(12) United States Patent
Bandiera et al.

(10) Patent No.: US 11,597,723 B2
(45) Date of Patent: Mar. 7, 2023

(54) PYRAZOLE DERIVATIVES FOR THE TREATMENT OF CYSTIC FIBROSIS

(71) Applicants: Fondazione Istituto Italiano Di Tecnologia, Genoa (IT); Istituto Giannina Gaslini, Genoa (IT); Fondazione Per La Ricerca Sulla Fibrosi Cistica—Onlus, Verona (IT)

(72) Inventors: Tiziano Bandiera, Genoa (IT); Fabio Bertozzi, Genoa (IT); Paolo Di Fruscia, Genoa (IT); Federico Sorana, Verona (IT); Emanuela Caci, Verona (IT); Loretta Ferrera, Verona (IT); Nicoletta Pedemonte, Genoa (IT); Luis Juan Vicente Galietta, Genoa (IT)

(73) Assignees: Fondazione Istituto Italiano Di Technologia, Genoa (IT); Istituto Giannina Gasiini, Genoa (IT); FondaZione Per La Ricerca Sulla Fibrosi Cristica—Onlus, Verona (IT)

( * ) Notice: Subject to any disclaimer, the term of this patent is extended or adjusted under 35 U.S.C. 154(b) by 0 days.

(21) Appl. No.: 16/493,457

(22) PCT Filed: Mar. 14, 2018

(86) PCT No.: PCT/IB2018/051714
§ 371 (c)(1),
(2) Date: Sep. 12, 2019

(87) PCT Pub. No.: WO2018/167695
PCT Pub. Date: Sep. 20, 2018

(65) Prior Publication Data
US 2020/0131157 A1  Apr. 30, 2020

(30) Foreign Application Priority Data
Mar. 14, 2017 (IT) .................. 102017000028127

(51) Int. Cl.
| | | |
|---|---|---|
| *C07D 401/12* | (2006.01) | |
| *C07D 403/12* | (2006.01) | |
| *C07D 407/12* | (2006.01) | |
| *C07D 407/14* | (2006.01) | |
| *C07D 413/12* | (2006.01) | |
| *C07D 487/04* | (2006.01) | |
| *C07D 405/12* | (2006.01) | |
| *C07D 231/16* | (2006.01) | |
| *C07D 403/14* | (2006.01) | |
| *C07D 409/12* | (2006.01) | |
| *C07D 417/12* | (2006.01) | |

(52) U.S. Cl.
CPC ......... *C07D 405/12* (2013.01); *C07D 231/16* (2013.01); *C07D 403/12* (2013.01); *C07D 403/14* (2013.01); *C07D 409/12* (2013.01); *C07D 413/12* (2013.01); *C07D 417/12* (2013.01)

(58) Field of Classification Search
CPC .. C07D 401/12; C07D 403/12; C07D 407/12; C07D 407/14; C07D 413/12; C07D 487/04
See application file for complete search history.

(56) References Cited

U.S. PATENT DOCUMENTS

2016/0304466 A1* 10/2016 Feng .................... C07D 401/14

FOREIGN PATENT DOCUMENTS

| EP | 1820795 A1 | 8/2007 |
|---|---|---|
| WO | 2003068749 A1 | 8/2003 |
| WO | 2004080972 A1 | 9/2004 |
| WO | 2005075435 A1 | 8/2005 |
| WO | 2007120647 A2 | 10/2007 |
| WO | 2008082487 A2 | 7/2008 |
| WO | 2011147764 A1 | 12/2011 |

OTHER PUBLICATIONS

RN 1241546-34-8 STN, 2010.*
RN 1242907-64-7 STN, 2010.*
RN 1319124-08-7 STN, 2011.*
RN 1427903-47-6, STN 2013, RN 1385992-43-7 STN 2012.*
RN 1839719-73-1 STN Registry of STNext. 2016.*
RN 1829213-54-8 STN Registry of STNext. 2015.*
RN 1825461-58-2 STN Registry of STNext. 2015.*
RN 1808821-79-5 STN Registry of STNext. 2015.*
RN 1825617-50-2 Registry in STN Registry of STNext.*
RN 1825541-66-9 Registry in STN Registry of STNext.*
International Search Report and Written Opinion for PCT Patent Application No. PCT/IB2018/051714 dated May 18, 2018.
Italian Search Report, Rapporto Di Ricerca for Italian Patent Application No. 2017000028127 dated Aug. 14, 2017.
Hu F L, et al., "Synthesis, Characterization and Luminescence Properties of Eu(III) and Tb(III) Complexes with Novel Pyrazole Derivatives and 1,10-Phenanthroline", Spectrochemica ACTA., Part A: Molecular and Biomolecular Spectroscopy, Elsevier, Amsterdam, NL, vol. 75, No. 2, Feb. 1, 2010.

(Continued)

*Primary Examiner* — Brian E McDowell
(74) *Attorney, Agent, or Firm* — McAndrews, Held & Malloy, Ltd.

(57) ABSTRACT

The present invention relates to compounds of Formula (I) or pharmaceutically acceptable salts or solvates thereof. It further discloses a pharmaceutical composition comprising the compounds of Formula (I) and their uses, in particular to modulate CFTR protein or ABC protein activities.

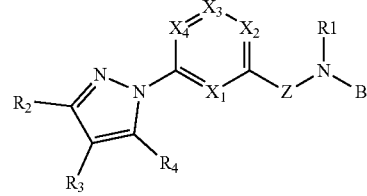

Formula (I)

2 Claims, 1 Drawing Sheet

(56) References Cited

OTHER PUBLICATIONS

Rong Jiang et al., "Design and Synthesis of 1-aryl-5-anilinoindazoles as c-Jun N-terminal kinase inhibitors", Bioorganic & Medicinal Chemistry Letters, vol. 23, No. 9, May 1, 2013.
Ke Zheng et al., "Design and Synthesis of Highly Potent and Isoform Selective JNK3 Inhibitors: SAR Studies on Aminopyrazole Derivatives", Journal of Medicinal Chemistry, vol. 57, No. 23, Dec. 11, 2014.

* cited by examiner

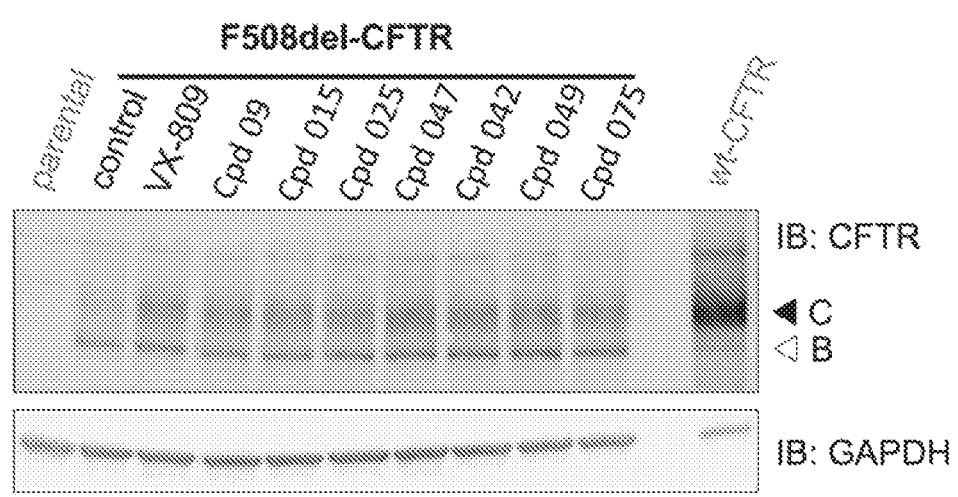

PYRAZOLE DERIVATIVES FOR THE TREATMENT OF CYSTIC FIBROSIS

PRIORITY CLAIM

The present application is filed pursuant to 35 U.S.C. 371 as a U.S. National Phase application of International Patent Application No. PCT/IB2018/051714, which was filed Mar. 14, 2018, claiming the benefit of priority from Italian Patent Application No. 102017000028127 filed on Mar. 14, 2017. The entire text of the aforementioned applications is incorporated herein by reference in its entirety.

TECHNICAL FIELD

The present invention relates to novel compounds to modulate CFTR protein or ABC protein activities, in particular for the treatment of cystic fibrosis.

BACKGROUND ART

Cystic fibrosis is an autosomal recessive genetic disorder caused by mutations of the gene encoding for the cystic fibrosis transmembrane conductance regulator (CFTR). The incidence of the disease among the Caucasian population is 1/2000-3000 newborns, whereas it is much lower among native Africans and Asians. Despite progress in the treatment of cystic fibrosis, there is no cure.

The cystic fibrosis transmembrane conductance regulator (CFTR) gene encodes an epithelial ion channel responsible for aiding in the regulation of salt and water absorption and secretion in various tissues.

Specifically, CFTR is a 1480 amino acid plasma membrane protein that belongs to the superfamily of ATP-binding cassette (ABC) transporters. CFTR structure consists of a cytosolic N-terminus followed by six transmembrane helices, a nucleotide-binding domain (NBD1), a regulatory (R) domain, six additional transmembrane helices, a second nucleotide-binding domain (NBD2), and a cytosolic C-terminus (Riordan, *Annu Rev Biochem* 77:701-726, 2008). The transmembrane helices form a pore permeable to chloride, bicarbonate, iodide, and other anions. Opening of the pore requires the phosphorylation of the R domain by the cAMP-dependent protein kinase A as well as binding of two ATP molecules in two pockets formed by the assembly of NBD1 and NBD2.

CFTR is a cAMP/ATP-modulated anion channel that is expressed in a variety of cells types, and particularly in epithelial cells of various organs including lungs, pancreas, liver, and intestine (Mall and Hartl, *Eur Respir J* 44:1042-1054, 2014). Physiological signals that increase intracellular cAMP levels elicit CFTR activation. In most tissues, opening of CFTR pore leads to chloride and bicarbonate secretion. A notable exception is represented by the sweat gland duct in which CFTR mediates chloride absorption and not secretion.

In epithelial cells, normal functioning of CFTR is critical for the maintenance of electrolyte transport throughout the body, including respiratory and digestive tissues.

The important role of CFTR is demonstrated by the severe pathological manifestations occurring in cystic fibrosis (CF), an inherited disease caused by mutations that lead to CFTR loss of function. In the lungs, lack of CFTR-dependent anion secretion impairs mucociliary clearance and innate antimicrobial mechanisms (Collawn and Matalon, *Am J Physiol* 307: L917-L923, 2014). Consequently, the airways become colonized by antibiotic-resistant bacteria that trigger a severe inflammatory response and a progressive loss of respiratory function.

The gene encoding CFTR has been identified and sequenced (See Gregory, R. J. et al. (1990) Nature 347:382-386; Rich, D. P. et al. (1990) Nature 347:358-362; Riordan, J. R. et al. (1989) Science 245:1066-1073). Defects in this gene cause mutations in CFTR protein resulting in cystic fibrosis, the most common fatal genetic disease in humans. Within the general United States population, up to 10 million people carry a single copy of the defective gene without apparent ill effects. In contrast, individuals with two copies of the cystic fibrosis associated gene suffer from the debilitating and fatal effects of cystic fibrosis, including chronic lung disease.

In addition to respiratory disease, cystic fibrosis patients typically suffer from gastrointestinal problems and pancreatic insufficiency. If left untreated, cystic fibrosis results in death. In addition, the majority of males with cystic fibrosis are infertile and fertility is decreased among females with cystic fibrosis. In contrast to the severe effects of two copies of the cystic fibrosis associated gene, individuals with a single copy of the cystic fibrosis associated gene may exhibit increased resistance to dehydration resulting from diarrhea. This heterozygote advantage could explain the relatively high frequency of the cystic fibrosis gene within the population.

Sequence analysis of the CFTR gene of cystic fibrosis patients has revealed a variety of disease causing mutations (Cutting, G. R. et al. (1990) Nature 346:366-369; Dean, M. et al. (1990) Cell 61:863-870; Kerem, B-S. et al. (1989) Science 245: 1073-1080; Kerem, B-S. et al. (1990) Proc. Natl. Acad. Sci. USA 87:8447-8451). To date, more than 2000 CF-causing mutations in the cystic fibrosis gene have been identified, involving 6 classes of molecular defects of the protein (Class I: premature stop of CFTR protein synthesis; Class II: defective maturation and intracellular localisation of the CFTR protein; Class III: impaired opening of CFTR pore; Class IV: reduced ability of CFTR pore to translocate anions; Class V: reduced CFTR protein synthesis due to altered RNA splicing; Class VI: reduced stability of CFTR at the plasma membrane leading to accelerated internalization and degradation).

A large majority of mutations have low or very low frequency (Bobadilla et al., *Hum Mutat* 19:575-606, 2002). However, a single mutation, F508del, is present in 50-90% of CF patients. F508del, i.e. loss of phenylalanine at position 508 within NBD1, causes multiple defects to CFTR protein (Okiyoneda et al., *Nat Chem Biol* 9:444-454, 2013). First of all, F508del-CFTR folding and stability are severely impaired. Such problems, which arise from the intrinsic instability of NBD1 and the altered interaction between NBD1 and the cytosolic loop 4, strongly reduce the trafficking of F508del-CFTR to the plasma membrane (trafficking defect). Indeed, mutant CFTR remains trapped in the endoplasmic reticulum (ER) where it is rapidly degraded by the ubiquitin-proteasome system (Lukacs and Verkman, *Trends Mol Med* 18:81-91, 2012). A second defect caused by F508del is the reduction of the open channel probability, i.e. the fraction of time spent by the channel in the open state (gating defect). Furthermore, if moved to the plasma membrane by rescue maneuvers, F508del-CFTR shows also a decreased half-time. Because of such defects, F508del mutation has combined class II, class III, and class VI characteristics.

The trafficking and gating defects can also be caused, often separately, by other CF mutations. For example, G85E, L1077P, A455E, and N1303K, defined as class II mutations, impair CFTR trafficking (Van Goor et al., *J Cyst Fibros* 13:29-36, 2014). Instead, G551D, G1349D, G178R, and G970R, defined as class III mutations, do not affect trafficking but strongly reduce CFTR open time (Yu et al., *J Cyst Fibros* 11:237-245, 2012).

The most prevalent mutation, i.e. the F508del, is associated with a severe disease.

The reduced number of channels in the membrane and the defective gating lead to reduced anion transport across epithelia leading to defective ion and fluid transport.

As discussed above, it is believed that the deletion of residue 508 in CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. This cellular phenomenon of defective ER processing of ABC transporters by the ER machinery has been shown to be the underlying basis not only for cystic fibrosis disease, but for other diseases (Loo et al., *Journal of Bioenergetics and Biomembranes*, 2005, 37, 501-507).

At present, the treatment of lung disorders in cystic fibrosis requires the development of innovative drugs aimed at the concomitant aspects of the disease and, consequently, modulators of the defective CFTR protein, new antibacterials and new anti-inflammatory agents, which can be used in parallel to obtain a synergistic action. Trafficking and gating defects caused by mutations in the CFTR protein are amenable to pharmacological treatment (Veit et al., *Mol Biol Cell* 27:424-433, 2016). Mistrafficking can be targeted with small molecules called correctors. Gating can be improved with so-called potentiators. There have been several attempts to identify potentiators and correctors (Galietta, *Pediatr Drugs* 15:393-402, 2013). The most advanced molecule is VX-770, also known as ivacaftor, developed by Vertex Pharmaceuticals (Van Goor et al., *Proc Natl Acad Sci USA* 106:18825-18830, 2009). Given its high efficacy in clinical trials (Ramsey et al., *N Engl J Med* 365:1663-1672, 2011), VX-770 has been approved for the treatment of patients with G551D and other eight mutations belonging to class III, who represent about 5% of all the cystic fibrosis patients. VX-770 has no significant therapeutic efficacy in patients who are homozygous for the F508del-CFTR mutation, confirming the need for customised treatments for sub-groups of patients suffering from cystic fibrosis depending on the specific CFTR protein molecular defect. For patients with the F508del-CFTR mutation, new molecules functioning as "correctors" of the mutated CFTR protein are under study. The VX-809 molecule, also known as lumacaftor, has been extensively characterized in cell models in vitro. In clinical trials on cystic fibrosis patients with F508del mutation, VX-809 did not show a clear therapeutic benefit (Clancy et al., *Thorax* 67:12-18, 2012). However, the combination of VX-809 and VX-770, commercially named Orkambi, elicited a significant although modest improvement in respiratory function (Wainwright et al., *N Engl J Med* 373: 220-231, 2015). Briefly, the treatment of cystic fibrosis patients requires different modulators of the mutated CFTR protein, namely "correctors" and/or "potentiators", depending on the mutations of the CFTR gene, which divide the patients into genetically distinct sub-groups, and complementary medicaments with an antibacterial action and an anti-inflammatory action.

Accordingly, there is a need for novel compounds to be used for the treatment of CFTR mediated diseases which involve CFTR modulator compounds.

DISCLOSURE OF INVENTION

The aim of the present invention is to provide novel compounds acting as CFTR modulators.

The aforementioned objective has been met according to compounds of claim 1, to a pharmaceutical composition of claim 5, to the uses of claims 6, 7 and 8. Preferred embodiments are set out within the dependent claims.

BRIEF DESCRIPTION OF THE DRAWINGS

The present invention will be now described in detail also with reference to the annexed FIGURE wherein:

FIG. 1 illustrates the analysis of electrophoretic mobility of mutant and wild type CFTR.

BEST MODE FOR CARRYING OUT THE INVENTION

The following paragraphs provide definitions of the various chemical moieties of the compounds according to the invention and are intended to apply uniformly through-out the specification and claims unless an otherwise expressly set out definition provides a broader definition.

The term "alkyl", as used herein, refers to saturated aliphatic hydrocarbon groups. Such term includes straight (unbranched) chains or branched chains.

Non-limiting examples of alkyl groups according to the invention are, for example, methyl, ethyl, propyl, isopropyl, n-butyl, iso-butyl, tert-butyl, n-pentyl, iso-pentyl, n-hexyl and the like.

Alkyl groups according to the present invention may be unsubstituted or substituted by one or more substituents as defined below.

The term "alkoxy", as used herein, refers to an alkyl group as defined above that is linked to the remainder of the compound by an oxygen atom.

The term "cycloalkyl", as used herein, refers to a saturated or partially unsaturated carbocyclic group having a single ring. It includes cycloalkenyl groups.

Non-limiting examples of cycloalkyl groups according to the invention are, for example, cyclopropane, cyclobutane, cyclopentane, cyclohexane, cycloheptane, cyclopentene, cyclohexene, cyclohexadiene and the like.

Cycloalkyl groups according to the present invention may be unsubstituted or substituted by one or more substituents as defined below.

The term "heterocycloalkyl" group, ("non-aromatic heterocycle" group), refers to a cycloalkyl group (non aromatic group) wherein at least one of the carbon atoms has been replaced by a heteroatom selected from nitrogen, oxygen and sulfur. Heterocycloalkyl groups can be unsubstituted or substituted by one or more substituents as defined below.

Examples of heterocycloalkyls include, but are not limited to, lactams, lactones, cyclic imides, cyclic thioimides, cyclic carbamates, 1-(1,2,5,6-tetrahydropyridyl), tetrahydrothiopyran, 4H-pyran, tetrahydropyran, piperidine (2-piperidinyl, 3-piperidinyl), 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, morpholine (4-morpholinyl, 3-morpholinyl, 2-morpholinyl) trioxane, hexahydro-1,3,5-triazine, tetrahydrothiophene, tetrahydrofuran (tetrahydrofuran-2-yl, tetrahydrofuran-3-yl), pyrroline, pyrrolidine, pyrrolidone, pyrrolidindione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane.

The term "halogen", as used herein, refers to fluorine, chlorine, bromine and iodine.

The term "aryl", as used herein, refers to a hydrocarbon consisting of an unsubstituted or substituted mono-, bi- or tricarbocyclic ring system, wherein the rings are fused together and at least one of the carbocyclic ring is aromatic. The term "aryl" means for example a cyclic aromatic such as a 6-membered hydrocarbon ring, a two six-membered fused hydrocarbon rings. Non-limiting examples of aryl groups are, for example, phenyl, alpha- or beta-naphthyl, 9,10-dihydroanthracenyl, indanyl, fluorenyl and the like. Aryl groups according to the present invention may be unsubstituted or substituted by one or more substituents as defined below.

The term "aromatic ring", as used herein, refers to a moiety wherein the constituent carbon atoms make up an unsaturated ring system, all atoms in the ring system are $sp^2$ hybridized and the total number of n-electrons is equal to 4n+2, wherein n is an integer.

The term "heteroaryl", as used herein, refers to an aryl as defined above wherein one to four carbon atoms are independently replaced by heteroatoms chosen from the group consisting of nitrogen, oxygen and sulphur. Non-limiting examples of heteroaryl groups are, for example, pyrrolyl, furyl, thiophenyl, imidazolyl, pyrazolyl, oxazolyl, isoxazolyl, triazolyl, isothiazolyl, indolyl, benzofuranyl, benzothiophenyl, benzimidazolyl, benzopyrazolyl, benzoxazolyl, benzoisoxazolyl, benzothiazolyl, benzoisothiazolyl, triazolyl, oxadiazolyl, tetrazolyl, pyridyl, pyrazinyl, pyrimidinyl, pyridazinyl, quinolinyl, isoquinolinyl, quinazolinyl, quinoxalinyl. Heteroaryl groups according to the present invention may be unsubstituted or substituted by one or more substituents as defined below.

Unless otherwise indicated, the term "substituted", as used herein, means that one or more hydrogen atoms of the above mentioned groups are replaced with another non-hydrogen atom or functional group referred to as substituent, provided that normal valencies are maintained and that the substitution results in a stable compound. Non-limiting example of substituents are, for example, OH, $C_{1-6}$alkyl, aryl, $C_{1-6}$alkylaryl, $C_{3-6}$ cycloalkyl, O—$C_{1-6}$alkyl, O—$C_{3-6}$ cycloalkyl, O-aryl, O—$C_{1-6}$alkylaryl, heteroaryl, O-heteroaryl, O-heterocycloalkyl, trifluoromethyl, difluoromethyl, trifluoromethoxy, difluoromethoxy, acyl, aroyl, heteroaroyl, halogen, nitro, cyano, COOR$^z$, alkylthio, arylthio, alkylsulfinyl, arylsulfinyl, alkylsulfonyl, arylsulfonyl, —O—C(=O)—NR$^h$R$^k$, —C(=O)—NR$^h$R$^k$, and —NR$^p$R$^q$, wherein each of R$^z$, R$^h$, and R$^k$, independently represents hydrogen, $C_{1-6}$alkyl, $C_{3-6}$cycloalkyl, aryl, $C_{1-6}$alkylaryl, heteroaryl, heteroC$_{3-6}$cycloalkyl, R$^p$ and R$^q$ independently represents hydrogen, $C_{1-6}$alkyl, $C_{3-6}$ cycloalkyl, aryl, $C_{1-6}$alkylaryl, heteroaryl, heteroC$_{3-6}$ cycloalkyl, COR$^z$, COOR$^z$, —C(=O)—NR$^h$R$^k$, —S(=O)$_2$—R$^z$, and —S(=O)$_2$—NR$^h$R$^k$, and when R$^h$ and R$^k$, or R$^p$ and R$^q$ are taken together with the nitrogen atom to which they are bound, the group —NR$^h$R$^k$ or the group NR$^p$R$^q$ represent a heterocycloalkyl residue, and wherein the terms alkyl, cycloalkyl, aryl, heteroaryl, heterocyclyl are as above defined.

Preferred substituents are OH, $C_{1-6}$alkyl, O—$C_{1-6}$alkyl, O—$C_{1-6}$alkylaryl, O-aryl, O—$C_{1-6}$alkylheteroaryl, $C_{1-6}$alkyl-O-aryl, $C_{1-6}$alkyl-O-heteroaryl, trifluoromethyl, difluoromethyl, halogen, $C_{3-6}$ cycloalkyl, O—$C_{3-6}$ cycloalkyl, trifluoromethoxy, difluoromethoxy, cyano, —NR$^p$R$^q$ and COOR$^z$ wherein R$^z$ is selected from the group consisting of H, methyl, ethyl, propyl, butyl, i-propyl, t-butyl, and R$^p$ and R$^q$ are independently selected from H, methyl, ethyl, butyl, i-propyl, phenyl, COR$^z$, COOR$^z$, —C(=O)—NR$^h$R$^k$, and —S(=O)$_2$—R$^z$. More preferred substituents are selected from OH, methyl, methoxy, chlorine, fluorine, trifluoromethyl, trifluoromethoxy, cyano, —NR$^p$R$^q$ and COOR$^z$ wherein R$^z$ is selected from the group consisting of H, methyl, ethyl and t-butyl, and R$^p$ and R$^q$ are independently selected from H, methyl, ethyl, butyl, i-propyl, phenyl, and acyl.

The term "pharmaceutically acceptable salts" refers to salts of the below identified compounds of Formula (I) that retain the desired biological activity and are accepted by regulatory authorities.

As used herein, the term "salt" refers to any salt of a compound according to the present invention prepared from an inorganic or organic acid or base and internally formed salts. Typically, such salts have a physiologically acceptable anion or cation.

Furthermore, the compounds of Formula (I) may form an acid addition salt or a salt with a base, depending on the kind of the substituents, and these salts are included in the present invention, as long as they are pharmaceutically acceptable salts.

Examples of such salts include, but are not restricted to acid addition salts formed with inorganic acids (e. g. hydrochloric acid, hydrobromic acid, sulfuric acid, phosphoric acid, nitric acid, and the like), salts formed with organic acids such as acetic acid, trifluoroacetic acid, oxalic acid, tartaric acid, succinic acid, malic acid, fumaric acid, maleic acid, ascorbic acid, benzoic acid, alginic acid, polyglutamic acid and naphthalene sulfonic acid.

The compounds of formula (I) containing acidic protons may be converted into their therapeutically active, non-toxic base addition salt forms, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Physiologically or pharmaceutically acceptable salts are particularly suitable for medical applications because of their greater aqueous solubility relative to the parent compound.

Pharmaceutically acceptable salts may also be prepared from other salts including other pharmaceutically acceptable salts of the compounds of Formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of the invention are within the scope of the invention. The compounds of Formula (I) may readily be isolated in association with solvent molecules by crystallization or evaporation of an appropriate solvent to give the corresponding solvates.

The compounds of Formula (I) may be in crystalline form. In certain embodiments, the crystalline forms of the compounds of Formula (I) are polymorphs.

The subject invention also includes isotopically-labelled compounds, which are identical to those recited in Formula (I) and following, but differ on the fact that one or more atoms are replaced by an atom having an atomic mass or mass number different from the atomic mass or mass number usually found in nature. Examples of isotopes that can be incorporated into the compounds of the invention and pharmaceutically acceptable salts thereof include isotopes of hydrogen, carbon, nitrogen, oxygen, sulfur, fluorine, and chlorine, such as $^2H$, $^3H$, $^{11}C$, $^{13}C$, $^{14}C$, $^{15}N$, $^{17}O$, $^{18}O$, $^{35}S$, $^{18}F$, $^{36}Cl$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e. $^3H$, and carbon-14, i.e. $^{14}C$, isotopes are particularly preferred for their ease of preparation and detectability. $^{11}C$ and $^{18}F$ isotopes are particularly useful in PET (Positron Emission Tomography). Furthermore, substitution with heavier isotopes such as deuterium, i.e. $^2H$, can afford certain therapeutic advantages resulting from greater metabolic stability, for example increased in vivo half-life or reduced dosage requirements and, hence, may be preferred in some circumstances. Isotopically-labelled compounds of Formula (I) and following of this invention can generally be prepared by carrying out the procedures disclosed in the Schemes and/or in the Examples below, by replacing a non-isotopically-labelled reagent with a readily available isotopically-labelled reagent.

Certain groups/substituents included in the present invention may be present as isomers or in one or more tautomeric forms. Accordingly, in certain embodiments, the compounds of Formula (I) may exist in the form of other tautomers or geometrical isomers in some cases, depending on the kinds of the substituents. In the present specification, the compounds may be described in only one form of such isomers, but the present invention includes all such isomers, isolated forms of the isomers, or a mixture thereof. Furthermore, the compounds of Formula (I) may have asymmetric carbon atoms or axial asymmetries in some cases and, correspondingly, they may exist in the form of optical isomers such as an (R)-form, an (S)-form, and the like. The present invention includes within the scope all such isomers, including racemates, enantiomers and mixtures thereof. In particular, within the scope of the present invention are included all stereoisomeric forms, including enantiomers, diastereoisomers, and mixtures thereof, including racemates, and the general reference to the compounds of Formula (I) includes all the stereoisomeric forms, unless otherwise indicated.

In general, the compounds or salts of the invention should be interpreted as excluding those compounds (if any) which are so chemically unstable, either per se or in water, that they are clearly unsuitable for pharmaceutical use through all administration routes, whether oral, parenteral, or otherwise. Such compounds are known to the skilled chemist.

According to a first aspect of the invention, compounds of Formula (I):

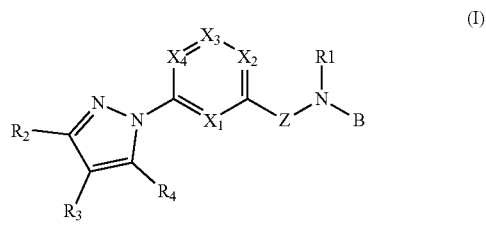

or pharmaceutically acceptable salts or solvates thereof are provided.

In the compounds of Formula (I):

$R_1$ is selected from the group consisting of $C_{1-6}$alkyl, $C_{3-6}$cycloalkyl, hydroxy-$C_{1-6}$alkyl;

$R_2$ and $R_3$, are independently selected from the group consisting of hydrogen, $C_{1-6}$alkyl, halo$C_{1-6}$alkyl, $C_{3-6}$cycloalkyl, aryl, heteroaryl, $COR^{viii}$, $COOR^{viii}$, heterocycloalkyl, $CONHR^{viii}$, $CONR^{viii}R^{ix}$, OH, O—$C_{1-6}$alkyl, O—$C_{3-6}$cycloalkyl, O-heterocycloalkyl, O-heteroaryl, O-aryl, O-halo$C_{1-6}$alkyl, $C_{1-6}$alkyl-O—$C_{1-6}$alkyl, $C_{1-6}$alkyl-O—$C_{3-6}$cycloalkyl, $C_{1-6}$alkyl-O-heterocycloalkyl, $C_{1-6}$alkyl-O-aryl, $C_{1-6}$alkyl-O-heteroaryl, CN, $NO_2$, $NR^xR^{xi}$, $N(R^{ix})COR^x$, $N(R^{ix})COOR^{xi}$, $N(R^{ix})CONR^{xi}R^x$, $N(R^{ix})SO_2R^x$, $SO_2R^x$, $SO_2NR^{ix}R^x$, halogen, hydroxy-$C_{1-6}$alkyl, and aryl-$C_{1-6}$alkyl;

or $R_2$ and $R_3$, taken together with the carbon atoms to whom they are bound, can form a saturated or unsaturated 5-membered, 6-membered or 7-membered carbocyclic ring or a 5-membered, 6-membered or 7-membered heterocycloalkyl containing from 1 to 3 heteroatoms selected from O, N, and S;

$R_4$ is hydrogen, $C_{1-6}$alkyl, halo$C_{1-6}$alkyl, $C_{3-6}$cycloalkyl, heterocycloalkyl, aryl, heteroaryl, $COR^{viii}$, $COOR^{viii}$, $CONHR^{viii}$, $CONR^{viii}R^{ix}$, $NR^xR^{xi}$, OH, O—$C_{1-6}$alkyl, O—$C_{1-6}$alkylaryl, O—$C_{1-6}$alkyl-$C_{3-6}$cycloalkyl, O—$C_{3-6}$cycloalkyl, O—$C_{1-6}$alkylheteroaryl, O-heterocycloalkyl, O-halo$C_{1-6}$alkyl, O-aryl, O-heteroaryl, $C_{1-6}$alkyl-O—$C_{3-6}$cycloalkyl, $C_{1-6}$alkyl-O-aryl, $C_{1-6}$alkyl-O-heteroaryl, $C_{1-6}$alkyl-O-heterocycloalkyl, CN, halogen, hydroxy-$C_{1-6}$alkyl, $NO_2$, $N(R^{ix})COR^x$, $N(R^{ix})COOR^{xi}$, $N(R^{ix})CONR^{xi}R^x$, $N(R^{ix})SO_2R^x$, $SO_2R^x$, $SO_2NR^{ix}R^x$, and aryl-$C_{1-6}$alkyl;

Z is C=O or $SO_2$;

$X_1$, $X_2$, $X_3$ and $X_4$ are independently selected from the group consisting of $CR^{vii}$ and N, with the proviso that the number of nitrogen atoms in the ring is comprised from 0 to 2;

B represents an unsubstituted or a substituted aromatic or heteroaromatic ring selected from the group consisting of:

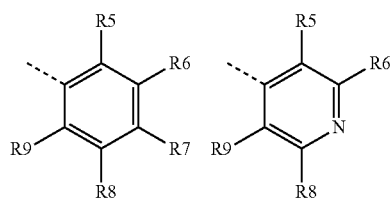

-continued

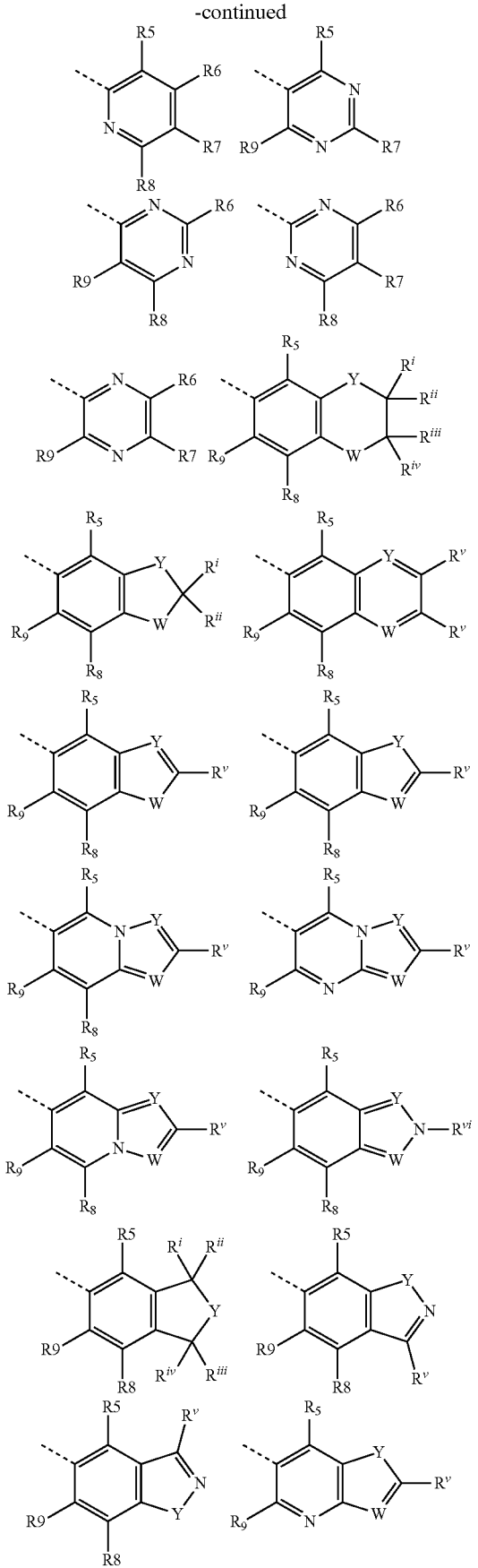
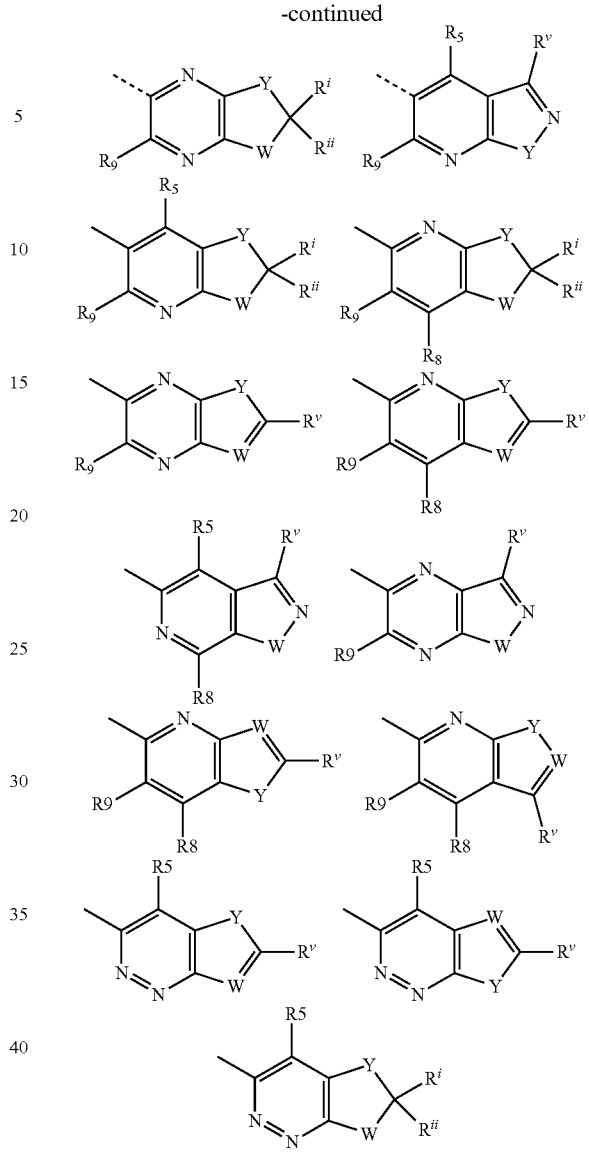

wherein

R$_5$, R$_6$, R$_7$, R$_8$, and R$_9$ are independently selected from the group consisting of hydrogen, halogen, C$_{1-6}$alkyl, haloC$_{1-6}$alkyl, C$_{3-6}$ cycloalkyl, O—C$_{3-6}$ cycloalkyl, O-heterocycloalkyl, COR$^{viii}$, COOR$^{viii}$, CONHR$^{viii}$, CONR$^{viii}$R$^{ix}$, OH, CN, NO$_2$, NR$^x$R$^{xi}$, N(R$^{ix}$)COR$^x$, N(R$^{ix}$)COOR$^{xi}$, N(R$^{ix}$)CONR$^x$R$^{xi}$, N(R$^{ix}$)SO$_2$R$^x$, SO$_2$R$^x$ and hydroxy-C$_{1-6}$alkyl or when R$_6$ and R$_7$ are present on a 6-membered heteroaromatic ring, taken together with the carbon atoms to whom they are bound, they can form a saturated or unsaturated 5-membered or 6-membered carbocyclic ring or a 5-membered or 6-membered heterocycloalkyl containing from 1 to 3 heteroatoms selected from O, N, and S or a 5-membered or 6-membered heteroaryl ring containing from 1 to 3 heteroatoms selected from O, N, and S;

Y and W are independently selected from the group consisting of O, S, SO$_2$, CR$^{iv}$R$^v$, CR$^v$, N, and NR$^{vi}$;

R$^i$, R$^{ii}$, R$^{iii}$ and R$^{iv}$ are independently selected from the group consisting of hydrogen, C$_{1-6}$alkyl, haloC$_{1-6}$alkyl, halogen, OH, O—C$_{1-6}$alkyl and O-haloC$_{1-6}$alkyl or when $R^i$ and $R^{ii}$, or $R^{iii}$ and $R^{iv}$ are taken together with the carbon atoms to whom they are bound, they can represent C=O;

$R^v$ is selected from the group consisting of hydrogen, $C_{1-6}$alkyl, haloC$_{1-6}$alkyl, O—C$_{1-6}$alkyl, halogen, $C_{3-6}$ cycloalkyl, OH, and O-haloC$_{1-6}$alkyl;

$R^{vi}$ is selected from the group consisting of hydrogen and $C_{1-6}$alkyl;

$R^{vii}$ is selected from the group consisting of hydrogen, $C_{1-6}$alkyl, $C_{3-6}$ cycloalkyl, haloC$_{1-6}$alkyl, O-haloC$_{1-6}$alkyl, COR$^{viii}$, COOR$^{viii}$, CONHR$^{viii}$, CONR$^{viii}$R$^{ix}$, OH, O—C$_{1-6}$alkyl, halogen, CN, NO$_2$, NR$^x$R$^{xi}$, N(R$^{ix}$)COR$^x$, N(R$^{ix}$)COOR$^{xi}$, N(R$^{ix}$)CONR$^x$R$^{xi}$, and N(R$^{ix}$)SO$_2$R$^x$;

$R^{viii}$ is selected from the group consisting of hydrogen, $C_{1-6}$alkyl, aryl, heteroaryl, hydroxy-$C_{1-6}$alkyl and $C_{1-6}$alkyl-O—C$_{1-6}$alkyl;

$R^{ix}$ is selected from the group consisting of hydrogen, $C_{1-6}$alkyl, hydroxy-$C_{1-6}$alkyl, and $C_{1-6}$alkyl-O—C$_{1-6}$alkyl;

$R^x$ is selected from the group consisting of hydrogen, $C_{1-6}$alkyl, $C_{3-6}$ cycloalkyl, heterocycloalkyl, aryl, heteroaryl, hydroxy-$C_{1-6}$alkyl, and $C_{1-6}$alkyl-O—C$_{1-6}$alkyl;

$R^{xi}$ is selected from the group consisting of hydrogen, $C_{1-6}$alkyl, hydroxy-$C_{1-6}$alkyl, aryl-$C_{1-6}$alkyl, heteroaryl-$C_{1-6}$alkyl, and heterocycloalkyl-$C_{1-6}$alkyl, provided that the compound of Formula (I) is not 3-(4-chloro-3,5-dimethyl-pyrazol-1-yl)-N-(2,3-dihydro-1,4-benzodioxin-6-yl)-N-methyl-benzamide.

According to a first embodiment:

$R_1$ is selected from the group consisting of $C_{1-6}$alkyl, $C_{3-6}$ cycloalkyl;

$R_2$ and $R_3$ are independently selected from the group consisting of hydrogen, $C_{1-6}$alkyl, haloC$_{1-6}$alkyl, $C_{3-6}$ cycloalkyl, aryl, heteroaryl, COR$^{viii}$, COOR$^{viii}$, CONHR$^{viii}$, CONR$^{viii}$R$^{ix}$, NR$^x$R$^{xi}$, O—C$_{1-6}$alkyl, O—C$_{1-6}$alkylaryl, O-heterocycloalkyl, O-haloC$_{1-6}$alkyl, O-aryl, $C_{1-6}$alkyl-O—C$_{1-6}$alkyl, $C_{1-6}$alkyl-O-aryl, CN, halogen, and hydroxy-$C_{1-6}$alkyl;

$R_4$ is hydrogen, $C_{1-6}$alkyl, haloC$_{1-6}$alkyl, $C_{3-6}$ cycloalkyl, heterocycloalkyl, aryl, heteroaryl, COR$^{viii}$, COOR$^{viii}$, CONHR$^{viii}$, CONR$^{viii}$R$^{ix}$, NR$^x$R$^{xi}$, O—C$_{1-6}$alkyl, O—C$_{1-6}$alkylaryl, O—C$_{1-6}$alkyl-$C_{3-6}$ cycloalkyl, O—C$_{3-6}$ cycloalkyl, O-heterocycloalkyl, O—C$_{1-6}$alkylheteroaryl, O-haloC$_{1-6}$alkyl, O-aryl, O-heteroaryl, O—C$_{1-6}$alkyl-O—C$_{1-6}$alkyl, $C_{1-6}$alkyl-O—C$_{3-6}$cycloalkyl, $C_{1-6}$alkyl-O-aryl, $C_{1-6}$alkyl-O-heteroaryl, $C_{1-6}$alkyl-O-heterocycloalkyl, CN, halogen, hydroxy-$C_{1-6}$alkyl;

Z is C=O or SO$_2$, $X_1$, $X_2$, $X_3$ and $X_4$ are independently selected from the group consisting of CR$^{vii}$ and N, with the proviso that the number of nitrogen atoms in the ring is comprised from 0 to 2;

B represents an unsubstituted or a substituted aromatic or heteroaromatic ring selected from the group consisting of:

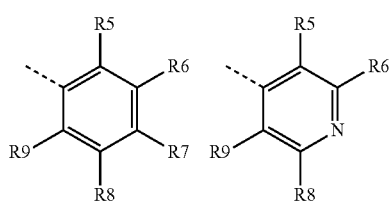

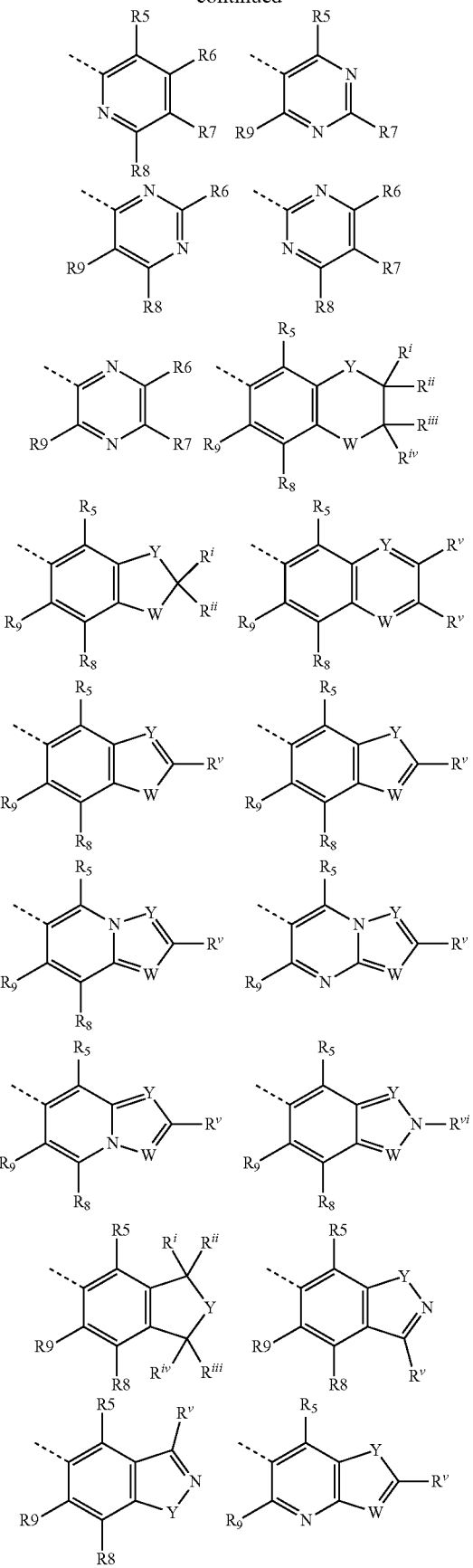

-continued

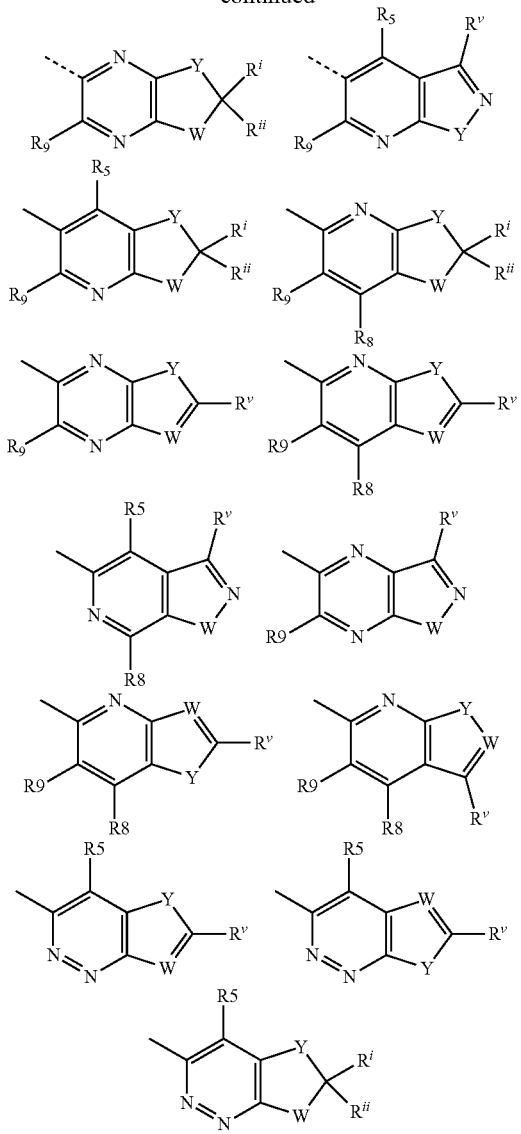

wherein $R_5$, $R_6$, $R_7$, $R_8$, and $R_9$ are independently selected from the group consisting of hydrogen, halogen, $C_{1-6}$alkyl, O—$C_{1-6}$alkyl, COR$^{viii}$, COOR$^{viii}$, NR$^x$R$^{xi}$, OH, CN and hydroxy-$C_{1-6}$alkyl;

or when $R_6$ and $R_7$ are present on a 6-membered heteroaromatic ring, taken together with the carbon atoms to whom they are bound, they can form a saturated or unsaturated 5-membered or 6-membered carbocyclic ring or a 5-membered or 6-membered heterocycloalkyl containing from 1 to 3 heteroatoms selected from O, N, and S or a 5-membered or 6-membered heteroaryl ring containing from 1 to 3 heteroatoms selected from O, N, and S;

Y and W are independently selected from the group consisting of O, S, CR$^i$R$^v$, CR$^v$, N, and NR$^{vi}$;

R$^i$, R$^{ii}$, R$^{iii}$ and R$^{iv}$ are independently selected from the group consisting of hydrogen, $C_{1-6}$alkyl and halogen;

R$^v$ is selected from the group consisting of hydrogen, $C_{1-6}$alkyl, halo$C_{1-6}$alkyl, halogen, O—$C_{1-6}$alkyl, $C_{3-6}$ cycloalkyl;

R$^{vi}$ is selected from the group consisting of hydrogen and $C_{1-6}$alkyl;

R$^{vii}$ is selected from the group consisting of hydrogen, $C_{1-6}$alkyl, halo$C_{1-6}$alkyl, halogen, OH, O—$C_{1-6}$alkyl, O-halo$C_{1-6}$alkyl, NR$^x$R$^{xi}$ and COOR$^{viii}$;

R$^{viii}$ is selected from the group consisting of hydrogen, $C_{1-6}$alkyl, aryl and hydroxy-$C_{1-6}$alkyl.

R$^{ix}$ is selected from the group consisting of hydrogen, $C_{1-6}$alkyl, and $C_{1-6}$alkyl-O—$C_{1-6}$alkyl;

R$^x$ is selected from the group consisting of hydrogen, $C_{1-6}$alkyl, $C_{3-6}$ cycloalkyl, heterocycloalkyl, aryl, heteroaryl, hydroxy-$C_{1-6}$alkyl;

R$^{xi}$ is selected from the group consisting of hydrogen, $C_{1-6}$alkyl, aryl-$C_{1-6}$alkyl, heteroaryl-$C_{1-6}$alkyl, and heterocycloalkyl-$C_{1-6}$alkyl.

According to a second embodiment:

$R_1$ is selected from the group consisting of $C_{1-4}$alkyl, $C_{3-4}$ cycloalkyl;

$R_2$ and $R_3$ are independently selected from the group consisting of hydrogen, $C_{1-4}$ alkyl, trifluoro$C_{1-4}$alkyl, $C_{3-4}$cycloalkyl, aryl, heteroaryl, COOR$^{viii}$, CONHR$^{viii}$, CONR$^{viii}$R$^{ix}$, NR$^x$R$^{xi}$, heterocycloalkyl, O-aryl, $C_{1-4}$alkyl-O—$C_{1-4}$alkyl, $C_{1-4}$ alkyl-O-aryl, CN, chlorine, fluorine, and hydroxy-$C_{1-4}$ alkyl;

$R_4$ is selected from the group consisting of hydrogen, $C_{1-4}$ alkyl, trifluoro$C_{1-4}$alkyl, $C_{3-4}$ cycloalkyl, aryl, heteroaryl, COOR$^{viii}$, CONHR$^{viii}$, CONR$^{viii}$R$^{ix}$, NR$^x$R$^{xi}$, O—$C_{1-4}$alkylaryl, O—$C_{1-4}$alkylheteroaryl, O-heterocycloalkyl, O-aryl, O-heteroaryl, $C_{1-4}$alkyl-O-aryl, $C_{1-4}$ alkyl-O-heteroaryl, CN, chlorine, fluorine, and hydroxy$C_{1-4}$ alkyl;

Z is C=O, $X_1$, $X_2$, $X_3$ and $X_4$ are independently selected from the group consisting of CR$^{vii}$ and N, with the proviso that the number of nitrogen atoms in the ring is comprised from 0 to 2;

B represents an unsubstituted or a substituted aromatic or heteroaromatic ring selected from the group consisting of:

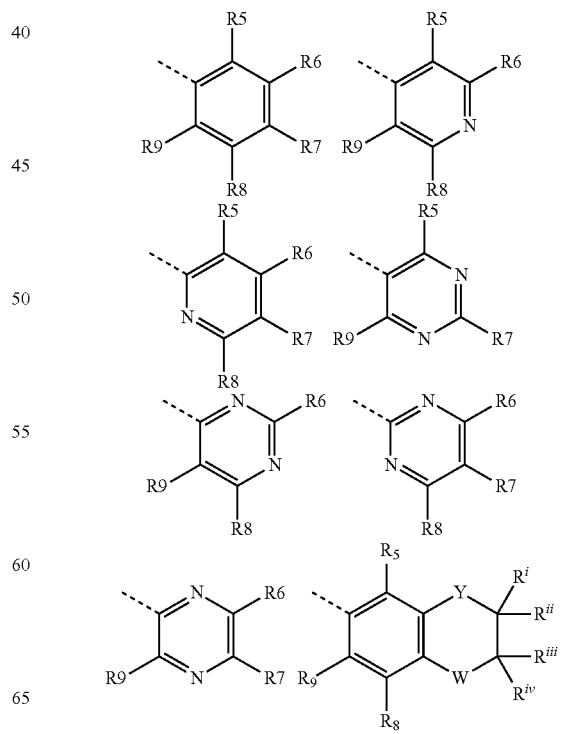

-continued

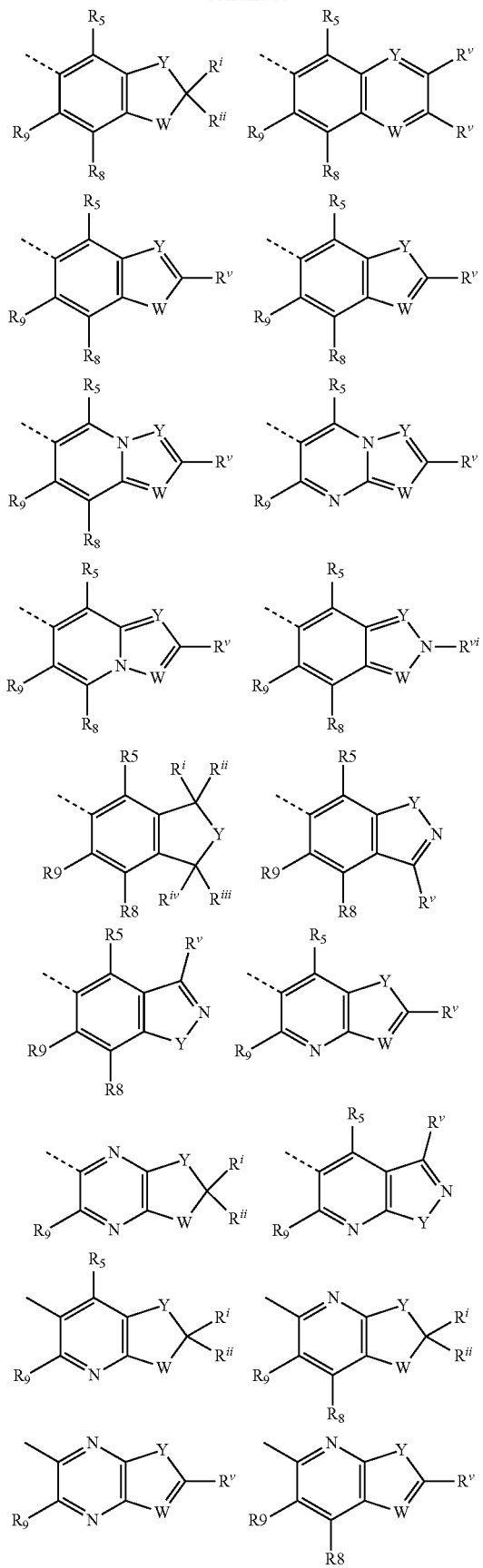

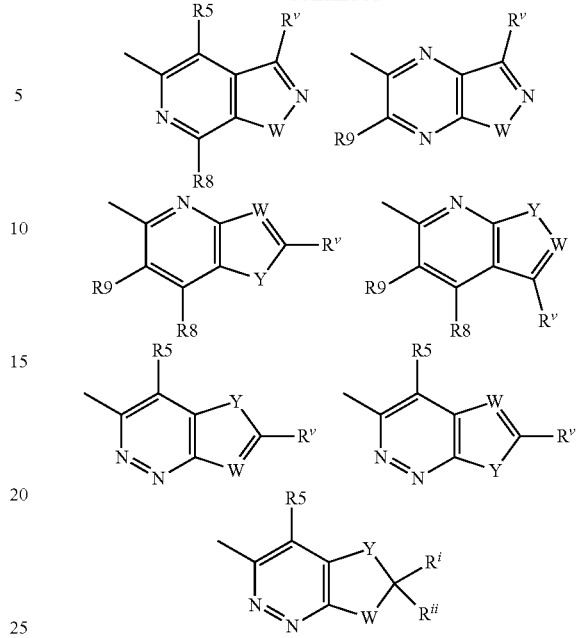

wherein $R_5$, $R_6$, $R_7$, $R_8$, and $R_9$ are independently selected from the group consisting of hydrogen, fluorine, chlorine, $C_{1-4}$alkyl, $COOR^{viii}$, $NR^x R^{xi}$, CN, and hydroxy-$C_{1-6}$alkyl;

or when $R_6$ and $R_7$ are present on a 6-membered heteroaromatic ring, taken together with the carbon atoms to whom they are bound, they can form a saturated or unsaturated 5-membered or 6-membered carbocyclic ring or a 5-membered or 6-membered heterocycloalkyl containing from 1 to 3 heteroatoms selected from O, N, and S or a 5-membered or 6-membered heteroaryl ring containing from 1 to 3 heteroatoms selected from O, N, and S;

Y and W are independently selected from the group consisting of O, S, $CR^{iv}R^v$, $CR^v$, N, and $NR^{vi}$;

$R^i$, $R^{ii}$, $R^{iii}$ and $R^{iv}$ are independently selected from the group consisting of hydrogen, $C_{1-4}$alkyl and fluorine;

$R^v$ is selected from the group consisting of hydrogen, $C_{1-4}$alkyl, trifluoromethyl, fluorine, O—$C_{1-4}$ alkyl, $C_{3-4}$cycloalkyl;

$R^{vi}$ is selected from the group consisting of hydrogen and $C_{1-4}$alkyl;

$R^{vii}$ is selected from the group consisting of hydrogen, $C_{1-4}$alkyl, trifluromethyl, fluorine, chlorine, OH, O—$C_{1-4}$alkyl, $NR^x R^{xi}$ and $COOR^{viii}$;

$R^{viii}$ is selected from the group consisting of hydrogen, $C_{1-4}$alkyl, and aryl;

$R^{ix}$ is selected from the group consisting of hydrogen, $C_{1-4}$alkyl, and $C_{1-4}$alkyl-O—$C_{1-4}$alkyl;

$R^x$ is selected from the group consisting of hydrogen, $C_{1-4}$ alkyl, $C_{3-4}$ cycloalkyl, heterocycloalkyl, aryl, and heteroaryl;

$R^{xi}$ is selected from the group consisting of hydrogen, $C_{1-4}$ alkyl, $C_{1-4}$alkyl-O—$C_{1-4}$alkyl; heteroaryl-$C_{1-6}$alkyl, and heterocycloalkyl-$C_{1-4}$ alkyl.

According to a third embodiment of the invention, the compounds of Formula (I) can be selected from the group consisting of:

| # | Substance Name |
|---|---|
| 3 | 3-(4-chloro-3,5-dimethyl-pyrazol-1-yl)-N-(2,3-dihydro-1,4-benzodioxin-6-yl)-N-isopropyl-benzamide |
| 4 | 3-(4-chloro-3,5-dimethyl-pyrazol-1-yl)-N-(2,3-dihydro-1,4-benzodioxin-6-yl)-N-ethyl-benzamide |
| 7 | 3-(4-chloro-3,5-dimethyl-pyrazol-1-yl)-N-methyl-N-phenyl-benzamide |
| 8 | 3-(4-chloro-3,5-dimethyl-pyrazol-1-yl)-N-methyl-N-(2,2,3,3-tetrafluoro-1,4-benzodioxin-6-yl)benzamide |
| 9 | 3-(4-chloro-3,5-dimethyl-pyrazol-1-yl)-N-(2,2-difluoro-1,3-benzodioxol-5-yl)-N-methyl-benzamide |
| 10 | N-(2,3-dihydro-1,4-benzodioxin-6-yl)-N-methyl-3-pyrazol-1-yl-benzamide |
| 11 | N-(2,3-dihydro-1,4-benzodioxin-6-yl)-3-(3,5-dimethylpyrazol-1-yl)-N-methyl-benzamide |
| 14 | 3-(4-chloro-3,5-dimethyl-pyrazol-1-yl)-N-(3,4-dimethoxyphenyl)-N-methyl-benzamide |
| 15 | N-(1,3-benzodioxol-5-yl)-3-(4-chloro-3,5-dimethyl-pyrazol-1-yl)-N-methyl-benzamide |
| 17 | N-(2,3-dihydro-1,4-benzodioxin-6-yl)-3-(3,5-dimethylpyrazol-1-yl)-N-methyl-benzenesulfonamide |
| 19 | 3-(4-chloro-3,5-dimethyl-pyrazol-1-yl)-N-(2,2-difluoro-1,3-benzodioxol-5-yl)-N-ethyl-benzamide |
| 20 | 3-(4-chloro-3,5-dimethyl-pyrazol-1-yl)-N-(2,3-dihydro-1,4-benzodioxin-6-yl)-N-methyl-benzenesulfonamide |
| 23 | 3-(4-chloro-3,5-dimethyl-pyrazol-1-yl)-N-indan-5-yl-N-methyl-benzamide |
| 24 | 3-(4-chloro-3,5-dimethyl-pyrazol-1-yl)-N-methyl-N-(1-methylbenzimidazol-5-yl)benzamide |
| 25 | 3-(4-chloro-3,5-dimethyl-pyrazol-1-yl)-N-methyl-N-(2-methyl-1,3-benzoxazol-5-yl)benzamide |
| 26 | 3-(4-chloro-3,5-dimethyl-pyrazol-1-yl)-N-(2,2-difluoro-1,3-benzodioxol-4-yl)-N-methyl-benzamide |
| 29 | N-(1,3-benzoxazol-5-yl)-3-(4-chloro-3,5-dimethyl-pyrazol-1-yl)-N-methyl-benzamide |
| 30 | 3-(4-chloro-3,5-dimethyl-pyrazol-1-yl)-N-cyclopropyl-N-(2,3-dihydro-1,4-benzodioxin-6-yl)benzamide |
| 31 | 5-(4-chloro-3,5-dimethyl-pyrazol-1-yl)-2,3-dihydro-1,4-benzodioxin-6-yl)-N,2-dimethyl-benzamide |
| 32 | N-(6-chloro-2,3-dihydro-1,4-benzodioxin-7-yl)-3-(4-chloro-3,5-dimethyl-pyrazol-1-yl)-N-methyl-benzamide |
| 33 | 3-(4-chloropyrazol-1-yl)-N-(2,3-dihydro-1,4-benzodioxin-6-yl)-N-methyl-benzamide |
| 34 | 3-(4-chloro-3,5-dimethyl-pyrazol-1-yl)-N-(2,2-dimethyl-1,3-benzodioxol-5-yl)-N-methyl-benzamide |
| 35 | 3-(4-chloro-3,5-dimethyl-pyrazol-1-yl)-N-(2,2-difluoro-1,3-benzodioxol-5-yl)-N-methyl-benzenesulfonamide |
| 36 | 3-(4-chloro-3,5-dimethyl-pyrazol-1-yl)-N-(3,4-dihydro-2H-1,4-benzoxazin-7-yl)-N-methyl-benzamide; 2,2,2-trifluoroacetic acid |
| 37 | 3-(4-tert-butyl-3,5-dimethyl-pyrazol-1-yl)-N-(2,3-dihydro-1,4-benzodioxin-6-yl)-N-methyl-benzamide |
| 38 | 3-(4-chloro-3,5-dimethyl-pyrazol-1-yl)-N-(3,4-dihydro-2H-1,4-benzoxazin-6-yl)-N-methyl-benzamide; 2,2,2-trifluoroacetic acid |
| 39 | 3-(4-chloro-3,5-dimethyl-pyrazol-1-yl)-N-(2,2-difluoro-1,3-benzodioxol-5-yl)-N-(trideuteriomethyl)benzamide |
| 42 | 3-(4-chloro-3,5-dimethyl-pyrazol-1-yl)-N-methyl-N-(6-methyl-1,3-benzodioxol-5-yl)benzamide |
| 43 | ethyl 1-[3-[1,3-benzodioxol-5-yl(methyl)carbamoyl]phenyl]-3,5-dimethyl-pyrazole-4-carboxylate |
| 44 | 3-(4-chloro-3,5-dimethyl-pyrazol-1-yl)-N-methyl-N-tetralin-6-yl-benzamide |
| 47 | 3-(4-chloro-3,5-dimethyl-pyrazol-1-yl)-N-methyl-N-(2-methyl-1,3-benzoxazol-6-yl)benzamide |
| 48 | 1-[3-[1,3-benzodioxol-5-yl(methyl)carbamoyl]phenyl]-3,5-dimethyl-pyrazole-4-carboxylic acid |
| 49 | N-(6-chloro-2,2-difluoro-1,3-benzodioxol-5-yl)-3-(4-chloro-3,5-dimethyl-pyrazol-1-yl)-N-methyl-benzamide |
| 50 | N-(1,3-benzodioxol-5-yl)-6-(4-chloro-3,5-dimethyl-pyrazol-1-yl)-N-methyl-pyridine-2-carboxamide |
| 55 | 3-(4-chloro-3,5-dimethyl-pyrazol-1-yl)-N-(2-cyclopropyl-1,3-benzoxazol-5-yl)-N-methyl-benzamide |
| 56 | 1-[3-[1,3-benzodioxol-5-yl(methyl)carbamoyl]phenyl]-3,5-dimethyl-pyrazole-4-carboxamide |
| 57 | 3-(4-chloro-3,5-dimethyl-pyrazol-1-yl)-N-(1,3-dihydroisobenzofuran-5-yl)-N-methyl-benzamide |
| 58 | 3-(4-chloro-3,5-dimethyl-pyrazol-1-yl)-N-(2,3-dihydrobenzofuran-5-yl)-N-methyl-benzamide |
| 59 | 1-[3-[1,3-benzodioxol-5-yl(methyl)carbamoyl]phenyl]-N-(2-hydroxyethyl)-3,5-dimethyl-pyrazole-4-carboxamide |
| 62 | 3-(4-chloro-3,5-dimethyl-pyrazol-1-yl)-N-(2-isopropyl-1,3-benzoxazol-5-yl)-N-methyl-benzamide |
| 64 | 3-(4-chloro-3,5-dimethyl-pyrazol-1-yl)-N-(2-methoxy-1,3-benzoxazol-5-yl)-N-methyl-benzamide |
| 65 | 2-[3-[1,3-benzodioxol-5-yl(methyl)carbamoyl]phenyl]-5-methyl-pyrazole-3-carboxylic acid |
| 66 | 1-[3-[1,3-benzodioxol-5-yl(methyl)carbamoyl]phenyl]-5-methyl-pyrazole-3-carboxylic acid |
| 67 | ethyl 1-[3-[1,3-benzodioxol-5-yl(methyl)carbamoyl]phenyl]-4-chloro-5-methyl-pyrazole-3-carboxylate |
| 68 | 3-(4-chloro-3,5-dimethyl-pyrazol-1-yl)-N-(3-methoxyphenyl)-N-methyl-benzamide |
| 69 | 1-[3-[1,3-benzodioxol-5-yl(methyl)carbamoyl]phenyl]-4-chloro-5-methyl-pyrazole-3-carboxylic acid |
| 70 | N-(1,3-benzodioxol-5-yl)-3-[5-(hydroxymethyl)-3-methyl-pyrazol-1-yl]-N-methyl-benzamide |
| 71 | N-(1,3-benzodioxol-5-yl)-3-(4-chloro-3,5-dimethyl-pyrazol-1-yl)-N-methyl-4-(trifluoromethyl)benzamide |
| 72 | N-(1,3-benzodioxol-5-yl)-2-(4-chloro-3,5-dimethyl-pyrazol-1-yl)-N-methyl-pyrimidine-4-carboxamide |
| 73 | N-(1,3-benzodioxol-5-yl)-3-[4-chloro-3-(hydroxymethyl)-5-methyl-pyrazol-1-yl]-N-methyl-benzamide |
| 74 | 1-[3-[1,3-benzodioxol-5-yl(methyl)carbamoyl]phenyl]-4-chloro-5-methyl-pyrazole-3-carboxamide |
| 75 | ethyl 2-[3-[1,3-benzodioxol-5-yl(methyl)carbamoyl]phenyl]-4-chloro-5-methyl-pyrazole-3-carboxylate |
| 76 | 3-(4-chloro-3,5-dimethyl-pyrazol-1-yl)-N-(2-ethyl-1,3-benzoxazol-6-yl)-N-methyl-benzamide |
| 77 | 3-(4-chloro-3,5-dimethyl-pyrazol-1-yl)-N-methyl-N-(2-methylimidazo[1,2-a]pyridin-6-yl)benzamide |
| 78 | 3-(4-chloro-3,5-dimethyl-pyrazol-1-yl)-N-methyl-N-[2-(trifluoromethyl)-1,3-benzoxazol-5-yl]benzamide |
| 79 | 3-(4-chloro-3,5-dimethyl-pyrazol-1-yl)-N-methyl-N-(2-methyl-[1,2,4]triazolo[1,5-a]pyridin-6-yl)benzamide |
| 80 | 3-(4-chloro-3,5-dimethyl-pyrazol-1-yl)-N-(5-chloro-2-methyl-1,3-benzoxazol-6-yl)-N-methyl-benzamide |
| 81 | N-(1,3-benzodioxol-5-yl)-3-(4-cyano-3,5-dimethyl-pyrazol-1-yl)-N-methyl-benzamide |
| 82 | N-(1,3-benzodioxol-5-yl)-3-(4-chloro-3,5-dimethyl-pyrazol-1-yl)-N,4-dimethyl-benzamide |
| 83 | 2-[3-[1,3-benzodioxol-5-yl(methyl)carbamoyl]phenyl]-4-chloro-5-methyl-pyrazole-3-carboxylic acid |
| 84 | 2-[3-[1,3-benzodioxol-5-yl(methyl)carbamoyl]phenyl]-4-chloro-5-methyl-pyrazole-3-carboxamide |
| 85 | 2-[3-[1,3-benzodioxol-5-yl(methyl)carbamoyl]phenyl]-4-chloro-N,5-dimethyl-pyrazole-3-carboxamide |
| 86 | ethyl 1-[3-[1,3-benzodioxol-5-yl(methyl)carbamoyl]phenyl]-4-chloro-5-isopropyl-pyrazole-3-carboxylate |
| 87 | ethyl 2-[3-[1,3-benzodioxol-5-yl(methyl)carbamoyl]phenyl]-4-chloro-5-isopropyl-pyrazole-3-carboxylate |
| 88 | 2-[3-[1,3-benzodioxol-5-yl(methyl)carbamoyl]phenyl]-4-chloro-N,N,5-trimethyl-pyrazole-3-carboxamide |
| 89 | tert-butyl 2-[3-[1,3-benzodioxol-5-yl(methyl)carbamoyl]phenyl]-4-chloro-5-methyl-pyrazole-3-carboxylate |
| 90 | N-(1,3-benzodioxol-5-yl)-3-[4-chloro-5-methyl-3-(trifluoromethyl)pyrazol-1-yl]-N-methyl-benzamide |
| 91 | N-(1,3-benzodioxol-5-yl)-N-methyl-3-[5-methyl-3-(trifluoromethyl)pyrazol-1-yl]benzamide |
| 92 | N-(1,3-benzodioxol-5-yl)-3-(4-chloro-3,5-diethyl-pyrazol-1-yl)-N-methyl-benzamide |
| 93 | N-(1,3-benzodioxol-5-yl)-3-(3,5-diethylpyrazol-1-yl)-N-methyl-benzamide |
| 94 | N-(1,3-benzodioxol-5-yl)-3-(4-chloro-5-cyclopropyl-3-methyl-pyrazol-1-yl)-N-methyl-benzamide |
| 95 | 3-[4-chloro-5-methyl-3-(trifluoromethyl)pyrazol-1-yl]-N-(2,2-difluoro-1,3-benzodioxol-5-yl)-N-methyl-benzamide |
| 96 | 3-[4-chloro-5-methyl-3-(trifluoromethyl)pyrazol-1-yl]-N-(2,3-dihydro-1,4-benzodioxin-6-yl)-N-methyl-benzamide |
| 97 | N-(1,3-benzodioxol-5-yl)-3-(5-cyclopropyl-3-methyl-pyrazol-1-yl)-N-methyl-benzamide |

| # | Substance Name |
|---|---|
| 98 | N-(1,3-benzodioxol-5-yl)-3-[4-bromo-5-methyl-3-(trifluoromethyl)pyrazol-1-yl]-N-methyl-benzamide |
| 99 | N-(1,3-benzodioxol-5-yl)-3-[3,5-dimethyl-4-(trifluoromethyl)pyrazol-1-yl]-N-methyl-benzamide |
| 100 | N-(1,3-benzodioxol-5-yl)-3-[5-isobutyl-3-(trifluoromethyl)pyrazol-1-yl]-N-methyl-benzamide |
| 101 | N-(1,3-benzodioxol-5-yl)-3-[4-chloro-5-isobutyl-3-(trifluoromethyl)pyrazol-1-yl]-N-methyl-benzamide |
| 102 | N-(1,3-benzodioxol-5-yl)-3-[4-chloro-3-methyl-5-(trifluoromethyl)pyrazol-1-yl]-N-methyl-benzamide |
| 103 | ethyl 4-chloro-2-[3-[2,3-dihydro-1,4-benzodioxin-6-yl(methyl)carbamoyl]phenyl]-5-methyl-pyrazole-3-carboxylate |
| 104 | N-(1,3-benzodioxol-5-yl)-3-[4-cyclopropyl-5-methyl-3-(trifluoromethyl)pyrazol-1-yl]-N-methyl-benzamide |
| 105 | N-(1,3-benzodioxol-5-yl)-3-[4-chloro-5-(hydroxymethyl)-3-methyl-pyrazol-1-yl]-N-methyl-benzamide |
| 106 | N-(6-chloro-1,3-benzodioxol-5-yl)-3-[4-chloro-5-methyl-3-(trifluoromethyl)pyrazol-1-yl]-N-methyl-benzamide |
| 107 | N-(1,3-benzodioxol-5-yl)-3-[4-chloro-5-(methoxymethyl)-3-methyl-pyrazol-1-yl]-N-methyl-benzamide |
| 108 | 3-[4-chloro-5-methyl-3-(trifluoromethyl)pyrazol-1-yl]-N-methyl-N-(2-methyl-1,3-benzoxazol-6-yl)benzamide |
| 109 | N-(1,3-benzodioxol-5-yl)-3-[4-chloro-5-[(R)-hydroxy(phenyl)methyl]-3-methyl-pyrazol-1-yl]-N-methyl-benzamide |
| 110 | N-(6-chloro-1,3-benzodioxol-5-yl)-3-[4-chloro-5-isobutyl-3-(trifluoromethyl)pyrazol-1-yl]-N-methyl-benzamide |
| 111 | N-(1,3-benzodioxol-5-yl)-3-[4-chloro-5-cyclopropyl-3-(trifluoromethyl)pyrazol-1-yl]-N-methyl-benzamide |
| 112 | N-(1,3-benzodioxol-5-yl)-3-(4-chloro-5-formyl-3-methyl-pyrazol-1-yl)-N-methyl-benzamide |
| 113 | N-(1,3-benzodioxol-5-yl)-3-[4-chloro-5-ethoxy-3-(trifluoromethyl)pyrazol-1-yl]-N-methyl-benzamide |
| 114 | N-(1,3-benzodioxol-5-yl)-3-[4-chloro-5-[(1R)-1-hydroxyethyl]-3-methyl-pyrazol-1-yl]-N-methyl-benzamide |
| 115 | N-(1,3-benzodioxol-5-yl)-3-[4-chloro-5-(1-hydroxy-1-methyl-ethyl)-3-methyl-pyrazol-1-yl]-N-methyl-benzamide |
| 116 | 3-(5-acetyl-4-chloro-3-methyl-pyrazol-1-yl)-N-(1,3-benzodioxol-5-yl)-N-methyl-benzamide |
| 117 | N-(1,3-benzodioxol-5-yl)-3-[4-chloro-5-[(R)-methoxy(phenyl)methyl]-3-methyl-pyrazol-1-yl]-N-methyl-benzamide |
| 118 | N-(1,3-benzodioxol-5-yl)-3-[4-chloro-3-methyl-5-(phenoxymethyl)pyrazol-1-yl]-N-methyl-benzamide |
| 119 | N-(1,3-benzodioxol-5-yl)-3-(5-benzoyl-4-chloro-3-methyl-pyrazol-1-yl)-N-methyl-benzamide |
| 122 | 3-[4-chloro-5-methyl-3-(trifluoromethyl)pyrazol-1-yl]-N-methyl-N-(2-methylindazol-6-yl)benzamide |
| 123 | N-(5-chloro-2-methyl-1,3-benzoxazol-6-yl)-3-[4-chloro-5-methyl-3-(trifluoromethyl)pyrazol-1-yl]-N-methyl-benzamide |
| 124 | N-(1,3-benzodioxol-5-yl)-3-[4-chloro-5-phenyl-3-(trifluoromethyl)pyrazol-1-yl]-N-methyl-benzamide |
| 125 | N-(1,3-benzodioxol-5-yl)-N-methyl-3-[5-phenyl-3-(trifluoromethyl)pyrazol-1-yl]benzamide |
| 126 | N-(1,3-benzodioxol-5-yl)-3-[4-fluoro-5-methyl-3-(trifluoromethyl)pyrazol-1-yl]-N-methyl-benzamide |
| 129 | N-(1,3-benzodioxol-5-yl)-3-[4-chloro-3-methyl-5-(5-methyl-1,3,4-oxadiazol-2-yl)pyrazol-1-yl]-N-methyl-benzamide |
| 130 | ethyl 2-[3-[1,3-benzodioxol-5-yl(methyl)carbamoyl]phenyl]-5-(trifluoromethyl)pyrazole-3-carboxylate |
| 131 | N-(1,3-benzodioxol-5-yl)-3-[5-isopropoxy-3-(trifluoromethyl)pyrazol-1-yl]-N-methyl-benzamide |
| 132 | N-(1,3-benzodioxol-5-yl)-3-[5-benzyloxy-3-(trifluoromethyl)pyrazol-1-yl]-N-methyl-benzamide |
| 133 | N-(1,3-benzodioxol-5-yl)-N-methyl-3-[5-phenethyloxy-3-(trifluoromethyl)pyrazol-1-yl]benzamide |
| 134 | N-(1,3-benzodioxol-5-yl)-3-[5-benzyloxy-4-chloro-3-(trifluoromethyl)pyrazol-1-yl]-N-methyl-benzamide |
| 135 | 3-[4-chloro-5-cyclopropyl-3-(trifluoromethyl)pyrazol-1-yl]-N-ethyl-N-(2-methyl-1,3-benzoxazol-6-yl)benzamide |
| 137 | 3-[4-chloro-5-cyclopropyl-3-(trifluoromethyl)pyrazol-1-yl]-N-methyl-N-(2-methyl-1,3-benzoxazol-6-yl)benzamide |
| 138 | 3-[4-chloro-5-cyclopropyl-3-(trifluoromethyl)pyrazol-1-yl]-N-(2-methyl-1,3-benzoxazol-6-yl)-N-(trideuteriomethyl)benzamide |
| 139 | 3-[4-chloro-5-cyclopropyl-3-(trifluoromethyl)pyrazol-1-yl]-N-(5-chloro-2-methyl-1,3-benzoxazol-6-yl)-N-methyl-benzamide |
| 140 | ethyl 3-[[2-[3-[1,3-benzodioxol-5-yl(methyl)carbamoyl]phenyl]-4-chloro-5-methyl-pyrazol-3-yl]methoxy]benzoate |
| 141 | ethyl 4-[[2-[3-[1,3-benzodioxol-5-yl(methyl)carbamoyl]phenyl]-4-chloro-5-methyl-pyrazol-3-yl]methoxy]benzoate |
| 142 | N-(1,3-benzodioxol-5-yl)-3-[4-chloro-5-isopropoxy-3-(trifluoromethyl)pyrazol-1-yl]-N-methyl-benzamide |
| 143 | 3-[[2-[3-[1,3-benzodioxol-5-yl(methyl)carbamoyl]phenyl]-4-chloro-5-methyl-pyrazol-3-yl]methoxy]benzoic acid |
| 144 | 4-[[2-[3-[1,3-benzodioxol-5-yl(methyl)carbamoyl]phenyl]-4-chloro-5-methyl-pyrazol-3-yl]methoxy]benzoic acid |
| 145 | tert-butyl 2-[[3-[4-chloro-5-cyclopropyl-3-(trifluoromethyl)pyrazol-1-yl]benzoyl]-(2-methyl-1,3-benzoxazol-6-yl)amino]acetate |
| 146 | 2-[[3-[4-chloro-5-cyclopropyl-3-(trifluoromethyl)pyrazol-1-yl]benzoyl]-(2-methyl-1,3-benzoxazol-6-yl)amino]acetic acid |
| 147 | N-(1,3-benzodioxol-5-yl)-3-[5-(2-furyl)-3-(trifluoromethyl)pyrazol-1-yl]-N-methyl-benzamide |
| 149 | 3-[4-chloro-5-methyl-3-(trifluoromethyl)pyrazol-1-yl]-N-methyl-N-(2-methyl-1,3-benzothiazol-6-yl)benzamide |
| 150 | ethyl 4-[[2-[3-[1,3-benzodioxol-5-yl(methyl)carbamoyl]phenyl]-4-chloro-5-(trifluoromethyl)pyrazol-3-yl]methoxy]benzoate |
| 151 | 4-[[2-[3-[1,3-benzodioxol-5-yl(methyl)carbamoyl]phenyl]-4-chloro-5-(trifluoromethyl)pyrazol-3-yl]methoxy]benzoic acid |
| 152 | methyl 4-[[2-[3-[1,3-benzodioxol-5-yl(methyl)carbamoyl]phenyl]-5-(trifluoromethyl)pyrazol-3-yl]oxymethyl]benzoate |
| 154 | 3-[4-chloro-5-methyl-3-(trifluoromethyl)pyrazol-1-yl]-N-(5-fluoro-2-methyl-1,3-benzoxazol-6-yl)-N-methyl-benzamide |
| 155 | methyl 4-[[2-[3-[1,3-benzodioxol-5-yl(methyl)carbamoyl]phenyl]-4-chloro-5-(trifluoromethyl)pyrazol-3-yl]oxymethyl]benzoate |
| 156 | methyl 4-[[4-chloro-2-[3-[(6-chloro-1,3-benzodioxol-5-yl)-methyl-carbamoyl]phenyl]-5-(trifluoromethyl)pyrazol-3-yl]oxymethyl]benzoate |
| 157 | tert-butyl 4-[2-[3-[1,3-benzodioxol-5-yl(methyl)carbamoyl]phenyl]-4-chloro-5-(trifluoromethyl)pyrazol-3-yl]oxypiperidine-1-carboxylate |
| 158 | N-(1,3-benzodioxol-5-yl)-3-[5-ethoxy-3-(trifluoromethyl)pyrazol-1-yl]-N-methyl-benzamide |
| 159 | 4-[[2-[3-[1,3-benzodioxol-5-yl(methyl)carbamoyl]phenyl]-4-chloro-5-(trifluoromethyl)pyrazol-3-yl]oxymethyl]benzoic acid |
| 161 | 3-[4-chloro-5-methyl-3-(trifluoromethyl)pyrazol-1-yl]-N-(6-formyl-1,3-benzodioxol-5-yl)-N-methyl-benzamide |
| 163 | 3-[4-chloro-5-methyl-3-(trifluoromethyl)pyrazol-1-yl]-N-(6-cyano-1,3-benzodioxol-5-yl)-N-methyl-benzamide |
| 164 | N-(1,3-benzodioxol-5-yl)-3-[5-(5-chloro-2-thienyl)-3-(trifluoromethyl)pyrazol-1-yl]-N-methyl-benzamide |
| 166 | N-(1,3-benzodioxol-5-yl)-N-methyl-3-[5-(2-thienyl)-3-(trifluoromethyl)pyrazol-1-yl]benzamide |
| 168 | 3-[4-chloro-5-methyl-3-(trifluoromethyl)pyrazol-1-yl]-N-[6-(hydroxymethyl)-1,3-benzodioxol-5-yl]-N-methyl-benzamide |
| 169 | N-(1,3-benzodioxol-5-yl)-N-methyl-2-[3-methyl-5-(trifluoromethyl)pyrazol-1-yl]pyridine-4-carboxamide |
| 170 | N-(1,3-benzodioxol-5-yl)-2-[4-chloro-3-methyl-5-(trifluoromethyl)pyrazol-1-yl]-N-methyl-pyridine-4-carboxamide |
| 171 | N-(1,3-benzodioxol-5-yl)-2-[4-chloro-5-methyl-3-(trifluoromethyl)pyrazol-1-yl]-N-methyl-pyridine-4-carboxamide |
| 175 | tert-butyl 4-[[4-chloro-2-[3-[(2,2-difluoro-1,3-benzodioxol-5-yl)-methyl-carbamoyl]phenyl]-5-(trifluoromethyl)pyrazol-3-yl]methoxy]benzoate |
| 176 | N-(1,3-benzodioxol-5-yl)-N-methyl-3-[3-(trifluoromethyl)-5-[2-(trifluoromethyl)phenyl]pyrazol-1-yl]benzamide |
| 177 | 4-[[4-chloro-2-[3-[(2,2-difluoro-1,3-benzodioxol-5-yl)-methyl-carbamoyl]phenyl]-5-(trifluoromethyl)pyrazol-3-yl]methoxy]benzoic acid |

| # | Substance Name |
|---|---|
| 179 | 6-[[3-[4-chloro-5-methyl-3-(trifluoromethyl)pyrazol-1-yl]benzoyl]-methyl-amino]-1,3-benzodioxole-5-carboxylic acid |
| 180 | N-(1,3-benzodioxol-5-yl)-3-[4-formyl-5-phenoxy-3-(trifluoromethyl)pyrazol-1-yl]-N-methyl-benzamide |
| 181 | tert-butyl 4-[[4-chloro-2-[3-[(2,2-difluoro-1,3-benzodioxol-5-yl)-(trideuteriomethyl)carbamoyl]phenyl]-5-(trifluoromethyl)pyrazol-3-yl]methoxy]benzoate |
| 182 | 4-[[4-chloro-2-[3-[(2,2-difluoro-1,3-benzodioxol-5-yl)-(trideuteriomethyl)carbamoyl]phenyl]-5-(trifluoromethyl)pyrazol-3-yl]methoxy]benzoic acid |
| 183 | N-(1,3-benzodioxol-5-yl)-3-[4-chloro-5-(2-methoxyphenyl)-3-(trifluoromethyl)pyrazol-1-yl]-N-methyl-benzamide |
| 184 | N-(1,3-benzodioxol-5-yl)-3-[5-(2-methoxyphenyl)-3-(trifluoromethyl)pyrazol-1-yl]-N-methyl-benzamide |
| 185 | N-(1,3-benzodioxol-5-yl)-3-[4-cyano-5-phenoxy-3-(trifluoromethyl)pyrazol-1-yl]-N-methyl-benzamide |
| 186 | N-(1,3-benzodioxol-5-yl)-3-[4-formyl-5-methyl-3-(trifluoromethyl)pyrazol-1-yl]-N-methyl-benzamide |
| 187 | N-(1,3-benzodioxol-5-yl)-3-[4-cyano-5-methyl-3-(trifluoromethyl)pyrazol-1-yl]-N-methyl-benzamide |
| 188 | tert-butyl 4-[[2-[3-[methyl-(2-methyl-1,3-benzoxazol-6-yl)carbamoyl]phenyl]-5-(trifluoromethyl)pyrazol-3-yl]oxymethyl]benzoate |
| 189 | tert-butyl 4-[[2-[3-[(5-fluoro-2-methyl-1,3-benzoxazol-6-yl)-methyl-carbamoyl]phenyl]-5-(trifluoromethyl)pyrazol-3-yl]oxymethyl]benzoate |
| 190 | tert-butyl 4-[[4-chloro-2-[3-[methyl-(2-methyl-1,3-benzoxazol-6-yl)carbamoyl]phenyl]-5-(trifluoromethyl)pyrazol-3-yl]oxymethyl]benzoate |
| 191 | tert-butyl 4-[[2-[3-[(2,2-difluoro-1,3-benzodioxol-5-yl)-methyl-carbamoyl]phenyl]-5-(trifluoromethyl)pyrazol-3-yl]oxymethyl]benzoate |
| 192 | N-(1,3-benzodioxol-5-yl)-N-methyl-3-[3-(2-pyridyl)-5-(trifluoromethyl)pyrazol-1-yl]benzamide |
| 193 | N-(1,3-benzodioxol-5-yl)-N-methyl-3-[5-(3-pyridyl)-3-(trifluoromethyl)pyrazol-1-yl]benzamide |
| 194 | N-(1,3-benzodioxol-5-yl)-N-methyl-3-[3-(3-pyridyl)-5-(trifluoromethyl)pyrazol-1-yl]benzamide |
| 195 | 4-[[2-[3-[methyl-(2-methyl-1,3-benzoxazol-6-yl)carbamoyl]phenyl]-5-(trifluoromethyl)pyrazol-3-yl]oxymethyl]benzoic acid |
| 196 | 4-[[2-[3-[(5-fluoro-2-methyl-1,3-benzoxazol-6-yl)-methyl-carbamoyl]phenyl]-5-(trifluoromethyl)pyrazol-3-yl]oxymethyl]benzoic acid |
| 197 | 4-[[2-[3-[(2,2-difluoro-1,3-benzodioxol-5-yl)-methyl-carbamoyl]phenyl]-5-(trifluoromethyl) pyrazol-3-yl]oxymethyl]benzoic acid |
| 198 | 4-[[4-chloro-2-[3-[methyl-(2-methyl-1,3-benzoxazol-6-yl)carbamoyl]phenyl]-5-(trifluoromethyl)pyrazol-3-yl]oxymethyl]benzoic acid |
| 200 | tert-butyl 4-[2-[3-[1,3-benzodioxol-5-yl(methyl)carbamoyl]phenyl]-4-cyano-5-(trifluoromethyl)pyrazol-3-yl]oxybenzoate |
| 201 | tert-butyl 4-[[4-chloro-2-[3-[(2,2-difluoro-1,3-benzodioxol-5-yl)-methyl-carbamoyl]phenyl]-5-(trifluoromethyl)pyrazol-3-yl]oxymethyl]benzoate |
| 202 | tert-butyl 4-[[4-chloro-2-[3-[(5-fluoro-2-methyl-i,3-benzoxazol-6-yl)-methyl-carbamoyl]phenyl]-5-(trifluoromethyl)pyrazol-3-yl]oxymethyl]benzoate |
| 204 | N-(1,3-benzodioxol-5-yl)-N-methyl-3-[5-methyl-3-(trifluoromethyl)pyrazol-1-yl]benzenesulfonamide |
| 207 | 3-[4-chloro-5-methyl-3-(trifluoromethyl)pyrazol-1-yl]-N-(4-formyl-1,3-benzodioxol-5-yl)-N-methyl-benzamide |
| 208 | 5-[[3-[4-chloro-5-methyl-3-(trifluoromethyl)pyrazol-1-yl]benzoyl]-methyl-amino]-1,3-benzodioxole-4-carboxylic acid |
| 209 | 3-[4-chloro-5-methyl-3-(trifluoromethyl)pyrazol-1-yl]-N-[4-(hydroxymethyl)-1,3-benzodioxol-5-yl]-N-methyl-benzamide |
| 210 | 4-[2-[3-[1,3-benzodioxol-5-yl(methyl)carbamoyl]phenyl]-4-cyano-5-(trifluoromethyl)pyrazol-3-yl]oxybenzoic acid |
| 211 | 4-[[4-chloro-2-[3-[(2,2-difluoro-1,3-benzodioxol-5-yl)-methyl-carbamoyl]phenyl]-5-(trifluoromethyl)pyrazol-3-yl]oxymethyl]benzoic acid |
| 212 | 4-[[4-chloro-2-[3-[(5-fluoro-2-methyl-1,3-benzoxazol-6-yl)-methyl-carbamoyl]phenyl]-5-(trifluoromethyl)pyrazol-3-yl]oxymethyl]benzoic acid |
| 213 | ethyl-cis-4-[2-[3-[1,3-benzodioxol-5-yl(methyl)carbamoyl]phenyl]-5-(trifluoromethyl)pyrazol-3-yl]oxycyclohexanecarboxylate |
| 214 | ethyl 4-[2-[3-[1,3-benzodioxol-5-yl(methyl)carbamoyl]phenyl]-5-(trifluoromethyl)pyrazol-3-yl]oxycyclohexanecarboxylate |
| 215 | 4-[2-[3-[1,3-benzodioxol-5-yl(methyl)carbamoyl]phenyl]-5-(trifluoromethyl)pyrazol-3-yl]oxycyclohexanecarboxylic acid |
| 216 | cis-4-[2-[3-[1,3-benzodioxol-5-yl(methyl)carbamoyl]phenyl]-5-(trifluoromethyl)pyrazol-3-yl]oxycyclohexanecarboxylic acid |
| 217 | 3-[4-chloro-5-(hydroxymethyl)-3-(trifluoromethyl)pyrazol-1-yl]-N-(2,2-difluoro-1,3-benzodioxol-5-yl)-N-methyl-benzamide |
| 218 | 4-[[2-[3-[(2,2-difluoro-1,3-benzodioxol-5-yl)-methyl-carbamoyl]phenyl]-5-(trifluoromethyl)pyrazol-3-yl]methoxy]benzoic acid |
| 219 | 3-[4-chloro-5-isobutyl-3-(trifluoromethyl)pyrazol-1-yl]-N-(2,2-difluoro-1,3-benzodioxol-5-yl)-N-methyl-benzamide |
| 220 | N-(2,2-difluoro-1,3-benzodioxol-5-yl)-3-[4-fluoro-5-methyl-3-(trifluoromethyl)pyrazol-1-yl]-N-methyl-benzamide |
| 221 | 3-[4-chloro-5-cyclopropyl-3-(trifluoromethyl)pyrazol-1-yl]-N-(2,2-difluoro-1,3-benzodioxol-5-yl)-N-methyl-benzamide |
| 222 | 4-[4-chloro-2-[3-[(2,2-difluoro-1,3-benzodioxol-5-yl)-methyl-carbamoyl]phenyl]-5-(trifluoromethyl)pyrazol-3-yl]oxycyclohexanecarboxylic acid |
| 223 | 4-[[4-cyano-2-[3-[(2,2-difluoro-1,3-benzodioxol-5-yl)-methyl-carbamoyl]phenyl]-5-(trifluoromethyl)pyrazol-3-yl]oxymethyl]benzoic acid |
| 224 | 4-[[4-cyano-2-[3-[(2,2-difluoro-1,3-benzodioxol-5-yl)-methyl-carbamoyl]phenyl]-5-(trifluoromethyl)pyrazol-3-yl]methoxy]benzoic acid |
| 225 | 2-[[4-chloro-2-[3-[(2,2-difluoro-1,3-benzodioxol-5-yl)-methyl-carbamoyl]phenyl]-5-(trifluoromethyl)pyrazol-3-yl]methoxy]thiazole-5-carboxylic acid |
| 226 | 5-[[4-chloro-2-[3-[(2,2-difluoro-1,3-benzodioxol-5-yl)-methyl-carbamoyl]phenyl]-5-(trifluoromethyl)pyrazol-3-yl]methoxy]pyrazine-2-carboxylic acid |
| 227 | 3-[[4-chloro-2-[3-[(2,2-difluoro-1,3-benzodioxol-5-yl)-methyl-carbamoyl]phenyl]-5-(trifluoromethyl)pyrazol-3-yl]methoxy]bicyclo[1.1.1]pentane-1-carboxylic acid |
| 228 | Trans-4-[[4-chloro-2-[3-[(2,2-difluoro-1,3-benzodioxol-5-yl)-methyl-carbamoyl]phenyl]-5-(trifluoromethyl)pyrazol-3-yl]methoxy]cyclohexanecarboxylic acid |
| 229 | 3-[2-[3-[methyl-(2-methyl-1,3-benzoxazol-6-yl)carbamoyl]phenyl]-5-(trifluoromethyl)pyrazol-3-yl]oxycyclobutanecarboxylic acid |
| 230 | 3-[4-chloro-5-methyl-3-(trifluoromethyl)pyrazol-1-yl]-N-methyl-pyridine-2-N-(1,3-benzodioxol-5-yl)-4-[4-chloro-5-methyl-3-carboxamide |
| 231 | 4-[[4-chloro-2-[3-[(2,2-difluoro-1,3-benzodioxol-5-yl)-methyl-carbamoyl]phenyl]-5-(trifluoromethyl)pyrazol-3-yl]methoxy]-2-fluoro-benzoic acid |
| 232 | 1-[2-[3-[1,3-benzodioxol-5-yl(methyl)carbamoyl]phenyl]-4-chloro-5-(trifluoromethyl)pyrazol-3-yl]piperidine-4-carboxylic acid |
| 233 | 4-[[4-chloro-2-[3-[methyl-(2-methyl-1,3-benzoxazol-6-yl)carbamoyl]phenyl]-5-(trifluoromethyl)pyrazol-3-yl]methoxy]benzoic acid |
| 234 | 4-[[4-chloro-2-[3-[(5-fluoro-2-methyl-1,3-benzoxazol-6-yl)-methyl-carbamoyl]phenyl]-5-(trifluoromethyl)pyrazol-3-yl]methoxy]benzoic acid |
| 235 | 4-[1-[2-[3-[1,3-benzodioxol-5-yl(methyl)carbamoyl]phenyl]-4-chloro-5-(trifluoromethyl)pyrazol-3-yl]-1-methyl-ethoxy]benzoic acid |
| 236 | 4-[[4-chloro-2-[3-[methyl-(2-methyl-[1,2,4]triazolo[1,5-a]pyridin-6-yl)carbamoyl]phenyl]-5-(trifluoromethyl)pyrazol-3-yl]methoxy]benzoic acid |

| # | Substance Name |
|---|---|
| 237 | 4-[[4-chloro-2-[3-[methyl-(3-methyl-1H-pyrazolo[3,4-b]pyridin-5-yl)carbamoyl]phenyl]-5-(trifluoromethyl)pyrazol-3-yl]methoxy]benzoic acid |
| 238 | 4-[[4-chloro-2-[3-[methyl-(2-methylpyrazolo[1,5-a]pyrimidin-6-yl)carbamoyl]phenyl]-5-(trifluoromethyl)pyrazol-3-yl]methoxy]benzoic acid |
| 239 | 4-[[4-chloro-2-[3-[methyl-(2-methylpyrazolo[1,5-a]pyridin-5-yl)carbamoyl]phenyl]-5-(trifluoromethyl)pyrazol-3-yl]methoxy]benzoic acid |
| 240 | 4-[[4-chloro-2-[3-[methyl(6-quinolyl)carbamoyl]phenyl]-5-(trifluoromethyl)pyrazol-3-yl]methoxy]benzoic acid |
| 241 | 4-[[4-chloro-2-[3-[methyl-(2-methyloxazolo[4,5-b]pyridin-6-yl)carbamoyl]phenyl]-5-(trifluoromethyl)pyrazol-3-yl]methoxy]benzoic acid |
| 242 | 1-[2-[3-[1,3-benzodioxol-5-yl(methyl)carbamoyl]phenyl]-4-chloro-5-(trifluoromethyl)pyrazol-3-yl]azetidine-3-carboxylic acid |
| 243 | 4-[[4-chloro-2-[5-[(2,2-difluoro-1,3-benzodioxol-5-yl)-methyl-carbamoyl]-3-pyridyl]-5-(trifluoromethyl)pyrazol-3-yl]methoxy]benzoic acid |
| 244 | 4-[[4-chloro-2-[3-[(1,1-dioxo-2,3-dihydrobenzothiophen-6-yl)-methyl-carbamoyl]phenyl]-5-(trifluoromethyl)pyrazol-3-yl]methoxy]benzoic acid |
| 245 | 4-[[4-chloro-2-[3-[methyl-(3-methyl-1,2-benzoxazol-6-yl)carbamoyl]phenyl]-5-(trifluoromethyl)pyrazol-3-yl]methoxy]benzoic acid |
| 246 | 3-[[4-chloro-2-[3-[(2,2-difluoro-1,3-benzodioxol-5-yl)-methyl-carbamoyl]phenyl]-5-(trifluoromethyl)pyrazol-3-yl]methoxy]isoxazole-5-carboxylic acid |
| 247 | 4-[[4-chloro-2-[3-[(2,2-difluoro-1,3-benzodioxol-5-yl)-methyl-carbamoyl]phenyl]-5-(trifluoromethyl)pyrazol-3-yl]methoxy]pyrrolidine-2-carboxylic acid |
| 248 | 6-[[4-chloro-2-[3-[(2,2-difluoro-1,3-benzodioxol-5-yl)-methyl-carbamoyl]phenyl]-5-(trifluoromethyl)pyrazol-3-yl]methoxy]pyridine-3-carboxylic acid |
| 249 | 4-[[4-chloro-2-[3-[(3-hydroxyindan-5-yl)-methyl-carbamoyl]phenyl]-5-(trifluoromethyl)pyrazol-3-yl]methoxy]benzoic acid |
| 250 | 4-[[4-chloro-2-[3-[(2,2-difluoro-[1,3]dioxolo[4,5-b]pyrazin-5-yl)-methyl-carbamoyl]phenyl]-5-(trifluoromethyl)pyrazol-3-yl]methoxy]benzoic acid |
| 251 | 4-[[4-chloro-2-[3-[methyl-(2-methyloxazolo[4,5-b]pyridin-6-yl)carbamoyl]phenyl]-5-(trifluoromethyl)pyrazol-3-yl]methoxy]benzoic acid |
| 252 | N-(2,2-difluoro-1,3-benzodioxol-5-yl)-N-methyl-3-[5-methyl-3-(p-tolylmethoxy)-6,7-dihydro-4H-pyrazolo[4,3-c]pyridin-2-yl]benzamide |
| 253 | N-(2,2-difluoro-1,3-benzodioxol-5-yl)-N-methyl-3-[3-(p-tolylmethoxy)-4,5,6,7-tetrahydroindazol-2-yl]benzamide |
| 254 | methyl 3-[[2-[3-[(2,2-difluoro-1,3-benzodioxol-5-yl)-methyl-carbamoyl]phenyl]-5-(trifluoromethyl)pyrazol-3-yl]oxymethyl]bicyclo[1.1.1]pentane-1-carboxylate |
| 255 | 3-[[2-[3-[(2,2-difluoro-1,3-benzodioxol-5-yl)-methyl-carbamoyl]phenyl]-5-(trifluoromethyl)pyrazol-3-yl]oxymethyl]bicyclo[1.1.1]pentane-1-carboxylic acid |
| 256 | 4-[[4-chloro-2-[3-[methyl-(2-methylimidazo[1,2-a]pyridin-6-yl)carbamoyl]phenyl]-5-(trifluoromethyl)pyrazol-3-yl]methoxy]benzoic acid |
| 257 | 3-[[4-chloro-2-[3-[(2,2-difluoro-1,3-benzodioxol-5-yl)-methyl-carbamoyl]phenyl]-5-(trifluoromethyl)pyrazol-3-yl]methoxy]cyclobutanecarboxylic acid |
| 258 | 3-[[4-chloro-2-[3-[(2,2-difluoro-1,3-benzodioxol-5-yl)-methyl-carbamoyl]phenyl]-5-(trifluoromethyl)pyrazol-3-yl]oxymethyl]bicyclo[1.1.1]pentane-1-carboxylic acid |
| 259 | tert-butyl 4-[[4-cyano-2-[3-[(2,2-difluoro-1,3-benzodioxol-5-yl)-methyl-carbamoyl]phenyl]-5-(trifluoromethyl)pyrazol-3-yl]methoxy]benzoate |
| 260 | ethyl 4-[4-[2-[3-[(2,2-difluoro-1,3-benzodioxol-5-yl)-methyl-carbamoyl]phenyl]-5-(trifluoromethyl)pyrazol-3-yl]oxy-1-piperidyl]-4-oxo-butanoate |
| 261 | 3-[4-chloro-5-methyl-3-(trifluoromethyl)pyrazol-1-yl]-N-methyl-N-(2-methyloxazolo[4,5-b]pyridin-6-yl)benzamide |
| 262 | 4-[[2-[3-[2,3-dihydrobenzofuran-6-yl(methyl)carbamoyl]phenyl]-5-(trifluoromethyl)pyrazol-3-yl]oxymethyl]benzoic acid |
| 263 | 4-[[2-[3-[methyl-(3-methyl-1,2-benzoxazol-6-yl)carbamoyl]phenyl]-5-(trifluoromethyl)pyrazol-3-yl]oxymethyl]benzoic acid |
| 264 | 4-[4-[2-[3-[(2,2-difluoro-1,3-benzodioxol-5-yl)-methyl-carbamoyl]phenyl]-5-(trifluoromethyl)pyrazol-3-yl]oxy-1-piperidyl]-4-oxo-butanoic acid |
| 265 | 1-[[2-[3-[(2,2-difluoro-1,3-benzodioxol-5-yl)-methyl-carbamoyl]phenyl]-5-(trifluoromethyl)pyrazol-3-yl]oxymethyl]cyclopropanecarboxylic acid |
| 266 | 4-[[2-[3-[(5-fluoro-2-methyl-1,3-benzoxazol-6-yl)-methyl-carbamoyl]phenyl]-5-(trifluoromethyl)pyrazol-3-yl]methoxy]benzoic acid |
| 267 | 4-[[4-chloro-2-[3-[[1,3]dioxolo[4,5-b]pyridin-6-yl(methyl)carbamoyl]phenyl]-5-(trifluoromethyl)pyrazol-3-yl]methoxy]benzoic acid |
| 268 | 4-[[4-cyano-2-[3-[(2,2-difluoro-1,3-benzodioxol-5-yl)-methyl-carbamoyl]phenyl]-5-(difluoromethyl)pyrazol-3-yl]methoxy]benzoic acid |
| 269 | 3-[4-chloro-5-methyl-3-(trifluoromethyl)pyrazol-1-yl]-N-methyl-N-(4-methyl-1,3-benzodioxol-5-yl)benzamide |
| 270 | 4-[[4-chloro-2-[3-[(2,2-difluoro-1,3-benzodioxol-5-yl)-methyl-carbamoyl]phenyl]-5-(difluoromethyl)pyrazol-3-yl]methoxy]benzoic acid |
| 271 | 4-[[4-chloro-5-(difluoromethyl)-2-[3-[methyl-(2-methyl-1,3-benzoxazol-6-yl)carbamoyl]phenyl]pyrazol-3-yl]methoxy]benzoic acid |
| 272 | 4-[[4-chloro-2-[3-[[2-(difluoromethoxy)pyrimidin-5-yl]-methyl-carbamoyl]phenyl]-5-(trifluoromethyl)pyrazol-3-yl]methoxy]benzoic acid |
| 273 | 4-[[4-chloro-5-(difluoromethyl)-2-[3-[methyl-(2-methyl-1,3-benzoxazol-6-yl)carbamoyl]phenyl]pyrazol-3-yl]oxymethyl]benzoic acid |
| 274 | 4-[[2-[3-[(2,2-difluoro-1,3-benzodioxol-5-yl)-methyl-carbamoyl]phenyl]-5-(difluoromethyl)pyrazol-3-yl]methoxy]benzoic acid |
| 275 | 4-[[4-chloro-2-[3-[(2,2-difluoro-3H-furo[3,2-b]pyridin-6-yl)-methyl-carbamoyl]phenyl]-5-(trifluoromethyl)pyrazol-3-yl]methoxy]benzoic acid |
| 276 | 4-[[4-cyano-5-(difluoromethyl)-2-[3-[methyl-(2-methyloxazolo[4,5-b]pyridin-6-yl)carbamoyl]phenyl]pyrazol-3-yl]methoxy]benzoic acid |
| 277 | 6-[[4-chloro-2-[3-[(2,2-difluoro-1,3-benzodioxol-5-yl)-methyl-carbamoyl]phenyl]-5-(trifluoromethyl)pyrazol-3-yl]methoxy]pyridazine-3-carboxylic acid |
| 278 | 4-[[4-chloro-2-[3-[methyl-(2-methylpyrazolo[1,5-a]pyrimidin-6-yl)carbamoyl]phenyl]-5-(trifluoromethyl)pyrazol-3-yl]oxymethyl]benzoic acid |
| 279 | 5-[[4-chloro-2-[3-[(2,2-difluoro-1,3-benzodioxol-5-yl)-methyl-carbamoyl]phenyl]-5-(trifluoromethyl)pyrazol-3-yl]methoxy]pyridine-2-carboxylic acid |
| 280 | 6-[[4-chloro-2-[3-[[2-(difluoromethoxy)pyrimidin-5-yl]-methyl-carbamoyl]phenyl]-5-(trifluoromethyl)pyrazol-3-yl]methoxy]pyridine-3-carboxylic acid |
| 281 | 5-[[2-[3-[(2,2-difluoro-1,3-benzodioxol-5-yl)-methyl-carbamoyl]phenyl]-5-(trifluoromethyl)pyrazol-3-yl]methoxy]pyridine-2-carboxylic acid |
| 282 | 2-[[4-chloro-2-[3-[(2,2-difluoro-1,3-benzodioxol-5-yl)-methyl-carbamoyl]phenyl]-5-(trifluoromethyl)pyrazol-3-yl]methoxy]pyridine-4-carboxylic acid |
| 283 | 4-[[4-cyano-2-[3-[[2-(difluoromethoxy)pyrimidin-5-yl]-methyl-carbamoyl]phenyl]-5-methyl-pyrazol-3-yl]methoxy]benzoic acid |
| 284 | 4-[[4-cyano-5-methyl-2-[3-[methyl-(2-methyloxazolo[4,5-b]pyridin-6-yl)carbamoyl]phenyl]pyrazol-3-yl]methoxy]benzoic acid |
| 285 | 4-[[5-methyl-2-[3-[methyl-(2-methylpyrazolo[1,5-a]pyrimidin-6-yl)carbamoyl]phenyl]pyrazol-3-yl]oxymethyl]benzoic acid |
| 286 | 4-[[2-[3-[(2,2-difluoro-1,3-benzodioxol-5-yl)-methyl-carbamoyl]phenyl]-4,5,6,7-tetrahydroindazol-3-yl]oxymethyl]benzoic acid |
| 287 | 4-[[2-[3-[(2,2-difluoro-1,3-benzodioxol-5-yl)-methyl-carbamoyl]phenyl]-5-methyl-6,7-dihydro-4H-pyrazolo[4,3-c]pyridin-3-yl]oxymethyl]benzoic acid |

In a further embodiment of the invention $R_2$ and $R_3$, can be independently selected from the group consisting of hydrogen, $C_{1-6}$alkyl, halo$C_{1-6}$alkyl, $C_{3-6}$ cycloalkyl, optionally substituted aryl, heteroaryl, $COR^{viii}$, $COOR^{viii}$, optionally substituted heterocycloalkyl, $CONHR^{viii}$, $CONR^{viii}R^{ix}$, OH, O—$C_{1-6}$alkyl, optionally substituted O—$C_{1-6}$alkylaryl, O—$C_{3-6}$cycloalkyl, optionally substituted O-heterocycloalkyl, O-heteroaryl, optionally substituted O-aryl, O-halo$C_{1-6}$alkyl, $C_{1-6}$alkyl-O—$C_{3-6}$cycloalkyl, $C_{1-6}$alkyl-O-heterocycloalkyl, optionally substituted $C_{1-6}$alkyl-O-aryl, $C_{1-6}$alkyl-O-heteroaryl, CN, $NO_2$, $NR^xR^{xi}$, $N(R^{ix})COR^x$, $N(R^{ix})COOR^{xi}$, $N(R^{ix})CONR^{xi}R^x$, $N(R^{ix})SO_2R^x$, $SO_2R^x$, $SO_2NR^{ix}R^x$, halogen, hydroxy-$C_{1-6}$alkyl, and aryl-$C_{1-6}$alkyl wherein the substitution is selected from the group consisting of hydroxy, O—$C_{1-6}$alkyl, COOH, COO—$C_{1-6}$alkyl, CO—$C_{1-6}$alkyl, halogen, halo-$C_{1-6}$alkyl.

In a further embodiment of the invention $R_4$ can be selected from the group consisting of hydrogen, $C_{1-6}$alkyl, halo$C_{1-6}$alkyl, $C_{3-6}$ cycloalkyl, optionally substituted aryl, heteroaryl, $COR^{viii}$, $COOR^{viii}$, optionally substituted heterocycloalkyl, $CONHR^{viii}$, $CONR^{viii}R^{ix}$, OH, O—$C_{1-6}$alkyl, optionally substituted O—$C_{1-6}$alkylaryl, O—$C_{3-6}$cycloalkyl, O—$C_{1-6}$alkylheteroaryl, optionally substituted O-heterocycloalkyl, O-heteroaryl, optionally substituted O-aryl, O-halo$C_{1-6}$alkyl, $C_{1-6}$alkyl-O—$C_{1-6}$alkyl, $C_{1-6}$alkyl-O—$C_{3-6}$cycloalkyl, optionally substituted $C_{1-6}$alkyl-O-heterocycloalkyl, optionally substituted $C_{1-6}$alkyl-O-aryl, optionally substituted $C_{1-6}$alkyl-O-heteroaryl, CN, $NO_2$, $NR^xR^{xi}$, $N(R^{ix})COR^x$, $N(R^{ix})COOR^{xi}$, $N(R^{ix})CONR^{xi}R^x$, $N(R^{ix})SO_2R^x$, $SO_2R^x$, $SO_2NR^{ix}R^x$, halogen, hydroxy-$C_{1-6}$alkyl, and aryl-$C_{1-6}$alkyl, optionally substituted O—$C_{1-6}$alkyl-$C_{3-6}$ cycloalkyl, optionally substituted O—$C_{3-6}$ cycloalkyl, optionally substituted O-heteroaryl, optionally substituted $C_{1-6}$alkyl-O—$C_{3-6}$ cycloalkyl, wherein the substitution is selected from the group consisting of hydroxy, COOH, COO—$C_{1-6}$alkyl, CO—$C_{1-6}$alkyl, halogen, halo-$C_{1-6}$alkyl.

In an alternative of the first and second embodiments, $R_2$ and $R_3$, taken together with the carbon atoms to whom they are bound, can form the following moiety:

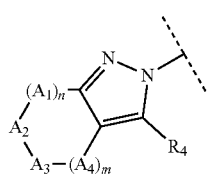

wherein $A_1$, $A_2$, $A_3$, and $A_4$, are independently selected from the group consisting of $CR^{xii}R^{xiii}$, O, $NR^{xiv}$, CO and $SO_2$, wherein $R^{xii}$ and $R^{xiii}$ are independently selected from the group consisting of hydrogen, $C_{1-6}$alkyl, $C_{3-6}$ cycloalkyl, heterocycloalkyl, halo$C_{1-6}$alkyl, $COR^{viii}$, $COOR^{viii}$, $CONHR^{viii}$, $CONR^{viii}R^{ix}$, OH, O—$C_{1-6}$alkyl, O-aryl, CN, halogen, $NR^xR^{xi}$, $N(R^{ix})COR^x$;

$R^{xiv}$ is selected from the group consisting of hydrogen, $C_{1-6}$alkyl, $C_{1-6}$alkylaryl, $C_{1-6}$alkyl-$C_{3-6}$ cycloalkyl, $C_{1-6}$alkyl-heterocycloalkyl, $C_{3-6}$ cycloalkyl, heterocycloalkyl, hydroxyl-$C_{1-6}$alkyl, $COR^{viii}$, $COOR^{viii}$, $CONHR^{viii}$, $CONR^{viii}R^{ix}$, $SO_2R^{viii}$, $C_{1-6}$alkyl-O—$C_{1-6}$alkyl, $C_{1-6}$alkyl-O-aryl, $C_{1-6}$alkyl-O-heteroaryl, $C_{1-6}$alkyl-O-heterocycloalkyl;

or when each of $A_1$ and $A_3$, or $A_2$ and $A_4$, or $A_1$ and $A_4$ represents $CR^{xii}R^{xiii}$, the two groups $R^{xii}$ can be linked together to form a ring and thus the moiety

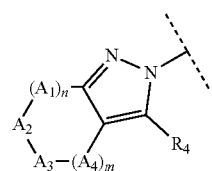

has a meaning selected from the group consisting of:

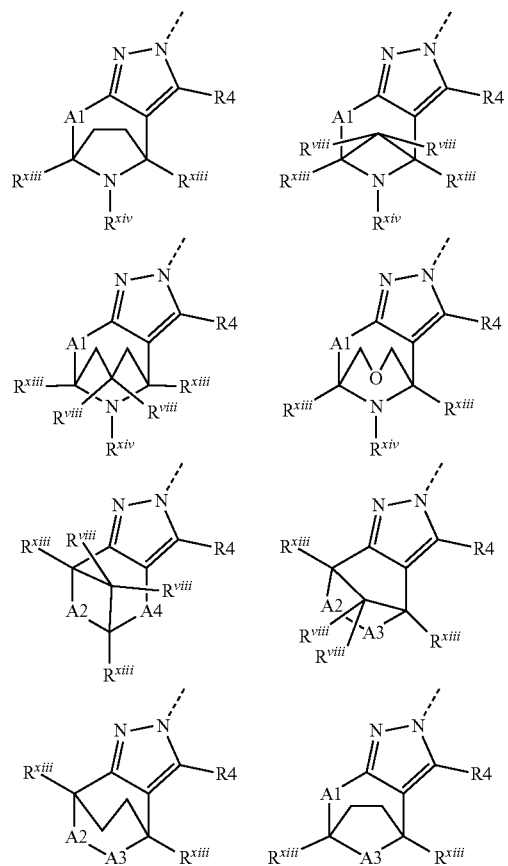

n and m are each independently selected from the group consisting of 0, 1, 2; and
$R_4$ is as above defined.

In a preferred embodiment $R_2$ and $R_3$, taken together with the carbon atoms to whom they are bound, can form the following moiety:

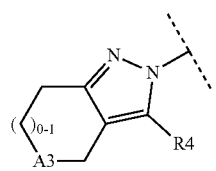

The compounds exemplified in this invention may be prepared from readily available starting materials using the following general methods and procedures for example exemplified in Michael B. Smith—March's Advanced Organic Chemistry: reactions, mechanisms, and structure—7th Edition, John Wiley & Sons Inc., 2013.

It is well known to one of ordinary skill in the art that transformation of a chemical function into another may require that one or more reactive centers in the compound containing this function be protected in order to avoid undesired side reactions. Protection of such reactive centers, and subsequent de-protection at the end of the synthetic transformations, can be accomplished following standard procedures described, for instance, in Peter G. M. Wuts— Green's Protective Groups in Organic Synthesis, Fifth Edition, John Wiley & Sons Inc., 2014.

It will be appreciated that where typical or preferred experimental conditions (i.e. reaction temperatures, time, moles of reagents, solvents, etc.) are given, other experimental conditions can also be used unless otherwise stated. Optimum reaction conditions may vary with the particular reactants or solvents used, but such conditions can be determined by the person skilled in the art, using routine optimization procedures.

The synthesis of a compound of Formula (I), according to the synthetic processes described below, can be conducted in a stepwise manner, whereby each intermediate is isolated and purified by standard purification techniques such as, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

The compounds of Formula (I), prepared with the methods described herein below, may be treated or purified by conventional techniques or means for example by filtration, distillation, chromatography, recrystallization and combination thereof.

The salts of compounds of Formula (I) may be prepared by reacting a basic compound with the desired acid in solution, or by reacting an acidic compound with the desired base in solution.

A second aspect of the present invention is related to a pharmaceutical composition comprising a compound of Formula (I) as disclosed above included 3-(4-chloro-3,5-dimethyl-pyrazol-1-yl)-N-(2,3-dihydro-1,4-benzodioxin-6-yl)-N-methyl-benzamide and a pharmaceutically acceptable carrier, stabilizer, diluent or excipient thereof.

A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral administration (including subcutaneous and intravenous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing a compound of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, subcutaneous, intravenous, intramuscular, intranasal and pulmonary routes. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampoules or syringes of the liquid compositions or pills, tablets, capsules or the like in the case of solid compositions.

Liquid forms suitable for oral administration may include a suitable aqueous or non-aqueous vehicle with buffers, suspending and dispensing agents, colorants, flavours and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel or corn starch; a lubricant such as magnesium stearate; a glidant such as colloidal silicon dioxide; a sweetening agent such as sucrose or saccharin; or a flavouring agent such as peppermint, methyl salicylate, or orange flavouring.

Injectable compositions are typically based upon injectable sterile saline or phosphate-buffered saline or other injectable carriers known in the art.

The pharmaceutical compositions may be in the form of tablets, pills, capsules, solutions, suspensions, emulsion, powders, suppository and as sustained release formulations.

If desired, tablets may be coated by standard aqueous or non-aqueous techniques. In certain embodiments, such compositions and preparations can contain at least 0.1 percent of active compound. The percentage of active compound in these compositions may, of course, be varied and may conveniently be between about 1 percent to about 60 percent of the weight of the unit. The amount of active compound in such therapeutically useful compositions is such that therapeutically active dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring agent such as cherry or orange flavor. To prevent breakdown during transit through the upper portion of the gastrointestinal tract, the composition be an enteric coated formulation.

Compositions for pulmonary administration include, but are not limited to, dry powder compositions consisting of the powder of a compound of Formula (I) or a salt thereof, and the powder of a suitable carrier and/or lubricant. The compositions for pulmonary administration can be inhaled from any suitable dry powder inhaler device known to a person skilled in the art.

Administration of the compositions is performed under a protocol and at a dosage sufficient to reduce the inflammation and pain in the subject. In some embodiments, in the pharmaceutical compositions of the present invention the active principle or active principles are generally formulated in dosage units. The dosage unit may contain from 0.1 to 1000 mg of a compound of Formula (I) per dosage unit for daily administration.

In some embodiments, the amounts effective for a specific formulation will depend on the severity of the disease, disorder or condition, previous therapy, the individual's health status and response to the drug. In some embodiments, the dose is in the range from 0.001% by weight to about 60% by weight of the formulation.

When used in combination with one or more other active ingredients, the compound of the present invention and the other active ingredient may be used in lower doses than when each is used singly.

Concerning formulations with respect to any variety of routes of administration, methods and formulations for the administration of drugs are disclosed in Remington's Pharmaceutical Sciences, 17th Edition, Gennaro et al. Eds., Mack Publishing Co., 1985, and Remington's Pharmaceutical Sciences, Gennaro A R ed. 20th Edition, 2000, Williams & Wilkins PA, USA, and Remington: The Science and Practice of Pharmacy, 21st Edition, Lippincott Williams & Wilkins Eds., 2005; and in Loyd V. Allen and Howard C. Ansel, Ansel's Pharmaceutical Dosage Forms and Drug Delivery Systems, 10th Edition, Lippincott Williams & Wilkins Eds., 2014.

The above described components for orally administered or injectable compositions are merely representative.

The compounds of this invention can also be administered in sustained release forms or from sustained release drug delivery systems.

A third aspect of the present invention is related to compounds of Formula (I) as disclosed above included 3-(4-chloro-3,5-dimethyl-pyrazol-1-yl)-N-(2,3-dihydro-1,4-benzodioxin-6-yl)-N-methyl-benzamide or the pharmaceutical composition thereof, for the use as a medicament.

A fourth aspect of the present invention relates to compounds of Formula (I) as disclosed above included 3-(4-chloro-3,5-dimethyl-pyrazol-1-yl)-N-(2,3-dihydro-1,4-benzodioxin-6-yl)-N-methyl-benzamide as well as those compounds of Formula (I) wherein $R_1$ can be hydrogen and/or wherein $R_5$, $R_6$, $R_7$, $R_8$, and $R_9$ can be $SO_2NR^{ix}R^x$ and/or wherein B can be

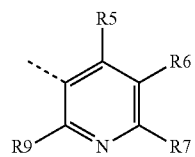

or a pharmaceutical composition thereof, for the use to modulate CFTR protein or ABC protein activities.

Compounds of Formula (I) as disclosed in the previous paragraph may also be effective for the treatment of patients with other protein misfolding diseases. In this respect, other, structurally different CFTR correctors were found to rescue proteins (AVPR2, HCNH2, and ABCC8) with mutations causing trafficking defects (Sampson et al., *Orphanet J Rare Dis* 8:11, 2013). The compounds of formula (I) included 3-(4-chloro-3,5-dimethyl-pyrazol-1-yl)-N-(2,3-dihydro-1,4-benzodioxin-6-yl)-N-methyl-benzamide as well as those compounds of Formula (I) wherein $R_1$ can be hydrogen and/or wherein $R_5$, $R_6$, $R_7$, $R_8$, and $R_9$ can be $SO_2NR^{ix}R^x$ and/or wherein B can be

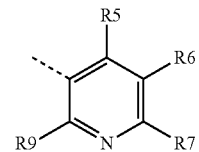

may be indicated in particular for ABC proteins that share with CFTR a similar structure, particularly at the level of nucleotide-binding domains (Rudashevskaya et al., *Drug Discov Today Technol* 12:e87-94, 2014). A list of ABC proteins with trafficking defects and associated diseases that could benefit from CFTR correctors includes: ABCA1 (Tangier disease), ABCA3 (fatal surfactant deficiency), ABCA4 (Stargardt disease), ABCB4 (progressive familial intrahepatic cholestasis type 3), ABCB11 (progressive familial intrahepatic cholestasis type 2), ABCC2 (Dubin-Johnson syndrome), ABCC8 (hyperinsulinemic hypoglycemia of infancy) and ABCG2 (gout).

According to a further aspect of the present invention, compounds of Formula (I) included 3-(4-chloro-3,5-dimethyl-pyrazol-1-yl)-N-(2,3-dihydro-1,4-benzodioxin-6-yl)-N-methyl-benzamide as well as those compounds of Formula (I) wherein $R_1$ can be hydrogen and/or wherein $R_5$, $R_6$, $R_7$, $R_9$, and $R_9$ can be $SO_2NR^{ix}R^x$ and/or wherein B can be

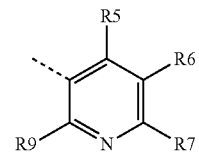

or the pharmaceutical composition thereof can be used in the treatment of a disease selected from the group consisting of cystic fibrosis, Tangier disease, fatal surfactant deficiency, Stargardt disease, progressive familial intrahepatic cholestasis type 3, progressive familial intrahepatic cholestasis type 2, Dubin-Johnson syndrome, hyperinsulinemic hypoglycemia of infancy and gout, in particular cystic fibrosis.

In the following, the present invention shall be illustrated by means of some examples, which are not construed to be viewed as limiting the scope of the invention.

The following abbreviations are hereinafter used in the accompanying examples: acetyl (Ac), Acetic acid (AcOH), aryl (Ar), Apparent triplet (app-t), Apparent doublet of triplet (app-dt), Apparent doublet (app-d), Apparent singlet (app-s), aqueous (aq), di-tert-butyl dicarbonate ($Boc_2O$), broad signal (bs), tert-butyl (tBu), normal-butyl lithium (nBuLi), carbon nuclear magnetic resonance spectroscopy ($^{13}C$ NMR), correlated spectroscopy (COSY), copper (II) acetate ($Cu(OAc)_2$) Cyclohexane (CyH), Deuterium (D), doublet (d), 1,8-diazabicyclo[5.4.0]undec-7-ene (DBU), dichloromethane (DCM), doublet of doublet (dd), doublet of doublet of triplets (ddt), diisopropyl azodicarboxylate (DIAD), ethyldiisopropylamine (DIPEA), doublet of quartet (dq), 4-N,N-dimethylformamide (DMF), Dess-Martin periodinane (DMP), dimethyl sulfoxide (DMSO), Hexadeuterodimethyl sulfoxide (DMSO-$d_6$), doublet of triplet (dt), N-(3-dimethylamino propyl)-N'-ethylcarbodiimide (EDC), half maximal effective concentration (EC50), equivalents (equiv. or eq.), enantiomeric ratio (e.r.), electrospray ionization (ESI), ethyl (Et), diethyl ether (Et$_2$O), ethyl acetate (EtOAc), hour (h), proton nuclear magnetic resonance spectroscopy ($^1$H NMR), 1-[bis (dimethylamino)methylene]-1H-1,2,3-triazolo[4,5-b] pyridinium 3-oxid hexafluorophosphate (HATU), 1-hydroxybenzotriazole hydrate (HOBt), high performance liquid chromatography (HPLC), hertz (Hz), infrared spectroscopy (IR), half maximal inhibitory concentration (IC50), half maximal effective concentration (EC50), isopropyl alcohol (IPA), coupling constant (J), Potassium carbonate (K$_2$CO$_3$), liter (L), Lithium Aluminum hydride (LiAlH$_4$) Lithium Hydroxide (LiOH), lithium diisopropylamide (LDA), molarity (M), multiplet (m), methyl (Me), acetonitrile (MeCN), Methylmagnesium bromide (MeMgBr), methanol (MeOH), Methyl Iodide (MeI), milligram (mg), megahertz (MHz), minutes (min), milliliter (mL), millimole (mmol), melting point (mp), Mass Spectrometry (MS), molecular weight (mw), Microwave (MW), number of atoms or counterions (n), Sodium hydride (NaH), Sodium bicarbonate (NaHCO$_3$), Sodium carbonate (Na$_2$CO$_3$), Sodium tert-butoxyde (NaOtBu), Sodium sulphate (Na$_2$SO$_4$), Sodium thiosulphate (Na$_2$S$_2$O$_3$), N-Bromosuccinimmide (NBS), N-Chlorosuccinimmide (NCS), Ammonium Chloride (NH$_4$C$_1$), not determined (nd), nanomolar (nM), Nuclear Magnetic Resonace (NMR), nuclear Overhauser enhancement (NOE), nuclear Overhauser enhancement spectroscopy (NOESY), nucleophile (Nu), Palladium Acetate (Pd(OAc)$_2$), palladium on charcoal (Pd/C), [1,1'-Bis(diphenylphosphino)ferrocene] dichloropalladium(II) (Pd(dppf)$_2$Cl$_2$), Tetrakis (triphenylphosphine)palladium(0) (Pd(PPh$_3$)$_4$), Tris(dibenzylideneacetone)dipalladium(0) (Pd$_2$(dba)$_3$), protecting group (Pg), phenyl (Ph), parts per million (ppm), Triphenylpospine (PPh$_3$), Phosphorous oxychloride (POCl$_2$), iso-propyl (i-Pr), quartet (q), substituent (R), racemic (rac), room temperature (rt), singlet (s), strong cation exchange cartridge (SCX), temperature (T), triplet or time (t), retention time (tr), tetrabutylammonium fluoride (TBAF), tert-butyldimethylsilyl (TBDMS), triethylamine (TEA), trifluoroacetic acid (TFA), tetrahydrofuran (THF), thin-layer chromatography (TLC), ultraviolet (UV), Ultra-Performance Liquid Chromotography-Mass Spectroscopy (UPLC-MS), anionic ligand, halide, substituent, or number (X), optical rotation ([α]), chemical shift (δ), microliter (μL), Micromolar (μM), Watt (W).

Chemicals, Materials and Methods

Solvents and reagents were obtained from commercial suppliers and were used without further purification.

Automated column chromatography purifications were performed on Teledyne ISCO apparatus (CombiFlash® Rf) with pre-packed silica gel columns of different sizes (Redisep). Hydrogenation reactions were performed on H-Cube® continuous hydrogenation equipment (SS-reaction line version), employing disposable catalyst cartridges (CatCart®) preloaded with the required heterogeneous catalyst. NMR experiments were run on a Bruker Avance III 400 system (400.13 MHz for $^1$H, and 100.62 MHz for $^{13}$C), equipped with a BBI probe and Z-gradients and Bruker FT NMR Avance III 600 MHz spectrometer equipped with a 5 mm CryoProbe™ QCI $^1$H/$^{19}$F-$^{13}$C/$^{15}$N-D quadruple resonance, a shielded z-gradient coil and the automatic sample changer SampleJet™ NMR system (600 MHz for $^1$H, 151 MHz for $^{13}$C and 565 MHz for $^{19}$F). Chemical shifts for $^1$H and $^{13}$C spectra were recorded in parts per million using the residual non-deuterated solvent as the internal standard (for CDCl$_3$: 7.26 ppm, $^1$H and 77.16 ppm, $^{13}$C; for DMSO-$d_6$: 2.50 ppm, $^1$H; 39.52 ppm, $^{13}$C, for D$_2$O: TSP as internal standard 0.00 ppm).

The analyses by UPLC/MS were run on a Waters ACQUITY UPLC/MS system consisting of a SQD (Single Quadrupole Detector) Mass Spectrometer equipped with an Electrospray Ionization interface and a Photodiode Array Detector. The PDA range was 210-400 nm. The analyses were performed on either an ACQUITY UPLC HSS T3 C$_{18}$ column (50×2.1 mmID, particle size 1.8 μm) with a VanGuard HSS T3 C$_{18}$ pre-column (5×2.1 mmID, particle size 1.8 μm) (Log D<1) or an ACQUITY UPLC BEH C$_{18}$ column (50×2.1 mmID, particle size 1.7 μm) with a VanGuard BEH C$_{18}$ pre-column (5×2.1 mmID, particle size 1.7 μm) (Log D>1).

The mobile phase was 10 mM NH$_4$OAc in H$_2$O at pH 5 adjusted with AcOH (A) and 10 mM NH$_4$OAc in MeCN—H$_2$O (95:5) at pH 5 (B).

Electrospray ionization in positive and negative mode was applied in the mass scan range 100-650 Da or 150-750 Da.

Analyses were performed either with "Polar method", "Generic method" and "Apolar Method" herein reported:

Polar Method:
Column: Waters ACQUITY UPLC HSS T3 C$_{18}$, 1.8 μm, 50×2.1 mmID
Pre-column: VanGuard HSS T3 C$_{18}$, 1.8 μm, 5×2.1 mmID
Linear gradient: 0-0.2 min: 0% B, 0.2-2.7 min: 0-50% B, 2.7-2.8 min: 50-100% B, 2.8-3.0 min: 100% B
Flow rate: 0.5 mL/min Generic Method:
Column: Waters ACQUITY UPLC BEH C$_{18}$, 1.7 μm, 50×2.1 mmID
Pre-column: VanGuard BEH C$_{18}$, 1.7 μm, 5×2.1 mmID
Linear gradient: 0-0.2 min: 5% B, 0.2-2.7 min: 5-95% B, 2.7-2.8 min: 95-100% B, 2.8-3.0 min: 100% B
Flow rate: 0.5 mL/min Apolar Method:
Column: Waters ACQUITY UPLC BEH C$_{18}$, 1.7 μm, 50×2.1 mmID
Pre-column: VanGuard BEH C$_{18}$, 1.7 μm, 5×2.1 mmID
Gradient: 0-0.2 min: 50% B, 0.2-2.7 min: 50-100% B, 2.7-3.0 min: 100% B
Flow rate: 0.5 mL/min With the aim of better illustrating the present invention, the syntheses of example compounds reported in table 1 are provided.

PREPARATIONS AND EXAMPLES

GENERAL PROTOCOL 1

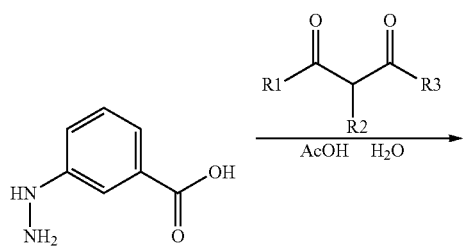

-continued

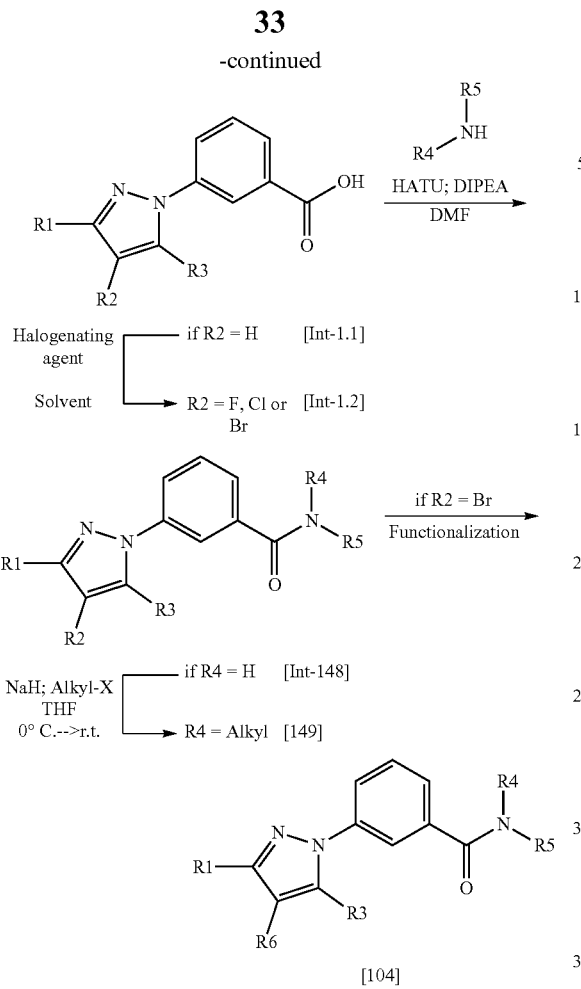

Procedure 1a:

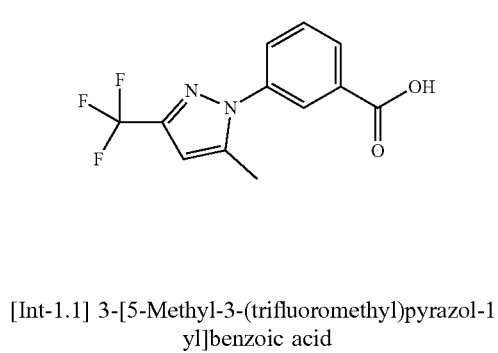

[Int-1.1] 3-[5-Methyl-3-(trifluoromethyl)pyrazol-1-yl]benzoic acid

To a solution of 3-hydrazinobenzoic acid (1.0 g, 6.58 mmol) in AcOH (10 mL) and H$_2$O (10 mL) was added 1,1,1-trifluoropentane-2,4-dione (1.06 g, 6.91 mmol) dropwise, and the mixture stirred at room temperature for 3 h. H$_2$O (50 mL) was added and the resultant precipitate collected by filtration. The product was purified by trituration, with H$_2$O as the solvent, to yield the title compound as a beige solid (1.3 g, 73%): $^1$H NMR (400 MHz, DMSO-d$_6$) δ 8.13-7.97 (m, 2H), 7.87 (ddd, J=8.0, 2.3, 1.1 Hz, 1H), 7.71 (app-t, J=7.9 Hz, 1H), 6.80 (s, 1H), 2.38 (s, 3H); UPLC-MS: t$_R$=1.55 min (generic method); MS (ESI) m/z calcd for C$_{12}$H$_{10}$F$_3$N$_2$O$_2$ (M+H)$^+$: 271.1, found: 271.1.

Procedure 1b

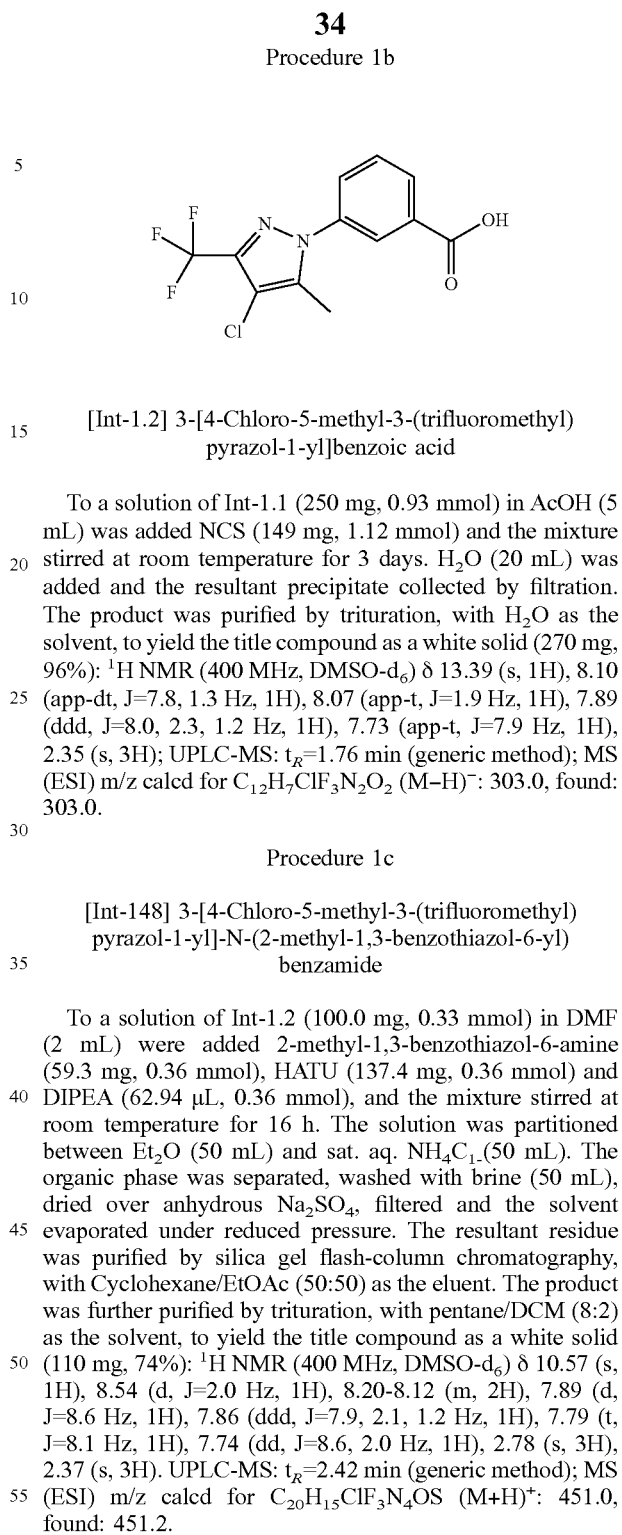

[Int-1.2] 3-[4-Chloro-5-methyl-3-(trifluoromethyl)pyrazol-1-yl]benzoic acid

To a solution of Int-1.1 (250 mg, 0.93 mmol) in AcOH (5 mL) was added NCS (149 mg, 1.12 mmol) and the mixture stirred at room temperature for 3 days. H$_2$O (20 mL) was added and the resultant precipitate collected by filtration. The product was purified by trituration, with H$_2$O as the solvent, to yield the title compound as a white solid (270 mg, 96%): $^1$H NMR (400 MHz, DMSO-d$_6$) δ 13.39 (s, 1H), 8.10 (app-dt, J=7.8, 1.3 Hz, 1H), 8.07 (app-t, J=1.9 Hz, 1H), 7.89 (ddd, J=8.0, 2.3, 1.2 Hz, 1H), 7.73 (app-t, J=7.9 Hz, 1H), 2.35 (s, 3H); UPLC-MS: t$_R$=1.76 min (generic method); MS (ESI) m/z calcd for C$_{12}$H$_7$ClF$_3$N$_2$O$_2$ (M−H)$^-$: 303.0, found: 303.0.

Procedure 1c

[Int-148] 3-[4-Chloro-5-methyl-3-(trifluoromethyl)pyrazol-1-yl]-N-(2-methyl-1,3-benzothiazol-6-yl)benzamide To a solution of Int-1.2 (100.0 mg, 0.33 mmol) in DMF (2 mL) were added 2-methyl-1,3-benzothiazol-6-amine (59.3 mg, 0.36 mmol), HATU (137.4 mg, 0.36 mmol) and DIPEA (62.94 μL, 0.36 mmol), and the mixture stirred at room temperature for 16 h. The solution was partitioned between Et$_2$O (50 mL) and sat. aq. NH$_4$Cl (50 mL). The organic phase was separated, washed with brine (50 mL), dried over anhydrous Na$_2$SO$_4$, filtered and the solvent evaporated under reduced pressure. The resultant residue was purified by silica gel flash-column chromatography, with Cyclohexane/EtOAc (50:50) as the eluent. The product was further purified by trituration, with pentane/DCM (8:2) as the solvent, to yield the title compound as a white solid (110 mg, 74%): $^1$H NMR (400 MHz, DMSO-d$_6$) δ 10.57 (s, 1H), 8.54 (d, J=2.0 Hz, 1H), 8.20-8.12 (m, 2H), 7.89 (d, J=8.6 Hz, 1H), 7.86 (ddd, J=7.9, 2.1, 1.2 Hz, 1H), 7.79 (t, J=8.1 Hz, 1H), 7.74 (dd, J=8.6, 2.0 Hz, 1H), 2.78 (s, 3H), 2.37 (s, 3H). UPLC-MS: t$_R$=2.42 min (generic method); MS (ESI) m/z calcd for C$_{20}$H$_{15}$ClF$_3$N$_4$OS (M+H)$^+$: 451.0, found: 451.2.

Procedure 1d

[149] 3-[4-Chloro-5-methyl-3-(trifluoromethyl)pyrazol-1-yl]-N-methyl-N-(2-methyl-1,3-benzothiazol-6-yl)benzamide To a solution of Int-148 (95.0 mg, 0.21 mmol) in THF (4 mL) NaH (60% dispersion in mineral oil, 25.3 mg, 0.63 mmol) was added at 0° C. and the suspension stirred at the same temperature for 15 min. MeI (39.3 μL, 0.63 mmol) was added and the mixture stirred at room temperature for 3 h. The suspension was quenched with sat. aq. NH$_4$Cl (10 mL), and the aqueous layer was extracted with EtOAc (50 mL). The organic phase was washed with brine (50 mL), dried over anhydrous Na$_2$SO$_4$, filtered and the solvent evaporated under reduced pressure. The resultant residue was purified by silica gel flash-column chromatography, with DCM/EtOAc (70:30) as the eluent to yield the title compound as a white solid (45 mg, 46): $^1$H NMR (400 MHz, DMSO-d$_6$) δ 7.97 (d, J=2.2 Hz, 1H), 7.78 (d, J=8.6 Hz, 1H), 7.53-7.38 (m, 4H), 7.33 (dd, J=8.6, 2.2 Hz, 1H), 3.44 (s, 3H), 2.76 (s, 3H), 1.91 (s, 3H). UPLC-MS: $t_R$=2.20 min (generic method); MS (ESI) m/z calcd for C$_{21}$H$_{17}$ClF$_3$N$_4$OS (M+H)$^+$: 465.1, found: 465.2.

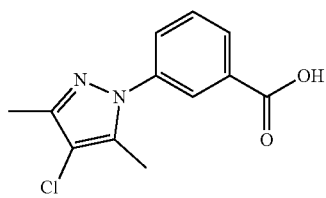 [SMILES: Cc1nn(-c2cccc(C(=O)O)c2)c(C)c1Cl]

[Int-1.3] 3-(4-Chloro-3,5-dimethyl-pyrazol-1-yl) benzoic acid

Following general procedure 1a, the title compound was obtained from 3-chloropentane-2,4-dione, after precipitation with H$_2$O, as a beige solid in 64% yield: $^1$H NMR (400 MHz, DMSO-d$_6$) δ 13.22 (bs, 1H), 8.01 (app-t, J=1.9 Hz, 1H), 7.97 (app-dt, J=7.7, 1.3 Hz, 1H), 7.79 (ddd, J=8.0, 2.3, 1.1 Hz, 1H), 7.65 (app-t, J=7.9 Hz, 1H), 2.32 (s, 3H), 2.21 (s, 3H); UPLC-MS: $t_R$=1.53 min (generic method); MS (ESI) m/z calcd for C$_{12}$H$_{12}$ClN$_2$O$_2$ (M+H)$^+$: 251.1, found: 251.0.

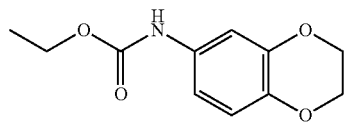 [SMILES: CCOC(=O)Nc1ccc2c(c1)OCCO2]

[Int-1.4] Ethyl N-(2,3-dihydro-1,4-benzodioxin-6-yl) carbamate

To a solution of 2,3-dihydro-1,4-benzodioxin-6-amine (500 mg, 3.31 mmol) in DCM (10 mL) were added ethyl chloroformate (346 μL, 3.64 mmol) and DIPEA (1.2 mL, 6.62 mmol), and the mixture stirred at room temperature for 3 h. The solution was partitioned between DCM (50 mL) and 1.0 M aq. HCl (50 mL). The organic phase was separated, washed with brine (50 mL), dried over anhydrous Na$_2$SO$_4$, filtered and the solvent evaporated under reduced pressure to yield the title compound as a dark oil: UPLC-MS: $t_R$=1.82 min (generic method); MS (ESI) m/z calcd for C$_{11}$H$_{14}$NO$_4$ (M+H)$^+$: 224.1, found: 224.1.

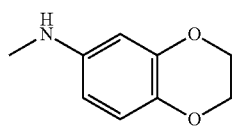

[Int-1.5] N-Methyl-2,3-dihydro-1,4-benzodioxin-6-amine

To a solution of Int-1.4 (700 mg, 3.14 mmol) in THF (15 mL) was added LiAlH$_4$ (2.0 M in THF, 7.8 mL, 15.70 mmol), and the mixture stirred at 70° C. for 1 h. The reaction was cooled to room temperature, H$_2$O (50 mL) added and the product extracted with EtOAc (50 mL). The organic phase was separated, washed with brine (50 mL), dried over anhydrous Na$_2$SO$_4$, filtered and the solvent evaporated under reduced pressure. The resultant residue was purified by silica gel flash-column chromatography, with cyclohexane/EtOAc (7:3) as the eluent, to yield the title compound as a yellow oil (514 mg, 94% over two steps): $^1$H NMR (400 MHz, DMSO-d$_6$) δ 6.58 (d, J=8.6 Hz, 1H), 6.04 (dd, J=8.6, 2.7 Hz, 1H), 6.01 (d, J=2.7 Hz, 1H), 5.16 (q, J=5.3 Hz, 1H), 4.51-3.85 (m, 4H), 2.58 (d, J=5.3 Hz, 3H); UPLC-MS: $t_R$=1.52 min (generic method); MS (ESI) m/z calcd for C$_9$H$_{12}$NO$_2$ (M+H)$^+$: 166.1, found: 166.1.

[001] 3-(4-Chloro-3,5-dimethyl-pyrazol-1-yl)-N-(2,3-dihydro-1,4-benzodioxin-6-yl)-N-methyl-benzamide Following general procedure 1d, the title compound was obtained from compound Int-002, after purification by silica gel flash-column chromatography with DCM/EtOAc (80:20) as the eluent, as a yellow solid in 98% yield: $^1$H NMR (400 MHz, DMSO-d$_6$) δ 7.44-7.39 (m, 2H), 7.38-7.32 (m, 2H), 6.82 (d, J=2.5 Hz, 1H), 6.72 (d, J=8.6 Hz, 1H), 6.63 (dd, J=8.6, 2.5 Hz, 1H), 4.17 (app-s, 4H), 3.31 (s, 3H), 2.17 (s, 3H), 2.04 (s, 3H); UPLC-MS: $t_R$=2.33 min (generic method); MS (ESI) m/z calcd for C$_{21}$H$_{21}$ClN$_3$O$_3$ (M+H)$^+$: 398.1, found: 398.1.

[Int-002] 3-(4-Chloro-3,5-dimethyl-pyrazol-1-yl)-N-(2,3-dihydro-1,4-benzodioxin-6-yl)benzamide Following general procedure 1c, the title compound was obtained from Int-1.3, after purification by silica gel flash-column chromatography with DCM/EtOAc (80:20) as the eluent, as a yellow solid in 78% yield: $^1$H NMR (400 MHz, DMSO-d$_6$) δ 10.18 (s, 1H), 8.05 (app-t, J=1.9 Hz, 1H), 7.98 (app-dt, J=7.6, 1.5 Hz, 1H), 7.72 (ddd, J=7.9, 2.2, 1.2 Hz, 1H), 7.66 (app-t, J=7.8 Hz, 1H), 7.39 (d, J=2.5 Hz, 1H), 7.20 (dd, J=8.7, 2.5 Hz, 1H), 6.83 (d, J=8.7 Hz, 1H), 4.29-4.18 (m, 4H), 2.33 (s, 3H), 2.23 (s, 3H); UPLC-MS: $t_R$=2.40 min (generic method); MS (ESI) m/z calcd for C$_{20}$H$_{29}$ClN$_3$O$_3$ (M+H)$^+$: 384.1, found: 384.0.

[003] 3-(4-Chloro-3,5-dimethyl-pyrazol-1-yl)-N-(2,3-dihydro-1,4-benzodioxin-6-yl)-N-isopropyl-benzamide Following general procedure 1d, the title compound was obtained from compound Int-002, after purification by silica gel flash-column chromatography with DCM/EtOAc (8:2) as the eluent, as a white solid in 35% yield: $^1$H NMR (400 MHz, DMSO-d$_6$) δ 7.46-7.25 (m, 4H), 6.79 (d, J=2.4 Hz, 1H), 6.72 (d, J=8.5 Hz, 1H), 6.66-6.55 (m, 1H), 4.88 (s, 1H), 4.18 (app-s, 4H), 2.18 (s, 3H), 2.10 (s, 3H), 1.12 (d, J=6.8 Hz, 6H); UPLC-MS: $t_R$=1.43 min (apolar method); MS (ESI) m/z calcd for C$_{23}$H$_{25}$ClN$_3$O$_3$ (M+H)$^+$: 426.2, found: 426.2.

[004] 3-(4-Chloro-3,5-dimethyl-pyrazol-1-yl)-N-(2,3-dihydro-1,4-benzodioxin-6-yl)-N-ethyl-benzamide Following general procedure 1d, the title compound was obtained from compound Int-002 upon treatment with iodoethane, after purification by silica gel flash-column chromatography with DCM/EtOAc (8:2) as the eluent, as a yellow solid in 33% yield: $^1$H NMR (400 MHz, DMSO-d$_6$) δ 7.48-7.27 (m, 4H), 6.80 (d, J=2.4 Hz, 1H), 6.72 (d, J=8.5 Hz, 1H), 6.59 (dd, J=8.5, 2.4 Hz, 1H), 4.17 (app-s, 4H), 3.79 (q, J=7.1 Hz, 2H), 2.17 (s, 3H), 2.04 (s, 3H), 1.09 (t, J=7.1 Hz, 3H); UPLC-MS: $t_R$=2.45 min (generic method); MS (ESI) m/z calcd for C$_{22}$H$_{23}$ClN$_3$O$_3$ (M+H)$^+$: 412.1, found: 412.1.

[Int-005] 3-(4-Chloro-3,5-dimethyl-pyrazol-1-yl)-N-(2,2,3,3-tetrafluoro-1,4-benzodioxin-6-yl)benzamide Following general procedure 1c, the title compound was obtained from Int-1.3, after purification by silica gel flash-column chromatography with DCM/EtOAc (95:5) as the eluent, as an off-white solid in 92% yield: $^1$H NMR (400 MHz, DMSO-d$_6$) δ 10.63 (s, 1H), 8.08 (app-t, J=1.9 Hz, 1H), 8.01 (app-dt, J=7.7, 1.4 Hz, 1H), 7.96 (d, J=2.3 Hz, 1H), 7.77 (ddd, J=8.0, 2.2, 1.2 Hz, 1H), 7.70 (d, J=7.8 Hz, 1H), 7.67 (dd, J=9.2, 2.3 Hz, 1H), 7.48 (d, J=9.2 Hz, 1H), 2.33 (s, 3H), 2.23 (s, 3H); UPLC-MS: $t_R$=2.14 min (apolar method); MS (ESI) m/z calcd for C$_{20}$H$_{15}$ClF$_4$N$_3$O$_3$ (M+H)$^+$: 456.1, found: 456.1.

[Int-006] 3-(4-Chloro-3,5-dimethyl-pyrazol-1-yl)-N-(2,2-difluoro-1,3-benzodioxol-5-yl)benzamide Following general procedure 1c, the title compound was obtained from Int-1.3, after purification by silica gel flash-column chromatography with DCM/EtOAc (95:5) as the eluent, as an off-white solid in 94% yield: $^1$H NMR (400 MHz, DMSO-d$_6$) δ 10.54 (s, 1H), 8.07 (app-t, J=1.9 Hz, 1H), 8.00 (app-dt, J=7.7, 1.5 Hz, 1H), 7.91 (d, J=2.1 Hz, 1H), 7.76 (ddd, J=8.0, 2.2, 1.2 Hz, 1H), 7.69 (app-t, J=7.8 Hz, 1H), 7.51 (dd, J=8.8, 2.1 Hz, 1H), 7.40 (d, J=8.7 Hz, 1H), 2.33 (s, 3H), 2.23 (s, 3H); UPLC-MS: $t_R$=1.80 min (apolar method); MS (ESI) m/z calcd for C$_{19}$H$_{15}$ClF$_2$N$_3$O$_3$ (M+H)$^+$: 406.1, found: 406.1.

[007] 3-(4-Chloro-3,5-dimethyl-pyrazol-1-yl)-N-methyl-N-phenyl-benzamide

Following general procedure 1c, the title compound was obtained from Int-1.3, after purification by silica gel flash-column chromatography with cyclohexane/EtOAc (7:3) as the eluent, as a yellow solid in 89% yield: $^1$H NMR (400 MHz, DMSO-d$_6$) δ 7.45-7.13 (m, 9H), 3.39 (s, 3H), 2.16 (s, 3H), 1.98 (s, 3H); UPLC-MS: $t_R$=1.28 min (apolar method); MS (ESI) m/z calcd for C$_{19}$H$_{19}$ClN$_3$O (M+H)$^+$: 340.1, found: 340.2.

[008] 3-(4-Chloro-3,5-dimethyl-pyrazol-1-yl)-N-methyl-N-(2,2,3,3-tetrafluoro-1,4-benzodioxin-6-yl)benzamide Following general procedure 1d, the title compound was obtained from compound Int-005, after purification by silica gel flash-column chromatography with DCM/EtOAc (8:2) as the eluent, as an off-white solid in 62% yield: $^1$H NMR (400 MHz, DMSO-d$_6$) δ 7.57 (d, J=2.4 Hz, 1H), 7.48-7.34 (m, 5H), 7.17 (dd, J=8.8, 2.4 Hz, 1H), 3.38 (s, 3H), 2.16 (s, 3H), 2.01 (s, 3H); UPLC-MS: $t_R$=1.96 min (apolar method); MS (ESI) m/z calcd for C$_{21}$H$_{17}$ClF$_4$N$_3$O$_3$ (M+H)$^+$: 470.1, found: 470.1.

[009] 3-(4-Chloro-3,5-dimethyl-pyrazol-1-yl)-N-(2,2-difluoro-1,3-benzodioxol-5-yl)-N-methyl-benzamide Following general procedure 1d, the title compound was obtained from compound Int-006, after purification by silica gel flash-column chromatography with DCM/EtOAc (9:1) as the eluent, as an off-white solid in 85% yield: $^1$H NMR (400 MHz, DMSO-d$_6$) δ 7.54 (d, J=2.1 Hz, 1H), 7.46-7.41 (m, 2H), 7.41-7.34 (m, 2H), 7.29 (d, J=8.6 Hz, 1H), 7.03 (dd, J=8.6, 2.1 Hz, 1H), 3.37 (s, 3H), 2.16 (s, 3H), 2.04 (s, 3H); UPLC-MS: $t_R$=1.64 min (apolar method); MS (ESI) m/z calcd for C$_{20}$H$_{17}$ClF$_2$N$_3$O$_3$ (M+H)$^+$: 420.1, found: 420.1.

[010] N-(2,3-Dihydro-1,4-benzodioxin-6-yl)-N-methyl-3-pyrazol-1-yl-benzamide

Following general procedure 1c, the title compound was obtained from 3-pyrazol-1-ylbenzoic acid, after purification by silica gel flash-column chromatography with DCM/EtOAc (8:2) as the eluent, as a white solid in 95% yield: $^1$H NMR (400 MHz, DMSO-d$_6$) δ 8.41 (d, J=2.5 Hz, 1H), 7.83 (app-t, J=1.9 Hz, 1H), 7.79-7.70 (m, 2H), 7.33 (app-t, J=7.9 Hz, 1H), 7.13 (d, J=7.6 Hz, 1H), 6.83 (d, J=2.4 Hz, 1H), 6.71 (d, J=8.6 Hz, 1H), 6.65 (dd, J=8.7, 2.5 Hz, 1H), 6.53 (dd, J=2.5, 1.8 Hz, 1H), 4.15 (app-s, 4H), 3.32 (s, 3H); UPLC-MS: $t_R$=1.93 min (generic method); MS (ESI) m/z calcd for C$_{19}$H$_{18}$N$_3$O$_3$ (M+H)$^+$: 336.1, found: 336.2.

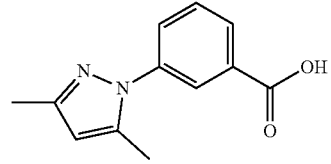 [SMILES: Cc1cc(C)n(-c2cccc(C(=O)O)c2)n1]

[Int-1.6] 3-(3,5-Dimethylpyrazol-1-yl)benzoic acid

Following general procedure 1a, the title compound was obtained from pentane-2,4-dione, after purification by trituration with H$_2$O as the solvent, as a beige solid in 60% yield: $^1$H NMR (400 MHz, DMSO-d$_6$) δ 13.19 (s, 1H), 8.01 (s, 1H), 7.92 (app-dt, J=7.7, 1.4 Hz, 1H), 7.76 (app-dt, J=8.0, 1.6 Hz, 1H), 7.61 (app-t, J=7.9 Hz, 1H), 6.09 (s, 1H), 2.32 (s, 3H), 2.19 (s, 3H); UPLC-MS: $t_R$=1.28 min (generic method); MS (ESI) m/z calcd for C$_{12}$H$_{13}$N$_2$O$_2$ (M+H)$^+$: 217.1, found: 217.1.

[011] N-(2,3-Dihydro-1,4-benzodioxin-6-yl)-3-(3,5-dimethyl pyrazol-1-yl)-N-methyl-benzamide Following general procedure 1c, the title compound was obtained from Int-1.6, after purification by silica gel flash-column chromatography with DCM/EtOAc (7:3) as the eluent, as a white solid in 65% yield: $^1$H NMR (400 MHz, DMSO-d$_6$) δ 7.44-7.26 (m, 4H), 6.83 (d, J=2.5 Hz, 1H), 6.71 (d, J=8.6 Hz, 1H), 6.62 (dd, J=8.6, 2.5 Hz, 1H), 6.02 (s, 1H), 4.16 (app-s, 4H), 3.31 (s, 3H), 2.15 (s, 3H), 2.04 (s, 3H); UPLC-MS: $t_R$=2.00 min (generic method); MS (ESI) m/z calcd for C$_{21}$H$_{22}$N$_3$O$_3$ (M+H)$^+$: 364.2, found: 364.2.

[Int-012] N-(1,3-Benzodioxol-5-yl)-3-(4-chloro-3,5-dimethyl-pyrazol-1-yl)benzamide Following general procedure 1c, the title compound was obtained from Int-1.3, after purification by silica gel flash-column chromatography with DCM/EtOAc (9:1) as the eluent, as a white solid in 26% yield: $^1$H NMR (400 MHz, DMSO-d$_6$) δ 10.25 (s, 1H), 8.05 (app-t, J=1.9 Hz, 1H), 7.98 (app-dt, J=7.6, 1.4 Hz, 1H), 7.73 (app-dt, J=8.2, 1.4 Hz, 1H), 7.67 (app-t, J=7.8 Hz, 1H), 7.43 (d, J=2.1 Hz, 1H), 7.19 (dd, J=8.4, 2.1 Hz, 1H), 6.90 (d, J=8.4 Hz, 1H), 6.01 (s, 2H), 2.33 (s, 3H), 2.23 (s, 3H); UPLC-MS: t$_R$=2.39 min (generic method); MS (ESI) m/z calcd for C$_{19}$H$_{17}$ClN$_3$O$_3$ (M+H)$^+$: 370.1, found: 370.1.

[Int-013] 3-(4-Chloro-3,5-dimethyl-pyrazol-1-yl)-N-(3,4-dimethoxyphenyl)benzamide Following general procedure 1c, the title compound was obtained from Int-1.3, after purification by silica gel flash-column chromatography with cyclohexane/EtOAc (7:3) as the eluent, as an off-white solid in 35% yield: $^1$H NMR (400 MHz, DMSO-d$_6$) δ 10.20 (s, 1H), 8.07 (app-t, J=1.9 Hz, 1H), 8.01 (app-dt, J=7.6, 1.5 Hz, 1H), 7.76-7.71 (m, 1H), 7.67 (app-t, J=7.8 Hz, 1H), 7.47 (d, J=2.4 Hz, 1H), 7.35 (dd, J=8.7, 2.4 Hz, 1H), 6.94 (d, J=8.7 Hz, 1H), 3.76 (s, 3H), 3.75 (s, 3H), 2.33 (s, 3H), 2.23 (s, 3H); UPLC-MS: t$_R$=2.30 min (generic method); MS (ESI) m/z calcd for C$_{20}$H$_{21}$ClN$_3$O$_3$ (M+H)$^+$: 386.1, found: 386.2.

[014] 3-(4-Chloro-3,5-dimethyl-pyrazol-1-yl)-N-(3,4-dimethoxyphenyl)-N-methyl-benzamide Following general procedure 1d, the title compound was obtained from Int-013, after purification by silica gel flash-column chromatography with cyclohexane/EtOAc (1:1) as the eluent, as an off-white solid in 86% yield: $^1$H NMR (400 MHz, DMSO-d$_6$) δ 7.47-7.18 (m, 4H), 6.91 (d, J=2.4 Hz, 1H), 6.80 (d, J=8.5 Hz, 1H), 6.68 (dd, J=8.5, 2.4 Hz, 1H), 3.68 (s, 3H), 3.64 (s, 3H), 3.36 (s, 3H), 2.17 (s, 3H), 2.02 (bs, 3H); UPLC-MS: t$_R$=0.98 min (apolar method); MS (ESI) m/z calcd for C$_{21}$H$_{23}$ClN$_3$O$_3$ (M+H)$^+$: 400.1, found: 400.2.

[015] N-(1,3-Benzodioxol-5-yl)-3-(4-chloro-3,5-dimethyl-pyrazol-1-yl)-N-methyl-benzamide Following general procedure 1d, the title compound was obtained from Int-012, after purification by silica gel flash-column chromatography with cyclohexane/EtOAc (1:1) as the eluent, as a white solid in 92% yield: $^1$H NMR (400 MHz, DMSO-d$_6$) δ 7.50-7.24 (m, 4H), 6.96 (d, J=2.1 Hz, 1H), 6.77 (d, J=8.2 Hz, 1H), 6.64 (dd, J=8.2, 2.1 Hz, 1H), 5.99 (s, 2H), 3.32 (s, 3H), 2.17 (s, 3H), 2.08 (s, 3H); UPLC-MS: t$_R$=1.12 min (apolar method); MS (ESI) m/z calcd for C$_{20}$H$_{49}$ClN$_3$O$_3$ (M+H)$^+$: 384.1, found: 384.1.

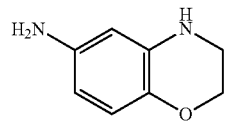 [SMILES: Nc1ccc2c(c1)NCCO2]

[Int-1.7] 3,4-Dihydro-2H-1,4-benzoxazin-6-amine

To a solution of 6-amino-4H-1,4-benzoxazin-3-one (300 mg, 1.83 mmol) in THF (10 mL) was added LiAlH$_4$ (2.0 M in THF, 4.6 mL, 9.15 mmol), and the mixture stirred at 70° C. for 3 h. The reaction was cooled to room temperature, H$_2$O (50 mL) added and the product extracted with EtOAc (50 mL). The organic phase was separated, washed with brine (50 mL), dried over anhydrous Na$_2$SO$_4$, filtered and the solvent evaporated under reduced pressure. The resultant residue was purified by silica gel flash-column chromatography, with DCM/EtOAc (1:1) as the eluent, to yield the title compound as a brown oil (160 mg, 58%): $^1$H NMR (400 MHz, DMSO-d$_6$) δ 6.31 (d, J=8.3 Hz, 1H), 5.84 (d, J=2.5 Hz, 1H), 5.73 (dd, J=8.3, 2.5 Hz, 1H), 5.42 (t, J=2.5 Hz, 1H), 4.30 (s, 2H), 4.00-3.93 (m, 2H), 3.22-3.14 (m, 2H); UPLC-MS: t$_R$=1.43 min (polar method); MS (ESI) m/z calcd for C$_8$H$_{11}$N$_2$O (M+H)$^+$: 151.1, found: 151.1.

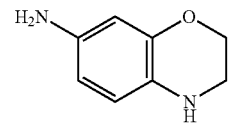 [SMILES: Nc1ccc2c(c1)OCCN2]

[Int-1.8] 3,4-Dihydro-2H-1,4-benzoxazin-7-amine

To a solution of 7-amino-4H-1,4-benzoxazin-3-one (300 mg, 1.83 mmol) in THF (10 mL) was added LiAlH$_4$ (2.0 M in THF, 4.6 mL, 9.15 mmol), and the mixture stirred at 70° C. for 3 h. The reaction was cooled to room temperature, H$_2$O (50 mL) added and the product extracted with EtOAc (50 mL). The organic phase was separated, washed with brine (50 mL), dried over anhydrous Na$_2$SO$_4$, filtered and the solvent evaporated under reduced pressure. The resultant residue was purified by silica gel flash-column chromatography, with DCM/EtOAc (6:4) as the eluent, to yield the title compound as a dark oil (120 mg, 44%): $^1$H NMR (400 MHz, DMSO-d$_6$) δ 6.30 (d, J=8.9 Hz, 1H), 6.03-5.94 (m, 2H), 4.07-3.98 (m, 2H), 3.21-3.07 (m, 2H); UPLC-MS: t$_R$=1.24 min (polar method); MS (ESI) m/z calcd for C$_8$H$_{11}$N$_2$O (M+H)$^+$: 151.1, found: 151.1.

[Int-016] 3-(4-Chloro-3,5-dimethyl-pyrazol-1-yl)-N-(3,4-dihydro-2H-1,4-benzoxazin-6-yl)benzamide Following general procedure 1c, the title compound was obtained from Int-1.3 and Int-1.7, after purification by silica gel flash-column chromatography with DCM/MeOH (95:5) as the eluent, as a pale yellow solid in 78% yield: $^1$H NMR (400 MHz, DMSO-d$_6$) δ 10.00 (s, 1H), 8.03 (app-t, J=1.9 Hz, 1H), 7.97 (app-dt, J=7.6, 1.5 Hz, 1H), 7.71 (app-dt, J=8.1, 1.5 Hz, 1H), 7.65 (app-t, J=7.8 Hz, 1H), 7.11 (d, J=2.5 Hz, 1H), 6.80 (dd, J=8.5, 2.5 Hz, 1H), 6.59 (d, J=8.5 Hz, 1H), 5.86 (t, J=2.4 Hz, 1H), 4.09 (t, J=4.3 Hz, 2H), 3.27 (td, J=4.3, 2.4 Hz, 2H), 2.33 (s, 3H), 2.23 (s, 3H); UPLC-MS: t$_R$=2.22 min (generic method); MS (ESI) m/z calcd for C$_{20}$H$_{20}$ClN$_4$O$_2$ (M+H)$^+$: 383.1, found: 383.1.

[Int-018] 3-(4-chloro-3,5-dimethyl-pyrazol-1-yl)-N-(3,4-dihydro-2H-1,4-benzoxazin-7-yl)benzamide Following general procedure 1c, the title compound was obtained from Int-1.3 and Int-1.8, after purification by silica gel flash-column chromatography with DCM/MeOH (95:5) as the eluent, as a green solid in 82% yield: $^1$H NMR (400 MHz, DMSO-d$_6$) δ 9.98 (s, 1H), 8.02 (d, J=2.0 Hz, 1H), 7.97 (app-dt, J=7.5, 1.5 Hz, 1H), 7.73-7.67 (m, 1H), 7.64 (app-t, J=7.7 Hz, 1H), 7.15 (d, J=2.3 Hz, 1H), 7.06 (dd, J=8.5, 2.3 Hz, 1H), 6.53 (d, J=8.5 Hz, 1H), 5.61 (t, J=2.6 Hz, 1H), 4.19-4.07 (m, 2H), 3.30-3.20 (m, 2H), 2.32 (s, 3H), 2.23 (s, 3H); UPLC-MS: $t_R$=2.21 min (generic method); MS (ESI) m/z calcd for $C_{20}H_2OClN_4O_2$ (M+H)$^+$: 383.1, found: 383.2.

[019] 3-(4-Chloro-3,5-dimethyl-pyrazol-1-yl)-N-(2,2-difluoro-1,3-benzodioxol-5-yl)-N-ethyl-benzamide Following general procedure 1d, the title compound was obtained from compound Int-006, upon treatment with iodoethane, after purification by silica gel flash-column chromatography with DCM/EtOAc (9:1) as the eluent, as a yellow solid in 55% yield: $^1$H NMR (400 MHz, DMSO-d$_6$) δ 7.54 (d, J=2.1 Hz, 1H), 7.47-7.34 (m, 4H), 7.29 (d, J=8.5 Hz, 1H), 6.99 (dd, J=8.5, 2.1 Hz, 1H), 3.85 (q, J=7.1 Hz, 2H), 2.16 (s, 3H), 2.03 (s, 3H), 1.11 (t, J=7.1 Hz, 3H); UPLC-MS: $t_R$=1.83 min (apolar method); MS (ESI) m/z calcd for $C_{21}H_{19}ClF_2N_3O_3$ (M+H)$^+$: 434.1, found: 434.2.

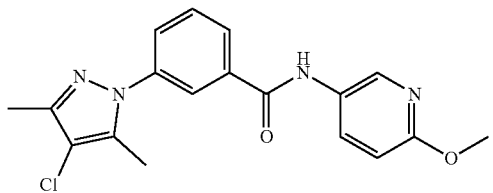

[Int-1.9] 3-(4-Chloro-3,5-dimethyl-pyrazol-1-yl)-N-(6-methoxy-3-pyridyl)benzamide Following general procedure 1c, the title compound was obtained from Int-1.3 as crude product, as a pale yellow solid UPLC-MS: $t_R$=2.27 min (Generic method); MS (ESI) m/z calcd for $C_{18}H_{18}ClN_4O_2$ (M+H)$^+$: 357.1, found: 357.2.

[021] 3-(4-Chloro-3,5-dimethyl-pyrazol-1-yl)-N-(6-methoxy-3-pyridyl)-N-methyl-benzamide Following general procedure 1d, the title compound was obtained from Int-1.9, after purification by silica gel flash-column chromatography with DCM/EtOAc (70:30) as the eluent, as a pale yellow solid in 65% yield: $^1$H NMR (400 MHz, DMSO-d$_6$) δ 8.00 (bs, 1H), 7.68 (dd, J=8.8, 2.8 Hz, 1H), 7.55-7.22 (m, 4H), 6.77 (d, J=8.8 Hz, 1H), 3.77 (s, 3H), 3.35 (s, 3H), 2.17 (s, 3H), 2.06 (s, 3H). UPLC-MS: $t_R$=2.26 min (generic method); MS (ESI) m/z calcd for $C_{19}H_{20}ClN_4O_2$ (M+H)$^+$: 371.1, found: 371.3.

[Int-022] 3-(4-Chloro-3,5-dimethyl-pyrazol-1-yl)-N-(2,2-difluoro-1,3-benzodioxol-4-yl)benzamide Following general procedure 1c, the title compound was obtained from Int-1.3, after purification by silica gel flash-column chromatography with DCM/EtOAc (80:20) as the eluent, as a pale yellow solid in 38% yield: $^1$H NMR (400 MHz, DMSO-d$_6$) δ 10.68 (s, 1H), 8.12 (app-t, J=1.8 Hz, 1H), 8.05 (app-dt, J=7.7, 1.3 Hz, 1H), 7.80 (ddd, J=8.0, 2.2, 1.1 Hz, 1H), 7.71 (app-t, J=7.9 Hz, 1H), 7.35-7.17 (m, 3H), 2.35 (s, 3H), 2.24 (s, 3H). UPLC-MS: $t_R$=2.63 min (Generic method); MS (ESI) m/z calcd for $C_{19}H_{15}ClF_2N_3O_3$ (M+H)$^+$: 406.1, found: 406.2.

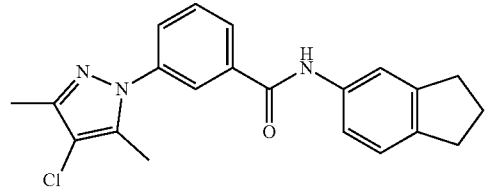 [SMILES: Cc1nn(-c2cccc(C(=O)Nc3ccc4c(c3)CCC4)c2)c(C)c1Cl]

[Int-1.10] 3-(4-Chloro-3,5-dimethyl-pyrazol-1-yl)-N-indan-5-yl-benzamide

Following general procedure 1c, the title compound was obtained from Int-1.3, after purification by silica gel flash-column chromatography with Cyclohexane/EtOAc (60:40) as the eluent, as a pale yellow solid in 72% yield: $^1$H NMR (400 MHz, DMSO-d$_6$) δ 10.23 (s, 1H), 8.06 (app-t, J=1.9 Hz, 1H), 8.00 (app-dt, J=7.6, 1.4 Hz, 1H), 7.73 (ddd, J=8.0, 2.2, 1.3 Hz, 1H), 7.70-7.63 (m, 2H), 7.48 (dd, J=8.1, 2.0 Hz, 1H), 7.19 (d, J=8.1 Hz, 1H), 2.93-2.76 (m, 4H), 2.33 (s, 3H), 2.23 (s, 3H), 2.02 (p, J=7.6 Hz, 2H). UPLC-MS: $t_R$=2.71 min (generic method); MS (ESI) m/z calcd for $C_{21}H_{21}ClN_3O$ (M+H)$^+$: 366.1, found: 366.3.

[023] 3-(4-chloro-3,5-dimethyl-pyrazol-1-yl)-N-indan-5-yl-N-methyl-benzamide

Following general procedure 1d, the title compound was obtained from compound Int-1.10, after purification by silica gel flash-column chromatography with DCM/MeOH (95:5) as the eluent, as a pale yellow solid in 81% yield: $^1$H NMR (400 MHz, DMSO-d$_6$) δ 7.48-7.33 (m, 3H), 7.31 (s, 1H), 7.13 (d, J=2.0 Hz, 1H), 7.08 (d, J=7.9 Hz, 1H), 6.88 (dd, J=7.9, 2.0 Hz, 1H), 3.35 (s, 3H), 2.75 (t, J=7.4 Hz, 4H), 2.16 (s, 3H), 2.03-1.88 (m, 5H). UPLC-MS: $t_R$=2.73 min (generic method); MS (ESI) m/z calcd for $C_{22}H_{23}ClN_3O$ (M+H)$^+$: 380.1, found: 380.3.

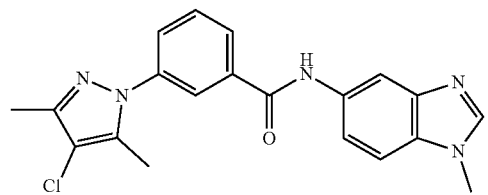 [SMILES: Cc1nn(-c2cccc(C(=O)Nc3ccc4c(c3)ncn4C)c2)c(C)c1Cl]

[Int-1.11] 3-(4-Chloro-3,5-dimethyl-pyrazol-1-yl)-N-(1-methylbenzimidazol-5-yl)benzamide Following general procedure 1c, the title compound was obtained from Int-1.3, after purification by silica gel flash-column chromatography with Cyclohexane/EtOAc (60:40) as the eluent, as a pale yellow solid in 82% yield: $^1$H NMR (400 MHz, DMSO-d$_6$) δ 10.34 (s, 1H), 8.16 (s, 1H), 8.12 (d, J=1.9 Hz, 1H), 8.10 (app-t, J=1.9 Hz, 1H), 8.04 (app-dt, J=7.5, 1.5 Hz, 1H), 7.74 (ddd, J=8.0, 2.1, 1.3 Hz, 1H), 7.69 (app-t, J=7.8 Hz, 1H), 7.62 (dd, J=8.7, 1.9 Hz, 1H), 7.54 (d, J=8.7 Hz, 1H), 3.84 (s, 3H), 2.34 (s, 3H), 2.24 (s, 3H). UPLC-MS: $t_R$=2.00 min (generic method); MS (ESI) m/z calcd for $C_{20}H_{19}ClN_5O$ (M+H)$^+$: 380.1, found: 380.2.

[024] 3-(4-Chloro-3,5-dimethyl-pyrazol-1-yl)-N-methyl-N-(1-methylbenzimidazol-5-yl)benzamide Following general procedure 1d, the title compound was obtained from compound Int-1.11, after purification by silica gel flash-column chromatography with DCM/EtOAc (80:20) as the eluent, as a pale yellow solid in 22% yield: $^1$H NMR (400 MHz, DMSO-$d_6$) δ 8.17 (s, 1H), 7.55 (d, J=2.0 Hz, 1H), 7.45 (d, J=8.5 Hz, 1H), 7.37 (s, 1H), 7.35-7.27 (m, 3H), 7.14 (dd, J=8.5, 2.0 Hz, 1H), 3.78 (s, 3H), 3.42 (s, 3H), 2.14 (s, 3H), 1.85 (s, 3H). UPLC-MS: $t_R$=1.90 min (generic method); MS (ESI) m/z calcd for $C_{21}H_{21}ClN_5O$ (M+H)$^+$: 394.1, found: 394.2.

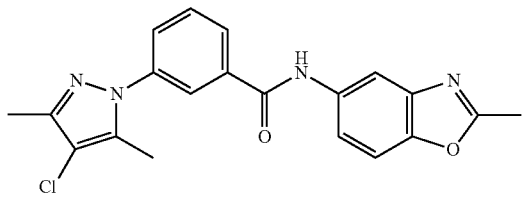

[Int-1.12] 3-(4-Chloro-3,5-dimethyl-pyrazol-1-yl)-N-(2-methyl-1,3-benzoxazol-5-yl)benzamide Following general procedure 1c, the title compound was obtained from Int-1.3, after purification by silica gel flash-column chromatography with DCM/MeOH (95:5) as the eluent, as a pale yellow solid in 78% yield: $^1$H NMR (400 MHz, DMSO-$d_6$) δ 10.47 (s, 1H), 8.15 (d, J=1.9 Hz, 1H), 8.11 (app-t, J=1.9 Hz, 1H), 8.05 (app-dt, J=7.5, 1.4 Hz, 1H), 7.76 (ddd, J=8.0, 2.1, 1.2 Hz, 1H), 7.70 (t, J=7.8 Hz, 1H), 7.68 (d, J=2.0 Hz, 1H), 7.64 (app-t, J=8.7 Hz, 1H), 2.62 (s, 3H), 2.35 (s, 3H), 2.25 (s, 3H). UPLC-MS: $t_R$=2.27 min (generic method); MS (ESI) m/z calcd for $C_{20}H_{18}ClN_4O_2$ (M+H)$^+$: 381.1, found: 381.2.

[025] 3-(4-Chloro-3,5-dimethyl-pyrazol-1-yl)-N-methyl-N-(2-methyl-1,3-benzoxazol-5-yl)benzamide Following general procedure 1d, the title compound was obtained from compound Int-1.12, after purification by silica gel flash-column chromatography with DCM/EtOAc (80:20) as the eluent, as a pale yellow solid in 22% yield: $^1$H NMR (400 MHz, DMSO-$d_6$) δ 7.59 (d, J=2.1 Hz, 1H), 7.55 (d, J=8.6 Hz, 1H), 7.35 (dd, J=15.4, 9.7 Hz, 4H), 7.22 (dd, J=8.6, 2.1 Hz, 1H), 3.42 (s, 3H), 2.56 (s, 3H), 2.15 (s, 3H), 1.95 (s, 3H). UPLC-MS: $t_R$=2.22 min (generic method); MS (ESI) m/z calcd for $C_{21}H_{20}ClN_4O_2$ (M+H)$^+$: 395.1, found: 395.2.

[026] 3-(4-Chloro-3,5-dimethyl-pyrazol-1-yl)-N-(2,2-difluoro-1,3-benzodioxol-4-yl)-N-methyl-benzamide Following general procedure 1d, the title compound was obtained from Int-022, after purification by silica gel flash-column chromatography with DCM/EtOAc (80:20) as the eluent, as a viscous oil in 61% yield: $^1$H NMR (400 MHz, DMSO-$d_6$) δ 7.54-7.47 (m, 1H), 7.46-7.39 (m, 1H), 7.39-7.32 (m, 2H), 7.27 (app-t, J=1.3 Hz, 1H), 7.25 (d, J=1.2 Hz, 1H), 7.22-7.14 (m, 1H), 3.40 (s, 3H), 2.16 (s, 3H). UPLC-MS: $t_R$=2.67 min (Generic method); MS (ESI) m/z calcd for $C_{20}H_{17}ClF_2N_3O_3$ (M+H)$^+$: 420.1, found: 420.2.

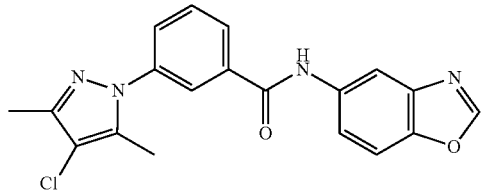 [SMILES: Cc1nn(-c2cccc(C(=O)Nc3ccc4ocnc4c3)c2)c(C)c1Cl]

[Int-1.13] N-(1,3-Benzoxazol-5-yl)-3-(4-chloro-3,5-dimethyl-pyrazol-1-yl)benzamide Following general procedure 1c, the title compound was obtained from Int-1.3, after purification by silica gel flash-column chromatography with cyclohexane/EtOAc (1:1) as the eluent, as a brown solid in 38% yield: UPLC-MS: $t_R$=2.20 min (generic method); MS (ESI) m/z calcd for $C_{19}H_{16}ClN_4O_2$ (M+H)$^+$: 367.1, found: 367.2.

[029] N-(1,3-Benzoxazol-5-yl)-3-(4-chloro-3,5-dimethyl-pyrazol-1-yl)-N-methyl-benzamide Following general procedure 1d, the title compound was obtained from compound Int-1.13, after purification by silica gel flash-column chromatography with cyclohexane/EtOAc (7:3) as the eluent, as a white solid in 99% yield: $^1$H NMR (400 MHz, DMSO-$d_6$) δ 8.74 (s, 1H), 7.78 (d, J=2.1 Hz, 1H), 7.68 (d, J=8.6 Hz, 1H), 7.47-7.23 (m, 5H), 3.43 (s, 3H), 2.14 (s, 3H), 1.91 (bs, 3H); UPLC-MS: $t_R$=2.11 min (generic method); MS (ESI) m/z calcd for $C_{20}H_{18}ClN_4O_2$ (M+H)$^+$: 381.1, found: 381.2.

[030] 3-(4-Chloro-3,5-dimethyl-pyrazol-1-yl)-N-cyclopropyl-N-(2,3-dihydro-1,4-benzodioxin-6-yl)benzamide To a solution of compound Int-002, (100 mg, 0.26 mmol) in toluene (3 mL) were added 2-cyclopropyl-4,4,5,5-tetramethyl-1,3,2-dioxaborolane (88 mg, 0.52 mmol), Cu(OAc)$_2$ (47 mg, 0.26 mmol), pyridine (63 μL, 0.78 mmol) and Cs$_2$CO$_3$ (42 mg, 0.13 mmol), and the mixture stirred at 130° C. for 32 h. The mixture was cooled to room temperature and partitioned between EtOAc (50 mL) and H$_2$O (50 mL). The organic phase was separated, washed with brine (50 mL), dried over anhydrous Na$_2$SO$_4$, filtered and the solvent evaporated under reduced pressure. The resultant residue was purified by silica gel flash-column chromatography, with DCM/EtOAc (8:2) as the eluent, to yield the title compound as an off-white solid (46 mg, 42%): 1H NMR (400 MHz, DMSO-$d_6$) δ 7.54-7.35 (m, 4H), 6.82 (d, J=2.4 Hz, 1H), 6.74 (d, J=8.5 Hz, 1H), 6.64 (dd, J=8.5, 2.4 Hz, 1H), 4.19 (app-s, 4H), 3.19 (tt, J=7.4, 4.0 Hz, 1H), 2.18 (s, 3H), 2.13 (s, 3H), 0.76-0.62 (m, 2H), 0.56-0.44 (m, 2H); UPLC-MS: $t_R$=1.27 min (apolar method); MS (ESI) m/z calcd for $C_{23}H_{23}ClN_3O_3$ (M+H)$^+$: 424.1, found: 424.3.

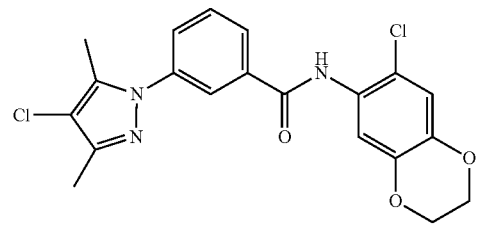 [SMILES: Cc1nn(-c2cccc(C(=O)Nc3cc4c(cc3Cl)OCCO4)c2)c(C)c1Cl]

[Int-1.14] N-(6-chloro-2,3-dihydro-1,4-benzodioxin-7-yl)-3-(4-chloro-3,5-dimethyl-pyrazol-1-yl)benzamide Following general procedure 1c, the title compound was obtained from Int-1.3, as crude product, as a pale yellow solid: UPLC-MS: $t_R$=2.55 min (Generic method); MS (ESI) m/z calcd for $C_{20}H_{28}C_{12}N_3O_3$ (M+H)$^+$: 418.1, found: 418.2.

[032] N-(6-chloro-2,3-dihydro-1,4-benzodioxin-7-yl)-3-(4-chloro-3,5-dimethyl-pyrazol-1-yl)-N-methyl-benzamide Following general procedure 1d, the title compound was obtained from Int-1.14, after purification by silica gel flash-column chromatography with Cyclohexane/EtOAc (50:50) as the eluent, as a pale yellow solid in 52% yield over two steps. $^1$H NMR Analysis showed the presence of rotamers; major product: $^1$H NMR (400 MHz, DMSO-d$_6$) δ 7.48-7.33 (m, 4H), 7.21 (s, 1H), 6.96 (s, 1H), 4.27-4.13 (m, 4H), 3.23 (s, 3H), 2.18 (s, 3H), 2.11 (s, 3H). UPLC-MS: $t_R$=2.50 min (Generic method); MS (ESI) m/z calcd for $C_{21}H_{20}C_{12}N_3O_3$ (M+H)$^+$: 432.1, found: 432.2.

[Int-1.15] 3-(4-Chloropyrazol-1-yl)benzoic acid

Following general procedure 1a, the title compound was obtained from 2-chloropropanedial, after purification by silica gel flash-column chromatography with DCM/MeOH (9:1) as the eluent, as a white solid in 7% yield: UPLC-MS: $t_R$=1.39 min (generic method); MS (ESI) m/z calcd for $C_{10}H_8ClN_2O_2$ (M+H)$^+$: 223.0, found: 223.1.

[033] 3-(4-Chloropyrazol-1-yl)-N-(2,3-dihydro-1,4-benzodioxin-6-yl)-N-methyl-benzamide Following general procedure 1c, the title compound was obtained from Int-1.15, after purification by silica gel flash-column chromatography with DCM/EtOAc (9:1) as the eluent, as a white solid in 42% yield: $^1$H NMR (400 MHz, DMSO-d$_6$) δ 8.71 (s, 1H), 7.87 (s, 1H), 7.80 (s, 1H), 7.72 (dd, J=8.1, 2.3 Hz, 1H), 7.35 (app-t, J=7.9 Hz, 1H), 7.16 (d, J=7.6 Hz, 1H), 6.83 (d, J=2.4 Hz, 1H), 6.70 (d, J=8.5 Hz, 1H), 6.64 (dd, J=8.6, 2.4 Hz, 1H), 4.16 (app-s, 4H), 3.31 (s, 3H); UPLC-MS: $t_R$=2.19 min (generic method); MS (ESI) m/z calcd for $C_{19}H_{17}ClN_3O_3$ (M+H)$^+$: 370.1, found: 370.2.

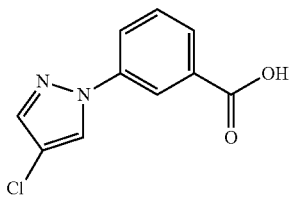 [SMILES: O=C(O)c1cccc(-n2cc(Cl)cn2)c1]

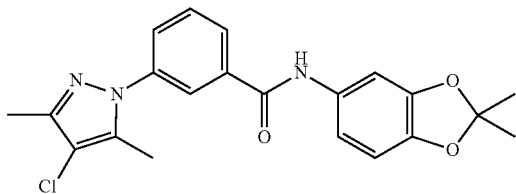

[Int-1.16] 3-(4-chloro-3,5-dimethyl-pyrazol-1-yl)-N-(2,2-dimethyl-1,3-benzodioxol-5-yl)benzamide Following general procedure 1c, the title compound was obtained from Int-1.3, after purification by silica gel flash-column chromatography with Cyclohexane/EtOAc (60:40) as the eluent, as a pale yellow solid in 72% yield: $^1$H NMR (400 MHz, DMSO-d$_6$) δ 10.21 (s, 1H), 8.05 (app-t, J=1.9 Hz, 1H), 7.99 (app-dt, J=7.6, 1.4 Hz, 1H), 7.73 (ddd, J=8.0, 2.2, 1.2 Hz, 1H), 7.67 (app-t, J=7.8 Hz, 1H), 7.34 (d, J=2.1 Hz, 1H), 7.15 (dd, J=8.4, 2.1 Hz, 1H), 6.81 (d, J=8.4 Hz, 1H), 2.34 (s, 3H), 2.24 (s, 3H), 1.65 (s, 6H). UPLC-MS: $t_R$=2.59 min (generic method); MS (ESI) m/z calcd for $C_{21}H_{21}ClN_3O_3$ (M+H)$^+$: 398.1, found: 398.2.

[034] 3-(4-Chloro-3,5-dimethyl-pyrazol-1-yl)-N-(2,2-dimethyl-1,3-benzodioxol-5-yl)-N-methyl-benzamide Following general procedure 1d, the title compound was obtained from compound Int-1.16, after purification by silica gel flash-column chromatography with cyclohexane/EtOAc (70:30) as the eluent, as a pale yellow solid in 22% yield: $^1$H NMR (400 MHz, DMSO-d$_6$) δ 7.49-7.35 (m, 3H), 7.30 (s, 1H), 6.87 (d, J=2.1 Hz, 1H), 6.66 (d, J=8.1 Hz, 1H), 6.55 (app-d, J=7.7 Hz, 1H), 3.31 (s, 3H), 2.16 (s, 3H), 2.05 (s, 3H), 1.57 (s, 6H). UPLC-MS: $t_R$=2.55 min (generic method); MS (ESI) m/z calcd for $C_{22}H_{23}ClN_3O_3$ (M+H)$^+$: 412.1, found: 412.2.

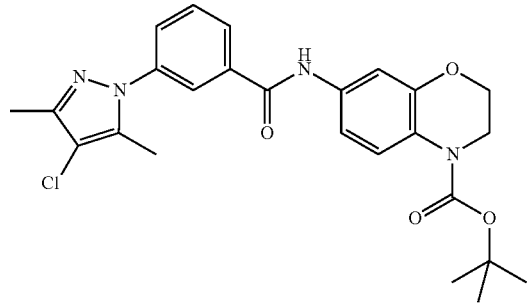 [SMILES: Cc1nn(-c2cccc(C(=O)Nc3ccc4c(c3)OCCN4C(=O)OC(C)(C)C)c2)c(C)c1Cl]

[Int-1.17] tert-Butyl 7-[[3-(4-chloro-3,5-dimethyl-pyrazol-1-yl)benzoyl]amino]-2,3-dihydro-1,4-benzoxazine-4-carboxylate To a solution of Int-018, (100 mg, 0.26 mmol) in DCM (5 mL) were added DIPEA (90 μL, 0.52 mmol) and (Boc)$_2$O (63 mg, 0.29 mmol), and the mixture stirred at room temperature for 6 days. The solution was partitioned between DCM (50 mL) and sat. aq. NH$_4$C$_1$ (50 mL). The organic phase was separated, washed with brine (50 mL), dried over anhydrous Na$_2$SO$_4$, filtered and the solvent evaporated under reduced pressure. The resultant residue was purified by silica gel flash-column chromatography, with cyclohexane/EtOAc (7:3) as the eluent, to yield the title compound as a pale pink solid (117 mg, 93%): $^1$H NMR (400 MHz, DMSO-d$_6$) δ 10.26 (s, 1H), 8.05 (app-t, J=1.9 Hz, 1H), 7.99 (app-dt, J=7.6, 1.5 Hz, 1H), 7.77-7.61 (m, 3H), 7.41 (d, J=2.4 Hz, 1H), 7.26 (dd, J=9.1, 2.4 Hz, 1H), 4.36-4.10 (m, 2H), 3.91-3.64 (m, 2H), 2.33 (s, 3H), 2.23 (s, 3H), 1.49 (s, 9H); UPLC-MS: $t_R$=1.80 min (apolar method); MS (ESI) m/z calcd for $C_{25}H_{28}ClN_4O_4$ (M+H)$^+$: 483.2, found: 483.3.

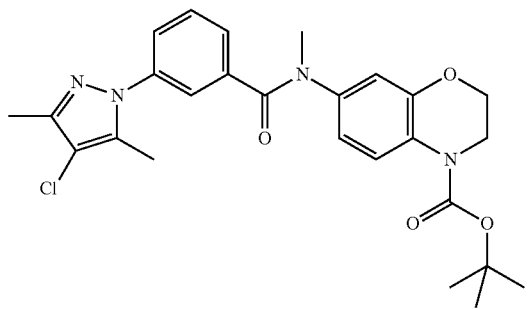 [SMILES: Cc1nn(-c2cccc(C(=O)N(C)c3ccc4c(c3)OCCN4C(=O)OC(C)(C)C)c2)c(C)c1Cl]

[Int-1.18] tert-Butyl 7-[[3-(4-chloro-3,5-dimethyl-pyrazol-1-yl)benzoyl]-methyl-amino]-2,3-dihydro-1,4-benzoxazine-4-carboxylate Following general procedure 1d, the title compound was obtained from Int-1.17, after purification by silica gel flash-column chromatography with cyclohexane/EtOAc (7:3) as the eluent, as a white solid in 83% yield: $^1$H NMR (400 MHz, DMSO-d$_6$) δ 7.59 (d, J=8.9 Hz, 1H), 7.47-7.34 (m, 3H), 7.32 (s, 1H), 6.79 (d, J=2.5 Hz, 1H), 6.66 (dd, J=8.9, 2.5 Hz, 1H), 4.15 (t, J=4.5 Hz, 2H), 3.71 (t, J=4.5 Hz, 2H), 3.34 (s, 3H), 2.16 (s, 3H), 1.98 (s, 3H), 1.43 (s, 9H); UPLC-MS: t$_R$=1.73 min (apolar method); MS (ESI) m/z calcd for C$_{26}$H$_{30}$ClN$_4$O$_4$ (M+H)$^+$: 497.2, found: 497.4.

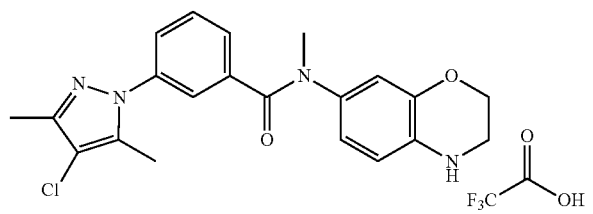

[036] 3-(4-Chloro-3,5-dimethyl-pyrazol-1-yl)-N-(3,4-dihydro-2H-1,4-benzoxazin-4-ium-7-yl)-N-methyl-benzamide 2,2,2-trifluoroacetate To a solution of Int-1.18 (100 mg, 0.20 mmol) in DCM (5 mL) was added TFA (306 μL, 4.00 mmol), and the mixture stirred at room temperature for 3 h. The solvent was evaporated under reduced pressure to yield the title compound as an off-white solid (97 mg, 94%): $^1$H NMR (400 MHz, DMSO-d$_6$) δ 7.57 (br s, 2H), 7.44-7.26 (m, 4H), 6.60 (d, J=2.3 Hz, 1H), 6.47 (dd, J=8.4, 2.3 Hz, 1H), 6.43 (d, J=8.4 Hz, 1H), 4.06 (t, J=4.3 Hz, 2H), 3.28 (s, 3H), 3.23 (t, J=4.3 Hz, 2H), 2.17 (s, 3H), 2.03 (s, 3H); UPLC-MS: t$_R$=2.12 min (generic method); MS (ESI) m/z calcd for C$_{21}$H$_{22}$ClN$_4$O$_2$ (M+H)$^+$: 397.1, found: 397.2.

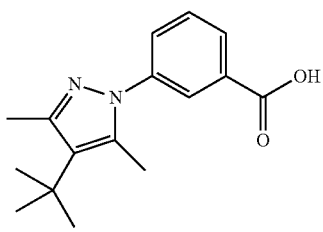 [SMILES: Cc1nn(-c2cccc(C(=O)O)c2)c(C)c1C(C)(C)C]

[Int-1.19] 3-(4-tert-Butyl-3,5-dimethyl-pyrazol-1-yl)benzoic acid

Following general procedure 1a, the title compound was obtained from 3-tert-butylpentane-2,4-dione, after purification by silica gel flash-column chromatography with DCM/MeOH (95:5) as the eluent, as an off-white solid in 5% yield: $^1$H NMR (400 MHz, DMSO-d$_6$) δ 13.17 (s, 1H), 7.94 (app-dt, J=7.3, 1.6 Hz, 1H), 7.87 (app-t, J=1.8 Hz, 1H), 7.69-7.57 (m, 2H), 2.32 (s, 3H), 2.31 (s, 3H), 1.36 (s, 9H); UPLC-MS: t$_R$=1.74 min (generic method); MS (ESI) m/z calcd for C$_{16}$H$_{21}$N$_2$O$_2$ (M+H)$^+$: 273.2, found: 273.3.

[037] 3-(4-tert-Butyl-3,5-dimethyl-pyrazol-1-yl)-N-(2,3-dihydro-1,4-benzodioxin-6-yl)-N-methyl-benzamide Following general procedure 1c, the title compound was obtained from Int-1.19, after purification by silica gel flash-column chromatography with cyclohexane/EtOAc (7:3) as the eluent, as a white solid in 30% yield: $^1$H NMR (400 MHz, DMSO-d$_6$) δ 7.45-7.26 (m, 3H), 7.17 (s, 1H), 6.82 (d, J=2.5 Hz, 1H), 6.71 (d, J=8.5 Hz, 1H), 6.62 (dd, J=8.6, 2.5 Hz, 1H), 4.17 (app-s, 4H), 3.30 (s, 3H), 2.26 (s, 3H), 2.02 (s, 3H); UPLC-MS: t$_R$=2.43 min (generic method); MS (ESI) m/z calcd for C$_{25}$H$_{30}$N$_3$O$_3$ (M+H)$^+$: 420.2, found: 420.4.

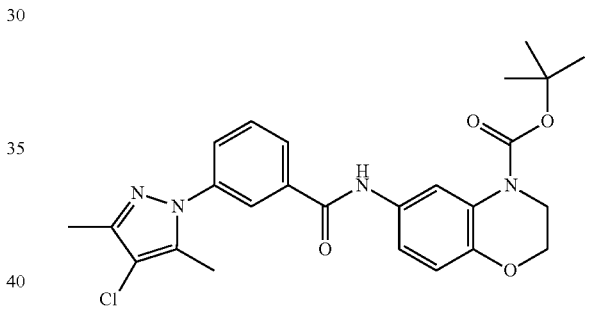

[Int-1.20] tert-Butyl 6-[[3-(4-chloro-3,5-dimethyl-pyrazol-1-yl)benzoyl]amino]-2,3-dihydro-1,4-benzoxazine-4-carboxylate To a solution of Int-016 (100 mg, 0.26 mmol) in DCM (5 mL) were added DIPEA (90 μL, 0.52 mmol) and (Boc)$_2$O (63 mg, 0.29 mmol), and the mixture stirred at room temperature for 10 days. The solution was partitioned between DCM (50 mL) and sat. aq. NH$_4$Cl (50 mL). The organic phase was separated, washed with brine (50 mL), dried over anhydrous Na$_2$SO$_4$, filtered and the solvent evaporated under reduced pressure. The resultant residue was purified by silica gel flash-column chromatography, with cyclohexane/EtOAc (7:3) as the eluent, to yield the title compound as a white solid (69 mg, 55%): $^1$H NMR (400 MHz, DMSO-d$_6$) δ 10.23 (s, 1H), 8.30 (d, J=2.5 Hz, 1H), 8.06 (app-t, J=2.0 Hz, 1H), 8.00 (app-dt, J=7.7, 1.4 Hz, 1H), 7.75-7.70 (m, 1H), 7.66 (app-t, J=7.8 Hz, 1H), 7.39 (dd, J=8.8, 2.5 Hz, 1H), 6.84 (d, J=8.8 Hz, 1H), 4.29-4.09 (m, 2H), 3.87-3.70 (m, 2H), 2.33 (s, 3H), 2.23 (s, 3H), 1.51 (s, 9H); UPLC-MS: t$_R$=1.77 min (apolar method); MS (ESI) m/z calcd for C$_{25}$H$_{28}$ClN$_4$O$_4$ (M+H)$^+$: 483.2, found: 483.4.

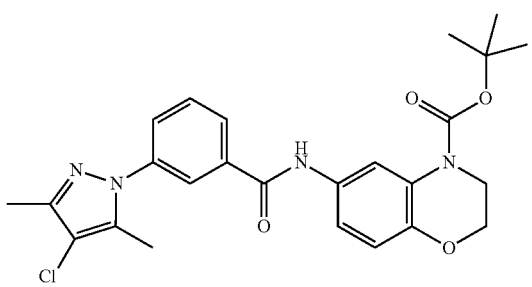 [SMILES: Cc1nn(-c2cccc(C(=O)Nc3ccc4c(c3)N(C(=O)OC(C)(C)C)CCO4)c2)c(C)c1Cl]

[Int-1.21] tert-Butyl 6-[[3-(4-chloro-3,5-dimethyl-pyrazol-1-yl)benzoyl]-methyl-amino]-2,3-dihydro-1,4-benzoxazine-4-carboxylate Following general procedure 1d, the title compound was obtained from Int-1.20, after purification by silica gel flash-column chromatography with cyclohexane/EtOAc (6:4) as the eluent, as a white solid in 99% yield: $^1$H NMR (400 MHz, DMSO-$d_6$) δ 7.73 (s, 1H), 7.49-7.26 (m, 4H), 6.78-6.66 (m, 2H), 4.15 (t, J=4.4 Hz, 2H), 3.73 (t, J=4.4 Hz, 2H), 3.33 (s, 3H), 2.16 (s, 3H), 2.01 (s, 3H), 1.46 (s, 9H); UPLC-MS: $t_R$=1.79 min (apolar method); MS (ESI) m/z calcd for $C_{26}H_{30}ClN_4O_4$ (M+H)$^+$: 497.2, found: 497.4.

[038] 3-(4-Chloro-3,5-dimethyl-pyrazol-1-yl)-N-(3,4-dihydro-2H-1,4-benzoxazin-4-ium-6-yl)-N-methyl-benzamide 2,2,2-trifluoroacetate To a solution of Int-1.21 (100 mg, 0.20 mmol) in DCM (5 mL) was added TFA (306 μL, 4.00 mmol), and the mixture stirred at room temperature for 3 h. The solvent was evaporated under reduced pressure to yield the title compound as an off-white solid (102 mg, 99%): $^1$H NMR (400 MHz, DMSO-$d_6$) δ 7.46-7.34 (m, 3H), 7.31 (s, 1H), 6.49 (d, J=8.4 Hz, 1H), 6.42 (d, J=2.5 Hz, 1H), 6.25 (dd, J=8.4, 2.5 Hz, 0H), 6.10 (br s, 2H), 4.04 (t, J=4.3 Hz, 1H), 3.29 (s, 3H), 3.21 (t, J=4.3 Hz, 2H), 2.17 (s, 3H), 2.02 (s, 3H); UPLC-MS: $t_R$=2.21 min (generic method); MS (ESI) m/z calcd for $C_{21}H_{22}ClN_4O_2$ (M+H)$^+$: 397.1, found: 397.3.

[039] 3-(4-Chloro-3,5-dimethyl-pyrazol-1-yl)-N-(2,2-difluoro-1,3-benzodioxol-5-yl)-N-(trideuteriomethyl) benzamide Following general procedure 1d, the title compound was obtained from compound Int-006 upon treatment with trideuterio(iodo)methane, after purification by silica gel flash-column chromatography with DCM/EtOAc (9:1) as the eluent, as a pale yellow solid in 99% yield: $^1$H NMR (400 MHz, DMSO-$d_6$) δ 7.54 (d, J=2.1 Hz, 1H), 7.47-7.33 (m, 4H), 7.29 (d, J=8.6 Hz, 1H), 7.03 (dd, J=8.6, 2.1 Hz, 1H), 2.16 (s, 3H), 2.04 (s, 3H); UPLC-MS: $t_R$=1.59 min (apolar method); MS (ESI) m/z calcd for $C_{20}D_3H_{14}ClF_2N_3O_3$ (M+H)$^+$: 423.1, found: 423.3.

[Int-040] 3-(4-Chloro-3,5-dimethyl-3,4-dihydropyrazol-2-yl)-N-tetralin-6-yl-benzamide Following general procedure 1c, the title compound was obtained from Int-1.3, after purification by silica gel flash-column chromatography with Cyclohexane/EtOAc (80:20) as the eluent, as a yellow solid in 66% yield: $^1$H NMR (400 MHz, DMSO-$d_6$): δ 10.19 (s, 1H), 8.08 (t, J=1.9 Hz, 1H), 8.01 (dt, J=7.6, 1.4 Hz, 1H), 7.74 (ddd, J=8.0, 2.1, 1.2 Hz, 1H), 7.67 (t, J=7.8 Hz, 1H), 7.54-7.42 (m, 2H), 7.03 (d, J=8.2 Hz, 1H), 2.70 (dd, J=11.1, 5.5 Hz, 4H), 2.34 (s, 3H), 2.24 (s, 3H), 1.74 (h, J=3.2, 2.7 Hz, 4H). UPLC-MS: $t_R$=2.79 min (generic method); MS (ESI) m/z calcd for $C_{22}H_{23}ClN_3O$ (M+H)$^+$: 380.1, found: 380.1.

[Int-041] 3-(4-Chloro-3,5-dimethyl-pyrazol-1-yl)-N-(6-methyl-1,3-benzodioxol-5-yl)benzamide Following general procedure 1c, the title compound was obtained Int-1.3, after purification by silica gel flash-column chromatography with DCM/EtOAc (80:20) as the eluent, as a white solid in 65% yield. $^1$H NMR (400 MHz, DMSO-$d_6$) δ 9.89 (s, 1H), 8.08 (app-t, J=1.9 Hz, 1H), 8.03 (app-d, J=7.4 Hz, 1H), 7.80-7.72 (m, 1H), 7.68 (app-t, J=7.8 Hz, 1H), 6.90 (s, 1H), 6.87 (s, 1H), 6.01 (s, 2H), 2.35 (s, 3H), 2.24 (s, 3H), 2.14 (s, 3H). UPLC-MS: $t_R$=2.37 min (Generic method); MS (ESI) m/z calcd for $C_{20}H_{29}ClN_3O_3$ (M+H)$^+$: 384.1, found: 384.1.

[042] 3-(4-chloro-3,5-dimethyl-pyrazol-1-yl)-N-methyl-N-(6-methyl-1,3-benzodioxol-5-yl)benzamide Following general procedure 1d, the title compound was obtained from Int-041, after purification by silica gel flash-column chromatography with DCM/EtOAc (75:25) as the eluent, as a white solid in 78% yield. $^1$H NMR Analysis showed the presence of rotamers. Major rotamer: $^1$H NMR (400 MHz, DMSO-$d_6$) δ 7.43-7.34 (m, 3H), 7.34-7.29 (m, 1H), 7.00 (s, 1H), 6.71 (s, 1H), 5.95 (d, J=0.9 Hz, 2H), 3.22 (s, 3H), 2.17 (s, 3H), 2.09 (s, 3H), 2.02 (s, 3H). UPLC-MS: $t_R$=2.41 min (Generic method); MS (ESI) m/z calcd for $C_{21}H_{21}ClN_3O_3$ (M+H)$^+$: 398.1, found: 398.2.

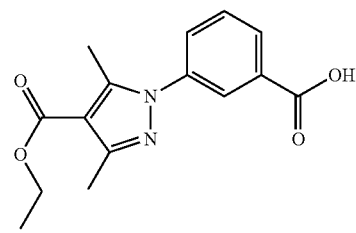 [SMILES: CCOC(=O)c1c(C)nn(-c2cccc(C(=O)O)c2)c1C]

[Int-1.22] 3-(4-Ethoxycarbonyl-3,5-dimethyl-pyrazol-1-yl) benzoic acid

Following general procedure 1a, the title compound was obtained ethyl 2-acetyl-3-oxo-butanoate, after precipitation with water, as a yellow solid in 68% yield: $^1$H NMR (400 MHz, DMSO-$d_6$) δ 13.31 (bs, 1H), 8.03 (app-dt, J=7.7, 1.4 Hz, 1H), 8.00 (app-t, J=1.8 Hz, 1H), 7.79 (ddd, J=8.0, 2.2, 1.1 Hz, 1H), 7.68 (app-t, J=7.8 Hz, 1H), 4.26 (q, J=7.1 Hz, 2H), 2.51 (s, 3H), 2.39 (s, 3H), 1.31 (t, J=7.1 Hz, 3H). UPLC-MS: $t_R$=1.50 min (Generic method); MS (ESI) m/z calcd for $C_{15}H_{17}N_2O_4$ (M+H)$^+$: 289.1, found: 289.2.

[043] Ethyl 1-[3-[1,3-benzodioxol-5-yl(methyl)carbamoyl]phenyl]-3,5-dimethyl-pyrazole-4-carboxylate Following general procedure 1c, the title compound was obtained from Int-1.22, after purification by silica gel flash-column chromatography with DCM/EtOAc (85:25) as the eluent, as a white solid in 90% yield: $^1$H NMR (400 MHz, DMSO-$d_6$) δ 7.56-7.20 (m, 4H), 6.96 (d, J=2.2 Hz, 1H), 6.77 (d, J=8.2 Hz, 1H), 6.64 (dd, J=8.2, 2.2 Hz, 1H), 5.98 (s, 2H), 4.23 (q, J=7.1 Hz, 2H), 3.32 (s, 3H), 2.35 (s, 3H), 2.23 (s, 3H), 1.29 (t, J=7.1 Hz, 3H). UPLC-MS: $t_R$=2.22 min (Generic method); MS (ESI) m/z calcd for $C_{23}H_{23}N_3O_5$ (M+H)$^+$: 422.2, found: 422.2.

[044] 3-(4-Chloro-3,5-dimethyl-3,4-dihydropyrazol-2-yl)-N-methyl-N-tetralin-6-yl-benzamide Following general procedure 1c, the title compound was obtained from Int-040, after purification by silica gel flash-column chromatography with Cyclohexane/EtOAc (50:50) as the eluent, as a yellow solid in 52% yield: $^1$H NMR (400 MHz, DMSO-$d_6$): δ 7.46-7.34 (m, 3H), 7.29 (s, 1H), 6.95 (s, 1H), 6.92 (d, J=8.1 Hz, 1H), 6.83 (dd, J=8.1, 2.3 Hz, 1H), 3.35 (s, 3H), 2.61 (q, J=5.6 Hz, 4H), 2.17 (s, 3H), 1.94 (s, 3H), 1.67 (h, J=2.9 Hz, 4H). UPLC-MS: $t_R$=2.84 min (generic method); MS (ESI) m/z calcd for $C_{23}H_{25}ClN_3O$ (M+H)$^+$: 394.2, found: 394.2.

[Int-045] 3-(4-Chloro-3,5-dimethyl-pyrazol-1-yl)-N-(2-methyl-1,3-benzoxazol-6-yl)benzamide Following general procedure 1c, the title compound was obtained from Int-1.3, after purification by silica gel flash-column chromatography with cyclohexane/EtOAc (7:3) as the eluent, as a pale yellow solid in 75% yield: $^1$H NMR (400 MHz, DMSO-$d_6$) δ 10.54 (s, 1H), 8.23 (d, J=1.3 Hz, 1H), 8.10 (app-t, J=1.9 Hz, 1H), 8.03 (app-dt, J=7.6, 1.5 Hz, 1H), 7.76 (ddd, J=8.0, 2.2, 1.2 Hz, 1H), 7.70 (app-t, J=7.8 Hz, 1H), 7.63 (app-d, J=1.2 Hz, 2H), 2.60 (s, 3H), 2.34 (s, 3H), 2.23 (s, 3H); UPLC-MS: $t_R$=2.28 min (generic method); MS (ESI) m/z calcd for $C_{20}H_{18}ClN_4O_2$ (M+H)$^+$: 381.1, found: 381.1.

[047] 3-(4-Chloro-3,5-dimethyl-pyrazol-1-yl)-N-methyl-N-(2-methyl-1,3-benzoxazol-6-yl)benzamide Following general procedure 1d, the title compound was obtained from Int-045, after purification by silica gel flash-column chromatography with cyclohexane/EtOAc (4:6) as the eluent, as a white solid in 20% yield: $^1$H NMR (400 MHz, DMSO-$d_6$) δ 7.66 (d, J=1.9 Hz, 1H), 7.53 (d, J=8.4 Hz, 1H), 7.42-7.29 (m, 4H), 7.20 (dd, J=8.4, 1.9 Hz, 1H), 3.42 (s, 3H), 2.57 (s, 3H), 2.15 (s, 3H), 1.95 (s, 3H); UPLC-MS: $t_R$=2.15 min (generic method); MS (ESI) m/z calcd for $C_{21}H_{20}ClN_4O_2$ (M+H)$^+$: 395.1, found: 395.2.

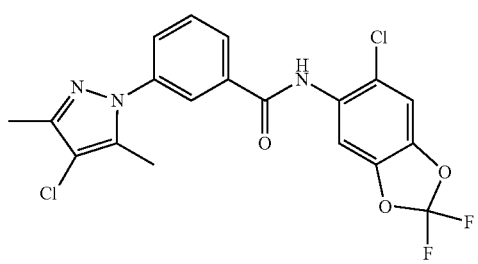 [SMILES: Cc1nn(-c2cccc(C(=O)Nc3cc4c(cc3Cl)OC(F)(F)O4)c2)c(C)c1Cl]

[Int-1.23] N-(6-Chloro-2,2-difluoro-1,3-benzodioxol-5-yl)-3-(4-chloro-3,5-dimethyl-pyrazol-1-yl)benzamide Following general procedure 1c, the title compound was obtained from Int-1.3, as crude product, as an oil in 28% yield: UPLC-MS: $t_R$=2.81 min (Generic method); MS (ESI) m/z calcd for $C_{19}H_{14}Cl_2F_2N_3O_3$ (M+H)$^+$: 440.0, found: 440.1.

[049] N-(6-Chloro-2,2-difluoro-1,3-benzodioxol-5-yl)-3-(4-chloro-3,5-dimethyl-pyrazol-1-yl)-N-methyl-benzamide Following general procedure 1d, the title compound was obtained from Int-1.23, after purification by silica gel flash-column chromatography with Cyclohexane/EtOAc (85:15) as the eluent, as a white solid in 55% yield. $^1$H NMR Analysis showed rotamers mixture. Major product: $^1$H NMR (400 MHz, DMSO-$d_6$) δ 7.94 (s, 1H), 7.71 (s, 1H), 7.52-7.33 (m, 4H), 3.28 (s, 3H), 2.17 (s, 3H), 2.09 (s, 3H). UPLC-MS: $t_R$=1.79 min (Apolar method); MS (ESI) m/z calcd for $C_{20}H_{15}Cl_2F_2N_3O_3$ (M+H)$^+$: 454.0, found: 454.2.

[Int-051] 3-(4-Chloro-3,5-dimethyl-3,4-dihydropyrazol-2-yl)-N-(1,3-dihydroisobenzofuran-5-yl)benzamide Following general procedure 1c, the title compound was obtained from Int-1.3, after purification by silica gel flash-column chromatography with Cyclohexane/EtOAc (80:20) as the eluent, as a white solid in 66% yield $^1$H NMR (400 MHz, DMSO-$d_6$): δ 10.40 (s, 1H), 8.08 (app-t, J=1.9 Hz, 1H), 8.02 (app-dt, J=7.6, 1.4 Hz, 1H), 7.82-7.78 (m, 1H), 7.75 (ddd, J=8.0, 2.2, 1.2 Hz, 1H), 7.69 (app-t, J=7.8 Hz, 1H), 7.63 (dd, J=8.2, 1.9 Hz, 1H), 7.30 (d, J=8.2 Hz, 1H), 5.07-4.91 (m, 4H), 2.34 (s, 3H), 2.24 (s, 3H). UPLC-MS: $t_R$=2.33 min (generic method); MS (ESI) m/z calcd for $C_{20}H_{19}ClN_3O_2$ (M+H)$^+$: 368.1, found: 368.2.

[Int-052] 3-(4-Chloro-3,5-dimethyl-3,4-dihydropyrazol-2-yl)-N-(2,3-dihydrobenzofuran-5-yl)benzamide Following general procedure 1c, the title compound was obtained from Int-1.3, after purification by silica gel flash-column chromatography with Cyclohexane/EtOAc (80:20) as the eluent, as a white solid in 66% yield: $^1$H NMR (400 MHz, DMSO-$d_6$): δ 10.19 (s, 1H), 8.06 (app-t, J=1.8 Hz, 1H), 8.00 (app-dt, J=7.6, 1.4 Hz, 1H), 7.73 (ddd, J=8.0, 2.2, 1.2 Hz, 1H), 7.71-7.64 (m, 2H), 7.41 (dd, J=8.6, 2.2 Hz, 1H), 6.75 (d, J=8.5 Hz, 1H), 4.53 (t, J=8.6 Hz, 2H), 3.20 (t, J=8.6 Hz, 2H), 2.34 (s, 3H), 2.24 (s, 3H). UPLC-MS: $t_R$=2.33 min (generic method); MS (ESI) m/z calcd for $C_{20}H_{19}ClN_3O_2$ (M+H)$^+$: 368.1, found: 368.2.

[Int-053] 3-(4-Chloro-3,5-dimethyl-pyrazol-1-yl)-N-(2-cyclopropyl-1,3-benzoxazol-5-yl)benzamide Following general procedure 1c, the title compound was obtained from Int-1.3, after purification by silica gel flash-column chromatography with cyclohexane/EtOAc (6:4) as the eluent, as a white solid in 88% yield: $^1$H NMR (400 MHz, DMSO-$d_6$) δ 10.44 (s, 1H), 8.11-8.06 (m, 2H), 8.03 (app-dt, J=7.6, 1.5 Hz, 1H), 7.78-7.73 (m, 1H), 7.70 (d, J=7.7 Hz, 1H), 7.68-7.57 (m, 2H), 2.34 (s, 3H), 2.31-2.24 (m, 1H), 2.23 (s, 3H), 1.26-1.05 (m, 4H); UPLC-MS: $t_R$=2.40 min (generic method); MS (ESI) m/z calcd for $C_{22}H_{20}ClN_4O_2$ (M+H)$^+$: 407.1, found: 407.2.

[054] 3-(4-Chloro-3,5-dimethyl-pyrazol-1-yl)-N-[2-(trifluoromethyl)-1,3-benzoxazol-5-yl]benzamide Following general procedure 1c, the title compound was obtained from Int-1.3, after purification by silica gel flash-column chromatography with cyclohexane/EtOAc (7:3) as the eluent, as a white solid in 90% yield: $^1$H NMR (400 MHz, DMSO-d$_6$) δ 10.67 (s, 1H), 8.47 (app-s, 1H), 8.12 (app-t, J=1.9 Hz, 1H), 8.05 (app-dt, J=7.7, 1.5 Hz, 1H), 7.97 (d, J=1.3 Hz, 2H), 7.80-7.75 (m, 1H), 7.71 (app-t, J=7.8 Hz, 1H), 2.35 (s, 3H), 2.24 (s, 3H); UPLC-MS: t$_R$=2.66 min (generic method); MS (ESI) m/z calcd for C$_{20}$H$_{15}$ClF$_3$N$_4$O$_2$ (M+H)$^+$: 435.1, found: 435.1.

[055] 3-(4-Chloro-3,5-dimethyl-pyrazol-1-yl)-N-(2-cyclopropyl-1,3-benzoxazol-5-yl)-N-methyl-benzamide Following general procedure 1d, the title compound was obtained from Int-053, after purification by silica gel flash-column chromatography with cyclohexane/EtOAc (1:1) as the eluent, as a white solid in 63% yield: $^1$H NMR (400 MHz, DMSO-d$_6$) δ 7.56 (d, J=2.1 Hz, 1H), 7.51 (d, J=8.6 Hz, 1H), 7.40-7.28 (m, 4H), 7.17 (dd, J=8.6, 2.1 Hz, 1H), 3.40 (s, 3H), 2.28-2.18 (m, 1H), 2.15 (s, 3H), 1.94 (s, 3H), 1.37-0.86 (m, 4H); UPLC-MS: t$_R$=2.39 min (generic method); MS (ESI) m/z calcd for C$_{23}$H$_{22}$ClN$_4$O$_2$ (M+H)$^+$: 421.1, found: 421.2.

[057] 3-(4-Chloro-3,5-dimethyl-3,4-dihydropyrazol-2-yl)-N-(1,3-dihydroisobenzofuran-5-yl)-N-methyl-benzamide Following general procedure 1d, the title compound was obtained from Int-051, after purification by silica gel flash-column chromatography with Cyclohexane/EtOAc (80:20) as the eluent, as a white solid in 56% yield: $^1$H NMR (400 MHz, DMSO-d$_6$): δ 7.46-7.38 (m, 2H), 7.39-7.33 (m, 2H), 7.29-7.22 (m, 1H), 7.19 (d, J=8.0 Hz, 1H), 7.07 (dd, J=8.3, 1.7 Hz, 1H), 4.91 (d, J=4.1 Hz, 4H), 3.39 (s, 3H), 2.17 (s, 3H), 1.99 (s, 3H). UPLC-MS: t$_R$=2.17 min (generic method); MS (ESI) m/z calcd for C$_{21}$H$_{21}$ClN$_3$O$_2$ (M+H)$^+$: 382.1, found: 382.2.

[058] 3-(4-Chloro-3,5-dimethyl-3,4-dihydropyrazol-2-yl)-N-(2,3-dihydrobenzofuran-5-yl)-N-methyl-benzamide Following general procedure 1d, the title compound was obtained from Int-052, after purification by silica gel flash-column chromatography with Cyclohexane/EtOAc (80:20) as the eluent, as a white solid in 90% yield: $^1$H NMR (400 MHz, DMSO-d$_6$): δ 7.54-7.22 (m, 4H), 7.25-6.95 (m, 1H), 6.89 (d, J=8.4 Hz, 1H), 6.61 (d, J=8.4 Hz, 1H), 4.49 (t, J=8.7 Hz, 2H), 3.33 (s, 3H), 3.08 (t, J=8.7 Hz, 2H), 2.18 (s, 3H), 2.05 (s, 3H). UPLC-MS: t$_R$=2.31 min (generic method); MS (ESI) m/z calcd for C$_{21}$H$_{21}$ClN$_3$O$_2$ (M+H)$^+$: 382.1, found: 382.2.

[Int-061] 3-(4-Chloro-3,5-dimethyl-pyrazol-1-yl)-N-(2-isopropyl-1,3-benzoxazol-5-yl)benzamide Following general procedure 1c, the title compound was obtained from Int-1.3, after purification by silica gel flash-column chromatography with cyclohexane/EtOAc (6:4) as the eluent, as a pale yellow solid in 80% yield: $^1$H NMR (400 MHz, DMSO-d$_6$) δ 10.47 (s, 1H), 8.15 (d, J=1.9 Hz, 1H), 8.10 (app-t, J=1.9 Hz, 1H), 8.04 (app-dt, J=7.6, 1.4 Hz, 1H), 7.79-7.73 (m, 1H), 7.73-7.62 (m, 3H), 3.25 (septet, J=6.9 Hz, 1H), 2.34 (s, 3H), 2.24 (s, 3H), 1.38 (d, J=6.9 Hz, 6H); UPLC-MS: t$_R$=2.50 min (generic method); MS (ESI) m/z calcd for C$_{22}$H$_{22}$ClN$_4$O$_2$ (M+H)$^+$: 409.1, found: 409.2.

[062] 3-(4-Chloro-3,5-dimethyl-pyrazol-1-yl)-N-(2-isopropyl-1,3-benzoxazol-5-yl)-N-methyl-benzamide Following general procedure 1d, the title compound was obtained from Int-061, after purification by silica gel flash-column chromatography with cyclohexane/EtOAc (1:1) as the eluent, as a white solid in 81% yield: $^1$H NMR (400 MHz, DMSO-d$_6$) δ 7.65 (d, J=2.1 Hz, 1H), 7.57 (d, J=8.6 Hz, 1H), 7.41-7.30 (m, 4H), 7.22 (dd, J=8.6, 2.1 Hz, 1H), 3.41 (s, 3H), 3.21 (septet, J=6.9 Hz, 1H), 2.14 (s, 3H), 1.92 (s, 3H), 1.33 (d, J=6.9 Hz, 6H); UPLC-MS: t$_R$=1.41 min (apolar method); MS (ESI) m/z calcd for C$_{23}$H$_{24}$ClN$_4$O$_2$ (M+H)$^+$: 423.2, found: 423.2.

[Int-063] 3-(4-Chloro-3,5-dimethyl-pyrazol-1-yl)-N-(2-methoxy-1,3-benzoxazol-5-yl)benzamide Following general procedure 1c, the title compound was obtained from Int-1.3, after purification by silica gel flash-column chromatography with cyclohexane/EtOAc (1:1) as the eluent, as a white solid in 51% yield: $^1$H NMR (400 MHz, DMSO-d$_6$) δ 10.41 (s, 1H), 8.08 (app-t, J=1.9 Hz, 1H), 8.02 (app-dt, J=7.5, 1.4 Hz, 1H), 7.98 (d, J=2.0 Hz, 1H), 7.75 (app-dt, J=8.1, 1.5 Hz, 1H), 7.69 (app-t, J=7.8 Hz, 1H), 7.57 (dd, J=8.8, 2.1 Hz, 1H), 7.51 (d, J=8.7 Hz, 1H), 4.18 (s, 3H), 2.34 (s, 3H), 2.23 (s, 3H); UPLC-MS: t$_R$=2.29 min (generic method); MS (ESI) m/z calcd for C$_{20}$H$_{18}$ClN$_4$O$_3$ (M+H)$^+$: 397.1, found: 397.1.

[064] 3-(4-Chloro-3,5-dimethyl-pyrazol-1-yl)-N-(2-methoxy-1,3-benzoxazol-5-yl)-N-methyl-benzamide Following general procedure 1d, the title compound was obtained from Int-063, after purification by silica gel flash-column chromatography with cyclohexane/EtOAc (4:6) as the eluent, as a white solid in 12% yield: $^1$H NMR (400 MHz, DMSO-d$_6$) δ 7.46 (d, J=2.2 Hz, 1H), 7.44 (d, J=8.6 Hz, 1H), 7.41-7.28 (m, 4H), 7.10 (dd, J=8.6, 2.2 Hz, 1H), 4.14 (s, 3H), 3.40 (s, 3H), 2.15 (s, 3H), 1.99 (s, 3H); UPLC-MS: t$_R$=2.25 min (generic method); MS (ESI) m/z calcd for C$_{21}$H$_{20}$ClN$_4$O$_3$ (M+H)$^+$: 411.1, found: 411.2.

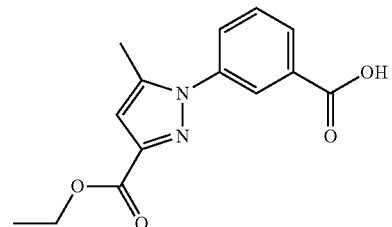

MIX of REGIOISOMERS

[Int-1.29] Mix of 3-(3-ethoxycarbonyl-5-methyl-pyrazol-1-yl)benzoic acid and 3-(5-ethoxycarbonyl-3-methyl-pyrazol-1-yl)benzoic acid Following general procedure 1a, a mix of regioisomers of title compounds was obtained from ethyl 2,4-dioxopentanoate, as a pale yellow solid in 54% total yield. $^1$H NMR Analysis showed a 1:1 ratio of regioisomers; UPLC-MS: $t_{R1}$=1.37 min, $t_{R2}$=1.48 min (Generic method); MS (ESI) m/z calcd for $C_{14}H_{15}N_2O_4$ (M+H)$^+$: 275.1, found: 275.2.

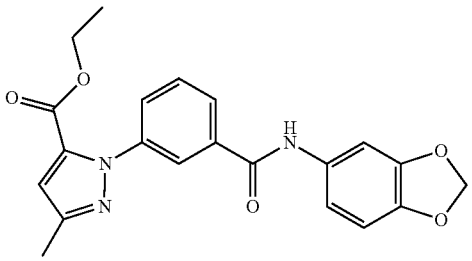 [SMILES: CCOC(=O)c1cc(C)nn1-c1cccc(C(=O)Nc2ccc3c(c2)OCO3)c1]

[Int-1.30] Ethyl 2-[3-(1,3-benzodioxol-5-ylcarbamoyl) phenyl]-5-methyl-pyrazole-3-carboxylate Following general procedure 1c, the title compound was obtained from Int-1.29, after purification from the other regioisomer by silica gel flash-column chromatography with Cyclohexane/EtOAc (70/30) as the eluent, as a white solid in 26% yield: $^1$H NMR (400 MHz, DMSO-$d_6$) δ 10.24 (s, 1H), 8.06-8.00 (m, 2H), 7.69-7.59 (m, 2H), 7.44 (d, J=2.1 Hz, 1H), 7.21 (dd, J=8.4, 2.1 Hz, 1H), 6.96 (d, J=0.6 Hz, 1H), 6.91 (d, J=8.4 Hz, 1H), 6.02 (s, 2H), 4.19 (q, J=7.1 Hz, 2H), 2.31 (s, 3H), 1.17 (t, J=7.1 Hz, 3H). 2D-NOESY: No dipolar coupling between 2.31 and aromatics. UPLC-MS: $t_R$=2.22 min (Generic method); MS (ESI) m/z calcd for $C_{21}H_{20}N_3O_5$ (M+H)$^+$: 394.1, found: 394.1.

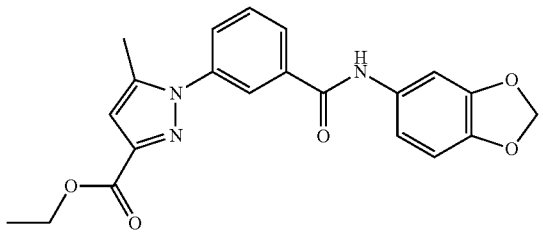 [SMILES: CCOC(=O)c1cc(C)n(-c2cccc(C(=O)Nc3ccc4c(c3)OCO4)c2)n1]

[Int-1.31] Ethyl 1-[3-(1,3-benzodioxol-5-ylcarbamoyl) phenyl]-5-methyl-pyrazole-3-carboxylate Following general procedure 1c, the title compound was obtained from Int-1.30, after purification from the other regioisomer by silica gel flash-column chromatography with Cyclohexane/EtOAc (70/30) as the eluent, as a white solid in 28% yield: $^1$H NMR (400 MHz, DMSO-$d_6$) δ 10.30 (s, 1H), 8.11 (app-t, J=1.9 Hz, 1H), 8.08 (app-dt, J=7.7, 1.4 Hz, 1H), 7.81 (ddd, J=8.0, 2.2, 1.2 Hz, 1H), 7.73 (app-t, J=7.8 Hz, 1H), 7.45 (d, J=2.1 Hz, 1H), 7.21 (dd, J=8.4, 2.1 Hz, 1H), 6.92 (d, J=8.4 Hz, 1H), 6.82 (d, J=0.9 Hz, 1H), 6.03 (s, 2H), 4.31 (q, J=7.1 Hz, 2H), 2.38 (s, 3H), 1.31 (t, J=7.1 Hz, 3H). 2D-NOESY: strong dipolar coupling between 2.38 ppm and 7.81 ppm, and strong dipolar coupling between 2.38 ppm and 8.11 ppm. UPLC-MS: $t_R$=2.16 min (Generic method); MS (ESI) m/z calcd for $C_{21}H_{20}N_3O_5$ (M+H)$^+$: 394.1, found: 394.1.

[065] 2-[3-[1,3-benzodioxol-5-yl(methyl)carbamoyl]phenyl]-5-methyl-pyrazole-3-carboxylic acid Following general procedure 1d, the title compound was obtained from Int-1.30 as ester hydrolysis product. After purification by silica gel flash-column chromatography with DCM/MeOH (95/5) as the eluent, product was obtained as a white solid in 45% yield: $^1$H NMR (400 MHz, DMSO-$d_6$) δ 13.19 (s, 1H), 7.39 (s, 1H), 7.36-7.18 (m, 3H), 6.93 (d, J=2.1 Hz, 1H), 6.75 (d, J=8.2 Hz, 1H), 6.62 (app-d, J=7.6 Hz, 1H), 5.99 (s, 2H), 3.31 (s, 3H), 2.24 (s, 3H). UPLC-MS: $t_R$=1.31 min (Generic method); MS (ESI) m/z calcd for $C_{20}H_{46}N_3O_5$ (M-H)$^-$: 378.1, found: 378.2.

[066] 1-[3-[1,3-Benzodioxol-5-yl(methyl)carbamoyl]phenyl]-5-methyl-pyrazole-3-carboxylic acid Following general procedure 1d, the title compound was obtained from Int-1.31 as ester hydrolysis product. After purification by silica gel flash-column chromatography with DCM/MeOH (95/5) as the eluent, product was obtained as a white solid in 45% yield: $^1$H NMR (400 MHz, DMSO-$d_6$) δ 12.77 (s, 1H), 7.57-7.36 (m, 4H), 6.98 (d, J=2.1 Hz, 1H), 6.77 (d, J=8.2 Hz, 1H), 6.69-6.63 (m, 2H), 6.00 (s, 2H), 3.32 (s, 3H), 2.12 (s, 3H). UPLC-MS: $t_R$=1.43 min (Generic method); MS (ESI) m/z calcd for $C_{20}H_{16}N_3O_5$ (M-H)$^-$: 378.1, found: 378.2.

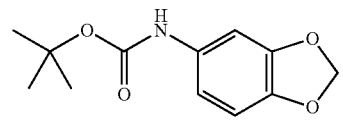 [SMILES: CC(C)(C)OC(=O)Nc1ccc2c(c1)OCO2]

[Int-1.32] tert-Butyl N-(1,3-benzodioxol-5-yl)carbamate

To a solution of 1,3-benzodioxol-5-amine (10.0 g, 73.0 mmol) in DCM (100 mL) were added tert-butoxycarbonyl tert-butyl carbonate (19.0 g, 87.6 mmol) and DIPEA (19 mL, 109.5 mmol), and the mixture stirred at room temperature for 16 h. The solution was washed with sat. aq. $NH_4C_{1.}$ (100 mL) and brine (100 mL), dried over anhydrous $Na_2SO_4$, filtered and the solvent evaporated under reduced pressure. The resultant residue was purified by silica gel flash-column chromatography, with cyclohexane/EtOAc (9:1) as the eluent. The product was further purified by trituration, with cyclohexane as the solvent, to yield the title compound as a white solid (13.0 g, 75%): $^1$H NMR (400 MHz, DMSO-$d_6$) δ 9.16 (s, 1H), 7.10 (d, J=2.1 Hz, 1H), 6.85 (dd, J=8.4, 2.1 Hz, 1H), 6.78 (d, J=8.4 Hz, 1H), 5.94 (s, 2H), 1.46 (s, 9H); UPLC-MS: $t_R$=2.41 min (generic method); MS (ESI) m/z calcd for $C_{12}H_{14}NO_4$ (M-H)$^-$: 236.1, found: 236.2.

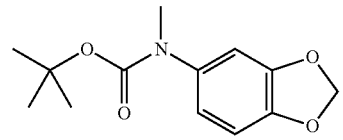 [SMILES: CN(C(=O)OC(C)(C)C)c1ccc2c(c1)OCO2]

[Int-1.33] tert-Butyl N-(1,3-benzodioxol-5-yl)-N-methyl-carbamate

Following general procedure 1d, the title compound was obtained from Int-1.32, after purification by silica gel flash-column chromatography with cyclohexane/EtOAc (9:1) as the eluent, as a yellow oil in 94% yield: $^1$H NMR (400 MHz, DMSO-$d_6$) δ 6.86 (d, J=2.1 Hz, 1H), 6.85 (d, J=8.3 Hz, 1H), 6.69 (dd, J=8.3, 2.1 Hz, 1H), 6.01 (s, 2H), 3.10 (s, 3H), 1.37 (s, 9H); UPLC-MS: $t_R$=2.04 min (generic method); MS (ESI) m/z calcd for $C_{13}H_{18}NO_4$ (M+H)$^+$: 252.1, found: 252.2.

[Int-1.34] 1,3-Benzodioxol-5-yl(methyl)ammonium chloride

To a solution of AcCl (22 mL, 310.8 mmol) in MeOH (100 mL) was added at 0° C. a solution of Int-1.33 in MeOH (50 mL) and the mixture stirred at room temperature for 3 h. The solvent was evaporated and the resultant residue purified by trituration, with cold MeOH as the solvent, to yield the title compound as a pale pink solid (9.5 g, 98%): $^1$H NMR (400 MHz, DMSO-d$_6$) δ 10.81 (br s, 2H), 7.09 (d, J=2.2 Hz, 1H), 7.00 (d, J=8.3 Hz, 1H), 6.94 (dd, J=8.3, 2.2 Hz, 1H), 6.08 (s, 2H), 2.84 (s, 3H); UPLC-MS: $t_R$=1.44 min (generic method); MS (ESI) m/z calcd for $C_8H_{10}NO_2$ (M+H)$^+$: 152.1, found: 152.1.

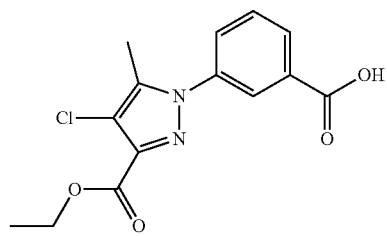

SINGLE REGIOISOMER

[Int-1.35] 3-(4-Chloro-3-ethoxycarbonyl-5-methyl-pyrazol-1-yl)benzoic acid

Following general procedure 1a, the title compounds was obtained from ethyl 3-chloro-2,4-dioxopentanoate, as single regioisomer, as a pale yellow solid in 78% yield: $^1$H NMR (400 MHz, DMSO-d$_6$) δ 13.35 (s, 1H), 8.09 (app-t, J=1.4 Hz, 1H), 8.08-8.05 (m, 1H), 7.88 (ddd, J=8.0, 2.3, 1.1 Hz, 1H), 7.72 (t, J=7.9 Hz, 1H), 4.33 (q, J=7.1 Hz, 2H), 2.33 (s, 3H), 1.31 (t, J=7.1 Hz, 3H). 2D-NOESY: strong dipolar coupling between signal at 2.33 ppm and signal at 7.88 ppm, and strong dipolar coupling between signal at 2.33 ppm and multiplet 8.08-8.05 ppm. UPLC-MS: =1.51 min (Generic method); MS (ESI) m/z calcd for $C_{14}H_{14}ClN_2O_4$ (M+H)$^+$: 309.0, found: 309.1.

[067] Ethyl 1-[3-[1,3-benzodioxol-5-yl(methyl)carbamoyl]phenyl]-4-chloro-5-methyl-pyrazole-3-carboxylate Following general procedure 1c, the title compound was obtained from Int-1.35. After purification by silica gel flash-column chromatography with Cyclohexane/EtOAc (60/40) as the eluent, product was obtained as a white solid in 69% yield: $^1$H NMR (400 MHz, DMSO-d$_6$) δ 7.54-7.37 (m, 4H), 6.96 (d, J=2.1 Hz, 1H), 6.77 (d, J=8.3 Hz, 1H), 6.65 (dd, J=8.3, 2.1 Hz, 1H), 5.99 (s, 2H), 4.31 (q, J=7.1 Hz, 2H), 3.32 (s, 3H), 2.09 (s, 3H). 2D-NOESY: strong dipolar coupling between peak at 2.09 ppm and multiplet at 7.54-7.37 ppm. UPLC-MS: $t_R$=2.26 min (Generic method); MS (ESI) m/z calcd for $C_{22}H_{21}ClN_3O_5$ (M+H)$^+$: 442.1, found: 442.2.

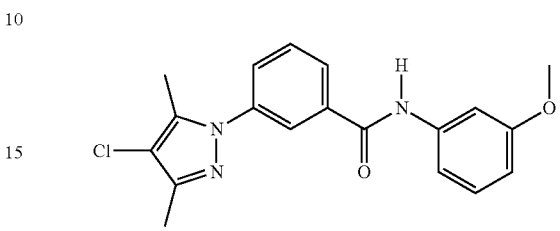

[Int-1.36] 3-(4-Chloro-3,5-dimethyl-pyrazol-1-yl)-N-(3-methoxyphenyl)benzamide

Following general procedure 1c, the title compound was obtained from Int-1.3, as crude product, as white solid in 65% yield: UPLC-MS: $t_R$=2.43 min (Generic method); MS (ESI) m/z calcd for $C_{19}H_{19}ClN_3O_2$ (M+H)$^+$: 356.1, found: 356.2.

[068] 3-(4-Chloro-3,5-dimethyl-pyrazol-1-yl)-N-(3-methoxy phenyl)-N-methyl-benzamide Following 1c, the title compound was obtained from Int-1.36, after purification by silica gel flash-column chromatography with DCM/EtOAc (80:20) as the eluent, as a white solid in 78% yield: $^1$H NMR (400 MHz, DMSO-d$_6$) δ 7.46-7.38 (m, 3H), 7.35 (app-dt, J=6.8, 1.8 Hz, 1H), 7.17 (t, J=8.1 Hz, 1H), 6.86 (t, J=2.3 Hz, 1H), 6.76 (d, J=2.2 Hz, 1H), 6.74 (d, J=2.7 Hz, 1H), 3.66 (s, 3H), 3.39 (s, 3H), 2.17 (s, 3H), 2.01 (s, 3H). UPLC-MS: $t_R$=2.39 min (generic method); MS (ESI) m/z calcd for $C_{20}H_{21}ClN_3O_2$ (M+H)$^+$: 370.1, found: 370.2.

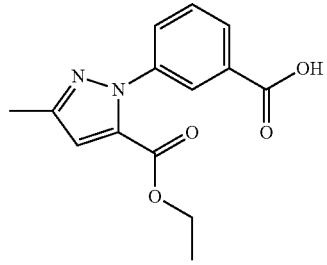

SINGLE REGIOISOMER

[Int-1.37] 3-(5-ethoxycarbonyl-3-methyl-pyrazol-1-yl) benzoic acid

Following general procedure 1a, and refluxing for 5 h, the title compounds was obtained from ethyl-2-methoxyimino-4-oxo-pentanoate (prepared following the procedure reported in Journal of Medicinal Chemistry 2003, 46, 5298-5315), as single regioisomer as yellow solid in 54% yield: $^1$H NMR (400 MHz, DMSO-d$_6$) δ 13.20 (s, 1H), 8.00

(app-dt, J=7.7, 1.4 Hz, 1H), 7.92 (app-t, J=1.9 Hz, 1H), 7.70 (ddd, J=8.0, 2.3, 1.2 Hz, 1H), 7.60 (app-t, J=7.8 Hz, 1H), 6.92 (s, 1H), 4.17 (q, J=7.1 Hz, 2H), 1.15 (t, J=7.1 Hz, 3H). UPLC-MS: $t_R$=1.48 min (Generic method); MS (ESI) m/z calcd for $C_{14}H_{15}N_2O_4$ (M+H)$^+$: 275.1, found: 275.1.

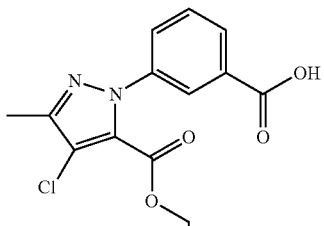

SINGLE REGIOISOMER

[Int-1.38] 3-(4-chloro-5-ethoxycarbonyl-3-methyl-pyrazol-1-yl)benzoic acid

Following general procedure 1b, the title compound was obtained from Int-1.37, after precipitation with water, as a yellow solid in 89% yield over two steps: UPLC-MS: $t_R$=1.69 min (Generic method); MS (ESI) m/z calcd for $C_{14}H_{14}ClN_2O_4$ (M+H)$^+$: 309.0, found: 309.0.

[075] Ethyl 2-[3-[[1,3-benzodioxol-5-yl(methyl)carbamoyl]phenyl]-4-chloro-5-methyl-pyrazole-3-carboxylate Following general procedure 1d, the title compound was obtained from [Int-1.38], after purification by silica gel flash-column chromatography with Cyclohexane/EtOAc (70/30) as the eluent, as a pale yellow solid in 24% yield: $^1$H NMR (400 MHz, DMSO-d$_6$) δ 7.38 (s, 1H), 7.36-7.26 (m, 3H), 6.93 (d, J=2.1 Hz, 1H), 6.76 (d, J=8.2 Hz, 1H), 6.64 (dd, J=8.2, 2.1 Hz, 1H), 4.15 (q, J=7.1 Hz, 2H), 3.30 (s, 3H), 2.25 (s, 3H), 1.04 (t, J=7.1 Hz, 3H). 2D-NOESY: No dipolar coupling between 2.25 and aromatics. UPLC-MS: $t_R$=2.48 min (Generic method); MS (ESI) m/z calcd for $C_{22}H_{21}ClN_3O_5$ (M+H)$^+$: 442.1, found: 442.2.

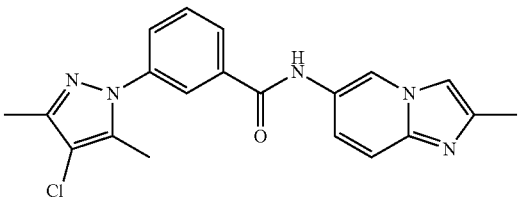

[Int-1.39] 3-(4-Chloro-3,5-dimethyl-pyrazol-1-yl)-N-(2-ethyl-1,3-benzoxazol-6-yl)benzamide Following general procedure 1c, the title compound was obtained from Int-1.3, after purification by silica gel flash-column chromatography with cyclohexane/EtOAc (6:4) as the eluent, as a pale yellow solid in 63% yield: $^1$H NMR (400 MHz, DMSO-d$_6$) δ 10.54 (s, 1H), 8.23 (d, J=1.5 Hz, 1H), 8.10 (app-t, J=1.9 Hz, 1H), 8.03 (app-dt, J=7.6, 1.5 Hz, 1H), 7.76 (app-dt, J=8.1, 1.5 Hz, 1H), 7.73-7.59 (m, 3H), 2.95 (q, J=7.6 Hz, 2H), 2.34 (s, 3H), 2.23 (s, 3H), 1.34 (t, J=7.6 Hz, 3H); UPLC-MS: $t_R$=2.41 min (generic method); MS (ESI) m/z calcd for $C_{21}H_{20}ClN_4O_2$ (M+H)$^+$: 395.1, found: 395.2.

[076] 3-(4-Chloro-3,5-dimethyl-pyrazol-1-yl)-N-(2-ethyl-1,3-benzoxazol-6-yl)-N-methyl-benzamide Following general procedure 1d, the title compound was obtained from Int-1.39, after purification by silica gel flash-column chromatography with cyclohexane/EtOAc (1:1) as the eluent, as a white solid in 92% yield: $^1$H NMR (400 MHz, DMSO-d$_6$) δ 7.68 (d, J=1.9 Hz, 1H), 7.54 (d, J=8.4 Hz, 1H), 7.41-7.30 (m, 4H), 7.20 (dd, J=8.4, 1.9 Hz, 1H), 3.42 (s, 3H), 2.91 (q, J=7.5 Hz, 2H), 2.14 (s, 3H), 1.94 (s, 3H), 1.30 (t, J=7.5 Hz, 3H); UPLC-MS: $t_R$=2.39 min (generic method); MS (ESI) m/z calcd for $C_{22}H_{22}ClN_4O_2$ (M+H)$^+$: 409.1, found: 409.2.

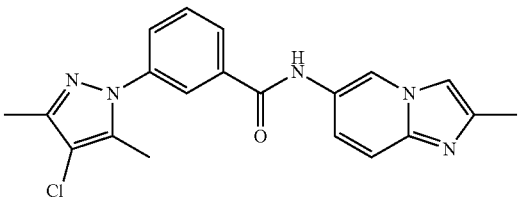

[Int-1.40] 3-(4-Chloro-3,5-dimethyl-pyrazol-1-yl)-N-(2-methylimidazo[1,2-a]pyridin-6-yl)benzamide Following general procedure 1c, the title compound was obtained from Int-1.3, after purification by silica gel flash-column chromatography with DCM/MeOH (95:5) as the eluent, as a pale yellow solid in 60% yield: $^1$H NMR (400 MHz, DMSO-d$_6$) δ 10.41 (s, 1H), 9.21 (app-s, 1H), 8.10 (app-t, J=1.9 Hz, 1H), 8.03 (app-dt, J=7.6, 1.5 Hz, 1H), 7.80-7.74 (m, 2H), 7.70 (app-t, J=7.8 Hz, 1H), 7.45 (d, J=9.5 Hz, 1H), 7.37 (dd, J=9.6, 2.0 Hz, 1H), 2.34 (s, 3H), 2.32 (s, 3H), 2.24 (s, 3H); UPLC-MS: $t_R$=2.02 min (generic method); MS (ESI) m/z calcd for $C_{20}H_{19}ClN_5O$ (M+H)$^+$: 380.1, found: 380.2.

[077] 3-(4-Chloro-3,5-dimethyl-pyrazol-1-yl)-N-methyl-N-(2-methylimidazo[1,2-a]pyridin-6-yl)benzamide Following general procedure 1d, the title compound was obtained from Int-1.40, after purification by silica gel flash-column chromatography with DCM/MeOH (95:5) as the eluent, as a white solid in 67% yield: $^1$H NMR (400 MHz, DMSO-d$_6$) δ 8.57 (app-s, 1H), 7.63 (app-s, 1H), 7.49-7.37 (m, 5H), 7.29 (d, J=9.6 Hz, 1H), 3.35 (s, 3H), 2.31 (s, 3H), 2.15 (s, 3H), 1.99 (br s, 3H); UPLC-MS: $t_R$=1.93 min (generic method); MS (ESI) m/z calcd for $C_{21}H_{21}ClN_5O$ (M+H)$^+$: 394.1, found: 394.2.

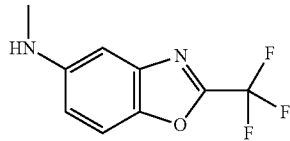

[Int-1.41] N-Methyl-2-(trifluoromethyl)-1,3-benzoxazol-5-amine

To a solution of 2-(trifluoromethyl)-1,3-benzoxazol-5-amine (50 mg, 0.25 mmol) in DCE (5 mL) were added paraformaldehyde (38 mg, 1.25 mmol), NaBH(OAc)$_3$ (159 mg, 0.75 mmol) and TsOH (5 mg, cat.), and the mixture stirred at room temperature for 2 days. The suspension was partitioned between DCM (50 mL) and H$_2$O (50 mL). The organic phase was separated, washed with brine (50 mL), dried over anhydrous Na$_2$SO$_4$, filtered and the solvent evaporated under reduced pressure. The resultant residue was purified by silica gel flash-column chromatography, with cyclohexane/EtOAc (9:1) as the eluent, to yield the title compound as a white solid (30 mg, 57%): UPLC-MS: $t_R$=0.94 min (apolar method); MS (ESI) m/z calcd for C$_9$H$_8$F$_3$N$_2$O (M+H)$^+$: 217.1, found: 217.0.

[078] 3-(4-Chloro-3,5-dimethyl-pyrazol-1-yl)-N-methyl-N-[2-(trifluoromethyl)-1,3-benzoxazol-5-yl]benzamide Following general procedure 1c, the title compound was obtained from Int-1.3, and Int-1.41, after purification by preparative HPLC, as a white solid in 5% yield: $^1$H NMR (400 MHz, DMSO-d$_6$) δ 8.01 (d, J=2.1 Hz, 1H), 7.89 (d, J=8.8 Hz, 1H), 7.57 (dd, J=8.8, 2.1 Hz, 1H), 7.45-7.29 (m, 4H), 3.45 (s, 3H), 2.14 (s, 3H), 2.00 (s, 3H); UPLC-MS: $t_R$=1.71 min (apolar method); MS (ESI) m/z calcd for C$_{21}$H$_{17}$ClF$_3$N$_4$O$_2$ (M+H)$^+$: 449.1, found: 449.1.

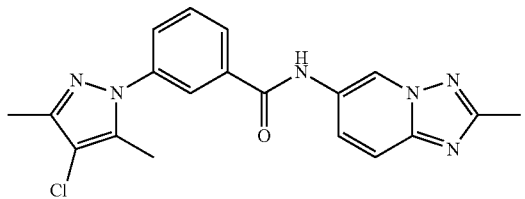

[Int-1.42] 3-(4-Chloro-3,5-dimethyl-pyrazol-1-yl)-N-(2-methyl-[1,2,4]triazolo[1,5-a]pyridin-6-yl)benzamide Following general procedure 1c, the title compound was obtained from Int-1.3, after purification by silica gel flash-column chromatography with DCM/MeOH (95:5) as the eluent, as a white solid in 53% yield: $^1$H NMR (400 MHz, DMSO-d$_6$) δ 10.66 (s, 1H), 9.46 (app-s, 1H), 8.12 (app-t, J=1.9 Hz, 1H), 8.05 (app-dt, J=7.6, 1.4 Hz, 1H), 7.84 (dd, J=9.5, 2.0 Hz, 1H), 7.79 (app-dt, J=8.2, 1.4 Hz, 1H), 7.76-7.68 (m, 2H), 2.46 (s, 3H), 2.34 (s, 3H), 2.24 (s, 3H); UPLC-MS: $t_R$=2.01 min (generic method); MS (ESI) m/z calcd for C$_{19}$H$_{18}$ClN$_6$O (M+H)$^+$: 381.1, found: 381.2.

[079] 3-(4-Chloro-3,5-dimethyl-pyrazol-1-yl)-N-methyl-N-(2-methyl-[1,2,4]triazolo[1,5-a]pyridin-6-yl)benzamide Following general procedure 1d, the title compound was obtained from Int-1.42, after purification by preparative HPLC, as a white solid in 35% yield: $^1$H NMR (400 MHz, DMSO-d$_6$) δ 8.98 (app-s, 1H), 7.63 (app-s, 2H), 7.47 (app-s, 1H), 7.41 (app-s, 3H), 3.41 (s, 3H), 2.42 (s, 3H), 2.15 (s, 3H), 1.99 (br s, 3H); UPLC-MS: $t_R$=1.93 min (generic method); MS (ESI) m/z calcd for C$_{20}$H$_{20}$ClN$_6$O (M+H)$^+$: 395.1, found: 395.2.

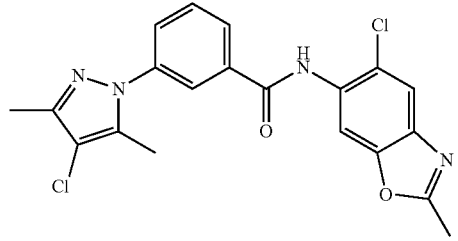

[Int-1.43] 3-(4-Chloro-3,5-dimethyl-pyrazol-1-yl)-N-(5-chloro-2-methyl-1,3-benzoxazol-6-yl)benzamide Following general procedure 1c, the title compound was obtained from Int-1.3, as crude product, as yellow solid at 35% yield: UPLC-MS: $t_R$=2.49 min (Generic method); MS (ESI) m/z calcd for C$_{20}$H$_{17}$C$_{12}$N$_4$O$_2$ (M+H)$^+$: 415.1, found: 415.1.

[080] 3-(4-Chloro-3,5-dimethyl-pyrazol-1-yl)-N-(5-chloro-2-methyl-1,3-benzoxazol-6-yl)-N-methyl-benzamide Following general procedure 1d, the title compound was obtained from [Int-1.43], after purification by preparative LC/MS, as a white solid in 31% yield. $^1$H NMR analysis showed rotamers mixture. Major rotamer: $^1$H NMR (600 MHz, DMSO-d$_6$) δ 8.09 (s, 1H), 7.83 (s, 1H), 7.42 (dd, J=1.5, 1.0 Hz, 1H), 7.38 (app-dt, J=7.1, 2.2 Hz, 1H), 7.36-7.30 (m, 2H), 3.31 (s, 3H), 2.59 (s, 3H), 2.14 (s, 3H), 2.03 (s, 3H). UPLC-MS: $t_R$=2.36 min (Generic method); MS (ESI) m/z calcd for C$_{21}$H$_{19}$C$_{12}$N$_4$O$_2$ (M+H)$^+$: 429.1, found: 429.1.

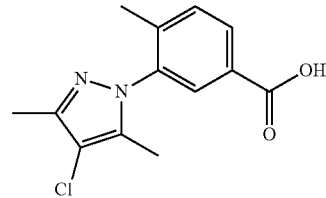 [SMILES: Cc1ccc(C(=O)O)cc1-n1nc(C)c(Cl)c1C]

[Int-1.44] 3-(4-Chloro-3,5-dimethyl-pyrazol-1-yl)-4-methyl-benzoic acid

Following general procedure 1a, the title compound was obtained from 3-chloropentane-2,4-dione and 3-hydrazino-4-methyl-benzoic acid, as crude product, as yellow solid at 35% yield: UPLC-MS: $t_R$=1.65 min (Generic method); MS (ESI) m/z calcd for C$_{13}$H$_{14}$ClN$_2$O$_2$ (M+H)$^+$: 265.1, found: 265.1.

[082] N-(1,3-Benzodioxol-5-yl)-3-(4-chloro-3,5-dimethyl-pyrazol-1-yl)-N,4-dimethyl-benzamide Following general procedure 1c, the title compound was obtained from Int-1.44, after purification by silica gel flash-column chromatography with DCM/EtOAc (70:30) as the eluent, as a white solid in 42% yield: $^1$H NMR (400 MHz, DMSO-$d_6$) δ 7.38 (dd, J=7.8, 1.7 Hz, 1H), 7.31 (d, J=7.9 Hz, 1H), 7.08 (s, 1H), 6.92 (d, J=2.1 Hz, 1H), 6.78 (d, J=8.2 Hz, 1H), 6.63 (dd, J=8.2, 2.1 Hz, 1H), 5.98 (s, 2H), 3.29 (s, 3H), 2.15 (s, 3H), 1.91 (s, 3H), 1.76 (s, 3H). UPLC-MS: $t_R$=2.36 min (Generic method); MS (ESI) m/z calcd for $C_{21}H_{21}ClN_3O_3$ (M+H)$^+$: 398.1, found: 398.1.

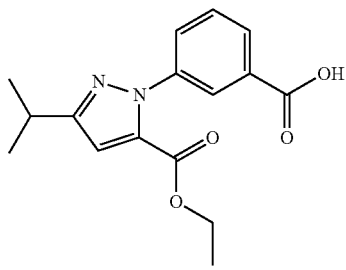

REGIOISOMERS MIX

[Int-1.45] Mix of 3-(5-Ethoxycarbonyl-3-isopropyl-pyrazol-1-yl)benzoic acid and 3-(3-Ethoxycarbonyl-5-isopropyl-pyrazol-1-yl)benzoic acid Following general procedure 1a, the title compound was obtained after precipitation with water, as a yellow solid in 80% yield as a mixture of regioisomers: UPLC-MS: $t_{R1}$=1.62 min $t_{R2}$=1.79 min (Generic method); MS (ESI) m/z calcd for $C_{16}H_{19}N_2O_4$ (M+H)$^+$: 303.1, found: 303.1.

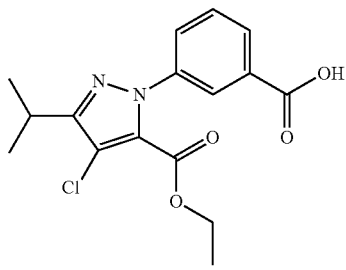

REGIOISOMERS MIX

[Int-1.46] Mix of 3-(4-chloro-5-ethoxycarbonyl-3-isopropyl-pyrazol-1-yl)benzoic acid and 3-(4-chloro-3-ethoxycarbonyl-5-isopropyl-pyrazol-1-yl)benzoic acid Following general procedure 1b, the title compound was obtained from Int-1.45, after precipitation with water, as a yellow solid in 62% yield: UPLC-MS: $t_{R1}$=1.75 min $t_{R2}$=1.96 min (Generic method); MS (ESI) m/z calcd for $C_{17}H_{22}ClN_2O_4$ (M+H)$^+$: 353.1, found: 353.0.

[086] Ethyl 1-[3-[1,3-benzodioxol-5-yl(methyl)car-bamoyl]phenyl]-4-chloro-5-isopropyl-pyrazole-3-carboxylate Following general procedure 1c, the title compound was obtained from Int-1.46, after purification from the other regioisomer by silica gel flash-column chromatography with Cyclohexane/EtOAc (70/30) as the eluent, as a pale yellow solid in 58% yield: $^1$H NMR (400 MHz, DMSO-$d_6$) δ 7.57-7.45 (m, 2H), 7.41 (app-dt, J=7.5, 1.9 Hz, 1H), 7.31 (bs, 1H), 6.93 (d, J=2.1 Hz, 1H), 6.76 (d, J=8.3 Hz, 1H), 6.64 (dd, J=8.3, 2.1 Hz, 1H), 5.98 (s, 2H), 4.29 (q, J=7.1 Hz, 2H), 3.32 (s, 3H), 2.71-2.57 (m, 1H), 1.28 (t, J=7.1 Hz, 3H), 1.18 (s, 3H), 1.17 (s, 3H). 2D-NOESY: strong dipolar coupling between multiplet at 2.71-2.57 ppm and signals at 7.31 ppm and 7.41 ppm. UPLC-MS: $t_R$=2.47 min (Generic method); MS (ESI) m/z calcd for $C_{24}H_{25}ClN_3O_5$ (M+H)$^+$: 470.1, found: 470.1.

[087] Ethyl 2-[3-[1,3-benzodioxol-5-yl(methyl)car-bamoyl]phenyl]-4-chloro-5-isopropyl-pyrazole-3-carboxylate Following general procedure 1c, the title compound was obtained from Int-1.46, after purification from the other regioisomer by silica gel flash-column chromatography with Cyclohexane/EtOAc (70/30) as the eluent, as a pale yellow solid in 58% yield: $^1$H NMR (400 MHz, DMSO-$d_6$) δ 7.38 (bs, 1H), 7.36-7.29 (m, 3H), 6.93 (d, J=2.1 Hz, 1H), 6.76 (d, J=8.2 Hz, 1H), 6.66 (dd, J=8.2, 2.1 Hz, 1H), 5.98 (s, 2H), 4.15 (q, J=7.1 Hz, 2H), 3.31 (s, 3H), 3.07 (h, J=6.9 Hz, 1H), 1.27 (s, 3H), 1.25 (s, 3H), 1.03 (t, J=7.1 Hz, 3H). 2D-NOESY: no dipolar coupling between signal at multiplet at 3.07 ppm and aromatics. UPLC-MS: $t_R$=2.71 min (Generic method); MS (ESI) m/z calcd for $C_{24}H_{25}ClN_3O_5$ (M+H)$^+$: 470.1, found: 470.2.

[090] N-(1,3-Benzodioxol-5-yl)-3-[4-chloro-5-methyl-3-(trifluoromethyl)pyrazol-1-yl]-N-methyl-benzamide Following general procedure 1c, the title compound was obtained from Int-1.2 and Int-1.34, after purification by silica gel flash-column chromatography with cyclohexane/EtOAc (7:3) as the eluent, as a white solid in 71% yield: $^1$H NMR (400 MHz, DMSO-$d_6$) δ 7.58-7.32 (m, 4H), 6.97 (d, J=2.1 Hz, 1H), 6.77 (d, J=8.2 Hz, 1H), 6.65 (dd, J=8.2, 2.1 Hz, 1H), 5.99 (s, 2H), 3.32 (s, 3H), 2.11 (s, 3H); UPLC-MS: $t_R$=1.44 min (apolar method); MS (ESI) m/z calcd for $C_{20}H_{16}ClF_3N_3O_3$ (M+H)$^+$: 438.1, found: 438.2.

[091] N-(1,3-Benzodioxol-5-yl)-N-methyl-3-[5-methyl-3-(trifluoromethyl)pyrazol-1-yl]benzamide Following general procedure 1c, the title compound was obtained from Int-1.1 and Int-1.34, after purification by silica gel flash-column chromatography with cyclohexane/EtOAc (6:4) as the eluent, as an off-white solid in 70% yield: $^1$H NMR (400 MHz, DMSO-$d_6$) δ 7.58-7.31 (m, 4H), 6.98 (d, J=2.1 Hz, 1H), 6.76 (d, J=8.4 Hz, 1H), 6.73 (s, 1H), 6.65 (dd, J=8.4, 2.1 Hz, 1H), 5.98 (s, 2H), 3.32 (s, 3H), 2.14 (s, 3H); UPLC-MS: $t_R$=1.11 min (apolar method); MS (ESI) m/z calcd for $C_{20}H_{17}F_3N_3O_3$ (M+H)$^+$: 404.1, found: 404.2.

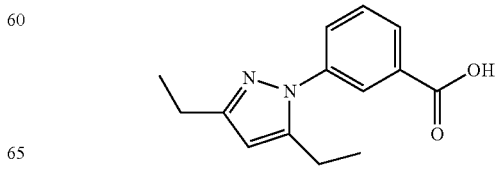

[Int-1.47] 3-(3,5-Diethylpyrazol-1-yl)benzoic acid

Following general procedure 1a, the title compound was obtained from 3-hydrazinobenzoic acid, after purification by trituration with pentane/DCM (9:1) as the solvent, as a brown solid in 75% yield: $^1$H NMR (400 MHz, DMSO-$d_6$) δ 13.20 (br s, 1H), 7.97 (app-t, J=1.9 Hz, 1H), 7.94 (app-dt, J=7.7, 1.4 Hz, 1H), 7.74 (ddd, J=8.0, 2.3, 1.2 Hz, 1H), 7.62 (app-t, J=7.8 Hz, 1H), 6.17 (s, 1H), 2.68 (q, J=7.4 Hz, 2H), 2.58 (q, J=7.6 Hz, 2H), 1.20 (t, J=7.6 Hz, 3H), 1.15 (t, J=7.4 Hz, 3H); UPLC-MS: $t_R$=1.56 min (generic method); MS (ESI) m/z calcd for $C_{14}H_{17}N_2O_2$ (M+H)$^+$: 245.1, found: 245.2.

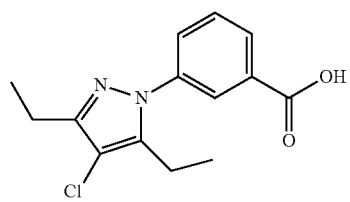 [SMILES: CCc1nn(-c2cccc(C(=O)O)c2)c(CC)c1Cl]

[Int-1.48] 3-(4-Chloro-3,5-diethyl-pyrazol-1-yl)benzoic acid

Following general procedure 1b, the title compound was obtained from Int-1.47, after purification by trituration with H$_2$O as the solvent, as a yellow solid in 91% yield: $^1$H NMR (400 MHz, DMSO-$d_6$) δ 13.30 (br s, 1H), 8.01 (app-dt, J=7.6, 1.4 Hz, 1H), 7.96 (app-t, J=1.9 Hz, 1H), 7.75 (ddd, J=8.0, 2.3, 1.2 Hz, 1H), 7.67 (app-t, J=7.8 Hz, 1H), 2.71 (q, J=7.6 Hz, 2H), 2.62 (q, J=7.5 Hz, 2H), 1.22 (t, J=7.6 Hz, 3H), 1.05 (t, J=7.5 Hz, 3H); UPLC-MS: $t_R$=1.81 min (generic method); MS (ESI) m/z calcd for $C_{14}H_{16}ClN_2O_2$ (M+H)$^+$: 279.1, found: 279.1.

[092] N-(1,3-Benzodioxol-5-yl)-3-(4-chloro-3,5-diethyl-pyrazol-1-yl)-N-methyl-benzamide Following general procedure 1c, the title compound was obtained from Int-1.48, after purification by silica gel flash-column chromatography with cyclohexane/EtOAc (7:3) as the eluent, as a yellow oil in 44% yield: $^1$H NMR (400 MHz, DMSO-$d_6$) δ 7.52-7.32 (m, 3H), 7.30 (br s, 1H), 6.96 (d, J=2.1 Hz, 1H), 6.77 (d, J=8.2 Hz, 1H), 6.64 (dd, J=8.3, 2.1 Hz, 1H), 5.99 (s, 2H), 2.57 (q, J=7.6 Hz, 2H), 2.45 (q, J=7.5 Hz, 2H), 1.19 (t, J=7.6 Hz, 3H), 0.83 (t, J=7.5 Hz, 3H); UPLC-MS: $t_R$=1.48 min (apolar method); MS (ESI) m/z calcd for $C_{22}H_{23}ClN_3O_3$ (M+H)$^+$: 412.1, found: 412.2.

[093] N-(1,3-Benzodioxol-5-yl)-3-(3,5-diethylpyrazol-1-yl)-N-methyl-benzamide Following general procedure 1c, the title compound was obtained from Int-1.47, after purification by silica gel flash-column chromatography with cyclohexane/EtOAc (6:4) as the eluent, as an orange oil in 32% yield: $^1$H NMR (400 MHz, DMSO-$d_6$) δ 7.45-7.32 (m, 3H), 7.29 (s, 1H), 6.95 (d, J=2.1 Hz, 1H), 6.78 (d, J=8.2 Hz, 1H), 6.64 (dd, J=8.2, 2.1 Hz, 1H), 6.10 (s, 1H), 5.99 (s, 2H), 3.32 (s, 3H), 2.58-2.52 (m, 2H), 2.42-2.28 (m, 2H), 1.18 (t, J=7.6 Hz, 3H), 1.03 (t, J=7.5 Hz, 3H); UPLC-MS: $t_R$=2.26 min (generic method); MS (ESI) m/z calcd for $C_{22}H_{24}N_3O_3$ (M+H)$^+$: 378.2, found: 378.2.

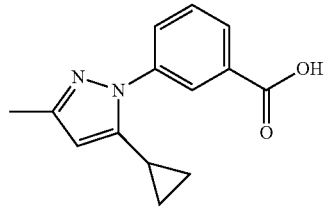 [SMILES: Cc1cc(C2CC2)n(-c2cccc(C(=O)O)c2)n1]

[Int-1.49] 3-(5-Cyclopropyl-3-methyl-pyrazol-1-yl)benzoic acid

Following general procedure 1a, the title compound was obtained from 3-hydrazinobenzoic acid, after purification by trituration with pentane/DCM (9:1) as the solvent, as a beige solid in 19% yield: $^1$H NMR (400 MHz, DMSO-$d_6$) δ 12.39 (br s, 1H), 8.19 (app-t, J=1.9 Hz, 1H), 7.96-7.77 (m, 2H), 7.63 (app-t, J=7.9 Hz, 1H), 5.96 (s, 1H), 2.17 (s, 3H), 1.84 (tt, J=8.3, 5.1 Hz, 1H), 1.04-0.89 (m, 2H), 0.78-0.65 (m, 2H); UPLC-MS: $t_R$=1.45 min (generic method); MS (ESI) m/z calcd for $C_{14}H_{15}N_2O_2$ (M+H)$^+$: 243.1, found: 243.1.

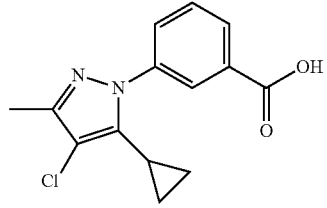 [SMILES: Cc1nn(-c2cccc(C(=O)O)c2)c(C2CC2)c1Cl]

[Int-1.50] 3-(4-Chloro-5-cyclopropyl-3-methyl-pyrazol-1-yl)benzoic acid

Following general procedure 1b, the title compound was obtained from Int-1.49, after purification by trituration with pentane/DCM (9:1) as the solvent, as a yellow solid in 60% yield: UPLC-MS: $t_R$=1.70 min (generic method); MS (ESI) m/z calcd for $C_{14}H_{12}ClN_2O_2$ (M−H)$^-$: 275.1, found: 275.0.

[094] N-(1,3-Benzodioxol-5-yl)-3-(4-chloro-5-cyclopropyl-3-methyl-pyrazol-1-yl)-N-methyl-benzamide Following general procedure 1c, the title compound was obtained from Int-1.50 and Int-1.34, after purification by silica gel flash-column chromatography with cyclohexane/EtOAc (6:4) as the eluent, as a white solid in 43% yield: $^1$H NMR (400 MHz, DMSO-$d_6$) δ 7.50-7.42 (m, 2H), 7.37 (app-t, J=8.1 Hz, 1H), 7.29 (d, J=7.7 Hz, 1H), 6.94 (d, J=2.1 Hz, 1H), 6.76 (d, J=8.2 Hz, 1H), 6.65 (dd, J=8.4, 2.1 Hz, 1H), 5.97 (s, 2H), 3.31 (s, 3H), 2.15 (s, 3H), 1.82-1.72 (m, 1H), 0.87-0.59 (m, 2H), 0.55-0.29 (m, 2H); UPLC-MS: $t_R$=1.28 min (apolar method); MS (ESI) m/z calcd for $C_{22}H_{21}ClN_3O_3$ (M+H)$^+$: 410.1, found: 410.1. (M+H)$^+$: 470.1, found: 470.2.

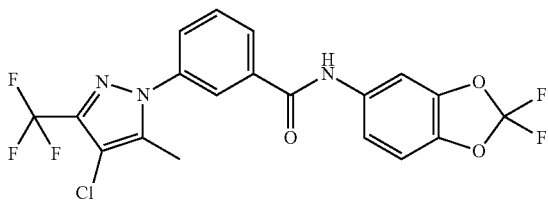 [SMILES: Cc1c(Cl)c(C(F)(F)F)nn1-c1cccc(C(=O)Nc2ccc3c(c2)OC(F)(F)O3)c1]

[Int-1.51] 3-[4-chloro-5-methyl-3-(trifluoromethyl) pyrazol-1-yl]-N-(2,2-difluoro-1,3-benzodioxol-5-yl) benzamide Following general procedure 1c, the title compound was obtained from Int-1.2, after purification by silica gel flash-column chromatography with Cyclohexane/EtOAc (70/30) as the eluent, as a white solid in 66% yield: UPLC-MS: $t_R$=2.52 min (Generic method); MS (ESI) m/z calcd for $C_{19}H_{12}ClF_5N_3O_3$ (M+H)$^+$: 460.0, found: 460.1.

[095] 3-[4-Chloro-5-methyl-3-(trifluoromethyl)pyrazol-1-yl]-N-(2,2-difluoro-1,3-benzodioxol-5-yl)-N-methyl-benzamide Following general procedure 1d, the title compound was obtained [Int-1.51], after purification by silica gel flash-column chromatography with Cyclohexane/EtOAc (80/20) as the eluent, as a white solid in 40% yield: $^1$H NMR (400 MHz, DMSO-$d_6$) δ 7.54 (d, J=2.1 Hz, 1H), 7.52 (app-d, J=1.5 Hz, 3H), 7.45 (bs, 1H), 7.30 (d, J=8.6 Hz, 1H), 7.04 (dd, J=8.6, 2.1 Hz, 1H), 3.37 (s, 3H), 2.07 (s, 3H). UPLC-MS: $t_R$=2.74 min (Generic method); MS (ESI) m/z calcd for $C_{20}H_{14}ClF_5N_3O_3$ (M+H)$^+$: 474.0, found: 474.1.

[096] 3-[4-Chloro-5-methyl-3-(trifluoromethyl)pyrazol-1-yl]-N-(2,3-dihydro-1,4-benzodioxin-6-yl)-N-methyl-benzamide Following general procedure 1c, the title compound was obtained from Int-1.2, after purification by silica gel flash-column chromatography with Cyclohexane/EtOAc (70/30) as the eluent, as a white solid in 24% yield: $^1$H NMR (400 MHz, DMSO-$d_6$) δ 7.54-7.47 (m, 3H), 7.45 (bs, 1H), 6.83 (d, J=2.5 Hz, 1H), 6.72 (d, J=8.6 Hz, 1H), 6.63 (dd, J=8.6, 2.5 Hz, 1H), 4.17 (s, 4H), 3.32 (s, 3H), 2.07 (s, 3H). UPLC-MS: $t_R$=2.53 min (Generic method); MS (ESI) m/z calcd for $C_{21}H_{18}ClF_3N_3O_3$ (M+H)$^+$: 452.1, found: 452.1.

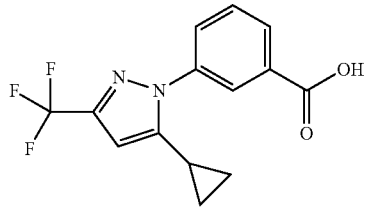 [SMILES: O=C(O)c1cccc(-n2nc(C(F)(F)F)cc2C2CC2)c1]

[Int-1.52] 3-[5-Cyclopropyl-3-(trifluoromethyl)pyrazol-1-yl]benzoic acid

Following general procedure 1a, the title compound was obtained from 3-hydrazinobenzoic acid, after purification by trituration with H$_2$O as the solvent, as a beige solid in 90% yield: $^1$H NMR (400 MHz, DMSO-$d_6$) δ 13.35 (br s, 1H), 8.17 (app-t, J=1.9 Hz, 1H), 8.07 (app-dt, J=7.8, 1.4 Hz, 1H), 7.96 (ddd, J=8.0, 2.3, 1.1 Hz, 1H), 7.72 (app-t, J=7.9 Hz, 1H), 6.69 (s, 1H), 1.88 (tt, J=8.3, 4.7 Hz, 1H), 1.04-0.96 (m, 2H), 0.90-0.83 (m, 2H); UPLC-MS: $t_R$=1.76 min (generic method); MS (ESI) m/z calcd for $C_{14}H_{12}F_3N_2O_2$ (M+H)$^+$: 297.1, found: 297.1.

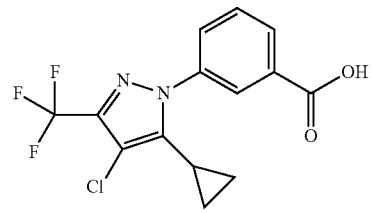 [SMILES: O=C(O)c1cccc(-n2nc(C(F)(F)F)c(Cl)c2C2CC2)c1]

[Int-1.53] 3-[4-Chloro-5-cyclopropyl-3-(trifluoromethyl) pyrazol-1-yl]benzoic acid Following general procedure 1b, the title compound was obtained from Int-1.52, after purification by trituration with H$_2$O as the solvent, as a white solid in 93% yield: $^1$H NMR (400 MHz, DMSO-$d_6$) δ 13.37 (br s, 1H), 8.15 (app-t, J=1.9 Hz, 1H), 8.09 (app-dt, J=7.8, 1.4 Hz, 1H), 7.96 (ddd, J=8.0, 2.3, 1.1 Hz, 1H), 7.71 (app-t, J=7.9 Hz, 1H), 2.03 (tt, J=8.5, 5.4 Hz, 1H), 0.92-0.85 (m, 2H), 0.66-0.60 (m, 2H); UPLC-MS: $t_R$=1.94 min (generic method); MS (ESI) m/z calcd for $C_{14}H_{11}ClF_3N_2O_2$ (M+H)$^+$: 331.0, found: 331.1.

[097] N-(1,3-Benzodioxol-5-yl)-3-(5-cyclopropyl-3-methyl-pyrazol-1-yl)-N-methyl-benzamide Following general procedure 1c, the title compound was obtained from Int-1.52, after purification by silica gel flash-column chromatography with cyclohexane/EtOAc (6:4) as the eluent, as a white solid in 33% yield: $^1$H NMR (400 MHz, DMSO-$d_6$) δ 7.55-7.45 (m, 2H), 7.38 (app-t, J=7.7 Hz, 1H), 7.27 (d, J=7.7 Hz, 1H), 6.95 (d, J=2.1 Hz, 1H), 6.75 (d, J=8.2 Hz, 1H), 6.63 (dd, J=8.2, 2.1 Hz, 1H), 5.97 (s, 2H), 5.88 (s, 1H), 3.32 (s, 3H), 2.13 (s, 3H), 1.61-1.36 (m, 1H), 0.95-0.80 (m, 2H), 0.71-0.54 (m, 2H); UPLC-MS: $t_R$=0.97 min (apolar method); MS (ESI) m/z calcd for $C_{22}H_{22}N_3O_3$ (M+H)$^+$: 376.2, found: 376.1.

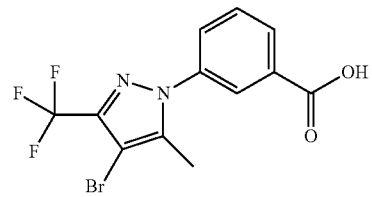 [SMILES: Cc1c(Br)c(C(F)(F)F)nn1-c1cccc(C(=O)O)c1]

[Int-1.54] 3-[4-Bromo-5-methyl-3-(trifluoromethyl) pyrazol-1-yl]benzoic acid Following general procedure 1b, the title compound was obtained from Int-1.1 and NBS, after purification by trituration with H$_2$O as the solvent, as a white solid in 60% yield: $^1$H NMR (400 MHz, DMSO-$d_6$) δ 13.39 (s, 1H), 8.10 (app-dt, J=7.8, 1.4 Hz, 1H), 8.06 (app-t, J=1.9 Hz, 1H), 7.89 (ddd, J=8.1, 2.4, 1.1 Hz, 1H), 7.73 (app-t, J=7.9 Hz, 1H), 2.35 (s, 3H); UPLC-MS: $t_R$=1.78 min (generic method); MS (ESI) m/z calcd for $C_{12}H_9BrF_3N_2O_2$ (M+H)$^+$: 349.0, found: 349.0.

[098] N-(1,3-Benzodioxol-5-yl)-3-[4-bromo-5-methyl-3-(trifluoromethyl)pyrazol-1-yl]-N-methyl-benzamide Following general procedure 1c, the title compound was obtained from Int-1.54 and Int-1.34, after purification by silica gel flash-column chromatography with cyclohexane/EtOAc (6:4) as the eluent, as a white solid in 75% yield: $^1$H NMR (400 MHz, DMSO-d$_6$) δ 7.59-7.39 (m, 4H), 6.96 (d, J=2.1 Hz, 1H), 6.77 (d, J=8.2 Hz, 1H), 6.65 (dd, J=8.2, 2.1 Hz, 1H), 5.99 (s, 2H), 3.32 (s, 3H), 2.11 (s, 3H); UPLC-MS: $t_R$=1.45 min (apolar method); MS (ESI) m/z calcd for $C_{20}H_{16}BrF_3N_3O_3$ (M+H)$^+$: 482.0, found: 482.0.

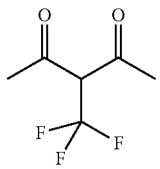

[Int-1.55] 3-(Trifluoromethyl)pentane-2,4-dione

To a solution of pentane-2,4-dione (1.0 g, 10.0 mmol), ICF$_3$ (2.55 M in DMSO, 12.0 mL, 30.0 mmol) and FeSO$_4$.7H$_2$O (834 mg, 3.0 mmol) in H$_2$O (3 mL) and DMSO (40 mL) was added H$_2$O$_2$ (30% wt. in H$_2$O, 2.0 mL, 20.0 mmol) dropwise, and the mixture stirred at room temperature for 2 h. The solution was partitioned between Et$_2$O (100 mL) and H$_2$O (100 mL). The organic phase was separated, washed with brine (100 mL), dried over anhydrous Na$_2$SO$_4$, filtered and the solvent evaporated under reduced pressure. The product was used in the next step without any purification.

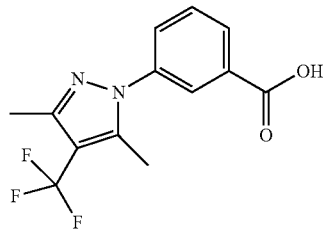 [SMILES: Cc1nn(-c2cccc(C(=O)O)c2)c(C)c1C(F)(F)F]

[Int-1.56] 3-[3,5-Dimethyl-4-(trifluoromethyl)pyrazol-1-yl]benzoic acid

Following general procedure 1a, the title compound was obtained from Int-1.55, after purification by trituration with pentane/DCM (9:1) as the solvent, as a beige solid in 90% yield: $^1$H NMR (400 MHz, DMSO-d$_6$) δ 13.27 (br s, 1H), 8.04 (app-dt, J=7.7, 1.4 Hz, 1H), 8.00 (app-t, J=1.9 Hz, 1H), 7.80 (ddd, J=8.0, 2.3, 1.2 Hz, 1H), 7.69 (app-t, J=7.9 Hz, 1H), 2.37 (s, 3H), 2.31 (s, 3H); UPLC-MS: $t_R$=1.60 min (generic method); MS (ESI) m/z calcd for $C_{13}H_{12}F_3N_2O_2$ (M+H)$^+$: 285.1, found: 285.1.

[099] N-(1,3-Benzodioxol-5-yl)-3-[3,5-dimethyl-4-(trifluoromethyl)pyrazol-1-yl]-N-methyl-benzamide Following general procedure 1c, the title compound was obtained from Int-1.56, after purification by silica gel flash-column chromatography with cyclohexane/EtOAc (6:4) as the eluent, as a white solid in 41% yield: $^1$H NMR (400 MHz, DMSO-d$_6$) δ 7.53-7.26 (m, 4H), 6.96 (d, J=2.1 Hz, 1H), 6.77 (d, J=8.2 Hz, 1H), 6.65 (dd, J=8.2, 2.1 Hz, 1H), 5.98 (s, 2H), 3.32 (s, 3H), 2.27 (q, J=1.3 Hz, 3H), 2.12 (s, 3H); UPLC-MS: $t_R$=1.18 min (apolar method); MS (ESI) m/z calcd for $C_{21}H_{19}F_3N_3O_3$ (M+H)$^+$: 418.1, found: 418.1.

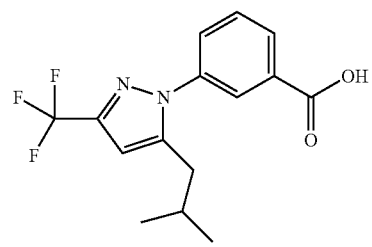 [SMILES: CC(C)Cc1cc(C(F)(F)F)nn1-c1cccc(C(=O)O)c1]

[Int-1.57] 3-[5-Isobutyl-3-(trifluoromethyl)pyrazol-1-yl]benzoic acid

Following general procedure 1a, the title compound was obtained from 3-hydrazinobenzoic acid, after purification by trituration with pentane as the solvent, as a beige solid in 85% yield: $^1$H NMR (400 MHz, DMSO-d$_6$) δ 13.37 (br s, 1H), 8.09 (app-dt, J=7.7, 1.4 Hz, 1H), 7.97 (app-t, J=1.9 Hz, 1H), 7.82 (ddd, J=8.0, 2.3, 1.2 Hz, 1H), 7.72 (app-t, J=7.8 Hz, 1H), 6.83 (s, 1H), 2.59 (d, J=7.2 Hz, 2H), 1.81 (app-nonet, J=6.8 Hz, 1H), 0.80 (d, J=6.6 Hz, 6H); UPLC-MS: $t_R$=1.90 min (generic method); MS (ESI) m/z calcd for $C_{15}H_{16}F_3N_2O_2$ (M+H)$^+$: 313.1, found: 313.1.

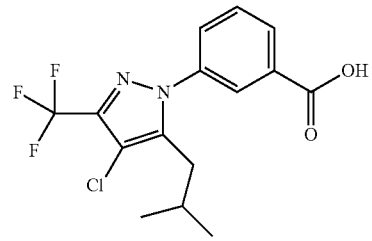 [SMILES: CC(C)Cc1c(Cl)c(C(F)(F)F)nn1-c1cccc(C(=O)O)c1]

[Int-1.58] 3-[4-Chloro-5-isobutyl-3-(trifluoromethyl)pyrazol-1-yl]benzoic acid

Following general procedure 1b, the title compound was obtained from Int-1.57, after purification by trituration with H$_2$O as the solvent, as a yellow solid in 14% yield: $^1$H NMR (400 MHz, DMSO-d$_6$) δ 11.04 (br s, 1H), 8.12 (app-dt, J=7.7, 1.4 Hz, 1H), 8.04 (app-t, J=1.9 Hz, 1H), 7.89 (ddd, J=8.0, 2.3, 1.1 Hz, 1H), 7.74 (app-t, J=7.9 Hz, 1H), 2.66 (d, J=7.4 Hz, 2H), 1.66 (app-nonet, J=6.9 Hz, 1H), 0.73 (d, J=6.6 Hz, 6H); UPLC-MS: $t_R$=2.08 min (generic method); MS (ESI) m/z calcd for $C_{15}H_{15}ClF_3N_2O_2$ (M+H)$^+$: 347.1, found: 347.1.

[100] N-(1,3-Benzodioxol-5-yl)-3-[5-isobutyl-3-(trifluoromethyl)pyrazol-1-yl]-N-methyl-benzamide Following general procedure 1c, the title compound was obtained from Int-1.57, after purification by silica gel flash-column chromatography with cyclohexane/EtOAc (7:3) as the eluent, as a white solid in 66% yield: $^1$H NMR (400 MHz, DMSO-d$_6$) δ 7.51-7.39 (m, 3H), 7.36 (app-s, 1H), 6.96 (d, J=2.1 Hz, 1H), 6.78-6.70 (m, 2H), 6.65 (dd, J=8.2, 2.1 Hz, 1H), 5.97 (s, 2H), 3.31 (s, 3H), 2.38 (d, J=7.1 Hz, 2H), 1.60 (app-nonet, J=6.7 Hz, 1H), 0.71 (d, J=6.6 Hz, 6H); UPLC-MS: t$_R$=1.58 min (apolar method); MS (ESI) m/z calcd for C$_{23}$H$_{23}$F$_3$N$_3$O$_3$ (M+H)$^+$: 446.2, found: 446.2.

[101] N-(1,3-Benzodioxol-5-yl)-3-[4-chloro-5-isobutyl-3-(trifluoromethyl)pyrazol-1-yl]-N-methyl-benzamide Following general procedure 1c, the title compound was obtained from Int-1.58, after purification by preparative HPLC, as an off-white solid in 26% yield: $^1$H NMR (400 MHz, DMSO-d$_6$) δ 7.59-7.36 (m, 4H), 6.96 (d, J=2.1 Hz, 1H), 6.74 (d, J=8.2 Hz, 1H), 6.65 (dd, J=8.2, 2.1 Hz, 1H), 5.97 (s, 2H), 3.30 (s, 3H), 2.47 (d, J=7.6 Hz, 2H), 1.42 (app-nonet, J=6.8 Hz, 1H), 0.63 (d, J=6.6 Hz, 6H); UPLC-MS: t$_R$=1.89 min (apolar method); MS (ESI) m/z calcd for C$_{23}$H$_{22}$ClF$_3$N$_3$O$_3$ (M+H)$^+$: 480.1, found: 480.1.

[102] N-(1,3-Benzodioxol-5-yl)-3-[4-chloro-3-methyl-5-(trifluoromethyl)pyrazol-1-yl]-N-methyl-benzamide Following general procedure 1d, the title compound was obtained from Int-1.2, after purification by silica gel flash-column chromatography with Cyclohexane/EtOAc (80/20) as the eluent, as a by-product of compound 090, as a Pale yellow solid in 1.5% yield (minor regioisomer): $^1$H NMR (400 MHz, DMSO-d$_6$) δ 7.50-7.31 (m, 4H), 6.90 (d, J=2.1 Hz, 1H), 6.74 (d, J=8.2 Hz, 1H), 6.60 (dd, J=8.2, 2.1 Hz, 1H), 5.97 (s, 2H), 3.31 (s, 3H), 2.26 (s, 3H). UPLC-MS: t$_R$=2.55 min (Generic method); MS (ESI) m/z calcd for C$_{20}$H$_{16}$ClF$_3$N$_3$O$_3$ (M+H)$^+$: 438.1, found: 438.1.

[103] Ethyl 4-chloro-2-[3-[2,3-dihydro-1,4-benzodioxin-6-yl(methyl)carbamoyl]phenyl]-5-methyl-pyrazole-3-carboxylate Following general procedure 1c, the title compound was obtained Int-1.38, after purification by silica gel flash-column chromatography with Cyclohexane/EtOAc (70/30) as the eluent, as a white solid in 31% yield: $^1$H NMR (400 MHz, DMSO-d$_6$) δ 7.41-7.27 (m, 4H), 6.80 (d, J=2.5 Hz, 1H), 6.72 (d, J=8.6 Hz, 1H), 6.64 (dd, J=8.6, 2.5 Hz, 1H), 4.18 (s, 4H), 4.16 (q, J=7.1 Hz, 2H), 3.30 (s, 3H), 2.26 (s, 3H), 1.05 (t, J=7.1 Hz, 3H). UPLC-MS: t$_R$=2.39 min (Generic method); MS (ESI) m/z calcd for C$_{23}$H$_{23}$ClN$_3$O$_5$ (M+H)$^+$: 456.1, found: 456.1.

[104] N-(1,3-Benzodioxol-5-yl)-3-[4-cyclopropyl-5-methyl-3-(trifluoromethyl)pyrazol-1-yl]-N-methyl-benzamide To a solution of compound 098 (70 mg, 0.15 mmol) in dioxane (3 mL) and water (1 mL), 2-cyclopropyl-4,4,5,5-tetramethyl-1,3,2-dioxaborolane (31.7 μL, 0.17 mmol) and K$_2$CO$_3$ (60.1 mg, 0.44 mmol) were added. Mixture was degassed with Nitrogen for 10 min and Pd(PPh$_3$)$_4$ (33.6 mg, 0.03 mmol) was added. Mixture was heated under microwave irradiation at 120° C. for 2 h, diluted with EtOAc (30 mL). Organic layer was washed with sat. aq. Na$_2$CO$_3$ (2×10 mL) and Brine (20 mL). The title compound was obtained, after purification by silica gel flash-column chromatography with Cyclohexane/EtOAc (70/30) as the eluent, as a white solid in 35% yield (23 mg): $^1$H NMR (400 MHz, DMSO-d$_6$) δ 7.50-7.36 (m, 4H), 7.01-6.93 (m, 1H), 6.77 (d, J=8.3 Hz, 1H), 6.65 (dd, J=8.3, 2.1 Hz, 1H), 5.98 (s, 2H), 3.32 (s, 3H), 2.10 (s, 3H), 1.69-1.56 (m, 1H), 0.94-0.86 (m, 2H), 0.58-0.52 (m, 2H). UPLC-MS: t$_R$=2.54 min (Generic method); MS (ESI) m/z calcd for C$_{23}$H$_{21}$F$_3$N$_3$O$_3$ (M+H)$^+$: 444.1, found: 444.1.

[106] N-(6-Chloro-1,3-benzodioxol-5-yl)-3-[4-chloro-5-methyl-3-(trifluoromethyl)pyrazol-1-yl]-N-methyl-benzamide Following general procedure 1b, the title compound was obtained from compound 090, after purification by silica gel flash-column chromatography with Cyclohexane/EtOAc (90/10) as the eluent, as a yellow solid in 30% yield. $^1$H NMR Analysis showed rotamers mixture. Major rotamer: $^1$H NMR (400 MHz, DMSO-d$_6$) δ 7.57-7.44 (m, 4H), 7.30 (s, 1H), 7.05 (s, $^1$H), 6.06 (d, J=0.9 Hz, 1H), 6.05 (d, J=0.9 Hz, 1H), 3.23 (s, 3H), 2.16 (s, 3H). UPLC-MS: t$_R$=2.64 min (Generic method); MS (ESI) m/z calcd for C$_{20}$H$_{15}$Cl$_2$F$_3$N$_3$O$_3$ (M+H)$^+$: 472.1, found: 472.0.

[108] 3-[4-Chloro-5-methyl-3-(trifluoromethyl)pyrazol-1-yl]-N-methyl-N-(2-methyl-1,3-benzoxazol-6-yl)benzamide Following general procedure 1d, the title compound was obtained from Int-1.2, after purification by silica gel flash-column chromatography with DCM/EtOAc (9:1) as the eluent, as a white solid in 97% yield: $^1$H NMR (400 MHz, DMSO-d$_6$) δ 7.68 (d, J=1.9 Hz, 1H), 7.53 (d, J=8.4 Hz, 1H), 7.50-7.40 (m, 4H), 7.20 (dd, J=8.4, 1.9 Hz, 1H), 3.43 (s, 3H), 2.57 (s, 3H), 1.98 (s, 3H); UPLC-MS: t$_R$=1.24 min (apolar method); MS (ESI) m/z calcd for C$_{21}$H$_{17}$ClF$_3$N$_4$O$_2$ (M+H)$^+$: 449.1, found: 449.1.

[110] N-(6-Chloro-1,3-benzodioxol-5-yl)-3-[4-chloro-5-isobutyl-3-(trifluoromethyl)pyrazol-1-yl]-N-methyl-benzamide Following general procedure 1b, the title compound was obtained from compound 100, and NCS (2.2 eq), after purification by preparative HPLC, as a white solid in 52% yield: $^1$H NMR (400 MHz, DMSO-d$_6$) δ 7.59-7.39 (m, 4H), 7.31 (s, 1H), 7.03 (s, 1H), 6.05 (d, J=5.0 Hz, 2H), 3.22 (s, 3H), 2.48 (d, J=6.7 Hz, 2H), 1.42 (app-nonet, J=6.9 Hz, 1H), 0.63 (app-dd, J=6.6, 1.9 Hz, 6H); UPLC-MS: t$_R$=2.08 min (apolar method); MS (ESI) m/z calcd for C$_{23}$H$_{21}$Cl$_2$F$_3$N$_3$O$_3$ (M+H)$^+$: 514.1, found: 514.1.

[111] N-(1,3-Benzodioxol-5-yl)-3-[4-chloro-5-cyclopropyl-3-(trifluoromethyl)pyrazol-1-yl]-N-methyl-benzamide Following general procedure 1c, the title compound was obtained from Int-1.53, after purification by silica gel flash-column chromatography with cyclohexane/EtOAc (7:3) as the eluent, as a white solid in 92% yield: $^1$H NMR (400 MHz, DMSO-d$_6$) δ 7.58-7.51 (m, 2H), 7.50-7.36 (m, 2H), 6.95 (d, J=2.1 Hz, 1H), 6.76 (d, J=8.2 Hz, 1H), 6.67 (dd, J=8.2, 2.1 Hz, 1H), 5.97 (s, 2H), 3.32 (s, 3H), 1.80 (tt, J=8.5, 5.3 Hz, 1H), 0.79-0.70 (m, 2H), 0.51-0.43 (m, 2H); UPLC-MS: $t_R$=1.62 min (apolar method); MS (ESI) m/z calcd for $C_{22}H_{18}ClF_3N_3O_3$ (M+H)$^+$: 464.1, found: 464.1.

[120] 3-[4-Chloro-5-methyl-3-(trifluoromethyl)pyrazol-1-yl]-N-(2-methyl-1,3-benzoxazol-6-yl)benzamide Following general procedure 1c, the title compound was obtained from Int-1.2, after purification by silica gel flash-column chromatography with cyclohexane/EtOAc (1:1) as the eluent, as a white solid in 89% yield: $^1$H NMR (400 MHz, DMSO-d$_6$) δ 10.58 (s, 1H), 8.22 (br s, 1H), 8.20-8.12 (m, 2H), 7.89-7.83 (m, 1H), 7.78 (app-t, J=8.1 Hz, 1H), 7.70-7.57 (m, 2H), 2.60 (s, 3H), 2.37 (s, 3H); UPLC-MS: $t_R$=2.48 min (generic method); MS (ESI) m/z calcd for $C_{20}H_{15}ClF_3N_4O_2$ (M+H)$^+$: 435.1, found: 435.1.

[Int-121] 3-[4-Chloro-5-methyl-3-(trifluoromethyl)pyrazol-1-yl]-N-(2-methylindazol-6-yl)benzamide Following general procedure 1c, the title compound was obtained from Int-1.2, after purification by silica gel flash-column chromatography with DCM/MeOH (95:5) as the eluent, as a pale pink solid in 63% yield: $^1$H NMR (400 MHz, DMSO-d$_6$) δ 10.37 (s, 1H), 8.27 (s, 1H), 8.20-8.10 (m, 3H), 7.89-7.82 (m, 1H), 7.77 (app-t, J=8.1 Hz, 1H), 7.66 (dd, J=8.9, 0.8 Hz, 1H), 7.32 (dd, J=9.0, 1.8 Hz, 1H), 4.14 (s, 3H), 2.37 (s, 3H); UPLC-MS: $t_R$=2.30 min (apolar method); MS (ESI) m/z calcd for $C_{20}H_{16}ClF_3N5O$ (M+H)$^+$: 434.1, found: 434.1.

[122] 3-[4-Chloro-5-methyl-3-(trifluoromethyl)pyrazol-1-yl]-N-methyl-N-(2-methylindazol-6-yl)benzamide Following general procedure 1d, the title compound was obtained from Int-121, after purification by silica gel flash-column chromatography with DCM/EtOAc (6:4) as the eluent, as a white solid in 83% yield: $^1$H NMR (400 MHz, DMSO-d$_6$) δ 8.28 (s, $^1$H), 7.63 (d, J=8.9 Hz, 1H), 7.55-7.34 (m, 5H), 6.95 (dd, J=8.8, 1.9 Hz, 1H), 4.10 (s, 3H), 3.42 (s, 3H), 1.87 (s, 3H); UPLC-MS: $t_R$=1.04 min (apolar method); MS (ESI) m/z calcd for $C_{21}H_{15}ClF_3N5O$ (M+H)$^+$: 448.1, found: 448.2.

[123] N-(5-Chloro-2-methyl-1,3-benzoxazol-6-yl)-3-[4-chloro-5-methyl-3-(trifluoromethyl)pyrazol-1-yl]-N-methyl-benzamide Following general procedure 1b, the title compound was obtained from compound 108, after purification by silica gel flash-column chromatography with DCM/EtOAc (95:5) as the eluent, as a white solid in 12% yield: $^1$H NMR (400 MHz, DMSO-d$_6$) δ 8.10 (s, 1H), 7.80 (s, 1H), 7.53-7.39 (m, 4H), 3.32 (s, 3H), 2.59 (s, 3H), 2.06 (s, 3H); UPLC-MS: $t_R$=1.52 min (apolar method); MS (ESI) m/z calcd for $C_{21}H_{16}Cl_2F_3N_4O_2$ (M+H)$^+$: 483.1, found: 483.0.

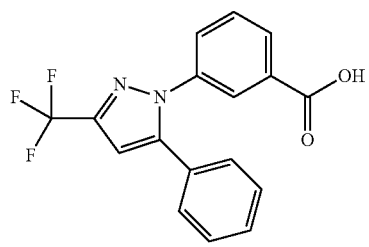 [SMILES: O=C(O)c1cccc(-n2nc(C(F)(F)F)cc2-c2ccccc2)c1]

[Int-1.59] 3-[5-Phenyl-3-(trifluoromethyl)pyrazol-1-yl]benzoic acid

Following general procedure 1a, the title compound was obtained from 3-hydrazinobenzoic acid in DMF. The product, as a solution in DMF, was used in the next step without any work-up or purification. UPLC-MS: $t_R$=1.88 min (generic method); MS (ESI) m/z calcd for $C_{17}H_{12}F_3N_2O_2$ (M+H)$^+$: 333.1, found: 333.1.

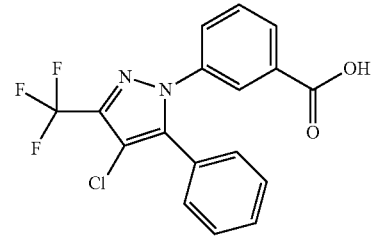 [SMILES: O=C(O)c1cccc(-n2nc(C(F)(F)F)c(Cl)c2-c2ccccc2)c1]

[Int-1.60] 3-[4-Chloro-5-phenyl-3-(trifluoromethyl)pyrazol-1-yl]benzoic acid

Following general procedure 1b, the title compound was obtained from Int-1.59 in DMF. The product, as a solution in DMF, was used in the next step without any work-up or purification: UPLC-MS: $t_R$=2.04 min (generic method); MS (ESI) m/z calcd for $C_{17}H_{11}ClF_3N_2O_2$ (M+H)$^+$: 367.0, found: 367.1.

[124] N-(1,3-Benzodioxol-5-yl)-3-[4-chloro-5-phenyl-3-(trifluoromethyl)pyrazol-1-yl]-N-methyl-benzamide Following general procedure 1c, the title compound was obtained from Int-1.60, after purification by preparative HPLC, as an off-white solid in 85% yield: $^1$H NMR (400 MHz, DMSO-d$_6$) δ 7.52-7.40 (m, 3H), 7.37 (s, 1H), 7.29-7.18 (m, 4H), 7.18-7.11 (m, 1H), 6.88 (d, J=2.1 Hz, 1H), 6.76 (d, J=8.2 Hz, 1H), 6.48 (d, J=8.2 Hz, 1H), 6.00 (s, 2H), 3.31 (s, 3H); UPLC-MS: $t_R$=1.75 min (apolar method); MS (ESI) m/z calcd for $C_{25}H_{18}ClF_3N_3O_3$ (M+H)$^+$: 500.1, found: 500.2.

[125] N-(1,3-Benzodioxol-5-yl)-N-methyl-3-[5-phenyl-3-(trifluoromethyl)pyrazol-1-yl]benzamide Following general procedure 1c, the title compound was obtained from Int-1.59, after purification by preparative HPLC, as an off-white solid in 91% yield: $^1$H NMR (400 MHz, DMSO-d$_6$) δ 7.46-7.21 (m, 6H), 7.18 (s, 1H), 7.13 (app-d, J=7.1 Hz, 3H), 6.92 (d, J=2.1 Hz, 1H), 6.79 (d, J=8.2 Hz, 1H), 6.56 (dd, J=8.2, 2.1 Hz, 1H), 5.98 (s, 2H), 3.31 (s, 3H); UPLC-MS: $t_R$=1.47 min (apolar method); MS (ESI) m/z calcd for $C_{25}H_{19}F_3N_3O_3$ (M+H)$^+$: 466.1, found: 466.2.

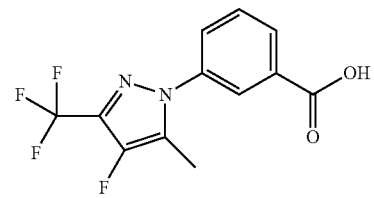 [SMILES: Cc1c(F)c(C(F)(F)F)nn1-c1cccc(C(=O)O)c1]

[Int-1.61] 3-[4-Fluoro-5-methyl-3-(trifluoromethyl)pyrazol-1-yl]benzoic acid To a solution of Int-1.1 (100 mg, 0.37 mmol) in MeCN (3 mL) was added selectfluor (138 mg, 0.39 mmol), and the mixture stirred at 100° C. for 2 days. The product, in MeCN, was used in the next step without any work-up or purification: UPLC-MS: $t_R$=1.68 min (generic method); MS (ESI) m/z calcd for $C_{12}H_9F_4N_2O_2$ (M+H)$^+$: 289.1, found: 289.1.

[126] N-(1,3-Benzodioxol-5-yl)-3-[4-fluoro-5-methyl-3-(trifluoromethyl)pyrazol-1-yl]-N-methylbenzamide Following general procedure 1c, the title compound was obtained from Int-1.61, after purification by silica gel flash-column chromatography with DCM/EtOAc (95:5) as the eluent, as a beige solid in 45% yield: $^1$H NMR (400 MHz, DMSO-d$_6$) δ 7.54-7.40 (m, 4H), 6.97 (d, J=2.2 Hz, 1H), 6.76 (d, J=8.3 Hz, 1H), 6.64 (dd, J=8.3, 2.2 Hz, 1H), 5.99 (s, 2H), 3.32 (s, 3H), 2.11 (s, 3H); UPLC-MS: $t_R$=1.29 min (apolar method); MS (ESI) m/z calcd for $C_{20}H_{16}F_4N_3O_3$ (M+H)$^+$: 422.1, found: 422.1.

[127] N-(6-Chloro-1,3-benzodioxol-5-yl)-3-[4-chloro-5-methyl-3-(trifluoromethyl)pyrazol-1-yl]benzamide Following general procedure 1b, the title compound was obtained from compound 128, after purification by silica gel flash-column chromatography with Cyclohexane/EtOAc (85/15) as the eluent, as a yellow solid in 30% yield: $^1$H NMR (400 MHz, DMSO-d$_6$) δ 10.15 (s, 1H), 8.24-8.06 (m, 2H), 7.87 (ddd, J=8.0, 2.1, 1.2 Hz, 1H), 7.76 (app-t, J=8.1 Hz, 1H), 7.19 (s, 1H), 7.13 (s, 1H), 6.12 (s, 2H), 2.37 (s, 3H). UPLC-MS: $t_R$=2.60 min (Generic method); MS (ESI) m/z calcd for $C_{19}H_{13}Cl_2F_3N_3O_3$ (M+H)$^+$: 458.0, found: 458.1.

[128] N-(1,3-Benzodioxol-5-yl)-3-[4-chloro-5-methyl-3-(trifluoromethyl)pyrazol-1-yl]benzamide Following general procedure 1c, the title compound was obtained Int-1.2, after purification by silica gel flash-column chromatography with Cyclohexane/EtOAc (70/30) as the eluent, as a white solid in 66% yield: $^1$H NMR (400 MHz, DMSO-d$_6$) δ 10.28 (s, 1H), 8.15-8.08 (m, 2H), 7.84 (app-dt, J=8.0, 1.4 Hz, 1H), 7.75 (app-t, J=8.1 Hz, 1H), 7.43 (d, J=2.1 Hz, 1H), 7.18 (dd, J=8.4, 2.1 Hz, 1H), 6.91 (d, J=8.4 Hz, 1H), 6.02 (s, 2H), 2.36 (s, 3H). UPLC-MS: $t_R$=2.53 min (Generic method); MS (ESI) m/z calcd for $C_{19}H_{14}ClF_3N_3O_3$ (M+H)$^+$: 424.0, found: 424.1.

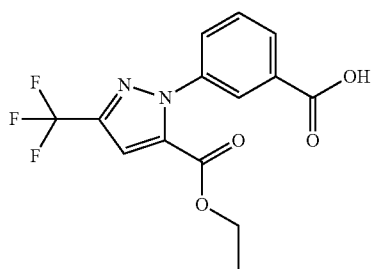 [SMILES: CCOC(=O)c1cc(C(F)(F)F)nn1-c1cccc(C(=O)O)c1]

[Int-1.62] 3-[5-ethoxycarbonyl-3-(trifluoromethyl)pyrazol-1-yl]benzoic acid

Following general procedure 1a, the title compound was obtained from ethyl 5,5,5-trifluoro-2,4-dioxopentanoate, after precipitation with water, as a yellow solid in 86% yield: UPLC-MS: $t_R$=1.77 min (Generic method); MS (ESI) m/z calcd for $C_{14}H_{10}F_3N_2O_4$ (M−H)$^-$: 327.1, found: 327.0.

[130] Ethyl 2-[3-[1,3-benzodioxol-5-yl(methyl)carbamoyl]phenyl]-5-(trifluoromethyl)pyrazole-3-carboxylate Following general procedure 1c, the title compound was obtained from Int-1.62, after purification by silica gel flash-column chromatography with Cyclohexane/EtOAc (70/30) as the eluent, as a pale yellow solid in 27% yield: $^1$H NMR (400 MHz, DMSO-d$_6$) δ 7.57 (bs, 1H), 7.53-7.45 (m, 2H), 7.43-7.36 (m, 2H), 6.94 (d, J=2.1 Hz, 1H), 6.77 (d, J=8.2 Hz, 1H), 6.67 (dd, J=8.2, 2.1 Hz, 1H), 5.99 (s, 2H), 4.18 (q, J=7.1 Hz, 2H), 3.32 (s, 3H), 1.13 (t, J=7.1 Hz, 3H). UPLC-MS: $t_R$=2.44 min (Generic method); MS (ESI) m/z calcd for $C_{22}H_{19}F_3N_3O_5$ (M+H)$^+$: 462.1, found: 462.1.

[135] 3-[4-Chloro-5-cyclopropyl-3-(trifluoromethyl)pyrazol-1-yl]-N-ethyl-N-(2-methyl-1,3-benzoxazol-6-yl)benzamide Following general procedure 1d, the title compound was obtained from Int-136, upon treatment with iodoethane, after purification by silica gel flash-column chromatography with DCM/EtOAc (9:1) as the eluent, as a white solid in 47% yield: $^1$H NMR (400 MHz, DMSO-d$_6$) δ 7.64 (d, J=1.9 Hz, 1H), 7.56-7.46 (m, 3H), 7.46-7.34 (m, 2H), 7.17 (dd, J=8.4, 1.9 Hz, 1H), 3.91 (q, J=7.1 Hz, 2H), 2.56 (s, 3H), 1.74-1.58 (m, 1H), 1.13 (t, J=7.1 Hz, 3H), 0.61-0.49 (m, 2H), 0.41-0.30 (m, 2H); UPLC-MS: $t_R$=1.59 min (apolar method); MS (ESI) m/z calcd for $C_{24}H_{21}ClF_3N_4O_2$ (M+H)$^+$: 489.1, found: 489.2.

[Int-136] 3-[4-Chloro-5-cyclopropyl-3-(trifluoromethyl)pyrazol-1-yl]-N-(2-methyl-1,3-benzoxazol-6-yl)benzamide Following general procedure 1c, the title compound was obtained from Int-1.53, after purification by silica gel flash-column chromatography with cyclohexane/EtOAc (1:1) as the eluent, as a white solid in 96% yield: $^1$H NMR (400 MHz, DMSO-d$_6$) δ 10.57 (s, 1H), 8.25-8.19 (m, 2H), 8.15 (app-dt, J=7.7, 1.3 Hz, 1H), 7.93 (ddd, J=8.0, 2.2, 1.0 Hz, 1H), 7.77 (app-t, J=7.9 Hz, 1H), 7.63 (app-s, 2H), 2.60 (s, 3H), 2.06 (tt, J=8.5, 5.3 Hz, 1H), 0.98-0.82 (m, 2H), 0.73-0.59 (m, 2H); UPLC-MS: $t_R$=1.60 min (apolar method); MS (ESI) m/z calcd for $C_{22}H_{17}ClF_3N_4O_2$ (M+H)$^+$: 461.1, found: 461.1.

[137] 3-[4-Chloro-5-cyclopropyl-3-(trifluoromethyl)pyrazol-1-yl]-N-methyl-N-(2-methyl-1,3-benzoxazol-6-yl)benzamide Following general procedure 1d, the title compound was obtained from Int-136, after purification by silica gel flash-column chromatography with DCM/EtOAc (8:2) as the eluent, as a white solid in 92% yield: $^1$H NMR (400 MHz, DMSO-d$_6$) δ 7.66 (d, J=1.9 Hz, 1H), 7.56-7.47 (m, 3H), 7.46-7.36 (m, 2H), 7.21 (dd, J=8.4, 1.9 Hz, 1H), 3.42 (s, 3H), 2.56 (s, 3H), 1.68 (tt, J=8.7, 5.3 Hz, 1H), 0.69-0.50 (m, 2H),

[138] 3-[4-Chloro-5-cyclopropyl-3-(trifluoromethyl) pyrazol-1-yl]-N-(2-methyl-1,3-benzoxazol-6-yl)-N-(trideuteriomethyl)benzamide Following general procedure 1d, the title compound was obtained from Int-136, upon treatment with trideuterio(iodo) methane, after purification by silica gel flash-column chromatography with DCM/EtOAc (8:2) as the eluent, as a white solid in 85% yield: $^1$H NMR (400 MHz, DMSO-$d_6$) δ 7.66 (d, J=2.0 Hz, 1H), 7.58-7.46 (m, 3H), 7.46-7.35 (m, 2H), 7.21 (dd, J=8.4, 2.0 Hz, 1H), 2.56 (s, 3H), 1.67 (tt, J=8.6, 7.9, 3.9 Hz, 1H), 0.63-0.53 (m, 2H), 0.42-0.33 (m, 2H); UPLC-MS: $t_R$=1.42 min (apolar method); MS (ESI) m/z calcd for $C_{23}D_3H_{16}ClF_3N_4O_2$ (M+H)$^+$: 478.1, found: 478.1.

[139] 3-[4-Chloro-5-cyclopropyl-3-(trifluoromethyl) pyrazol-1-yl]-N-(5-chloro-2-methyl-1,3-benzoxazol-6-yl)-N-methyl-benzamide Following general procedure 1b, the title compound was obtained from compound 137, after purification by preparative HPLC, as a white solid in 30% yield: $^1$H NMR (400 MHz, DMSO-$d_6$) δ 8.08 (s, 1H), 7.80 (s, 1H), 7.60-7.49 (m, 2H), 7.48-7.34 (m, 2H), 3.32 (s, 3H), 2.58 (s, 3H), 1.85-1.61 (m, 1H), 0.65-0.50 (m, 2H), 0.44-0.29 (m, 2H); UPLC-MS: $t_R$=1.68 min (apolar method); MS (ESI) m/z calcd for $C_{23}H_{18}Cl_2F_3N_4O_2$ (M+H)$^+$: 509.1, found: 509.1.

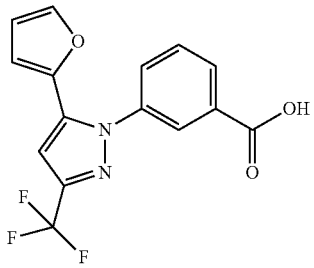 [SMILES: O=C(O)c1cccc(-n2nc(C(F)(F)F)cc2-c2ccco2)c1]

[Int-1.63] 3-[5-(2-Furyl)-3-(trifluoromethyl)pyrazol-1-yl]benzoic acid

Following general procedure 1a, the title compound was obtained 4,4,4-trifluoro-1-(2-furyl)butane-1,3-dione, after precipitation with water, as a yellow solid in 30% yield: UPLC-MS: $t_R$=1.80 min (Generic method); MS (ESI) m/z calcd for $C_{15}H_{10}F_3N_2O_3$ (M+H)$^+$: 323.0, found: 323.10.

[147] N-(1,3-Benzodioxol-5-yl)-3-[5-(2-furyl)-3-(trifluoromethyl)pyrazol-1-yl]-N-methyl-benzamide Following general procedure 1c, the title compound was obtained Int-1.63, after purification by silica gel flash-column chromatography with Cycohexane/EtOAc (50:50) as the eluent, as a white solid in 30% yield $^1$H NMR (400 MHz, DMSO-$d_6$) δ 7.75 (dd, J=1.8, 0.7 Hz, 1H), 7.53-7.34 (m, 4H), 7.22 (s, 1H), 6.93 (d, J=2.0 Hz, 1H), 6.77 (d, J=8.1 Hz, 1H), 6.64 (dd, J=8.1, 2.0 Hz, 1H), 6.51 (dd, J=3.5, 1.8 Hz, 1H), 5.96 (s, 2H), 5.87 (bs, 1H), 3.30 (s, 3H). UPLC-MS: $t_R$=2.52 min (Generic method); MS (ESI) m/z calcd for $C_{23}H_{17}F_3N_3O_4$ (M+H)$^+$: 456.1, found: 456.2.

[Int-153] 3-[4-Chloro-5-methyl-3-(trifluoromethyl)pyrazol-1-yl]-N-(5-fluoro-2-methyl-1,3-benzoxazol-6-yl)benzamide Following the general procedure 1d, the title compound was prepared from Int-1.2 and 5-fluoro-2-methyl-1,3-benzoxazol-6-amine. Subsequent flash chromatography, eluting a gradient of 100% Cyclohexane to 50% AcOEt in Cyclohexane, afforded the title compound as white solid in 42% yield. $^1$H NMR (400 MHz, DMSO-$d_6$) δ 10.40 (s, 1H), 8.20-8.15 (m, 2H), 7.97 (d, J=6.4 Hz, 1H), 7.91-7.85 (m, 2H), 7.78 (app-t, J=8.2 Hz, 1H), 7.67 (d, J=10.0 Hz, 1H), 2.63 (s, 3H), 2.37 (s, 3H). UPLC-MS: $t_R$=2.24 (Generic method); MS (ESI) m/z calcd for $C_{20}H_{12}ClF_4N_4O_2$ (M–H)$^-$: 451.1 found: 451.1.

[154] 3-[4-Chloro-5-methyl-3-(trifluoromethyl)pyrazol-1-yl]-N-(5-fluoro-2-methyl-1,3-benzoxazol-6-yl)-N-methyl-benzamide Following the general procedure 1d, the title compound was prepared from Int-153. Subsequent silica gel flash chromatography, eluting a gradient of 100% Cyclohexane to 20% AcOEt in Cyclohexane, afforded the title compound as white solid in 82% yield. $^1$H NMR (400 MHz, DMSO-d6) δ 7.98 (d, J=6.6 Hz, 1H), 7.58-7.39 (m, 5H), 3.37 (s, 3H), 2.59 (s, 3H), 2.04 (s, 3H). UPLC-MS: $t_R$=2.16 min (Generic method); MS (ESI) m/z calcd for $C_{21}H_{16}ClF_4N_4O_2$(M+H)$^+$: 467.1, found: 467.2.

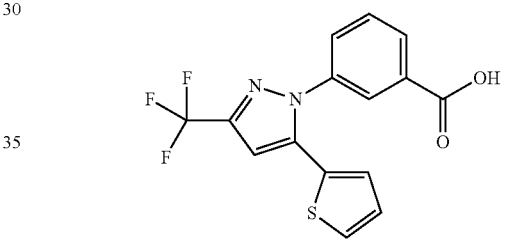

[Int-1.64] 3-[5-(2-Thienyl)-3-(trifluoromethyl)pyrazol-1-yl]benzoic acid

Following general procedure 1a, the title compound was obtained from 3-hydrazinobenzoic acid, after purification by trituration with $H_2O$ as the solvent, as a brown solid in 56% yield: $^1$H NMR (400 MHz, DMSO-$d_6$) δ 13.33 (br s, 1H), 8.11 (app-dt, J=7.6, 1.5 Hz, 1H), 7.96 (app-t, J=1.9 Hz, 1H), 7.78-7.73 (m, 1H), 7.71-7.64 (m, 2H), 7.33 (s, 1H), 7.23 (dd, J=3.7, 1.2 Hz, 1H), 7.10 (dd, J=5.1, 3.7 Hz, 1H); UPLC-MS: $t_R$=1.79 min (generic method); MS (ESI) m/z calcd for $C_{15}H_{10}F_3N_2O_2S$ (M+H)$^+$: 339.0, found: 339.4.

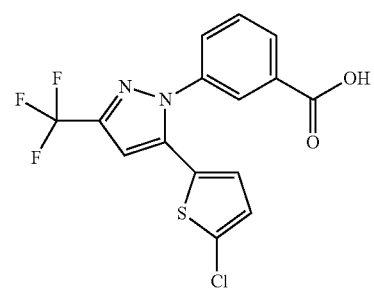 [SMILES: O=C(O)c1cccc(-n2nc(C(F)(F)F)cc2-c2ccc(Cl)s2)c1]

[Int-1.65] 3-[5-(5-Chloro-2-thienyl)-3-(trifluoromethyl) pyrazol-1-yl]benzoic acid Following general procedure 1b, the title compound was obtained from Int-1.64. A mixture of SM/product was obtained and used in the next step without any purification: UPLC-MS: $t_R$=1.79 min (generic method); MS (ESI) m/z calcd for $C_{15}H_9ClF_3N_2O_2S$ (M+H)$^+$: 373.0, found: 373.0.

[164] N-(1,3-Benzodioxol-5-yl)-3-[5-(5-chloro-2-thienyl)-3-(trifluoromethyl)pyrazol-1-yl]-N-methyl-benzamide Following general procedure 1c, the title compound was obtained from Int-1.65 and Int-1.32, after purification by preparative HPLC, as a pale pink solid in 65% yield: $^1$H NMR (400 MHz, DMSO-d$_6$) δ 7.53-7.36 (m, 4H), 7.34 (s, 1H), 7.12 (d, J=4.0 Hz, 1H), 7.01 (d, J=4.0 Hz, 1H), 6.96 (d, J=2.1 Hz, 1H), 6.73 (d, J=8.2 Hz, 1H), 6.61 (dd, J=8.2, 2.1 Hz, 1H), 5.95 (s, 2H), 3.30 (s, 3H); UPLC-MS: $t_R$=1.69 min (apolar method); MS (ESI) m/z calcd for $C_{23}H_{16}ClF_3N_3O_3S$ (M+H)$^+$: 506.1, found: 506.5.

[165] N-(1,3-Benzodioxol-5-yl)-3-[4-chloro-5-cyclopropyl-3-(trifluoromethyl)pyrazol-1-yl]benzamide Following general procedure 1c, the title compound was obtained from Int-1.53, after purification by silica gel flash-column chromatography with cyclohexane/EtOAc (7:3) as the eluent, as a beige solid in 92% yield: $^1$H NMR (400 MHz, DMSO-d$_6$) δ 10.27 (s, 1H), 8.17 (app-t, J=1.9 Hz, 1H), 8.10 (app-dt, J=7.8, 1.4 Hz, 1H), 7.90 (ddd, J=8.0, 2.2, 1.1 Hz, 1H), 7.74 (app-t, J=7.9 Hz, 1H), 7.43 (d, J=2.1 Hz, 1H), 7.19 (dd, J=8.4, 2.1 Hz, 1H), 6.91 (d, J=8.4 Hz, 1H), 6.01 (s, 2H), 2.16-1.93 (m, 1H), 1.00-0.81 (m, 2H), 0.75-0.54 (m, 2H); UPLC-MS: $t_R$=1.66 min (apolar method); MS (ESI) m/z calcd for $C_{21}H_{16}ClF_3N_3O_3$ (M+H)$^+$: 450.1, found: 450.2.

[166] N-(1,3-Benzodioxol-5-yl)-N-methyl-3-[5-(2-thienyl)-3-(trifluoromethyl)pyrazol-1-yl]benzamide Following general procedure 1c, the title compound was obtained from Int-1.64 and Int-1.34, after purification by silica gel flash-column chromatography with cyclohexane/EtOAc (7:3) as the eluent, as a white solid in 54% yield: $^1$H NMR (400 MHz, DMSO-d$_6$) δ 7.63 (dd, J=5.0, 1.2 Hz, 1H), 7.50-7.30 (m, 4H), 7.27 (s, 1H), 7.06 (dd, J=5.0, 3.6 Hz, 1H), 7.04-7.00 (m, 1H), 6.91 (d, J=2.1 Hz, 1H), 6.77 (d, J=8.2 Hz, 1H), 6.62 (dd, J=8.2, 2.1 Hz, 1H), 5.96 (s, 2H), 3.29 (s, 3H); UPLC-MS: $t_R$=1.34 min (apolar method); MS (ESI) m/z calcd for $C_{23}H_{17}F_3N_3O_3S$ (M+H)$^+$: 472.1, found: 472.5.

Procedure 1e

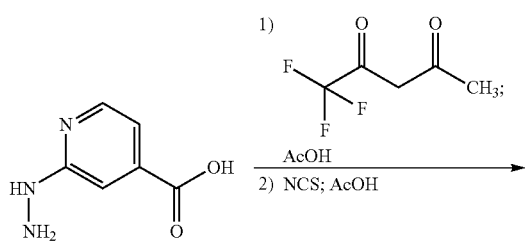

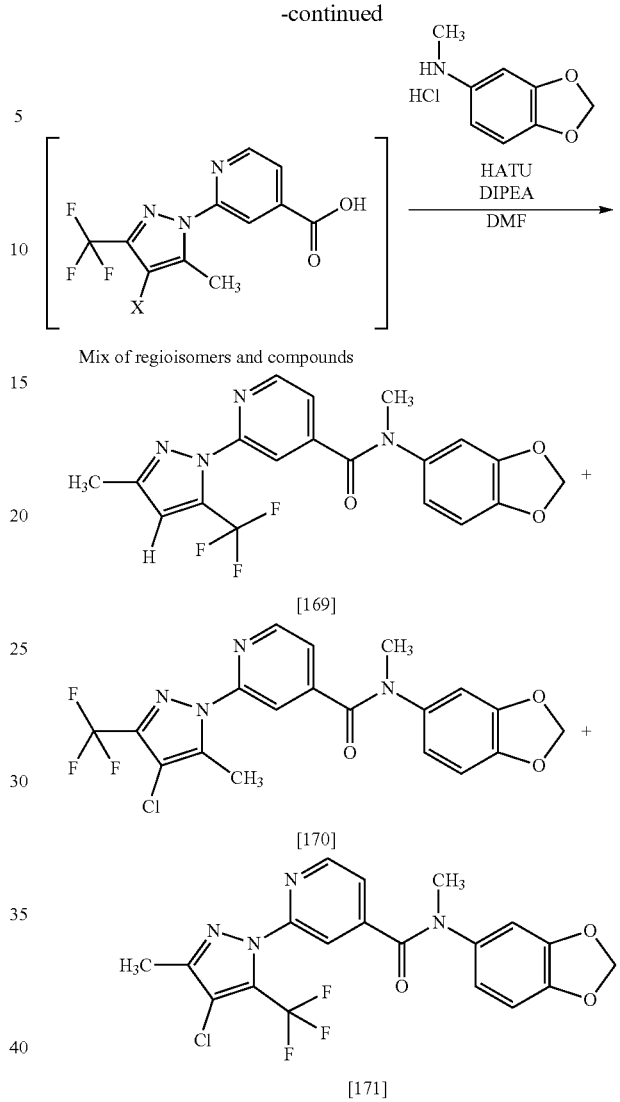

[169] N-(1,3-Benzodioxol-5-yl)-N-methyl-2-[3-methyl-5-(trifluoromethyl)pyrazol-1-yl]pyridine-4-carboxamide To a suspension of 2-hydrazinopyridine-4-carboxylic acid (200 mg, 1.31 mmol) in AcOH (5 mL), 1,1,1-trifluoropentane-2,4-dione (174.3 µL, 1.1 mmol) was added and mixture stirred at room temperature for 3 h and refluxed for 18 h. Solution was cooled to room temperature and was heated at 90° C. until complete dissolution. Then, the mixture was cooled to room temperature and water (10 mL) was added, with the formation of a precipitate. The solid was filtered, dried and dissolved in AcOH (2 mL). NCS (99.2 mg, 0.74 mmol) was added to the solution and mixture stirred for 18 h. Water (10 mL) was added again, with the formation of a precipitate. The precipitate was filtered, dried under vacuum. Solid was dissolved in DMF (2 mL) and HATU (87.1 mg, 0.46 mmol), DIPEA (161.8 µL, 0.93 mmol) and N-methyl-1,3-benzodioxol-5-amine hydrochloride (87.1 mg, 0.46 mmol) were added. Mixture was stirred at room temperature for 16 h and diluted with Et$_2$O (15 mL). Organic layer was washed with sat. aq. NH$_4$C$_{1-}$(20 mL), water (20 mL) and brine (20 mL). Solvent was dried with Na$_2$SO$_4$, filtered and evaporated. The title compound was obtained, after purification with preparative LC/MS, as a white solid with 19% of yield: $^1$H NMR (400 MHz, DMSO-d$_6$) δ 8.40-8.31 (m, 1H), 7.93-7.81 (m, 1H), 7.68 (d, J=8.5 Hz, 1H), 7.07-6.96 (m, 2H), 6.78 (d, J=8.2 Hz, 1H), 6.69 (dd, J=8.2, 2.1 Hz, 1H), 5.99 (s, 2H), 3.34 (s, 3H), 2.29 (s, 3H). UPLC-MS: t$_R$=2.25 min (Generic method); MS (ESI) m/z calcd for C$_{19}$H$_{16}$F$_3$N$_4$O$_3$ (M+H)$^+$: 405.1, found: 405.5.

[170] N-(1,3-Benzodioxol-5-yl)-2-[4-chloro-3-methyl-5-(trifluoromethyl)pyrazol-1-yl]-N-methyl-pyridine-4-carboxamide Following procedure 1e, the title compound was obtained as by product of compound 169, after purification with preparative LC/MS, as a white solid with 21% of yield: $^1$H NMR (400 MHz, DMSO-d$_6$) δ 8.38 (s, 1H), 7.94 (d, J=8.4 Hz, 1H), 7.65 (d, J=8.4 Hz, 1H), 7.01 (d, J=2.1 Hz, 1H), 6.77 (d, J=8.2 Hz, 1H), 6.69 (dd, J=8.2, 2.1 Hz, 1H), 5.99 (s, 2H), 3.35 (s, 3H), 2.28 (s, 3H). UPLC-MS: t$_R$=2.42 min (Generic method); MS (ESI) m/z calcd for C$_{19}$H$_{15}$ClF$_3$N$_4$O$_3$ (M+H)$^+$: 439.1, found: 439.5.

[171] N-(1,3-Benzodioxol-5-yl)-2-[4-chloro-5-methyl-3-(trifluoromethyl)pyrazol-1-yl]-N-methyl-pyridine-4-carboxamide Following procedure 1e, the title compound was obtained as by product of compound 169, after purification with preparative LC/MS, as a white solid with 21% of yield: $^1$H NMR (400 MHz, DMSO-d$_6$) δ 8.50-8.41 (m, 1H), 7.93 (d, J=8.5 Hz, 1H), 7.74 (d, J=8.5 Hz, 1H), 7.03 (d, J=2.1 Hz, 1H), 6.79 (d, J=8.2 Hz, 1H), 6.70 (dd, J=8.2, 2.1 Hz, 1H), 6.00 (s, 3H), 3.35 (s, 3H), 2.55 (s, 3H). UPLC-MS: t$_R$=2.54 min (Generic method); MS (ESI) m/z calcd for C$_{19}$H$_{15}$ClF$_3$N$_4$O$_3$ (M+H)$^+$: 439.1, found: 439.5.

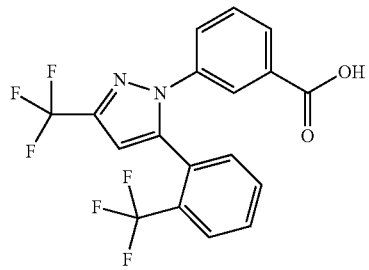 [SMILES: O=C(O)c1cccc(-n2nc(C(F)(F)F)cc2-c2ccccc2C(F)(F)F)c1]

[Int-1.66] 3-[3-(Trifluoromethyl)-5-[2-(trifluoromethyl) phenyl]pyrazol-1-yl]benzoic acid Following general procedure 1a, the title compound was obtained from 3-hydrazinobenzoic acid, after purification by trituration with H$_2$O as the solvent, as a beige solid in 63% yield: $^1$H NMR (400 MHz, DMSO-d$_6$) δ 13.19 (br s, 1H), 7.94-7.83 (m, 2H), 7.79 (app-t, J=1.9 Hz, 1H), 7.74-7.67 (m, 2H), 7.65-7.57 (m, 1H), 7.56-7.42 (m, 2H), 7.17 (s, 1H); UPLC-MS: t$_R$=1.74 min (generic method); MS (ESI) m/z calcd for C$_{15}$H$_{11}$F$_6$N$_2$O$_2$ (M+H)$^+$: 401.1, found: 401.1.

[176] N-(1,3-Benzodioxol-5-yl)-N-methyl-3-[3-(trifluoromethyl)-5-[2-(trifluoromethyl)phenyl]pyrazol-1-yl]benzamide Following general procedure 1c, the title compound was obtained from Int-1.66 and Int-1.34, after purification by silica gel flash-column chromatography with cyclohexane/EtOAc (7:3) as the eluent, as a white solid in 67% yield: $^1$H NMR (400 MHz, DMSO-d$_6$) δ 7.90 (dd, J=7.4, 1.8 Hz, 1H), 7.79-7.61 (m, 2H), 7.51-7.40 (m, 1H), 7.27 (d, J=2.2 Hz, 1H), 7.24-7.16 (m, 2H), 7.12 (s, 1H), 7.09 (app-dt, J=7.3, 2.1 Hz, 1H), 6.82 (d, J=2.1 Hz, 1H), 6.71 (d, J=8.2 Hz, 1H), 6.40 (d, J=8.2 Hz, 1H), 6.00 (s, 2H), 3.25 (s, 3H); UPLC-MS: t$_R$=1.54 min (apolar method); MS (ESI) m/z calcd for C$_{26}$H$_{18}$F$_6$N$_3$O$_3$ (M+H)$^+$: 534.1, found: 534.5.

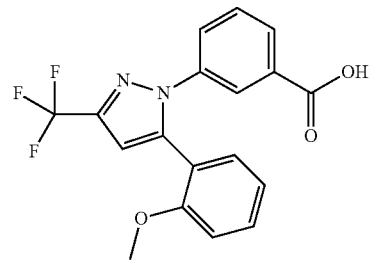 [SMILES: COc1ccccc1-c1cc(C(F)(F)F)nn1-c1cccc(C(=O)O)c1]

[Int-1.67] 3-[5-(2-Methoxyphenyl)-3-(trifluoromethyl) pyrazol-1-yl]benzoic acid

Following general procedure 1a, the title compound was obtained from 3-hydrazinobenzoic acid, after purification by trituration with H$_2$O as the solvent, as a beige solid in 86% yield: UPLC-MS: t$_R$=1.69 min (generic method); MS (ESI) m/z calcd for C$_{15}$H$_{14}$F$_3$N$_2$O$_3$ (M+H)$^+$: 363.1, found: 363.1.

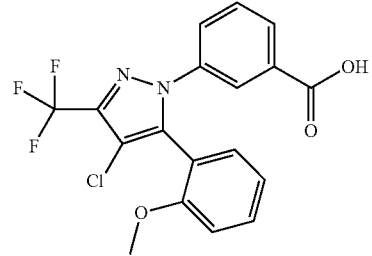 [SMILES: COc1ccccc1-c1c(Cl)c(C(F)(F)F)nn1-c1cccc(C(=O)O)c1]

[Int-1.68] 3-[4-Chloro-5-(2-methoxyphenyl)-3-(trifluoro methyl)pyrazol-1-yl]benzoic acid Following general procedure 1b, the title compound was obtained from Int-1.67, after purification by trituration with H$_2$O as the solvent, as a white solid in 91% yield: UPLC-MS: t$_R$=2.01 min (generic method); MS (ESI) m/z calcd for C$_{15}$H$_{13}$ClF$_3$N$_2$O$_3$ (M+H)$^+$: 397.1, found: 397.4.

[183] N-(1,3-Benzodioxol-5-yl)-3-[4-chloro-5-(2-methoxyphenyl)-3-(trifluoromethyl)pyrazol-1-yl]-N-methyl-benzamide Following general procedure 1c, the title compound was obtained from Int-1.68 and Int-1.34, after purification by silica gel flash-column chromatography with cyclohexane/EtOAc (7:3) as the eluent, as a white solid in 68% yield: $^1$H NMR (400 MHz, DMSO-d$_6$) δ 7.55-7.46 (m, 2H), 7.37 (app-s, 1H), 7.25-7.06 (m, 4H), 7.03 (d, J=8.6 Hz, 1H), 6.89 (d, J=2.1 Hz, 1H), 6.77 (d, J=8.2 Hz, 1H), 6.53 (dd, J=8.2, 2.1 Hz, 1H), 6.01 (s, 2H), 3.28-3.23 (m, 6H); UPLC-MS:

$t_R$=1.73 min (apolar method); MS (ESI) m/z calcd for $C_{26}H_{20}ClF_3N_3O_4$ (M+H)$^+$: 530.1, found: 530.5.

[184] N-(1,3-Benzodioxol-5-yl)-3-[5-(2-methoxyphenyl)-3-(trifluoromethyl)pyrazol-1-yl]-N-methylbenzamide Following general procedure 1c, the title compound was obtained from Int-1.67 and Int-1.34, after purification by silica gel flash-column chromatography with cyclohexane/EtOAc (7:3) as the eluent, as a white solid in 75% yield: $^1$H NMR (400 MHz, DMSO-d$_6$) δ 7.46 (app-td, J=7.9, 1.8 Hz, 1H), 7.36-7.27 (m, 2H), 7.24-6.95 (m, 6H), 6.86 (d, J=2.1 Hz, 1H), 6.78 (d, J=8.2 Hz, 1H), 6.51 (dd, J=8.2, 2.1 Hz, 1H), 6.01 (s, 2H), 3.31 (s, 3H), 3.26 (s, 3H); UPLC-MS: $t_R$=1.52 min (apolar method); MS (ESI) m/z calcd for $C_{26}H_{21}F_3N_3O_4$ (M+H)$^+$: 496.2, found: 496.5.

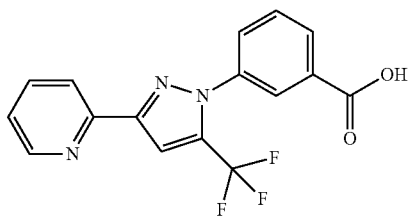 [SMILES: O=C(O)c1cccc(-n2nc(-c3ccccn3)cc2C(F)(F)F)c1]

[Int-1.69] 3-[3-(2-Pyridyl)-5-(trifluoromethyl)pyrazol-1-yl]benzoic acid

Following the general procedure 1a, the title compound was prepared from 3-hydrazinobenzoic acid and sodium 1,1,1-trifluoro-4-oxo-4-(pyridin-2-yl)but-2-en-2-olate, after purification by trituration with water, as a beige solid in 84% yield. UPLC-MS: $t_R$=2.29 min (Generic method); MS (ESI) m/z calcd for $C_{16}H_{11}F_3N_3O_2$ (M+H)$^+$: 334.1, found: 334.4.

[192] N-(1,3-benzodioxol-5-yl)-N-methyl-3-[3-(2-pyridyl)-5-(trifluoromethyl)pyrazol-1-yl]benzamide Following the general procedure 1c, the title compound was prepared from Int-1.69 and Int-1.34. Subsequent silica gel flash chromatography, eluting a gradient of 100% DCM to 20% AcOEt in DCM, afforded the title compound as white solid in 62% yield. $^1$H NMR (400 MHz, DMSO-d$_6$) δ 8.66 (ddd, J=4.9, 1.8, 1.0 Hz, 1H), 7.99 (dt, J=7.9, 1.1 Hz, 1H), 7.91 (td, J=7.7, 1.8 Hz, 1H), 7.58 (s, 1H), 7.55-7.45 (m, 4H), 7.43 (ddd, J=7.5, 4.8, 1.2 Hz, 1H), 6.93 (d, J=2.1 Hz, 1H), 6.76 (dd, J=8.2, 1.8 Hz, 1H), 6.63 (d, J=7.7 Hz, 1H), 5.97 (s, 2H), 3.33 (s, 3H). UPLC-MS: $t_R$=2.29 min (Generic method); MS (ESI) m/z calcd for $C_{24}H_{18}F_3N_4O_3$ (M+H)$^+$: 467.1, found: 467.5.

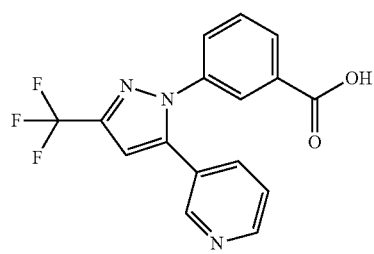

-continued

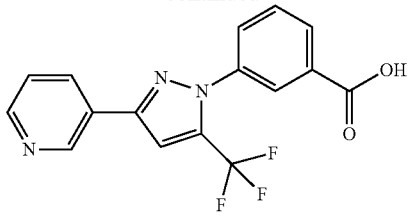

[Int-1.70 and Int-1.71] 3-[5-(3-Pyridyl)-3-(trifluoromethyl)pyrazol-1-yl]benzoic acid and 3-[3-(3-pyridyl)-5-(trifluoromethyl)pyrazol-1-yl]benzoic acid Following the general procedure 1a, the title compound was prepared from 3-hydrazinobenzoic acid and sodium 1,1,1-trifluoro-4-oxo-4-pyridin-3-ylbut-2-en-2-olate, after purification by trituration with water, as a mixture of regioisomers in 74% yield. UPLC-MS: $t_R$=1.52 min (Generic method); MS (ESI) m/z calcd for $C_{16}H_{11}F_3N_3O_2$ (M+H)$^+$: 334.1, found: 334.4.

[193] N-(1,3-Benzodioxol-5-yl)-N-methyl-3-[5-(3-pyridyl)-3-(trifluoromethyl)pyrazol-1-yl]benzamide Following the general procedure 1c, the title compound was prepared from the mixture of Int-1.70/Int-1.71 and Int-1.34. Subsequent silica gel flash chromatography, eluting a gradient of 100% DCM to 20% AcOEt in DCM, afforded the title compound as white solid in 52% yield. $^1$H NMR (600 MHz, DMSO-d$_6$) δ 8.59 (dd, J=4.8, 1.6 Hz, 1H), 8.45 (d, J=2.5 Hz, 1H), 7.50-7.44 (m, 1H), 7.42 (bs, 1H), 7.36 (dd, J=7.9, 4.8 Hz, 1H), 7.34 (s, 1H), 7.33-7.26 (m, 2H), 7.25-7.19 (m, 1H), 6.93 (d, J=2.1 Hz, 1H), 6.76 (d, J=8.2 Hz, 1H), 6.53 (d, J=8.2 Hz, 1H), 6.00 (s, 2H), 3.35 (s, 3H). UPLC-MS: $t_R$=2.16 min (Generic method); MS (ESI) m/z calcd for $C_{24}H_{18}F_3N_4O_3$ (M+H)$^+$: 467.1, found: 467.5.

[194] N-(1,3-Benzodioxol-5-yl)-N-methyl-3-[3-(3-pyridyl)-5-(trifluoromethyl)pyrazol-1-yl]benzamide The title compound was isolated from the slower eluting fraction of the flash chromatography of 193 as a white solid in 13% yield. $^1$H NMR (600 MHz, DMSO-d$_6$) δ 9.12 (dd, J=2.3, 0.8 Hz, 1H), 8.60 (dd, J=4.8, 1.7 Hz, 1H), 8.27 (dt, J=8.0, 1.9 Hz, 1H), 7.81 (s, 1H), 7.54-7.42 (m, 4H), 6.95 (d, J=2.1 Hz, 1H), 6.75 (d, J=8.2 Hz, 1H), 6.62 (d, J=8.2 Hz, 1H), 5.98 (s, 2H), 3.35 (s, 3H). UPLC-MS: $t_R$=2.14 min MS (ESI) m/z calcd for $C_{24}H_{18}F_3N_4O_3$ (M+H)$^+$: 467.1, found: 467.5.

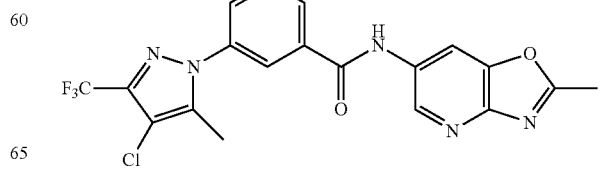

[Int-1.72] 3-[4-chloro-5-methyl-3-(trifluoromethyl)pyrazol-1-yl]-N-(2-methyloxazolo[4,5-b]pyridin-6-yl)benzamide Step 1. tert-butyl N-(2-methyloxazolo[4,5-b]pyridin-6-yl)carbamate: a flame-dried Schlenk tube was loaded with Pd$_2$(dba)$_3$ (77 mg, 0.084 mmol) and (5-diphenylphosphanyl-9,9-dimethyl-xanthen-4-yl)-diphenyl-phosphane (122 mg, 0.21 mmol). The vial was purged with nitrogen and toluene (26 mL) was added. The solution was allowed to stir for 15 min at rt. Following the order, tert-butyl carbamate (295 mg, 0.2.52 mmol), Cs$_2$CO$_3$ (1.36 g, 4.00 mmol) and 6-bromo-2-methyloxazolo[4,5-b]pyridine (450 mg, 2.10 mmol) were added and the mixture was degassed (vacuum/nitrogen 5-6 times) and put in the pre-heated bath. The resulting solution was stirred 16 h at 120° C., filtered over a short pad of Celite using AcOEt, and concentrated. The compound was obtained after purification by flash-column chromatography (alumina pH=7), eluting a gradient of 100% DCM to 10% of a solution of EtOH 20% in DCM, as a yellow solid in 23% yield. $^1$H NMR (400 MHz, DMSO-d$_6$) δ 9.79 (s, 1H), 8.40 (d, J=2.3 Hz, 1H), 8.24 (s, 1H), 2.63 (s, 3H), 1.49 (s, 9H).

column chromatography, eluting a gradient of 100% DCM to 50% AcOEt in DCM, as a yellowish solid in 18% yield: $^1$H NMR (400 MHz, DMSO-d$_6$) δ 10.80 (s, 1H), 8.72 (d, J=2.2 Hz, 1H), 8.59 (d, J=2.2 Hz, 1H), 8.20-8.16 (m, 2H), 7.93-7.87 (m, 1H), 7.83-7.76 (m, 1H), 2.67 (s, 3H), 2.37 (s, 3H). UPLC-MS: t$_R$=2.30 min (Generic method); MS (ESI) m/z calcd for C$_{19}$H$_{12}$ClF$_3$N$_5$O$_2$ (M−H)$^-$: 434.1, found: 434.4.

[261] 3-[4-Chloro-5-methyl-3-(trifluoromethyl)pyrazol-1-yl]-N-methyl-N-(2-methyloxazolo[4,5-b]pyridin-6-yl)benzamide following general procedure 1d, the title compound was obtained from compound Int-1.72, after purification by silica gel flash-column chromatography, eluting a gradient of DCM 100% to 40% TMBE in DCM, as a white solid in 67% yield: $^1$H NMR (400 MHz, DMSO-d$_6$) δ 8.31 (bs, 1H), 8.26 (d, J=2.2 Hz, 1H), 7.59-7.42 (m, 4H), 3.45 (s, 3H), 2.65 (s, 3H), 2.03 (bs, 3H). UPLC-MS: t$_R$=0.95 min (Apolar method); MS (ESI) m/z calcd for C$_{20}$H$_{16}$ClF$_3$N$_5$O$_2$ (M+H)$^+$: 450.1, found: 450.4.

GENERAL PROTOCOL 2

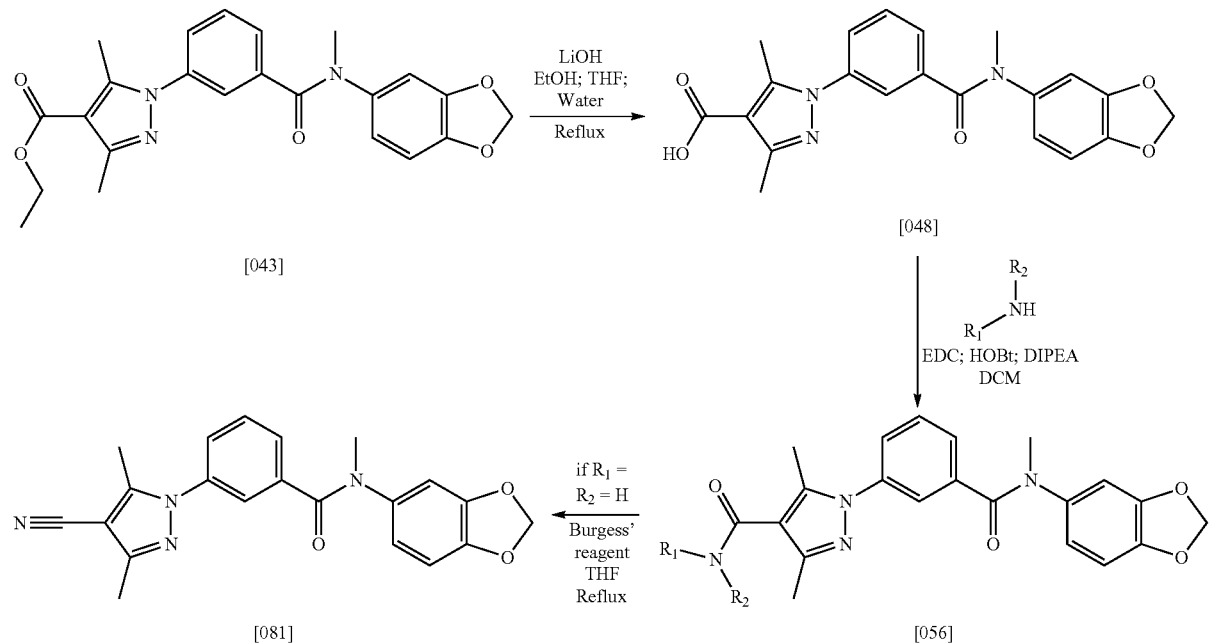

Step 2. 2-methyloxazolo[4,5-b]pyridin-6-amine: was dissolved in a solution of 10% TFA in DCM (1.0 mL) and stirred for 4 h. The solution was poured into a saturated aqueous solution of NaHCO$_3$ and extracted with AcOEt (3×). The organics were dried over Na$_2$SO$_4$, filtered and concentrated. The compound was obtained after purification by flash-column chromatography (alumina pH=7), eluting a gradient of 100% DCM to 20% of a solution of MeOH in DCM, as a yellow solid in 52% yield. $^1$H NMR (400 MHz, DMSO-d$_6$) δ 7.83 (d, J=2.4 Hz, 1H), 7.11 (d, J=2.4 Hz, 1H), 5.45 (bs, 2H), 2.53 (s, 3H).

Step 3 Following the general procedure 1c, the title compound was prepared from Int-1.2 and 2-methyloxazolo[4,5-b]pyridin-6-amine, after purification by silica gel flash- Procedure 2a

[048] 1-[3-[1,3-Benzodioxol-5-yl(methyl)carbamoyl]phenyl]-3,5-dimethyl-pyrazole-4-carboxylic acid To a solution of compound 043 (150.0 mg, 0.36 mmol) in a mixture of THF (10 mL) water (5 mL) and EtOH (5 mL), LiOH (17 mg, 0.71 mmol) was added. Mixture was refluxed for 5 h. After completion of the reaction mixture was cooled to room temperature and quenched with 1M HCl$_{aq}$ until pH 5/6. Aqueous layer was extracted with EtOAc (3×40 mL). Collected organic layers were washed with water (20 mL) and Brine (20 mL), dried over Na$_2$SO$_4$, filtered and solvent evaporated. The title compound was obtained, after purification by silica gel flash-column chromatography with DCM/EtOAc (40:60) as the eluent, as a white solid in 25% yield (35 mg, 0.09 mmol): $^1$H NMR (400 MHz, DMSO-$d_6$) δ 12.39 (bs, 1H), 7.49-7.31 (m, 4H), 6.95 (d, J=2.1 Hz, 1H), 6.78 (d, J=8.2 Hz, 1H), 6.65 (dd, J=8.1, 2.1 Hz, 1H), 5.98 (s, 2H), 3.32 (s, 3H), 2.33 (s, 3H), 2.23 (s, 3H). UPLC-MS: $t_R$=1.65 min (Generic method); MS (ESI) m/z calcd for $C_{21}H_{20}N_3O_5$ (M+H)$^+$: 394.1, found: 394.2.

Procedure 2b

[056] 1-[3-[1,3-Benzodioxol-5-yl(methyl)carbamoyl]phenyl]-3,5-dimethyl-pyrazole-4-carboxamide To a solution of compound 048 (100 mg, 0.25 mmol) in DCM (5 mL) Ammonium Chloride (17.7 mg, 0.33 mmol), DIPEA (110.7 μL, 0.64 mmol), HOBt (34.3 mg, 0.25 mmol), and EDC (53.6 mg, 0.28 mmol) were added. Mixture was stirred at room temperature for 18 h. Mixture was diluted with DCM (20 mL) and organic layer was washed with water (20 mL) and brine (20 mL). Solvent was dried over Na$_2$SO$_4$, filtered and evaporated. The title compound was obtained, after purification by silica gel flash-column chromatography with DCM/MeOH (95:5) as the eluent, as a white solid in 67% yield (66 mg, 0.17 mmol): $^1$H NMR (400 MHz, DMSO-$d_6$) δ 7.51-7.26 (m, 4H), 7.11 (bs, 2H), 6.95 (d, J=2.1 Hz, 1H), 6.77 (d, J=8.2 Hz, 1H), 6.65 (dd, J=8.2, 2.1 Hz, 1H), 5.98 (s, 2H), 3.32 (s, 3H), 2.30 (s, 3H), 2.17 (s, 3H). UPLC-MS: $t_R$=1.59 min (Generic method); MS (ESI) m/z calcd for $C_{21}H_{21}N_4O_4$ (M+H)$^+$: 393.1, found: 393.2.

Procedure 2c

[081] N-(1,3-Benzodioxol-5-yl)-3-(4-cyano-3,5-dimethyl-pyrazol-1-yl)-N-methyl-benzamide To a solution of compound 056 (95 mg, 0.25 mmol) in THF (5 mL), Burgess' reagent (78.9 mg, 0.33 mmol) was added. Mixture was stirred at reflux for 5 h. DCM (20 mL) was added and organic layer was washed with water (2×15 mL) and brine (2×15 mL). Solvent was evaporated. The title compound was obtained, after purification by preparative LC/MS, as a white solid in 25% yield (23.2 mg, 0.06 mmol): $^1$H NMR (600 MHz, DMSO-$d_6$) δ 7.50-7.36 (m, 4H), 6.97 (d, J=2.1 Hz, 1H), 6.77 (d, J=8.2 Hz, 1H), 6.63 (app-d, J=8.2 Hz, 1H), 5.99 (s, 2H), 3.32 (s, 3H), 2.29 (s, 3H), 2.20 (s, 3H). UPLC-MS: $t_R$=2.02 min (Generic method); MS (ESI) m/z calcd for $C_{21}H_{19}N_4O_3$ (M+H)$^+$: 375.1, found: 375.1.

[059] 1-[3-[1,3-Benzodioxol-5-yl(methyl)carbamoyl]phenyl]-N-(2-hydroxyethyl)-3,5-dimethyl-pyrazole-4-carboxamide Following general procedure 2b, the title compound was obtained from compound 048, after purification by silica gel flash-column chromatography with DCM/MeOH (95:5) as the eluent, as a white solid in 26% yield: $^1$H NMR (400 MHz, DMSO-$d_6$) δ 7.53 (t, J=5.6 Hz, 1H), 7.45-7.29 (m, 4H), 6.96 (d, J=2.1 Hz, 1H), 6.77 (d, J=8.2 Hz, 1H), 6.64 (dd, J=8.2, 2.1 Hz, 1H), 5.98 (s, 2H), 4.69 (t, J=5.4 Hz, 1H), 3.49 (q, J=6.0 Hz, 2H), 3.32 (s, 3H), 3.29 (q, J=6.0 Hz, 2H), 2.28 (s, 3H), 2.15 (s, 3H). UPLC-MS: $t_R$=1.54 min (Generic method); MS (ESI) m/z calcd for $C_{23}H_{25}N_4O_5$ (M+H)$^+$: 437.2, found: 437.3.

GENERAL PROTOCOL 3

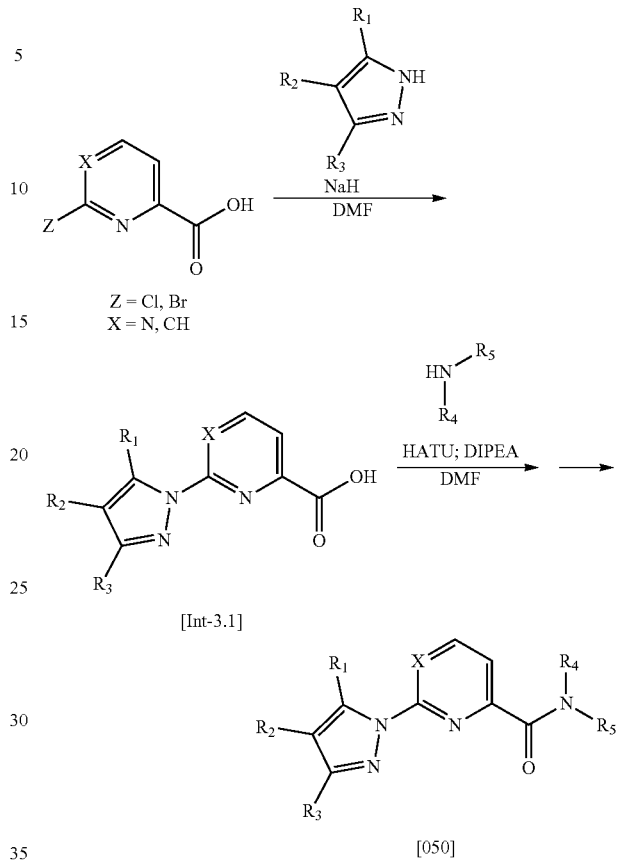

Procedure 3a

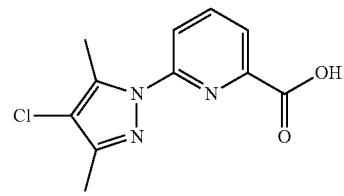 [SMILES: Cc1nn(-c2cccc(C(=O)O)n2)c(C)c1Cl]

[Int-3.1] 6-(4-Chloro-3,5-dimethyl-pyrazol-1-yl)pyridine-2-carboxylic acid

To a solution of 4-chloro-3,5-dimethyl-1H-pyrazole (181 mg, 1.39 mmol) in DMF (5 mL), NaH (60% dispersion in mineral oil, 64.8 mg, 1.62 mmol) was added. Mixture was stirred at room temperature for 30 min and methyl 6-bromopyridine-2-carboxylate (250 mg, 1.16 mmol) was added. Mixture was stirred for 4 h at 80° C. Mixture was quenched with sat. aq. NH$_4$Cl and aqueous layer was extracted with EtOAC (3×15 mL). Collected organic layers were washed with water (20 mL) and Brine (20 mL), dried over Na$_2$SO$_4$, filtered and solvent evaporated. The title compound was obtained, after purification by silica gel flash-column chromatography with Cyclohexane/EtOAc (60:40) as the eluent, as a yellow solid in 34% yield (100 mg, 0.40 mmol):

UPLC-MS: $t_R$=0.52 min (Generic method); MS (ESI) m/z calcd for $C_{22}H_{22}ClN_3O_2$ (M+H)$^+$: 252.0, found: 252.1.

[050] N-(1,3-Benzodioxol-5-yl)-6-(4-chloro-3,5-dimethyl-pyrazol-1-yl)-N-methyl-pyridine-2-carboxamide Following general procedure 1c, the title compound was obtained from Int-3.1, after purification by silica gel flash-column chromatography with DCM/EtOAc (80:20) as the eluent, as a pink solid in 26% yield over two steps: $^1$H NMR (400 MHz, DMSO-d$_6$) δ 7.94 (app-t, J=7.9 Hz, 1H), 7.70 (d, J=8.3 Hz, 1H), 7.43 (d, J=7.6 Hz, 1H), 6.92 (s, 1H), 6.72 (d, J=8.1 Hz, 1H), 6.57 (bs, 1H), 5.95 (s, 2H), 3.35 (s, 3H), 2.34 (bs, 3H), 2.19 (s, 3H). UPLC-MS: $t_R$=2.36 min (Generic method); MS (ESI) m/z calcd for $C_{29}H_{28}ClN_4O_3$ (M+H)$^+$: 385.1, found: 385.2.

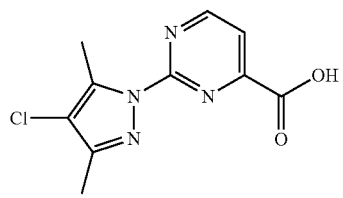 [SMILES: Cc1nn(-c2nccc(C(=O)O)n2)c(C)c1Cl]

[Int-3.2] 2-(4-Chloro-3,5-dimethyl-pyrazol-1-yl)pyrimidine-4-carboxylic acid

Following general procedure 3a, the title compound was obtained from 2-chloropyrimidine-4-carboxylic acid, as crude product in 15% yield: UPLC-MS: $t_R$=1.33 min (Generic method); MS (ESI) m/z calcd for $C_{10}H_{10}ClN_4O_2$ (M+H)$^+$: 253.0, found: 253.1.

[072] N-(1,3-Benzodioxol-5-yl)-2-(4-chloro-3,5-dimethyl-pyrazol-1-yl)-N-methyl-pyrimidine-4-carboxamide Following general procedure 1c, the title compound was obtained from Int-3.2, after purification by preparative LC/MS, as a white solid in 15% yield over two steps: $^1$H NMR (400 MHz, DMSO-d$_6$) δ 8.84 (d, J=5.0 Hz, 1H), 7.48 (d, J=5.0 Hz, 1H), 7.02 (d, J=2.1 Hz, 1H), 6.74 (d, J=8.2 Hz, 1H), 6.64 (dd, J=8.2, 2.1 Hz, 1H), 5.98 (s, 2H), 3.37 (s, 3H), 2.41 (s, 3H), 2.22 (s, 3H). UPLC-MS: $t_R$=2.13 min (Generic method); MS (ESI) m/z calcd for $C_{15}H_{17}ClN_5O_3$ (M+H)$^+$: 386.1, found: 386.1.

GENERAL PROTOCOL 4

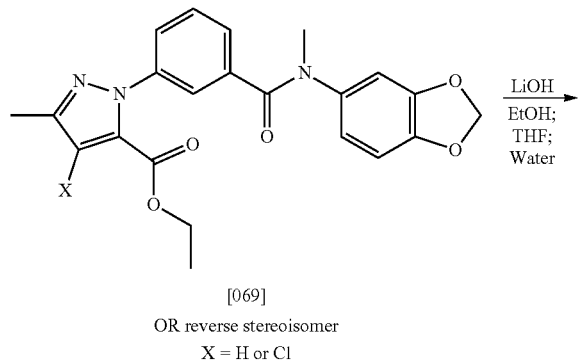

[069]

OR reverse stereoisomer
X = H or Cl

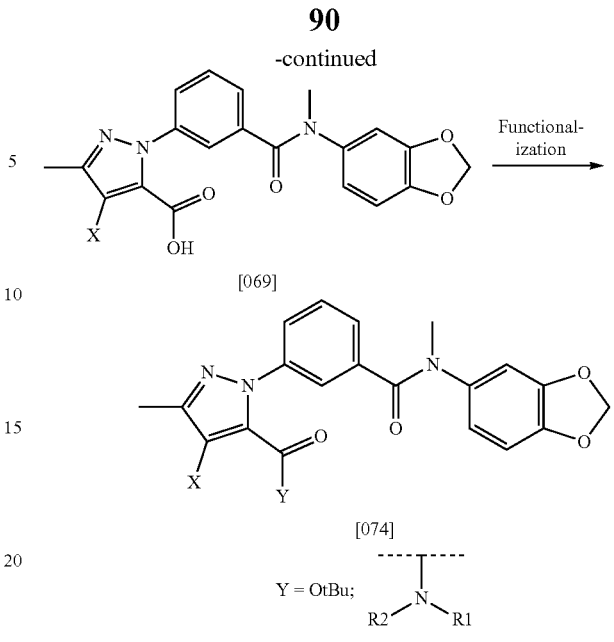

[069] 1-[3-[1,3-Benzodioxol-5-yl(methyl)carbamoyl]phenyl]-4-chloro-5-methyl-pyrazole-3-carboxylic acid To a solution of compound 067 (45.0 mg, 0.10 mmol) in THF (2 mL) and water (2 mL), LiOH (3.4 mg, 0.14 mmol) was added. Mixture was stirred at room temperature for 5 h and quenched with 2M HCl aq. solution until pH=4-5. Aqueous layer was extracted with EtOAc (3×15 mL). Collected organic layers were washed with Brine (20 mL) dried with Na$_2$SO$_4$, filtered and solvent evaporated. The title compound was obtained, as crude product, as a white solid in 92% yield (38.0 mg): $^1$H NMR (400 MHz, DMSO-d$_6$) δ 13.16 (s, 1H), 7.53-7.37 (m, 4H), 6.97 (d, J=2.1 Hz, 1H), 6.77 (d, J=8.3 Hz, 1H), 6.65 (dd, J=8.3, 2.1 Hz, 1H), 5.99 (s, 2H), 3.32 (s, 3H), 2.09 (s, 3H). UPLC-MS: $t_R$=1.46 min (Generic method); MS (ESI) m/z calcd for $C_{20}H_{17}ClN_3O_5$ (M+H)$^+$: 414.1, found: 414.2.

[074] 1-[3-[1,3-Benzodioxol-5-yl(methyl)carbamoyl]phenyl]-4-chloro-5-methyl-pyrazole-3-carboxamide Following general procedure 2b, the title compound was obtained from compound 069, after purification by silica gel flash-column chromatography with DCM/MeOH (95:5) as the eluent, as a white solid in 78% yield: $^1$H NMR (400 MHz, DMSO-d$_6$) δ 7.65-7.30 (m, 6H), 6.97 (d, J=2.1 Hz, 1H), 6.77 (d, J=8.2 Hz, 1H), 6.65 (dd, J=8.2, 2.1 Hz, 1H), 5.99 (s, 2H), 3.32 (s, 3H), 2.09 (s, 3H). UPLC-MS: $t_R$=1.88 min (Generic method); MS (ESI) m/z calcd for $C_{20}H_{18}ClN_4O_4$ (M+H)$^+$: 413.1, found: 413.1.

[083] 2-[3-[1,3-Benzodioxol-5-yl(methyl)carbamoyl]phenyl]-4-chloro-5-methyl-pyrazole-3-carboxylic acid Following general procedure 4a, the title compound was obtained from compound 075, after purification by silica gel flash-column chromatography with DCM/MeOH (95/5) as the eluent, as a white solid in 85% yield $^1$H NMR (400 MHz, DMSO-$d_6$) δ 13.81 (s, $^1$H), 7.48-7.21 (m, 4H), 6.93 (d, J=2.1 Hz, 1H), 6.75 (d, J=8.2 Hz, 1H), 6.60 (d, J=8.3 Hz, 1H), 5.99 (s, 2H), 3.30 (s, 3H), 2.24 (s, 3H). 2D-NOESY: No dipolar coupling between 2.25 and aromatics. UPLC-MS: $t_R$=1.42 min (Generic method); MS (ESI) m/z calcd for $C_{20}H_{17}ClN_3O_5$ (M+H)$^+$: 414.1, found: 414.1.

[084] 2-[3-[1,3-benzodioxol-5-yl(methyl)carbamoyl]phenyl]-4-chloro-5-methyl-pyrazole-3-carboxamide Following general procedure 2b, the title compound was obtained compound 083, after purification by silica gel flash-column chromatography with DCM/MeOH (95:5) as the eluent, as a white solid in 68% yield: $^1$H NMR (400 MHz, DMSO-$d_6$) δ 8.17 (s, 1H), 8.09-7.99 (m, 1H), 7.50 (app-t, J=1.8 Hz, 1H), 7.42-7.35 (m, 1H), 7.32 (app-t, J=7.8 Hz, 1H), 7.19 (app-d, J=7.5 Hz, 1H), 6.92 (d, J=2.1 Hz, 1H), 6.76 (d, J=8.2 Hz, 1H), 6.65-6.55 (m, 1H), 5.99 (s, 2H), 3.31 (s, 3H), 2.23 (s, 3H). UPLC-MS: $t_R$=1.88 min (Generic method); MS (ESI) m/z calcd for $C_{20}H_{18}ClN_4O_4$ (M+H)$^+$: 413.1, found: 413.1.

[085] 2-[3-[1,3-benzodioxol-5-yl(methyl)carbamoyl]phenyl]-4-chloro-N,5-dimethyl-pyrazole-3-carboxamide Following general procedure 2b, the title compound was obtained compound 083, after purification by silica gel flash-column chromatography with DCM/EtOAc (50:50) as the eluent, as a white solid in 83% yield: $^1$H NMR (400 MHz, DMSO-$d_6$) δ 8.71 (q, J=4.7 Hz, 1H), 7.51-7.46 (m, 1H), 7.37-7.26 (m, 2H), 7.18 (bs, 1H), 6.93 (d, J=2.1 Hz, 1H), 6.76 (d, J=8.3 Hz, 1H), 6.60 (dd, J=8.3, 2.1 Hz, 1H), 6.00 (s, 2H), 3.31 (s, 3H), 2.73 (d, J=4.7 Hz, 3H), 2.24 (s, 3H). UPLC-MS: $t_R$=1.88 min (Generic method); MS (ESI) m/z calcd for $C_{21}H_{20}ClN_4O_4$ (M+H)$^+$: 427.1, found: 427.1.

[088] 2-[3-[1,3-benzodioxol-5-yl(methyl)carbamoyl]phenyl]-4-chloro-N,N,5-trimethyl-pyrazole-3-carboxamide Following general procedure 2b, the title compound was obtained compound 083, after purification by silica gel flash-column chromatography with DCM/EtOAc (60:40) as the eluent, as a white solid in 83% yield: $^1$H NMR (400 MHz, DMSO-$d_6$) δ 7.43 (app-t, J=1.9 Hz, 1H), 7.38-7.29 (m, 1H), 7.29-7.18 (m, 2H), 6.93 (d, J=2.1 Hz, 1H), 6.76 (d, J=8.2 Hz, 1H), 6.61 (dd, J=8.2, 2.1 Hz, 1H), 5.98 (s, 2H), 3.31 (s, 3H), 2.95 (s, 3H), 2.72 (s, 3H), 2.25 (s, 3H). UPLC-MS: $t_R$=2.06 min (Generic method); MS (ESI) m/z calcd for $C_{22}H_{22}ClN_4O_4$ (M+H)$^+$: 441.1, found: 441.1.

[089] Tert-butyl 2-[3-[1,3-benzodioxol-5-yl(methyl)carbamoyl]phenyl]-4-chloro-5-methyl-pyrazole-3-carboxylate To a solution of compound 083 (55 mg, 0.13 mmol) in DCM (5 mL), under nitrogen, 2-tert-butyl-1,3-diisopropylisourea (66.6 mg, 0.33 mmol) was added. Mixture was stirred at refluxing temperature for 3 h and cooled to room temperature. Obtained precipitate was filtered over a short pad of celite, eluting with EtOAc. Filtrate was evaporated. The title compound was obtained, after purification by silica gel flash-column chromatography with Cyclohexane/EtOAc (70/30) as the eluent, as a white solid in 61% yield: $^1$H NMR (400 MHz, DMSO-$d_6$) δ 7.42 (bs, 1H), 7.38-7.32 (m, 2H), 7.29 (bs, 1H), 6.95 (d, J=2.1 Hz, 1H), 6.77 (d, J=8.2 Hz, 1H), 6.67 (dd, J=8.2, 2.1 Hz, 1H), 6.00 (s, 2H), 3.32 (s, 3H), 2.25 (s, 3H), 1.28 (s, 9H). UPLC-MS: $t_R$=2.63 min (Generic method); MS (ESI) m/z calcd for $C_{24}H_{25}ClN_3O_5$ (M+H)$^+$: 470.1, found: 470.2.

GENERAL PROTOCOL 5

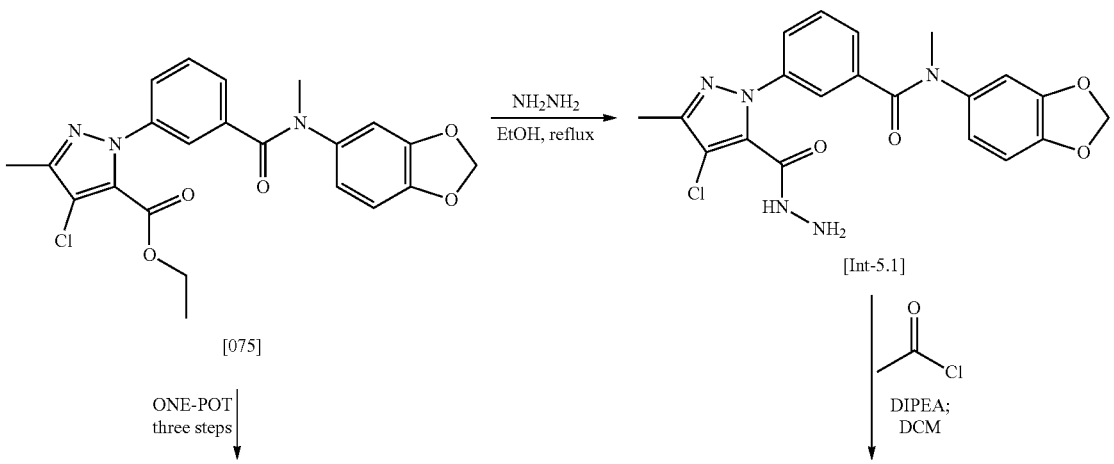

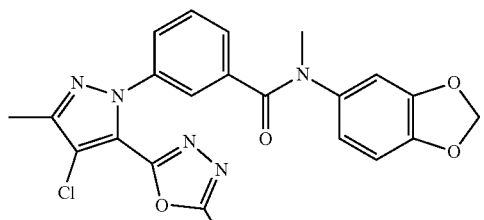 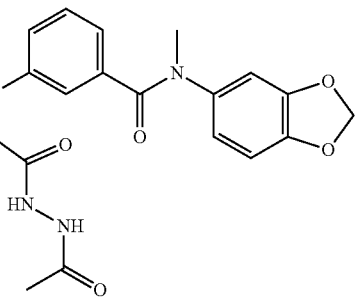

[129]                                       [Int-5.2]

Procedure 5a

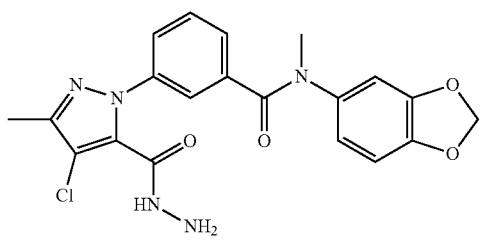 [SMILES: Cc1nn(-c2cccc(C(=O)N(C)c3ccc4c(c3)OCO4)c2)c(C(=O)NN)c1Cl]

[Int-5.1] N-(1,3-Benzodioxol-5-yl)-3-[4-chloro-5-(hydrazinecarbonyl)-3-methyl-pyrazol-1-yl]-N-methyl-benzamide To a solution of compound 075 (190 mg, 0.43 mmol) in EtOH (5 mL), hydrazine hydrate (0.5 mL) was added. Mixture was stirred at refluxing temperature for 8 h. Solvent was evaporated and the title compound was obtained, as crude product. UPLC-MS: $t_R$=0.65 min (Isocratic B2); MS (ESI) m/z calcd for $C_{20}H_{19}ClN_5O_4$ (M+H)$^+$: 428.1, found: 428.1.

Procedure 5b

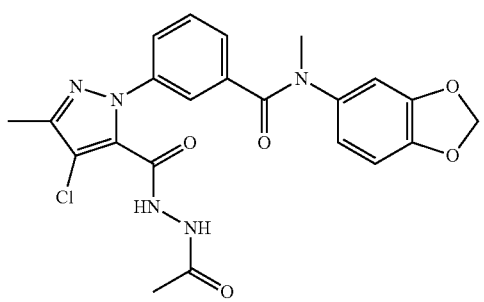 [SMILES: CC(=O)NNC(=O)c1c(Cl)c(C)nn1-c1cccc(C(=O)N(C)c2ccc3c(c2)OCO3)c1]

[Int-5.2] 3-[5-(acetamidocarbamoyl)-4-chloro-3-methyl-pyrazol-1-yl]-N-(1,3-benzodioxol-5-yl)-N-methyl-benzamide To a solution of Int-5.1 (187 mg, 0.42 mmol) in DCM (5 mL), DIPEA (63.1 µL, 0.89 mmol) and AcCl (155.5 µL, 0.89 mmol) was added. Mixture was stirred for 18 h and diluted with EtOH (5 mL). Mixture was quenched with 2M LiOH aq. sol. (4 mL). Mixture was stirred for 30 min. Layers were separated and aqueous layer extracted with DCM (4×10 mL). Collected organic layers were washed with brine, dried with Na$_2$SO$_4$, filtered and solvent evaporated. The title compound was obtained, as crude product. UPLC-MS: $t_R$=0.65 min (Isocratic B2); MS (ESI) m/z calcd for $C_{22}H_{21}ClN_5O_5$ (M+H)$^+$: 470.1, found: 470.1.

Procedure 5c

[129] N-(1,3-Benzodioxol-5-yl)-3-[4-chloro-3-methyl-5-(5-methyl-1,3,4-oxadiazol-2-yl)pyrazol-1-yl]-N-methyl-benzamide To a solution of Int-5.2 (185 mg, 0.13 mmol) in THF$_{dry}$ (5 mL), under Nitrogen, TEA (11 µL, 0.08 mmol), and Burgess' reagent (122 mg, 0.51 mmol) were added. Mixture was stirred at 50° C. for 5 h and cooled to room temperature. Mixture was diluted with DCM (20 mL) and organic layer was washed with sat. aq. NH$_4$Cl solution (10 mL), water (10 mL) and Brine (10 mL). organic layer was dried over Na$_2$SO$_4$, filtered ad solvent evaporated. The title compound was obtained, after purification by silica gel flash-column chromatography with DCM/EtOAc (50/50) as the eluent, as a white solid in 36% yield: $^1$H NMR (400 MHz, DMSO-d$_6$) δ 7.41 (s, 1H), 7.38-7.20 (m, 3H), 6.93 (d, J=2.1 Hz, 1H), 6.75 (d, J=8.2 Hz, 1H), 6.61 (dd, J=8.2, 2.1 Hz, 2H), 5.99 (s, 2H), 3.29 (s, 3H), 2.49 (s, 3H), 2.31 (s, 3H). UPLC-MS: $t_R$=2.12 min (Generic method); MS (ESI) m/z calcd for $C_{22}H_{19}ClN_5O_4$ (M+H)$^+$: 452.1, found: 452.2.

GENERAL PROTOCOL 6

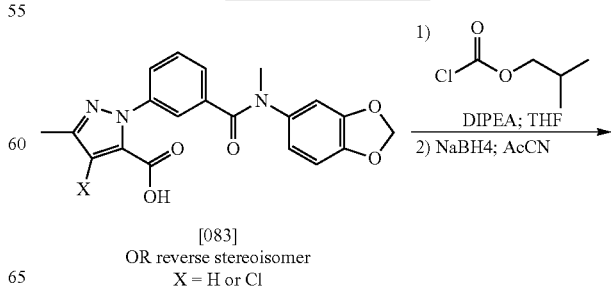

[083] OR reverse stereoisomer
X = H or Cl

-continued

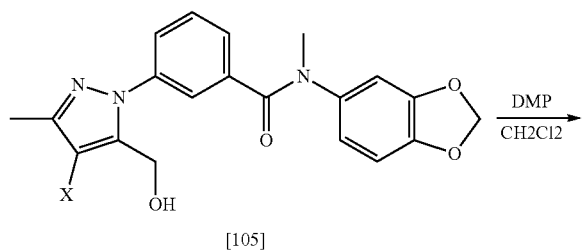

[105]

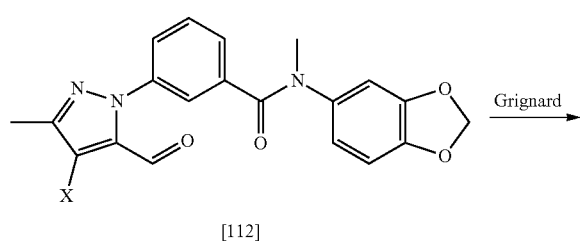

[112]

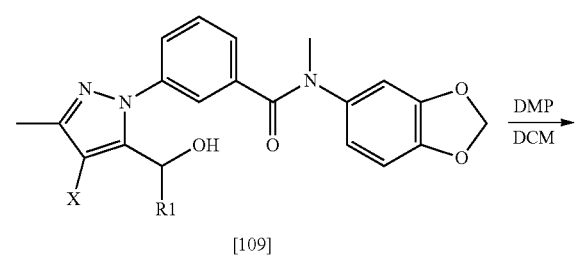

[109]

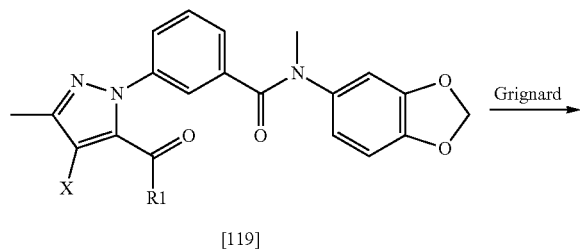

[119]

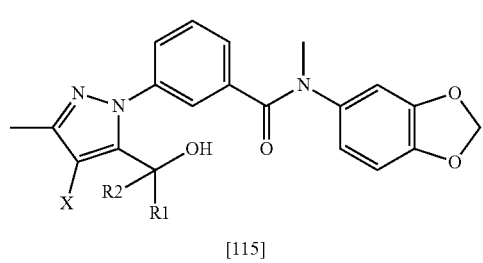

[115]

General Protocol 6a

[070] N-(1,3-Benzodioxol-5-yl)-3-[5-(hydroxymethyl)-3-methyl-pyrazol-1-yl]-N-methyl-benzamide To a solution of compound 065 (27.2 mg, 0.07 mmol) in THF (3 mL), DIPEA (17.49 μL, 0.1 mmol) and isobutyl chloroformiate (12 μL, 0.09 mmol) were added. Reaction mixture was stirred until complete formation of intermediate (2 h). Mixture was diluted with 6 mL of AcCN and $NaBH_4$ (13.6 mg, 0.36 mmol) was added. Mixture was stirred for 5 h at room temperature, and quenched with MeOH (5 mL). Solution was evaporated. Obtained solid was dissolved in water (5 mL) and EtOAc (5 mL). Layers were divided and aqueous layer was extracted with EtOAc (3×10 mL). Collected organic layers were washed with and Brine (10 mL), dried over $Na_2SO_4$, filtered and solvent evaporated. The title compound was obtained, after purification by silica gel flash-column chromatography with Cyclohexane/EtOAc (50/50) as the eluent, as a white solid in 55% yield (14 mg, 0.038 mmol): $^1$H NMR (400 MHz, DMSO-$d_6$) δ 7.55 (bs, $^1$H), 7.51 (d, J=8.4 Hz, 1H), 7.34 (t, J=7.8 Hz, 1H), 7.22 (d, J=7.6 Hz, 1H), 6.94 (d, J=2.1 Hz, 1H), 6.75 (d, J=8.2 Hz, 1H), 6.62 (dd, J=8.2, 1.8 Hz, 1H), 6.22 (s, 1H), 5.99 (s, 2H), 5.41 (t, J=5.5 Hz, 1H), 4.30 (d, J=5.5 Hz, 2H), 3.32 (s, 3H), 2.19 (s, 3H). UPLC-MS: $t_R$=1.69 min (Generic method); MS (ESI) m/z calcd for $C_{20}H_{20}N_3O_4$ (M+H)$^+$: 366.1, found: 366.2.

[073] N-(1,3-Benzodioxol-5-yl)-3-[4-chloro-3-(hydroxyl methyl)-5-methyl-pyrazol-1-yl]-N-methyl-benzamide Following general procedure 6a, the title compound was obtained from compound 069. After purification by silica gel flash-column chromatography with Cyclohexane/EtOAc (60/40) as the eluent, product was obtained as a white solid in 40% yield: $^1$H NMR (400 MHz, DMSO-$d_6$) δ 7.46-7.38 (m, 3H), 7.38-7.31 (m, 1H), 6.96 (d, J=2.1 Hz, 1H), 6.77 (d, J=8.2 Hz, 1H), 6.64 (dd, J=8.2, 2.1 Hz, 1H), 5.99 (s, 2H), 5.13 (t, J=5.6 Hz, 1H), 4.42 (d, J=5.6 Hz, 2H), 3.32 (s, 3H), 2.09 (s, 3H). UPLC-MS: $t_R$=1.95 min (Generic method); MS (ESI) m/z calcd for $C_{20}H_{19}ClN_3O_4$ (M+H)$^+$: 400.1, found: 400.1.

[105] N-(1,3-benzodioxol-5-yl)-3-[4-chloro-5-(hydroxyl methyl)-3-methyl-pyrazol-1-yl]-N-methyl-benzamide Following general procedure 6a, the title compound was obtained from compound 083, after purification by silica gel flash-column chromatography with Cyclohexane/EtOAc (50/50) as the eluent, as a white solid in 52% yield (150 mg): $^1$H NMR (400 MHz, DMSO-$d_6$) δ 7.66 (app-t, J=1.8 Hz, 1H), 7.63-7.55 (m, 1H), 7.38 (app-t, J=7.9 Hz, 1H), 7.27 (app-d, J=7.7 Hz, 1H), 6.94 (d, J=2.1 Hz, 1H), 6.77 (d, J=8.2 Hz, 1H), 6.63 (dd, J=8.2, 2.1 Hz, 1H), 6.00 (s, 2H), 5.59 (t, J=5.0 Hz, 1H), 4.32 (d, J=5.0 Hz, 2H), 3.33 (s, 3H), 2.22 (s, 3H). UPLC-MS: $t_R$=1.96 min (Generic method); MS (ESI) m/z calcd for $C_{20}H_{19}ClN_3O_4$ (M+H)$^+$: 400.1, found: 400.1.

General Protocol 6b

[112] N-(1,3-benzodioxol-5-yl)-3-(4-chloro-5-formyl-3-methyl-pyrazol-1-yl)-N-methyl-benzamide To a solution of compound 105 (1 g, 2.5 mmol) in DCM (30 mL), under Nitrogen, DMP (1.27 g, 3.0 mmol) was added. Mixture was stirred for 3 h and quenched with 30 mL of a 1:1 solution of sat. aq. $NaHCO_3$ and sat. aq. $Na_2S_2O_3$. Mixture was stirred for 30 min and layers were separated. Aqueous layer was washed with DCM (3×40 mL). Collected organic layers were washed with water (20 mL) and Brine (20 mL) dried with $Na_2SO_4$, filtered and solvent evaporated. The title compound was obtained, after purification by silica gel flash-column chromatography with Cyclohexane/EtOAc (60/40) as the eluent, as a white solid in 60% yield (605 mg): $^1$H NMR (400 MHz, DMSO-$d_6$) δ 9.45 (s, $^1$H), 7.59-7.36 (m, 4H), 6.95 (d, J=2.0 Hz, 1H), 6.76 (d, J=8.2 Hz, 1H), 6.62 (app-d, J=8.2 Hz, 1H), 6.02 (d, J=1.1 Hz, 2H), 3.32 (s, 3H), 2.28 (s, 3H). UPLC-MS: $t_R$=1.96 min (Generic method); MS (ESI) m/z calcd for $C_{20}H_{17}ClN_3O_4$ (M+H)$^+$: 398.1, found: 398.1.

General Protocol 6c

[109] N-(1,3-benzodioxol-5-yl)-3-[4-chloro-5-[(rac)-hydroxy(phenyl)methyl]-3-methyl-pyrazol-1-yl]-N-methyl-benzamide To a solution of compound 112 (30 mg, 0.08 mmol) in THF (3 mL), under Nitrogen, Phenyl Magnesium Bromide (3M solution in ether, 33 µL, 0.11 mmol) was added at −78° C. Mixture was stirred for 1 h at low temperature and quenched with 5 mL of sat. aq. $NH_4C_1$. Aqueous layer was washed with EtOAc (3×10 mL). Collected organic layers were washed with water (20 mL) and Brine (20 mL) dried with $Na_2SO_4$, filtered and solvent evaporated. The title compound was obtained, after purification by silica gel flash-column chromatography with Cyclohexane/EtOAc (60/40) as the eluent, as a white solid in 66% yield (25 mg): $^1$H NMR (400 MHz, DMSO-$d_6$) δ 7.44 (app-t, J=1.9 Hz, 1H), 7.36-7.14 (m, 6H), 7.11-7.02 (m, 2H), 6.86 (d, J=2.1 Hz, 1H), 6.67 (d, J=8.2 Hz, 1H), 6.54 (dd, J=8.2, 2.1 Hz, 1H), 6.33 (d, J=3.7 Hz, 1H), 5.91 (d, J=1.0 Hz, 1H), 5.88 (d, J=1.0 Hz, 1H), 5.73 (d, J=3.7 Hz, 1H), 3.29 (s, 3H), 2.17 (s, 3H). UPLC-MS: $t_R$=2.28 min (Generic method); MS (ESI) m/z calcd for $C_{26}H_{23}ClN_3O_4$ (M+H)$^+$: 476.1, found: 476.1.

[114] N-(1,3-benzodioxol-5-yl)-3-[4-chloro-5-[(rac)-1-hydroxyethyl]-3-methyl-pyrazol-1-yl]-N-methyl-benzamide Following general procedure 6c, the title compound was obtained from compound 112, after purification by silica gel flash-column chromatography with Cyclohexane/EtOAc (70:30) as the eluent, as a white solid in 63% yield: $^1$H NMR (400 MHz, DMSO-$d_6$) δ 7.52-7.29 (m, 4H), 6.92 (d, J=2.1 Hz, 1H), 6.74 (d, J=8.2 Hz, 1H), 6.61 (dd, J=8.2, 2.1 Hz, 1H), 5.98 (app-q, J=1.0 Hz, 2H), 5.48 (d, J=3.8 Hz, 1H), 4.67-4.48 (m, 1H), 3.32 (s, 3H), 2.16 (s, 3H), 1.27 (d, J=6.7 Hz, 3H). UPLC-MS: $t_R$=1.99 min (Generic method); MS (ESI) m/z calcd for $C_{21}H_{21}ClN_3O_4$ (M+H)$^+$: 414.1, found: 414.1.

[115] N-(1,3-Benzodioxol-5-yl)-3-[4-chloro-5-(1-hydroxy-1-methyl-ethyl)-3-methyl-pyrazol-1-yl]-N-methyl-benzamide Following general procedure 6c, the title compound was obtained from compound 116, after purification by silica gel flash-column chromatography with DCM/EtOAc (70:30) as the eluent, as a white solid in 43% yield: $^1$H NMR (400 MHz, DMSO-$d_6$) δ 7.36-7.25 (m, 3H), 7.23 (s, 1H), 6.90 (d, J=2.1 Hz, 1H), 6.73 (d, J=8.3 Hz, 1H), 6.60 (dd, J=8.3, 2.1 Hz, 1H), 5.98 (s, 2H), 5.07 (s, 1H), 3.30 (s, 3H), 2.12 (s, 3H), 1.31 (s, 6H). UPLC-MS: $t_R$=2.07 min (Generic method); MS (ESI) m/z calcd for $C_{22}H_{23}ClN_3O_4$ (M+H)$^+$: 428.1, found: 428.1.

[116] 3-(5-Acetyl-4-chloro-3-methyl-pyrazol-1-yl)-N-(1,3-benzodioxol-5-yl)-N-methyl-benzamide Following general procedure 6b, the title compound was obtained from compound 114, after purification by silica gel flash-column chromatography with Cyclohexane/EtOAc (70:30) as the eluent, as a white solid in 98% yield: $^1$H NMR (400 MHz, DMSO-$d_6$) δ 7.44-7.22 (m, 4H), 6.90 (d, J=2.1 Hz, 1H), 6.75 (d, J=8.3 Hz, 1H), 6.62 (dd, J=8.3, 2.1 Hz, 1H), 3.30 (s, 3H), 2.38 (s, 3H), 2.25 (s, 3H). UPLC-MS: $t_R$=2.22 min (Generic method); MS (ESI) m/z calcd for $C_{21}H_{18}ClN_3O_4$ (M+H)$^+$: 412.1, found: 412.1.

[119] N-(1,3-benzodioxol-5-yl)-3-(5-benzoyl-4-chloro-3-methyl-pyrazol-1-yl)-N-methyl-benzamide Following general procedure 6b, the title compound was obtained from compound 109, after purification by silica gel flash-column chromatography with Cyclohexane/EtOAc (70:30) as the eluent, as a white solid in 54% yield: $^1$H NMR (400 MHz, DMSO-$d_6$) δ 7.81-7.77 (m, 2H), 7.75-7.67 (m, 1H), 7.59-7.51 (m, 2H), 7.35 (s, 1H), 7.25-7.17 (m, 2H), 7.13 (bs, 1H), 6.84 (d, J=2.1 Hz, 1H), 6.65 (d, J=8.2 Hz, 1H), 6.44 (t, J=8.2, 2.1 Hz, 1H), 5.99 (s, 2H), 3.25 (s, 3H), 2.31 (s, 3H). UPLC-MS: $t_R$=2.49 min (Generic method); MS (ESI) m/z calcd for $C_{26}H_{21}ClN_3O_4$ (M+H)$^+$: 474.1, found: 474.2.

GENERAL PROTOCOL 7

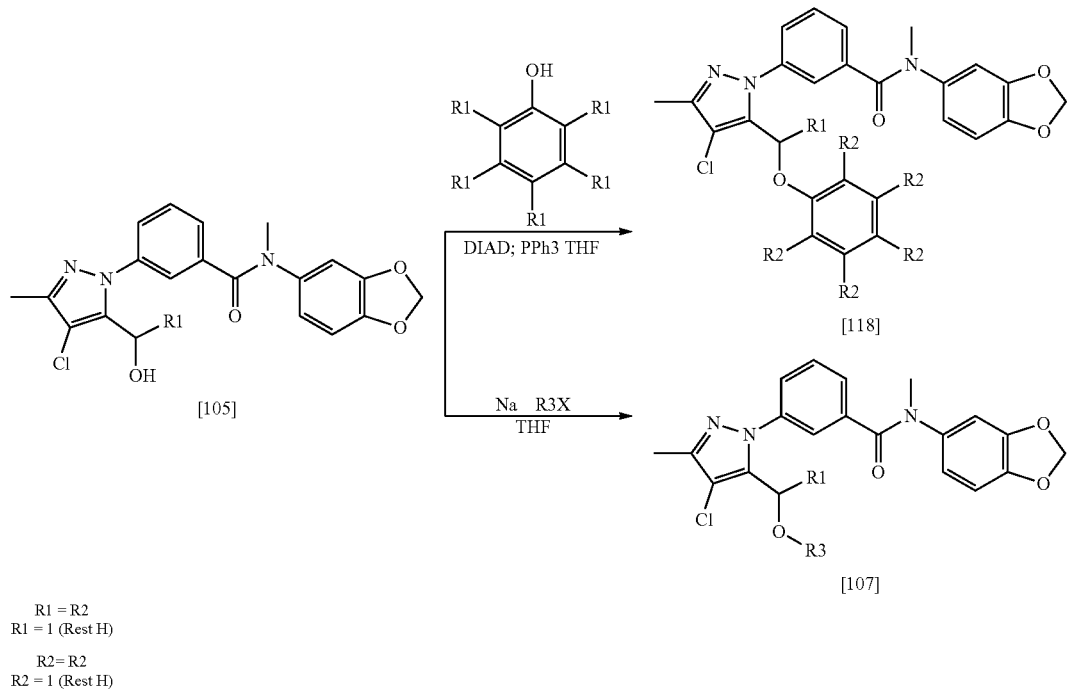

R1 = R2
R1 = 1 (Rest H)

R2= R2
R2 = 1 (Rest H)

General Protocol 7a

[107] N-(1,3-benzodioxol-5-yl)-3-[4-chloro-5-(methoxy methyl)-3-methyl-pyrazol-1-yl]-N-methyl-benzamide To a solution of 105 (89.0 mg, 0.22 mmol) in THF (4 mL) NaH (60% dispersion in mineral oil, 16.0 mg, 0.67 mmol) was added at 0° C. and the suspension stirred at the same temperature for 15 min. MeI (41.57 µL, 0.63 mmol) was added and the mixture stirred at room temperature for 3 h. The suspension was partitioned between EtOAc (50 mL) and H$_2$O (50 mL). The organic phase was separated, washed with brine (50 mL), dried over anhydrous Na$_2$SO$_4$, filtered and the solvent evaporated under reduced pressure. The resultant residue was purified by silica gel flash-column chromatography with Cyclohexane/EtOAc (70:30) as the eluent, obtaining a white solid in 63% yield (58 mg): $^1$H NMR (400 MHz, DMSO-d$_6$) δ 7.57-7.51 (m, 1H), 7.51-7.45 (m, 1H), 7.39 (app-t, J=7.8 Hz, 1H), 7.29 (app-d, J=7.7 Hz, 1H), 6.94 (d, J=2.1 Hz, 1H), 6.76 (d, J=8.2 Hz, 1H), 6.62 (dd, J=8.2, 2.1 Hz, 1H), 5.99 (s, 2H), 4.27 (s, 2H), 3.32 (s, 3H), 3.21 (s, 3H), 2.23 (s, 3H). UPLC-MS: t$_R$=2.06 min (Generic method); MS (ESI) m/z calcd for C$_{21}$H$_{21}$ClN$_3$O$_4$ (M+H)$^+$: 414.1, found: 414.1.

[117] N-(1,3-Benzodioxol-5-yl)-3-[4-chloro-5-[(rac)-methoxy (phenyl)methyl]-3-methyl-pyrazol-1-yl]-N-methyl-benzamide Following general procedure 7a, the title compound was obtained from compound 109, after purification by silica gel flash-column chromatography with DCM/EtOAc (80:20) as the eluent, as a white solid in 57% yield: $^1$H NMR (400 MHz, DMSO-d$_6$) δ 7.33-7.21 (m, 6H), 7.14 (app-dt, J=7.0, 2.1 Hz, 1H), 7.06-7.00 (m, 2H), 6.87 (d, J=2.1 Hz, 1H), 6.69 (d, J=8.2 Hz, 1H), 6.56 (dd, J=8.2, 2.1 Hz, 1H), 5.92 (d, J=1.0 Hz, 1H), 5.91 (d, J=1.0 Hz, 1H), 5.35 (s, 1H), 3.29 (s, 3H), 3.23 (s, 3H), 2.20 (s, 3H). UPLC-MS: t$_R$=2.58 min (Generic method); MS (ESI) m/z calcd for C$_{27}$H$_{25}$ClN$_3$O$_4$ (M+H)$^+$: 490.1, found: 490.2.

General Procedure 7b

[118] N-(1,3-Benzodioxol-5-yl)-3-[4-chloro-3-methyl-5-(phenoxymethyl)pyrazol-1-yl]-N-methyl-benzamide To a solution of alcohol 105 (100 mg, 0.25 mmol) in THF (5 mL), under Nitrogen, phenol (28.2 mg, 0.30 mmol), PPh$_3$ (78.7 mg, 0.3 mmol) and DIAD (60.7 µL, 0.30 mmol) were added at room temperature. Mixture was stirred for 18 h and quenched with sat. aq. NH$_4$Cl (10 mL). Aqueous layer was extracted with EtOAc (3×15 mL). Collected organic layers were washed with water (20 mL) and Brine (20 mL) dried with Na$_2$SO$_4$, filtered and solvent evaporated. The title compound was obtained, after purification by preparative LC/MS, as a white solid in 30% yield (25 mg): $^1$H NMR (400 MHz, DMSO-d$_6$) δ 7.54 (app-t, J=1.8 Hz, 1H), 7.44 (app-d, J=8.0 Hz, 1H), 7.35 (app-d, J=7.7 Hz, 1H), 7.33-7.22 (m, 3H), 6.99 (tt, J=7.3, 1.1 Hz, 1H), 6.95-6.89 (m, 2H), 6.84 (d, J=2.1 Hz, 1H), 6.63 (d, J=8.2 Hz, 1H), 6.45 (dd, J=8.2, 2.1 Hz, 1H), 5.95 (s, 2H), 4.96 (s, 2H), 3.24 (s, 3H), 2.24 (s, 3H). UPLC-MS: t$_R$=2.57 min (Generic method); MS (ESI) m/z calcd for C$_{26}$H$_{23}$ClN$_3$O$_4$ (M+H)$^+$: 476.1, found: 476.1.

[140] Ethyl 3-[[2-[3-[1,3-benzodioxol-5-yl(methyl) carbamoyl]phenyl]-4-chloro-5-methyl-pyrazol-3-yl] methoxy]benzoate Following general procedure 7b, the title compound was obtained from compound 105, after purification by silica gel flash-column chromatography with Cyclohexane/EtOAc (70:30) as the eluent, as a white solid in 72% yield: $^1$H NMR (400 MHz, DMSO-$d_6$) δ 7.60 (app-dt, J=7.8, 1.2 Hz, 1H), 7.53 (bs, J=1.8 Hz, 1H), 7.48-7.41 (m, 3H), 7.36 (t, J=7.8 Hz, 1H), 7.27 (d, J=7.8 Hz, 1H), 7.18 (ddd, J=8.3, 2.7, 1.0 Hz, 1H), 6.85 (d, J=2.1 Hz, 1H), 6.63 (d, J=8.2 Hz, 1H), 6.47 (dd, J=8.1, 2.1 Hz, 1H), 5.94 (s, 2H), 5.05 (s, 2H), 4.31 (q, J=7.1 Hz, 2H), 3.25 (s, 3H), 2.25 (s, 3H), 1.32 (t, J=7.1 Hz, 3H). UPLC-MS: $t_R$=2.63 min (Generic method); MS (ESI) m/z calcd for $C_{29}H_{27}ClN_3O_6$ (M+H)$^+$: 548.2, found: 548.2.

[141] Ethyl 4-[[2-[3-[1,3-benzodioxol-5-yl(methyl)carbamoyl]phenyl]-4-chloro-5-methyl-pyrazol-3-yl]methoxy]benzoate Following general procedure 7b, the title compound was obtained from compound 105, after purification by silica gel flash-column chromatography with Cyclohexane/EtOAc (70:30) as the eluent, as a white solid in 77% yield: $^1$H NMR (400 MHz, DMSO-$d_6$) δ 7.93-7.85 (m, 2H), 7.52 (app-t, J=1.8 Hz, 1H), 7.43 (app-d, J=8.1 Hz, 1H), 7.34 (app-t, J=7.8 Hz, 1H), 7.26 (app-d, J=7.7 Hz, 1H), 7.06-6.97 (m, 2H), 6.87 (d, J=2.1 Hz, 1H), 6.64 (d, J=8.2 Hz, 1H), 6.48 (dd, J=8.2, 2.1 Hz, 1H), 5.95 (s, 2H), 5.07 (s, 2H), 4.27 (q, J=7.1 Hz, 2H), 3.25 (s, 3H), 2.25 (s, 3H), 1.30 (t, J=7.1 Hz, 3H). UPLC-MS: $t_R$=2.61 min (Generic method); MS (ESI) m/z calcd for $C_{29}H_{27}ClN_3O_6$ (M+H)$^+$: 548.2, found: 548.2.

[143] 3-[[2-[3-[1,3-Benzodioxol-5-yl(methyl)carbamoyl]phenyl]-4-chloro-5-methyl-pyrazol-3-yl]methoxy]benzoic acid Following general procedure 4a, the title compound was obtained from compound 140, after purification by silica gel flash-column chromatography with DCM/MeOH (95:5) as the eluent, as a white solid in 75% yield: $^1$H NMR (400 MHz, DMSO-$d_6$) δ 13.04 (bs, 1H), 7.58 (app-dt, J=7.7, 1.2 Hz, 1H), 7.53 (app-t, J=1.8 Hz, 1H), 7.49-7.38 (m, 3H), 7.35 (d, J=7.7 Hz, 1H), 7.25 (d, J=7.7 Hz, 1H), 7.15 (ddd, J=8.3, 2.7, 1.0 Hz, 1H), 6.85 (d, J=2.1 Hz, 1H), 6.61 (d, J=8.2 Hz, 1H), 6.44 (dd, J=8.2, 2.1 Hz, 2H), 5.94 (s, 2H), 5.03 (s, 2H), 3.24 (s, 3H), 2.24 (s, 3H). UPLC-MS: $t_R$=1.94 min (Generic method); MS (ESI) m/z calcd for $C_{27}H_{23}ClN_3O_6$ (M+H)$^+$: 520.1, found: 520.2.

[144] 4-[[2-[3-[1,3-Benzodioxol-5-yl(methyl)carbamoyl]phenyl]-4-chloro-5-methyl-pyrazol-3-yl]methoxy]benzoic acid Following general procedure 4a, the title compound was obtained from compound 141, after purification by silica gel flash-column chromatography with DCM/MeOH (95:5) as the eluent, as a white solid in 75% yield: $^1$H NMR (400 MHz, DMSO-$d_6$) δ 12.71 (bs, 1H), 7.94-7.83 (m, 2H), 7.53 (app-t, J=1.9 Hz, 1H), 7.44 (app-d, J=7.6 Hz, 1H), 7.35 (app-t, J=7.8 Hz, 1H), 7.26 (app-d, J=7.7 Hz, 1H), 7.05-6.93 (m, 2H), 6.87 (d, J=2.1 Hz, 1H), 6.64 (d, J=8.2 Hz, 1H), 6.47 (dd, J=8.2, 2.1 Hz, 1H), 5.95 (s, 2H), 5.06 (s, 2H), 3.25 (s, 3H), 2.26 (s, 3H). UPLC-MS: $t_R$=1.93 min (Generic method); MS (ESI) m/z calcd for $C_{27}H_{23}ClN_3O_6$ (M+H)$^+$: 520.1, found: 520.2.

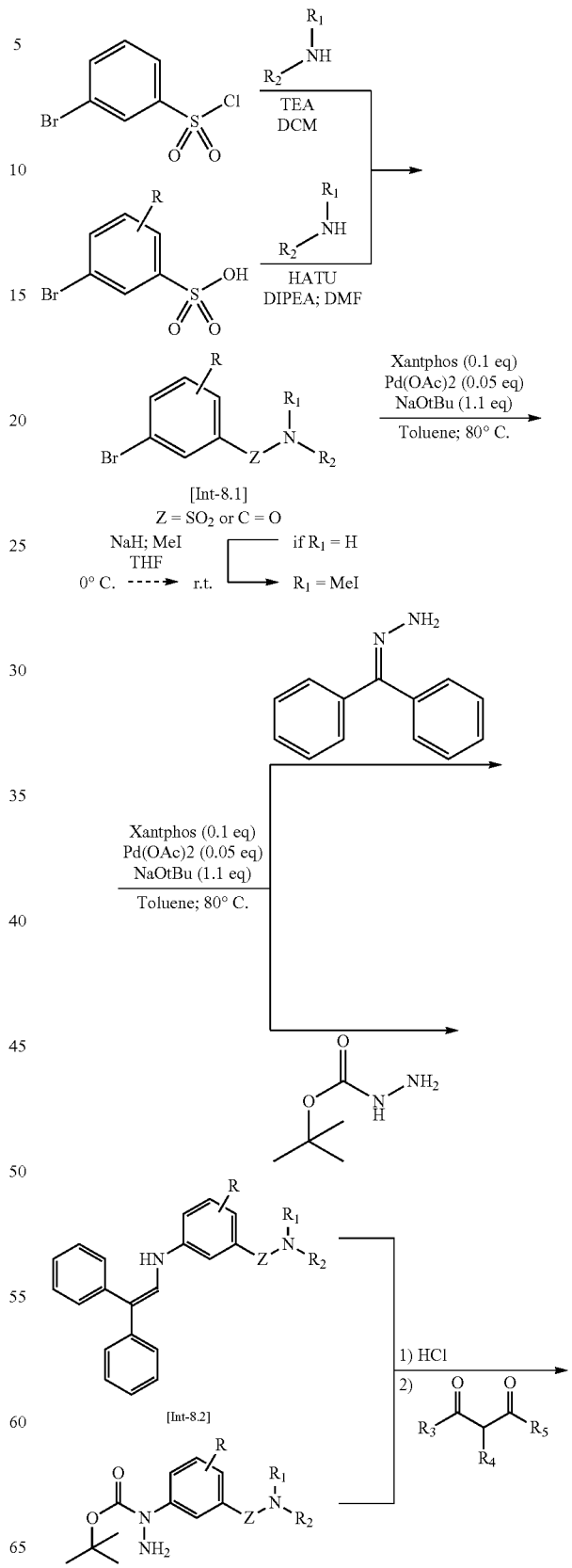

GENERAL PROTOCOL 8

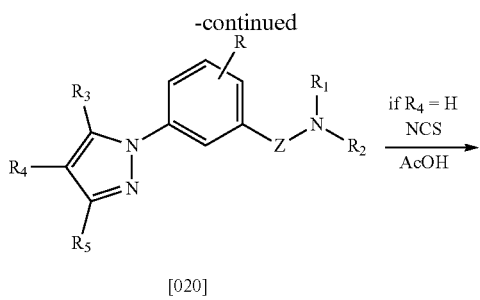

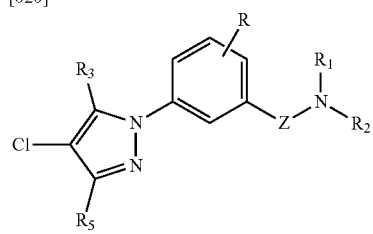

General Procedure 8a

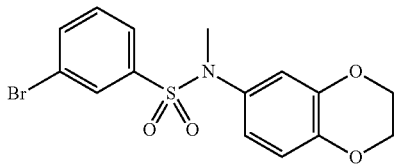 [SMILES: CN(c1ccc2c(c1)OCCO2)S(=O)(=O)c1cccc(Br)c1]

[Int-8.1] 3-Bromo-N-(2,3-dihydro-1,4-benzodioxin-6-yl)-N-methyl-benzenesulfonamide To a solution of 3-Bromobenzenesulfonyl chloride (450 mg; 1.76 mmol) in DCM (5 mL), TEA (270 μL; 1.94 mmol) was added under nitrogen. Mixture was cooled to 0° C. and N-methyl-2,3-dihydro-1,4-benzodioxin-6-amine was added slowly. Mixture was stirred at room temperature for 2 h and diluted with DCM (20 mL). Organic layer was washed with sat. aq. $NH_4Cl$ (10 mL), water (10 mL), sat. aq. $NaHCO_3$ (10 mL) and brine. The title compound was obtained, after purification by silica gel flash-column chromatography with DCM/EtOAc (85:15) as the eluent, as a clear oil in 67% yield: UPLC-MS: $t_R$=2.34 min (generic method); MS (ESI) m/z calcd for $C_{15}H_{15}BrNO_4S$ (M+H)$^+$: 384.0, found: 384.0.

General Procedure 8b

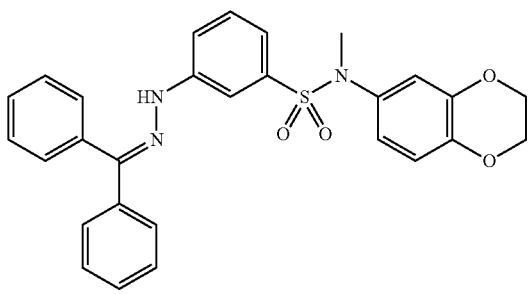 [SMILES: CN(c1ccc2c(c1)OCCO2)S(=O)(=O)c1cccc(NN=C(c2ccccc2)c2ccccc2)c1]

[Int-8.2] 3-(2-benzhydrylidenehydrazino)-N-(2,3-dihydro-1,4-benzodioxin-6-yl)-N-methyl-benzenesulfonamide To a solution of Int-8.1 (120 mg, 0.31 mmol) in dry Toluene (4 mL), diphenyl-hydrazone (36 mg, 1.3 mmol), Xanthpos (10 mol %), $Pd_2(dba)_3$ (5 mol %), and NaOtBu (33 mg, 0.34 mmol) were added and mixture was degassed with nitrogen. Mixture was stirred at 80° C. for 16 h and cooled to room temperature. EtOAc (20 mL) was added and organic layer was washed with water (10 mL) and brine (10 mL). Organic layer was dried with Sodium sulphate, filtered, and solvent evaporated. The title compound was obtained, after purification by silica gel flash-column chromatography with Cyclohexane/EtOAc (85:15) as the eluent, as a pale yellow solid in 71% yield: UPLC-MS: $t_R$=2.11 min (Apolar method); MS (ESI) m/z calcd for $C_{28}H_{26}N_3O_4S$ (M+H)$^+$: 500.2, found: 500.2.

General Procedure 8c

[020] 3-(4-chloro-3,5-dimethyl-pyrazol-1-yl)-N-(2,3-dihydro-1,4-benzodioxin-6-yl)-N-methyl-benzenesulfonamide To a solution of Int-8.2 (110 mg, 0.22 mmol) in EtOH (6 mL), 2 mL of $HCl_{conc.}$ was added. Reaction was stirred at refluxing temperature for 3 h. Solvent was partially evaporated and mixture diluted with water (5 mL). Aqueous layer was washed with $Et_2O$ (10 mL) and evaporated. Obtained solid was dissolved in EtOH (5 mL) and 3-chloropentane-2,4-dione (1.1 eq.) was added. Reaction was stirred for 3 h at r.t. and solvent was evaporated. Obtained oil was dissolved in EtOAc (30 mL). Organic layer was washed with water (10 mL), and sat. aq. $NaHCO_3$ (10 mL). Organic layer was dried with Sodium sulphate, filtered, and solvent evaporated. The title compound was obtained, after purification by silica gel flash-column chromatography with DCM/EtOAc (85:15) as the eluent, as a pale yellow solid in 63% yield: $^1$H NMR (400 MHz, DMSO-$d_6$) δ 7.89 (ddd, J=8.1, 2.2, 1.0 Hz, 1H), 7.76 (t, J=7.9 Hz, 1H), 7.64-7.54 (m, 2H), 6.81 (d, J=8.5 Hz, 1H), 6.63-6.56 (m, 2H), 4.41-4.09 (m, 4H), 3.13 (s, 3H), 2.27 (s, 3H), 2.22 (s, 3H). UPLC-MS: $t_R$=2.60 min (generic method); MS (ESI) m/z calcd for $C_{20}H_{21}ClN_3O_4S$ (M+H)$^+$: 434.1, found: 434.2.

[017] N-(2,3-dihydro-1,4-benzodioxin-6-yl)-3-(3,5-dimethyl pyrazol-1-yl)-N-methyl-benzenesulfonamide Following general procedure 8c, the title compound was obtained from Int-8.2 and 3-chloropentane-2,4-dione, after purification by silica gel flash-column chromatography with Cyclohexane/EtOAc (90:10) as the eluent, as a white solid in 14% yield $^1$H NMR (400 MHz, DMSO-$d_6$) δ 7.88 (ddd, J=8.1, 2.1, 1.0 Hz, 1H), 7.73 (t, J=7.9 Hz, 1H), 7.57 (t, J=1.8 Hz, 2H), 7.53 (ddd, J=7.7, 1.8, 1.0 Hz, 1H), 6.81 (dd, J=8.4, 0.6 Hz, 1H), 6.62-6.57 (m, 2H), 6.13 (s, 1H), 4.29-4.16 (m, 8H), 3.13 (s, 3H), 2.27 (s, 3H), 2.19 (s, 3H). UPLC-MS: $t_R$=2.31 min (generic method); MS (ESI) m/z calcd for $C_{20}H_{22}N_3O_4S$ (M+H)$^+$: 400.1, found: 400.2.

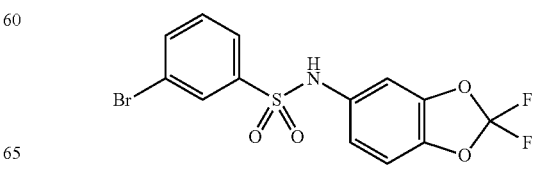

[Int-8.3] 3-bromo-N-(2,2-difluoro-1,3-benzodioxol-5-yl) benzenesulfonamide

Following general procedure 8a, the title compound was obtained from 2,2-difluoro-1,3-benzodioxol-5-amine, after purification by silica gel flash-column chromatography with Cyclohexane/EtOAc (90:10) as the eluent, as a white solid in 45% yield: $^1$H NMR (400 MHz, DMSO-d$_6$) δ 10.50 (s, 1H), 7.87 (t, J=1.8 Hz, 1H), 7.85 (ddd, J=7.9, 2.0, 1.0 Hz, 1H), 7.70 (ddd, J=7.9, 1.8, 1.0 Hz, 1H), 7.52 (t, J=7.9 Hz, 1H), 7.29 (d, J=8.7 Hz, 1H), 7.13 (d, J=2.1 Hz, 1H), 6.83 (dd, J=8.7, 2.1 Hz, 1H); UPLC-MS: t$_R$=1.45 min (Apolar method); MS (ESI) m/z calcd for C$_{13}$H$_{12}$BrF$_2$N$_2$O$_4$S (M+NH$_4$)$^+$: 408.9, found: 409.0.

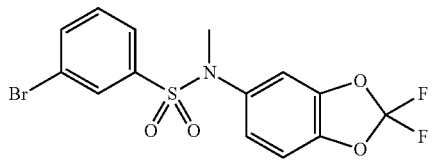 [SMILES: CN(c1ccc2c(c1)OC(F)(F)O2)S(=O)(=O)c1cccc(Br)c1]

[Int-8.4] 3-bromo-N-(2,2-difluoro-1,3-benzodioxol-5-yl) benzenesulfonamide

Following general procedure 1d, the title compound was obtained from Int-8.3, after purification by silica gel flash-column chromatography with Cyclohexane/EtOAc (80:20) as the eluent, as an Oil in 91% yield: $^1$H NMR (400 MHz, DMSO-d$_6$) δ 7.95 (ddd, J=7.8, 2.0, 1.3 Hz, 1H), 7.64 (t, J=1.8 Hz, 1H), 7.57 (t, J=7.8 Hz, 1H), 7.52 (dt, J=7.8, 1.5 Hz, 1H), 7.41 (d, J=8.7 Hz, 1H), 7.31 (d, J=2.2 Hz, 1H), 6.97 (dd, J=8.7, 2.2 Hz, 1H), 3.15 (s, 3H). UPLC-MS: t$_R$=1.74 min (Apolar method); MS (ESI) m/z calcd for C$_{14}$H$_{11}$BrF$_2$NO$_4$S (M+H)$^+$: 406.0, found: 406.1.

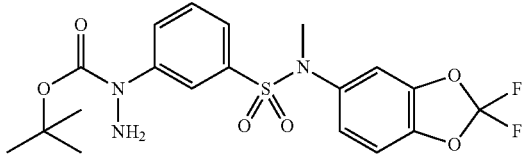 [SMILES: CN(c1ccc2c(c1)OC(F)(F)O2)S(=O)(=O)c1cccc(N(N)C(=O)OC(C)(C)C)c1]

[Int-8.5] Tert-butyl N-[3-[(2,2-difluoro-1,3-benzodioxol-5-yl)-methyl-sulfamoyl]anilino]carbamate Following general procedure 8b and using tert-butyl N-aminocarbamate as nuchleophyle, the title compound was obtained from Int-8.4, after purification by silica gel flash-column chromatography with Cyclohexane/EtOAc (60:40) as the eluent, as a Yellow Oil in 26% yield: UPLC-MS: t$_R$=2.6 min (Apolar method); MS (ESI) m/z calcd for C$_{19}$H$_{25}$F$_2$N4O6S (M+H)$^+$: 475.5, found: 475.3.

[035] 3-(4-Chloro-3,5-dimethyl-pyrazol-1-yl)-N-(2,2-difluoro-1,3-benzodioxol-5-yl)-N-methyl-benzenesulfonamide Following general procedure 8c, the title compound was obtained from Int-8.5, after purification by silica gel flash-column chromatography with Cyclohexane/EtOAc (60:40) as the eluent, as a white solid in 61% yield: $^1$H NMR (400 MHz, DMSO-d$_6$) δ 7.90 (ddd, J=8.1, 2.1, 1.1 Hz, 1H), 7.76 (t, J=8.2 Hz, 1H), 7.63-7.53 (m, 2H), 7.40 (d, J=8.7 Hz, 1H), 7.29 (d, J=2.2 Hz, 1H), 7.01 (dd, J=8.7, 2.2 Hz, 1H), 3.17 (s, 3H), 2.26 (s, 3H), 2.19 (s, 3H). UPLC-MS: t$_R$=2.60 min (generic method); MS (ESI) m/z calcd for C$_{19}$H$_{17}$ClF$_2$N$_3$O$_4$S (M+H)$^+$: 456.0, found: 456.2.

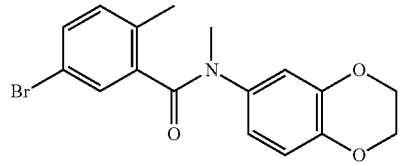 [SMILES: Cc1ccc(Br)cc1C(=O)N(C)c1ccc2c(c1)OCCO2]

[Int-8.6] 5-Bromo-N-(2,3-dihydro-1,4-benzodioxin-6-yl)-N,2-dimethyl-benzamide Following general procedure 1c, the title compound was obtained from 5-bromo-2-methyl-benzoic acid, after purification by silica gel flash-column chromatography with Cyclohexane/EtOAc (85:15) as the eluent, as an oil in 96% yield. UPLC-MS: t$_R$=2.22 min (Generic method); MS (ESI) m/z calcd for C$_{17}$H$_{17}$BrNO$_3$ (M+H)$^+$: 362.0, found: 362.1.

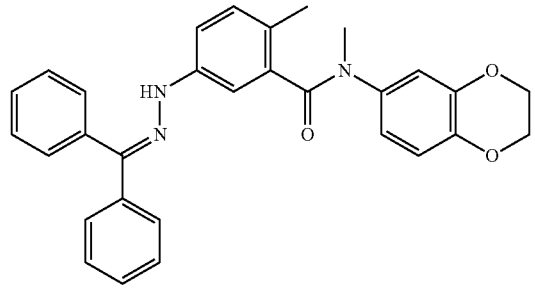 [SMILES: Cc1ccc(NN=C(c2ccccc2)c2ccccc2)cc1C(=O)N(C)c1ccc2c(c1)OCCO2]

[Int-8.7] 5-(2-Benzhydrylidenehydrazino)-N-(2,3-dihydro-1,4-benzodioxin-6-yl)-N,2-dimethyl-benzamide Following general procedure 8b, the title compound was obtained from Int-8.6, after purification by silica gel flash-column chromatography with Cyclohexane/EtOAc (70:30) as the eluent, as a pale yellow foam in 82% yield. UPLC-MS: t$_R$=2.71 min (Generic method); MS (ESI) m/z calcd for C$_{30}$H$_{28}$N$_3$O$_3$ (M+H)$^+$: 478.2, found: 478.4.

[031] 5-(4-chloro-3,5-dimethyl-pyrazol-1-yl)-N-(2,3-dihydro-1,4-benzodioxin-6-yl)-N,2-dimethyl-benzamide Following general procedure 8c, the title compound was obtained from Int-8.7, after purification by silica gel flash-column chromatography with Cyclohexane/EtOAc (50:50) as the eluent, as a pale yellow foam in 36% yield: $^1$H NMR (400 MHz, DMSO-d$_6$) δ 7.32-7.14 (m, 3H), 6.88-6.78 (m, 1H), 6.66 (app-d, J=8.1 Hz, 1H), 6.62 (app-dd, J=8.1 Hz, 1H), 4.14 (s, 4H), 3.32 (s, 3H), 2.30 (s, 3H), 2.16 (s, 3H), 2.00 (s, 3H). UPLC-MS: t$_R$=2.31 min (Generic method); MS (ESI) m/z calcd for C$_{22}$H$_{23}$ClN$_3$O$_3$ (M+H)$^+$: 412.1, found: 412.2.

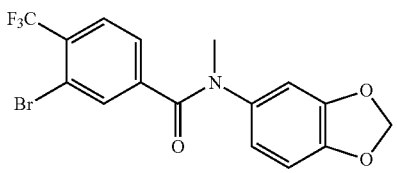 [SMILES: CN(C(=O)c1ccc(C(F)(F)F)c(Br)c1)c1ccc2c(c1)OCO2]

[Int-8.8] N-(1,3-Benzodioxol-5-yl)-3-bromo-N-methyl-4-(trifluoromethyl)benzamide Following general procedure 1c, the title compound was obtained from 3-bromo-4-(trifluoromethyl)benzoic acid, after purification by silica gel flash-column chromatography with Cyclohexane/EtOAc (70:30) as the eluent, as a yellow solid in 90% yield: UPLC-MS: $t_R$=2.36 min (generic method); MS (ESI) m/z calcd for $C_{16}H_{12}BrF_3NO_3$ (M+NH$_4$)+: 402.0, found: 402.1.

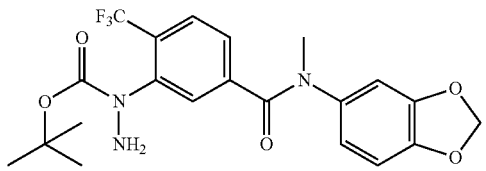 [SMILES: CN(C(=O)c1ccc(C(F)(F)F)c(N(N)C(=O)OC(C)(C)C)c1)c1ccc2c(c1)OCO2]

[Int-8.9] tert-Butyl N-amino-N-[5-[1,3-benzodioxol-5-yl (methyl)carbamoyl]-2-(trifluoromethyl)phenyl] carbamate Following general procedure 8b, the title compound was obtained from Int-8.8, after purification by silica gel flash-column chromatography with Cyclohexane/EtOAc (60:40) as the eluent, as an oil in 55% yield: UPLC-MS: $t_R$=2.27 min (generic method); MS (ESI) m/z calcd for $C_{21}H_{23}F_3N_3O_5$ (M+H)+: 454.2, found: 454.3.

[071] N-(1,3-Benzodioxol-5-yl)-3-(4-chloro-3,5-dimethyl-pyrazol-1-yl)-N-methyl-4-(trifluoromethyl) benzamide Following general procedure 8c, the title compound was obtained from Int-8.9, after purification by preparative LC/MS as yellow solid in 8.6% yield over two steps: $^1$H NMR (400 MHz, DMSO-d$_6$) δ 7.89 (d, J=8.2 Hz, 1H), 7.72 (d, J=8.1 Hz, 1H), 7.40 (s, 1H), 7.01 (d, J=2.1 Hz, 1H), 6.79 (d, J=8.2 Hz, 1H), 6.69 (d, J=8.2 Hz, 1H), 6.00 (s, 2H), 3.33 (s, 3H), 2.16 (s, 3H), 1.77 (s, 3H). UPLC-MS: $t_R$=2.52 min (generic method); MS (ESI) m/z calcd for $C_{21}H_{15}ClF_3N_3O_3$ (M+H)+: 452.1, found: 452.2.

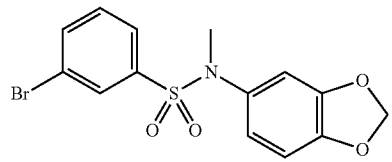 [SMILES: CN(c1ccc2c(c1)OCO2)S(=O)(=O)c1cccc(Br)c1]

[Int-8.10] N-(1,3-Benzodioxol-5-yl)-3-bromo-N-methyl-benzenesulfonamide

Following the general procedure 8a, the title compound was prepared from Int-1.34 and 3-bromobenzenesulfonyl chloride. The title compound was obtained, after purification by silica gel flash chromatography (DCM/EtOAc=85:15) as a colourless oil in 78% yield. $^1$H NMR (400 MHz, DMSO-d$_6$) δ 7.93 (dt, J=7.3, 1.9 Hz, 1H), 7.63-7.61 (m, 1H), 7.60-7.49 (m, 2H), 6.86 (d, J=8.3 Hz, 1H), 6.71 (d, J=2.2 Hz, 1H), 6.53 (dd, J=8.3, 2.2 Hz, 1H), 6.05 (s, 2H), 3.11 (s, 3H). UPLC-MS: $t_R$=2.27 min (Generic method); MS (ESI) m/z calcd for $C_{14}H_{13}BrNO_4S$ (M+H)+: 370.0, found: 370.3.

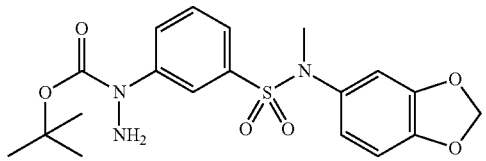 [SMILES: CN(c1ccc2c(c1)OCO2)S(=O)(=O)c1cccc(N(N)C(=O)OC(C)(C)C)c1]

[Int-8.11] tert-Butyl N-amino-N-[3-[1,3-benzodioxol-5-yl (methyl) sulfamoyl]phenyl]carbamate Following general procedure 8b and using tert-butyl N-aminocarbamate as nucleophile, the title compound was obtained from Int-8.10 and used in the next step without any purification. UPLC-MS: $t_R$=2.18 min (Generic method); MS (ESI) m/z calcd for $C_{19}H_{24}N_3O_6S$ (M+H)+: 422.2, found: 422.5.

[204] N-(1,3-Benzodioxol-5-yl)-N-methyl-3-[5-methyl-3-(trifluoromethyl)pyrazol-1-yl]benzenesulfonamide Following the general procedure 8c, the title compound was prepared from Int-8.11 and 1,1,1-trifluoropentane-2,4-dione. Subsequent silica gel flash chromatography (cyclohexane/AcOEt=9:1) afforded the title compound as red solid in 43% yield. $^1$H NMR (400 MHz, DMSO-d$_6$) δ 7.98-7.94 (m, 1H), 7.83-7.77 (m, 1H), 7.69-7.65 (m, 2H), 6.85 (d, J=8.3 Hz, 1H), 6.80-6.79 (m, 1H), 6.72 (d, J=2.1 Hz, 1H), 6.58 (dd, J=8.3, 2.2 Hz, 1H), 6.03 (s, 2H), 3.14 (s, 3H), 2.34 (s, 3H). UPLC-MS: $t_R$=2.57 min (Generic method); MS (ESI) m/z calcd for $C_{19}H_{17}F_3N_3O_4S$ (M+H)+: 440.1, found: 440.4.

GENERAL PROTOCOL 10

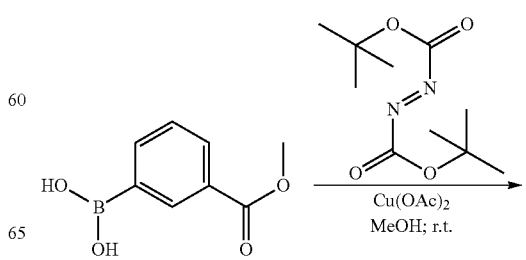

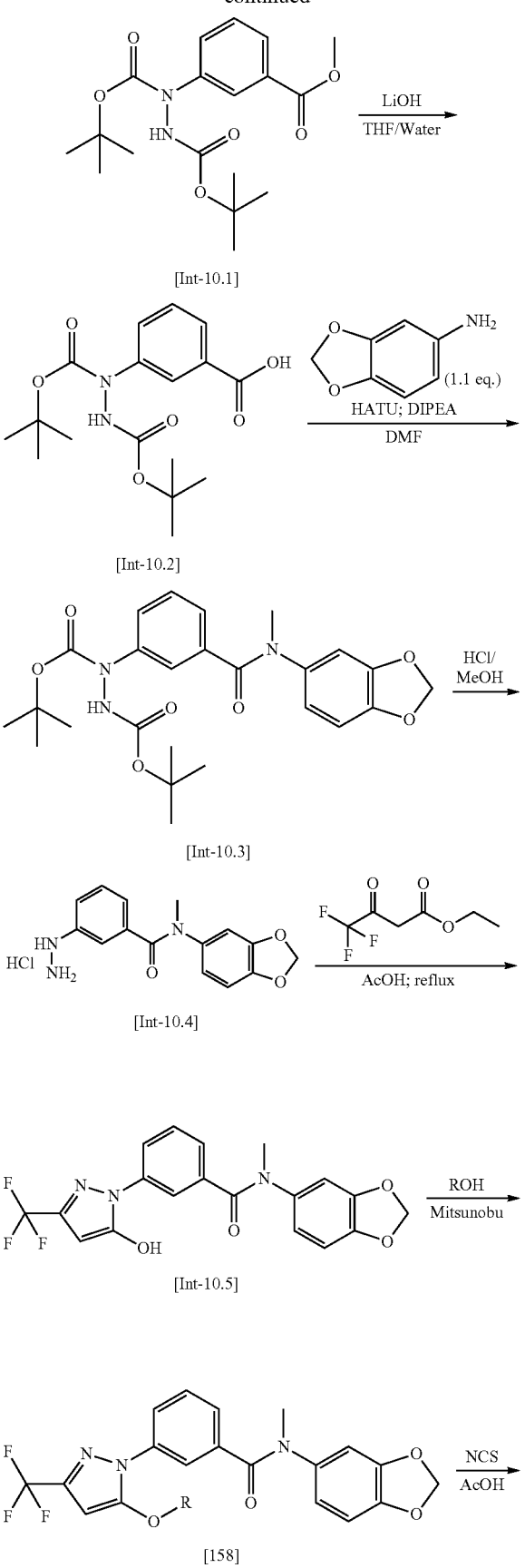

[Int-10.1]

[Int-10.2]

[Int-10.3]

[Int-10.4]

[Int-10.5]

[158]

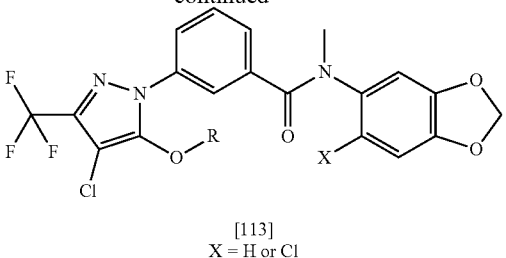

[113]
X = H or Cl

General Procedure 10a

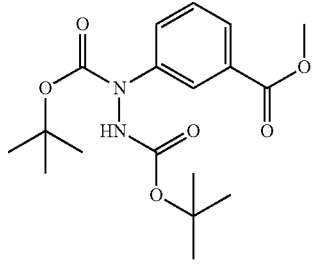 [SMILES: COC(=O)c1cccc(N(NC(=O)OC(C)(C)C)C(=O)OC(C)(C)C)c1]

[Int-10.1] Methyl 3-[tert-butoxycarbonyl-(tert-butoxy carbonylamino)amino]benzoate To a solution of (3-methoxycarbonylphenyl)boronic acid (10 g, 55.6 mmol) in MeOH (200 mL), tert-butyl (NE)-N-tert-butoxycarbonyliminocarbamate (14.1 g, 61.12 mmol) and Cu(OAc)$_2$ (504.6 mg, 2.78 mmol) were added. The mixture was stirred for 8 h, the brownish precipitate was filtered-off, and the filtrate evaporated. The obtained solid was dissolved in boiling MeOH (about 50 mL) and the solution leave to stand for 1 h. The white precipitate was filtered and washed with MeOH. The title compound was obtained as a white solid in 64% yield (13.1 g). $^1$H NMR Analysis showed the presence of two rotamers. Major form: $^1$H NMR (400 MHz, DMSO-d$_6$) δ 9.70 (s, 1H), 7.98 (t, J=2.0 Hz, 1H), 7.73 (app-dt, J=7.8, 1.4 Hz, 1H), 7.64-7.59 (m, 1H), 7.48 (app-t, J=7.9 Hz, 1H), 3.86 (s, 3H), 1.45 (bs, 18H). UPLC-MS: t$_R$=2.42 min (Generic method); MS (ESI) m/z calcd for C$_{18}$H$_{27}$N$_2$O$_6$ (M+H)$^+$: 367.2, found: 367.2.

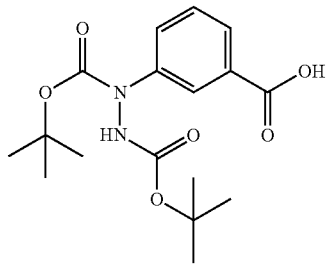 [SMILES: CC(C)(C)OC(=O)NN(C(=O)OC(C)(C)C)c1cccc(C(=O)O)c1]

[Int-10.2] 3-[Tert-butoxycarbonyl-(tert-butoxycarbonyl amino)amino]benzoic acid

Following general procedure 4a, the title compound was obtained from Int-10.1, as a pale yellow solid in 82% yield.

¹H NMR Analysis showed the presence of two rotamers. Major rotamer: ¹H NMR (400 MHz, DMSO-$d_6$) δ 9.66 (s, 1H), 7.94 (s, 1H), 7.71 (d, J=7.9 Hz, 1H), 7.49 (app-d, J=8.4 Hz, 1H), 7.38 (app-t, J=7.7 Hz, 1H), 1.44 (s, 18H). UPLC-MS: $t_R$=1.59 min (Generic method); MS (ESI) m/z calcd for $C_{17}H_{23}N_2O_6$ (M–H)⁻: 351.2, found: 351.2.

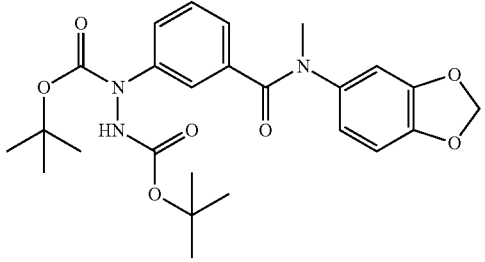 [SMILES: CN(C(=O)c1cccc(N(NC(=O)OC(C)(C)C)C(=O)OC(C)(C)C)c1)c1ccc2c(c1)OCO2]

[Int-10.3] Tert-butyl N-[3-[1,3-benzodioxol-5-yl (methyl) carbamoyl]phenyl]-N-(tert-butoxycarbonylamino)carbamate Following general procedure 1c, the title compound was obtained from Int-10.2, as a pale yellow solid in 74% yield. ¹H NMR Analysis showed the presence of two rotamers. Major form: ¹H NMR (400 MHz, DMSO-$d_6$) δ 9.54 (s, 1H), 7.37 (s, 1H), 7.24 (app-d, J=7.6 Hz, 1H), 7.16 (app-t, J=7.8 Hz, 1H), 6.97 (app-d, J=7.6 Hz, 1H), 6.85 (d, J=2.2 Hz, 1H), 6.73 (d, J=8.1 Hz, 1H), 6.55 (dd, J=8.1, 2.2 Hz, 1H), 5.99 (s, 2H), 1.44 (s, 9H), 1.42 (s, 9H). UPLC-MS: $t_R$=2.37 min (Generic method); MS (ESI) m/z calcd for $C_{25}H_{32}N_3O_7$ (M+H)⁺: 486.2, found: 486.3.

General Procedure 10b

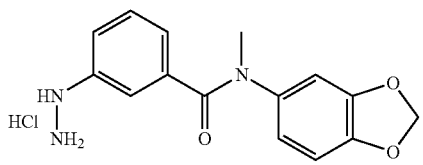 [SMILES: Cl ; CN(C(=O)c1cccc(NN)c1)c1ccc2c(c1)OCO2]

[Int-10.4] N-(1,3-Benzodioxol-5-yl)-3-hydrazino-N-methyl-benzamide hydrochloride Int-10.3 (1.61 g, 3.32 mmol) was dissolved in a HCl solution in MeOH (3 M, 40 mL). The mixture was stirred for 5 h at room temperature and the solvent was evaporated. The title compound was obtained, after trituration with Et₂O, as a pale yellow solid in 94% yield (223 mg): ¹H NMR (400 MHz, DMSO-$d_6$) δ 10.29 (s, 3H), 8.37 (s, 1H), 7.10 (app-t, J=7.9 Hz, 1H), 7.02 (app-t, J=1.9 Hz, 1H), 6.95-6.89 (m, 1H), 6.86 (d, J=2.1 Hz, 1H), 6.75 (d, J=8.2 Hz, 1H), 6.72 (app-d, J=7.8 Hz, 1H), 6.57 (dd, J=8.2, 2.1 Hz, 1H), 5.99 (s, 2H), 3.28 (s, 3H). UPLC-MS: $t_R$=1.46 min (Generic method); MS (ESI) m/z calcd for $C_{15}H_{16}N_3O_3$ (M+H)⁺: 286.1, found: 286.2.

General Procedure 10c

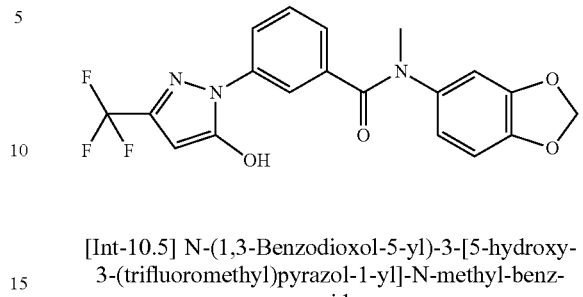

[Int-10.5] N-(1,3-Benzodioxol-5-yl)-3-[5-hydroxy-3-(trifluoromethyl)pyrazol-1-yl]-N-methyl-benzamide To a solution of Int-10.4 (533.0 mg, 1.66 mmol) in AcOH (5 mL), ethyl 4,4,4-trifluoro-3-oxo-butanoate (249.80 μL, 1.70 mmol) was added and mixture refluxed for 5 h. The solvent was evaporated and the crude product purified. The title compound was obtained, after purification by silica gel flash-column chromatography with DCM/EtOAc (70/30) as the eluent, as a white solid in 75% yield (504 mg): ¹H NMR (400 MHz, DMSO-$d_6$) δ 12.52 (s, 1H), 7.75 (app-t, J=1.8 Hz, 1H), 7.66 (ddd, J=8.2, 2.3, 1.1 Hz, 1H), 7.35 (app-t, J=7.9 Hz, 1H), 7.20 (app-d, J=7.7 Hz, 1H), 6.94 (d, J=2.1 Hz, 1H), 6.75 (d, J=8.2 Hz, 1H), 6.63 (dd, J=8.2, 2.1 Hz, 1H), 5.98 (s, 2H), 5.91 (s, 1H), 3.32 (s, 3H). ¹³C NMR (101 MHz, DMSO) δ 168.47, 153.83, 147.49, 145.76, 140.41 (q, J=39.0, 37.1 Hz), 138.18, 137.37, 137.29, 126.39, 123.93 (q, J=268.5 Hz), 122.46, 121.45, 120.88, 108.25, 108.01, 101.48, 85.70. UPLC-MS: $t_R$=1.64 min (Generic method); MS (ESI) m/z calcd for $C_{19}H_{15}F_3N_3O_4$ (M+H)⁺: 406.1, found: 406.2.

General Procedure 10d

[158] N-(1,3-benzodioxol-5-yl)-3-[5-ethoxy-3-(trifluoro methyl)pyrazol-1-yl]-N-methyl-benzamide To a solution of Int-10.5 (100.0 mg, 0.25 mmol) in THF (5 mL), under Nitrogen, Ethanol (20 μL, 0.30 mmol), PPh₃ (77.7 mg, 0.3 mmol) and DIAD (58.3 μL, 0.30 mmol) were added at room temperature. Mixture was stirred for 18 h and quenched with sat. aq. NH₄C1.(10 mL). Aqueous layer was washed with EtOAc (3×15 mL). Collected organic layers were washed with water (20 mL) and Brine (20 mL) dried with Na₂SO₄, filtered and solvent evaporated. The title compound was obtained, after purification by silica gel flash-column chromatography with DCM/EtOAc (80/20) as the eluent, as a white solid in 70% yield (75 mg): ¹H NMR (400 MHz, DMSO-$d_6$) δ 7.68 (app-t, J=1.8 Hz, 1H), 7.62 (ddd, J=8.2, 2.3, 1.1 Hz, 1H), 7.37 (app-t, J=7.9 Hz, 1H), 7.24 (app-d, J=7.7 Hz, 1H), 6.95 (d, J=2.1 Hz, 1H), 6.76 (d, J=8.2 Hz, 1H), 6.64 (dd, J=8.2, 2.1 Hz, 1H), 6.44 (s, 1H), 5.98 (s, 2H), 4.29 (q, J=7.0 Hz, 2H), 3.32 (s, 3H), 1.36 (t, J=7.0 Hz, 3H). UPLC-MS: $t_R$=2.11 min (Generic method); MS (ESI) m/z calcd for $C_{21}H_{19}F_3N_3O_4$ (M+H)⁺: 434.1, found: 434.2.

[131] N-(1,3-benzodioxol-5-yl)-3-[5-isopropoxy-3-(trifluoro methyl)pyrazol-1-yl]-N-methyl-benzamide Following general procedure 10d, the title compound was obtained from Int-10.5, after purification by silica gel flash-column chromatography with cyclohexane/EtOAc (70/30)

as the eluent, as a white solid in 50% yield: $^1$H NMR (400 MHz, DMSO-d$_6$) δ 7.68 (app-t, J=1.9 Hz, 1H), 7.60 (ddd, J=8.1, 2.3, 1.1 Hz, 1H), 7.36 (app-t, J=7.9 Hz, 1H), 7.22 (app-d, J=7.7 Hz, 1H), 6.96 (d, J=2.1 Hz, 1H), 6.75 (d, J=8.2 Hz, 1H), 6.63 (dd, J=8.2, 2.1 Hz, 1H), 6.47 (s, 1H), 5.98 (s, 2H), 4.67 (kept, J=6.1 Hz, 1H), 3.32 (s, 3H), 1.34 (d, J=6.1 Hz, 6H). UPLC-MS: $t_R$=1.46 min (Apolar method); MS (ESI) m/z calcd for $C_{22}H_{21}F_3N_3O_4$ (M+H)$^+$: 448.1, found: 448.1.

[132] N-(1,3-benzodioxol-5-yl)-3-[5-benzyloxy-3-(trifluoro methyl)pyrazol-1-yl]-N-methyl-benzamide Following general procedure 10d, the title compound was obtained from Int-10.5, after purification by silica gel flash-column chromatography with cyclohexane/EtOAc (70/30) as the eluent, as a white solid in 70% yield: $^1$H NMR (400 MHz, DMSO-d$_6$) δ 7.71 (app-t, J=1.9 Hz, 1H), 7.60 (app-dt, J=8.1, 1.6 Hz, 1H), 7.50-7.45 (m, 2H), 7.45-7.32 (m, 4H), 7.23 (d, J=7.7 Hz, 1H), 6.89 (d, J=2.1 Hz, 1H), 6.70 (d, J=8.2 Hz, 1H), 6.60-6.54 (m, 1H), 6.54 (s, 1H), 5.96 (s, 2H), 5.34 (s, 2H), 3.29 (s, 3H). UPLC-MS: $t_R$=1.61 min (Apolar method); MS (ESI) m/z calcd for $C_{26}H_{21}F_3N_3O_4$ (M+H)$^+$: 496.1, found: 496.1.

[133] N-(1,3-Benzodioxol-5-yl)-N-methyl-3-[5-phenethyloxy-3-(trifluoromethyl)pyrazol-1-yl]benzamide Following general procedure 10d, the title compound was obtained from Int-10.5, after purification by silica gel flash-column chromatography with cyclohexane/EtOAc (70/30) as the eluent, as a white solid in 65% yield: $^1$H NMR (400 MHz, DMSO-d$_6$) δ 7.62 (app-t, J=1.8 Hz, 1H), 7.53-7.42 (m, 1H), 7.36-7.18 (m, 7H), 6.88 (d, J=2.1 Hz, 1H), 6.74 (d, J=8.2 Hz, 1H), 6.56 (dd, J=8.2, 2.1 Hz, 1H), 6.50 (s, 1H), 5.98 (s, 2H), 4.48 (t, J=6.6 Hz, 2H), 3.33 (s, 3H), 3.09 (t, J=6.6 Hz, 2H). UPLC-MS: $t_R$=1.71 min (Apolar method); MS (ESI) m/z calcd for $C_{27}H_{23}F_3N_3O_4$ (M+H)$^+$: 510.2, found: 510.1.

[152] Methyl-4-[[2-[3-[1,3-benzodioxol-5-yl (methyl) carbamoyl]phenyl]-5-(trifluoromethyl) pyrazol-3-yl]oxymethyl]benzoate Following general procedure 10d, the title compound was obtained from Int-10.5, after purification by silica gel flash-column chromatography with cyclohexane/EtOAc (80/20) as the eluent, as a white solid in 79% yield: $^1$H NMR (400 MHz, DMSO-d$_6$) δ 8.05-7.94 (m, 2H), 7.73 (app-t, J=1.8 Hz, 1H), 7.66-7.55 (m, 3H), 7.37 (app-t, J=7.9 Hz, 1H), 7.24 (app-d, J=7.7 Hz, 1H), 6.91 (d, J=2.2 Hz, 1H), 6.71 (d, J=8.2 Hz, 1H), 6.59 (dd, J=8.2, 2.2 Hz, 1H), 6.52 (s, 1H), 5.95 (s, 2H), 5.44 (s, 2H), 3.86 (s, 3H), 3.30 (s, 3H). UPLC-MS: $t_R$=2.23 min (Generic method); MS (ESI) m/z calcd for $C_{28}H_{23}F_3N_3O_6$ (M+H)$^+$: 554.1, found: 554.3.

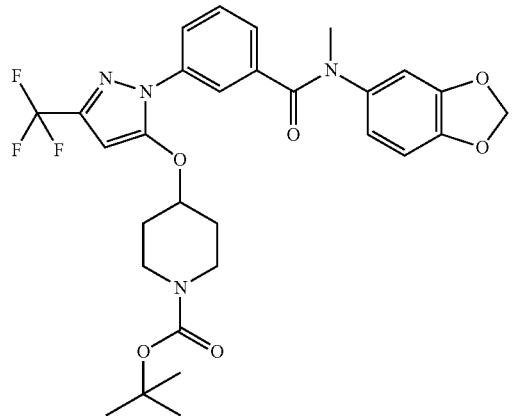 [SMILES: CN(C(=O)c1cccc(-n2nc(C(F)(F)F)cc2OC2CCN(C(=O)OC(C)(C)C)CC2)c1)c1ccc2c(c1)OCO2]

[Int-10.6] Tert-butyl 4-[2-[3-[1,3-benzodioxol-5-yl (methyl)carbamoyl]phenyl]-5-(trifluoromethyl)pyrazol-3-yl]oxypiperidine-1-carboxylate Following general procedure 10d, the title compound was obtained from Int-10.5, after purification by silica gel flash-column chromatography with cyclohexane/EtOAc (80/20) as the eluent, as a white solid in 81% yield: $^1$H NMR (400 MHz, DMSO-d$_6$) δ 7.71 (app-t, J=1.9 Hz, 1H), 7.61 (app-d, J=8.1 Hz, 1H), 7.36 (app-t, J=8.0 Hz, 1H), 7.21 (app-d, J=7.8 Hz, 1H), 6.95 (d, J=2.1 Hz, 1H), 6.73 (d, J=8.2 Hz, 1H), 6.61 (dd, J=8.2, 2.1 Hz, 1H), 6.56 (s, 1H), 5.98 (s, 2H), 4.73-4.63 (m, 1H), 3.71-3.58 (m, 1H), 3.57-3.45 (m, 2H), 3.32 (s, 3H), 3.28-3.20 (m, 1H), 1.98-1.88 (m, 2H), 1.72-1.57 (m, 2H), 1.40 (s, 9H). UPLC-MS: $t_R$=2.37 min (Generic method); MS (ESI) m/z calcd for $C_{29}H_{32}F_3N_4O_6$ (M+H)$^+$: 589.2, found: 589.3.

General Procedure 10e

[113] N-(1,3-Benzodioxol-5-yl)-3-[4-chloro-5-ethoxy-3-(trifluoromethyl)pyrazol-1-yl]-N-methyl-benzamide To a solution of compound 158 (60 mg, 0.13 mmol) in AcOH (2 mL), NCS (24.3 mg, 0.18 mmol) was added. The mixture was stirred at room temperature for 18 h and quenched with water. The aqueous layer was washed with EtOAc (3×15 mL). The collected organic layers were washed with sat. aq. NaHCO$_3$ (3×10 mL) and Brine (20 mL) dried with Na$_2$SO$_4$, filtered and solvent evaporated. The title compound was obtained, after purification by silica gel flash-column chromatography with Cyclohexane/EtOAc (70/30) as the eluent, as a white solid in 27% yield (15 mg): $^1$H NMR (400 MHz, DMSO-d$_6$) δ 7.61 (app-t, J=1.9 Hz, 1H), 7.59-7.53 (m, 1H), 7.42 (app-t, J=7.9 Hz, 1H), 7.33 (app-d, J=7.7 Hz, 1H), 6.95 (d, J=2.1 Hz, 1H), 6.75 (d, J=8.2 Hz, 1H), 6.64 (dd, J=8.2, 2.1 Hz, 1H), 5.98 (s, 2H), 4.30 (q, J=7.0 Hz, 2H), 3.32 (s, 3H), 1.19 (t, J=7.0 Hz, 3H). UPLC-MS: $t_R$=2.63 min (Generic method); MS (ESI) m/z calcd for $C_{24}H_{48}ClF_3N_3O_4$ (M+H)$^+$: 468.1, found: 468.1.

[134] N-(1,3-Benzodioxol-5-yl)-3-[5-benzyloxy-4-chloro-3-(trifluoromethyl)pyrazol-1-yl]-N-methyl-benzamide Following general procedure 10e, the title compound was obtained from compound 132, after purification by silica gel flash-column chromatography with cyclohexane/EtOAc (70/30) as the eluent, as a white solid in 60% yield: $^1$H NMR (400 MHz, DMSO-$d_6$) δ 7.58 (app-t, J=1.8 Hz, 1H), 7.43 (app-d, J=8.0 Hz, 1H), 7.40-7.26 (m, 5H), 7.26-7.20 (m, 2H), 6.91 (d, J=2.1 Hz, 1H), 6.72 (d, J=8.2 Hz, 1H), 6.59 (dd, J=8.2, 2.1 Hz, 1H), 5.92 (s, 2H), 5.28 (s, 2H), 3.31 (s, 3H). UPLC-MS: $t_R$=1.98 min (Apolar method); MS (ESI) m/z calcd for $C_{26}H_{20}ClF_3N_3O_4$ (M+H)$^+$: 530.1, found: 530.1.

[142] N-(1,3-Benzodioxol-5-yl)-3-[4-chloro-5-isopropoxy-3-(trifluoromethyl)pyrazol-1-yl]-N-methylbenzamide Following general procedure 10e, the title compound was obtained from compound 131, after purification by silica gel flash-column chromatography with cyclohexane/EtOAc (80/20) as the eluent, as a white solid in 50% yield: $^1$H NMR (400 MHz, DMSO-$d_6$) δ 7.59 (app-t, J=1.8 Hz, 1H), 7.55 (app-dt, J=8.1, 1.6 Hz, 1H), 7.42 (app-t, J=7.9 Hz, 1H), 7.34 (app-d, J=7.7 Hz, 1H), 6.95 (d, J=2.1 Hz, 1H), 6.73 (d, J=8.2 Hz, 1H), 6.64 (dd, J=8.2, 2.1 Hz, 1H), 5.97 (s, 2H), 4.49 (kept, J=6.1 Hz, 1H), 3.32 (s, 3H), 1.14 (d, J=6.2 Hz, 6H). UPLC-MS: $t_R$=2.69 min (Generic method); MS (ESI) m/z calcd for $C_{22}H_{20}ClF_3N_3O_4$ (M+H)$^+$: 482.1, found: 482.2.

[155] Methyl 4-[[2-[3-[1,3-benzodioxol-5-yl(methyl) carbamoyl]phenyl]-4-chloro-5-(trifluoromethyl)pyrazol-3-yl]oxymethyl]benzoate Following general procedure 10e, the title compound was obtained from compound 152, after purification by silica gel flash-column chromatography with cyclohexane/EtOAc (80/20) as the eluent, as a white solid in 21% yield: $^1$H NMR (400 MHz, DMSO-$d_6$) δ 7.93-7.83 (m, 2H), 7.60 (app-t, J=1.8 Hz, 1H), 7.46 (app-d, J=7.9 Hz, 1H), 7.42-7.37 (m, 2H), 7.37-7.27 (m, 2H), 6.91 (d, J=2.1 Hz, 1H), 6.71 (d, J=8.2 Hz, 1H), 6.58 (dd, J=8.2, 2.1 Hz, 1H), 5.93 (s, 2H), 5.39 (s, 2H), 3.85 (s, 3H), 3.31 (s, 3H). UPLC-MS: $t_R$=2.38 min (Generic method); MS (ESI) m/z calcd for $C_{28}H_{22}ClF_3N_3O_6$ (M+H)$^+$: 538.1, found: 538.1.

[156] Methyl 4-[[4-chloro-2-[3-[(6-chloro-1,3-benzodioxol-5-yl)-methyl-carbamoyl]phenyl]-5-(trifluoromethyl)pyrazol-3-yl]oxymethyl]benzoate Following general procedure 10e, the title compound was obtained as by-product from compound 152, after purification by silica gel flash-column chromatography with cyclohexane/EtOAc (80/20) as the eluent, as a white solid in 26% yield $^1$H NMR (400 MHz, DMSO-$d_6$) δ 7.90-7.82 (m, 2H), 7.61 (app-t, J=1.6 Hz, 1H), 7.47 (dt, J=7.2, 2.3 Hz, 1H), 7.43-7.32 (m, 4H), 7.21 (s, 1H), 6.99 (s, 1H), 6.03 (s, 1H), 5.96 (s, 1H), 5.38 (s, 2H), 3.85 (s, 3H), 3.22 (s, 3H). UPLC-MS: $t_R$=2.46 min (Generic method); MS (ESI) m/z calcd for $C_{28}H_{21}Cl_2F_3N_3O_6$ (M+H)$^+$: 622.1, found: 622.2.

[157] Tert-butyl 4-[2-[3-[1,3-benzodioxol-5-yl(methyl)carbamoyl]phenyl]-4-chloro-5-(trifluoromethyl) pyrazol-3-yl]oxypiperidine-1-carboxylate Following general procedure 10e, the title compound was obtained from Int-10.6, after purification by silica gel flash-column chromatography with cyclohexane/EtOAc (80/20) as the eluent, as a white solid in 25% yield: $^1$H NMR (400 MHz, DMSO-$d_6$) δ 7.64 (t, J=1.9 Hz, 1H), 7.56 (app-dd, J=8.0, 1.9 Hz, 1H), 7.41 (app-t, J=7.9 Hz, 1H), 7.30 (app-d, J=7.7 Hz, 1H), 6.97 (d, J=2.1 Hz, 1H), 6.71 (d, J=8.2 Hz, 1H), 6.60 (dd, J=8.2, 2.1 Hz, 1H), 5.98 (s, 2H), 4.61-4.48 (m, 1H), 3.47-3.34 (m, 2H), 3.32 (s, 3H), 3.18-3.02 (m, 2H), 1.83-1.69 (m, 2H), 1.51-1.41 (m, 2H), 1.37 (s, 9H). UPLC-MS: $t_R$=2.51 min (Generic method); MS (ESI) m/z calcd for $C_{29}H_{31}ClF_3N_4O_6$ (M+H)$^+$: 623.2, found: 623.3.

[159] 4-[[2-[3-[1,3-Benzodioxol-5-yl(methyl)carbamoyl]phenyl]-4-chloro-5-(trifluoromethyl)pyrazol-3-yl]oxymethyl]benzoic acid Following general procedure 4a, the title compound was obtained from compound 156, after purification by silica gel flash-column chromatography with DCM/MeOH (95/5) as the eluent, as a white solid in 67% yield (31 mg): $^1$H NMR (400 MHz, DMSO-$d_6$) δ 13.00 (bs, 1H), 7.92-7.80 (m, 2H), 7.61 (t, J=1.8 Hz, 1H), 7.46 (app-d, J=7.9 Hz, 1H), 7.41-7.27 (m, 4H), 6.91 (d, J=2.1 Hz, 1H), 6.70 (d, J=8.2 Hz, 1H), 6.57 (dd, J=8.2, 2.1 Hz, 1H), 5.93 (s, 2H), 5.38 (s, 2H), 3.31 (s, 3H). UPLC-MS: $t_R$=2.08 min (Generic method); MS (ESI) m/z calcd for $C_{27}H_{19}ClF_3N_3O_6$ (M+H)$^+$: 574.1, found: 574.2.

[213] Ethyl-cis-4-[2-[3-[1,3-benzodioxol-5-yl (methyl) carbamoyl]phenyl]-5-(trifluoromethyl) pyrazol-3-yl]oxycyclohexanecarboxylate Following general procedure 10d, the title compound was obtained from [Int-10.5], after purification by preparative LC/MS, as a single diastereoisomer, as a white solid in 54% yield: $^1$H NMR (400 MHz, DMSO-$d_6$) δ 7.73 (app-t, J=1.9 Hz, 1H), 7.68-7.60 (m, 1H), 7.37 (app-t, J=7.9 Hz, 1H), 7.22 (app-d, J=7.7 Hz, 1H), 6.96 (d, J=2.1 Hz, 1H), 6.74 (d, J=8.2 Hz, 1H), 6.62 (app-d, J=8.2 Hz, 1H), 6.52 (s, 1H), 5.98 (s, 2H), 4.75-4.61 (m, 1H), 4.06 (q, J=7.1 Hz, 2H), 3.32 (s, 3H), 2.50-2.42 (m, 1H), 2.02-1.86 (m, 2H), 1.82-1.58 (m, 6H), 1.17 (t, J=7.1 Hz, 3H). UPLC-MS: $t_R$=2.59 min (Generic method); MS (ESI) m/z calcd for $C_{28}H_{29}F_3N_3O_6$ (M+H)$^+$: 560.2, found: 560.5.

[214] Ethyl 4-[2-[3-[1,3-benzodioxol-5-yl(methyl) carbamoyl]phenyl]-5-(trifluoromethyl)pyrazol-3-yl] oxycyclohexane carboxylate Following general procedure 10d, the title compound was obtained from [Int-10.5], after purification by preparative LC/MS, as a 1:1 mixture of diastereoisomers as a white solid in 64% yield: $^1$H NMR (400 MHz, DMSO-$d_6$) δ 7.73 (app-t, J=1.9 Hz, 1H, cis-), 7.69 (app-t, J=1.9 Hz, 1H, trans-), 7.67-7.56 (m, 2H, cis-/trans-mix), 7.45-7.31 (m, 2H, cis-/trans-mix), 7.29-7.16 (m, 2H, cis-/trans-mix), 6.97 (d, J=2.1 Hz, 1H, trans-), 6.96 (d, J=2.1 Hz, 1H, cis-), 6.75 (m, 2H, cis-/trans-mix), 6.68-6.59 (m, 2H, cis-/trans-mix), 6.57 (s, 1H, trans-), 6.52 (s, 1H cis-), 5.99 (s, 4H, cis-/trans-mix), 4.68 (m, 1H, cis-), 4.44 (dt, J=9.8, 5.1 Hz, 1H, trans-), 4.06 (m, 4H, cis-/trans-mix), 3.33 (s, 3H, trans-), 3.32 (s, 3H, cis-), 2.50-2.44 (m, 1H, cis-), 2.41-2.31 (m, 1H, trans-), 2.18-2.10 (m, 2H, trans-), 1.97-1.89 (m, 2H, cis-), 1.80-1.62 (m, 6H, cis-), 1.62-1.43 (m, 6H, trans), 1.23-1.12 (m, 6H, cis-/trans-mix). UPLC-MS: $t_R$=2.59 min (Generic method); MS (ESI) m/z calcd for $C_{28}H_{29}F_3N_3O_6$ (M+H)$^+$: 560.2, found: 560.5.

[215] 4-[2-[3-[1,3-Benzodioxol-5-yl(methyl)carbamoyl]phenyl]-5-(trifluoromethyl)pyrazol-3-yl]oxycyclohexane carboxylic acid Following general procedure 4a, the title compound was obtained from compound 214 as a 1:1 mixture of diastereoismers, after purification by silica gel flash-column chromatography with DCM/EtOAc (70/30) as the eluent, as a white solid in 36% yield: ¹H NMR (400 MHz, DMSO-d₆) δ 12.17 (s, 2H, cis-/trans-mix), 7.71 (app-t, J=1.9 Hz, 1H, cis-), 7.68 (app-t, J=1.9 Hz, 1H, trans-), 7.65-7.57 (m, 2H, cis-/trans-mix), 7.36 (app-t, J=7.9 Hz, 2H, cis-/trans-mix), 7.22 (d, J=7.7 Hz, 2H, cis-/trans-mix), 6.96 (d, J=2.1 Hz, 1H, cis-), 6.95 (d, J=2.1 Hz, 1H, trans-), 6.79-6.72 (m, 2H, cis-/trans-mix), 6.67-6.58 (m, 2H, cis-/trans-mix), 6.55 (s, 1H, trans-), 6.50 (s, 1H, cis-), 4.65 (bs, 1H, cis-), 4.54-4.34 (m, 1H, trans-), 3.32 (s, 6H, cis-/trans-mix), 2.39 (p, J=5.1 Hz, 1H, cis-), 2.32-2.22 (m, 1H, trans-), 2.20-2.08 (m, 2H, cis-), 1.98-1.84 (m, 2H, trans-), 1.81-1.59 (m, 6H, cis-), 1.61-1.40 (m, 6H, trans-). UPLC-MS: $t_{R\text{-}trans}$=2.10 min $t_{R\text{-}cis}$=2.20 min (Generic method); MS (ESI) m/z calcd for $C_{26}H_{23}F_3N_3O_6$ (M–H)⁻: 530.2, found: 530.5.

[216] Cis-4-[2-[3-[1,3-benzodioxol-5-yl(methyl)carbamoyl]phenyl]-5-(trifluoromethyl)pyrazol-3-yl]oxycyclohexane carboxylic acid Following general procedure 4a, the title compound was obtained from compound 213, after purification by silica gel flash-column chromatography with DCM/EtOAc (70/30) as the eluent, as a white solid in 21% yield ¹H NMR (400 MHz, DMSO-d₆) δ 12.20 (bs, 1H), 7.72 (app-t, J=1.9 Hz, 1H), 7.63 (app-dt, J=8.1, 1.5 Hz, 1H), 7.37 (app-t, J=7.9 Hz, 1H), 7.23 (app-d, J=7.7 Hz, 1H), 6.96 (d, J=2.1 Hz, 1H), 6.75 (d, J=8.2 Hz, 1H), 6.62 (dd, J=8.2, 2.1 Hz, 1H), 6.51 (s, 1H), 5.98 (s, 2H), 4.72-4.60 (m, 1H), 3.32 (s, 3H), 2.39 (p, J=4.9 Hz, 1H), 2.05-1.85 (m, 2H), 1.80-1.57 (m, 6H). UPLC-MS: $t_R$=2.17 min (Generic method); MS (ESI) m/z calcd for $C_{26}H_{23}F_3N_3O_6$ (M–H)⁻: 530.2, found: 530.5.

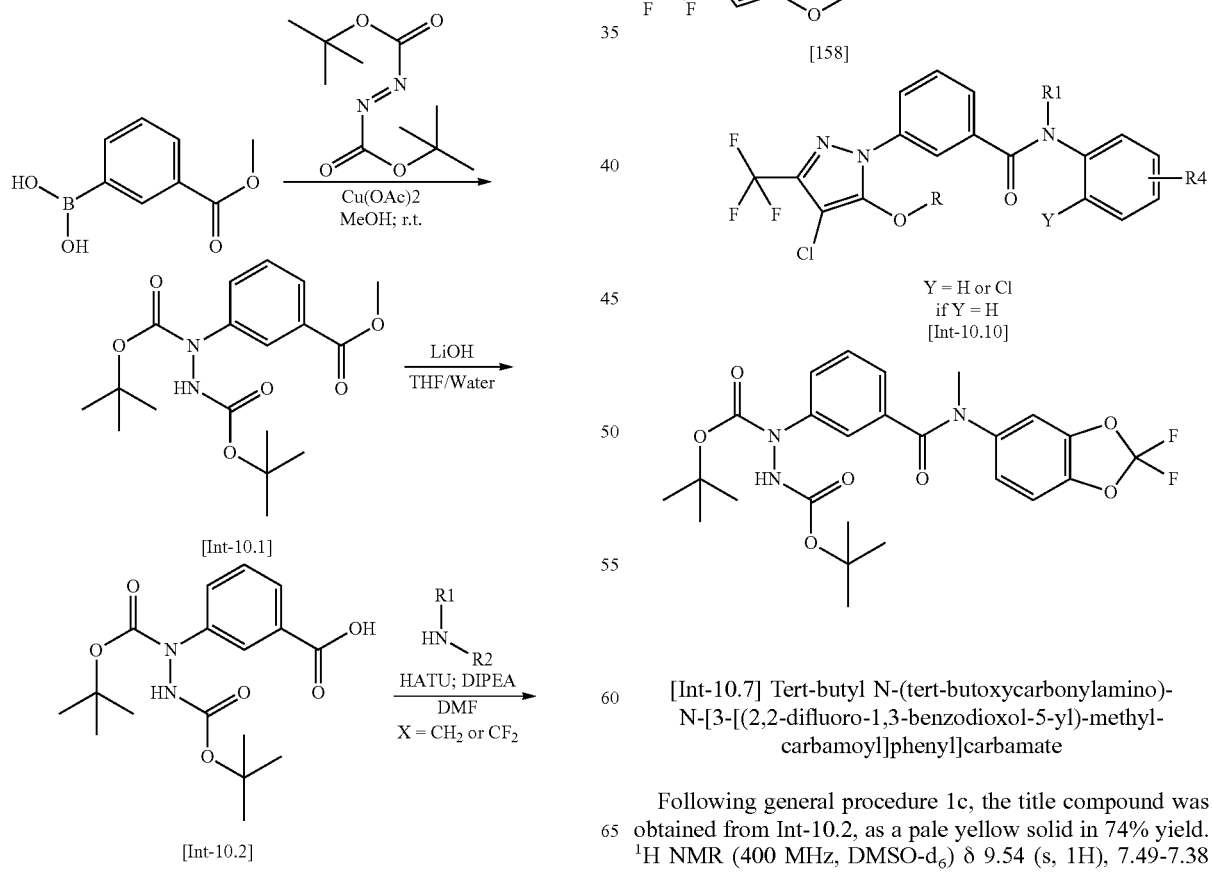

[Int-10.7] Tert-butyl N-(tert-butoxycarbonylamino)-N-[3-[(2,2-difluoro-1,3-benzodioxol-5-yl)-methyl-carbamoyl]phenyl]carbamate Following general procedure 1c, the title compound was obtained from Int-10.2, as a pale yellow solid in 74% yield. ¹H NMR (400 MHz, DMSO-d₆) δ 9.54 (s, 1H), 7.49-7.38 (m, 1H), 7.36-7.17 (m, 4H), 7.14-7.05 (m, 1H), 6.99-6.88

(m, 1H), 3.34 (s, 3H), 1.46-1.36 (m, 18H). UPLC-MS: $t_R$=2.63 min (Generic method); MS (ESI) m/z calcd for $C_{25}H_{30}F_2N_3O_7$ (M+H)$^+$: 522.2, found: 522.3.

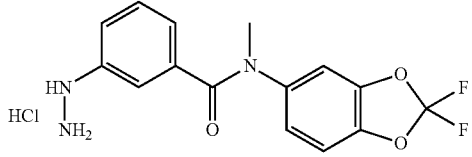 [SMILES: Cl ; CN(C(=O)c1cccc(NN)c1)c1ccc2c(c1)OC(F)(F)O2]

[Int-10.8] N-(2,2-Difluoro-1,3-benzodioxol-5-yl)-3-hydrazino-N-methyl-benzamide hydrochloride Following general procedure 1c, the title compound was obtained from Int-10.7, as a pale yellow solid in 90% yield. UPLC-MS: $t_R$=1.85 min (Generic method); MS (ESI) m/z calcd for $C_{15}H_{14}F_2N_3O_3$ (M+H)$^+$: 322.1, found: 322.2.

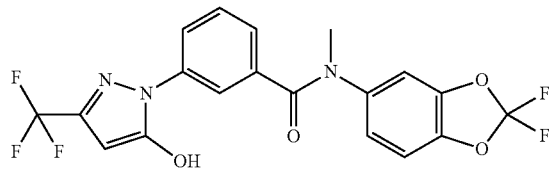 [SMILES: CN(C(=O)c1cccc(-n2nc(C(F)(F)F)cc2O)c1)c1ccc2c(c1)OC(F)(F)O2]

[Int-10.9] N-(2,2-Difluoro-1,3-benzodioxol-5-yl)-3-[5-hydroxy-3-(trifluoromethyl)pyrazol-1-yl]-N-methyl-benzamide Following general procedure 1c, the title compound was obtained from Int-10.8, as a pale yellow solid in 71% yield. $^1$H NMR (400 MHz, DMSO-$d_6$) δ 12.59 (bs, $^1$H), 7.78-7.62 (m, 2H), 7.53 (d, J=2.1 Hz, 1H), 7.38 (t, J=7.9 Hz, 1H), 7.27 (d, J=8.6 Hz, 1H), 7.24 (d, J=8.0 Hz, 1H), 7.04 (dd, J=8.6, 2.1 Hz, 1H), 5.90 (s, 1H), 3.36 (s, 3H).

[254] Methyl 3-[[2-[3-[(2,2-difluoro-1,3-benzodioxol-5-yl)-methyl-carbamoyl]phenyl]-5-(trifluoromethyl)pyrazol-3-yl]oxymethyl]bicyclo[1.1.1]pentane-1-carboxylate Following general procedure 10d, the title compound was obtained from Int-10.9, after purification by silica gel flash-column chromatography with cyclohexane/EtOAc (80/20) as the eluent, as a white solid in 89% yield $^1$H NMR (400 MHz, DMSO-$d_6$) δ 7.71 (app-t, J=1.9 Hz, 1H), 7.66-7.61 (m, 1H), 7.54 (d, J=2.1 Hz, 1H), 7.42 (t, J=7.9 Hz, 1H), 7.29 (d, J=8.6 Hz, 1H), 7.26 (d, J=7.6 Hz, 1H), 7.05 (app-dd, J=8.5, 2.1 Hz, 1H), 6.47 (s, 1H), 4.30 (s, 2H), 3.61 (s, 3H), 3.38 (s, 3H), 2.00 (s, 6H). UPLC-MS: $t_R$=1.88 min (Apolar method); MS (ESI) m/z calcd for $C_{27}H_{23}F_5N_3O_6$ (M+H)$^+$: 580.1, found: 580.4.

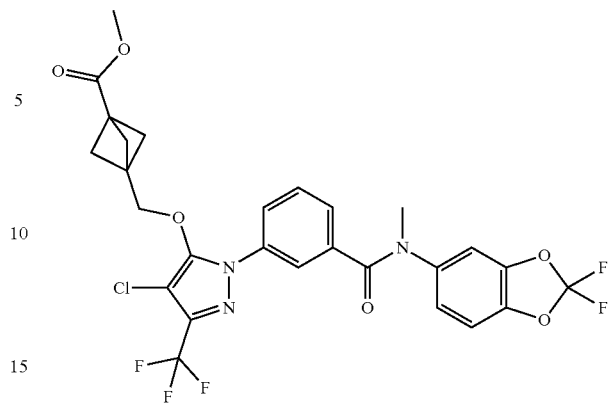

[Int-10.10] Methyl 3-[[4-chloro-2-[3-[(2,2-difluoro-1,3-benzodioxol-5-yl)-methyl-carbamoyl]phenyl]-5-(trifluoromethyl)pyrazol-3-yl]oxymethyl]bicyclo[1.1.1]pentane-1-carboxylate Following general procedure 10e, the title compound was obtained from compound 254, as a pale yellow solid as a crude compound: UPLC-MS: $t_R$=2.16 min (Apolar method); MS (ESI) m/z calcd for $C_{27}H_{22}ClF_5N_3O_6$ (M+H)$^+$: 614.1, found: 614.4.

[255] 3-[[2-[3-[(2,2-Difluoro-1,3-benzodioxol-5-yl)-methyl-carbamoyl]phenyl]-5-(trifluoromethyl)pyrazol-3-yl]oxymethyl]bicyclo[1.1.1]pentane-1-carboxylic acid Following general procedure 4a, the title compound was obtained from compound 254, after purification by silica gel flash-column chromatography with DCM/EtOAc (70/30) as the eluent, as a white solid in 63% yield: $^1$H NMR (400 MHz, DMSO-$d_6$) δ 12.40 (bs, 1H), 7.71 (app-t, J=1.9 Hz, 1H), 7.67-7.61 (m, 1H), 7.54 (d, J=2.1 Hz, 1H), 7.43 (t, J=7.9 Hz, 1H), 7.35-7.20 (m, 2H), 7.04 (app-dd, J=8.5, 2.1 Hz, 1H), 6.47 (s, 1H), 4.29 (s, 2H), 3.38 (s, 3H), 1.96 (s, 6H). UPLC-MS: $t_R$=2.19 min (Generic method); MS (ESI) m/z calcd for $C_{26}H_{19}F_5N_3O_6$ (M−H)$^-$: 564.1, found: 564.4.

[258] 3-[[4-Chloro-2-[3-[(2,2-difluoro-1,3-benzodioxol-5-yl)-methyl-carbamoyl]phenyl]-5-(trifluoromethyl)pyrazol-3-yl]oxymethyl]bicyclo[1.1.1]pentane-1-carboxylic acid Following general procedure 4a, the title compound was obtained from Int-10.10, after purification by silica gel flash-column chromatography with DCM/EtOAc (70/30) as the eluent, as a white solid in 32% yield: $^1$H NMR (400 MHz, DMSO-$d_6$) δ 12.05 (bs, 1H), 7.64-7.56 (m, 2H), 7.54 (d, J=2.1 Hz, 1H), 7.46 (t, J=8.1 Hz, 1H), 7.37 (d, J=7.7 Hz, 1H), 7.28 (d, J=8.5 Hz, 1H), 7.03 (dd, J=8.7, 2.1 Hz, 1H), 4.33 (s, 2H), 3.36 (s, 3H), 1.78 (s, 6H). UPLC-MS: $t_R$=2.24 min (Generic method); MS (ESI) m/z calcd for $C_{26}H_{18}ClF_5N_3O_6$ (M−H)$^-$: 598.1, found: 598.4.

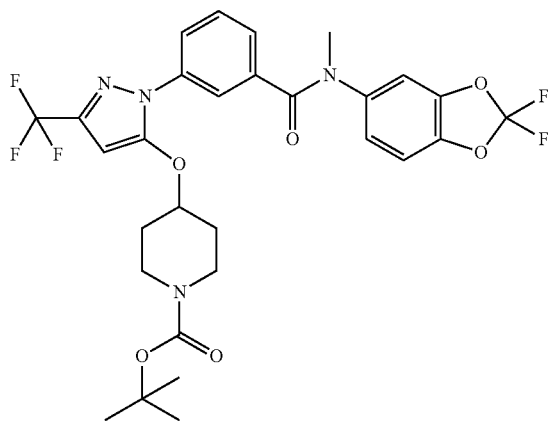 [SMILES: CN(C(=O)c1cccc(-n2nc(C(F)(F)F)cc2OC2CCN(C(=O)OC(C)(C)C)CC2)c1)c1ccc2c(c1)OC(F)(F)O2]

[Int-10.11] Tert-butyl 4-[2-[3-[(2,2-difluoro-1,3-benzodioxol-5-yl)-methyl-carbamoyl]phenyl]-5-(trifluoromethyl)pyrazol-3-yl]oxypiperidine-1-carboxylate Following general procedure 10d, the title compound was obtained from Int-10.9, after purification by silica gel flash-column chromatography with cyclohexane/EtOAc (50/50) as the eluent, as a white solid in 81% yield: UPLC-MS: $t_R$=2.13 min (Apolar method); MS (ESI) m/z calcd for $C_{29}H_{30}F_5N_4O_6$ (M+H)$^+$: 625.2, found: 625.4.

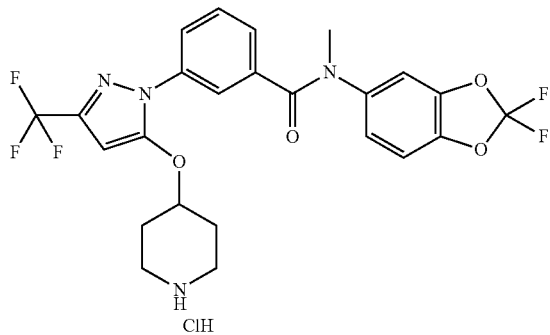 [SMILES: CN(C(=O)c1cccc(-n2nc(C(F)(F)F)cc2OC2CCNCC2)c1)c1ccc2c(c1)OC(F)(F)O2 ; Cl]

[Int-10.12] N-(2,2-Difluoro-1,3-benzodioxol-5-yl)-N-methyl-3-[5-(4-piperidyloxy)-3-(trifluoromethyl)pyrazol-1-yl]benzamide hydrochloride Following general procedure 1c, the title compound was obtained from Int-10.11, as a white solid in 95% yield UPLC-MS: $t_R$=2.12 min (Generic method); MS (ESI) m/z calcd for $C_{24}H_{22}F_5N_4O_4$ (M+H)$^+$: 525.1, found: 525.3.

[260] Ethyl 4-[4-[2-[3-[(2,2-difluoro-1,3-benzodioxol-5-yl)-methyl-carbamoyl]phenyl]-5-(trifluoromethyl)pyrazol-3-yl]oxy-1-piperidyl]-4-oxo-butanoate To a solution of Int-10.12 (117.0 mg, 0.21 mmol) in DCM (5 mL), under Nitrogen and cooled to 0° C., DIPEA (79.9 µL, 0.46 mmol) was added followed by ethyl 4-chloro-4-oxo-butanoate (35.8 µL, 0.25 mmol. Mixture was stirred for 18 h at room temperature and quenched with sat. aq. NH$_4$Cl (10 mL). Aqueous layer was extracted with EtOAc (3×15 mL). Collected organic layers were washed with water (20 mL), Brine (20 mL), dried with Na$_2$SO$_4$, filtered and solvent evaporated. The title compound was obtained, after purification by silica gel flash-column chromatography with Cyclohexane/EtOAc (80/20) as the eluent, as a white solid in 82% yield (113 mg): $^1$H NMR (400 MHz, DMSO-d$_6$) δ 7.70 (app-t, J=1.9 Hz, 1H), 7.65 (ddd, J=8.1, 2.3, 1.1 Hz, 1H), 7.55 (d, J=2.1 Hz, 1H), 7.40 (app-t, J=7.9 Hz, 1H), 7.31-7.22 (m, 2H), 7.04 (dd, J=8.6, 2.1 Hz, 1H), 6.59 (s, 1H), 4.88-4.61 (m, 1H), 4.03 (q, J=7.1 Hz, 2H), 3.76-3.56 (m, 2H), 3.46-3.35 (m, 2H), 3.37 (s, 3H), 2.64-2.57 (m, 2H), 2.50-2.46 (m, 2H), 2.08-2.00 (m, 1H), 1.96-1.88 (m, 1H), 1.79-1.67 (m, 1H), 1.67-1.54 (m, 1H), 1.17 (t, J=7.1 Hz, 3H). UPLC-MS: $t_R$=2.11 min (Apolar method); MS (ESI) m/z calcd for $C_{30}H_{30}F_5N_4O_7$ (M+H)$^+$: 653.2, found: 653.4.

[264] 4-[4-[2-[3-[(2,2-Difluoro-1,3-benzodioxol-5-yl)-methyl-carbamoyl]phenyl]-5-(trifluoromethyl)pyrazol-3-yl]oxy-1-piperidyl]-4-oxo-butanoic acid Following general procedure 4a, the title compound was obtained from compound 260, after purification by silica gel flash-column chromatography with DCM/EtOAc (50/50) as the eluent, as a white solid in 32% yield: $^1$H NMR (400 MHz, DMSO-d$_6$) δ 11.99 (s, 1H), 7.68 (app-t, J=1.8 Hz, 1H), 7.65 (app-dt, J=8.6, 1.2 Hz, 1H), 7.54 (d, J=2.1 Hz, 1H), 7.40 (t, J=7.9 Hz, 1H), 7.31-7.19 (m, 2H), 7.03 (dd, J=8.5, 2.2 Hz, 1H), 6.58 (s, 1H), 4.83-4.67 (m, 1H), 3.73-3.56 (m, 2H), 3.46-3.39 (m, 2H), 3.36 (s, 3H), 2.60-2.53 (m, 2H), 2.46-2.38 (m, 2H), 2.08-1.97 (m, 1H), 1.95-1.88 (m, 1H), 1.78-1.67 (m, 1H), 1.66-1.57 (m, 1H). UPLC-MS: $t_R$=2.19 min (Generic method); MS (ESI) m/z calcd for $C_{28}H_{24}F_5N_4O_7$ (M−H)$^-$: 623.2, found: 623.4.

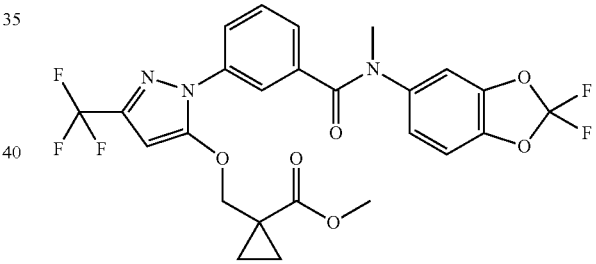

[Int-10.13] Ethyl 1-[[2-[3-[(2,2-difluoro-1,3-benzodioxol-5-yl)-methyl-carbamoyl]phenyl]-5-(trifluoromethyl)pyrazol-3-yl]oxymethyl]cyclopropanecarboxylate Following general procedure 10d, the title compound was obtained from Int-10.9, after purification by silica gel chromatography eluting with cyclohexane/EtOAc (80/20), as a white solid in 81% yield: $^1$H NMR (400 MHz, DMSO-d$_6$) δ 7.70 (app-t, J=1.8 Hz, 1H), 7.64 (dd, J=8.1, 1.5 Hz, 1H), 7.52 (d, J=2.1 Hz, 1H), 7.39 (t, J=7.9 Hz, 1H), 7.29 (d, J=8.5 Hz, 1H), 7.25 (d, J=7.7 Hz, 1H), 7.07-6.98 (m, 1H), 6.48 (s, 1H), 4.38 (s, 2H), 3.36 (s, 3H), 1.28-1.23 (m, 0H), 1.14-1.10 (m, 2H).

[265] 1-[[2-[3-[(2,2-Difluoro-1,3-benzodioxol-5-yl)-methyl-carbamoyl]phenyl]-5-(trifluoromethyl)pyrazol-3-yl]oxymethyl]cyclopropanecarboxylic acid Following general procedure 4a, the title compound was obtained from Int-10.13, after purification by silica gel flash-column chromatography with DCM/EtOAc (70/30) as the eluent, as a white solid in 30% yield: $^1$H NMR (400 MHz, DMSO-$d_6$) δ 12.55 (s, 1H), 7.70 (app-t, J=1.9 Hz, 1H), 7.68-7.62 (m, 1H), 7.53 (d, J=2.1 Hz, 1H), 7.39 (t, J=7.9 Hz, 1H), 7.32-7.18 (m, 2H), 7.02 (dd, J=8.7, 2.1 Hz, 1H), 6.45 (s, 1H), 4.34 (s, 2H), 3.36 (s, 3H), 1.22 (app-q, J=3.9 Hz, 2H), 1.06 (app-q, J=4.0 Hz, 2H). UPLC-MS: $t_R$=2.28 min (Generic method); MS (ESI) m/z calcd for $C_{24}H_{19}F_5N_3O_6$ (M+H)$^+$: 540.1, found: 540.4.
GENERAL PROTOCOL 11
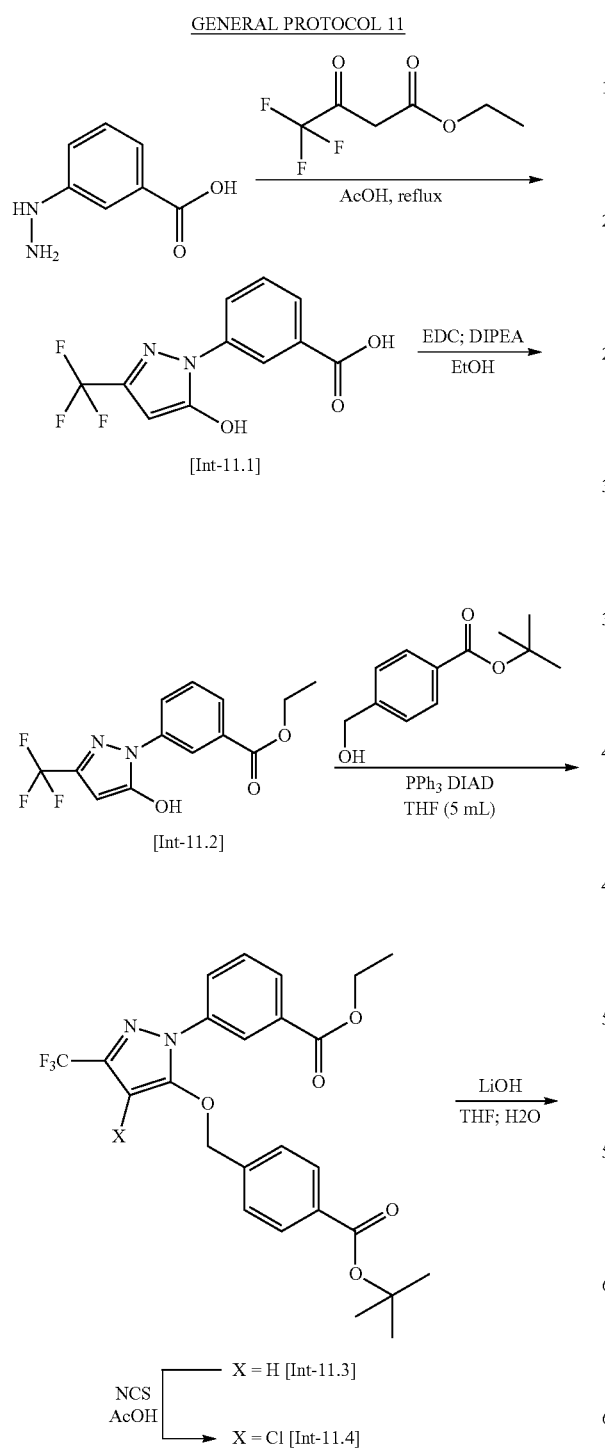
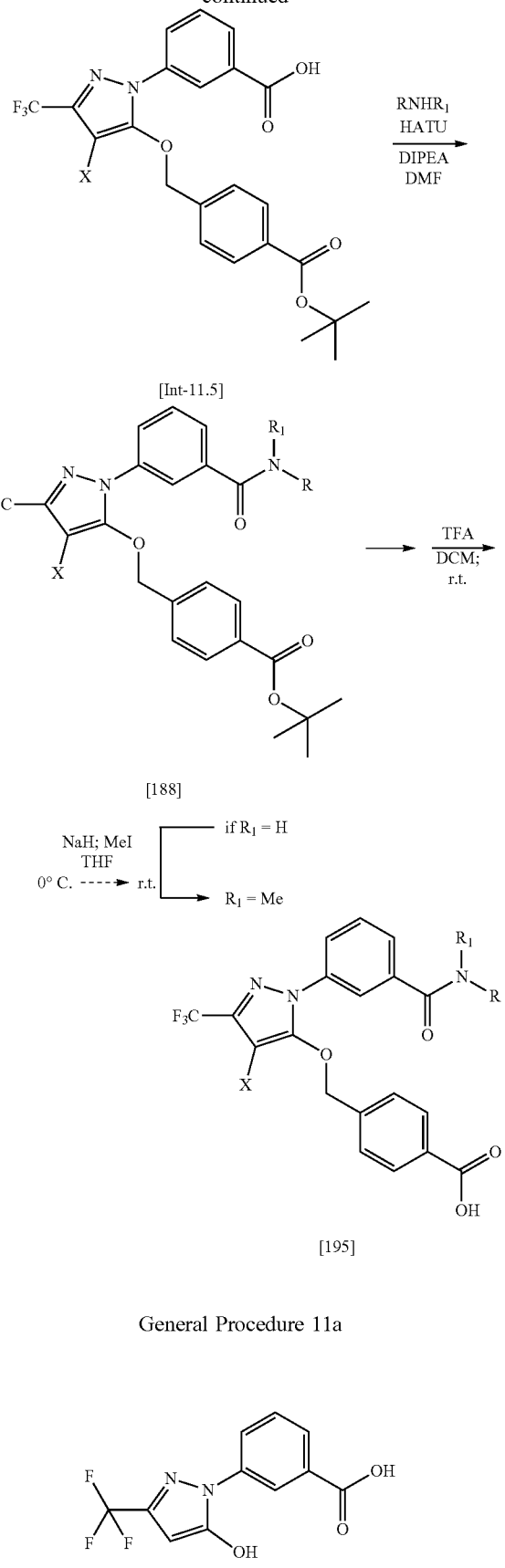
General Procedure 11a

[Int-11.1] 3-[5-Hydroxy-3-(trifluoromethyl)pyrazol-1-yl]benzoic acid

To a solution of 3-hydrazinobenzoic acid (5.0 g, 32.9 mmol) in AcOH (30 mL), ethyl 4,4,4-trifluoro-3-oxo-butanoate (4.9 mL, 33.5 mmol) was added. The mixture was refluxed for 5 h and cooled to room temperature. Water (100 mL) was added, with the formation of a precipitate. The precipitate was filtered and washed with water. The obtained solid was dissolved in EtOAc. The organic layer was dried over $Na_2SO_4$, filtered and the solvent evaporated. The title compound was obtained as a pale yellow solid in 79% yield (7.1 g): $^1$H NMR (400 MHz, DMSO-$d_6$) δ 13.25 (s, 1H), 12.71 (s, 1H), 8.30 (t, J=1.9 Hz, 1H), 8.01 (ddd, J=8.1, 2.3, 1.1 Hz, 1H), 7.94 (app-dt, J=7.8, 1.3 Hz, 1H), 7.65 (app-t, J=7.9 Hz, 1H), 5.98 (s, 1H). UPLC-MS: $t_R$=1.30 min (Generic method); MS (ESI) m/z calcd for $C_{11}H_8F_3N_2O_3$ (M+H)$^+$: 273.0, found: 273.1.

General Procedure 11b

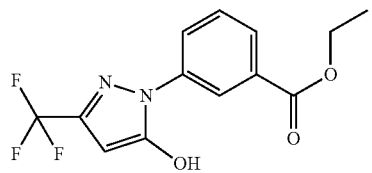 [SMILES: CCOC(=O)c1cccc(-n2nc(C(F)(F)F)cc2O)c1]

[Int-11.2] Ethyl 3-[5-hydroxy-3-(trifluoromethyl)pyrazol-1-yl]benzoate

To a solution of Int-11.1 (1.0 g, 3.67 mmol) in EtOH (20 mL), EDC.HCl (684.5 mg, 4.41 mmol) and DIPEA (768.22 μL, 4.41 mmol) were added. The mixture was stirred at room temperature for 24 h and the solvent was evaporated. The obtained solid was dissolved in EtOAc (50 mL) and the organic layer was washed with water (30 mL) and Brine (20 mL). The organic layer was dried over $Na_2SO_4$, filtered and the solvent evaporated. The title compound was obtained as a crude product as pale yellow solid in 90% yield (1.0 g): $^1$H NMR (400 MHz, DMSO-$d_6$) δ 8.35 (app-t, J=1.9 Hz, 1H), 8.08 (ddd, J=8.2, 2.3, 1.1 Hz, 1H), 7.92 (app-dt, J=7.8, 1.4 Hz, 1H), 7.65 (app-t, J=8.0 Hz, 1H), 5.86 (s, 1H), 4.36 (q, J=7.1 Hz, 2H), 1.34 (t, J=7.1 Hz, 3H). UPLC-MS: $t_R$=1.87 min (Generic method); MS (ESI) m/z calcd for $C_{13}H_{12}F_3N_2O_3$ (M+H)$^+$: 301.1, found: 301.5.

[Int-11.3] Ethyl 3-[5-[(4-tert-butoxycarbonylphenyl)methoxy]-3-(trifluoromethyl)pyrazol-1-yl]benzoate Following general procedure 10d, the title compound was obtained from compound Int-11.2, after purification by silica gel flash-column chromatography with Cyclohexane/EtOAc (70/30) as the eluent, as a white solid in 79% yield: $^1$H NMR (400 MHz, DMSO-$d_6$) δ 8.28 (app-t, J=1.9 Hz, 1H), 8.04-7.97 (m, 2H), 7.97-7.91 (m, 2H), 7.70 (app-t, J=8.0 Hz, 1H), 7.62 (d, J=8.2 Hz, 2H), 6.62 (s, 1H), 5.46 (s, 2H), 4.35 (q, J=7.1 Hz, 2H), 1.55 (s, 9H), 1.31 (t, J=7.1 Hz, 3H). UPLC-MS: $t_R$=2.50 min (Apolar method); MS (ESI) m/z calcd for $C_{25}H_{26}F_3N_2O_5$ (M+H)$^+$: 491.2, found: 491.6.

General Procedure 11c

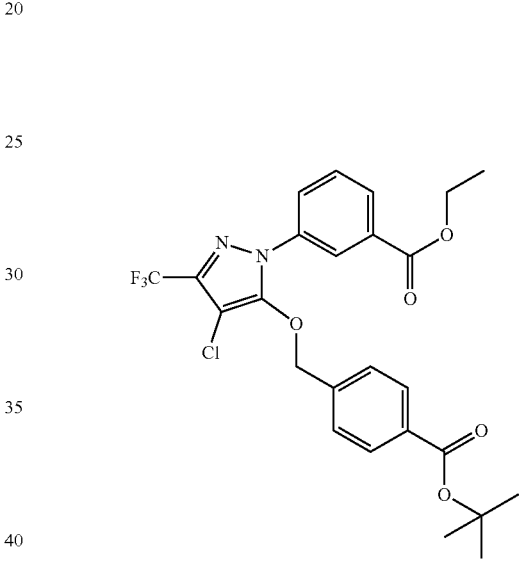

[Int-11.4] Ethyl 3-[5-[(4-tert-butoxycarbonylphenyl)methoxy]-4-chloro-3-(trifluoromethyl)pyrazol-1-yl]benzoate To a solution of Int-11.3 (750 mg, 1.53 mmol) in AcOH (5 mL), NCS (306.3 mg, 2.29 mmol) was added and the mixture was stirred for 4 days. Water was added (30 mL) and the aqueous layer was extracted with EtOAc (3×30 mL). The collected organic layers were washed with sat. aq. $NaHCO_3$ (4×20 mL), aq. sat. $Na_2S_2O_3$ (2×10 mL), brine (20 mL), dried with $Na_2SO_4$, filtered and the solvent evaporated. The title compound was obtained, after purification by silica gel flash-column chromatography with Cyclohexane/EtOAc (85/15) as the eluent, as a yellow solid in 86% yield (706 mg): $^1$H NMR (400 MHz, DMSO-$d_6$) δ 8.07-7.99 (m, 2H), 7.87 (ddd, J=8.1, 2.3, 1.2 Hz, 1H), 7.82-7.78 (m, 2H), 7.67 (app-t, J=7.8 Hz, 1H), 7.44-7.37 (m, 2H), 5.48 (s, 2H), 4.34 (q, J=7.1 Hz, 2H), 1.54 (s, 9H), 1.31 (t, J=7.1 Hz, 3H).

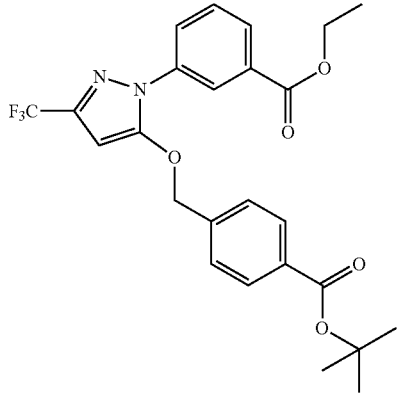 [SMILES: CCOC(=O)c1cccc(-n2nc(C(F)(F)F)cc2OCc2ccc(C(=O)OC(C)(C)C)cc2)c1]

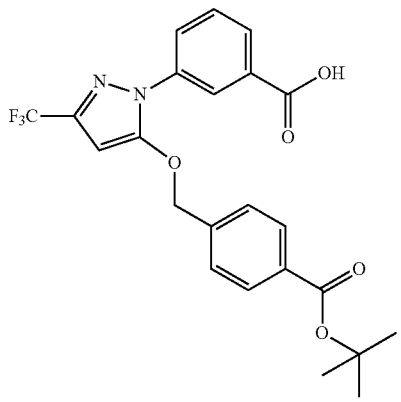 [SMILES: CC(C)(C)OC(=O)c1ccc(COc2cc(C(F)(F)F)nn2-c2cccc(C(=O)O)c2)cc1]

[Int-11.5] 3-[5-[(4-Tert-butoxycarbonylphenyl)methoxy]-3-(trifluoromethyl)pyrazol-1-yl]benzoic acid Following general procedure 4a, the title compound was obtained from compound Int-11.3, as crude product, as a white solid in 93% yield (430): $^1$H NMR (400 MHz, DMSO-$d_6$) δ 13.27 (bs, 1H), 8.30 (app-t, J=1.9 Hz, 1H), 8.00-7.95 (m, 2H), 7.95-7.90 (m, 2H), 7.67 (t, J=8.0 Hz, 1H), 7.64-7.56 (m, 2H), 6.59 (s, 1H), 5.46 (s, 2H), 1.54 (s, 9H).

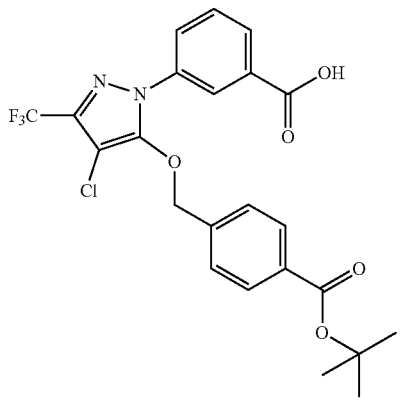 [SMILES: CC(C)(C)OC(=O)c1ccc(COc2c(Cl)c(C(F)(F)F)nn2-c2cccc(C(=O)O)c2)cc1]

[Int-11.6] 3-[5-[(4-Tert-butoxycarbonylphenyl)methoxy]-4-chloro-3-(trifluoromethyl)pyrazol-1-yl]benzoic acid Following general procedure 4a, the title compound was obtained from Int-11.4 as crude product, as a white solid in 91% yield: $^1$H NMR (400 MHz, DMSO-$d_6$) δ 13.36 (bs, 1H), 8.08 (app-t, J=1.9 Hz, 1H), 8.00 (app-dt, J=7.7, 1.3 Hz, 1H), 7.83 (ddd, J=8.3, 2.4, 1.3 Hz, 1H), 7.81-7.76 (m, 2H), 7.64 (app-t, J=7.9 Hz, 1H), 7.46-7.34 (m, 2H), 5.47 (s, 2H), 1.53 (s, 9H).

Tert-butyl 4-[[2-[3-[methyl-(2-methyl-1,3-benzoxazol-6-yl)carbamoyl]phenyl]-5-(trifluoromethyl)pyrazol-3-yl]oxymethyl]benzoate Following general procedure 1c, the title compound was obtained from compound Int-11.5, after purification by silica gel flash-column chromatography with Cyclohexane/EtOAc (50/50) as the eluent, as a yellow solid in 76% yield (79 mg): $^1$H NMR (400 MHz, DMSO-$d_6$) δ 7.99-7.86 (m, 2H), 7.73 (t, J=1.8 Hz, 1H), 7.63 (d, J=1.9 Hz, 1H), 7.57 (d, J=8.2 Hz, 1H), 7.53 (d, J=8.1 Hz, 2H), 7.48 (d, J=8.4 Hz, 1H), 7.32 (t, J=7.9 Hz, 1H), 7.23 (d, J=7.8 Hz, 1H), 7.14 (dd, J=8.4, 2.0 Hz, 1H), 6.50 (s, 1H), 5.38 (s, 2H), 3.41 (s, 3H), 2.52 (s, 3H), 1.53 (d, J=1.2 Hz, 9H). UPLC-MS: $t_R$=2.01 min (Generic method); MS (ESI) m/z calcd for $C_{20}H_{14}ClF_3N_3O_4$ (M+H)$^+$: 452.0, found: 452.1. UPLC-MS: $t_R$=1.92 min (Apolar method); MS (ESI) m/z calcd for $C_{32}H_{30}F3N4O5$ (M−H)$^-$: 607.2, found: 607.5.

[190] Tert-butyl 4-[[4-chloro-2-[3-[methyl-(2-methyl-1,3-benzoxazol-6-yl)carbamoyl]phenyl]-5-(trifluoromethyl) pyrazol-3-yl]oxymethyl]benzoate Following general procedure 1c, the title compound was obtained from compound Int-11.6, after purification by silica gel flash-column chromatography with Cyclohexane/EtOAc (50:50) as the eluent, as a white solid in 79% yield: $^1$H NMR (400 MHz, DMSO-$d_6$) δ 7.88-7.77 (m, 2H), 7.65-7.61 (m, 1H), 7.60 (d, J=2.0 Hz, 1H), 7.48 (d, J=8.4 Hz, 1H), 7.46-7.39 (m, 1H), 7.37-7.25 (m, 4H), 7.13 (dd, J=8.4, 2.0 Hz, 1H), 5.34 (s, 2H), 3.42 (s, 3H), 2.49 (s, 3H), 1.52 (s, 9H). UPLC-MS: $t_R$=2.17 min (Apolar method); MS (ESI) m/z calcd for $C_{32}H_{29}ClF_3N4O5$ (M+H)$^+$: 641.2, found: 641.5.

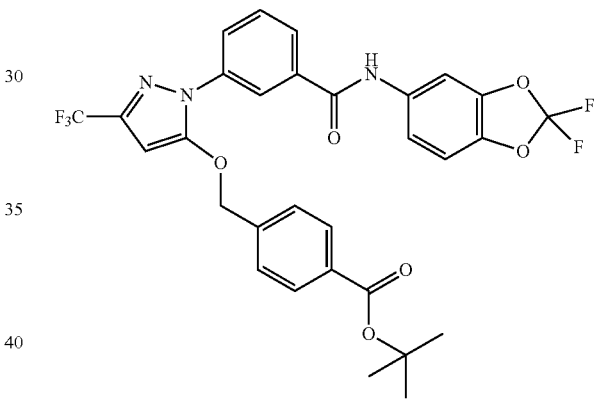

[Int-11.7] Tert-butyl 4-[[2-[3-[(2,2-difluoro-1,3-benzodioxol-5-yl)carbamoyl]phenyl]-5-(trifluoromethyl) pyrazol-3-yl]oxymethyl]benzoate Following general procedure 1c, the title compound was obtained from compound Int-11.5, after purification by silica gel flash-column chromatography with Cyclohexane/EtOAc (70:30) as the eluent, as a white solid in 75% yield: $^1$H NMR (400 MHz, DMSO-$d_6$) δ 10.60 (s, 1H), 8.29 (app-t, J=1.9 Hz, 1H), 8.01 (app-dt, J=7.9, 1.2 Hz, 1H), 7.97-7.86 (m, 4H), 7.72 (app-t, J=8.0 Hz, 1H), 7.65-7.58 (m, 2H), 7.51 (dd, J=8.8, 2.1 Hz, 1H), 7.42 (d, J=8.8 Hz, 1H), 6.63 (s, 1H), 5.47 (s, 2H), 1.53 (s, 9H). UPLC-MS: $t_R$=2.50 min (Apolar method); MS (ESI) m/z calcd for $C_{30}H_{24}ClF_5N_3O_6$ (M+H)$^+$: 618.1, found: 618.5.

[191] Tert-butyl 4-[[2-[3-[(2,2-difluoro-1,3-benzodioxol-5-yl)-methyl-carbamoyl]phenyl]-5-(trifluoromethyl)pyrazol-3-yl]oxymethyl]benzoate Following general procedure 1d, the title compound was obtained from compound Int-11.7, after purification by silica gel flash-column chromatography with Cyclohexane/EtOAc (70/30) as the eluent, as a white solid in 85% yield (91 mg): ¹H NMR (400 MHz, DMSO-d₆) δ 7.98-7.88 (m, 2H), 7.69 (app-t, J=1.9 Hz, 1H), 7.64 (app-dt, J=8.1, 1.5 Hz, 1H), 7.59-7.53 (m, 2H), 7.50 (d, J=2.1 Hz, 1H), 7.40 (app-t, J=7.9 Hz, 1H), 7.32-7.22 (m, 2H), 7.00 (dd, J=8.6, 2.1 Hz, 1H), 6.52 (s, 1H), 5.41 (s, 2H), 3.34 (s, 3H), 1.53 (s, 9H). UPLC-MS: $t_R$=2.35 min (Apolar method); MS (ESI) m/z calcd for $C_{31}H_{27}F_5N_3O_6$ (M+H)⁺: 632.2, found: 632.5.

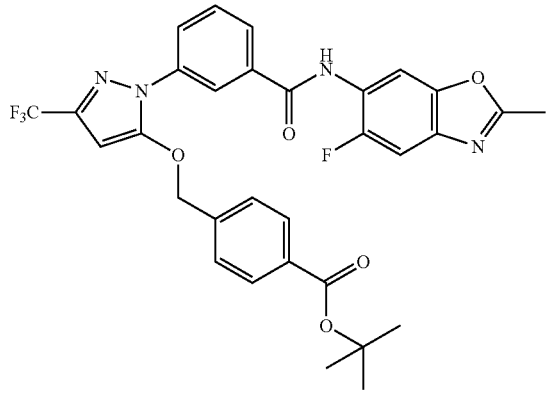

[Int-11.9] Tert-butyl 4-[[2-[3-[(5-fluoro-2-methyl-1,3-benzoxazol-6-yl)carbamoyl]phenyl]-5-(trifluoromethyl) pyrazol-3-yl]oxymethyl]benzoate Following general procedure 1c, the title compound was obtained from compound Int-11.5, after purification by silica gel flash-column chromatography with Cyclohexane/EtOAc (70:30) as the eluent, as a white solid in 65% yield: ¹H NMR (400 MHz, DMSO-d₆) δ 10.42 (s, 1H), 8.34 (app-t, J=2.0 Hz, 1H), 8.06 (app-dt, J=8.0, 1.3 Hz, 1H), 8.00-7.94 (m, 2H), 7.94-7.88 (m, 2H), 7.72 (t, J=7.9 Hz, 1H), 7.68 (d, J=10.0 Hz, 1H), 7.65-7.57 (m, 2H), 6.62 (s, 1H), 5.48 (s, 2H), 2.64 (s, 3H), 1.53 (s, 9H). UPLC-MS: $t_R$=2.07 min (Apolar method); MS (ESI) m/z calcd for $C_{31}H_{27}F_4N_4O_5$ (M+H)⁺: 611.2, found: 611.5.

[189] Tert-butyl 4-[[2-[3-[(5-fluoro-2-methyl-1,3-benzoxazol-6-yl)-methyl-carbamoyl]phenyl]-5-(trifluoro methyl)pyrazol-3-yl]oxymethyl]benzoate Following general procedure 1d, the title compound was obtained from Int-11.9, after purification by silica gel flash-column chromatography with Cyclohexane/EtOAc (60:40) as the eluent, as a white solid in 74% yield: ¹H NMR (400 MHz, DMSO-d₆) δ 8.04-7.86 (m, 3H), 7.78-7.68 (m, 1H), 7.62 (bs, 1H), 7.58-7.48 (m, 3H), 7.44-7.15 (m, 2H), 6.51 (s, 1H), 5.41 (s, 2H), 3.34 (s, 3H), 2.54 (s, 3H), 1.54 (s, 9H). UPLC-MS: $t_R$=2.00 min (Apolar method); MS (ESI) m/z calcd for $C_{32}H_{29}F_4N_4O_5$ (M+H)⁺: 625.2, found: 625.5.

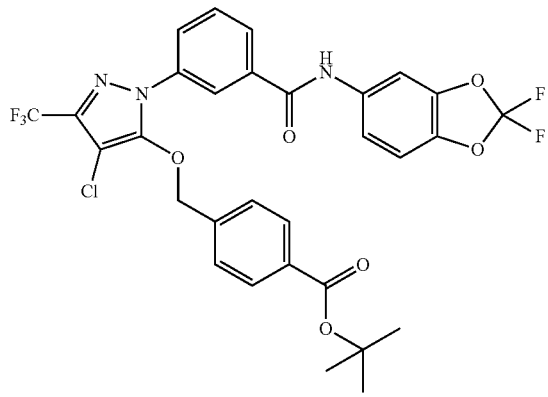 [SMILES: CC(C)(C)OC(=O)c1ccc(COc2c(Cl)c(C(F)(F)F)nn2-c2cccc(C(=O)Nc3ccc4c(c3)OC(F)(F)O4)c2)cc1]

[Int-11.8] Tert-butyl 4-[[4-chloro-2-[3-[(2,2-difluoro-1,3-benzodioxol-5-yl)carbamoyl]phenyl]-5-(trifluoromethyl) pyrazol-3-yl]oxymethyl]benzoate Following general procedure 1c, the title compound was obtained from compound Int-11.6, after purification by silica gel flash-column chromatography with Cyclohexane/EtOAc (80:20) as the eluent, as a white solid in 94% yield: ¹H NMR (400 MHz, DMSO-d₆) δ 10.55 (s, 1H), 8.10 (app-t, J=1.9 Hz, 1H), 8.06 (app-dt, J=7.6, 1.3 Hz, 1H), 7.91 (d, J=2.0 Hz, 1H), 7.82 (ddd, J=8.1, 2.2, 1.1 Hz, 1H), 7.80-7.74 (m, 2H), 7.70 (app-t, J=7.9 Hz, 1H), 7.49 (dd, J=8.8, 2.1 Hz, 1H), 7.45-7.37 (m, 3H), 5.49 (s, 2H), 1.49 (s, 9H).

[201] Tert-butyl 4-[[4-chloro-2-[3-[(2,2-difluoro-1,3-benzodioxol-5-yl)-methyl-carbamoyl]phenyl]-5-(trifluoro methyl)pyrazol-3-yl]oxymethyl]benzoate Following general procedure 1d, the title compound was obtained from Int-11.8, after purification by silica gel flash-column chromatography with cyclohexane/EtOAc (70:30) as the eluent, as a white solid in 53% yield: ¹H NMR (400 MHz, DMSO-d₆) δ 7.87-7.78 (m, 2H), 7.61-7.54 (m, 1H), 7.53-7.43 (m, 2H), 7.43-7.30 (m, 4H), 7.25 (d, J=8.5 Hz, 1H), 6.98 (d, J=8.6 Hz, 1H), 5.40 (s, 2H), 3.36 (s, 3H), 1.53 (s, 9H). UPLC-MS: $t_R$=2.60 min (Apolar method); MS (ESI) m/z calcd for $C_{31}H_{26}ClF_5N_3O_6$ (M+H)⁺: 666.1, found: 666.4.

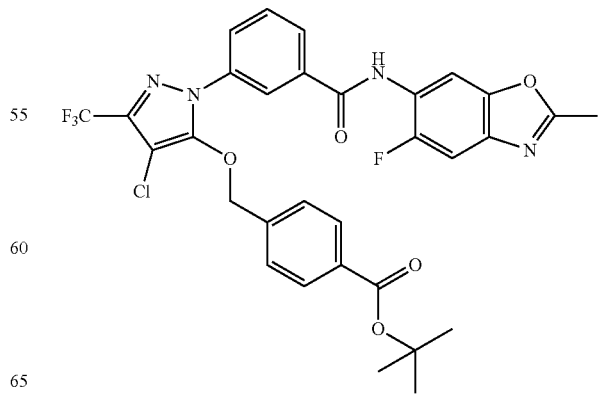

[Int-11.10] Tert-butyl 4-[[4-chloro-2-[3-[(5-fluoro-2-methyl-1,3-benzoxazol-6-yl)carbamoyl]phenyl]-5-(trifluoro methyl)pyrazol-3-yl]oxymethyl]benzoate Following general procedure 1c, the title compound was obtained from compound Int-11.6, after purification by silica gel flash-column chromatography with Cyclohexane/EtOAc (60:40) as the eluent, as a white solid in 61% yield: $^1$H NMR (400 MHz, DMSO-d$_6$) δ 10.40 (s, 1H), 8.20 (app-t, J=1.9 Hz, 1H), 8.12 (app-d, J=7.7 Hz, 1H), 7.97 (app-d, J=6.3 Hz, 1H), 7.87-7.79 (m, 3H), 7.77-7.64 (m, 2H), 7.50-7.40 (m, 2H), 5.50 (s, 2H), 2.64 (s, 3H), 1.51 (s, 9H).

[202] Tert-butyl 4-[[4-chloro-2-[3-[(5-fluoro-2-methyl-1,3-benzoxazol-6-yl)-methyl-carbamoyl] phenyl]-5-(trifluoro methyl)pyrazol-3-yl]oxymethyl] benzoate Following general procedure 1d, the title compound was obtained from compound Int-11.10, after purification by silica gel flash-column chromatography with DCM/EtOAc (70:30) as the eluent, as a white solid in 73% yield: $^1$H NMR (400 MHz, DMSO-d$_6$) δ 7.90 (d, J=6.6 Hz, 1H), 7.83-7.75 (m, 2H), 7.59 (s, 1H), 7.52 (app-d, J=9.6 Hz, 1H), 7.45 (bs, 1H), 7.31 (d, J=8.2 Hz, 4H), 5.34 (s, 2H), 3.35 (s, 3H), 2.49 (s, 3H), 1.53 (s, 9H). UPLC-MS: t$_R$=2.29 min (Apolar method); MS (ESI) m/z calcd for C$_{32}$H$_{28}$ClF$_4$N4O5 (M+H)$^+$: 659.2, found: 659.3.

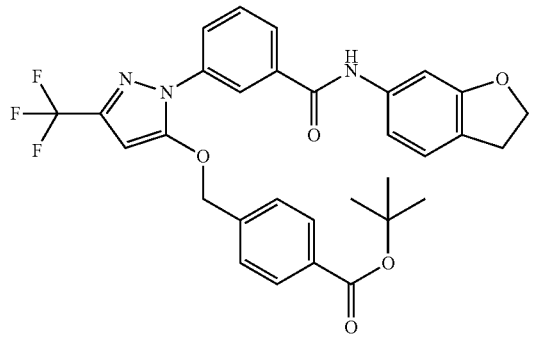 [SMILES: CC(C)(C)OC(=O)c1ccc(COc2cc(C(F)(F)F)nn2-c2cccc(C(=O)Nc3ccc4c(c3)OCC4)c2)cc1]

[Int-11.11] tert-Butyl 4-[[2-[3-(2,3-dihydrobenzofuran-6-ylcarbamoyl)phenyl]-5-(trifluoromethyl)pyrazol-3-yl]oxymethyl]benzoate following general procedure 1c, the title compound was obtained from compound Int-11.5 and 2,3-dihydrobenzofuran-6-amine, after purification by silica gel flash-column chromatography with Cyclohexane/EtOAc as the eluent, as a white solid in 53% yield: $^1$H NMR (400 MHz, DMSO-d$_6$) δ 10.38 (s, 1H), 8.26-8.21 (m, 1H), 8.12 (dt, J=7.7, 1.3 Hz, 1H), 7.93-7.86 (m, 2H), 7.83-7.78 (m, 2H), 7.72 (td, J=7.9, 2.5 Hz, 1H), 7.68-7.62 (m, 1H), 7.24 (s, 1H), 7.08-7.01 (m, 2H), 5.31 (s, 2H), 2.62 (s, 3H), 1.51 (s, 9H). UPLC-MS: t$_R$=2.24 min (Apolar method); MS (ESI) m/z calcd for C$_{31}$H$_{29}$F$_3$N$_3$O$_5$ (M+H)$^+$: 579.6, found: 579.4.

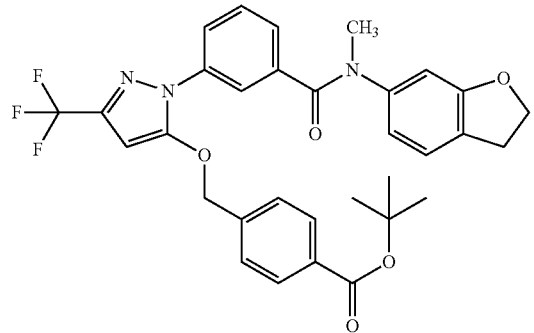 [SMILES: CN(C(=O)c1cccc(-n2nc(C(F)(F)F)cc2OCc2ccc(C(=O)OC(C)(C)C)cc2)c1)c1ccc2c(c1)OCC2]

[Int-11.12] tert-Butyl 4-[[2-[3-[2,3-dihydrobenzofuran-6-yl(methyl)carbamoyl]phenyl]-5-(trifluoromethyl)pyrazol-3-yl]oxymethyl]benzoate following general procedure 1d, the title compound was obtained from compound Int-11.11, after purification by silica gel flash-column chromatography with Cyclohexane/EtOAc (65:35) as the eluent, as a white solid in 86% yield: $^1$H NMR (400 MHz, DMSO-d$_6$) δ 7.96-7.92 (m, 2H), 7.74 (t, J=1.9 Hz, 1H), 7.64-7.60 (m, 1H), 7.57 (d, J=8.2 Hz, 2H), 7.37 (t, J=7.9 Hz, 1H), 7.24 (d, J=7.7 Hz, 1H), 7.03 (d, J=7.8 Hz, 1H), 6.69 (d, J=1.9 Hz, 1H), 6.56 (dd, J=7.8, 1.9 Hz, 1H), 6.53 (s, 1H), 5.43 (s, 2H), 4.47 (t, J=8.7 Hz, 2H), 3.32 (s, 3H), 3.05 (t, J=8.7 Hz, 2H), 1.55 (s, 9H). UPLC-MS: t$_R$=2.18 min (Apolar method); MS (ESI) m/z calcd for C$_{32}$H$_{31}$F$_3$N$_3$O$_5$ (M+H)$^+$: 594.6, found: 594.5.

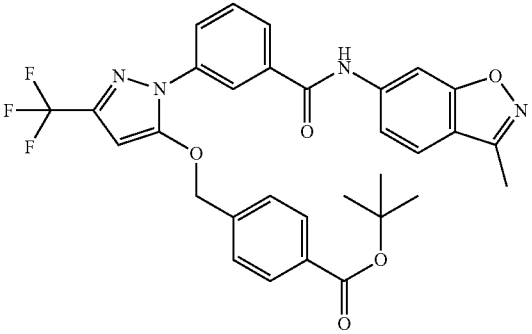 [SMILES: Cc1noc2cc(NC(=O)c3cccc(-n4nc(C(F)(F)F)cc4OCc4ccc(C(=O)OC(C)(C)C)cc4)c3)ccc12]

[Int-11.13] tert-Butyl 4-[[2-[3-[(3-Methyl-1,2-benzoxazol-6-yl)carbamoyl]phenyl]-5-(trifluoromethyl)pyrazol-3-yl]oxymethyl]benzoate following general procedure 1c, the title compound was obtained from compound Int-11.5 and 3-methyl-1,2-benzoxazol-6-amine, after purification by silica gel flash-column chromatography with Cyclohexane/EtOAc as the eluent, as a white solid in 79% yield: $^1$H NMR (400 MHz, DMSO-d$_6$) δ 10.61 (s, 1H), 8.32 (s, 1H), 8.05 (dt, J=7.8, 1.3 Hz, 1H), 7.94 (ddd, J=8.1, 2.2, 1.0 Hz, 1H), 7.92-7.87 (m, 3H), 7.76-7.69 (m, 2H), 7.65-7.59 (m, 2H), 6.62 (s, 1H), 5.47 (s, 2H), 2.56 (s, 3H), 1.51 (s, 9H). UPLC-MS: t$_R$=2.20 min (Apolar method); MS (ESI) m/z calcd for C$_{31}$H$_{28}$F$_3$N$_4$O$_5$ (M+H)$^+$: 593.6, found: 593.4.

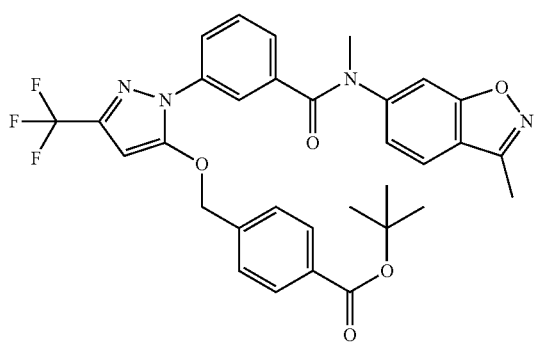 [SMILES: Cc1noc2cc(N(C)C(=O)c3cccc(-n4nc(C(F)(F)F)cc4OCc4ccc(C(=O)OC(C)(C)C)cc4)c3)ccc12]

[Int-11.14] tert-Butyl 4-[[2-[3-[methyl-(3-Methyl-1,2-benzoxazol-6-yl)carbamoyl]phenyl]-5-(trifluoromethyl) pyrazol-3-yl]oxymethyl]benzoate following general procedure 1d, the title compound was obtained from compound Int-11.13, after purification by silica gel flash-column chromatography with Cyclohexane/EtOAc (50/50) as the eluent, as a white solid in 74% yield: $^1$H NMR (400 MHz, DMSO-$d_6$) δ 7.95-7.89 (m, 2H), 7.83 (d, J=2.0 Hz, 1H), 7.73 (s, 1H), 7.59 (d, J=8.3 Hz, 1H), 7.56-7.50 (m, 3H), 7.46-7.40 (m, 1H), 7.34 (app-t, J=7.4 Hz, 1H), 7.25 (s, 1H), 5.37 (s, 2H), 3.41 (s, 3H), 2.44 (s, 3H), 1.53 (s, 9H). UPLC-MS: $t_R$=2.10 min (Apolar method); MS (ESI) m/z calcd for $C_{32}H_{30}F_3N_4O_5$ (M+H)$^+$: 607.6, found: 607.5.

General Procedure 11 d

[195] 4-[[2-[3-[Methyl-(2-methyl-1,3-benzoxazol-6-yl) carbamoyl]phenyl]-5-(trifluoromethyl)pyrazol-3-yl]oxy methyl]benzoic acid To a solution of compound 188 (63.0 mg, 0.10 mmol) in DCM (1 mL) a 15% solution of TFA in DCM (1 mL) was added. Solution was stirred at room temperature for 8 h and solvent was evaporated. The title compound was obtained, after purification by silica gel flash-column chromatography with DCM/EtOAc (70/30) as the eluent, as a white solid in 75% yield (41 mg): $^1$H NMR (400 MHz, DMSO-$d_6$) δ 13.04 (bs, 1H), 8.01-7.93 (m, 2H), 7.74 (app-t, J=1.9 Hz, 1H), 7.63 (d, J=2.0 Hz, 1H), 7.57 (app-dt, J=8.1, 1.4 Hz, 1H), 7.55-7.51 (m, 2H), 7.47 (d, J=8.4 Hz, 1H), 7.31 (app-t, J=7.9 Hz, 1H), 7.22 (d, J=7.7 Hz, 1H), 7.14 (dd, J=8.4, 2.0 Hz, 1H), 6.51 (s, 1H), 5.39 (s, 2H), 3.41 (s, 3H), 2.51 (s, 3H). UPLC-MS: $t_R$=0.48 min (Apolar method); MS (ESI) m/z calcd for $C_{28}H_{20}F_3N_4O_5$ (M-H)$^-$: 549.1, found: 549.3.

[196] 4-[[2-[3-[(5-Fluoro-2-methyl-1,3-benzoxazol-6-yl)-methyl-carbamoyl]phenyl]-5-(trifluoromethyl) pyrazol-3-yl]oxymethyl]benzoic acid Following general procedure 11d, the title compound was obtained from compound 189, after purification by silica gel flash-column chromatography with DCM/EtOAc (80:20) as the eluent, as a white solid in 80% yield: $^1$H NMR (400 MHz, DMSO-$d_6$) δ 13.06 (s, 1H), 8.02-7.88 (m, 3H), 7.73 (bs, 1H), 7.67-7.57 (m, 1H), 7.57-7.47 (m, 3H), 7.40-7.18 (m, 2H), 6.52 (s, 1H), 5.41 (s, 2H), 3.35 (s, 3H), 2.53 (s, 3H). UPLC-MS: $t_R$=0.48 min (Apolar method); MS (ESI) m/z calcd for $C_{28}H_{19}F_4N_4O_5$ (M-H)$^-$: 567.1, found: 567.5.

[197] 4-[[2-[3-[(2,2-difluoro-1,3-benzodioxol-5-yl)-methyl-carbamoyl]phenyl]-5-(trifluoromethyl)pyrazol-3-yl]oxymethyl]benzoic acid Following general procedure 11d, the title compound was obtained from compound 191, after purification by silica gel flash-column chromatography with DCM/EtOAc (90:10) as the eluent, as a white solid in 75% yield: $^1$H NMR (400 MHz, DMSO-$d_6$) δ 13.05 (bs, 1H), 8.03-7.93 (m, 2H), 7.71 (app-t, J=1.8 Hz, 1H), 7.65 (app-dt, J=8.2, 2.2 Hz, 1H), 7.60-7.54 (m, 2H), 7.51 (d, J=2.1 Hz, 1H), 7.41 (app-t, J=7.9 Hz, 1H), 7.34-7.21 (m, 2H), 7.01 (dd, J=8.6, 2.1 Hz, 1H), 6.54 (s, 1H), 5.43 (s, 2H), 3.34 (s, 3H). UPLC-MS: $t_R$=0.88 min (Apolar method); MS (ESI) m/z calcd for $C_{27}H_{17}F_5N_3O_6$ (M-H)$^-$: 574.1, found: 574.4.

[198] 4-[[4-Chloro-2-[3-[methyl-(2-methyl-1,3-benzoxazol-6-yl)carbamoyl]phenyl]-5-(trifluoromethyl) pyrazol-3-yl]oxymethyl]benzoic acid Following general procedure 11d, the title compound was obtained from compound 190, after purification by silica gel flash-column chromatography with DCM/EtOAc (70:30) as the eluent, as a white solid in 68% yield: $^1$H NMR (400 MHz, DMSO-$d_6$) δ 13.04 (bs, 1H), 7.89-7.79 (m, 2H), 7.66-7.58 (m, 2H), 7.47 (d, J=8.4 Hz, 1H), 7.45-7.37 (m, 1H), 7.36-7.25 (m, 4H), 7.14 (dd, J=8.4, 2.0 Hz, 1H), 5.31 (s, 2H), 3.41 (s, 3H), 2.48 (s, 3H). UPLC-MS: $t_R$=0.56 min (Apolar method); MS (ESI) m/z calcd for $C_{28}H_{19}F_4N_4O_5$ (M-H)$^-$: 567.1, found: 583.4.

[211] 4-[[4-Chloro-2-[3-[(2,2-difluoro-1,3-benzodioxol-5-yl)-methyl-carbamoyl]phenyl]-5-(trifluoromethyl)pyrazol-3-yl]oxymethyl]benzoic acid Following general procedure 11d, the title compound was obtained from compound 201, after purification by silica gel flash-column chromatography with DCM/EtOAc (90:10) as the eluent, as a white solid in 61% yield: $^1$H NMR (400 MHz, DMSO-$d_6$) δ 13.01 (s, 1H), 7.92-7.82 (m, 2H), 7.55 (app-t, J=1.8 Hz, 1H), 7.51-7.45 (m, 2H), 7.43-7.30 (m, 4H), 7.24 (d, J=8.5 Hz, 1H), 6.99 (dd, J=8.5, 2.1 Hz, 1H), 5.38 (s, 2H), 3.35 (s, 3H). UPLC-MS: $t_R$=1.16 min (Apolar method); MS (ESI) m/z calcd for $C_{27}H_{18}ClF_5N_3O_6$ (M-H)$^-$: 608.1, found: 608.4.

[212] 4-[[4-Chloro-2-[3-[(5-fluoro-2-methyl-1,3-benzoxazol-6-yl)-methyl-carbamoyl]phenyl]-5-(trifluoromethyl)pyrazol-3-yl]oxymethyl]benzoic acid Following general procedure 11d, the title compound was obtained from compound 202, after purification by silica gel flash-column chromatography with DCM/EtOAc (70:30) as the eluent, as a white solid in 79% yield: $^1$H NMR (400 MHz, DMSO-$d_6$) δ 13.07 (s, 1H), 7.91 (d, J=6.6 Hz, 1H), 7.87-7.79 (m, 2H), 7.61 (bs, 1H), 7.56-7.41 (m, 2H), 7.40-7.25 (m, 4H), 5.33 (s, 2H), 3.35 (s, 3H), 2.51 (s, 3H). UPLC-MS: $t_R$=0.72 min (Apolar method); MS (ESI) m/z calcd for $C_{28}H_{18}ClF_4N_4O_5$ (M-H)$^-$: 601.1, found: 601.5.

135

[262] 4-[[2-[3-[2,3-Dihydrobenzofuran-6-yl(methyl) carbamoyl]phenyl]-5-(trifluoromethyl)pyrazol-3-yl] oxymethyl]benzoic acid following general procedure 11d, the title compound was obtained from compound Int-11.12, after purification by silica gel flash-column chromatography with DCM/MeOH (99:1) as the eluent, as a white solid in 77% yield: $^1$H NMR (400 MHz, DMSO-$d_6$) δ 13.02 (bs, 1H), 7.98 (d, J=8.3 Hz, 2H), 7.76 (app-t, J=1.9 Hz, 1H), 7.62 (ddd, J=8.2, 2.3, 1.1 Hz, 1H), 7.57 (d, J=8.3 Hz, 2H), 7.37 (app-t, J=7.9 Hz, 1H), 7.24 (d, J=7.7 Hz, 1H), 7.03 (d, J=7.8 Hz, 1H), 6.69 (d, J=1.9 Hz, 1H), 6.56 (dd, J=8.0, 2.1 Hz, 1H), 6.54 (s, 1H), 5.43 (s, 2H), 4.46 (t, J=8.7 Hz, 2H), 3.32 (s, 3H), 3.05 (t, J=8.7 Hz, 2H). UPLC-MS: $t_R$=2.01 min (Apolar method); MS (ESI) m/z calcd for $C_{28}H_{23}F_3N_3O_5$ (M+H)$^+$: 538.5, found: 538.4.

136

[263] 4-[[2-[3-[Methyl-(3-methyl-1,2-benzoxazol-6-yl) carbamoyl]phenyl]-5-(trifluoromethyl)pyrazol-3-yl]oxymethyl]benzoic acid following general procedure 11d, the title compound was obtained from compound Int-11.14, after purification by silica gel flash-column chromatography with DCM/MeOH (99:1) as the eluent, as a white solid in 67% yield: $^1$H NMR (400 MHz, DMSO-$d_6$) δ 13.02 (s, 1H), 8.00-7.94 (m, 2H), 7.83 (d, J=2.1 Hz, 1H), 7.74 (s, 1H), 7.60 (d, J=8.2 Hz, 1H), 7.54 (d, J=8.2 Hz, 3H), 7.43 (d, J=8.9 Hz, 1H), 7.38-7.29 (m, 1H), 7.28-7.20 (m, 1H), 6.51 (s, 1H), 5.38 (s, 2H), 3.41 (s, 3H), 2.44 (s, 3H). UPLC-MS: $t_R$=1.97 min (Generic method); MS (ESI) m/z calcd for $C_{28}H_{22}F_3N_4O_5$ (M+H)$^+$: 551.5, found: 551.4.

GENERAL PROTOCOL 12

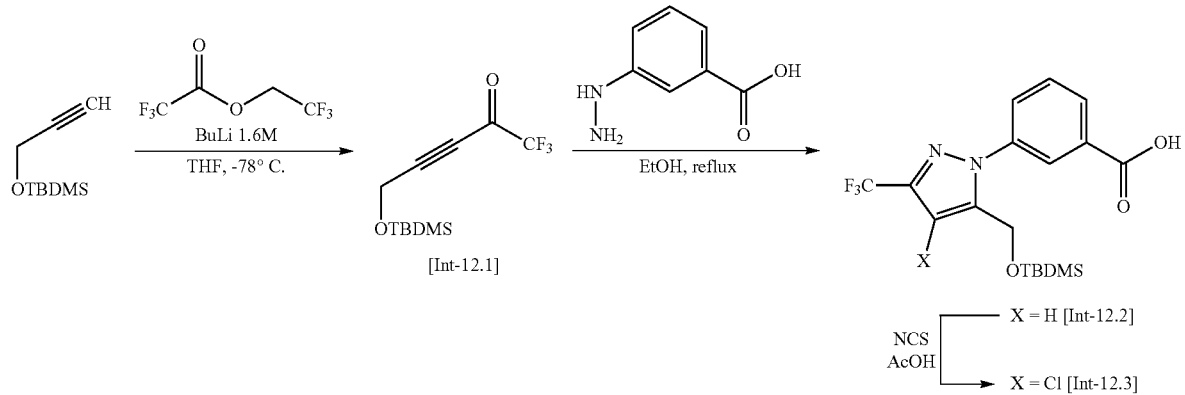

Pathway A

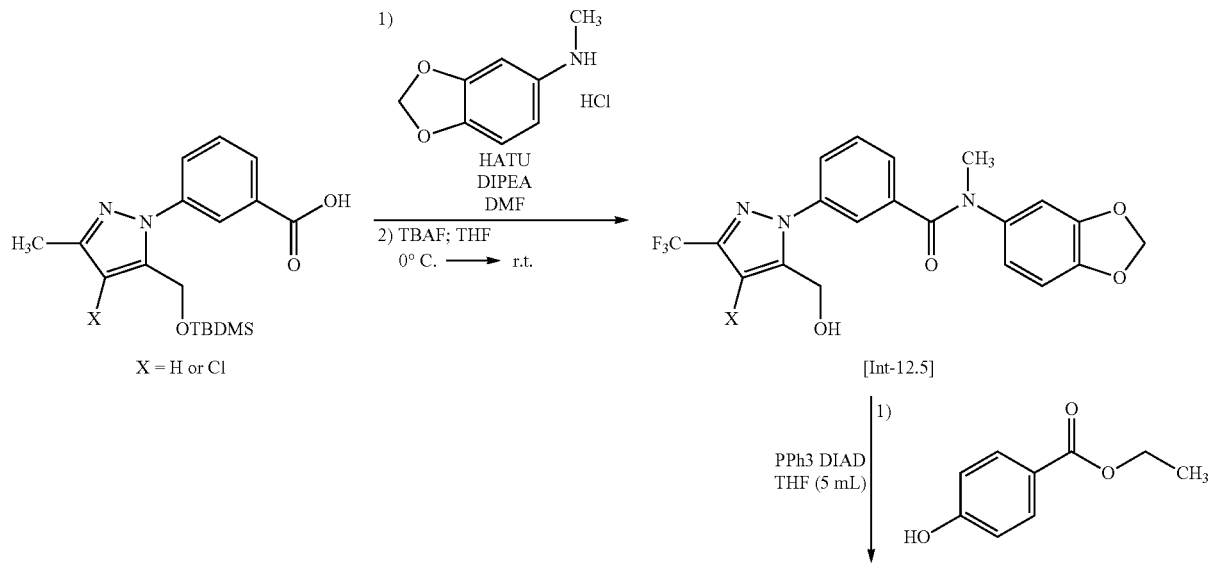

137 138
-continued
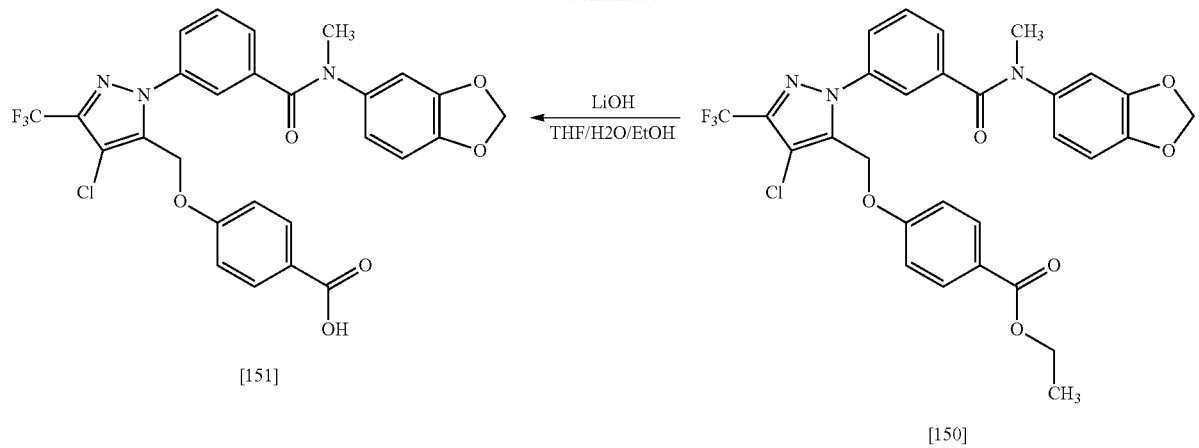
[151]
[150]
Pathway B
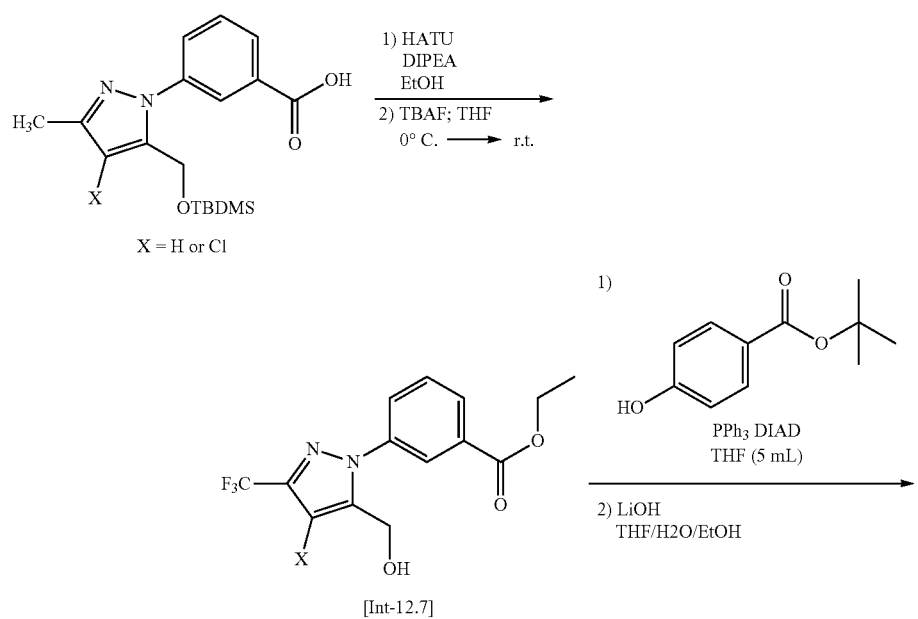
X = H or Cl
[Int-12.7]
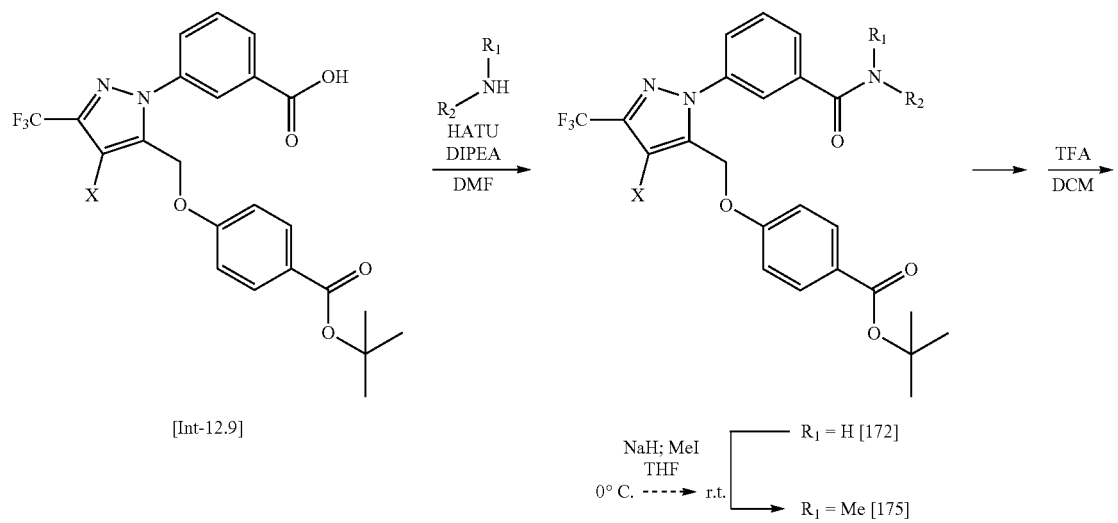
[Int-12.9]
R₁ = H [172]
R₁ = Me [175]

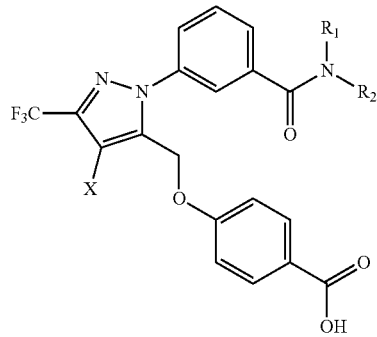

[177]

General Procedure 12a

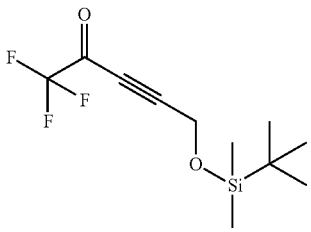 [SMILES: CC(C)(C)[Si](C)(C)OCC#CC(=O)C(F)(F)F]

[Int-12.1] 5-[Tert-butyl(dimethyl)silyl]oxy-1,1,1-trifluoro-pent-3-yn-2-one

To a solution of tert-butyl-dimethyl-prop-2-ynoxy-silane (1.0 g, 5.85 mmol) in dry THF (20 mL) under nitrogen and cooled to −78° C., BuLi (1.6 M in Hexane, 4.77 mL, 7.63 mmol) was added dropwise over a period of 20 min. Mixture was stirred at −78° C. for further 30 min and 2,2,2-trifluoroethyl 2,2,2-trifluoroacetate (827.8 µL, 6.16 mmol) was added dropwise. The solution was stirred for 4 h at low temperature and quenched with sat. aq. NH$_4$C$_{1-}$(10 mL) and water (10 mL). The aqueous layer was extracted with EtOAc (3×30 mL). Collected organic layers were washed with water and brine, and dried over Na$_2$SO$_4$. After filtration, the solvent was evaporated. The title compound was obtained, after purification by silica gel flash-column chromatography with Cyclohexane/EtOAc (95/5) as the eluent, as an oil in 45% yield (710 mg): $^1$H NMR (400 MHz, DMSO-d$_6$) δ 4.74 (s, 2H), 0.88 (s, 9H), 0.12 (s, 6H). $^{13}$C NMR (101 MHz, DMSO-d$_6$) δ 166.29 (q, J=42.1 Hz), 114.82 (q, J=268.0 Hz), 102.34, 60.12, 51.74, 25.86, 18.17, −5.08.

General Procedure 12b

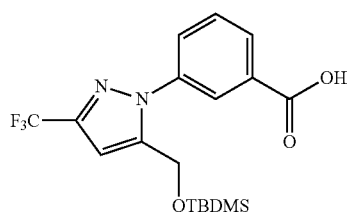 [SMILES: CC(C)(C)[Si](C)(C)OCc1cc(C(F)(F)F)nn1-c1cccc(C(=O)O)c1]

[Int-12.2] 3-[5-(Hydroxymethyl)-3-(trifluoromethyl)pyrazol-1-yl]benzoic acid

To a solution of Int-12.1 (676 mg, 2.54 mmol) in EtOH (20 mL), 3-hydrazinobenzoic acid (367.2 mg, 2.41 mmol) was added. The mixture was refluxed for 18 h and the solvent was evaporated. The title compound was obtained, after purification by silica gel flash-column chromatography with Cyclohexane/EtOAc (90/10) as the eluent, as a white solid in 55% yield (560 mg): $^1$H NMR (400 MHz, DMSO-d$_6$) δ 13.13 (s, 1H), 8.17 (app-t, J=2.2 Hz, 1H), 8.07 (dt, J=7.8, 1.4 Hz, 1H), 7.93-7.89 (m, 1H), 7.70 (t, J=7.9 Hz, 1H), 4.77 (s, 2H), 0.76 (s, 9H), −0.02 (s, 6H). 2D-NOESY: strong dipolar coupling between singlet at 4.77 ppm and signal at 8.17 ppm and multiplet at 7.93-7.89 ppm.

General Procedure 12c

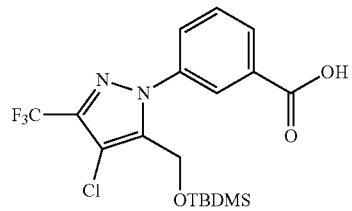 [SMILES: CC(C)(C)[Si](C)(C)OCc1c(Cl)c(C(F)(F)F)nn1-c1cccc(C(=O)O)c1]

[Int-12.3] 3-[4-Chloro-5-(hydroxymethyl)-3-(trifluoromethyl)pyrazol-1-yl]benzoic acid To a solution of Int-12.2 (530 mg, 1.32 mmol) in AcOH (5 mL), NCS (229.7 mg, 1.72 mmol) was added and the mixture stirred for 48 h. The mixture was quenched with water (20 mL), and the aqueous layer extracted with DCM (4×20 mL). The collected organic layer was washed with brine, dried with Na$_2$SO$_4$, filtered and the solvent evaporated. The title compound was obtained, after purification by silica gel flash-column chromatography with Cyclohexane/EtOAc (85/15) as the eluent, as a yellow solid in 44% yield (253 mg): UPLC-MS: t$_R$=2.28 min (Generic method); MS (ESI) m/z calcd for C$_{28}$H$_{22}$ClF$_3$N$_2$O$_3$Si (M−H)$^−$: 433.1, found: 433.1.

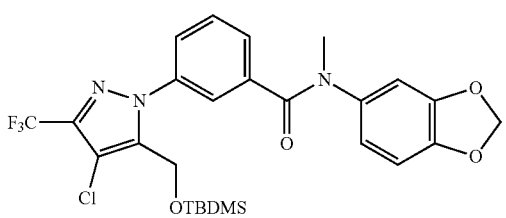 [SMILES: CN(C(=O)c1cccc(-n2nc(C(F)(F)F)c(Cl)c2CO[Si](C)(C)C(C)(C)C)c1)c1ccc2c(c1)OCO2]

[Int-12.4] N-(1,3-Benzodioxol-5-yl)-3-[4-chloro-5-(hydroxyl methyl)-3-(trifluoromethyl)pyrazol-1-yl]-N-methyl-benzamide Following general procedure 1c, the title compound was obtained from Int-12.3, after purification by silica gel flash-column chromatography with Cyclohexane/EtOAc (90/10) as the eluent, as a yellow solid in 56% yield (215 mg): $^1$H NMR (400 MHz, DMSO-d$_6$) δ 7.66 (s, 1H), 7.58 (app-d, J=7.9 Hz, 1H), 7.51-7.36 (m, 2H), 6.93 (d, J=2.2 Hz, 1H), 6.75 (d, J=8.1 Hz, 1H), 6.62 (dd, J=8.1, 2.2 Hz, 1H), 5.99 (s, 2H), 4.60 (s, 2H), 3.31 (s, 3H), 0.80 (s, 9H), −0.01 (s, 6H). UPLC-MS: $t_R$=2.69 min (Apolar method); MS (ESI) m/z calcd for $C_{26}H_{30}ClF_3N_3O_4Si$ (M+H)$^+$: 568.2, found: 568.3.

General Procedure 12d

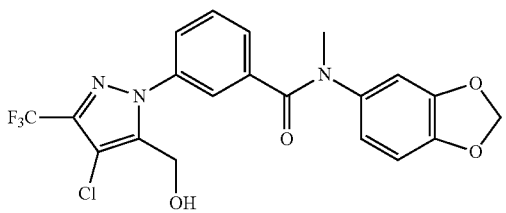 [SMILES: CN(C(=O)c1cccc(-n2nc(C(F)(F)F)c(Cl)c2CO)c1)c1ccc2c(c1)OCO2]

[Int-12.5] N-(1,3-Benzodioxol-5-yl)-3-[4-chloro-5-(hydroxyl methyl)-3-(trifluoromethyl)pyrazol-1-yl]-N-methyl-benzamide To a solution of Int-12.4 (198 mg, 0.35 mmol) in THF (5 mL) cooled to 0° C., TBAF solution (1M in THF, 380 μL, 0.38 mmol) was added. The mixture was stirred at room temperature for 5 h and quenched with water (5 mL). The aqueous layer was extracted with EtOAc (3×20 mL). The collected organic layer was washed with brine (20 mL), dried with Na$_2$SO$_4$, filtered, and the solvent evaporated. The title compound was obtained, after purification by silica gel flash-column chromatography with DCM/EtOAc (50/50) as the eluent, as a white solid in 96% yield (158 mg): $^1$H NMR (400 MHz, DMSO-d$_6$) δ 7.65 (s, 1H), 7.61 (app-d, J=8.0 Hz, 1H), 7.46 (app-t, J=7.7 Hz, 1H), 7.41 (app-d, J=7.7 Hz, 1H), 6.95 (d, J=2.1 Hz, 1H), 6.76 (d, J=8.2 Hz, 1H), 6.64 (dd, J=8.2, 2.1 Hz, 1H), 5.98 (s, 2H), 5.69 (t, J=4.4 Hz, 1H), 4.35 (d, J=4.0 Hz, 2H), 3.32 (s, 3H). UPLC-MS: $t_R$=1.05 min (Apolar method); MS (ESI) m/z calcd for $C_{20}H_{16}ClF_3N_3O_4$ (M+H)$^+$: 454.1, found: 454.2.

[150] Ethyl 4-[[2-[3-[1,3-benzodioxol-5-yl(methyl) carbamoyl]phenyl]-4-chloro-5-(trifluoromethyl) pyrazol-3-yl]methoxy]benzoate Following general procedure 7b, the title compound was obtained from [Int-12.5], after purification by silica gel flash-column chromatography with Cyclohexane/EtOAc (80/20) as the eluent, as a white solid in 81% yield (166 mg): $^1$H NMR (400 MHz, DMSO-d$_6$) δ 7.98-7.82 (m, 2H), 7.61 (s, 1H), 7.52 (app-d, J=7.1 Hz, 1H), 7.47-7.32 (m, 2H), 7.05-6.94 (m, 2H), 6.90 (d, J=2.0 Hz, 1H), 6.62 (d, J=8.2 Hz, 1H), 6.51 (dd, J=8.1, 2.0 Hz, 1H), 5.94 (s, 2H), 5.13 (s, 2H), 4.27 (q, J=7.1 Hz, 2H), 3.30 (s, 3H), 1.30 (t, J=7.1 Hz, 3H). 2D-NOESY: strong dipolar coupling between singlet at 5.13 ppm and signals at 7.61 ppm and 7.52 ppm. UPLC-MS: $t_R$=2.49 min (Generic method); MS (ESI) m/z calcd for $C_{29}H_{24}ClF_3N_3O_6$ (M+H)$^+$: 602.1, found: 602.2.

[151] 4-[[2-[3-[1,3-benzodioxol-5-yl(methyl)carbamoyl]phenyl]-4-chloro-5-(trifluoromethyl)pyrazol-3-yl]methoxy]benzoic acid Following general procedure 4a, the title compound was obtained from compound 150, after purification by silica gel flash-column chromatography with DCM/MeOH (95/5) as the eluent, as a white solid in 74% yield (90 mg): $^1$H NMR (400 MHz, DMSO-d$_6$) δ 12.71 (s, 1H), 7.95-7.80 (m, 2H), 7.66-7.57 (m, 1H), 7.52 (app-d, J=7.6 Hz, 1H), 7.40 (d, J=8.1 Hz, 2H), 7.00-6.93 (m, 2H), 6.90 (d, J=2.1 Hz, 1H), 6.60 (d, J=8.2 Hz, 1H), 6.49 (dd, J=8.2, 2.1 Hz, 1H), 5.93 (s, 2H), 5.12 (s, 2H), 3.27 (s, 3H). UPLC-MS: $t_R$=2.63 min (Generic method); MS (ESI) m/z calcd for $C_{27}H_{20}ClF_3N_3O_6$ (M+H)$^+$: 574.1, found: 574.2.

General Procedure 12e

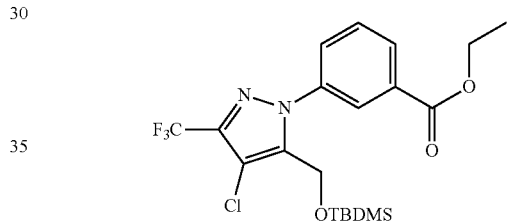

[Int-12.6] Ethyl 3-[4-chloro-5-(hydroxymethyl)-3-(trifluoro methyl)pyrazol-1-yl]benzoate To a solution of Int-12.3 (1.45 g, 3.52 mmol) in EtOH (10 mL), HATU (1.47 mg, 3.88 mmol) and DIPEA (675.58 μL) were added. Mixture was stirred at room temperature for 20 h and the solvent partially evaporated. Et$_2$O (100 mL) was added, and the organic layer was washed with water (30 mL), aq. sat. NH$_4$Cl (50 mL), and brine (50 mL). The solvent was dried with Na$_2$SO$_4$, filtered and evaporated. The title compound was obtained, as crude product, as a pale yellow oil in 68% yield (1.11 g): $^1$H NMR (400 MHz, DMSO-d$_6$) δ 8.19 (app-t, J=1.9 Hz, 1H), 8.16-8.11 (m, 1H), 7.99-7.93 (m, 1H), 7.76 (app-t, J=7.9 Hz, 1H), 4.70 (s, 2H), 4.36 (q, J=7.1 Hz, 2H), 1.33 (t, J=7.1 Hz, 3H), 0.77 (s, 9H), 0.00 (s, 6H).

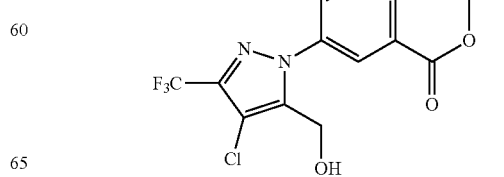

[Int-12.7] Ethyl 3-[4-chloro-5-(hydroxymethyl)-3-(trifluoro methyl)pyrazol-1-yl]benzoate Following general procedure 12d, the title compound was obtained from Int-12.6, after purification by silica gel flash-column chromatography with DCM/EtOAc (50/50) as the eluent, as a white solid in 50% yield (420 mg): $^1$H NMR (400 MHz, DMSO-$d_6$) δ 8.26 (app-t, J=1.9 Hz, 1H), 8.13 (app-dt, J=7.9, 1.3 Hz, 1H), 8.02 (ddd, J=8.1, 2.3, 1.1 Hz, 1H), 7.77 (app-t, J=7.9 Hz, 1H), 5.76 (t, J=5.2 Hz, 1H), 4.51 (d, J=5.2 Hz, 2H), 4.37 (q, J=7.1 Hz, 2H), 1.35 (t, J=7.1 Hz, 3H).

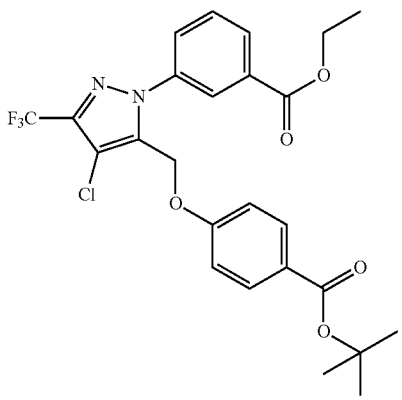 [SMILES: CCOC(=O)c1cccc(-n2nc(C(F)(F)F)c(Cl)c2COc2ccc(C(=O)OC(C)(C)C)cc2)c1]

[Int-12.8] Ethyl 3-[5-[(4-tert-butoxycarbonyl phenoxy) methyl]-4-chloro-3-(trifluoromethyl)pyrazol-1-yl] benzoate Following general procedure 7b, the title compound was obtained from Int-12.7, after purification by silica gel flash-column chromatography with Cyclohexane/EtOAc (80/20) as the eluent, as a white solid in 73% yield (390 mg): $^1$H NMR (400 MHz, DMSO-$d_6$) δ 8.15-8.07 (m, 2H), 7.92 (ddd, J=8.1, 2.3, 1.1 Hz, 1H), 7.87-7.80 (m, 2H), 7.73 (t, J=7.9 Hz, 1H), 7.09-6.99 (m, 2H), 5.21 (s, 2H), 4.27 (q, J=7.1 Hz, 2H), 1.52 (s, 9H), 1.23 (t, J=7.1 Hz, 3H).

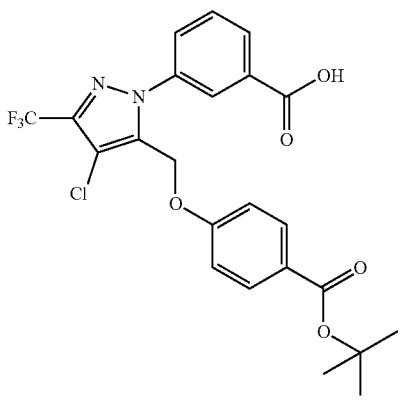 [SMILES: CC(C)(C)OC(=O)c1ccc(OCc2c(Cl)c(C(F)(F)F)nn2-c2cccc(C(=O)O)c2)cc1]

[Int-12.9] 3-[5-[(4-Tert-butoxycarbonylphenoxy) methyl]-4-chloro-3-(trifluoromethyl)pyrazol-1-yl] benzoic acid Following general procedure 4a, the title compound was obtained from Int-12.8, as crude product, as a white solid in 96% yield (350 mg): $^1$H NMR (400 MHz, DMSO-$d_6$) δ 13.28 (s, 1H), 8.15 (app-t, J=1.9 Hz, 1H), 8.09 (app-dt, J=7.8, 1.3 Hz, 1H), 7.89 (ddd, J=8.1, 2.3, 1.2 Hz, 1H), 7.86-7.79 (m, 2H), 7.70 (t, J=7.9 Hz, 1H), 7.13-7.00 (m, 2H), 5.22 (s, 2H), 1.53 (s, 9H).

[Int-172] Tert-butyl 4-[[4-chloro-2-[3-[(2,2-difluoro-1,3-benzodioxol-5-yl)carbamoyl]phenyl]-5-(trifluoromethyl) pyrazol-3-yl]methoxy]benzoate Following general procedure 1c, the title compound was obtained from Int-12.9, after purification by silica gel flash-column chromatography with Cyclohexane/EtOAc (90/10) as the eluent, as a white solid in 91% yield (250 mg): $^1$H NMR (400 MHz, DMSO-$d_6$) δ 10.50 (s, 1H), 8.17 (app-t, J=1.9 Hz, 1H), 8.10 (app-dt, J=7.8, 1.3 Hz, 1H), 7.87 (ddd, J=8.0, 2.2, 1.1 Hz, 1H), 7.82 (d, J=2.0 Hz, 1H), 7.79-7.68 (m, 3H), 7.44 (dd, J=8.8, 2.1 Hz, 1H), 7.38 (d, J=8.8 Hz, 1H), 7.08-6.98 (m, 2H), 5.24 (s, 2H), 1.50 (s, 9H). UPLC-MS: $t_R$=2.53 min (Apolar method); MS (ESI) m/z calcd for $C_{30}H_{24}ClF_5N_3O_6$ (M+H)$^+$: 652.1, found: 652.5.

[175] Tert-butyl 4-[[4-chloro-2-[3-[(2,2-difluoro-1,3-benzodioxol-5-yl)-methyl-carbamoyl]phenyl]-5-(trifluoro methyl)pyrazol-3-yl]methoxy]benzoate Following general procedure 1d, the title compound was obtained from Int-172, after purification by silica gel flash-column chromatography with cyclohexane/EtOAc (80/20) as the eluent, as a white solid in 88% yield (100 mg): $^1$H NMR (400 MHz, DMSO-$d_6$) δ 7.85-7.78 (m, 2H), 7.62-7.56 (m, 1H), 7.53 (q, J=3.6, 2.3 Hz, 1H), 7.45 (d, J=2.1 Hz, 1H), 7.43 (d, J=4.8 Hz, 2H), 7.18 (d, J=8.5 Hz, 1H), 6.96 (dd, J=8.5, 2.1 Hz, 1H), 6.94-6.90 (m, 2H), 5.13 (s, 2H), 3.32 (s, 3H), 1.51 (s, 9H). UPLC-MS: $t_R$=2.42 min (Apolar method); MS (ESI) m/z calcd for $C_{31}H_{26}ClF_5N_3O_6$ (M+H)$^+$: 666.1, found: 666.5.

[181] Tert-butyl 4-[[4-chloro-2-[3-[(2,2-difluoro-1,3-benzodioxol-5-yl)-(trideuteriomethyl)carbamoyl] phenyl]-5-(trifluoromethyl)pyrazol-3-yl]methoxy] benzoate Following general procedure 1d, the title compound was obtained from Int-172 and CD$_3$I, after purification by silica gel flash-column chromatography with cyclohexane/EtOAc (80/20) as the eluent, as a white solid in 83% yield: $^1$H NMR (400 MHz, DMSO-$d_6$) δ 7.88-7.76 (m, 2H), 7.61-7.56 (m, 1H), 7.57-7.50 (m, 1H), 7.44 (dd, J=5.7, 3.4 Hz, 3H), 7.18 (d, J=8.6 Hz, 1H), 7.01-6.88 (m, 3H), 5.13 (s, 2H), 1.51 (s, 9H). UPLC-MS: $t_R$=2.39 min (Apolar method); MS (ESI) m/z calcd for $C_{31}D_3H_{23}ClF_5N_3O_6$ (M+H)$^+$: 669.2 found: 669.5.

[174] 4-[[4-Chloro-2-[3-[(2,2-difluoro-1,3-benzodioxol-5-yl)carbamoyl]phenyl]-5-(trifluoromethyl) pyrazol-3-yl]methoxy] benzoic acid Following general procedure 11d, the title compound was obtained from Int-172, after purification by silica gel flash-column chromatography with DCM/EtOAc (90/10) as the eluent, as a white solid in 77% yield (23 mg): $^1$H NMR (400 MHz, DMSO-$d_6$) δ 12.66 (bs, 1H), 10.53 (s, 1H), 8.18 (app-t, J=1.9 Hz, 1H), 8.11 (app-d, J=7.8 Hz, 1H), 7.87 (dd, J=7.8, 2.1 Hz, 1H), 7.84-7.79 (m, 3H), 7.73 (app-t, J=7.9 Hz, 1H), 7.45 (dd, J=8.8, 2.0 Hz, 1H), 7.38 (d, J=8.8 Hz, 1H), 5.24 (s, 2H). UPLC-MS: $t_R$=1.28 min (Apolar method); MS (ESI) m/z calcd for $C_{26}H_{14}ClF_5N_3O_6$ (M−H)⁻: 594.0, found: 594.5.

[177] 4-[[4-chloro-2-[3-[(2,2-difluoro-1,3-benzodioxol-5-yl)-methyl-carbamoyl]phenyl]-5-(trifluoromethyl)pyrazol-3-yl]methoxy]benzoic acid Following general procedure 11d, the title compound was obtained from compound 175, after purification by silica gel flash-column chromatography with DCM/EtOAc (90/10) as the eluent, as a white solid in 69% yield: ¹H NMR (400 MHz, DMSO-$d_6$) δ 12.68 (bs, 1H), 7.91-7.81 (m, 2H), 7.61-7.57 (m, 1H), 7.56-7.50 (m, 1H), 7.46 (d, J=2.1 Hz, 1H), 7.45-7.41 (m, 2H), 7.18 (d, J=8.6 Hz, 1H), 7.01-6.89 (m, 3H), 5.13 (s, 2H), 3.32 (s, 3H). UPLC-MS: $t_R$=2.27 min (Generic method); MS (ESI) m/z calcd for $C_{27}H_{16}ClF_5N_3O_6$ (M+H)⁺: 608.1 found: 608.5.

[182] 4-[[4-Chloro-2-[3-[(2,2-difluoro-1,3-benzodioxol-5-yl)-(trideuteriomethyl)carbamoyl]phenyl]-5-(trifluoro methyl)pyrazol-3-yl]methoxy]benzoic acid Following general procedure 11d, the title compound was obtained from compound 181 after purification by silica gel flash-column chromatography with DCM/EtOAc (90/10) as the eluent, as a white solid in 77% yield: ¹H NMR (400 MHz, DMSO-$d_6$) δ 12.69 (bs, 1H), 7.63-7.58 (m, 1H), 7.55 (td, J=4.7, 2.2 Hz, 1H), 7.47 (d, J=2.2 Hz, 1H), 7.46-7.42 (m, 2H), 7.18 (d, J=8.6 Hz, 1H), 7.02-6.90 (m, 3H), 5.14 (s, 2H). UPLC-MS: $t_R$=1.07 min (Apolar method); MS (ESI) m/z calcd for $C_{27}D_3H_{13}ClF_5N_3O_6$ (M+H)⁺: 611.1 found: 611.5.

[Int-12.10] 3-[5-[[tert-butyl(dimethyl)silyl]oxymethyl]-4-chloro-3-(trifluoromethyl)pyrazol-1-yl]-N-(2,2-difluoro-1,3-benzodioxol-5-yl)-N-methyl-benzamide Following general procedure 1c, the title compound was obtained from [Int-12.3], after purification by silica gel flash-column chromatography with Cyclohexane/EtOAc (90/10) as the eluent, as a yellow solid in 82% yield: UPLC-MS: $t_R$=2.80 min (Apolar method); MS (ESI) m/z calcd for $C_{26}H_{28}ClF_5N_3O_4Si$ (M+H)⁺: 604.1, found: 604.4.

[217] 3-[4-Chloro-5-(hydroxymethyl)-3-(trifluoromethyl) pyrazol-1-yl]-N-(2,2-difluoro-1,3-benzodioxol-5-yl)-N-methyl-benzamide Following general procedure 12d, the title compound was obtained from compound Int-12.10, after purification by silica gel flash-column chromatography with cyclohexane/EtOAc (50/50) as the eluent, as a white solid in 96% yield: ¹H NMR (400 MHz, DMSO-$d_6$) δ 7.65 (app-dt, J=7.2, 2.1 Hz, 1H), 7.59 (bs, 1H), 7.53 (d, J=2.1 Hz, 1H), 7.52-7.44 (m, 2H), 7.29 (d, J=8.6 Hz, 1H), 7.04 (dd, J=8.6, 2.1 Hz, 1H), 5.68 (t, J=5.3 Hz, 1H), 4.33 (d, J=5.3 Hz, 2H), 3.38 (s, 3H). UPLC-MS: $t_R$=1.29 min (Apolar method); MS (ESI) m/z calcd for $C_{20}H_{14}ClF_5N_3O_4$ (M+H)⁺: 490.0, found: 490.4.

[Int-12.11] 3-[5-[[tert-butyl(dimethyl)silyl]oxymethyl]-3-(trifluoromethyl)pyrazol-1-yl]-N-(2,2-difluoro-1,3-benzodioxol-5-yl)-N-methyl-benzamide Following general procedure 1c, the title compound was obtained from [Int-12.2], after purification by silica gel flash-column chromatography with Cyclohexane/EtOAc (90/10) as the eluent, as a yellow solid in 67% yield: UPLC-MS: $t_R$=2.51 min (Apolar method); MS (ESI) m/z calcd for $C_{26}H_{29}F_5N_3O_4Si$ (M+H)⁺: 570.2, found: 570.4.

[Int-12.12] N-(2,2-difluoro-1,3-benzodioxol-5-yl)-3-[5-(hydroxymethyl)-3-(trifluoromethyl)pyrazol-1-yl]-N-methyl-benzamide Following general procedure 12d, the title compound was obtained from compound [Int-12.11], after purification by silica gel flash-column chromatography with cyclohexane/EtOAc (50/50) as the eluent, as a white solid in 96% yield: UPLC-MS: $t_R$=1.15 min (Apolar method); MS (ESI) m/z calcd for $C_{20}H_{15}F_5N_3O_4$ (M+H)⁺: 456.1, found: 456.4.

[Int-12.13] Tert-butyl 4-[[2-[3-[(2,2-difluoro-1,3-benzodioxol-5-yl)-methyl-carbamoyl]phenyl]-5-(trifluoromethyl)pyrazol-3-yl]methoxy]benzoate Following general procedure 7b, the title compound was obtained from compound [Int-12.12], after purification by silica gel flash-column chromatography with cyclohexane/EtOAc (70/30) as the eluent, as a white solid in 96% yield: UPLC-MS: $t_R$=2.39 min (Apolar method); MS (ESI) m/z calcd for $C_{31}H_{27}F_5N_3O_6$ (M+H)⁺: 632.2, found: 632.4.

[218] 4-[[2-[3-[(2,2-difluoro-1,3-benzodioxol-5-yl)-methyl-carbamoyl]phenyl]-5-(trifluoromethyl)pyrazol-3-yl]methoxy]benzoic acid Following general procedure 11d, the title compound was obtained from compound [Int-12.13] after purification by silica gel flash-column chromatography with DCM/EtOAc (90/10) as the eluent, as a white solid in 67% yield: ¹H NMR (400 MHz, DMSO-$d_6$) δ 12.69 (s, 1H), 7.91-7.82 (m, 2H), 7.65-7.52 (m, 2H), 7.50 (d, J=2.1 Hz, 1H), 7.43 (d, J=7.5 Hz, 2H), 7.20 (d, J=8.5 Hz, 1H), 7.15 (s, 1H), 7.04-6.87 (m, 3H), 5.17 (s, 2H), 3.33 (s, 3H). UPLC-MS: $t_R$=1.05 min (Apolar method); MS (ESI) m/z calcd for $C_{27}H_{19}F_5N_3O_6$ (M+H)⁺: 576.1 found: 576.4.

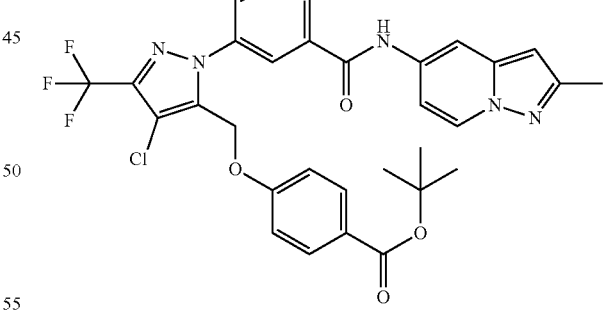

[Int-12.14] tert-Butyl 4-[[4-chloro-2-[3-[(2-methylpyrazolo[1,5-a]pyridin-5-yl)carbamoyl]phenyl]-5-(trifluoromethyl)pyrazol-3-yl]methoxy]benzoate following general procedure 1c, the title compound was obtained from compound Int-12.9 and 2-methylpyrazolo[1,5-a]pyridin-5-amine, after purification by silica gel flash-column chromatography with DCM/AcOEt (70:30) as the eluent, as a white solid in 83% yield: ¹H NMR (400 MHz, DMSO-$d_6$) δ 10.50 (bs, 1H), 8.49 (d, J=7.5, 0.8 Hz, 1H), 8.19 (t, J=1.9 Hz, 1H), 8.12 (dt, J=7.9, 1.3 Hz, 1H), 8.09 (dd, J=2.3, 0.8 Hz, 1H), 7.87 (ddd, J=8.0, 2.2, 1.0 Hz, 1H), 7.79-7.71 (m, 3H), 7.07-6.99 (m, 3H), 6.30 (s, 1H), 5.24 (s, 2H), 2.35 (s, 3H), 1.47 (s, 9H). UPLC-MS: $t_R$=2.32 min (Apolar method); MS (ESI) m/z calcd for $C_{31}H_{28}ClF_3N_5O_4$ (M+H)$^+$: 626.2, found: 626.4.

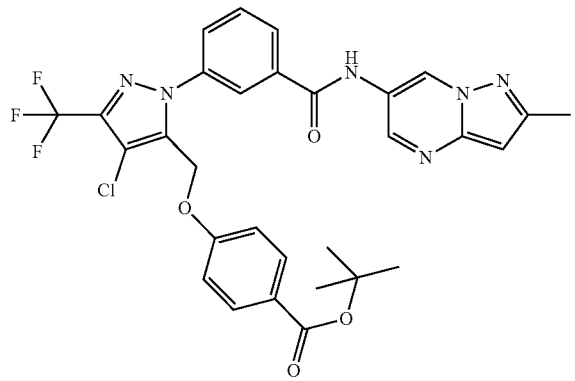

[Int-12.16] tert-Butyl 4-[[4-chloro-2-[3-[(2-methylpyrazolo[1,5-a]pyrimidin-6-yl)carbamoyl]phenyl]-5-(trifluoromethyl)pyrazol-3-yl]methoxy]benzoate following general procedure 1c, the title compound was obtained from compound Int-12.9 and 2-methylpyrazolo[1,5-a]pyrimidin-6-amine, after purification by silica gel flash-column chromatography with DCM/AcOEt (70:30) as the eluent, as a white solid in 86% yield: $^1$H NMR (400 MHz, DMSO-d$_6$) δ 10.69 (s, 1H), 9.41 (dd, J=2.4, 0.9 Hz, 1H), 8.64 (d, J=2.4 Hz, 1H), 8.22 (app-t, J=1.9 Hz, 1H), 8.17-8.14 (m, 1H), 7.90 (ddd, J=8.0, 2.2, 1.1 Hz, 1H), 7.80-7.74 (m, 3H), 7.06-7.00 (m, 2H), 6.52 (s, 1H), 5.25 (s, 2H), 2.42 (s, 3H), 1.47 (s, 9H). UPLC-MS: $t_R$=2.17 min (Apolar method); MS (ESI) m/z calcd for $C_{30}H_{27}ClF_3N_6O_4$ (M+H)$^+$: 627.2, found: 627.3.

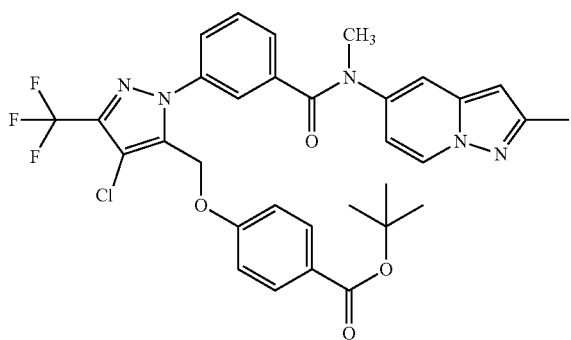 [SMILES: Cc1cc2cc(N(C)C(=O)c3cccc(-n4nc(C(F)(F)F)c(Cl)c4COc4ccc(C(=O)OC(C)(C)C)cc4)c3)ccn2n1]

[Int-12.15] tert-Butyl 4-[[4-chloro-2-[3-[methyl-(2-methylpyrazolo[1,5-a]pyridin-5-yl)carbamoyl]phenyl]-5-(trifluoromethyl)pyrazol-3-yl]methoxy]benzoate following general procedure 1d, the title compound was obtained from compound Int-12.14, after purification by silica gel flash-column chromatography. eluting a gradient of 100% DCM to 40% AcOEt in DCM, as a white solid in 82% yield: $^1$H NMR (400 MHz, DMSO-d$_6$) δ 8.39 (dd, J=7.3, 0.9 Hz, 1H), 7.81 (dd, J=8.9, 1.0 Hz, 2H), 7.74 (t, J=1.7 Hz, 1H), 7.55 (dt, J=6.9, 2.2 Hz, 1H), 7.44-7.36 (m, 2H), 7.23 (app d, J=2.3 Hz, 1H), 6.93 (d, J=8.0 Hz, 2H), 6.67 (dd, J=7.5, 2.4 Hz, 1H), 6.11 (s, 1H), 5.12 (s, 2H), 3.34 (s, 3H), 2.28 (s, 3H), 1.51 (s, 9H). UPLC-MS: $t_R$=2.23 min (Apolar method); MS (ESI) m/z calcd for $C_{32}H_{30}ClF_3N_5O_4$ (M+H)$^+$: 640.2, found: 640.4.

[239] 4-[[4-Chloro-2-[3-[methyl-(2-methylpyrazolo[1,5-a]pyridin-5-yl)carbamoyl]phenyl]-5-(trifluoromethyl) pyrazol-3-yl]methoxy]benzoic acid following general procedure 11d, the title compound was obtained from compound Int-12.15, after purification by silica gel flash-column chromatography, eluting a gradient of 100% DCM to 10% MeOH in DCM, as a white solid in 61% yield: $^1$H NMR (400 MHz, DMSO-d$_6$) δ 12.71 (bs, 1H), 8.38 (app d, J=7.4 Hz, 1H), 7.88-7.84 (m, 2H), 7.74-7.72 (m, 1H), 7.55 (dt, J=6.7, 2.3 Hz, 1H), 7.45-7.37 (m, 2H), 7.24 (d, J=2.1 Hz, 1H), 6.96-6.91 (m, 2H), 6.66 (dd, J=7.4, 2.4 Hz, 1H), 6.13 (s, 1H), 5.11 (s, 2H), 3.34 (s, 3H), 2.28 (s, 3H). UPLC-MS: $t_R$=0.82 min (Apolar method); MS (ESI) m/z calcd for $C_{28}H_{22}ClF_3N_5O_4$ (M+H)$^+$: 584.2, found: 584.4.

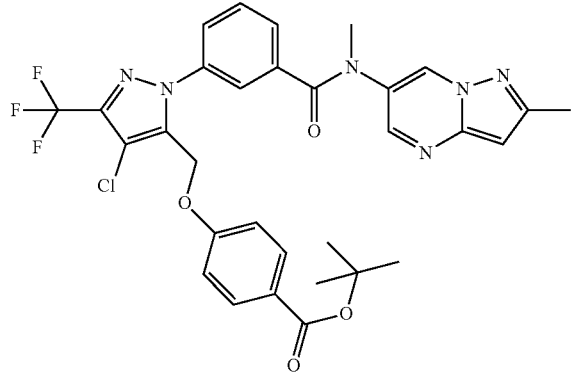 [SMILES: Cc1cc2ncc(N(C)C(=O)c3cccc(-n4nc(C(F)(F)F)c(Cl)c4COc4ccc(C(=O)OC(C)(C)C)cc4)c3)cn2n1]

[Int-12.17] tert-Butyl 4-[ [4-chloro-2-[3-[methyl-(2-methylpyrazolo[1,5-a]pyrimidin-6-yl) carbamoyl] phenyl]-5-(trifluoromethyl)pyrazol-3-yl]methoxy] benzoate following general procedure 1d, the title compound was obtained from compound Int-12.16, after purification by silica gel flash-column chromatography. eluting a gradient of 100% DCM to 40% AcOEt in DCM, as a white solid in 77% yield: $^1$H NMR (400 MHz, DMSO-d$_6$) δ 9.17 (d, J=2.4 and 0.7 Hz, 1H), 8.43 (s, 1H), 7.95 (s, 1H), 7.83-7.71 (m, 3H), 7.61-7.35 (m, 3H), 6.84 (bs, 2H), 6.45 (s, 1H), 5.13 (s, 2H), 3.38 (bs, 3H), 2.34 (bs, 3H), 1.51 (s, 9H). UPLC-MS: $t_R$=2.12 min (Apolar method); MS (ESI) m/z calcd for $C_{31}H_{29}ClF_3N_6O_4$ (M+H)$^+$: 641.2, found: 641.4.

[238] 4-[[4-Chloro-2-[3-[methyl-(2-methylpyrazolo [1,5-a]pyrimidin-6-yl) carbamoyl]phenyl]-5-(trifluoromethyl) pyrazol-3-yl]methoxy]benzoic acid following general procedure 11d, the title compound was obtained from compound Int-12.17, after purification by silica gel flash-column chromatography, eluting a gradient of 100% DCM to 10% MeOH in DCM, as a white solid in 79% yield: $^1$H NMR (400 MHz, DMSO-$d_6$) δ 12.71 (s, 1H), 9.18 (d, J=2.3 Hz, 1H), 8.43 (bs, $^1$H), 7.83 (d, J=6.8 Hz, 2H), 7.75 (s, 1H), 7.60-7.36 (m, 3H), 6.86 (bs, 2H), 6.46 (s, 1H), 5.14 (s, 2H), 3.39 (s, 3H), 2.35 (s, 3H). UPLC-MS: $t_R$=2.01 min (Generic method); MS (ESI) m/z calcd for $C_{27}H_{21}ClF_3N_6O_4$ (M+H)$^+$: 585.1, found: 585.4.

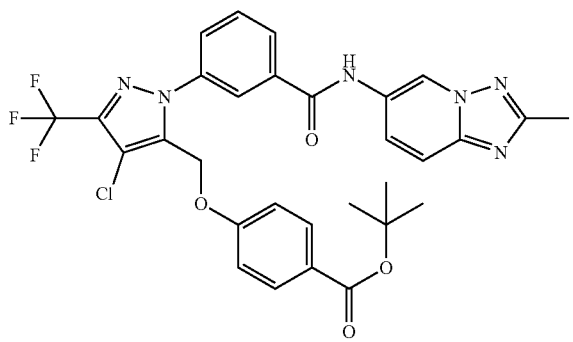 [SMILES: Cc1nc2ccc(NC(=O)c3cccc(-n4nc(C(F)(F)F)c(Cl)c4COc4ccc(C(=O)OC(C)(C)C)cc4)c3)cn2n1]

[173] tert-Butyl 4-[[4-chloro-2-[3-[(2-methyl-[1,2,4] triazolo[1,5-a]pyridin-6-yl)carbamoyl]phenyl]-5-(trifluoromethyl)pyrazol-3-yl]methoxy]benzoate following general procedure 1c, the title compound was obtained from compound Int-12.9 and 2-methylpyrazolo[1,5-a]pyrimidin-6-amine, after purification by flash-column chromatography using alumina pH=7 with DCM/MeOH (99:1), as a white solid in 68% yield: $^1$H NMR (400 MHz, DMSO-$d_6$) δ 10.64 (s, 1H), 9.40 (dd, J=1.8, 0.7 Hz, 1H), 8.21 (s, 1H), 8.14 (dt, J=7.8, 1.4 Hz, 1H), 7.89 (ddd, J=8.0, 2.2, 1.1 Hz, 1H), 7.79-7.70 (m, 5H), 7.07-7.00 (m, 2H), 5.25 (s, 2H), 2.45 (s, 3H), 1.46 (s, 9H). UPLC-MS: $t_R$=1.97 min (Apolar method); MS (ESI) m/z calcd for $C_{30}H_{27}ClF_3N_6O_4$ (M+H)$^+$: 627.2, found: 627.4.

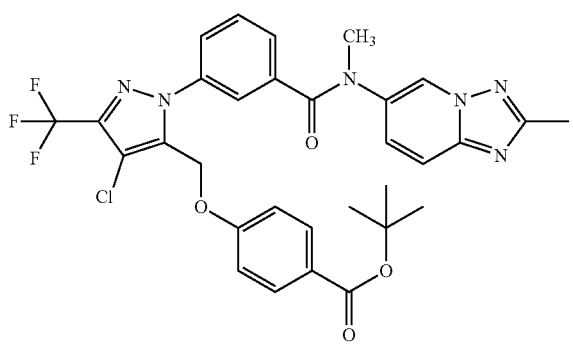 [SMILES: Cc1nc2ccc(N(C)C(=O)c3cccc(-n4nc(C(F)(F)F)c(Cl)c4COc4ccc(C(=O)OC(C)(C)C)cc4)c3)cn2n1]

[Int-12.19] tert-Butyl 4-[[4-chloro-2-[3-[methyl-(2-methyl-[1,2,4]triazolo[1,5-a]pyridin-6-yl)carbamoyl]phenyl]-5-(trifluoromethyl)pyrazol-3-yl]methoxy]benzoate following general procedure 1d, the title compound was obtained from compound 173, after purification by silica gel flash-column chromatography. eluting a gradient of 100% DCM to 5% MeOH in DCM, as a white solid in 99% yield: $^1$H NMR (400 MHz, DMSO-$d_6$) δ 8.96 (t, J=1.4 Hz, 1H), 7.82-7.74 (m, 2H), 7.70 (s, 1H), 7.57 (bs, 2H), 7.54-7.44 (m, 2H), 7.44-7.37 (m, 1H), 6.85 (d, J=8.4 Hz, 2H), 5.12 (s, 2H), 3.36 (s, 3H), 2.38 (s, 3H), 1.51 (s, 9H). UPLC-MS: $t_R$=1.89 min (Apolar method); MS (ESI) m/z calcd for $C_{31}H_{29}ClF_3N_6O_4$ (M+H)$^+$: 641.2, found: 641.4.

[236] 4-[[4-Chloro-2-[3-[methyl-(2-methyl-[1,2,4] triazolo[1,5-a]pyridin-6-yl)carbamoyl]phenyl]-5-(trifluoromethyl) pyrazol-3-yl]methoxy]benzoic acid following general procedure 11d, the title compound was obtained from compound Int-12.19, after purification by silica gel flash-column chromatography, eluting a gradient of 100% DCM to 5% MeOH in DCM, as a white solid in 83% yield: $^1$H NMR (400 MHz, DMSO-$d_6$) δ 12.72 (bs, 1H), 8.98 (t, J=1.4 Hz, 1H), 7.88-7.79 (m, 2H), 7.71 (s, 1H), 7.59-7.38 (m, 5H), 6.87 (d, J=8.4 Hz, 2H), 5.12 (s, 2H), 3.37 (s, 3H), 2.38 (s, 3H). UPLC-MS: $t_R$=1.92 min (Generic method); MS (ESI) m/z calcd for $C_{27}H_{21}ClF_3N_6O_4$ (M+H)$^+$: 585.1, found: 585.4.

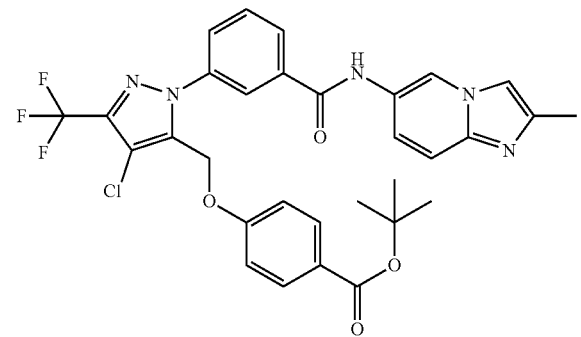 [SMILES: Cc1cn2cc(NC(=O)c3cccc(-n4nc(C(F)(F)F)c(Cl)c4COc4ccc(C(=O)OC(C)(C)C)cc4)c3)ccc2n1]

[Int-12.20] tert-Butyl 4-[[4-chloro-2-[3-[(2-methylimidazo[1,2-a]pyridin-6-yl)carbamoyl]phenyl]-5-(trifluoromethyl)pyrazol-3-yl]methoxy]benzoate following general procedure 1c, the title compound was obtained from compound Int-12.9 and 2-methylimidazo[1,2-a]pyridin-6-amine, after purification by flash-column chromatography using alumina pH=7 with DCM/MeOH (99:1), as a white solid in 69% yield: $^1$H NMR (400 MHz, DMSO-$d_6$) δ 10.40 (s, 1H), 9.16 (s, 1H), 8.22-8.19 (m, 1H), 8.13 (d, J=7.8, 1.5 Hz, 1H), 7.87 (ddd, J=8.0, 2.2, 1.1 Hz, 1H), 7.80-7.71 (m, 4H), 7.43 (d, J=9.5, 0.8 Hz, 1H), 7.29 (dt, J=9.6, 2.2 Hz, 1H), 7.07-7.02 (m, 2H), 5.24 (s, 2H), 2.31 (s, 3H), 1.47 (s, 9H). UPLC-MS: $t_R$=2.01 min (Generic method); MS (ESI) m/z calcd for $C_{31}H_{28}ClF_3N_5O_4$ (M+H)$^+$: 626.2, found: 626.4.

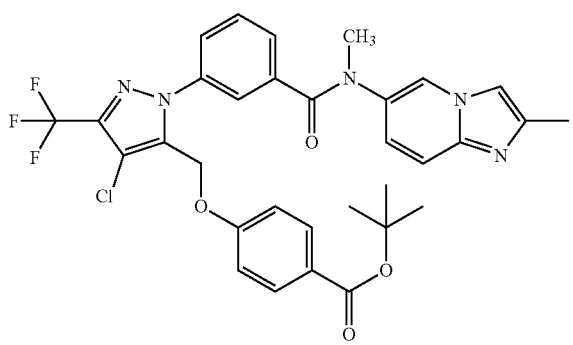 [SMILES: Cc1cn2cc(N(C)C(=O)c3cccc(-n4nc(C(F)(F)F)c(Cl)c4COc4ccc(C(=O)OC(C)(C)C)cc4)c3)ccc2n1]

[Int-12.21] tert-Butyl 4-[[4-chloro-2-[3-[methyl-(2-methylimidazo[1,2-a]pyridin-6-yl)carbamoyl]phenyl]-5-(trifluoromethyl)pyrazol-3-yl]methoxy]benzoate following general procedure 1d, the title compound was obtained from compound Int-12.20, after purification by silica gel flash-column chromatography. eluting a gradient of 100% DCM to 5% MeOH in DCM, as a white solid in 99% yield: $^1$H NMR (400 MHz, DMSO-d$_6$) δ 8.41 (s, 1H), 7.83-7.76 (m, 2H), 7.70 (bs, 1H), 7.56-7.47 (m, 1H), 7.39 (bs, 3H), 7.30 (d, J=9.5 Hz, 1H), 7.12 (dd, J=9.5, 2.1 Hz, 1H), 6.88 (d, J=8.4 Hz, 2H), 5.10 (s, 2H), 3.33 (s, 3H), 2.23 (s, 3H), 1.51 (s, 9H). UPLC-MS: t$_R$=1.88 min (Generic method); MS (ESI) m/z calcd for C$_{32}$H$_{30}$ClF$_3$N$_5$O$_4$ (M+H)$^+$: 640.2, found: 640.5.

[256] 4-[[4-Chloro-2-[3-[methyl-(2-methylimidazo[1,2-a]pyridin-6-yl)carbamoyl]phenyl]-5-(trifluoromethyl) pyrazol-3-yl]methoxy]benzoic acid following general procedure 11d, the title compound was obtained from compound Int-12.21, after purification by silica gel flash-column chromatography, eluting a gradient of 100% DCM to 5% MeOH in DCM, as a white solid in 88% yield: $^1$H NMR (400 MHz, DMSO-d$_6$) δ 12.76 (bs, 1H), 8.86-8.79 (m, 1H), 7.88-7.78 (m, 3H), 7.74-7.63 (m, 3H), 7.59 (d, J=7.8 Hz, 1H), 7.53 (d, J=7.6 Hz, 1H), 7.47 (t, J=7.8 Hz, 1H), 6.92 (d, J=8.5 Hz, 2H), 5.15 (s, 2H), 3.36 (s, 3H), 2.37 (s, 3H). UPLC-MS: t$_R$=0.51 min (Generic method); MS (ESI) m/z calcd for C$_{28}$H$_{22}$ClF$_3$N$_5$O$_4$ (M+H)$^+$: 584.1, found: 584.4.

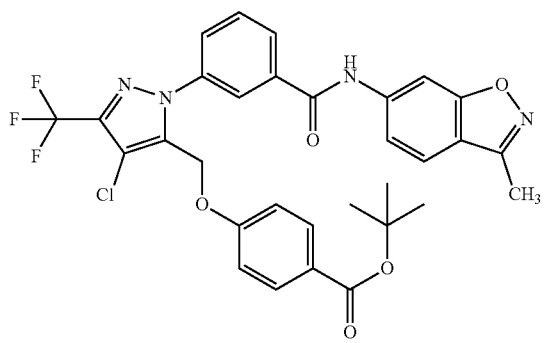 [SMILES: Cc1noc2cc(NC(=O)c3cccc(-n4nc(C(F)(F)F)c(Cl)c4COc4ccc(C(=O)OC(C)(C)C)cc4)c3)ccc12]

[Int-12.22] tert-butyl 4-[[4-chloro-2-[3-[(3-methyl-1,2-benzoxazol-6-yl)carbamoyl]phenyl]-5-(trifluoromethyl) pyrazol-3-yl]methoxy]benzoate following general procedure 1c, the title compound was obtained from compound Int-12.9 and 3-methyl-1,2-benzoxazol-6-amine, after purification by silica gel flash-column chromatography with DCM/MeOH (95:5) as the eluent, as a white solid in 79% yield: $^1$H NMR (400 MHz, DMSO-d$_6$) δ 10.70 (s, 1H), 8.21 (s, 2H), 8.14 (app d, J=8.1 Hz, 1H), 7.88 (ddd, J=8.0, 2.2, 1.1 Hz, 1H), 7.80 (d, J=8.6 Hz, 1H), 7.78-7.72 (m, 3H), 7.62 (dd, J=8.6, 1.6 Hz, 1H), 7.07-7.00 (m, 2H), 5.25 (s, 2H), 2.53 (s, 3H), 1.47 (s, 9H). UPLC-MS: t$_R$=2.40 min (Apolar method); MS (ESI) m/z calcd for C$_{31}$H$_{27}$ClF$_3$N$_4$O$_5$ (M+H)$^+$: 627.2, found: 627.2.

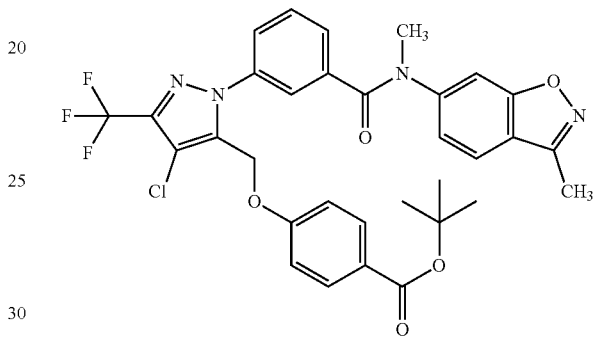

[Int-12.23] tert-Butyl 4-[[4-chloro-2-[3-[methyl-(3-methyl-1,2-benzoxazol-6-yl)carbamoyl]phenyl]-5-(trifluoromethyl) pyrazol-3-yl]methoxy]benzoate following general procedure 1d, the title compound was obtained from compound Int-12.22, after purification by silica gel flash-column chromatography with DCM/MeOH (95:5) as the eluent, as a white solid in 87% yield: $^1$H NMR (400 MHz, DMSO-d$_6$) δ 7.83-7.78 (m, 2H), 7.67-7.65 (m, 1H), 7.61 (d, J=1.7 Hz, 1H), 7.55 (d, J=8.4 Hz, 1H), 7.52 (dt, J=6.8, 2.3 Hz, 1H), 7.40-7.33 (m, 2H), 7.13 (dd, J=8.4, 1.7 Hz, 1H), 6.93-6.87 (m, 2H), 5.08 (s, 2H), 3.41 (s, 3H), 2.43 (s, 3H), 1.51 (s, 9H). UPLC-MS: t$_R$=2.33 min (Apolar method); MS (ESI) m/z calcd for C$_{32}$H$_{29}$ClF$_3$N$_4$O$_5$ (M+H)$^+$: 641.2, found: 641.2.

[245] 4-[[4-Chloro-2-[3-[methyl-(3-methyl-1,2-benzoxazol-6-yl)carbamoyl]phenyl]-5-(trifluoromethyl) pyrazol-3-yl]methoxy]benzoic acid following general procedure 11d, the title compound was obtained from compound Int-12.23, after purification by silica gel flash-column chromatography with DCM/MeOH (99:1) as the eluent, as a white solid in 69% yield: $^1$H NMR (400 MHz, DMSO-d$_6$) δ 12.72 (bs, 1H), 7.89-7.82 (m, 2H), 7.66 (t, J=1.4 Hz, 1H), 7.62 (d, J=1.6 Hz, 1H), 7.57-7.50 (m, 2H), 7.42-7.33 (m, 2H), 7.12 (dd, J=8.4, 1.7 Hz, 1H), 6.94-6.88 (m, 2H), 5.08 (s, 2H), 3.41 (s, 3H), 2.43 (s, 3H). UPLC-MS: t$_R$=0.89 min (Apolar method); MS (ESI) m/z calcd for C$_{28}$H$_{21}$ClF$_3$N$_4$O$_5$ (M+H)$^+$: 584.1, found: 584.5.

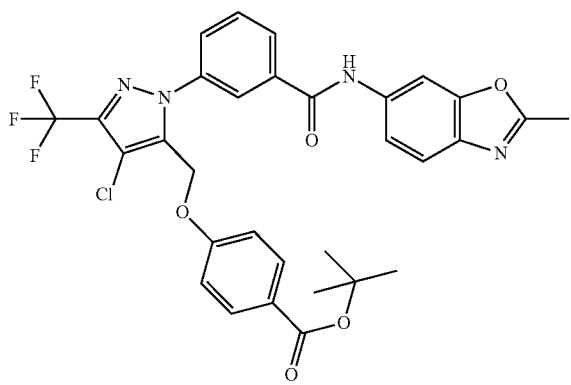 [SMILES: Cc1nc2ccc(NC(=O)c3cccc(-n4nc(C(F)(F)F)c(Cl)c4COc4ccc(C(=O)OC(C)(C)C)cc4)c3)cc2o1]

[Int-12.24] tert-Butyl 4-[[4-chloro-2-[3-[(2-methyl-1,3-benzoxazol-6-yl)carbamoyl]phenyl]-5-(trifluoromethyl) pyrazol-3-yl]methoxy]benzoate following general procedure 1c, the title compound was obtained from compound Int-12.9 and 2-methyl-1,3-benzoxazol-6-amine, after purification by silica gel flash-column chromatography with Cyclohexane/EtOAc as the eluent, as a white solid in 50% yield: 1H NMR (400 MHz, DMSO-$d_6$) δ 10.53 (s, 1H), 8.21 (app-t, J=1.9 Hz, 1H), 8.17 (d, J=1.8 Hz, 1H), 8.14 (dt, J=7.9, 1.5 Hz, 1H), 7.87 (ddd, J=8.0, 2.2, 1.0 Hz, 1H), 7.78-7.69 (m, 3H), 7.62 (d, J=8.6 Hz, 1H), 7.55 (dd, J=8.6, 1.9 Hz, 1H), 7.08-7.01 (m, 2H), 5.25 (s, 2H), 2.61 (s, 3H), 1.49 (s, 9H). UPLC-MS: $t_R$=2.26 min (Apolar method); MS (ESI) m/z calcd for $C_{31}H_{27}ClF_3N_4O_5$ (M+H)$^+$: 628.0, found: 627.4.

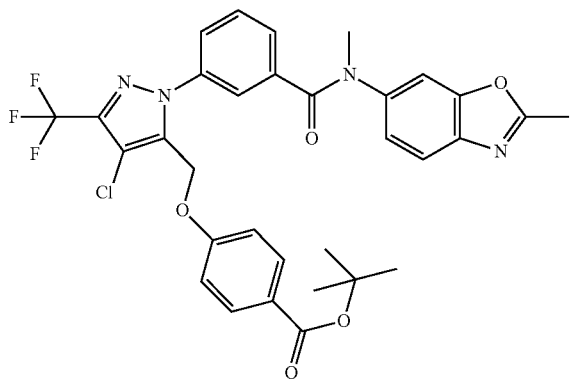 [SMILES: Cc1nc2ccc(N(C)C(=O)c3cccc(-n4nc(C(F)(F)F)c(Cl)c4COc4ccc(C(=O)OC(C)(C)C)cc4)c3)cc2o1]

[Int-12.25] tert-Butyl 4-[[4-chloro-2-[3-[methyl-(2-methyl-1,3-benzoxazol-6-yl)carbamoyl]phenyl]-5-(trifluoromethyl) pyrazol-3-yl]methoxy]benzoate following general procedure 1d, the title compound was obtained from compound Int-12.24, as crude, as a white solid. UPLC-MS: $t_R$=2.64 min (Apolar method); MS (ESI) m/z calcd for $C_{32}H_{29}ClF_3N_4O_5$ (M+H)$^+$: 641.2, found: 641.2.

[233] 4-[[4-Chloro-2-[3-[methyl-(2-methyl-1,3-benzoxazol-6-yl)carbamoyl]phenyl]-5-(trifluoromethyl) pyrazol-3-yl]methoxy]benzoic acid following general procedure 11d, the title compound was obtained from compound Int-12.25, after purification by silica gel flash-column chromatography with DCM/MeOH (99:1) as the eluent, as a white solid in 87% yield (over two steps): $^1$H NMR (400 MHz, DMSO-$d_6$) δ 7.85 (d, J=8.6 Hz, 2H), 7.64 (bs, 1H), 7.61 (d, J=1.9 Hz, 1H), 7.53-7.47 (m, 1H), 7.41 (d, J=8.4 Hz, 1H), 7.38-7.32 (m, 2H), 7.08 (dd, J=8.4, 2.0 Hz, 1H), 6.88 (d, J=8.5 Hz, 2H), 5.07 (s, 2H), 3.38 (s, 3H), 2.51 (s, 3H). UPLC-MS: $t_R$=2.05 min (Apolar method); MS (ESI) m/z calcd for $C_{28}H_{21}ClF_3N_4O_5$ (M+H)$^+$: 585.1, found: 585.2.

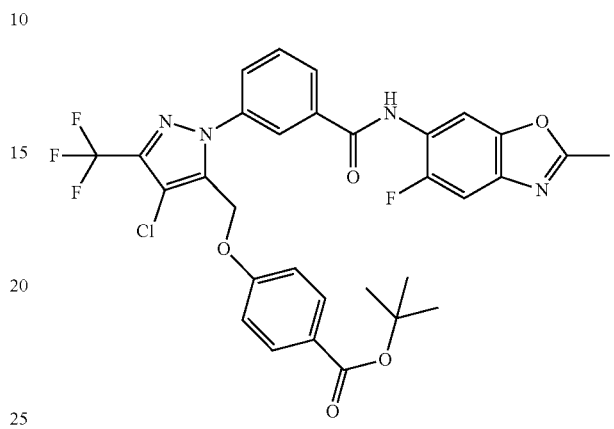

[Int-12.26] tert-Butyl 4-[[4-chloro-2-[3-[(5-fluoro-2-methyl-1,3-benzoxazol-6-yl)carbamoyl]phenyl]-5-(trifluoromethyl)pyrazol-3-yl]methoxy]benzoate following general procedure 1c, the title compound was obtained from compound Int-12.9 and 5-fluoro-2-methyl-1,3-benzoxazol-6-amine, after purification by silica gel flash-column chromatography with CyHex/AcOEt (60:40) as the eluent, as a white solid in 86% yield: $^1$H NMR (400 MHz, DMSO-$d_6$) δ 10.37 (s, 1H), 8.23 (t, J=1.9 Hz, 1H), 8.15 (dt, J=7.9, 1.2 Hz, 1H), 7.92-7.86 (m, 2H), 7.81-7.77 (m, 2H), 7.73 (app-t, J=7.9 Hz, 1H), 7.65 (app d, J=9.9 Hz, 1H), 7.06-7.01 (m, 2H), 5.25 (s, 2H), 2.62 (s, 3H), 1.51 (s, 9H). UPLC-MS: $t_R$=2.31 min (Apolar method); MS (ESI) m/z calcd for $C_{31}H_{26}ClF_4N_4O_5$ (M+H)$^+$: 645.1, found: 645.4.

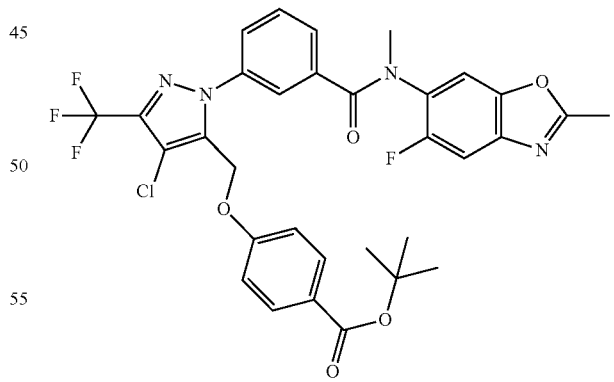

[Int-12.27] tert-Butyl 4-[[4-chloro-2-[3-[(5-fluoro-2-methyl-1,3-benzoxazol-6-yl)-methyl-carbamoyl] phenyl]-5-(trifluoromethyl)pyrazol-3-yl]methoxy] benzoate following general procedure 1d, the title compound was obtained from compound Int-12.26, after purification by silica gel flash-column chromatography with CyHex/AcOEt (60:40) as the eluent, as a white solid in 78% yield: $^1$H NMR (400 MHz, DMSO-$d_6$) δ 7.91 (d, J=6.6 Hz, 1H), 7.83-7.76 (m, 2H), 7.62 (s, 1H), 7.55-7.32 (m, 4H), 6.88 (d, J=8.4 Hz, 2H), 5.11 (s, 2H), 3.32 (s, 3H), 2.53 (s, 3H), 1.52 (s, 9H). UPLC-MS: $t_R$=2.28 min (Apolar method); MS (ESI) m/z calcd for $C_{32}H_{28}ClF_4N_4O_5$ (M+H)$^+$: 659.2, found: 659.4.

[234] 4-[[4-Chloro-2-[3-[(5-fluoro-2-methyl-1,3-benzoxazol-6-yl)-methyl-carbamoyl]phenyl]-5-(trifluoromethyl)pyrazol-3-yl]methoxy]benzoic acid following general procedure 11d, the title compound was obtained from compound Int-12.27, after purification by silica gel flash-column chromatography with DCM/AcOEt (60:40) as the eluent, as a white solid in 74% yield: $^1$H NMR (400 MHz, DMSO-$d_6$) δ 12.72 (s, 1H), 7.91 (d, J=6.6 Hz, 1H), 7.87-7.80 (m, 2H), 7.63 (s, 1H), 7.52 (s, 1H), 7.46-7.31 (m, 3H), 6.89 (d, J=8.4 Hz, 2H), 5.10 (s, 2H), 3.32 (s, 3H), 2.53 (s, 3H). UPLC-MS: $t_R$=0.85 min (Apolar method); MS (ESI) m/z calcd for $C_{28}H_{20}ClF_4N_4O_5$ (M+H)$^+$: 603.1, found: 603.4.

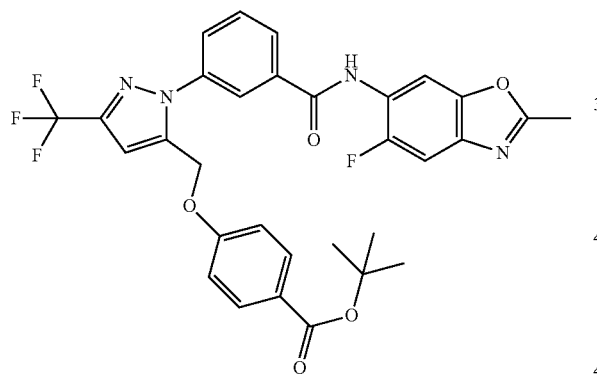

[Int-12.28] tert-Butyl 4-[[2-[3-[(5-fluoro-2-methyl-1,3-benzoxazol-6-yl)carbamoyl]phenyl]-5-(trifluoromethyl) pyrazol-3-yl]methoxy]benzoate following general procedure 1c, the title compound was obtained from compound Int-12.9 and 5-fluoro-2-methyl-1,3-benzoxazol-6-amine, after purification by silica gel flash-column chromatography with DCM/AcOEt (80:20) as the eluent, as a white solid in 84% yield: $^1$H NMR (400 MHz, DMSO-$d_6$) δ 10.39 (s, 1H), 8.24 (app-t, J=1.9 Hz, 1H), 8.12 (dt, J=7.9, 1.3 Hz, 1H), 7.91 (d, J=6.4 Hz, 1H), 7.90-7.86 (m, 1H), 7.83-7.78 (m, 2H), 7.73 (app-t, J=7.9 Hz, 1H), 7.65 (d, J=10.0 Hz, 1H), 7.25 (s, 1H), 7.09-7.01 (m, 2H), 5.31 (s, 2H), 2.62 (s, 3H), 1.51 (s, 9H). UPLC-MS: $t_R$=2.03 min (Apolar method); MS (ESI) m/z calcd for $C_{31}H_{27}F_4N_4O_5$ (M+H)$^+$: 611.1, found: 611.5.

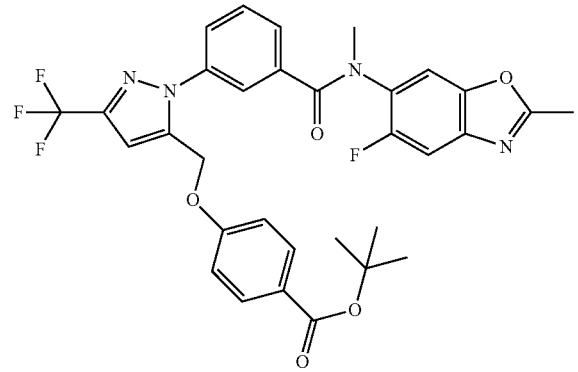 [SMILES: Cc1nc2cc(F)c(N(C)C(=O)c3cccc(-n4nc(C(F)(F)F)cc4COc4ccc(C(=O)OC(C)(C)C)cc4)c3)cc2o1]

[Int-12.29] tert-Butyl 4-[[2-[3-[(5-fluoro-2-methyl-1,3-benzoxazol-6-yl)-methyl-carbamoyl]phenyl]-5-(trifluoromethyl)pyrazol-3-yl]methoxy]benzoate following general procedure 1d, the title compound was obtained from compound Int-12.28, after purification by silica gel flash-column chromatography with DCM/TMBE (90:10) as the eluent, as a white solid in 50% yield: $^1$H NMR (400 MHz, DMSO-$d_6$) δ 7.94 (d, J=6.6 Hz, 1H), 7.85-7.77 (m, 2H), 7.61 (bs, 1H), 7.55-7.44 (m, 2H), 7.37 (bs, 2H), 7.12 (s, 1H), 6.90 (d, J=8.4 Hz, 2H), 5.13 (bs, 2H), 3.34 (s, 3H), 2.52 (s, 3H), 1.52 (s, 9H). UPLC-MS: $t_R$=2.00 min (Apolar method); MS (ESI) m/z calcd for $C_{32}H_{29}F_4N_4O_5$ (M+H)$^+$: 625.2, found: 625.5.

[266] 4-[[2-[3-[(5-Fluoro-2-methyl-1,3-benzoxazol-6-yl)-methyl-carbamoyl]phenyl]-5-(trifluoromethyl) pyrazol-3-yl]methoxy]benzoic acid following general procedure 11d, the title compound was obtained from compound Int-12.29, after purification by silica gel flash-column chromatography with DCM/AcOEt (50:50) as the eluent, as a white solid in 62% yield: $^1$H NMR (400 MHz, DMSO-$d_6$) δ 12.70 (bs, 1H), 7.94 (d, J=6.5 Hz, 1H), 7.89-7.83 (m, 2H), 7.62 (bs, 1H), 7.58-7.34 (m, 4H), 7.13 (s, 1H), 6.91 (app d, J=8.4 Hz, 2H), 5.14 (s, 2H), 3.34 (s, 3H), 2.56-2.49 (m, 3H). UPLC-MS: $t_R$=0.63 min (Apolar method); MS (ESI) m/z calcd for $C_{28}H_{21}F_4N_4O_5$ (M+H)$^+$: 569.1, found: 569.5.

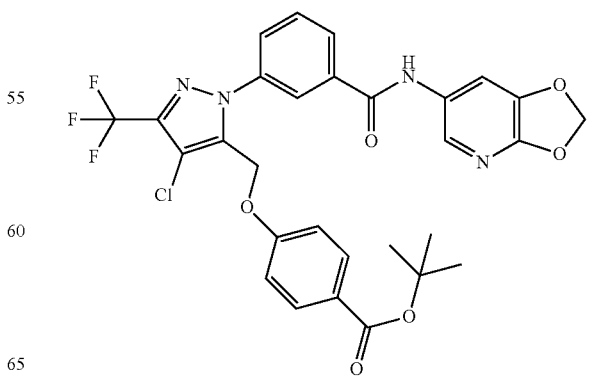

[Int-12.30] tert-Butyl 4-[[4-chloro-2-[3-[[1,3]di-oxolo[4,5-b]pyridin-6-yl(methyl)carbamoyl]phenyl]-5-(trifluoromethyl) pyrazol-3-yl]methoxy]benzoate Step 1. tert-Butyl N-([1,3]dioxolo[4,5-b]pyridin-6-yl)carbamate: a flame-dried Schlenk tube was loaded with Pd$_2$(dba)$_3$ (11 mg, 0.012 mmol) and (5-diphenylphosphanyl-9,9-dimethyl-xanthen-4-yl)-diphenyl-phosphane (17 mg, 0.030 mmol). The vial was purged with nitrogen and toluene (3.7 mL) was added. The solution was allowed to stir for 15 min at rt. Following the order, tert-butyl carbamate (42 mg, 0.36 mmol), Cs$_2$CO$_3$ (195 mg, 0.60 mmol) and 6-bromo-[1,3]dioxolo[4,5-b]pyridine (60 mg, 0.30 mmol) were added and the mixture was degassed (vacuum/nitrogen 5-6 times) and put in the pre-heated bath. The resulting solution was stirred 16 h at 120° C., filtered over a short pad of Celite using AcOEt, and concentrated. The compound was obtained after purification by flash-column chromatography (alumina pH=7), eluting a gradient of 100% DCM to 100% of AcOEt, as a white solid in 41% yield. $^1$H NMR (400 MHz, DMSO-d$_6$) δ 9.33 (s, 1H), 7.62 (d, J=2.1 Hz, 1H), 7.39-7.31 (m, 1H), 6.09 (s, 2H), 1.46 (s, 9H).

Step 2. [1,3]Dioxolo[4,5-b]pyridin-6-amine: tert-butyl N-([1,3]dioxolo[4,5-b]pyridin-6-yl)carbamate (28 mg, 0.11 mmol) was dissolved in a solution of 10% TFA in DCM (1.0 mL) and stirred for 6 h. The solution was poured into a saturated aqueous solution of NaHCO$_3$ and extracted with AcOEt (3×). The organics were dried over Na$_2$SO$_4$, filtered and concentrated. The compound was used in the next step without purification (86% Yield). $^1$H NMR (400 MHz, DMSO-d$_6$) δ 6.90 (d, J=2.2 Hz, 1H), 6.59 (d, J=2.2 Hz, 1H), 5.95 (s, 2H), 4.87 (s, 2H).

Step 3. Following general procedure 1c, the title compound was obtained from compound Int-12.9 and [1,3]dioxolo[4,5-b]pyridin-6-amine, after purification by silica gel flash-column chromatography with DCM/AcOEt (70:30) as the eluent, as a white solid in 61% yield: $^1$H NMR (400 MHz, DMSO-d$_6$) δ 10.38 (s, 1H), 8.16 (t, J=2.0 Hz, 1H), 8.10 (dt, J=8.0, 1.3 Hz, 1H), 7.91-7.85 (m, 1H), 7.86 (ddd, J=7.9, 2.2, 1.0 Hz 1H), 7.80-7.76 (m, 2H), 7.73 (app t, J=7.9 Hz, 1H), 7.57 (d, J=2.1 Hz, 1H), 7.05-6.98 (m, 2H), 6.16 (s, 2H), 1.51 (s, 9H). UPLC-MS: t$_R$=2.14 min (Apolar method); MS (ESI) m/z calcd for C$_{29}$H$_{25}$ClF$_3$N$_4$O$_6$ (M+H)$^+$: 617.1, found: 617.5.

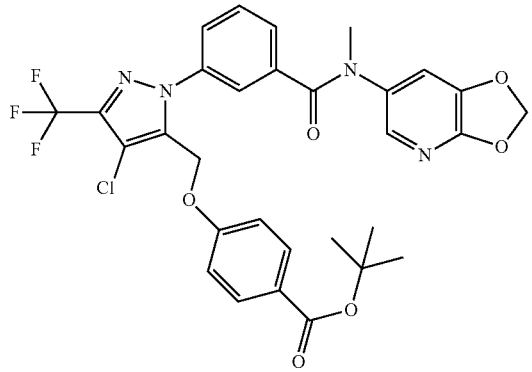 [SMILES: CN(C(=O)c1cccc(-n2nc(C(F)(F)F)c(Cl)c2COc2ccc(C(=O)OC(C)(C)C)cc2)c1)c1cnc2c(c1)OCO2]

[Int-12.31] tert-Butyl 4-[[4-chloro-2-[3-[[1,3]di-oxolo[4,5-b]pyridin-6-yl(methyl)carbamoyl]phenyl]-5-(trifluoromethyl) pyrazol-3-yl]methoxy]benzoate Following general procedure 1d, the title compound was obtained from compound Int-12.30, after purification by silica gel flash-column chromatography with DCM/AcOEt (70:30) as the eluent, as a white solid in 79% yield: $^1$H NMR (400 MHz, DMSO-d$_6$) δ 7.85-7.78 (m, 2H), 7.64 (bs, 1H), 7.58-7.51 (m, 1H), 7.47-7.39 (m, 2H), 7.36 (d, J=2.1 Hz, 1H), 7.32 (bs, 1H), 6.94 (d, J=8.7 Hz, 2H), 6.10 (s, 2H), 5.17 (s, 2H), 3.28 (s, 3H), 1.52 (s, 9H). UPLC-MS: t$_R$=2.07 min (Apolar method); MS (ESI) m/z calcd for C$_{30}$H$_{27}$ClF$_3$N$_4$O$_6$ (M+H)$^+$: 631.2, found: 631.5.

[267] 4-[[4-Chloro-2-[3-[[1,3]dioxolo[4,5-b]pyridin-6-yl (methyl)carbamoyl]phenyl]-5-(trifluoromethyl) pyrazol-3-yl]methoxy]benzoic acid Following general procedure 11d, the title compound was obtained from compound Int-12.31, after purification by silica gel flash-column chromatography with DCM/AcOEt (50:50) as the eluent, as a white solid in 62% yield: $^1$H NMR (400 MHz, DMSO-d$_6$) δ 12.71 (bs, 1H), 7.89-7.82 (m, 2H), 7.64 (bs, 1H), 7.58-7.51 (m, 1H), 7.47-7.39 (m, 2H), 7.35 (d, J=2.2 Hz, 1H), 7.31 (bs, 1H), 6.96 (d, J=8.7 Hz, 2H), 6.10 (s, 2H), 5.16 (s, 2H), 3.28 (s, 3H). UPLC-MS: t$_R$=2.02 min (Generic method); MS (ESI) m/z calcd for C$_{26}$H$_{19}$ClF$_3$N$_4$O$_6$ (M+H)$^+$: 575.1, found: 575.4.

Pathway C

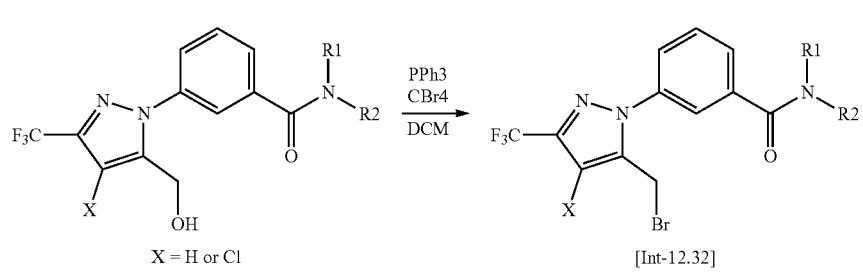

X = H or Cl

[Int-12.32]

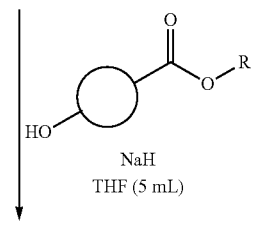

NaH
THF (5 mL)

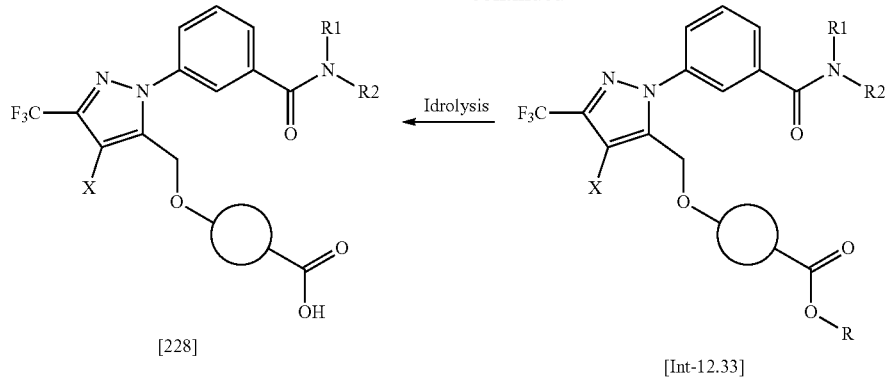

[228] ← Idrolysis ← [Int-12.33]

General Procedure 12e

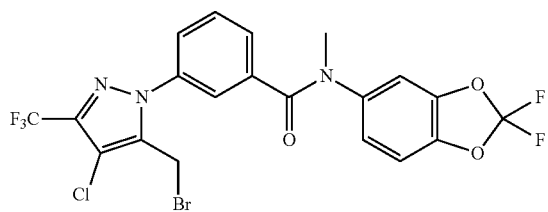 [SMILES: CN(C(=O)c1cccc(-n2nc(C(F)(F)F)c(Cl)c2CBr)c1)c1ccc2c(c1)OC(F)(F)O2]

[Int-12.32] 3-[5-(Bromomethyl)-4-chloro-3-(trifluoromethyl) pyrazol-1-yl]-N-(2,2-difluoro-1,3-benzodioxol-5-yl)-N-methyl-benzamide To a solution of compound 217 (393 mg, 0.8 mmol) in DCM (5 mL), cooled to 0° C., PPh$_3$ (316 mg, 1.20 mmol) and CBr$_4$ (399 mg, 1.20 mmol) were added. Mixture was stirred at room temperature for 16 h, and solvent was remove under reduced pression. Obtained oil was purified with silica gel flash chromatography, eluing with Cyclohexne/EtOAc (60/40). The title compound was obtained, as a white solid in 90% yield (398 mg): UPLC-MS: t$_R$=1.99 min (Apolar method); MS (ESI) m/z calcd for C$_{20}$H$_{13}$BrClF$_5$N$_3$O$_3$ (M+H)$^+$: 552.0 found: 552.1.

General Procedure 12f

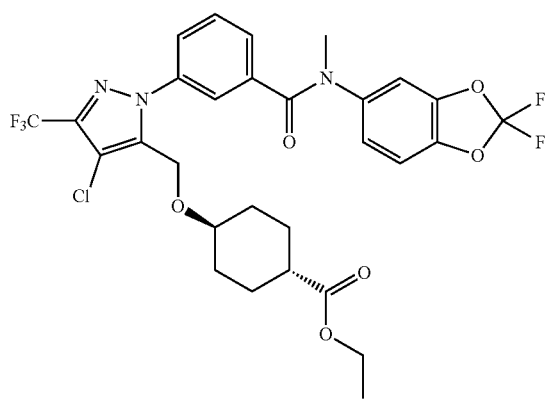 [SMILES: CCOC(=O)[C@H]1CC[C@H](OCc2c(Cl)c(C(F)(F)F)nn2-c2cccc(C(=O)N(C)c3ccc4c(c3)OC(F)(F)O4)c2)CC1]

[Int-12.33] Trans-ethyl 4-[[4-chloro-2-[3-[(2,2-difluoro-1,3-benzodioxol-5-yl)-methyl-carbamoyl]phenyl]-5-(trifluoromethyl)pyrazol-3-yl]methoxy]cyclohexane carboxylate To A solution of trans-ethyl 4-hydroxycyclohexanecarboxylate (20 mg, 0.12 mmol) and Int-12.32 (60 mg, 0.11 mmol) in THF (3 mL), cooled to 0° C., NaH (60% in mineral oil dispersion, 5 mg, 0.12 mmol) was added. Mixture was stirred at room temperature for 8 h and quenched with sat. aq. NH$_4$C$_{1-}$(5 ml). Aqueous layer was extracted with EtOAc (3×10 mL). Collected organic layers were washed with water (2×10 mL) brine (10 mL), dried with Na$_2$SO$_4$, filtered and solvent evaporated. The title compound was obtained, after purification by silica gel flash chromatography with Cyclohexane/EtOAc (70/30), as a white solid in 60% yield (398 mg): UPLC-MS: t$_R$=2.37 min (Apolar method); MS (ESI) m/z calcd for C$_{29}$H$_{28}$ClF$_5$N$_3$O$_6$ (M+H)$^+$: 644.2.0 found: 644.3.

[228] Trans-4-[[4-chloro-2-[3-[(2,2-difluoro-1,3-benzodioxol-5-yl)-methyl-carbamoyl]phenyl]-5-(trifluoromethyl)pyrazol-3-yl]methoxy]cyclohexanecarboxylic acid Following general procedure 4a, the title compound was obtained from [Int-12.33] after purification by silica gel flash-column chromatography with DCM/EtOAc (70/30) as the eluent, as a white solid in 81% yield: $^1$H NMR (400 MHz, DMSO-d$_6$) δ 12.05 (s, 1H), 7.76-7.55 (m, 2H), 7.53 (d, J=2.1 Hz, 1H), 7.52-7.40 (m, 2H), 7.30 (d, J=8.5 Hz, 1H), 7.04 (dd, J=8.5, 2.1 Hz, 1H), 4.39 (s, 2H), 3.36 (s, 3H), 3.19 (app-tt, J=9.9, 3.5 Hz, 1H), 2.11 (app-tt, J=11.4, 3.5 Hz, 1H), 1.88-1.74 (m, 4H), 1.38-1.25 (m, 2H), 1.16-1.03 (m, 2H). UPLC-MS: t$_R$=1.43 min (Apolar method); MS (ESI) m/z calcd for C$_{27}$H$_{24}$ClF$_5$N$_3$O$_6$ (M+H)$^+$: 616.1 found: 616.3.

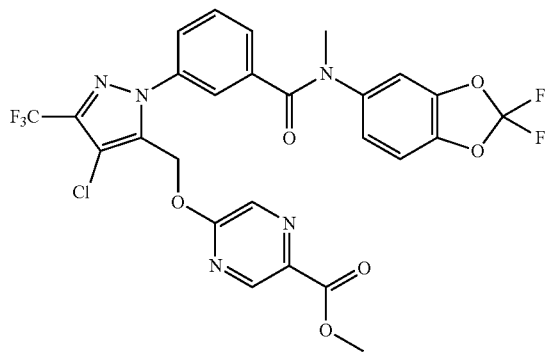 [SMILES: COC(=O)c1cnc(OCc2c(Cl)c(C(F)(F)F)nn2-c2cccc(C(=O)N(C)c3ccc4c(c3)OC(F)(F)O4)c2)cn1]

[Int-12.34] Methyl 5-[[4-chloro-2-[3-[(2,2-difluoro-1,3-benzodioxol-5-yl)-methyl-carbamoyl]phenyl]-5-(trifluoromethyl)pyrazol-3-yl]methoxy]pyrazine-2-carboxylate Following general procedure 12f, the title compound was obtained from [Int-12.32] after purification by silica gel flash-column chromatography with cyclohexane/EtOAc (60/40) as the eluent, as a white solid in 21% yield: $^1$H NMR (400 MHz, DMSO-$d_6$) δ 8.61 (d, J=1.3 Hz, 1H), 8.33 (d, J=1.3 Hz, 1H), 7.61-7.52 (m, 2H), 7.51-7.46 (m, 3H), 7.24 (d, J=8.6 Hz, 1H), 7.04 (dd, J=8.6, 2.2 Hz, 1H), 5.34 (s, 2H), 3.87 (s, 3H), 3.35 (s, 3H). UPLC-MS: $t_R$=1.79 min (Apolar method); MS (ESI) m/z calcd for $C_{26}H_{18}ClF_5N_5O_6$ (M+H)$^+$: 626.1 found: 626.3.

[226] 5-[[4-Chloro-2-[3-[(2,2-difluoro-1,3-benzodioxol-5-yl)-methyl-carbamoyl]phenyl]-5-(trifluoromethyl)pyrazol-3-yl]methoxy]pyrazine-2-carboxylic acid Following general procedure 4a, the title compound was obtained from [Int-12.34] after purification by silica gel flash-column chromatography with DCM/EtOAc (0% to 100%) as the eluent, as a white solid in 73% yield: $^1$H NMR (400 MHz, DMSO-$d_6$) δ 13.35 (bs, 1H), 8.58 (d, J=1.3 Hz, 1H), 8.29 (d, J=1.3 Hz, 1H), 7.64-7.52 (m, 2H), 7.53-7.39 (m, 3H), 7.23 (d, J=8.5 Hz, 1H), 7.03 (dd, J=8.6, 2.2 Hz, 1H), 5.32 (s, 2H), 3.35 (s, 3H). UPLC-MS: $t_R$=0.67 min (Apolar method); MS (ESI) m/z calcd for $C_{25}H_{14}ClF_5N_5O_6$ (M−H)$^-$: 610.1 found: 610.2.

[257] 3-[[4-Chloro-2-[3-[(2,2-difluoro-1,3-benzodioxol-5-yl)-methyl-carbamoyl]phenyl]-5-(trifluoromethyl)pyrazol-3-yl]methoxy]cyclobutanecarboxylic acid Following general procedure 12f, the title compound was obtained directly as carboxylic acid from [Int-12.32] after purification by silica gel flash-column chromatography with DCM/EtOAc (70/30) as the eluent, as a white solid in 22% yield: $^1$H NMR (400 MHz, DMSO-$d_6$) δ 12.19 (s, 1H), 7.63-7.58 (m, 1H), 7.55 (bs, 1H), 7.53 (d, J=2.1 Hz, 1H), 7.51-7.47 (m, 2H), 7.29 (d, J=8.5 Hz, 1H), 7.04 (dd, J=8.6, 2.1 Hz, 1H), 4.27 (s, 2H), 3.80 (p, J=7.3 Hz, 1H), 2.61-2.52 (m, 1H), 2.38-2.23 (m, 2H), 1.92-1.81 (m, 2H). UPLC-MS: $t_R$=0.50 min (Apolar method); MS (ESI) m/z calcd for $C_{25}H_{20}ClF_5N_3O_6$ (M+H)$^+$: 588.1 found: 588.3.

GENERAL PROTOCOL 13

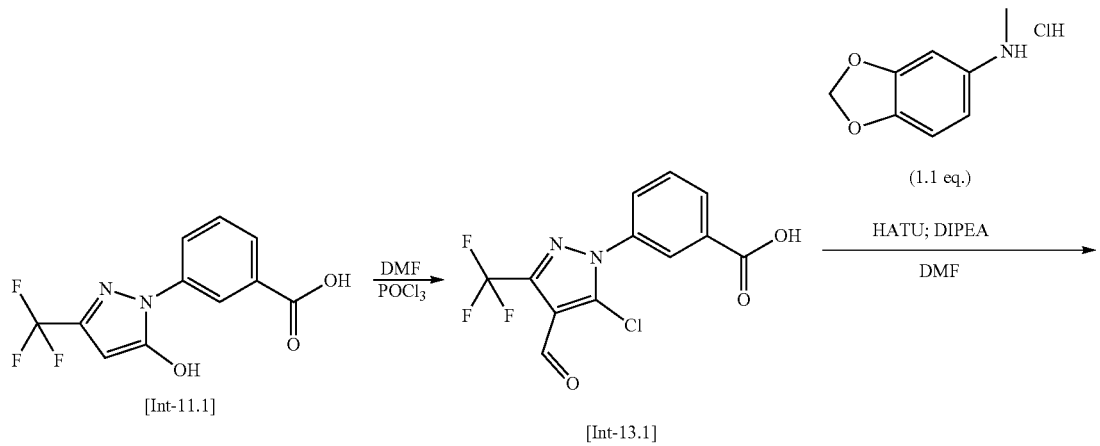

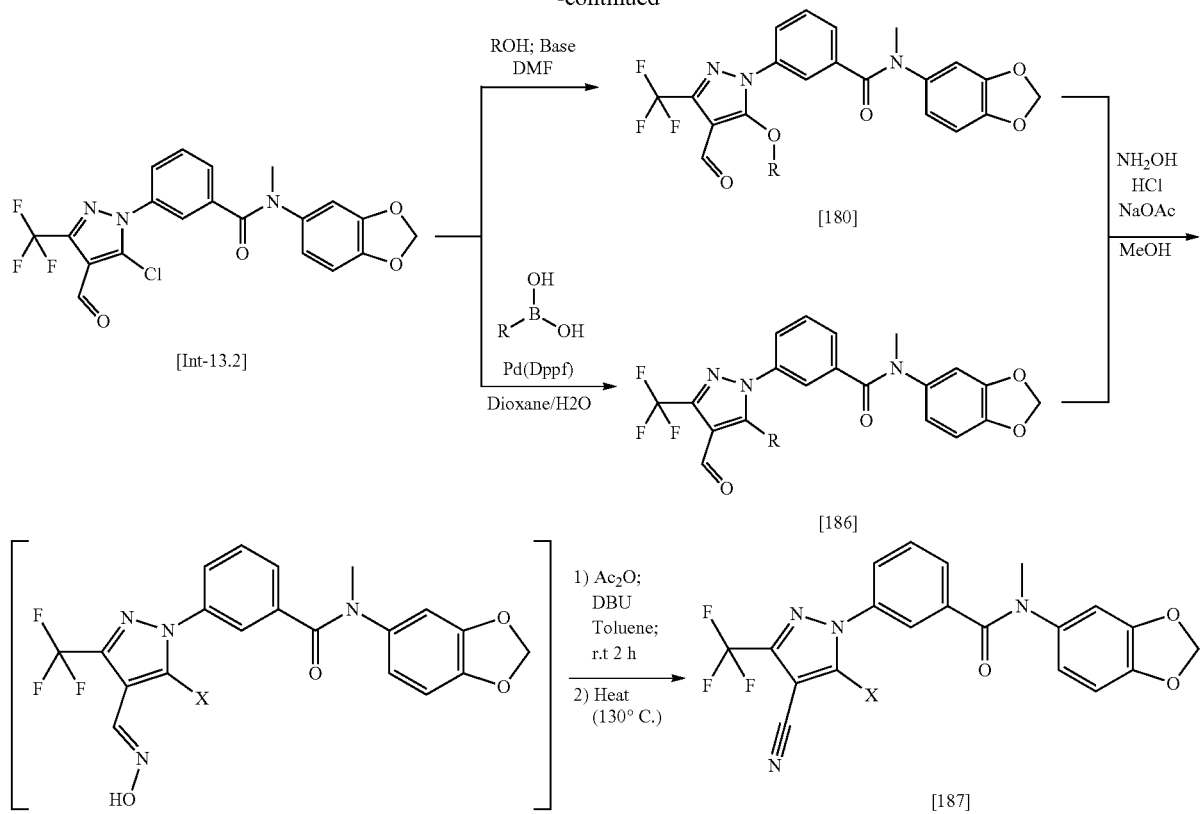

General Procedure 13a

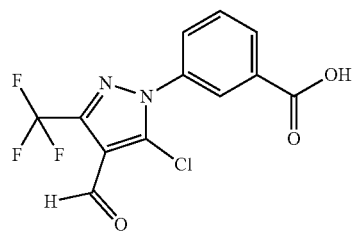 [SMILES: O=Cc1c(C(F)(F)F)nn(-c2cccc(C(=O)O)c2)c1Cl]

[Int-13.1] 3-[5-Chloro-4-formyl-3-(trifluoromethyl)pyrazol-1-yl]benzoic acid

To a solution of [Int-11.1] (100 mg, 0.37 mmol) in POCl₃ (500 μL), DMF (114.0 μL, 1.47 mmol) was added. The mixture was refluxed for 5 h and cooled to 0° C. The reaction was quenched with water (5 mL), and the aqueous layer was extracted with EtOAc (3×10 mL). The collected organic layers were washed with brine (10 mL), dried over Na₂SO₄, filtered and the solvent evaporated. The title compound was obtained as a pale yellow solid in 85% yield (100 mg): $^1$H NMR (400 MHz, DMSO-d₆) δ 9.96 (d, J=0.8 Hz, 1H), 8.20 (t, J=1.9 Hz, 1H), 8.17 (app-dt, J=7.8, 1.3 Hz, 1H), 7.98 (ddd, J=8.0, 2.3, 1.2 Hz, 1H), 7.95 (s, 1H), 7.79 (t, J=7.9 Hz, 1H). UPLC-MS: $t_R$=1.44 min (Generic method); MS (ESI) m/z calcd for $C_{11}H_8F_3N_2O_3$ (M−H)⁻: 317.1, found: 317.3.

General Procedure 13b

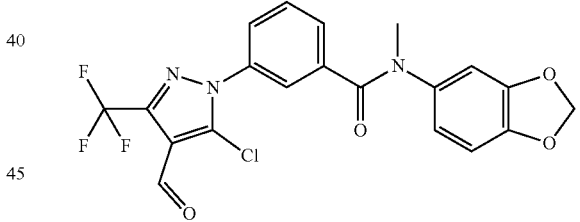

[Int-13.2] N-(1,3-benzodioxol-5-yl)-3-[5-chloro-4-formyl-3-(trifluoromethyl)pyrazol-1-yl]-N-methylbenzamide To a solution of [Int-13.1] (60.0 mg, 0.19 mmol) in DMF (2 mL), N-methyl-1,3-benzodioxol-5-amine hydrochloride (33.6 mg, 0.95 mmol), HATU (71.6 mg, 0.19 mmol) and DIPEA (65.6 μL, 0.38 mmol) were added. The mixture was stirred at room temperature for 6 h and diluted with Et₂O (40 mL). The organic layer was washed with sat. aq. NH₄Cl₍₎ (3×10 mL), water (20 mL), and brine (20 mL). The organic layer was dried with Na₂SO₄, filtered and solvent evaporated. The title compound was obtained, after purification by silica gel flash-column chromatography with Cyclohexane/EtOAc (50/50) as the eluent, as a yellow solid in 65% yield (56 mg): $^1$H NMR (400 MHz, DMSO-d₆) δ 9.93 (s, 1H), 7.70-7.45 (m, 4H), 6.96 (d, J=2.1 Hz, 1H), 6.79 (d, J=8.2 Hz, 1H), 6.66 (dd, J=8.2, 2.1 Hz, 1H), 6.00 (s, 2H), 3.34 (s, 3H).

UPLC-MS: $t_R$=2.01 min (Generic method); MS (ESI) m/z calcd for $C_{20}H_{14}ClF_3N_3O_4$ (M+H)$^+$: 452.0, found: 452.1.

General Procedure 13c

[180] N-(1,3-Benzodioxol-5-yl)-3-[4-formyl-5-phenoxy-3-(trifluoromethyl)pyrazol-1-yl]-N-methylbenzamide To a solution of Phenol (79.7 mg, 0.85 mmol) in DMF (5 mL) under nitrogen, $K_2CO_3$ (159.5 mg, 1.16 mmol) was added and mixture stirred for 20 min. Int-13.2 (348 mg, 0.77 mmol) was added and mixture stirred at 50° C. for 5 h. Mixture was cooled to room temperature and diluted with $Et_2O$ (50 mL). Organic layer was washed with water (20 mL), Brine (20 mL), dried with $Na_2SO_4$, filtered and solvent evaporated. The title compound was obtained, after purification by silica gel flash-column chromatography with Cyclohexane/EtOAc (70/30) as the eluent, as a white solid in 35% yield (140 mg): $^1$H NMR (400 MHz, DMSO-$d_6$) δ 9.49 (s, 1H), 7.69 (app-t, J=1.9 Hz, 1H), 7.65-7.57 (m, 1H), 7.47-7.36 (m, 3H), 7.33 (d, J=7.7 Hz, 1H), 7.28-7.22 (m, 1H), 7.22-7.17 (m, 2H), 6.90 (d, J=2.1 Hz, 1H), 6.62 (d, J=8.2 Hz, 1H), 6.52 (app-d, J=8.2 Hz, 1H), 5.96 (s, 2H), 3.30 (s, 3H). UPLC-MS: $t_R$=2.33 min (Generic method); MS (ESI) m/z calcd for $C_{26}H_1F_3N_3O_5$ (M+H)$^+$: 510.1, found: 510.5.

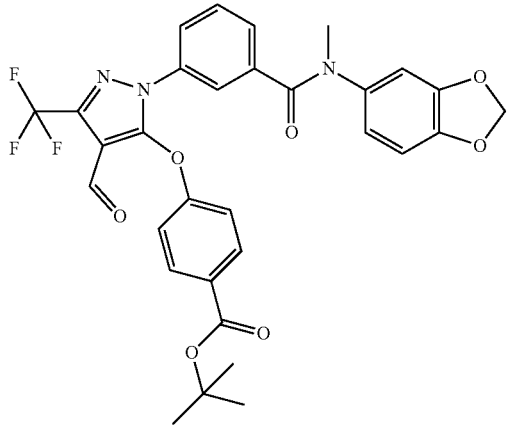 [SMILES: CN(C(=O)c1cccc(-n2nc(C(F)(F)F)c(C=O)c2Oc2ccc(C(=O)OC(C)(C)C)cc2)c1)c1ccc2c(c1)OCO2]

[Int-13.3] Tert-butyl 4-[2-[3-[1,3-benzodioxol-5-yl (methyl)carbamoyl]phenyl]-4-formyl-5-(trifluoromethyl) pyrazol-3-yl]oxybenzoate Following general procedure 13c, the title compound was obtained from Int-13.2, after purification by silica gel flash-column chromatography with DCM/EtOAc (70/30) as the eluent, as a white solid in 79% yield: $^1$H NMR (400 MHz, DMSO-$d_6$) δ 9.65 (d, J=0.9 Hz, 1H), 7.95-7.84 (m, 2H), 7.72-7.64 (m, 1H), 7.57 (app-d, J=8.0 Hz, 1H), 7.38 (app-t, J=7.9 Hz, 1H), 7.33-7.21 (m, 3H), 6.92 (d, J=2.1 Hz, 1H), 6.59 (d, J=8.2 Hz, 1H), 6.46 (dd, J=8.2, 2.1 Hz, 1H), 5.97 (s, 2H), 3.29 (s, 3H), 1.53 (s, 9H).

[186] N-(1,3-Benzodioxol-5-yl)-3-[4-formyl-5-methyl-3-(trifluoromethyl)pyrazol-1-yl]-N-methylbenzamide To a solution of Int-13.2 (100 mg, 0.22 mmol) in dioxane (2 mL) and water (2 mL), trimethylboroxine (309.36 µL, 2.21 mmol), Pd(dppf) (36.1 mg, 0.04 mmol) and $Na_2CO_3$ (234.5 mg, 2.21 mmol) were added. The mixture was degassed with Nitrogen and heated at 100° C. under microwave irradiation for 1.5 h. The mixture was then diluted with EtOAc (30 mL), and washed with sat. aq. $Na_2CO_3$ (10 mL), Brine (20 mL), dried with $Na_2SO_4$, filtered, and the solvent evaporated. The title compound was obtained, after purification by silica gel flash-column chromatography with Cyclohexane/EtOAc (60/40) as the eluent, as a white solid in 79% yield (75 mg): $^1$H NMR (400 MHz, DMSO-$d_6$) δ 10.00 (d, J=0.9 Hz, 1H), 7.55-7.44 (m, 4H), 6.96 (d, J=2.1 Hz, 1H), 6.77 (d, J=8.2 Hz, 1H), 6.65 (dd, J=8.2, 2.1 Hz, 1H), 5.99 (s, 2H), 3.33 (s, 3H), 2.35 (s, 3H). UPLC-MS: $t_R$=2.18 min (Generic method); MS (ESI) m/z calcd for $C_{21}H_{17}F_3N_3O_4$ (M+H)$^+$: 432.1, found: 432.5.

General Procedure 13d

[187] N-(1,3-Benzodioxol-5-yl)-3-[4-cyano-5-methyl-3-(trifluoromethyl)pyrazol-1-yl]-N-methylbenzamide To a solution of compound 186 (63.0 mg, 0.15 mmol) in MeOH (4 mL), Sodium acetate (18.0 mg, 0.22 mmol) and hydroxylamine hydrochloride (11.3 mg, 0.18 mmol) were added. Solution was stirred for 18 h and solvent was evaporated. The obtained solid was rinsed with EtOAc (20 mL), and the organic layer was washed with water (2×20 mL), dried with $Na_2SO_4$, filtered and the solvent evaporated. The obtained solid was dissolved in Toluene (4 mL), and DBU (65.4 µL, 0.44 mmol) and Acetic anhydride (41.4 µL, 0.44 mmol) were added. The mixture was stirred at room temperature for 2 h and at refluxing temperature for further 6 h. The mixture was cooled to room temperature and diluted with EtOAc (30 mL). The organic layer was washed with water (20 mL), 0.5 N HCl aq. sol. (2×20 mL), sat. aq. $NaHCO_3$ (2×10 mL) and brine (20 mL). The organic layer was dried with $Na_2SO_4$, filtered and the solvent evaporated. The title compound was obtained, after purification by silica gel flash-column chromatography with Cyclohexane/EtOAc (70/30) as the eluent, as a white solid in 66% yield over three steps (42 mg): $^1$H NMR (400 MHz, DMSO-$d_6$) δ 7.52 (d, J=9.4 Hz, 4H), 6.96 (d, J=2.1 Hz, 1H), 6.77 (d, J=8.2 Hz, 1H), 6.64 (dd, J=8.2, 2.1 Hz, 1H), 5.99 (s, 2H), 3.33 (s, 3H), 2.27 (s, 3H). UPLC-MS: $t_R$=2.27 min (Generic method); MS (ESI) m/z calcd for $C_{21}H_{16}F_3N_4O_3$ (M+H)$^+$: 429.1, found: 429.5.

[185] N-(1,3-Benzodioxol-5-yl)-3-[4-cyano-5-phenoxy-3-(trifluoromethyl)pyrazol-1-yl]-N-methylbenzamide Following general procedure 13d, the title compound was obtained from compound 180, after purification by silica gel flash-column chromatography with DCM/EtOAc (70/30) as the eluent, as a white solid in 65% yield: $^1$H NMR (400 MHz, DMSO-$d_6$) δ 7.75 (app-t, J=1.9 Hz, 1H), 7.68 (app-d, J=8.1 Hz, 1H), 7.57-7.43 (m, 5H), 7.43-7.34 (m, 2H), 6.90 (d, J=1.9 Hz, 1H), 6.71-6.50 (m, 2H), 5.91 (s, 2H), 3.31 (s, 3H). UPLC-MS: $t_R$=2.19 min (Generic method); MS (ESI) m/z calcd for $C_{26}H_{18}F_3N_4O_4$ (M+H)$^+$: 507.1, found: 507.4.

167

[200] Tert-butyl 4-[2-[3-[1,3-benzodioxol-5-yl(methyl)carbamoyl]phenyl]-4-cyano-5-(trifluoromethyl)pyrazol-3-yl]oxybenzoate Following general procedure 13d the title compound was obtained from [Int-13.3], after purification by silica gel flash-column chromatography with DCM/EtOAc (70/30) as the eluent, as a white solid in 66% yield: $^1$H NMR (400 MHz, DMSO-d$_6$) δ 8.09-7.94 (m, 2H), 7.76-7.70 (m, 1H), 7.65 (app-d, J=7.9 Hz, 1H), 7.58 (d, J=8.8 Hz, 2H), 7.45 (app-t, J=7.8 Hz, 1H), 7.38 (d, J=7.8 Hz, 1H), 6.90 (d, J=2.0 Hz, 1H), 6.70-6.46 (m, 2H), 5.93 (s, 2H), 3.30 (s, 4H), 1.56 (s, 9H). UPLC-MS: $t_R$=2.75 min (Generic method); MS (ESI) m/z calcd for $C_{31}H_{26}F_3N4O6$ (M+H)$^+$: 607.2, found: 607.5.

168

[210] 4-[2-[3-[1,3-Benzodioxol-5-yl(methyl)carbamoyl]phenyl]-4-cyano-5-(trifluoromethyl)pyrazol-3-yl]oxybenzoic acid Following general procedure 13d the title compound was obtained from compound [200], after purification by silica gel flash-column chromatography with DCM/EtOAc (80/20) as the eluent, as a white solid in 82% yield (68 mg): $^1$H NMR (400 MHz, DMSO-d$_6$) δ 13.16 (bs, 1H), 8.10-8.00 (m, 2H), 7.73 (app-t, J=1.8 Hz, 1H), 7.71-7.62 (m, 1H), 7.60-7.54 (m, 2H), 7.46 (app-t, J=7.9 Hz, 1H), 7.39 (app-d, J=7.5 Hz, 1H), 6.89 (d, J=2.0 Hz, 1H), 6.66-6.50 (m, 2H), 5.91 (s, 2H), 3.30 (s, 3H). UPLC-MS: $t_R$=0.48 min (Apolar method); MS (ESI) m/z calcd for $C_{27}H_{16}F_3N4O6$ (M−H)$^-$: 549.1, found: 549.5.

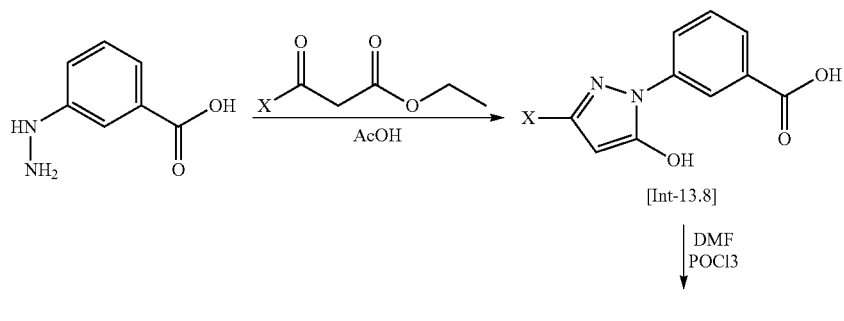

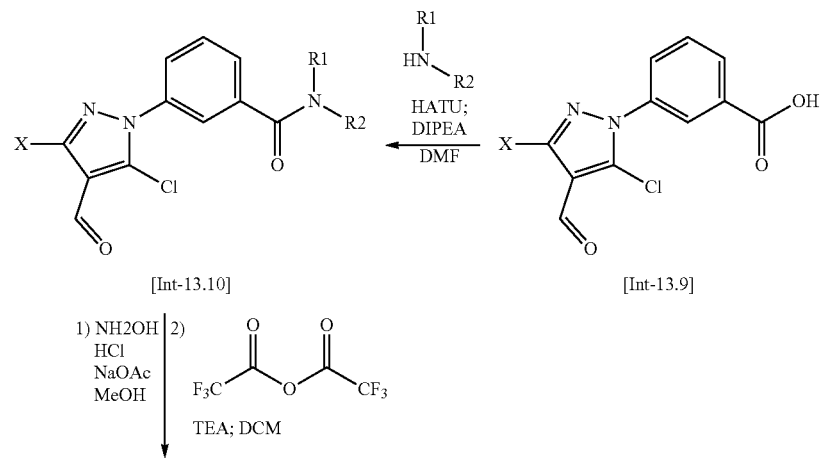

-continued
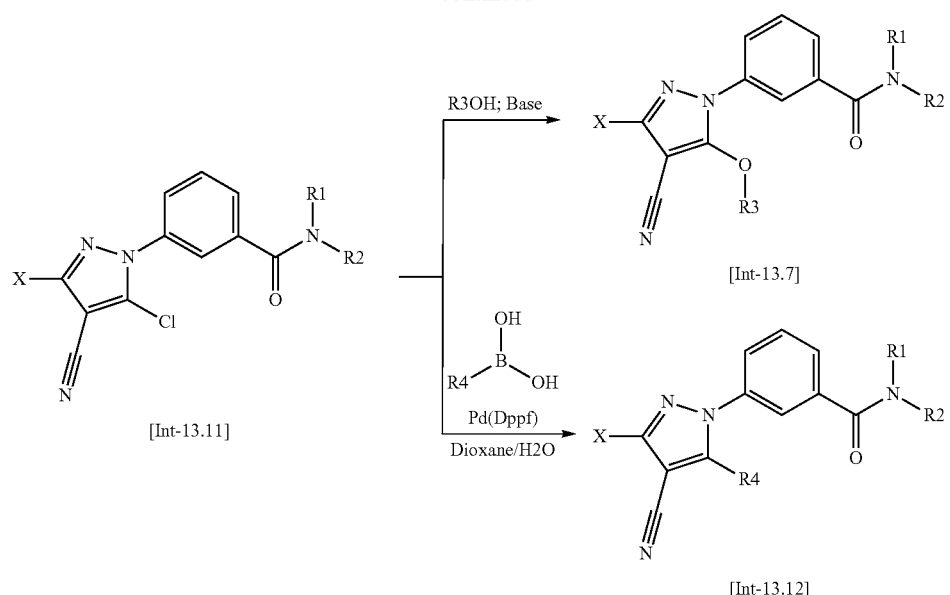
[Int-13.11]
[Int-13.7]
[Int-13.12]
if R4 =
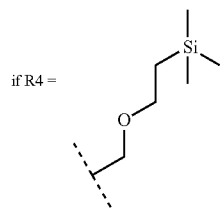
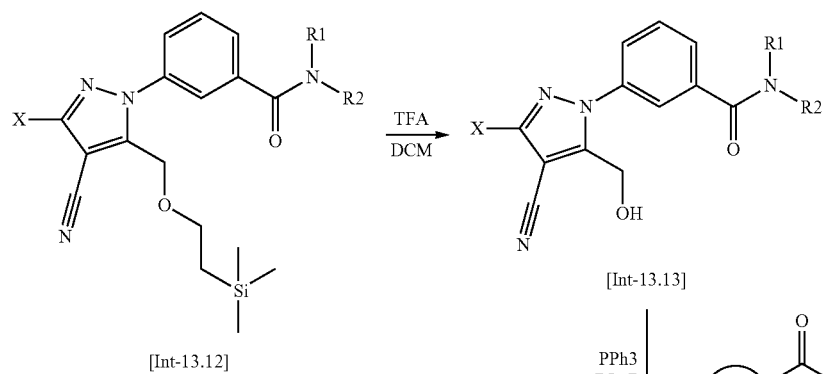
[Int-13.12]
[Int-13.13]
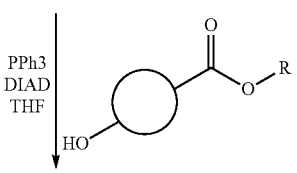
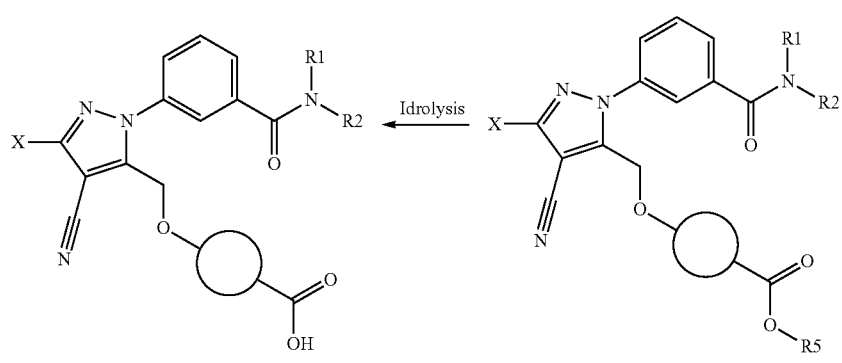
[244]
[Int-13.14]

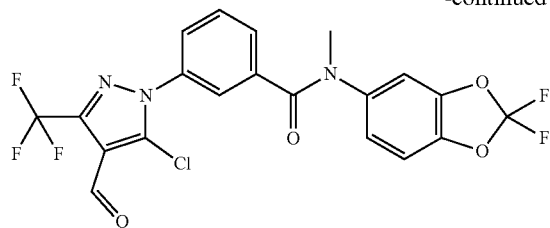

[Int-13.15] 3-[5-Chloro-4-formyl-3-(trifluoromethyl)pyrazol-1-yl]-N-(2,2-difluoro-1,3-benzodioxol-5-yl)-N-methyl-benzamide Following general procedure 13b, the title compound was obtained from [Int-13.1], after purification by silica gel flash-column chromatography with DCM/EtOAc (50/50) as the eluent, as a pale yellow solid in 42% yield: $^1$H NMR (400 MHz, DMSO-$d_6$) δ 9.91 (s, 1H), 7.64-7.54 (m, 4H), 7.53 (d, J=2.1 Hz, 1H), 7.31 (d, J=8.5 Hz, 1H), 7.05 (dd, J=8.5, 2.2 Hz, 1H), 3.38 (s, 3H).

General Procedure 13e

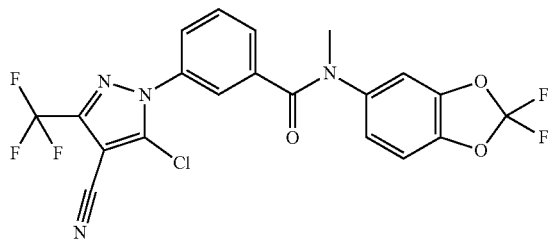 [SMILES: CN(C(=O)c1cccc(-n2nc(C(F)(F)F)c(C#N)c2Cl)c1)c1ccc2c(c1)OC(F)(F)O2]

[Int-13.4] 3-[5-Chloro-4-cyano-3-(trifluoromethyl)pyrazol-1-yl]-N-(2,2-difluoro-1,3-benzodioxol-5-yl)-N-methyl-benzamide To a solution of [Int-13.15] (330 mg, 0.68 mmol) in MeOH (5 mL), sodium acetate (52 mg, 0.81 mmol) and hydroxylamine hydrochloride (83 mg, 1.01 mmol) were added. Mixture was stirred at room temperature for 18 h and solvent was evaporated. Remaining oil was dissolved in EtOAc (20 mL), and organic layer was washed with water (3×10 mL), brine (10 mL), dried with Na$_2$SO$_4$, filtered and solvent evaporated. Obtained solid was dissolved in DCM dry (5 mL), and solution cooled to 0° C., under Nitrogen. TEA (283 µL, 2.03 mmol) was added and Trifluoroacetic anhydride (142 µL, 1.01 mmol) was dropped-over. Mixture was stirred at room temperature for 3 h and quenched with sat. aq. NaHCO$_3$. Aqueous layer was extracted with EtOAc (3×15 mL), and collected organic layer were washed with brine (15 mL), dried over Na$_2$SO$_4$, filtered and solvent evaporated. The title compound was obtained as a yellow solid in 90% yield (296 mg): $^1$H NMR (400 MHz, DMSO-$d_6$) δ 7.68-7.54 (m, 4H), 7.53 (d, J=2.1 Hz, 1H), 7.31 (d, J=8.6 Hz, 1H), 7.09-6.98 (m, 1H), 3.38 (s, 3H).

General Procedure 13f

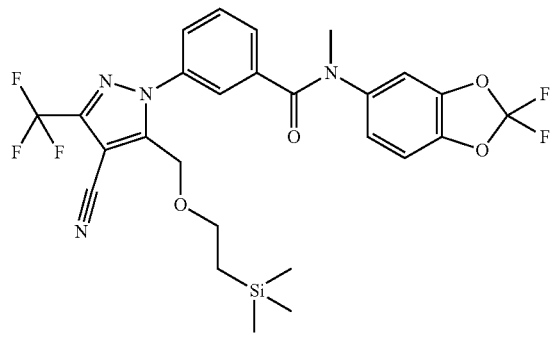 [SMILES: CN(C(=O)c1cccc(-n2nc(C(F)(F)F)c(C#N)c2COCC[Si](C)(C)C)c1)c1ccc2c(c1)OC(F)(F)O2]

[Int-13.5] 3-[4-Cyano-3-(trifluoromethyl)-5-(2-trimethyl silylethoxymethyl)pyrazol-1-yl]-N-(2,2-difluoro-1,3-benzodioxol-5-yl)-N-methyl-benzamide To a mixture of [Int-13.4] (278 mg, 0.57 mmol) in dioxane (8 mL) and water (8 mL), Potassium (2-trimethylsilyl)-ethoxymethyl trifluoroborate (164 mg, 0.5 mL), and Na$_2$CO$_3$ (303 mg, 2.87 mmol) were added. Mixture was degassed with Nitrogen, while stirring, for 10 min, and Pd(dppf)CH$_2$Cl$_2$ (93.7 mg, 0.11 mmol) was added. Mixture was stirred at 80° C. for 48 h, cooled to room temperature, and diluted with EtOAc (30 mL). Organic layer was washed with sat.aq. Na$_2$CO$_3$ (2×10 mL), brine (20 mL), dried over Na$_2$SO$_4$, filtered and solvent evaporated. The title compound was obtained, after purification by silica-gel flash chromatography eluting with cyclohexane/EtOAc (50:50), as a white solid in 69% yield (230 mg): $^1$H NMR (400 MHz, DMSO-$d_6$) δ 7.84-7.49 (m, 5H), 7.31 (d, J=8.5 Hz, 1H), 7.06 (dd, J=8.5, 1.9 Hz, 1H), 4.44 (s, 2H), 3.73-3.56 (m, 2H), 3.38 (s, 3H), 1.81-1.74 (m, 2H), −0.04 (s, 9H).

General Procedure 13g

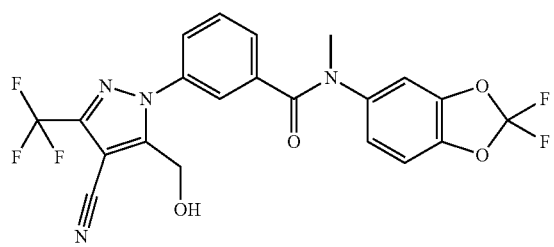

[Int-13.6] 3-[4-Cyano-5-(hydroxymethyl)-3-(trifluoromethyl) pyrazol-1-yl]-N-(2,2-difluoro-1,3-benzodioxol-5-yl)-N-methyl-benzamide To a solution of [Int-13.5] (200 mg, 0.34 mmol) in DCM (0.5 mL), 20% TFA in DCM (0.5 mL) was added. Solution was stirred at room temperature for 4 h and solvent was evaporated. The title compound was obtained, after purification by silica-gel flash chromathography eluting with DCM/EtOAc (60:40), as a white solid in 79% yield (130 mg $^1$H NMR (400 MHz, DMSO-d$_6$) δ 7.65-7.57 (m, 1H), 7.56-7.49 (m, 4H), 7.29 (d, J=8.5 Hz, 1H), 7.12-7.01 (m, 1H), 5.99 (t, J=5.7 Hz, 1H), 4.43 (d, J=5.7 Hz, 2H), 3.37 (s, 3H).

[259] Tert-butyl 4-[[4-cyano-2-[3-[(2,2-difluoro-1,3-benzodioxol-5-yl)-methyl-carbamoyl]phenyl]-5-(trifluoromethyl)pyrazol-3-yl]methoxy]benzoate Following general procedure 7b the title compound was obtained from [Int-13.6], after purification by silica gel flash-column chromatography with cyclohexane/EtOAc (70/30) as the eluent, as a white solid in 68% yield: $^1$H NMR (400 MHz, DMSO-d$_6$) δ 7.91-7.76 (m, 2H), 7.65-7.57 (m, 2H), 7.53-7.45 (m, 3H), 7.21 (d, J=8.5 Hz, 1H), 7.02 (dd, J=8.6, 2.1 Hz, 1H), 6.99-6.92 (m, 2H), 5.31 (s, 2H), 3.35 (s, 3H), 1.52 (s, 9H). UPLC-MS: t$_R$=2.29 min (Apolar method); MS (ESI) m/z calcd for C$_{32}$H$_{26}$F$_5$N$_4$O$_6$ (M+H)$^+$: 657.2, found: 657.4.

[224] 4-[[4-Cyano-2-[3-[(2,2-difluoro-1,3-benzodioxol-5-yl)-methyl-carbamoyl]phenyl]-5-(trifluoromethyl)pyrazol-3-yl]methoxy]benzoic acid Following general procedure 11d the title compound was obtained from compound [259], after purification by silica gel flash-column chromatography with DCM/EtOAc (50/50) as the eluent, as a white solid in 56% yield: $^1$H NMR (400 MHz, DMSO-d$_6$) δ 12.74 (s, 1H), 7.94-7.83 (m, 2H), 7.66-7.56 (m, 2H), 7.55-7.45 (m, 3H), 7.21 (d, J=8.6 Hz, 1H), 7.02 (dd, J=8.6, 2.1 Hz, 1H), 7.00-6.94 (m, 2H), 5.31 (s, 2H), 3.35 (s, 3H). UPLC-MS: t$_R$=1.01 min (Apolar method); MS (ESI) m/z calcd for C$_{28}$H$_{18}$F$_5$N$_4$O$_6$ (M+H)$^+$: 601.1, found: 601.3.

General Procedure 13 h

[Int-13.7] Tert-butyl 4-[[4-cyano-2-[3-[(2,2-difluoro-1,3-benzodioxol-5-yl)-methyl-carbamoyl]phenyl]-5-(trifluoromethyl)pyrazol-3-yl]oxymethyl]benzoate To a solution of tert-butyl 4-(hydroxymethyl)benzoate (35 mg, 0.17 mmol) in THF (3 mL), cooled to 0° C., NaH (60% dispersion in mineral oil, 8 mg, 0.18 mmol) was added. Mixture was stirred for 10 min and [Int-13.4], dissolved in sTHF (3 mL), was added dropwise. Mixture was stirred at room temperature for 4 h, quenched with sat. aq. NH$_4$C$_1$, and diluted with EtOAc (30 mL). Organic layer was washed with brine (20 mL), dried over Na$_2$SO$_4$, filtered and solvent evaporated. The title compound was obtained, after purification by silica-gel flash chromathography eluting with cyclohexane/EtOAc (50:50), as a white solid in 69% yield (230 mg): $^1$H NMR (400 MHz, DMSO-d$_6$) δ 8.05-7.81 (m, 2H), 7.63 (bs, 1H), 7.60-7.49 (m, 3H), 7.48-7.39 (app-d, J=7.8 Hz, 1H), 7.22 (d, J=8.5 Hz, 1H), 6.92 (app-d, J=8.5 Hz, 1H), 5.76 (s, 2H), 3.33 (s, 3H), 1.53 (s, 9H).

[223] 4-[[4-Cyano-2-[3-[(2,2-difluoro-1,3-benzodioxol-5-yl)-methyl-carbamoyl]phenyl]-5-(trifluoromethyl)pyrazol-3-yl]oxymethyl]benzoic acid Following general procedure 11d the title compound was obtained from compound [Int-13.7], after purification by silica gel flash-column chromatography with DCM/EtOAc (50/50) as the eluent, as a white solid in 67% yield: $^1$H NMR (400 MHz, DMSO-d$_6$) δ 13.06 (s, 1H), 7.96 (d, J=8.2 Hz, 2H), 7.63 (bs, 1H), 7.61-7.51 (m, 3H), 7.49-7.39 (m, 2H), 7.36 (d, J=7.8 Hz, 1H), 7.22 (d, J=8.6 Hz, 1H), 6.93 (d, J=8.5 Hz, 1H), 5.76 (s, 2H), 3.34 (s, 3H). UPLC-MS: t$_R$=0.92 min (Apolar method); MS (ESI) m/z calcd for C$_{28}$H$_{18}$F$_5$N$_4$O$_6$ (M+H)$^+$: 601.1, found: 601.5.

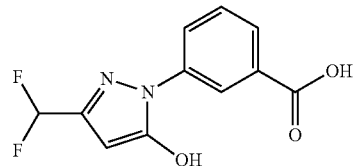

[Int-13.8] 3-[5-Hydroxy-3-(difluoromethyl)pyrazol-1-yl]benzoic acid

Following general procedure 11b, the title compound was obtained from 3-hydrazinobenzoic acid and ethyl 4,4-difluoro-3-oxo-butanoate, after purification by silica gel flash-column chromatography with DCM/MeOH (85/15) as the eluent, as a yellow solid in 40% yield. $^1$H NMR (400 MHz, DMSO-d$_6$) δ 13.21 (bs, 1H), 12.35 (bs, 1H), 8.31 (t, J=1.9 Hz, 1H), 8.00 (ddd, J=8.2, 2.3, 1.1 Hz, 1H), 7.90 (app-dt, J=7.8, 1.4 Hz, 1H), 7.62 (app-t, J=8.0 Hz, 1H), 6.89 (t, J=54.6 Hz, 1H), 5.80 (s, 1H). UPLC-MS: t$_R$=1.03 min (Generic method); MS (ESI) m/z calcd for C$_{11}$H$_9$F$_2$N$_2$O$_3$ (M+H)$^+$: 255.0, found: 255.4.

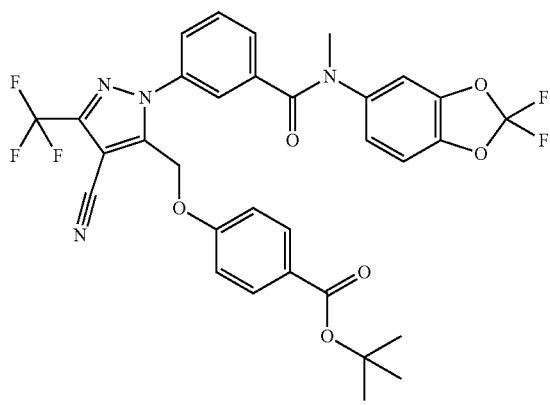 [SMILES: CN(C(=O)c1cccc(-n2nc(C(F)(F)F)c(C#N)c2COc2ccc(C(=O)OC(C)(C)C)cc2)c1)c1ccc2c(c1)OC(F)(F)O2]

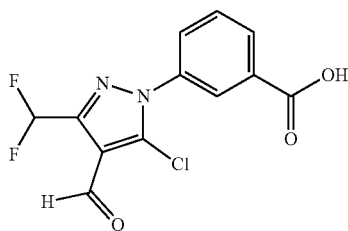 [SMILES: O=Cc1c(C(F)F)nn(-c2cccc(C(=O)O)c2)c1Cl]

[Int-13.9] 3-[5-Chloro-4-formyl-3-(difluoromethyl)pyrazol-1-yl]benzoic acid

Following general procedure 13a, the title compound was obtained from Int-13.8, after purification by silica gel flash-column chromatography with DCM/EtOAc (60/40) as the eluent, as a pale-yellow solid in 65% yield. $^1$H NMR (400 MHz, CDCl$_3$) δ 10.07 (s, 1H), 8.31 (app-t, J=1.9 Hz, 1H), 8.26 (app-dt, J=7.9, 1.3 Hz, 1H), 7.82 (ddd, J=8.0, 2.2, 1.1 Hz, 1H), 7.68 (app-t, J=7.9 Hz, 1H), 6.98 (t, J=53.5 Hz, 1H). UPLC-MS: t$_R$=1.32 min (Generic method); MS (ESI) m/z calcd for C$_{12}$H$_6$ClF$_2$N$_2$O$_3$ (M−H)$^-$: 299.0, found: 299.3.

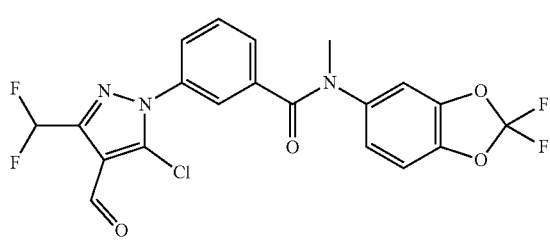 [SMILES: CN(C(=O)c1cccc(-n2nc(C(F)F)c(C=O)c2Cl)c1)c1ccc2c(c1)OC(F)(F)O2]

[Int-13.10] 3-[5-Chloro-4-formyl-3-(difluoromethyl)pyrazol-1-yl]-N-(2,2-difluoro-1,3-benzodioxol-5-yl)-N-methyl-benzamide Following general procedure 13b, the title compound was obtained from [Int-13.9], after purification by silica gel flash-column chromatography with DCM/EtOAc (85/15) as the eluent, as a pale-yellow solid in 28% yield. $^1$H NMR (400 MHz, CDCl$_3$) δ 10.00 (s, 1H), 7.54-7.41 (m, 4H), 6.95 (d, J=8.45 Hz, 1H), 6.92 (t, J=53.5 Hz, 1H), 6.88 (d, J=2.0 Hz, 1H), 6.80 (dd, J=8.4, 2.1 Hz, 1H), 3.48 (s, 3H). UPLC-MS: t$_R$=2.34 min (Generic method); MS (ESI) m/z calcd for C$_{20}$H$_{13}$ClF$_4$N$_3$O$_4$ (M+H)$^+$: 470.0, found: 470.4.

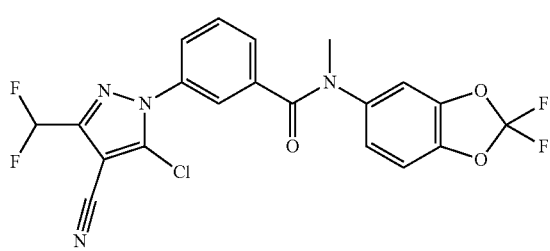 [SMILES: CN(C(=O)c1cccc(-n2nc(C(F)F)c(C#N)c2Cl)c1)c1ccc2c(c1)OC(F)(F)O2]

[Int-13.11] 3-[5-Chloro-4-cyano-3-(difluoromethyl)pyrazol-1-yl]-N-(2,2-difluoro-1,3-benzodioxol-5-yl)-N-methyl-benzamide Following general procedure 13e, the title compound was obtained from [Int-13.10], after purification by silica gel flash-column chromatography with Cyclohexane/EtOAc (70/30) as the eluent, as a pale-yellow viscous oil in 90% yield. $^1$H NMR (400 MHz, CDCl$_3$) δ 7.50-7.43 (m, 4H), 6.94 (d, J=8.4 Hz, 1H), 6.88 (d, J=2.1 Hz, 1H), 6.78 (dd, J=8.5, 2.1 Hz, 1H), 6.67 (t, J=52.6 Hz, 1H), 3.48 (s, 3H). UPLC-MS: t$_R$=1.30 min (Apolar method); MS (ESI) m/z calcd for C$_{20}$H$_{12}$ClF$_4$N$_4$O$_3$ (M+H)$^+$: 467.0, found: 467.5.

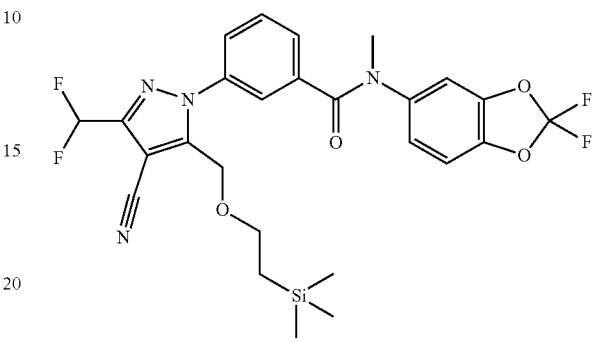

[Int-13.12] 3-[4-Cyano-3-(difluoromethyl)-5-(2-trimethyl silylethoxymethyl)pyrazol-1-yl]-N-(2,2-difluoro-1,3-benzodioxol-5-yl)-N-methyl-benzamide Following general procedure 13f, the title compound was obtained from [Int-13.11], after purification by silica gel flash-column chromatography with Cyclohexane/EtOAc (60/40) as the eluent, as a pale-yellow viscous oil in 35% yield. $^1$H NMR (400 MHz, CDCl$_3$) δ 7.65 (bs, 1H), 7.61 (app-dt, J=6.7, 2.2 Hz, 1H), 7.42-7.36 (m, 2H), 6.92 (d, J=8.4 Hz, 1H), 6.90 (d, J=2.2 Hz, 1H), 6.77 (dd, J=8.4, 2.2 Hz, 1H), 6.73 (t, J=53.70, 1H), 4.41 (s, 2H), 3.65 (m, 2H), 3.48 (s, 3H), 0.99 (m, 2H), 0.03 (s, 9H). UPLC-MS: t$_R$=2.10 min (Apolar method); MS (ESI) m/z calcd for C$_{26}$H$_{27}$F$_4$N$_4$O$_4$Si (M−H)$^-$: 561.1, found: 561.5.

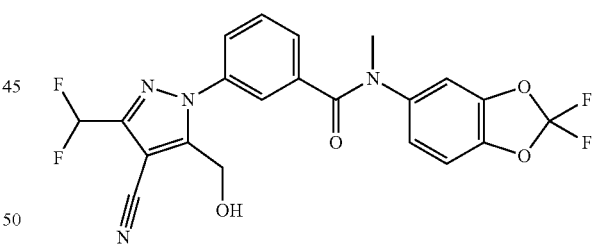

[Int-13.13] 3-[4-Cyano-5-(hydroxymethyl)-3-(difluoromethyl) pyrazol-1-yl]-N-(2,2-difluoro-1,3-benzodioxol-5-yl)-N-methyl-benzamide Following general procedure 13g, the title compound was obtained from [Int-13.12], after purification by silica gel flash-column chromatography with DCM/EtOAc (50/50) as the eluent, as a pale-yellow viscous oil in 77% yield. $^1$H NMR (400 MHz, CDCl$_3$) δ 7.66 (bs, 1H), 7.59 (m, 1H), 7.40 (m, 2H), 6.93 (d, J=8.7 Hz, 1H), 6.92 (d, J=2.2 Hz, 1H), 6.78 (dd, J=8.6, 1.8 Hz, 1H), 6.72 (t, J=53.70 Hz, 1H), 4.60 (bs, 2H), 3.48 (s, 3H). UPLC-MS: t$_R$=0.88 min (Apolar method); MS (ESI) m/z calcd for C$_{21}$H$_{15}$F$_2$N$_4$O$_4$ (M+H)$^+$: 463.1, found: 463.5.

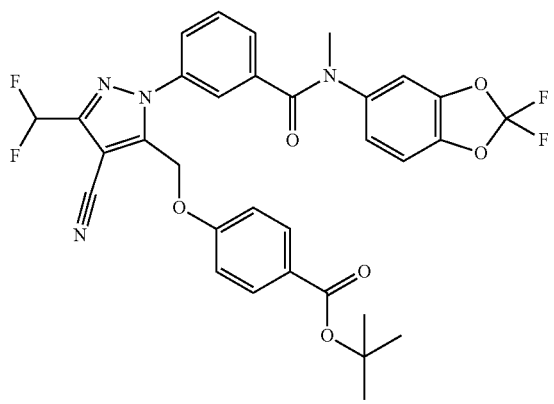 [SMILES: CN(C(=O)c1cccc(-n2nc(C(F)F)c(C#N)c2COc2ccc(C(=O)OC(C)(C)C)cc2)c1)c1ccc2c(c1)OC(F)(F)O2]

[Int-13.14] Tert-butyl 4-[[4-cyano-2-[3-[(2,2-difluoro-1,3-benzodioxol-5-yl)-methyl-carbamoyl]phenyl]-5-(difluoromethyl)pyrazol-3-yl]methoxy]benzoate Following general procedure 7b the title compound was obtained from [Int-13.13], after purification by silica gel flash-column chromatography with DCM/EtOAc (80/20) as the eluent, as a viscous yellow oil in 59% yield. $^1$H NMR (400 MHz, CDCl$_3$) δ 7.96 (m, 2H), 7.60 (bs, 1H), 7.46 (app-dt, J=7.7, 2.2 Hz, 1H), 7.38 (d, J=7.8 Hz, 1H), 7.34 (app-t, J=7.8 Hz, 1H), 6.90-6.86 (m, 3H), 6.79 (d, J=2.0 Hz, 1H), 6.75 (t, J=53.50 Hz, 1H), 6.68 (dd, J=8.4, 2.0 Hz, 1H), 5.07 (s, 2H), 3.44 (s, 3H), 1.57 (s, 9H). UPLC-MS: t$_R$=1.96 min (Apolar method); MS (ESI) m/z calcd for C$_{32}$H$_{27}$F$_4$N4O6 (M+H)$^+$: 639.2, found: 639.5.

[268] 4-[[4-Cyano-2-[3-[(2,2-difluoro-1,3-benzodioxol-5-yl)-methyl-carbamoyl]phenyl]-5-(difluoromethyl)pyrazol-3-yl]methoxy]benzoic acid Following general procedure 11d the title compound was obtained from compound [Int-13.14], after purification by silica gel flash-column chromatography with DCM/EtOAc (60/40) as the eluent, as a white solid in 90% yield: $^1$H NMR (400 MHz, DMSO-d$_6$) δ 7.90-7.87 (m, 2H), 7.64 (bs, 1H), 7.57 (app-dt, J=7.3, 1.8 Hz, 1H), 7.50 (d, J=2.1 Hz, 1H), 7.46 (m, 2H), 7.26 (t, J=53.1 Hz, 1H), 7.21 (d, J=8.7 Hz, 1H), 7.01 (dd, J=8.6, 1.8 Hz, 1H), 7.02-6.94 (m, 2H), 5.27 (s, 2H), 3.34 (s, 3H). UPLC-MS: t$_R$=2.02 min (Generic method); MS (ESI) m/z calcd for C$_{28}$H$_{19}$F$_4$N$_4$O$_6$ (M+H)$^+$: 583.1, found: 583.5.

GENERAL PROTOCOL 14

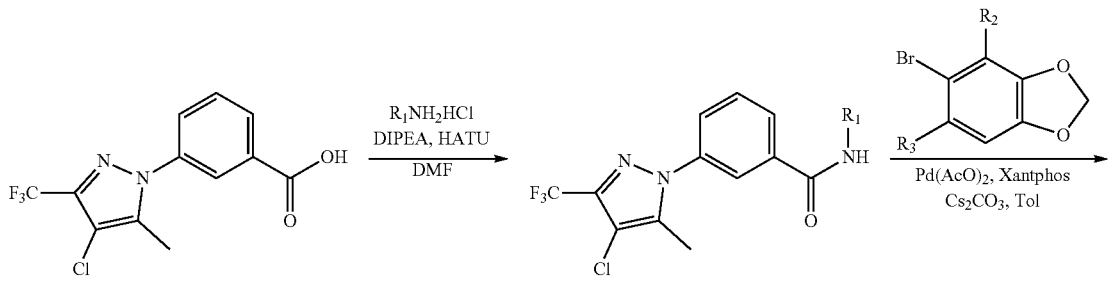

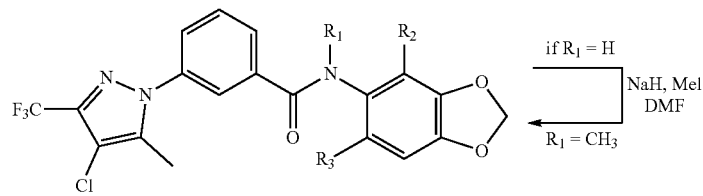

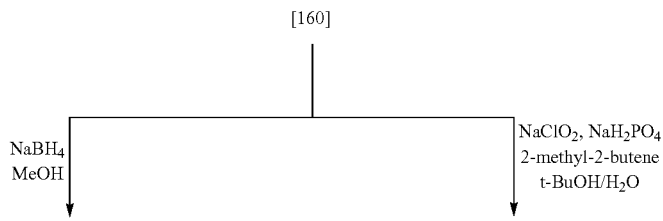

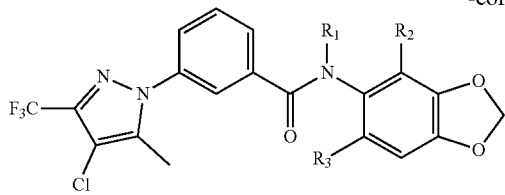

[167]

When R₂ = H and R₃ = CHO or R2 = CHO and R₃ = H then
R₂ = H and R₃ = CH₂OH or R₂ = CH₂OH and R₃ = H

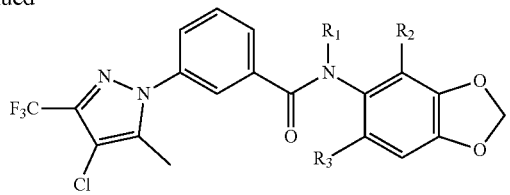

[178]

When R₂ = H and R₃ = CHO or R2 = CHO and R₃ = H then
R₂ = H and R₃ = COOH or R₂ = COOH and R₃ = H General Procedure 14a

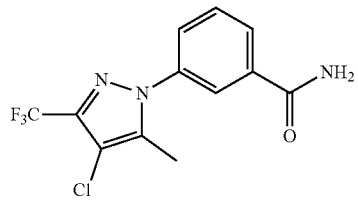 [SMILES: Cc1c(Cl)c(C(F)(F)F)nn1-c1cccc(C(N)=O)c1]

[Int-14.1] 3-[4-Chloro-5-methyl-3-(trifluoromethyl)pyrazol-1-yl]benzamide

To a solution of Int-1.2 (500 mg, 1.64 mmol) in DMF (4.0 mL), HATU (686 mg, 1.80 mmol) and DIPEA (932 mg, 7.38 mmol) were added at 0° C. The resulting mixture was stirred 30 minutes and NH₄HCl (263 mg, 4.92 mmol) was added. After 1 h of stirring at room temperature, the solution was diluted with Et₂O (30 mL) and quenched with NH₄C₁_std solution (15 mL). The organic layer was washed with Brine (10 mL), dried over Na₂SO₄ and concentrated. The title compound was purified by flash chromatography, eluting with a gradient of 100% DCM to 20% AcOEt in DCM, to afford a white solid in 73% yield (365 mg, 1.20 mmol). ¹H NMR (400 MHz, DMSO-d₆) δ 8.12 (bs, 1H), 8.10-8.01 (m, 2H), 7.78 (app dt, J=8.0, 1.4 Hz, 1H), 7.68 (app-t, J=7.7 Hz, 1H), 7.56 (bs, 1H), 2.34 (s, 3H). UPLC-MS: t_R=2.02 min (Generic method); MS (ESI) m/z calcd for C₁₂H₁₀ClF₃N₃O (M+H)⁺: 304.0, found: 304.4.

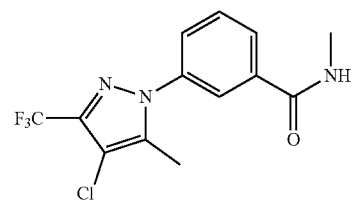 [SMILES: CNC(=O)c1cccc(-n2nc(C(F)(F)F)c(Cl)c2C)c1]

[Int-14.2] 3-[4-Chloro-5-methyl-3-(trifluoromethyl)pyrazol-1-yl]-N-methyl-benzamide Following the general procedure 14a, the title compound was prepared from Int-1.2 and methylamine hydrochloride. Subsequent flash chromatography, eluting with a gradient of 100% DCM to 20% AcOEt in DCM, afforded a white solid in 71% yield. ¹H NMR (400 MHz, DMSO-d₆) δ 8.59 (q, J=4.8 Hz, 1H), 8.02-7.98 (m, 2H), 7.77 (ddd, J=7.9, 2.2, 1.2 Hz, 1H), 7.69 (app t, J=7.7 Hz, 1H), 2.81 (d, J=4.5 Hz, 3H), 2.34 (s, 3H). UPLC-MS: t_R=2.08 min (Generic method); MS (ESI) m/z calcd for C₁₃H₁₀ClF₃N₃O (M−H)⁻: 316.0, found: 316.4.

General Procedure 14b

[Int-160] 3-[4-Chloro-5-methyl-3-(trifluoromethyl)pyrazol-1-yl]-N-(6-formyl-1,3-benzodioxol-5-yl)benzamide A flame-dried Schlenk tube was loaded with Int-14.1 (69 mg, 0.30 mmol), 6-bromo-1,3-benzodioxole-5-carbaldehyde (109 mg, 0.36 mmol), 4,5-bis(diphenylphosphino)-9,9-dimethylxanthene (18 mg, 0.03 mmol), palladium(II) acetate (4 mg, 0.015 mmol), cesium carbonate (293 mg, 0.90 mmol) and toluene (6.0 mL). The mixture was degassed with nitrogen and allowed to stir for 4 h at 90° C. The reaction was filtered over a short pad of Celite, concentrated and purified by flash chromatography, eluting with a gradient of 100% DCM to 40% AcOEt in DCM. The title compound was obtained as white solid in 74% yield (101 mg, 0.22 mmol). ¹H NMR (400 MHz, DMSO-d₆) δ 11.90 (s, 1H), 9.87 (s, 1H), 8.18-8.09 (m, 2H), 7.98 (s, 1H), 7.92 (dt, J=7.9, 1.4 Hz, 1H), 7.84 (app t, J=7.8 Hz, 1H), 7.47 (s, 1H), 6.21 (s, 2H), 2.41 (s, 3H). UPLC-MS: t_R=2.73 min (Generic method); MS (ESI) m/z calcd for C₂₀H₁₂ClF₃N₃O₄ (M−H)⁻: 450.0, found: 450.4.

[161] 3-[4-Chloro-5-methyl-3-(trifluoromethyl)pyrazol-1-yl]-N-(6-formyl-1,3-benzodioxol-5-yl)-N-methyl-benzamide Following the general procedure 14b, the title compound was prepared from Int-14.2 and 6-bromo-1,3-benzodioxole-5-carbaldehyde. Purification by silica gel flash-column chromatography, eluting with a gradient of 100% DCM to 10% AcOEt in DCM, gave a white solid in 43% yield. ¹H NMR (400 MHz, DMSO-d₆, 60° C.) δ 9.86 (s, 1H), 7.81-7.30 (m, 4H), 7.23 (s, 1H), 7.14 (s, 1H), 6.15 (s, 2H), 3.37 (s, 3H), 2.13 (bs, 3H). UPLC-MS: t_R=2.36 min (Generic method); MS (ESI) m/z calcd for C₂₁H₁₆ClF₃N₃O₄ (M+H)⁺: 466.8, found: 466.5.

[162] 3-[4-Chloro-5-methyl-3-(trifluoromethyl)pyrazol-1-yl]-N-(6-cyano-1,3-benzodioxol-5-yl)benzamide Following the general procedure 14b, the title compound was prepared from Int-14.1 and 6-bromo-1,3-benzodioxole-5-carbonitrile.

Purification by silica gel flash-column chromatography, eluting a gradient of 100% DCM to 10% AcOEt in DCM, gave a white solid in 28% yield. $^1$H NMR (400 MHz, DMSO-d$_6$) δ 10.62 (s, 1H), 8.19-8.11 (m, 2H), 7.89 (app d, J=8.7 Hz, 1H), 7.82-7.75 (m, 1H), 7.44 (s, 1H), 7.19 (s, 1H), 6.21 (s, 2H), 2.38 (s, 3H). UPLC-MS: t$_R$=2.41 min (Generic method); MS (ESI) m/z calcd for C$_{20}$H$_{11}$ClF$_3$N$_4$O$_3$ (M−H)$^-$: 447.1, found: 447.4.

[163] 3-[4-Chloro-5-methyl-3-(trifluoromethyl)pyrazol-1-yl]-N-(6-cyano-1,3-benzodioxol-5-yl)-N-methyl-benzamide Following the general procedure 14b, the title compound was prepared from Int-14.2 and 6-bromo-1,3-benzodioxole-5-carbonitrile. Purification by silica gel flash-column chromatography, eluting a gradient of 100% DCM to 10% AcOEt in DCM, gave a white solid in 28% yield. $^1$H NMR (400 MHz, DMSO-d$_6$) δ 7.69-7.45 (m, 4H), 7.43 (s, 1H), 7.31 (s, $^1$H), 6.18 (s, 2H), 3.35 (bs, 3H), 2.17 (bs, 3H). UPLC-MS: t$_R$=2.36 min (Generic method); MS (ESI) m/z calcd for C$_{21}$H$_{15}$ClF$_3$N$_4$O$_3$ (M+H)$^+$: 463.1, found: 463.5.

[Int-203] 3-[4-Chloro-5-methyl-3-(trifluoromethyl)pyrazol-1-yl]-N-(4-formyl-1,3-benzodioxol-5-yl)benzamide Following the general procedure 14b, the title compound was prepared from Int-14.1 and 5-bromo-1,3-benzodioxole-4-carbaldehyde. Purification by silica gel flash-column chromatography, eluting a gradient of 100% cyclohexanes to 10% AcOEt in cyclohexanes, gave a yellow solid in 80% yield. $^1$H NMR (400 MHz, DMSO-d$_6$) δ 11.27 (s, 1H), 10.09 (s, $^1$H), 8.14-8.10 (m, 2H), 7.92-7.88 (m, 1H), 7.81 (app t, J=7.8 Hz, 1H), 7.68 (d, J=8.5 Hz, 1H), 7.27 (dd, J=8.5, 0.7 Hz, 1H), 6.24 (s, 2H), 2.40 (s, 3H). UPLC-MS: t$_R$=2.76 min (Generic method); MS (ESI) m/z calcd for C$_{20}$H$_{14}$ClF$_3$N$_3$O$_4$ (M+H)$^+$: 451.1, found: 452.5.

General Procedure 14c

[207] 3-[4-Chloro-5-methyl-3-(trifluoromethyl)pyrazol-1-yl]-N-(4-formyl-1,3-benzodioxol-5-yl)-N-methyl-benzamide A solution of Int-203 (452 mg, 1.00 mmol) in DMF (5.0 mL) was treated with NaH (60% dispersion in mineral oil, 50 mg, 1.25 mmol) at 0° C. After 30 minutes of stirring, Iodomethane (213 mg, 1.50 mmol) was added dropwise and the mixture was allowed to react overnight at room temperature. The reaction was quenched with NH$_4$C$_{1-}$std solution (20 mL) and AcOEt (25 mL). The organic layer was washed with Brine (15 mL) and water (15 mL), dried over Na$_2$SO$_4$. The title compound was obtained, after silica gel flash chromatography (Cyclohexanes/AcOEt=8/2), as yellowish solid in 80% yield. NMR (400 MHz, DMSO-d$_6$, 87° C.) δ 10.08 (s, 1H), 7.66-7.31 (m, 4H), 7.08 (d, J=8.2 Hz, 1H), 6.90 (d, J=8.2 Hz, 1H), 6.18 (s, 2H), 3.29 (s, 3H), 2.17 (bs, 3H). UPLC-MS: t$_R$=2.33 min (Generic method); MS (ESI) m/z calcd for C$_{21}$H$_{16}$ClF$_3$N$_3$O$_4$ (M+H)$^+$: 466.1, found: 466.4.

General Procedure 14d

[Int-167] 3-[4-Chloro-5-methyl-3-(trifluoromethyl)pyrazol-1-yl]-N-[6-(hydroxymethyl)-1,3-benzodioxol-5-yl]benzamide A solution of Int-160 (30 mg, 0.07 mmol) in MeOH was treated with NaBH$_4$ (5 mg, 0.14 mmol) at 0° C. After 30 minutes of stirring, the reaction was quenched with NH$_4$C$_{1-}$std solution (3.0 mL) and AcOEt (3.0 mL). The aqueous phase was extracted with AcOEt (5.0 mL) and the combined organic phases were dried over Na$_2$SO$_4$ and concentrated. Purification by silica gel flash-column chromatography, eluting a gradient of 100% cyclohexane to 50% AcOEt in cyclohexanes, afforded the title compound as a white solid in 86% yield. $^1$H NMR (400 MHz, DMSO-d$_6$) δ 10.06 (s, 1H), 8.13-8.06 (m, 2H), 7.85 (dt, J=8.2, 1.4 Hz, 1H), 7.76 (app t, J=8.1 Hz, 1H), 7.14 (s, 1H), 7.00 (s, 1H), 6.03 (s, 2H), 5.34 (s, 1H), 4.47 (s, 2H), 2.37 (s, 3H). UPLC-MS: t$_R$=2.28 min (Generic method); MS (ESI) m/z calcd for C$_{20}$H$_{14}$ClF$_3$N$_3$O$_4$ (M−H)$^-$: 452.1, found: 452.5.

[168] 3-[4-Chloro-5-methyl-3-(trifluoromethyl)pyrazol-1-yl]-N-[6-(hydroxymethyl)-1,3-benzodioxol-5-yl]-N-methyl-benzamide Following the general procedure 14d, the title compound was prepared from 161. Purification by silica gel flash-column chromatography, eluting with a gradient of 100% Cyclohexanes to 50% AcOEt in Cyclohexane, gave a white solid in 92% yield. $^1$H NMR spectrum showed a mixture of rotamers, major rotamer (400 MHz, DMSO-d$_6$) δ 7.54-7.41 (m, 4H), 6.95 (s, 1H), 6.87 (t, J=1.2 Hz, 1H), 5.98 (d, J=7.1 Hz, 2H), 5.22 (t, J=5.5 Hz, 1H), 4.37 (dd, J=13.4, 5.2 Hz, 1H), 4.23 (dd, J=13.7, 5.5 Hz, 1H), 3.25 (s, 3H), 2.10 (s, 3H). UPLC-MS: t$_R$=2.18 min (Generic method); MS (ESI) m/z calcd for C$_{21}$H$_{18}$ClF$_3$N$_3$O$_4$ (M+H)$^+$: 468.1, found: 468.5.

[206] 3-[4-Chloro-5-methyl-3-(trifluoromethyl)pyrazol-1-yl]-N-[4-(hydroxymethyl)-1,3-benzodioxol-5-yl]benzamide Following the general procedure 14d, the title compound was prepared from Int-203. Purification by silica gel flash-column chromatography, eluting with a gradient of 100% cyclohexanes to 50% AcOEt in Cyclohexane, gave a white solid in 94% yield. $^1$H NMR (400 MHz, DMSO-d$_6$) δ 10.15 (s, 1H), 8.15-8.00 (m, 2H), 7.86 (dt, J=8.2, 1.5 Hz, 1H), 7.77 (app t, J=8.1 Hz, 1H), 7.24 (d, J=8.4 Hz, 1H), 6.88 (d, J=8.3 Hz, 1H), 6.05 (s, 2H), 5.44 (s, 1H), 4.55 (s, 2H), 2.37 (s, 3H). UPLC-MS: t$_R$=2.47 min (Generic method); MS (ESI) m/z calcd for C$_{20}$H$_{16}$ClF$_3$N$_3$O$_4$ (M+H)$^+$: 454.1, found: 454.4.

[209] 3-[4-Chloro-5-methyl-3-(trifluoromethyl)pyrazol-1-yl]-N-[4-(hydroxymethyl)-1,3-benzodioxol-5-yl]-N-methyl-benzamide Following the general procedure 14d, the title compound was prepared from 207. Purification by silica gel flash-column chromatography, eluting with a gradient of 100% Cyclohexane to 50% AcOEt in Cyclohexane, gave a white solid in 92% yield. $^1$H NMR spectrum showed a mixture of rotamers, major rotamer (400 MHz, DMSO-d$_6$) δ 7.55-7.48 (m, 2H), 7.48-7.40 (m, 2H), 6.71 (d, J=8.2 Hz, 1H), 6.62 (d, J=8.2 Hz, 1H), 6.03 (dd, J=6.5, 0.9 Hz, 2H), 5.28 (s, 1H), 4.43 (s, 2H), 3.30 (s, 3H), 2.07 (s, 3H). UPLC-MS: t$_R$=2.24 min (Generic method); MS (ESI) m/z calcd for C$_{21}$H$_{18}$ClF$_3$N$_3$O$_4$ (M+H)$^+$: 468.1, found: 468.5.

General Procedure 14e

[Int-178] 6-[[3-[4-Chloro-5-methyl-3-(trifluoromethyl)pyrazol-1-yl]benzoyl]amino]-1,3-benzodioxole-5-carboxylic acid To a solution of Int-160 (36 mg, 0.08 mmol) in t-BuOH (0.5 mL) and water (0.10 mL), NaH$_2$PO$_4$ (85 mg, 0.64 mmol), NaClO$_2$ (29 mg, 0.32 mmol) and 2-methyl-2-butene (56 mg, 0.80 mmol) were added and the resulting mixture was allowed to stir 24 h at room temperature. The reaction was quenched by adding a solution of HCl until pH=4 and the aqueous phase was extracted with AcOEt (3×10 mL). The combined organic layers were dried over Na$_2$SO$_4$ and concentrated. Purification by silica gel flash-column chromatography (DCM/MeOH=95:5) gave a white solid in 54% yield. $^1$H NMR (400 MHz, DMSO-d$_6$) δ 12.50 (s, 1H), 8.28 (s, 1H), 8.11-8.04 (m, 2H), 7.88 (dt, J=8.0, 1.4 Hz, 1H), 7.83-7.77 (m, 1H), 7.46 (s, 1H), 6.14 (s, 2H), 3.35 (bs, 1H), 2.39 (s, 3H). UPLC-MS: t$_R$=1.92 min (Generic method); MS (ESI) m/z calcd for C$_{20}$H$_{14}$ClF$_3$N$_3$O$_5$ (M+H)$^+$: 468.1, found: 468.4.

[179] 6-[[3-[4-Chloro-5-methyl-3-(trifluoromethyl)pyrazol-1-yl]benzoyl]-methyl-amino]-1,3-benzodioxole-5-carboxylic acid Following the general procedure 14e, the title compound was prepared from 161, after purification by silica gel flash-column chromatography (DCM/MeOH=95:5), as a white solid in 37% yield. $^1$H NMR spectrum showed a mixture of rotamers, major rotamer (400 MHz, DMSO-d$_6$) δ 12.97 (bs, $^1$H), 7.48 (dt, J=8.0, 1.7 Hz, 1H), 7.46-7.40 (m, 2H), 7.36 (dt, J=7.5, 1.5 Hz, 1H), 7.20 (s, 1H), 7.14 (s, 1H), 6.11 (d, J=3.2 Hz, 2H), 3.26 (s, 3H), 2.12 (s, 3H). UPLC-MS: t$_R$=1.81 min (Generic method); MS (ESI) m/z calcd for C$_{21}$H$_{16}$ClF$_3$N$_3$O$_5$ (M+H)$^+$: 482.1, found: 482.5.

[208] 5-[[3-[4-Chloro-5-methyl-3-(trifluoromethyl)pyrazol-1-yl]benzoyl]-methyl-amino]-1,3-benzodioxole-4-carboxylic acid Following the general procedure 14e, the title compound was prepared from 207, after purification by silica gel flash-column chromatography (DCM/MeOH=95:5), as a white solid in 55% yield. $^1$H NMR spectrum showed a mixture of rotamers, major rotamer (400 MHz, DMSO-d$_6$) δ 7.52-7.43 (m, 4H), 6.92 (d, J=8.3 Hz, 1H), 6.82 (d, J=8.2 Hz, 1H), 6.07 (s, 2H), 3.24 (s, 3H), 2.12 (s, 3H). UPLC-MS: t$_R$=1.77 min (Generic method); MS (ESI) m/z calcd for C$_{21}$H$_{16}$ClF$_3$N$_3$O$_5$ (M+H)$^+$: 482.1, found: 482.5.

[205] 5-[[3-[4-Chloro-5-methyl-3-(trifluoromethyl)pyrazol-1-yl]benzoyl]amino]-1,3-benzodioxole-4-carboxylic acid Following the general procedure 14e, the title compound was prepared from 207, after purification by silica gel flash-column chromatography (DCM/MeOH=95:5), as a white solid in 44% yield. $^1$H NMR (400 MHz, DMSO-d$_6$) δ 11.65 (s, 1H), 8.13-8.04 (m, 2H), 7.90-7.86 (m, 1H), 7.84 (dd, J=8.6, 1.8 Hz, 1H), 7.80 (app-t, J=8.1 Hz, 1H), 7.16 (d, J=8.6 Hz, 1H), 6.14 (s, 2H), 2.39 (s, 3H). UPLC-MS: t$_R$=1.94 min (Generic method); MS (ESI) m/z calcd for C$_{20}$H$_{14}$ClF$_3$N$_3$O$_5$ (M+H)$^+$: 468.1, found: 468.4.

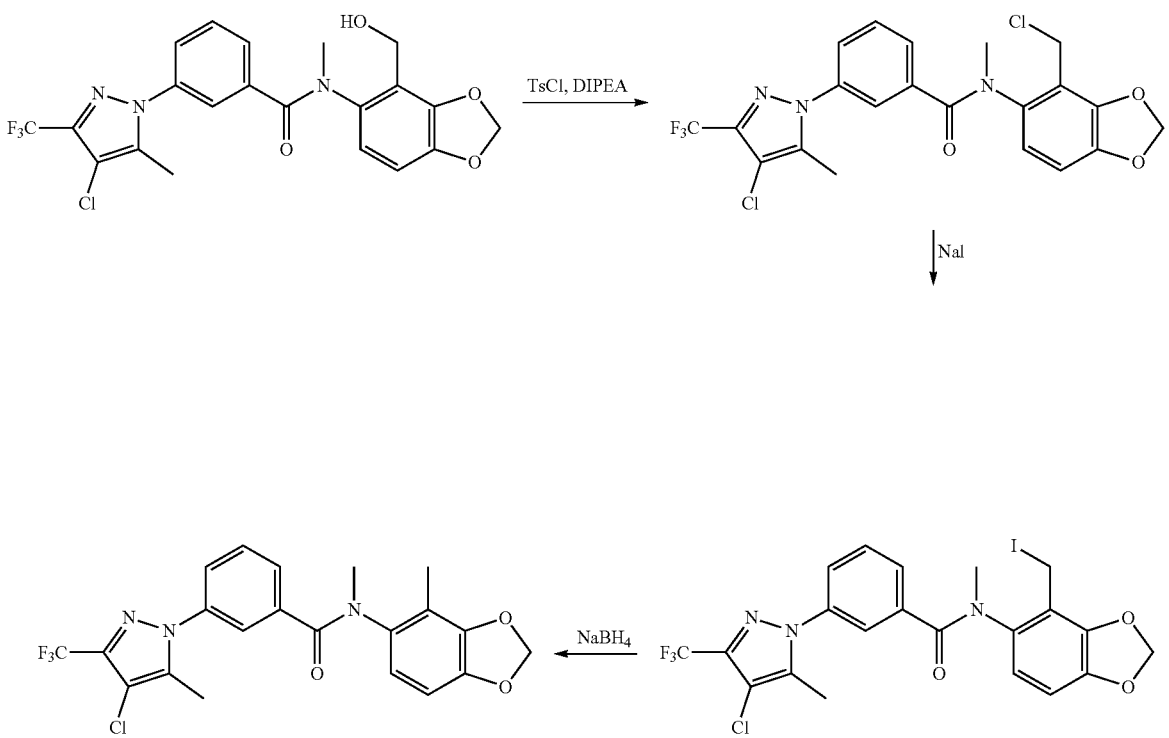

General Procedure 14f

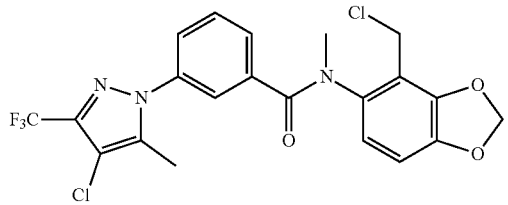 [SMILES: Cc1c(Cl)c(C(F)(F)F)nn1-c1cccc(C(=O)N(C)c2ccc3c(c2CCl)OCO3)c1]

[Int-14.3] N-[4-(Chloromethyl)-1,3-benzodioxol-5-yl]-3-[4-chloro-5-methyl-3-(trifluoromethyl)pyrazol-1-yl]-N-methyl-benzamide

[209] (200 mg, 0.43 mmol) was dissolved in DCM (2.9 mL). the mixture was cooled at 0° C. and DIPEA (134 mg, 1.04 mmol) and 4-toluenesulfonyl chloride (198 mg, 1.04 mmol) were added. The ice-bath was removed and the reaction was allowed to stir for 48 h at room temperature. An aqueous saturated solution of $NH_4Cl$ was added and the resulting aqueous layer was extracted with DCM (2×), The combined organic phase were dried over $Na_2SO_4$, filtered and concentrated. The title compound was obtained after purification by silica gel flash-column chromatography with CyHex/AcOEt (50:50) as the eluent, as a white solid in 39% yield: $^1$H NMR (400 MHz, DMSO-$d_6$) δ 7.53-7.42 (m, 4H), 6.82 (d, J=8.2 Hz, 1H), 6.76 (d, J=8.2 Hz, 1H), 6.11 (dd, J=20.6, 0.9 Hz, 2H), 4.78-4.61 (m, 2H), 3.32 (s, 3H), 2.11 (s, 3H). UPLC-MS: $t_R$=1.54 min (Apolar method); MS (ESI) m/z calcd for $C_{21}H_{17}Cl_2F_3N_3O_3$ (M+H)$^+$: 486.0, found: 486.4.

General Procedure 14g

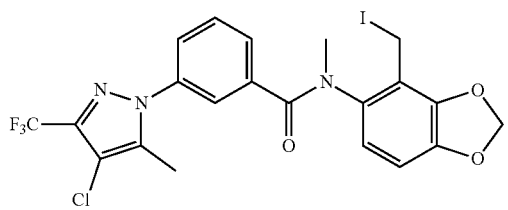 [SMILES: Cc1c(Cl)c(C(F)(F)F)nn1-c1cccc(C(=O)N(C)c2ccc3c(c2CI)OCO3)c1]

[Int-14.4] 3-[4-Chloro-5-methyl-3-(trifluoromethyl)pyrazol-1-yl]-N-[4-(iodomethyl)-1,3-benzodioxol-5-yl]-N-methyl-benzamide Int-14.3 (75 mg, 0.15 mmol) was dissolved in acetone (0.50 mL). Sodium iodide (45 mg, 0.30 mmol) was added and the resulting suspension was stirred 30 minutes at room temperature, filtered and concentrated. The crude was used in the next step without purification. UPLC-MS: $t_R$=2.64 min (Generic method); MS (ESI) m/z calcd for $C_{21}H_{17}ClF_3IN_3O_3$ (M+H)$^+$: 578.0, found: 578.2.

General Procedure 14 h: 3-[4-Chloro-5-methyl-3-(trifluoromethyl)pyrazol-1-yl]-N-methyl-N-(4-methyl-1,3-benzodioxol-5-yl)benzamide Int-14.4 (86 mg, 0.15 mmol) was dissolved in methanol (1.0 mL) and sodium borohydride (9 mg, 0.23 mmol) was added to the solution portionwise at 0° C. The ice-bath was removed and the reaction was allowed to react 24 h at room temperature. Removal of the solvent gave a crude which was subjected to flash chromatography with CyHex/AcOEt=70:30 as eluent, to afford the title compound as white solid (19%): $^1$H NMR (400 MHz, DMSO-$d_6$) δ 7.52-7.40 (m, 4H), 6.75 (d, J=8.2 Hz, 1H), 6.66 (d, J=7.7 Hz, 1H), 5.99 (dd, J=7.5, 1.0 Hz, 2H), 3.24 (s, 3H), 2.11 (s, 3H), 2.05 (s, 3H). UPLC-MS: $t_R$=2.62 min (Generic method); MS (ESI) m/z calcd for $C_{21}H_{18}ClF_3N_3O_3$ (M+H)$^+$: 452.1, found: 452.2.

Methods

Fluorescence Assay for CFTR Activity

Mutant CFTR activity was determined with the functional assay based on the halide-sensitive yellow fluorescent protein, HS-YFP (Galietta et al., FEBS Lett 499:220-224, 2001). CFBE4lo- and FRT cells with stable expression of mutant CFTR and HS-YFP were plated on clear-bottom 96-well black microplates (Code 3603, Corning Life Sciences) at a density of 50,000 cells/well and kept at 37° C. in 5% $CO_2$ for 24 hours. For the corrector assay, cells were treated for further 24 hours with test compounds, vehicle (DMSO), or the positive control VX-809. After treatment, the culture medium was removed and cells in each well were stimulated for 30 min at 37° C. with 60 μL PBS (containing 137 mM NaCl, 2.7 mM KCl, 8.1 mM $Na_2HPO_4$, 1.5 mM $KH_2PO_4$, 1 mM $CaCl_2$, and 0.5 mM $MgCl_2$) plus forskolin (20 μM) and genistein (50 μM).

For determination of potentiator activity on F508del-CFTR, cells were incubated for 24 hours at 27° C. to allow trafficking of the mutant protein to plasma membrane. Cells were then stimulated with for 30 min with PBS containing forskolin (20 μM) plus the compound to be tested at the desired concentration.

For determination of potentiator activity on G551D-CFTR or G1349D-CFTR, cells were directly stimulated with forskolin plus test compound without previous incubation at low temperature. At the time of assay, microplates carrying CFBE4lo- or FRT cells were transferred to microplate readers (BMG Labtech) equipped with high-quality excitation (HQ500/20X: 500±10 nm) and emission (HQ535/30M: 535±15 nm) filters for YFP (Chroma Technology). The assay consisted of a continuous 14 s fluorescence reading with 2 s before and 12 s after injection of an iodide-containing solution (165 μL of a modified PBS containing I$^-$ instead of Cl$^-$; final I$^-$ concentration in the well: 100 mM). Data were normalized to the initial background-subtracted fluorescence. Enhanced CFTR activity, induced by correctors and/or potentiators, results in accelerated I$^-$ influx that in turn causes faster HS-YFP quenching (Pedemonte et al., Mol Pharmacol 68:1736-1746, 2005; Pedemonte et al., J Clin Invest 115:2564-2571, 2015). To determine fluorescence quenching rate associated with I$^-$ influx, the final 10 s of data for each well were fitted with an exponential function to extrapolate initial slope (dF/dt).

$EC_{50}$ obtained are illustrated in table 1 wherein +: $EC_{50}$>2 μM; ++: 1.0 μM<$EC_{50}$<2 μM; +++: $EC_{50}$<1 μM.

TABLE 1

| # | Compound structure | Substance Name | Substance Formula | EC$_{50}$ |
|---|---|---|---|---|
| Int-002 | 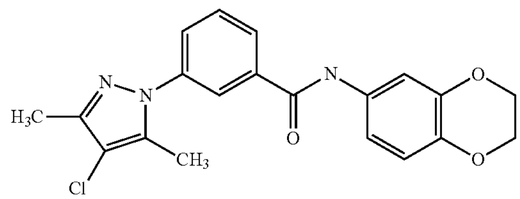 [SMILES: Cc1nn(-c2cccc(C(=O)Nc3ccc4c(c3)OCCO4)c2)c(C)c1Cl] | 3-(4-chloro-3,5-dimethyl-pyrazol-1-yl)-N-(2,3-dihydro-1,4-benzodioxin-6-yl)benzamide | C20H18ClN3O3 | + |
| 003 | 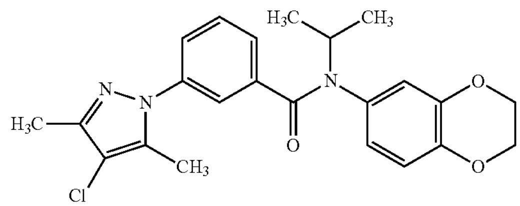 [SMILES: Cc1nn(-c2cccc(C(=O)N(c3ccc4c(c3)OCCO4)C(C)C)c2)c(C)c1Cl] | 3-(4-chloro-3,5-dimethyl-pyrazol-1-yl)-N-(2,3-dihydro-1,4-benzodioxin-6-yl)-N-isopropyl-benzamide | C23H24ClN3O3 | + |
| 004 | 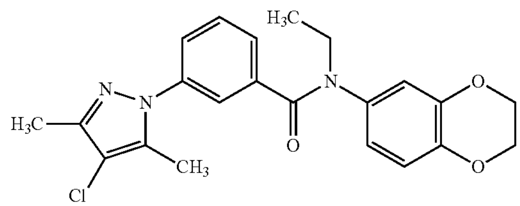 [SMILES: CCN(C(=O)c1cccc(-n2nc(C)c(Cl)c2C)c1)c1ccc2c(c1)OCCO2] | 3-(4-chloro-3,5-dimethyl-pyrazol-1-yl)-N-(2,3-dihydro-1,4-benzodioxin-6-yl)-N-ethyl-benzamide | C22H22ClN3O3 | +++ |
| Int-005 | 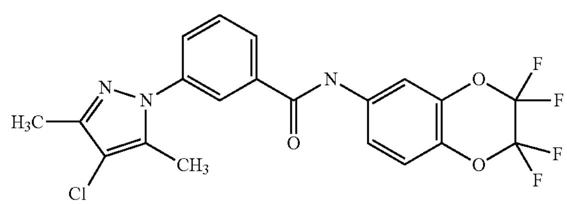 [SMILES: Cc1nn(-c2cccc(C(=O)Nc3ccc4c(c3)OC(F)(F)C(F)(F)O4)c2)c(C)c1Cl] | 3-(4-chloro-3,5-dimethyl-pyrazol-1-yl)-N-(2,2,3,3-tetrafluoro-1,4-benzodioxin-6-yl)benzamide | C20H14ClF4N3O3 | + |
| Int-006 | 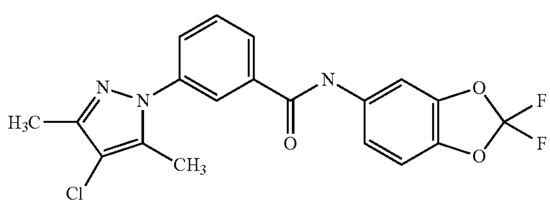 [SMILES: Cc1nn(-c2cccc(C(=O)Nc3ccc4c(c3)OC(F)(F)O4)c2)c(C)c1Cl] | 3-(4-chloro-3,5-dimethyl-pyrazol-1-yl)-N-(2,2-difluoro-1,3-benzodioxol-5-yl)benzamide | C19H14ClF2N3O3 | + |
| 007 | 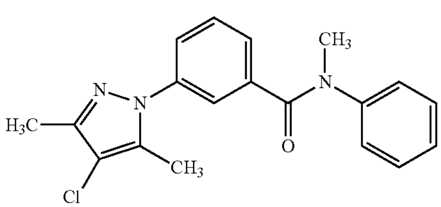 [SMILES: Cc1nn(-c2cccc(C(=O)N(C)c3ccccc3)c2)c(C)c1Cl] | 3-(4-chloro-3,5-dimethyl-pyrazol-1-yl)-N-methyl-N-phenyl-benzamide | C19H18ClN3O | + |
| 008 | 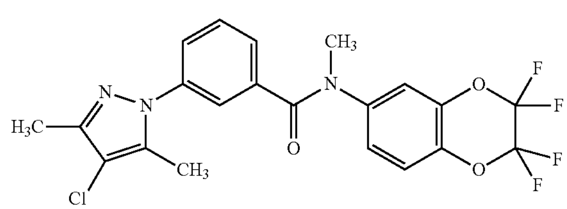 [SMILES: Cc1nn(-c2cccc(C(=O)N(C)c3ccc4c(c3)OC(F)(F)C(F)(F)O4)c2)c(C)c1Cl] | 3-(4-chloro-3,5-dimethyl-pyrazol-1-yl)-N-methyl-N-(2,2,3,3-tetrafluoro-1,4-benzodioxin-6-yl)benzamide | C21H16ClF4N3O3 | + |

TABLE 1-continued

| # | Compound structure | Substance Name | Substance Formula | EC$_{50}$ |
|---|---|---|---|---|
| 009 | 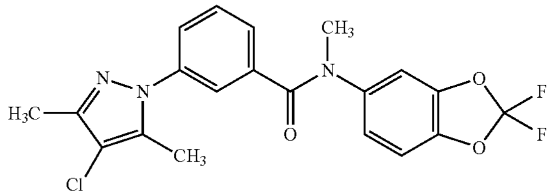 [SMILES: Cc1nn(-c2cccc(C(=O)N(C)c3ccc4c(c3)OC(F)(F)O4)c2)c(C)c1Cl] | 3-(4-chloro-3,5-dimethyl-pyrazol-1-yl)-N-(2,2-difluoro-1,3-benzodioxol-5-yl)-N-methyl-benzamide | C20H16ClF2N3O3 | ++ |
| 010 | 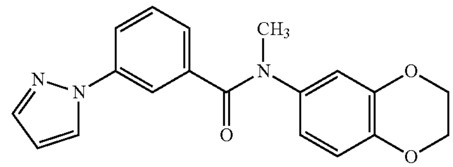 [SMILES: CN(C(=O)c1cccc(-n2cccn2)c1)c1ccc2c(c1)OCCO2] | N-(2,3-dihydro-1,4-benzodioxin-6-yl)-N-methyl-3-pyrazol-1-yl-benzamide | C19H17N3O3 | + |
| 011 | 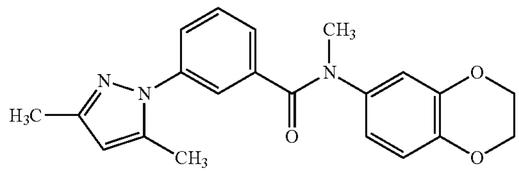 [SMILES: Cc1cc(C)n(-c2cccc(C(=O)N(C)c3ccc4c(c3)OCCO4)c2)n1] | N-(2,3-dihydro-1,4-benzodioxin-6-yl)-3-(3,5-dimethylpyrazol-1-yl)-N-methyl-benzamide | C21H21N3O3 | + |
| Int-012 | 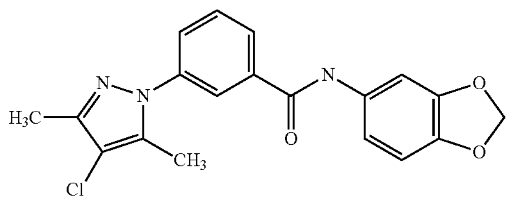 [SMILES: Cc1nn(-c2cccc(C(=O)Nc3ccc4c(c3)OCO4)c2)c(C)c1Cl] | N-(1,3-benzodioxol-5-yl)-3-(4-chloro-3,5-dimethyl-pyrazol-1-yl)benzamide | C19H16ClN3O3 | + |
| Int-013 | 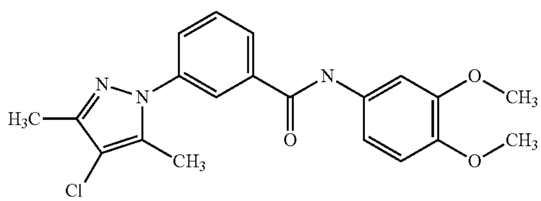 | 3-(4-chloro-3,5-dimethyl-pyrazol-1-yl)-N-(3,4-dimethoxyphenyl)benzamide | C20H20ClN3O3 | + |
| 014 | 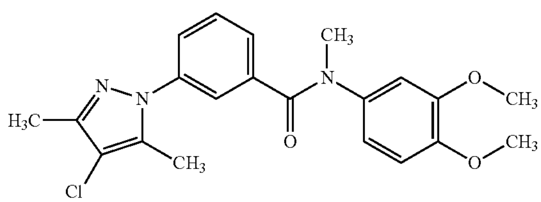 | 3-(4-chloro-3,5-dimethyl-pyrazol-1-yl)-N-(3,4-dimethoxyphenyl)-N-methyl-benzamide | C21H22ClN3O3 | + |
| 015 | 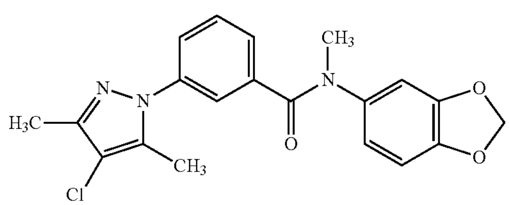 [SMILES: Cc1nn(-c2cccc(C(=O)N(C)c3ccc4c(c3)OCO4)c2)c(C)c1Cl] | N-(1,3-benzodioxol-5-yl)-3-(4-chloro-3,5-dimethyl-pyrazol-1-yl)-N-methyl-benzamide | C20H18ClN3O3 | +++ |
| Int-016 | 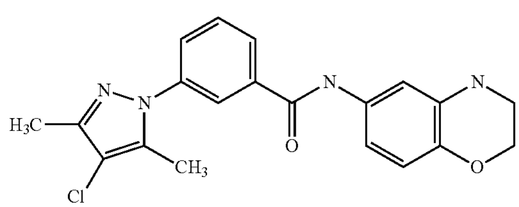 [SMILES: Cc1nn(-c2cccc(C(=O)Nc3ccc4c(c3)NCCO4)c2)c(C)c1Cl] | 3-(4-chloro-3,5-dimethyl-pyrazol-1-yl)-N-(3,4-dihydro-2H-1,4-benzoxazin-6-yl)benzamide | C20H19ClN4O2 | + |

TABLE 1-continued

| # | Compound structure | Substance Name | Substance Formula | EC$_{50}$ |
|---|---|---|---|---|
| 017 | 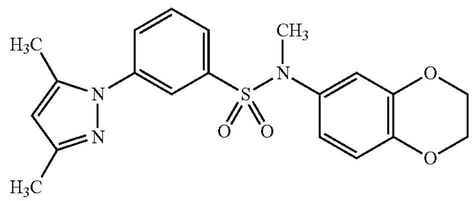 [SMILES: Cc1cc(C)n(-c2cccc(S(=O)(=O)N(C)c3ccc4c(c3)OCCO4)c2)n1] | N-(2,3-dihydro-1,4-benzodioxin-6-yl)-3-(3,5-dimethylpyrazol-1-yl)-N-methyl-benzenesulfonamide | C20H21N3O4S | + |
| Int-018 | 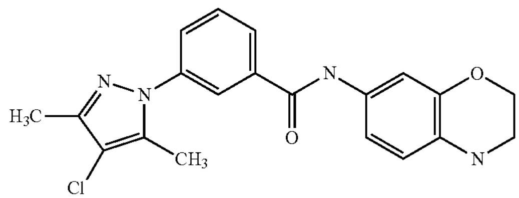 [SMILES: Cc1nn(-c2cccc(C(=O)Nc3ccc4c(c3)OCCN4)c2)c(C)c1Cl] | 3-(4-chloro-3,5-dimethyl-pyrazol-1-yl)-N-(3,4-dihydro-2H-1,4-benzoxazin-7-yl)benzamide | C20H19ClN4O2 | + |
| 019 | 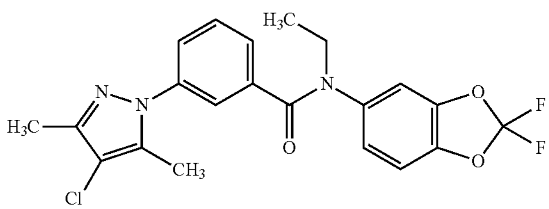 [SMILES: CCN(C(=O)c1cccc(-n2nc(C)c(Cl)c2C)c1)c1ccc2c(c1)OC(F)(F)O2] | 3-(4-chloro-3,5-dimethyl-pyrazol-1-yl)-N-(2,2-difluoro-1,3-benzodioxol-5-yl)-N-ethyl-benzamide | C21H18ClF2N3O3 | ++ |
| 020 | 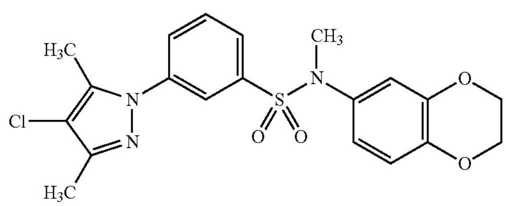 [SMILES: Cc1nn(-c2cccc(S(=O)(=O)N(C)c3ccc4c(c3)OCCO4)c2)c(C)c1Cl] | 3-(4-chloro-3,5-dimethyl-pyrazol-1-yl)-N-(2,3-dihydro-1,4-benzodioxin-6-yl)-N-methyl-benzenesulfonamide | C20H20ClN3O4S | ++ |
| 021 | 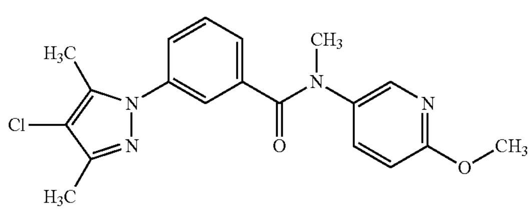 [SMILES: COc1ccc(N(C)C(=O)c2cccc(-n3nc(C)c(Cl)c3C)c2)cn1] | 3-(4-chloro-3,5-dimethyl-pyrazol-1-yl)-N-(6-methoxy-3-pyridyl)-N-methyl-benzamide | C19H19ClN4O2 | + |
| Int-022 | 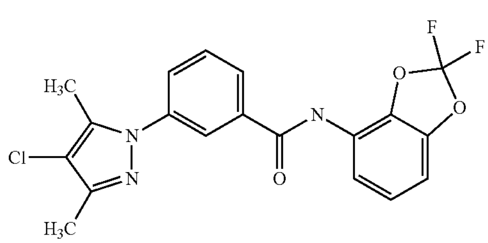 [SMILES: Cc1nn(-c2cccc(C(=O)Nc3cccc4c3OC(F)(F)O4)c2)c(C)c1Cl] | 3-(4-chloro-3,5-dimethyl-pyrazol-1-yl)-N-(2,2-difluoro-1,3-benzodioxol-4-yl)benzamide | C19H14ClF2N3O3 | ++ |
| 023 | 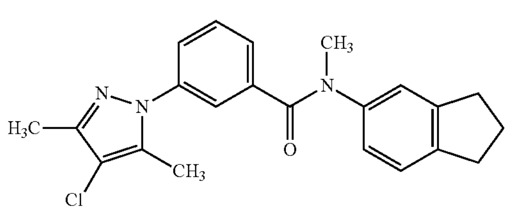 [SMILES: Cc1nn(-c2cccc(C(=O)N(C)c3ccc4c(c3)CCC4)c2)c(C)c1Cl] | 3-(4-chloro-3,5-dimethyl-pyrazol-1-yl)-N-indan-5-yl-N-methyl-benzamide | C22H22ClN3O | +++ |

TABLE 1-continued

| # | Compound structure | Substance Name | Substance Formula | $EC_{50}$ |
|---|---|---|---|---|
| 024 | 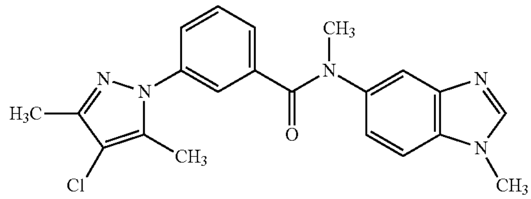 [SMILES: Cc1nn(-c2cccc(C(=O)N(C)c3ccc4c(c3)ncn4C)c2)c(C)c1Cl] | 3-(4-chloro-3,5-dimethyl-pyrazol-1-yl)-N-methyl-N-(1-methylbenzimidazol-5-yl)benzamide | C21H20ClN5O | + |
| 025 | 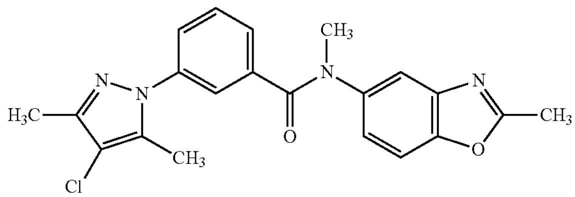 | 3-(4-chloro-3,5-dimethyl-pyrazol-1-yl)-N-methyl-N-(2-methyl-1,3-benzoxazol-5-yl)benzamide | C21H19ClN4O2 | + |
| 026 | 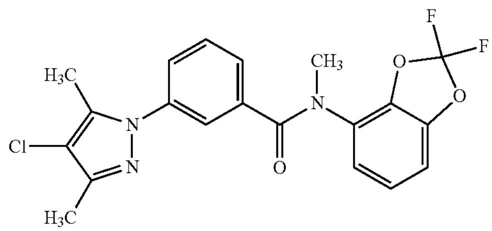 [SMILES: Cc1nn(-c2cccc(C(=O)N(C)c3cccc4c3OC(F)(F)O4)c2)c(C)c1Cl] | 3-(4-chloro-3,5-dimethyl-pyrazol-1-yl)-N-(2,2-difluoro-1,3-benzodioxol-4-yl)-N-methyl-benzamide | C20H16ClF2N3O3 | + |
| 029 | 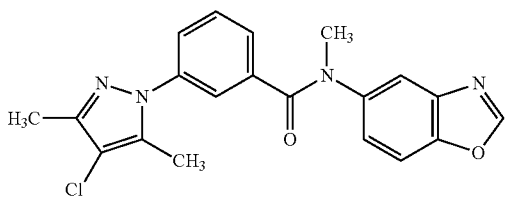 [SMILES: Cc1nn(-c2cccc(C(=O)N(C)c3ccc4ocnc4c3)c2)c(C)c1Cl] | N-(1,3-benzoxazol-5-yl)-3-(4-chloro-3,5-dimethyl-pyrazol-1-yl)-N-methyl-benzamide | C20H17ClN4O2 | + |
| 030 | 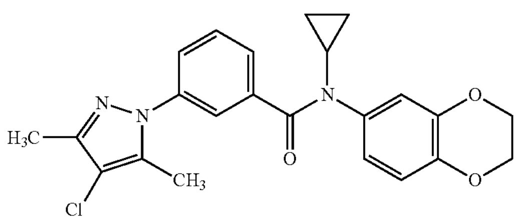 [SMILES: Cc1nn(-c2cccc(C(=O)N(c3ccc4c(c3)OCCO4)C3CC3)c2)c(C)c1Cl] | 3-(4-chloro-3,5-dimethyl-pyrazol-1-yl)-N-cyclopropyl-N-(2,3-dihydro-1,4-benzodioxin-6-yl)benzamide | C23H22ClN3O3 | + |
| 031 | 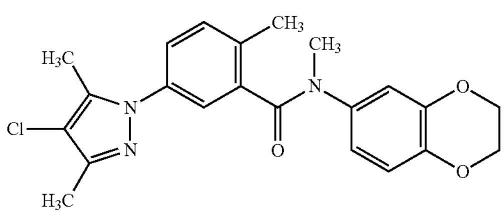 [SMILES: Cc1ccc(-n2nc(C)c(Cl)c2C)cc1C(=O)N(C)c1ccc2c(c1)OCCO2] | 5-(4-chloro-3,5-dimethyl-pyrazol-1-yl)-N-(2,3-dihydro-1,4-benzodioxin-6-yl)-N,2-dimethyl-benzamide | C22H22ClN3O3 | + |
| 032 | 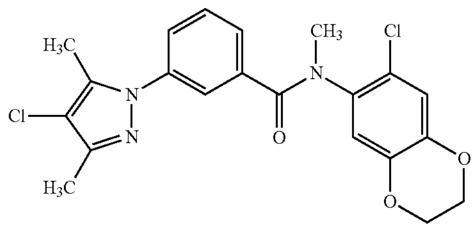 [SMILES: Cc1nn(-c2cccc(C(=O)N(C)c3cc4c(cc3Cl)OCCO4)c2)c(C)c1Cl] | N-(6-chloro-2,3-dihydro-1,4-benzodioxin-7-yl)-3-(4-chloro-3,5-dimethyl-pyrazol-1-yl)-N-methyl-benzamide | C21H19Cl2N3O3 | +++ |

TABLE 1-continued

| # | Compound structure | Substance Name | Substance Formula | EC$_{50}$ |
|---|---|---|---|---|
| 033 | 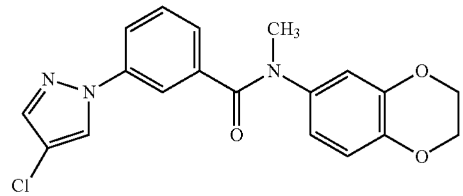 [SMILES: CN(C(=O)c1cccc(-n2cc(Cl)cn2)c1)c1ccc2c(c1)OCCO2] | 3-(4-chloropyrazol-1-yl)-N-(2,3-dihydro-1,4-benzodioxin-6-yl)-N-methyl-benzamide | C19H16ClN3O3 | + |
| 034 | 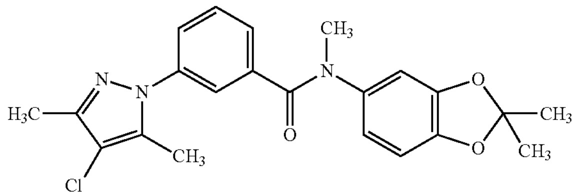 | 3-(4-chloro-3,5-dimethyl-pyrazol-1-yl)-N-(2,2-dimethyl-1,3-benzodioxol-5-yl)-N-methyl-benzamide | C22H22ClN3O3 | + |
| 035 | 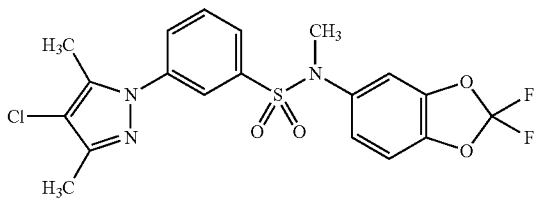 [SMILES: Cc1nn(-c2cccc(S(=O)(=O)N(C)c3ccc4c(c3)OC(F)(F)O4)c2)c(C)c1Cl] | 3-(4-chloro-3,5-dimethyl-pyrazol-1-yl)-N-(2,2-difluoro-1,3-benzodioxol-5-yl)-N-methyl-benzenesulfonamide | C19H16ClF2N3O4S | + |
| 036 | 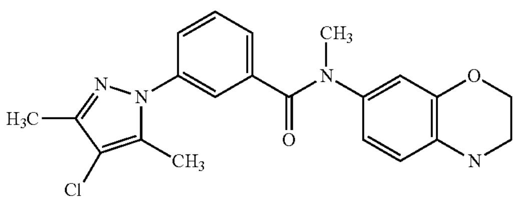 [SMILES: Cc1nn(-c2cccc(C(=O)N(C)c3ccc4c(c3)OCCN4)c2)c(C)c1Cl] | 3-(4-chloro-3,5-dimethyl-pyrazol-1-yl)-N-(3,4-dihydro-2H-1,4-benzoxazin-7-yl)-N-methyl-benzamide; 2,2,2-trifluoroacetic acid | C21H21ClN4O2•C2HF3O2 | + |
| 037 | 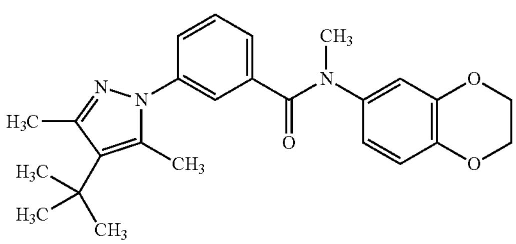 [SMILES: Cc1nn(-c2cccc(C(=O)N(C)c3ccc4c(c3)OCCO4)c2)c(C)c1C(C)(C)C] | 3-(4-tert-butyl-3,5-dimethyl-pyrazol-1-yl)-N-(2,3-dihydro-1,4-benzodioxin-6-yl)-N-methyl-benzamide | C25H29N3O3 | ++ |
| 038 | 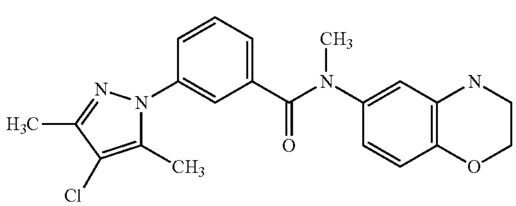 [SMILES: Cc1nn(-c2cccc(C(=O)N(C)c3ccc4c(c3)NCCO4)c2)c(C)c1Cl] | 3-(4-chloro-3,5-dimethyl-pyrazol-1-yl)-N-(3,4-dihydro-2H-1,4-benzoxazin-6-yl)-N-methyl-benzamide; 2,2,2-trifluoroacetic acid | C2HF3O2•C21H21ClN4O2 | + |
| 039 | 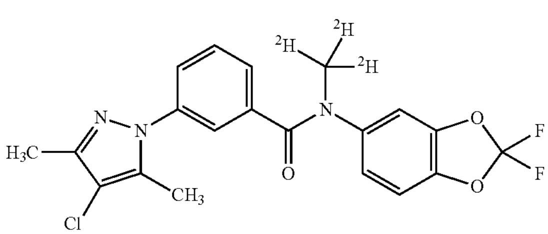 [SMILES: [2H]C([2H])([2H])N(C(=O)c1cccc(-n2nc(C)c(Cl)c2C)c1)c1ccc2c(c1)OC(F)(F)O2] | 3-(4-chloro-3,5-dimethyl-pyrazol-1-yl)-N-(2,2-difluoro-1,3-benzodioxol-5-yl)-N-(trideuteriomethyl)benzamide | C20H13ClD3F2N3O3 | ++ |

TABLE 1-continued

| # | Compound structure | Substance Name | Substance Formula | EC$_{50}$ |
|---|---|---|---|---|
| Int-040 | 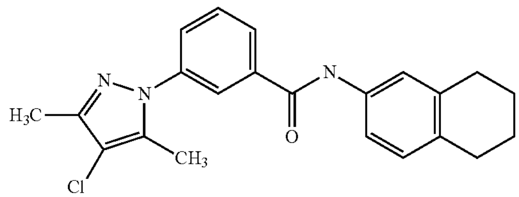 [SMILES: Cc1nn(-c2cccc(C(=O)Nc3ccc4c(c3)CCCC4)c2)c(C)c1Cl] | 3-(4-chloro-3,5-dimethyl-pyrazol-1-yl)-N-tetralin-6-yl-benzamide | C22H22ClN3O | + |
| Int-041 | 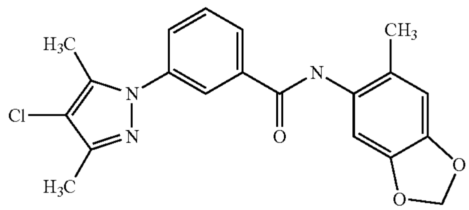 [SMILES: Cc1cc2c(cc1NC(=O)c1cccc(-n3nc(C)c(Cl)c3C)c1)OCO2] | 3-(4-chloro-3,5-dimethyl-pyrazol-1-yl)-N-(6-methyl-1,3-benzodioxol-5-yl)benzamide | C20H18ClN3O3 | + |
| 042 | 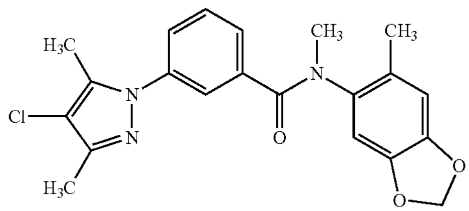 [SMILES: Cc1cc2c(cc1N(C)C(=O)c1cccc(-n3nc(C)c(Cl)c3C)c1)OCO2] | 3-(4-chloro-3,5-dimethyl-pyrazol-1-yl)-N-methyl-N-(6-methyl-1,3-benzodioxol-5-yl)benzamide | C21H20ClN3O3 | ++ |
| 043 | 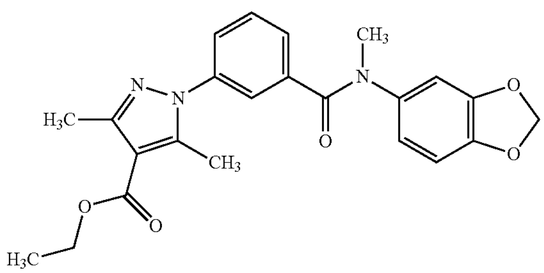 [SMILES: CCOC(=O)c1c(C)nn(-c2cccc(C(=O)N(C)c3ccc4c(c3)OCO4)c2)c1C] | ethyl 1-[3-[1,3-benzodioxol-5-yl(methyl)carbamoyl]phenyl]-3,5-dimethyl-pyrazole-4-carboxylate | C23H23N3O5 | + |
| 044 | 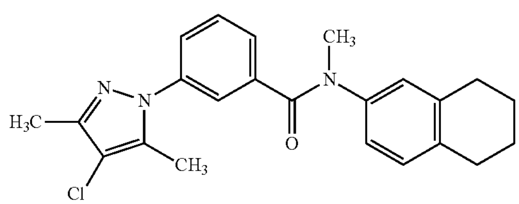 [SMILES: Cc1nn(-c2cccc(C(=O)N(C)c3ccc4c(c3)CCCC4)c2)c(C)c1Cl] | 3-(4-chloro-3,5-dimethyl-pyrazol-1-yl)-N-methyl-N-tetralin-6-yl-benzamide | C23H24ClN3O | + |
| Int-045 | 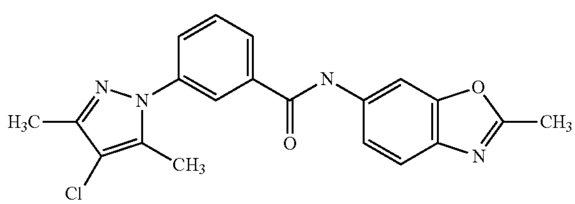 | 3-(4-chloro-3,5-dimethyl-pyrazol-1-yl)-N-(2-methyl-1,3-benzoxazol-6-yl)benzamide | C20H17ClN4O2 | + |
| 047 | 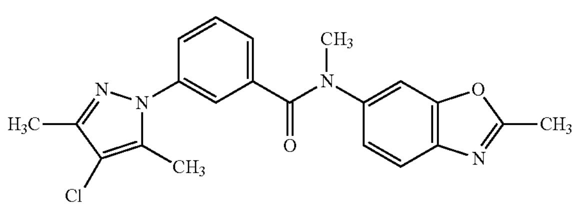 | 3-(4-chloro-3,5-dimethyl-pyrazol-1-yl)-N-methyl-N-(2-methyl-1,3-benzoxazol-6-yl)benzamide | C21H19ClN4O2 | +++ |

TABLE 1-continued

| # | Substance Name | Substance Formula | EC$_{50}$ |
|---|---|---|---|
| 048 | 1-[3-[1,3-benzodioxol-5-yl(methyl)carbamoyl]phenyl]-3,5-dimethyl-pyrazole-4-carboxylic acid | C21H19N3O5 | + |
| 049 | N-(6-chloro-2,2-difluoro-1,3-benzodioxol-5-yl)-3-(4-chloro-3,5-dimethyl-pyrazol-1-yl)-N-methyl-benzamide | C20H15Cl2F2N3O3 | +++ |
| 050 | N-(1,3-benzodioxol-5-yl)-6-(4-chloro-3,5-dimethyl-pyrazol-1-yl)-N-methyl-pyridine-2-carboxamide | C19H17ClN4O3 | + |
| Int-051 | 3-(4-chloro-3,5-dimethyl-pyrazol-1-yl)-N-(1,3-dihydroisobenzofuran-5-yl)benzamide | C20H18ClN3O2 | + |
| Int-052 | 3-(4-chloro-3,5-dimethyl-pyrazol-1-yl)-N-(2,3-dihydrobenzofuran-5-yl)benzamide | C20H18ClN3O2 | + |
| Int-053 | 3-(4-chloro-3,5-dimethyl-pyrazol-1-yl)-N-(2-cyclopropyl-1,3-benzoxazol-5-yl)benzamide | C22H19ClN4O2 | + |
| 054 | 3-(4-chloro-3,5-dimethyl-pyrazol-1-yl)-N-[2-(trifluoromethyl)-1,3-benzoxazol-5-yl]benzamide | C20H14ClF3N4O2 | ++ |

TABLE 1-continued

| # | Compound structure | Substance Name | Substance Formula | EC$_{50}$ |
|---|---|---|---|---|
| 055 | 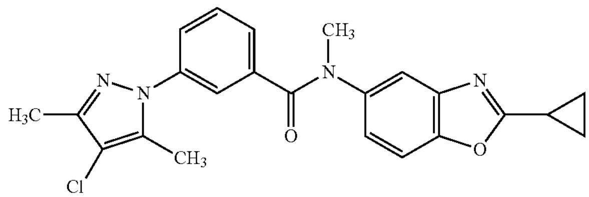 [SMILES: Cc1nn(-c2cccc(C(=O)N(C)c3ccc4oc(C5CC5)nc4c3)c2)c(C)c1Cl] | 3-(4-chloro-3,5-dimethyl-pyrazol-1-yl)-N-(2-cyclopropyl-1,3-benzoxazol-5-yl)-N-methyl-benzamide | C23H21ClN4O2 | ++ |
| 056 | 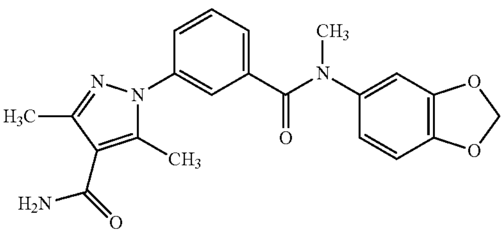 [SMILES: Cc1nn(-c2cccc(C(=O)N(C)c3ccc4c(c3)OCO4)c2)c(C)c1C(N)=O] | 1-[3-[1,3-benzodioxol-5-yl(methyl)carbamoyl]phenyl]-3,5-dimethyl-pyrazole-4-carboxamide | C21H20N4O4 | + |
| 057 | 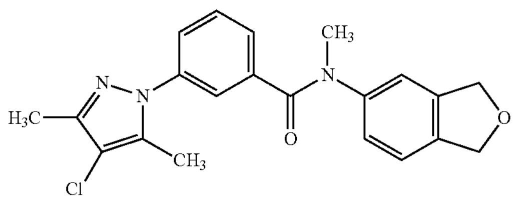 [SMILES: Cc1nn(-c2cccc(C(=O)N(C)c3ccc4c(c3)COC4)c2)c(C)c1Cl] | 3-(4-chloro-3,5-dimethyl-pyrazol-1-yl)-N-(1,3-dihydroisobenzofuran-5-yl)-N-methyl-benzamide | C21H20ClN3O2 | ++ |
| 058 | 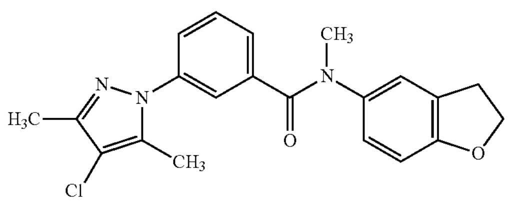 | 3-(4-chloro-3,5-dimethyl-pyrazol-1-yl)-N-(2,3-dihydrobenzofuran-5-yl)-N-methyl-benzamide | C21H20ClN3O2 | +++ |
| 059 | 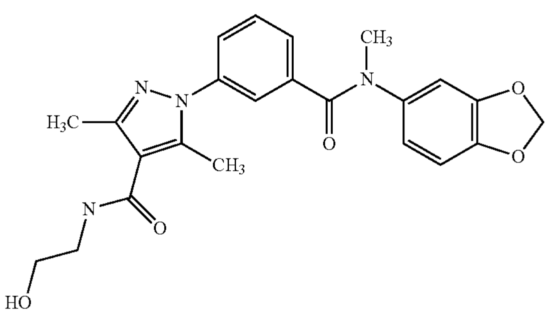 [SMILES: Cc1nn(-c2cccc(C(=O)N(C)c3ccc4c(c3)OCO4)c2)c(C)c1C(=O)NCCO] | 1-[3-[1,3-benzodioxol-5-yl(methyl)carbamoyl]phenyl]-N-(2-hydroxyethyl)-3,5-dimethyl-pyrazole-4-carboxamide | C23H24N4O5 | + |
| Int-061 | 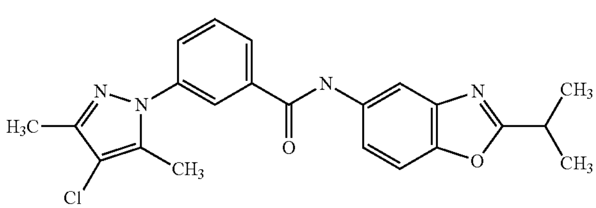 [SMILES: Cc1nn(-c2cccc(C(=O)Nc3ccc4oc(C(C)C)nc4c3)c2)c(C)c1Cl] | 3-(4-chloro-3,5-dimethyl-pyrazol-1-yl)-N-(2-isopropyl-1,3-benzoxazol-5-yl)benzamide | C22H21ClN4O2 | + |
| 062 | 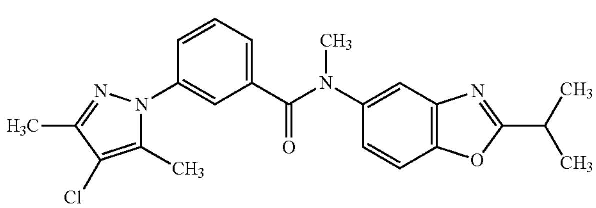 [SMILES: Cc1nn(-c2cccc(C(=O)N(C)c3ccc4oc(C(C)C)nc4c3)c2)c(C)c1Cl] | 3-(4-chloro-3,5-dimethyl-pyrazol-1-yl)-N-(2-isopropyl-1,3-benzoxazol-5-yl)-N-methyl-benzamide | C23H23ClN4O2 | + |

TABLE 1-continued

| # | Compound structure | Substance Name | Substance Formula | EC$_{50}$ |
|---|---|---|---|---|
| Int-063 | 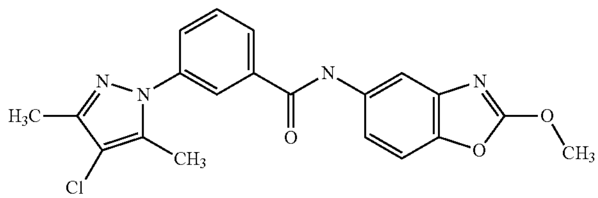 | 3-(4-chloro-3,5-dimethyl-pyrazol-1-yl)-N-(2-methoxy-1,3-benzoxazol-5-yl)benzamide | C20H17ClN4O3 | + |
| 064 | 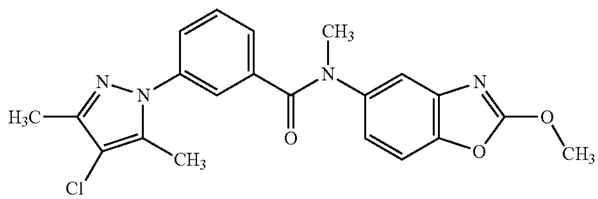 | 3-(4-chloro-3,5-dimethyl-pyrazol-1-yl)-N-(2-methoxy-1,3-benzoxazol-5-yl)-N-methyl-benzamide | C21H19ClN4O3 | + |
| 065 | 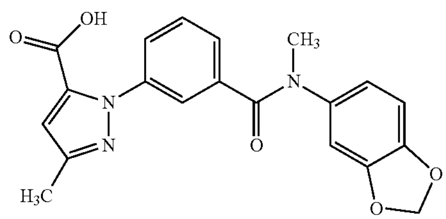 [SMILES: Cc1cc(C(=O)O)n(-c2cccc(C(=O)N(C)c3ccc4c(c3)OCO4)c2)n1] | 2-[3-[1,3-benzodioxol-5-yl(methyl)carbamoyl]phenyl]-5-methyl-pyrazole-3-carboxylic acid | C20H17N3O5 | + |
| 066 | 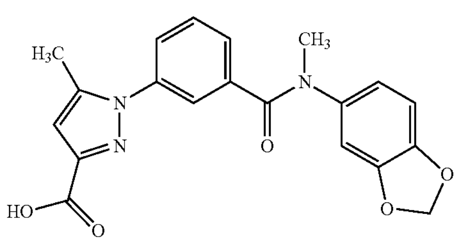 [SMILES: Cc1cc(C(=O)O)nn1-c1cccc(C(=O)N(C)c2ccc3c(c2)OCO3)c1] | 1-[3-[1,3-benzodioxol-5-yl(methyl)carbamoyl]phenyl]-5-methyl-pyrazole-3-carboxylic acid | C20H17N3O5 | + |
| 067 | 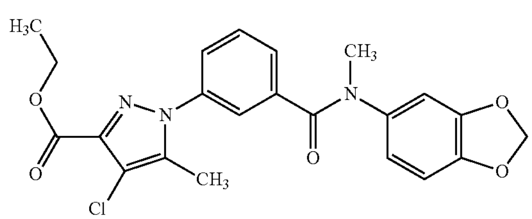 [SMILES: CCOC(=O)c1nn(-c2cccc(C(=O)N(C)c3ccc4c(c3)OCO4)c2)c(C)c1Cl] | ethyl 1-[3-[1,3-benzodioxol-5-yl(methyl)carbamoyl]phenyl]-4-chloro-5-methyl-pyrazole-3-carboxylate | C22H20ClN3O5 | + |
| 068 | 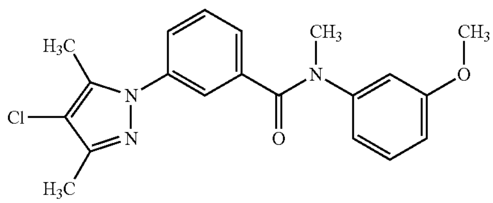 [SMILES: COc1cccc(N(C)C(=O)c2cccc(-n3nc(C)c(Cl)c3C)c2)c1] | 3-(4-chloro-3,5-dimethyl-pyrazol-1-yl)-N-(3-methoxyphenyl)-N-methyl-benzamide | C20H20ClN3O2 | +++ |
| 069 | 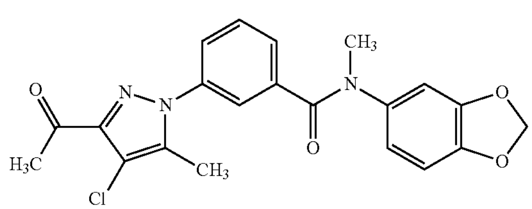 [SMILES: CC(=O)c1nn(-c2cccc(C(=O)N(C)c3ccc4c(c3)OCO4)c2)c(C)c1Cl] | 1-[3-[1,3-benzodioxol-5-yl(methyl)carbamoyl]phenyl]-4-chloro-5-methyl-pyrazole-3-carboxylic acid | C20H16ClN3O5 | + |

TABLE 1-continued

| # | Compound structure | Substance Name | Substance Formula | EC$_{50}$ |
|---|---|---|---|---|
| 070 | 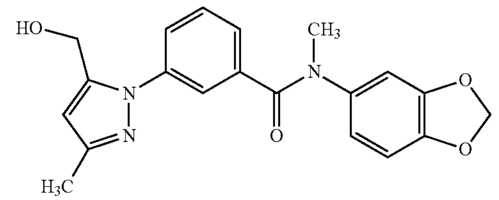 [SMILES: Cc1cc(CO)n(-c2cccc(C(=O)N(C)c3ccc4c(c3)OCO4)c2)n1] | N-(1,3-benzodioxol-5-yl)-3-[5-hydroxymethyl-3-methyl-pyrazol-1-yl]-N-methyl-benzamide | C20H19N3O4 | + |
| 071 | 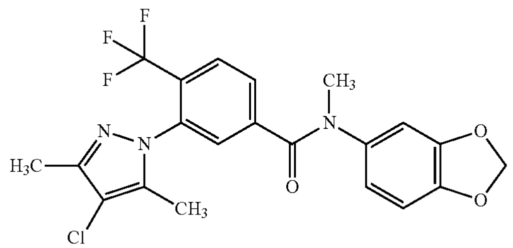 [SMILES: Cc1nn(-c2cc(C(=O)N(C)c3ccc4c(c3)OCO4)ccc2C(F)(F)F)c(C)c1Cl] | N-(1,3-benzodioxol-5-yl)-3-(4-chloro-3,5-dimethyl-pyrazol-1-yl)-N-methyl-4-(trifluoromethyl)benzamide | C21H17ClF3N3O3 | + |
| 072 | 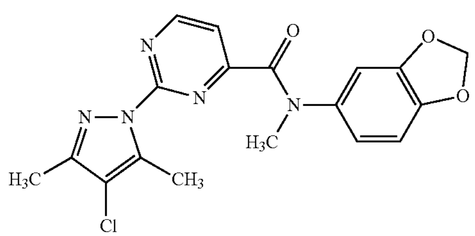 [SMILES: Cc1nn(-c2nccc(C(=O)N(C)c3ccc4c(c3)OCO4)n2)c(C)c1Cl] | N-(1,3-benzodioxol-5-yl)-2-(4-chloro-3,5-dimethyl-pyrazol-1-yl)-N-methyl-pyrimidine-4-carboxamide | C18H16ClN5O3 | + |
| 073 | 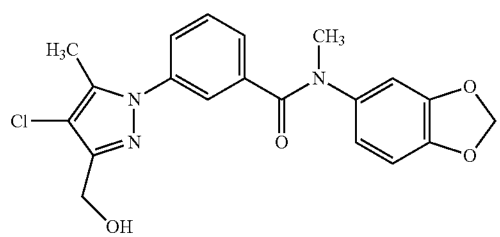 [SMILES: Cc1c(Cl)c(CO)nn1-c1cccc(C(=O)N(C)c2ccc3c(c2)OCO3)c1] | N-(1,3-benzodioxol-5-yl)-3-[4-chloro-3-(hydroxymethyl)-5-methyl-pyrazol-1-yl]-N-methyl-benzamide | C20H18ClN3O4 | + |
| 074 | 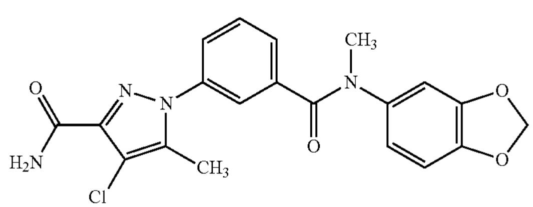 [SMILES: Cc1c(Cl)c(C(N)=O)nn1-c1cccc(C(=O)N(C)c2ccc3c(c2)OCO3)c1] | 1-[3-[1,3-benzodioxol-5-yl(methyl)carbamoyl]phenyl]-4-chloro-5-methyl-pyrazole-3-carboxamide | C20H17ClN4O4 | + |
| 075 | 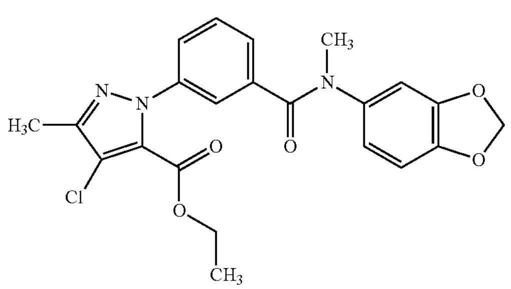 [SMILES: CCOC(=O)c1c(Cl)c(C)nn1-c1cccc(C(=O)N(C)c2ccc3c(c2)OCO3)c1] | ethyl 2-[3-[1,3-benzodioxol-5-yl(methyl)carbamoyl]phenyl]-4-chloro-5-methyl-pyrazole-3-carboxylate | C22H20ClN3O5 | +++ |

TABLE 1-continued

| # | Compound structure | Substance Name | Substance Formula | EC$_{50}$ |
|---|---|---|---|---|
| 076 | 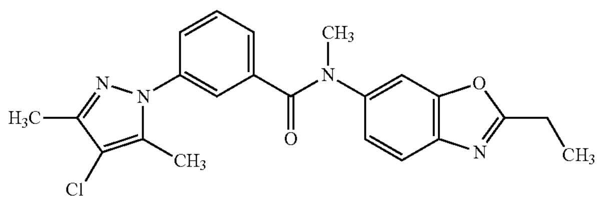 [SMILES: CCc1nc2ccc(N(C)C(=O)c3cccc(-n4nc(C)c(Cl)c4C)c3)cc2o1] | 3-(4-chloro-3,5-dimethyl-pyrazol-1-yl)-N-(2-ethyl-1,3-benzoxazol-6-yl)-N-methyl-benzamide | C22H21ClN4O2 | +++ |
| 077 | 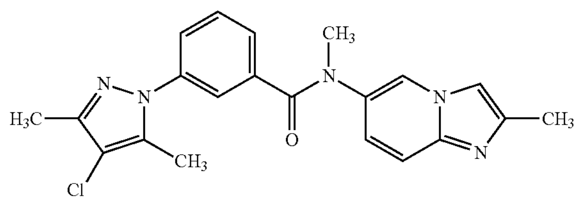 | 3-(4-chloro-3,5-dimethyl-pyrazol-1-yl)-N-methyl-N-(2-methylimidazo[1,2-a]pyridin-6-yl)benzamide | C21H20ClN5O | +++ |
| 078 | 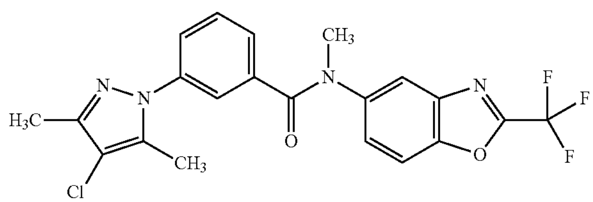 [SMILES: Cc1nn(-c2cccc(C(=O)N(C)c3ccc4oc(C(F)(F)F)nc4c3)c2)c(C)c1Cl] | 3-(4-chloro-3,5-dimethyl-pyrazol-1-yl)-N-methyl-N-[2-(trifluoromethyl)-1,3-benzoxazol-5-yl]benzamide | C21H16ClF3N4O2 | + |
| 079 | 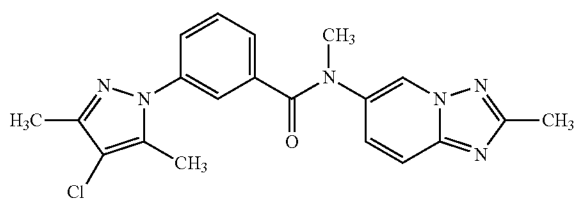 | 3-(4-chloro-3,5-dimethyl-pyrazol-1-yl)-N-methyl-N-(2-methyl-[1,2,4]triazolo[1,5-a]pyridin-6-yl)benzamide | C20H19ClN6O | + |
| 080 | 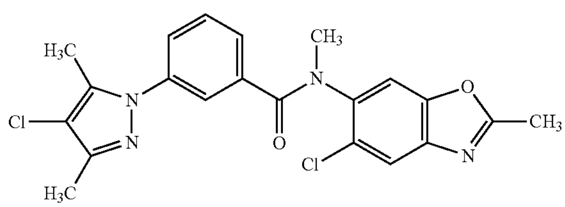 [SMILES: Cc1nc2cc(Cl)c(N(C)C(=O)c3cccc(-n4nc(C)c(Cl)c4C)c3)cc2o1] | 3-(4-chloro-3,5-dimethyl-pyrazol-1-yl)-N-(5-chloro-2-methyl-1,3-benzoxazol-6-yl)-N-methyl-benzamide | C21H18Cl2N4O2 | +++ |
| 081 | 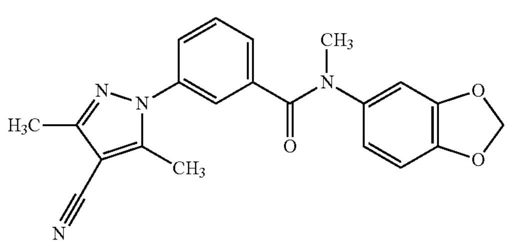 [SMILES: Cc1nn(-c2cccc(C(=O)N(C)c3ccc4c(c3)OCO4)c2)c(C)c1C#N] | N-(1,3-benzodioxol-5-yl)-3-(4-cyano-3,5-dimethyl-pyrazol-1-yl)-N-methyl-benzamide | C21H18N4O3 | + |
| 082 | 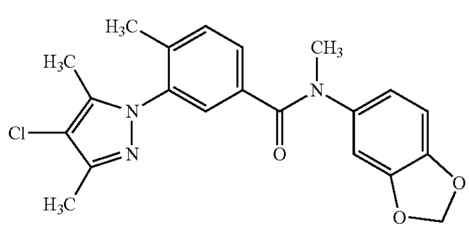 [SMILES: Cc1ccc(C(=O)N(C)c2ccc3c(c2)OCO3)cc1-n1nc(C)c(Cl)c1C] | N-(1,3-benzodioxol-5-yl)-3-(4-chloro-3,5-dimethyl-pyrazol-1-yl)-N,4-dimethyl-benzamide | C21H20ClN3O3 | ++ |

TABLE 1-continued

| # | Compound structure | Substance Name | Substance Formula | $EC_{50}$ |
|---|---|---|---|---|
| 083 | 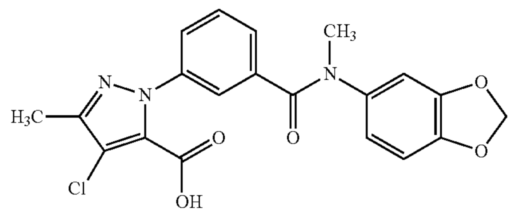 [SMILES: Cc1nn(-c2cccc(C(=O)N(C)c3ccc4c(c3)OCO4)c2)c(C(=O)O)c1Cl] | 2-[3-[1,3-benzodioxol-5-yl(methyl)carbamoyl]phenyl]-4-chloro-5-methyl-pyrazole-3-carboxylic acid | C20H16ClN3O5 | + |
| 084 | 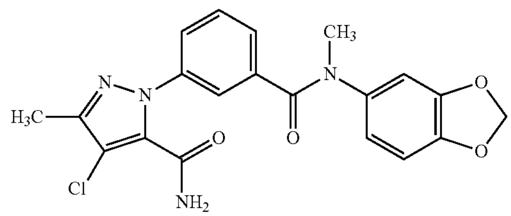 [SMILES: Cc1nn(-c2cccc(C(=O)N(C)c3ccc4c(c3)OCO4)c2)c(C(N)=O)c1Cl] | 2-[3-[1,3-benzodioxol-5-yl(methyl)carbamoyl]phenyl]-4-chloro-5-methyl-pyrazole-3-carboxamide | C20H17ClN4O4 | + |
| 085 | 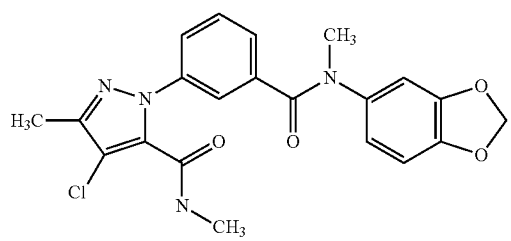 [SMILES: CNC(=O)c1c(Cl)c(C)nn1-c1cccc(C(=O)N(C)c2ccc3c(c2)OCO3)c1] | 2-[3-[1,3-benzodioxol-5-yl(methyl)carbamoyl]phenyl]-4-chloro-N,5-dimethyl-pyrazole-3-carboxamide | C21H19ClN4O4 | + |
| 086 | 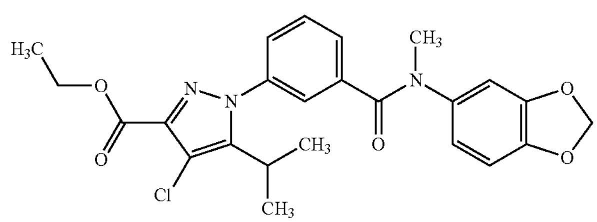 [SMILES: CCOC(=O)c1nn(-c2cccc(C(=O)N(C)c3ccc4c(c3)OCO4)c2)c(C(C)C)c1Cl] | ethyl 1-[3-[1,3-benzodioxol-5-yl(methyl)carbamoyl]phenyl]-4-chloro-5-isopropyl-pyrazole-3-carboxylate | C24H24ClN3O5 | + |
| 087 | 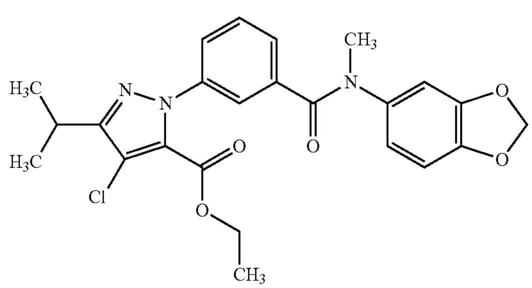 [SMILES: CCOC(=O)c1c(Cl)c(C(C)C)nn1-c1cccc(C(=O)N(C)c2ccc3c(c2)OCO3)c1] | ethyl 2-[3-[1,3-benzodioxol-5-yl(methyl)carbamoyl]phenyl]-4-chloro-5-isopropyl-pyrazole-3-carboxylate | C24H24ClN3O5 | +++ |
| 088 | 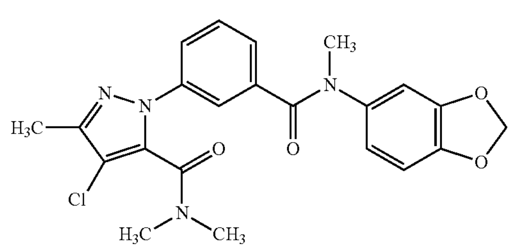 [SMILES: Cc1nn(-c2cccc(C(=O)N(C)c3ccc4c(c3)OCO4)c2)c(C(=O)N(C)C)c1Cl] | 2-[3-[1,3-benzodioxol-5-yl(methyl)carbamoyl]phenyl]-4-chloro-N,N,5-trimethyl-pyrazole-3-carboxamide | C22H21ClN4O4 | + |

TABLE 1-continued

| # | Compound structure | Substance Name | Substance Formula | EC$_{50}$ |
|---|---|---|---|---|
| 089 | 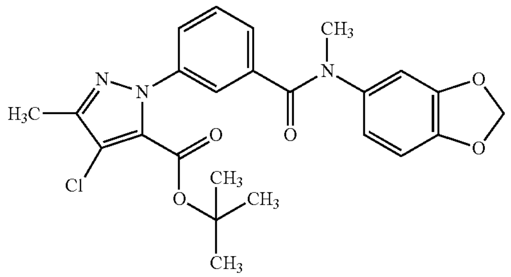 [SMILES: Cc1nn(-c2cccc(C(=O)N(C)c3ccc4c(c3)OCO4)c2)c(C(=O)OC(C)(C)C)c1Cl] | tert-butyl 2-[3-[1,3-benzodioxol-5-yl(methyl)carbamoyl]phenyl]-4-chloro-5-methyl-pyrazole-3-carboxylate | C24H24ClN3O5 | +++ |
| 090 | 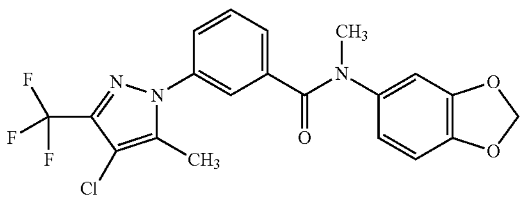 | N-(1,3-benzodioxol-5-yl)-3-[4-chloro-5-methyl-3-(trifluoromethyl)pyrazol-1-yl]-N-methyl-benzamide | C20H15ClF3N3O3 | +++ |
| 091 | 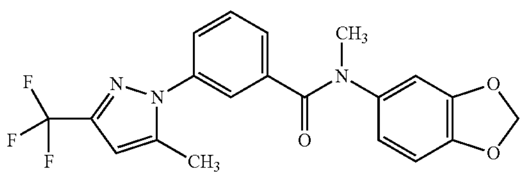 [SMILES: Cc1cc(C(F)(F)F)nn1-c1cccc(C(=O)N(C)c2ccc3c(c2)OCO3)c1] | N-(1,3-benzodioxol-5-yl)-N-methyl-3-[5-methyl-3-(trifluoromethyl)pyrazol-1-yl]benzamide | C20H16F3N3O3 | ++ |
| 092 | 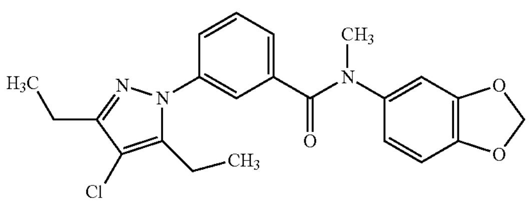 [SMILES: CCc1nn(-c2cccc(C(=O)N(C)c3ccc4c(c3)OCO4)c2)c(CC)c1Cl] | N-(1,3-benzodioxol-5-yl)-3-(4-chloro-3,5-diethyl-pyrazol-1-yl)-N-methyl-benzamide | C22H22ClN3O3 | +++ |
| 093 | 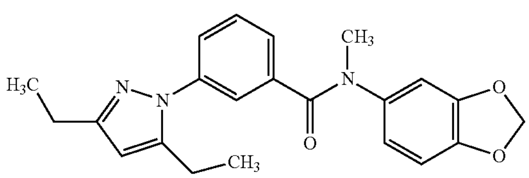 [SMILES: CCc1cc(CC)n(-c2cccc(C(=O)N(C)c3ccc4c(c3)OCO4)c2)n1] | N-(1,3-benzodioxol-5-yl)-3-(3,5-diethylpyrazol-1-yl)-N-methyl-benzamide | C22H23N3O3 | ++ |
| 094 | 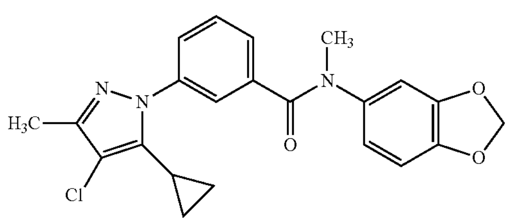 [SMILES: Cc1nn(-c2cccc(C(=O)N(C)c3ccc4c(c3)OCO4)c2)c(C2CC2)c1Cl] | N-(1,3-benzodioxol-5-yl)-3-(4-chloro-5-cyclopropyl-3-methyl-pyrazol-1-yl)-N-methyl-benzamide | C22H20ClN3O3 | +++ |
| 095 | 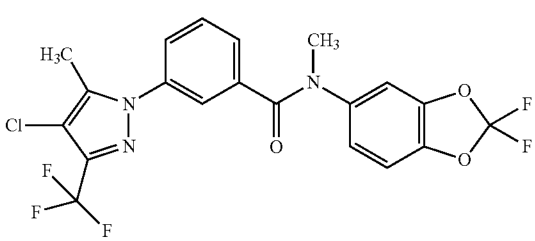 [SMILES: Cc1c(Cl)c(C(F)(F)F)nn1-c1cccc(C(=O)N(C)c2ccc3c(c2)OC(F)(F)O3)c1] | 3-[4-chloro-5-methyl-3-(trifluoromethyl)pyrazol-1-yl]-N-(2,2-difluoro-1,3-benzodioxol-5-yl)-N-methyl-benzamide | C20H13ClF5N3O3 | +++ |

TABLE 1-continued

| # | Compound structure | Substance Name | Substance Formula | EC$_{50}$ |
|---|---|---|---|---|
| 096 | 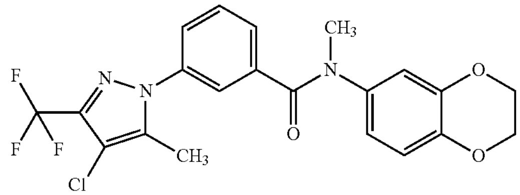 [SMILES: Cc1c(Cl)c(C(F)(F)F)nn1-c1cccc(C(=O)N(C)c2ccc3c(c2)OCCO3)c1] | 3-[4-chloro-5-methyl-3-(trifluoromethyl)pyrazol-1-yl]-N-(2,3-dihydro-1,4-benzodioxin-6-yl)-N-methyl-benzamide | C21H17ClF3N3O3 | +++ |
| 097 | 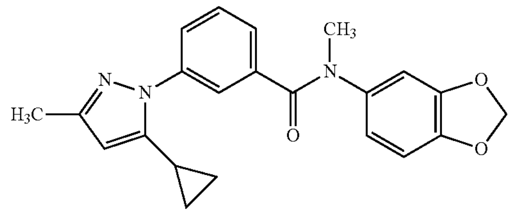 [SMILES: Cc1cc(C2CC2)n(-c2cccc(C(=O)N(C)c3ccc4c(c3)OCO4)c2)n1] | N-(1,3-benzodioxol-5-yl)-3-(5-cyclopropyl-3-methyl-pyrazol-1-yl)-N-methyl-benzamide | C22H21N3O3 | +++ |
| 098 | 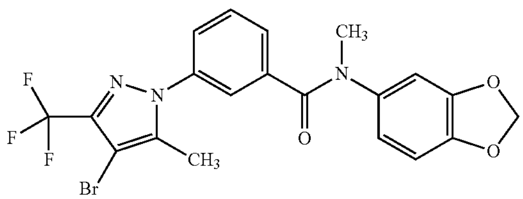 | N-(1,3-benzodioxol-5-yl)-3-[4-bromo-5-methyl-3-(trifluoromethyl)pyrazol-1-yl]-N-methyl-benzamide | C20H15BrF3N3O3 | +++ |
| 099 | 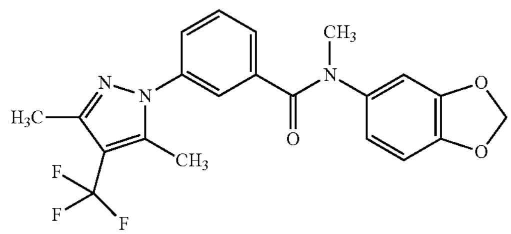 [SMILES: Cc1nn(-c2cccc(C(=O)N(C)c3ccc4c(c3)OCO4)c2)c(C)c1C(F)(F)F] | N-(1,3-benzodioxol-5-yl)-3-[3,5-dimethyl-4-(trifluoromethyl)pyrazol-1-yl]-N-methyl-benzamide | C21H18F3N3O3 | +++ |
| 100 | 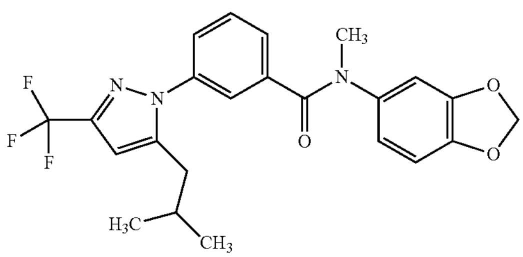 [SMILES: CC(C)Cc1cc(C(F)(F)F)nn1-c1cccc(C(=O)N(C)c2ccc3c(c2)OCO3)c1] | N-(1,3-benzodioxol-5-yl)-3-[5-isobutyl-3-(trifluoromethyl)pyrazol-1-yl]-N-methyl-benzamide | C23H22F3N3O3 | +++ |
| 101 | 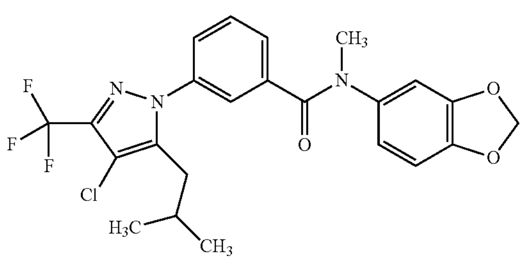 | N-(1,3-benzodioxol-5-yl)-3-[4-chloro-5-isobutyl-3-(trifluoromethyl)pyrazol-1-yl]-N-methyl-benzamide | C23H21ClF3N3O3 | +++ |
| 102 | 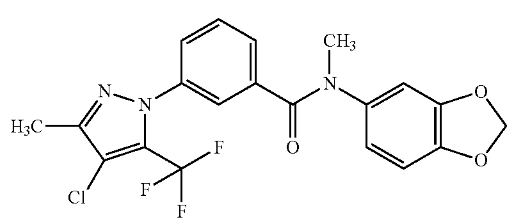 [SMILES: Cc1nn(-c2cccc(C(=O)N(C)c3ccc4c(c3)OCO4)c2)c(C(F)(F)F)c1Cl] | N-(1,3-benzodioxol-5-yl)-3-[4-chloro-3-methyl-5-(trifluoromethyl)pyrazol-1-yl]-N-methyl-benzamide | C20H15ClF3N3O3 | +++ |

TABLE 1-continued

| # | Compound structure | Substance Name | Substance Formula | $EC_{50}$ |
|---|---|---|---|---|
| 103 | 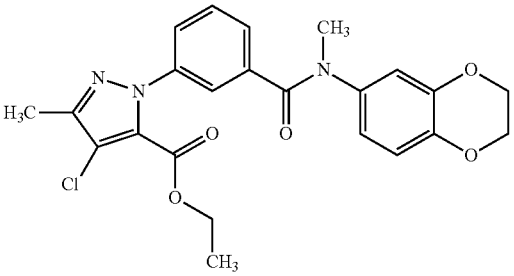 [SMILES: CCOC(=O)c1c(Cl)c(C)nn1-c1cccc(C(=O)N(C)c2ccc3c(c2)OCCO3)c1] | ethyl 4-chloro-2-[3-[2,3-dihydro-1,4-benzodioxin-6-yl(methyl)carbamoyl]phenyl]-5-methyl-pyrazole-3-carboxylate | C23H22ClN3O5 | +++ |
| 104 | 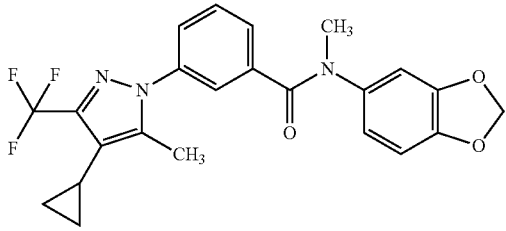 [SMILES: Cc1c(C2CC2)c(C(F)(F)F)nn1-c1cccc(C(=O)N(C)c2ccc3c(c2)OCO3)c1] | N-(1,3-benzodioxol-5-yl)-3-[4-cyclopropyl-5-methyl-3-(trifluoromethyl)pyrazol-1-yl]-N-methyl-benzamide | C23H20F3N3O3 | +++ |
| 105 | 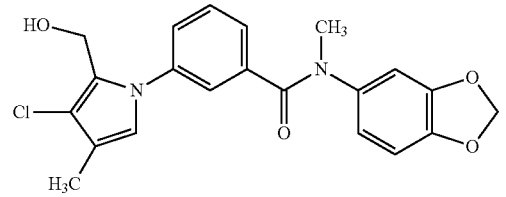 [SMILES: Cc1cn(-c2cccc(C(=O)N(C)c3ccc4c(c3)OCO4)c2)c(CO)c1Cl] | N-(1,3-benzodioxol-5-yl)-3-[4-chloro-5-(hydroxymethyl)-3-methyl-pyrazol-1-yl]-N-methyl-benzamide | C20H18ClN3O4 | ++ |
| 106 | 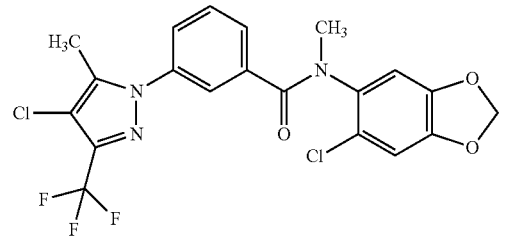 [SMILES: Cc1c(Cl)c(C(F)(F)F)nn1-c1cccc(C(=O)N(C)c2cc3c(cc2Cl)OCO3)c1] | N-(6-chloro-1,3-benzodioxol-5-yl)-3-[4-chloro-5-methyl-3-(trifluoromethyl)pyrazol-1-yl]-N-methyl-benzamide | C20H14Cl2F3N3O3 | +++ |
| 107 | 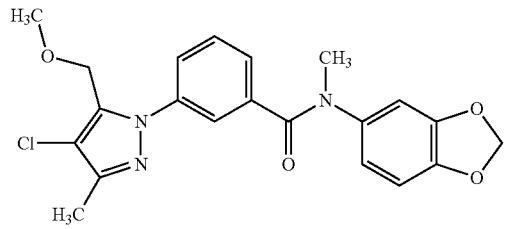 [SMILES: COCc1c(Cl)c(C)nn1-c1cccc(C(=O)N(C)c2ccc3c(c2)OCO3)c1] | N-(1,3-benzodioxol-5-yl)-3-[4-chloro-5-(methoxymethyl)-3-methyl-pyrazol-1-yl]-N-methyl-benzamide | C21H20ClN3O4 | +++ |
| 108 | 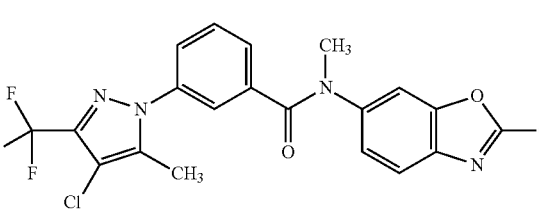 | 3-[4-chloro-5-methyl-3-(trifluoromethyl)pyrazol-1-yl]-N-methyl-N-(2-methyl-1,3-benzoxazol-6-yl)benzamide | C21H16ClF3N4O2 | +++ |

TABLE 1-continued

| # | Compound structure | Substance Name | Substance Formula | $EC_{50}$ |
|---|---|---|---|---|
| 109 | 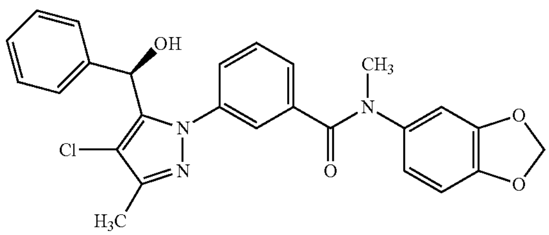 | N-(1,3-benzodioxol-5-yl)-3-[4-chloro-5-[(R)-hydroxy(phenyl)methyl]-3-methyl-pyrazol-1-yl]-N-methyl-benzamide | C26H22ClN3O4 | +++ |
| 110 | 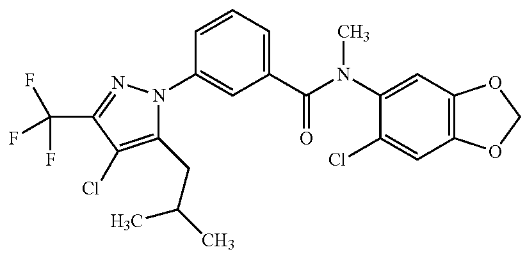 [SMILES: CC(C)Cc1c(Cl)c(C(F)(F)F)nn1-c1cccc(C(=O)N(C)c2cc3c(cc2Cl)OCO3)c1] | N-(6-chloro-1,3-benzodioxol-5-yl)-3-[4-chloro-5-isobutyl-3-(trifluoromethyl)pyrazol-1-yl]-N-methyl-benzamide | C23H20Cl2F3N3O3 | +++ |
| 111 | 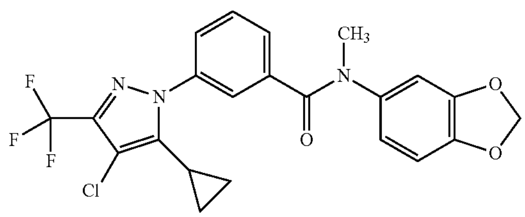 [SMILES: CN(C(=O)c1cccc(-n2nc(C(F)(F)F)c(Cl)c2C2CC2)c1)c1ccc2c(c1)OCO2] | N-(1,3-benzodioxol-5-yl)-3-[4-chloro-5-cyclopropyl-3-(trifluoromethyl)pyrazol-1-yl]-N-methyl-benzamide | C22H17ClF3N3O3 | +++ |
| 112 | 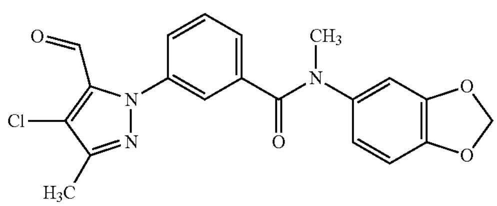 [SMILES: Cc1nn(-c2cccc(C(=O)N(C)c3ccc4c(c3)OCO4)c2)c(C=O)c1Cl] | N-(1,3-benzodioxol-5-yl)-3-(4-chloro-5-formyl-3-mthyl-pyrazol-1-yl)-N-methyl-benzamide | C20H16ClN3O4 | +++ |
| 113 | 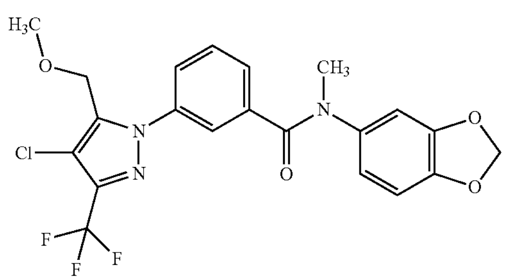 [SMILES: COCc1c(Cl)c(C(F)(F)F)nn1-c1cccc(C(=O)N(C)c2ccc3c(c2)OCO3)c1] | N-(1,3-benzodioxol-5-yl)-3-[4-chloro-5-ethoxy-3-(trifluoromethyl)pyrazol-1-yl]-N-methyl-benzamide | C21H17ClF3N3O4 | ++ |
| 114 | 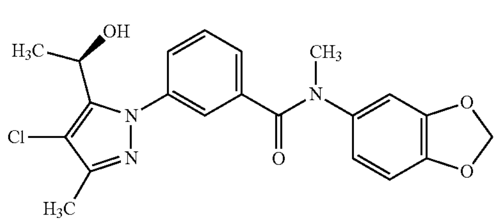 [SMILES: Cc1nn(-c2cccc(C(=O)N(C)c3ccc4c(c3)OCO4)c2)c([C@@H](C)O)c1Cl] | N-(1,3-benzodioxol-5-yl)-3-[4-chloro-5-[(1R)-1-hydroxyethyl]-3-methyl-pyrazol-1-yl]-N-methyl-benzamide | C21H20ClN3O4 | + |

TABLE 1-continued

| # | Compound structure | Substance Name | Substance Formula | EC$_{50}$ |
|---|---|---|---|---|
| 115 | 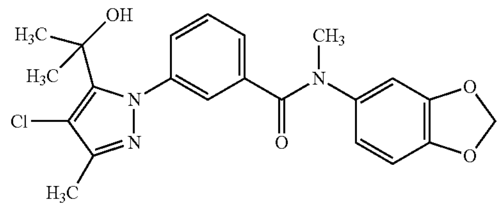 [SMILES: Cc1nn(-c2cccc(C(=O)N(C)c3ccc4c(c3)OCO4)c2)c(C(C)(C)O)c1Cl] | N-(1,3-benzodioxol-5-yl)-3-[4-chloro-5-(1-hydroxy-1-methyl-ethyl)-3-methyl-pyrazol-1-yl]-N-methyl-benzamide | C22H22ClN3O4 | ++ |
| 116 | 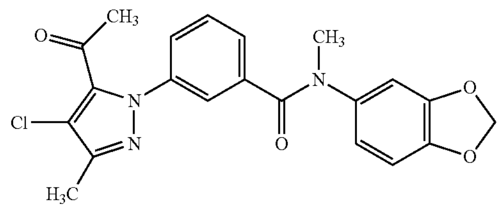 [SMILES: CC(=O)c1c(Cl)c(C)nn1-c1cccc(C(=O)N(C)c2ccc3c(c2)OCO3)c1] | 3-(5-acetyl-4-chloro-3-methyl-pyrazol-1-yl)-N-(1,3-benzodioxol-5-yl)-N-methyl-benzamide | C21H18ClN3O4 | +++ |
| 117 | 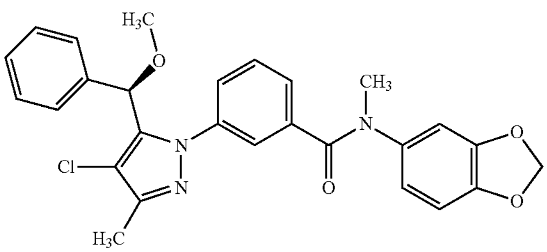 [SMILES: CO[C@H](c1ccccc1)c1c(Cl)c(C)nn1-c1cccc(C(=O)N(C)c2ccc3c(c2)OCO3)c1] | N-(1,3-benzodioxol-5-yl)-3-[4-chloro-5-[(R)-methoxy(phenyl)methyl]-3-methyl-pyrazol-1-yl]-N-methyl-benzamide | C27H24ClN3O4 | +++ |
| 118 | 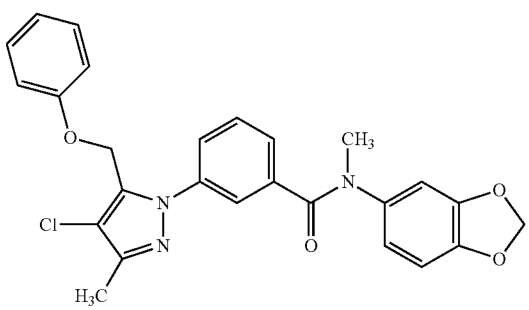 [SMILES: Cc1nn(-c2cccc(C(=O)N(C)c3ccc4c(c3)OCO4)c2)c(COc2ccccc2)c1Cl] | N-(1,3-benzodioxol-5-yl)-3-[4-chloro-3-methyl-5-(phenoxymethyl)pyrazol-1-yl]-N-methyl-benzamide | C26H22ClN3O4 | +++ |
| 119 | 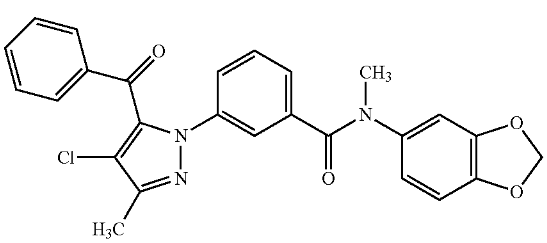 [SMILES: Cc1nn(-c2cccc(C(=O)N(C)c3ccc4c(c3)OCO4)c2)c(C(=O)c2ccccc2)c1Cl] | N-(1,3-benzodioxol-5-yl)-3-(5-benzoyl-4-chloro-3-methyl-pyrazol-1-yl)-N-methyl-benzamide | C26H20ClN3O4 | +++ |
| 120 | 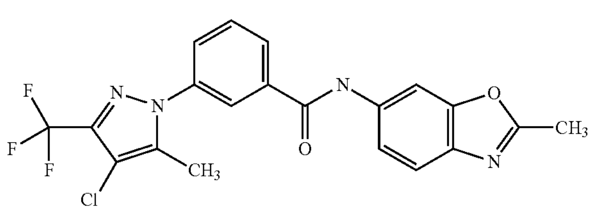 [SMILES: Cc1nc2ccc(NC(=O)c3cccc(-n4nc(C(F)(F)F)c(Cl)c4C)c3)cc2o1] | 3-[4-chloro-5-methyl-3-(trifluoromethyl)pyrazol-1-yl]-N-(2-methyl-1,3-benzoxazol-6-yl)benzamide | C20H14ClF3N4O2 | ++ |

TABLE 1-continued

| # | Compound structure | Substance Name | Substance Formula | EC$_{50}$ |
|---|---|---|---|---|
| Int-121 | 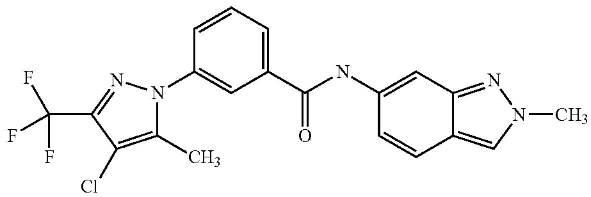 [SMILES: Cc1c(Cl)c(C(F)(F)F)nn1-c1cccc(C(=O)Nc2ccc3cn(C)nc3c2)c1] | 3-[4-chloro-5-methyl-3-(trifluoromethyl)pyrazol-1-yl]-N-(2-methylindazol-6-yl)benzamide | C20H15ClF3N5O | + |
| 122 | 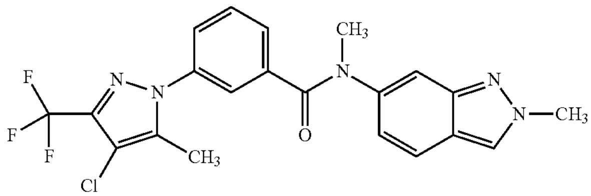 [SMILES: Cc1c(Cl)c(C(F)(F)F)nn1-c1cccc(C(=O)N(C)c2ccc3cn(C)nc3c2)c1] | 3-[4-chloro-5-methyl-3-(trifluoromethyl)pyrazol-1-yl]-N-methyl-N-(2-methylindazol-6-yl)benzamide | C21H17ClF3N5O | ++ |
| 123 | 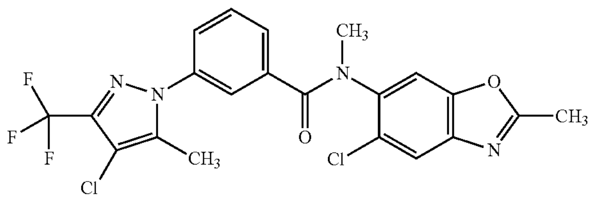 [SMILES: Cc1nc2cc(Cl)c(N(C)C(=O)c3cccc(-n4nc(C(F)(F)F)c(Cl)c4C)c3)cc2o1] | N-(5-chloro-2-methyl-1,3-benzoxazol-6-yl)-3-[4-chloro-5-methyl-3-(trifluoromethyl)pyrazol-1-yl]-N-methyl-benzamide | C21H15Cl2F3N4O2 | +++ |
| 124 | 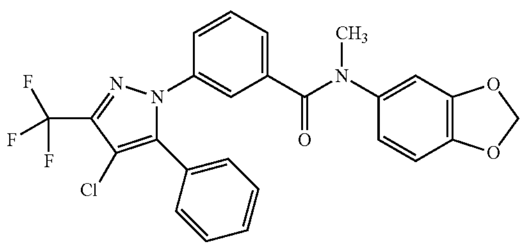 [SMILES: CN(C(=O)c1cccc(-n2nc(C(F)(F)F)c(Cl)c2-c2ccccc2)c1)c1ccc2c(c1)OCO2] | N-(1,3-benzodioxol-5-yl)-3-[4-chloro-5-phenyl-3-(trifluoromethyl)pyrazol-1-yl]-N-methyl-benzamide | C25H17ClF3N3O3 | +++ |
| 125 | 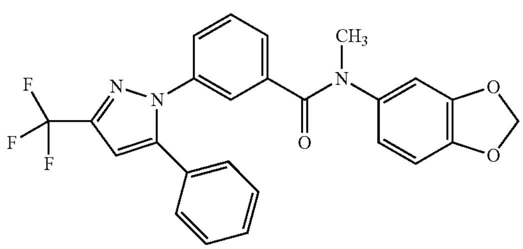 [SMILES: CN(C(=O)c1cccc(-n2nc(C(F)(F)F)cc2-c2ccccc2)c1)c1ccc2c(c1)OCO2] | N-(1,3-benzodioxol-5-yl)-N-methyl-3-[5-phenyl-3-(trifluoromethyl)pyrazol-1-yl]benzamide | C25H18F3N3O3 | +++ |
| 126 | 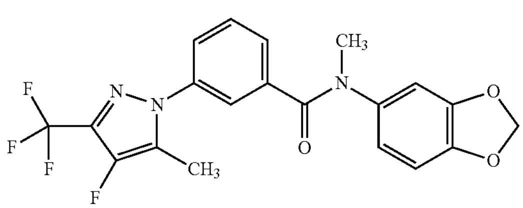 [SMILES: Cc1c(F)c(C(F)(F)F)nn1-c1cccc(C(=O)N(C)c2ccc3c(c2)OCO3)c1] | N-(1,3-benzodioxol-5-yl)-3-[4-fluoro-5-methyl-3-(trifluoromethyl)pyrazol-1-yl]-N-methyl-benzamide | C20H15F4N3O3 | +++ |
| 127 | 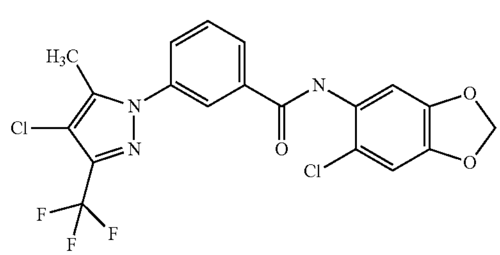 [SMILES: Cc1c(Cl)c(C(F)(F)F)nn1-c1cccc(C(=O)Nc2cc3c(cc2Cl)OCO3)c1] | N-(6-chloro-1,3-benzodioxol-5-yl)-3-[4-chloro-5-methyl-3-(trifluoromethyl)pyrazol-1-yl]benzamide | C19H12Cl2F3N3O3 | + |

TABLE 1-continued

| # | Compound structure | Substance Name | Substance Formula | EC$_{50}$ |
|---|---|---|---|---|
| 128 | 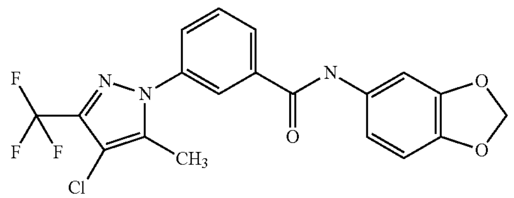 [SMILES: Cc1c(Cl)c(C(F)(F)F)nn1-c1cccc(C(=O)Nc2ccc3c(c2)OCO3)c1] | N-(1,3-benzodioxol-5-yl)-3-[4-chloro-5-methyl-3-(trifluoromethyl)pyrazol-1-yl]benzamide | C19H13ClF3N3O3 | + |
| 129 | 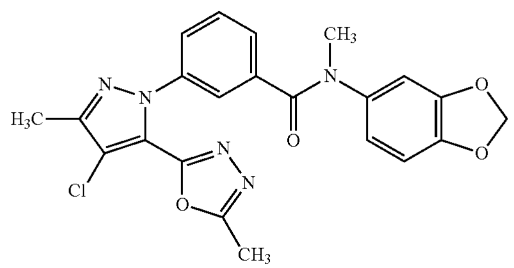 [SMILES: Cc1nnc(-c2c(Cl)c(C)nn2-c2cccc(C(=O)N(C)c3ccc4c(c3)OCO4)c2)o1] | N-(1,3-benzodioxol-5-yl)-3-[4-chloro-3-methyl-5-(5-methyl-1,3,4-oxadiazol-2-yl)pyrazol-1-yl]-N-methyl-benzamide | C22H18ClN5O4 | +++ |
| 130 | 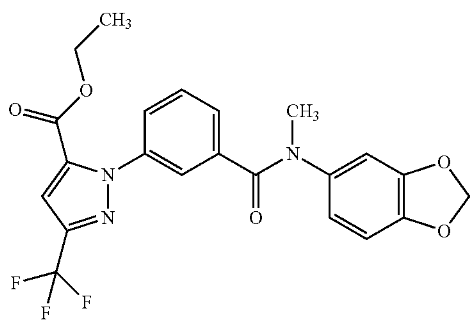 [SMILES: CCOC(=O)c1cc(C(F)(F)F)nn1-c1cccc(C(=O)N(C)c2ccc3c(c2)OCO3)c1] | ethyl 2-[3-[1,3-benzodioxol-5-yl(methyl)carbamoyl]phenyl]-5-(trifluoromethyl)pyrazole-3-carboxylate | C22H18F3N3O5 | +++ |
| 131 | 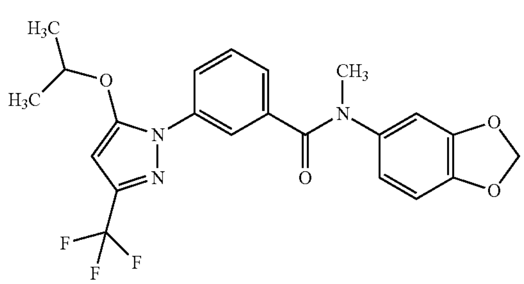 [SMILES: CC(C)Oc1cc(C(F)(F)F)nn1-c1cccc(C(=O)N(C)c2ccc3c(c2)OCO3)c1] | N-(1,3-benzodioxol-5-yl)-3-[5-isopropoxy-3-(trifluoromethyl)pyrazol-1-yl]-N-methyl-benzamide | C22H20F3N3O4 | +++ |
| 132 | 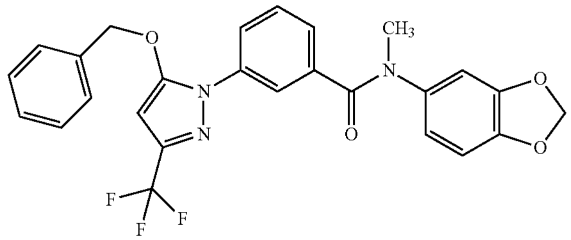 [SMILES: CN(C(=O)c1cccc(-n2nc(C(F)(F)F)cc2OCc2ccccc2)c1)c1ccc2c(c1)OCO2] | N-(1,3-benzodioxol-5-yl)-3-[5-benzyloxy-3-(trifluoromethyl)pyrazol-1-yl]-N-methyl-benzamide | C26H20F3N3O4 | +++ |

TABLE 1-continued

| # | Compound structure | Substance Name | Substance Formula | $EC_{50}$ |
|---|---|---|---|---|
| 133 | 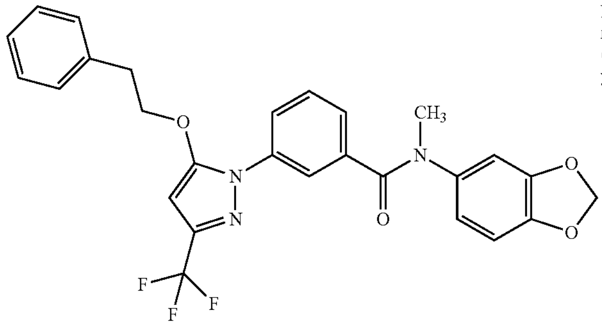 [SMILES: CN(C(=O)c1cccc(-n2nc(C(F)(F)F)cc2OCCc2ccccc2)c1)c1ccc2c(c1)OCO2] | N-(1,3-benzodioxol-5-yl)-N-methyl-3-[5-phenethyloxy-3-(trifluoromethyl)pyrazol-1-yl]benzamide | C27H22F3N3O4 | +++ |
| 134 | 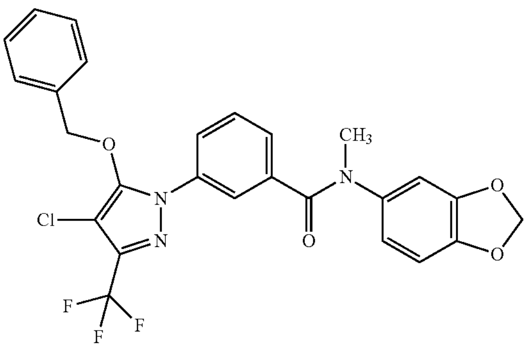 [SMILES: CN(C(=O)c1cccc(-n2nc(C(F)(F)F)c(Cl)c2OCc2ccccc2)c1)c1ccc2c(c1)OCO2] | N-(1,3-benzodioxol-5-yl)-3-[5-benzyloxy-4-chloro-3-(trifluoromethyl)pyrazol-1-yl]-N-methyl-benzamide | C26H19ClF3N3O4 | +++ |
| 135 | 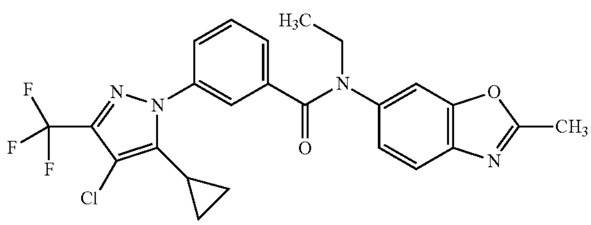 [SMILES: CCN(C(=O)c1cccc(-n2nc(C(F)(F)F)c(Cl)c2C2CC2)c1)c1ccc2nc(C)oc2c1] | 3-[4-chloro-5-cyclopropyl-3-(trifluoromethyl)pyrazol-1-yl]-N-ethyl-N-(2-methyl-1,3-benzoxazol-6-yl)benzamide | C24H20ClF3N4O2 | +++ |
| Int-136 | 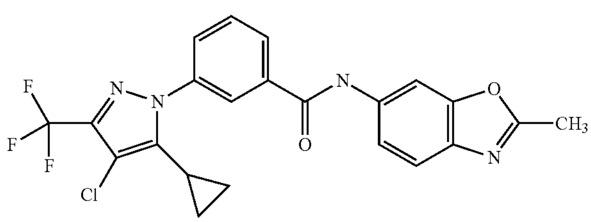 [SMILES: Cc1nc2ccc(NC(=O)c3cccc(-n4nc(C(F)(F)F)c(Cl)c4C4CC4)c3)cc2o1] | 3-[4-chloro-5-cyclopropyl-3-(trifluoromethyl)pyrazol-1-yl]-N-(2-methyl-1,3-benzoxazol-6-yl)benzamide | C22H16ClF3N4O2 | +++ |
| 137 | 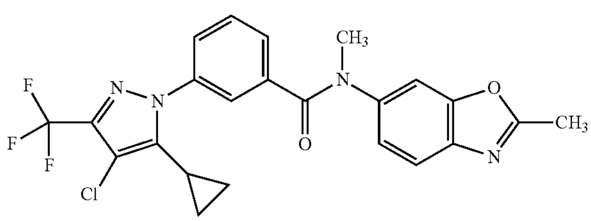 [SMILES: Cc1nc2ccc(N(C)C(=O)c3cccc(-n4nc(C(F)(F)F)c(Cl)c4C4CC4)c3)cc2o1] | 3-[4-chloro-5-cyclopropyl-3-(trifluoromethyl)pyrazol-1-yl]-N-methyl-N-(2-methyl-1,3-benzoxazol-6-yl)benzamide | C23H18ClF3N4O2 | +++ |
| 138 | 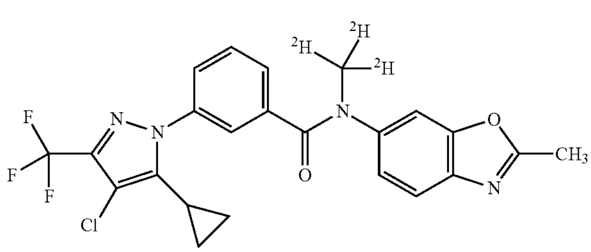 [SMILES: [2H]C([2H])([2H])N(C(=O)c1cccc(-n2nc(C(F)(F)F)c(Cl)c2C2CC2)c1)c1ccc2nc(C)oc2c1] | 3-[4-chloro-5-cyclopropyl-3-(trifluoromethyl)pyrazol-1-yl]-N-(2-methyl-1,3-benzoxazol-6-yl)-N-(trideuteriomethyl)benzamide | C23H15ClD3F3N4O2 | +++ |

TABLE 1-continued

| # | Substance Name | Substance Formula | EC$_{50}$ |
|---|---|---|---|
| 139 | 3-[4-chloro-5-cyclopropyl-3-(trifluoromethyl)pyrazol-1-yl]-N-(5-chloro-2-methyl-1,3-benzoxazol-6-yl)-N-methyl-benzamide | C23H17Cl2F3N4O2 | +++ |
| 140 | ethyl 3-[[2-[3-[1,3-benzodioxol-5-yl(methyl)carbamoyl]phenyl]-4-chloro-5-methyl-pyrazol-3-yl]methoxy]benzoate | C29H26ClN3O6 | +++ |
| 141 | ethyl 4-[[2-[3-[1,3-benzodioxol-5-yl(methyl)carbamoyl]phenyl]-4-chloro-5-methyl-pyrazol-3-yl]methoxy]benzoate | C29H26ClN3O6 | +++ |
| 142 | N-(1,3-benzodioxol-5-yl)-3-[4-chloro-5-isopropoxy-3-(trifluoromethyl)pyrazol-1-yl]-N-methyl-benzamide | C22H19ClF3N3O4 | +++ |
| 143 | 3-[[2-[3-[1,3-benzodioxol-5-yl(methyl)carbamoyl]phenyl]-4-chloro-5-methyl-pyrazol-3-yl]methoxy]benzoic acid | C27H22ClN3O6 | ++ |

TABLE 1-continued

| # | Compound structure | Substance Name | Substance Formula | $EC_{50}$ |
|---|---|---|---|---|
| 144 | 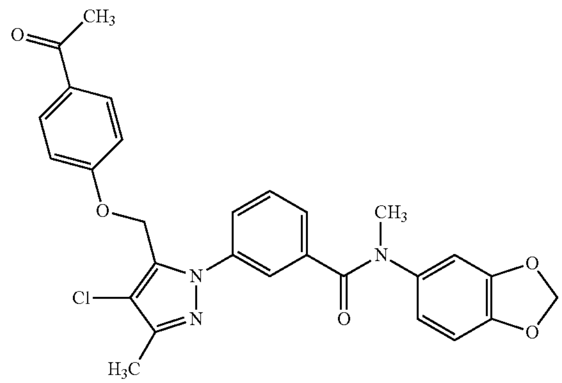 [SMILES: CC(=O)c1ccc(OCc2c(Cl)c(C)nn2-c2cccc(C(=O)N(C)c3ccc4c(c3)OCO4)c2)cc1] | 4-[[2-[3-[1,3-benzodioxol-5-yl(methyl)carbamoyl]phenyl]-4-chloro-5-methyl-pyrazol-3-yl]methoxy]benzoic acid | C27H22ClN3O6 | +++ |
| 147 | 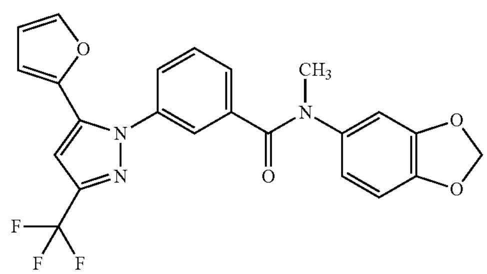 [SMILES: CN(C(=O)c1cccc(-n2nc(C(F)(F)F)cc2-c2ccco2)c1)c1ccc2c(c1)OCO2] | N-(1,3-benzodioxol-5-yl)-3-[5-(2-furyl)-3-(trifluoromethyl)pyrazol-1-yl]-N-methyl-benzamide | C23H16F3N3O4 | +++ |
| Int-148 | 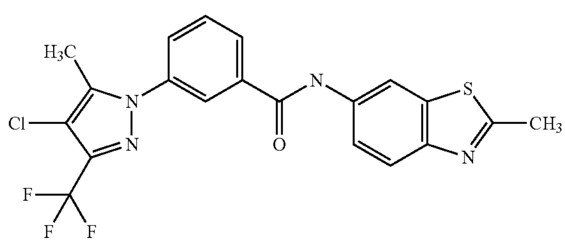 [SMILES: Cc1nc2ccc(NC(=O)c3cccc(-n4nc(C(F)(F)F)c(Cl)c4C)c3)cc2s1] | 3-[4-chloro-5-methyl-3-(trifluoromethyl)pyrazol-1-yl]-N-(2-methyl-1,3-benzothiazol-6-yl)benzamide | C20H14ClF3N4OS | +++ |
| 149 | 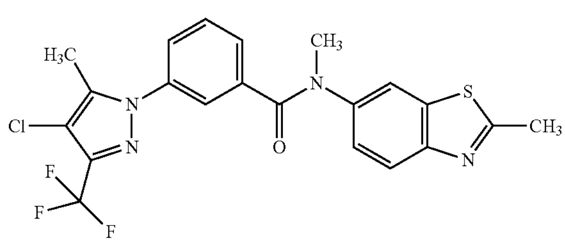 [SMILES: Cc1nc2ccc(N(C)C(=O)c3cccc(-n4nc(C(F)(F)F)c(Cl)c4C)c3)cc2s1] | 3-[4-chloro-5-methyl-3-(trifluoromethyl)pyrazol-1-yl]-N-methyl-N-(2-methyl-1,3-benzothiazol-6-yl) benzamide | C21H16ClF3N4OS | ++ |

TABLE 1-continued

| # | Compound structure | Substance Name | Substance Formula | $EC_{50}$ |
|---|---|---|---|---|
| 150 | 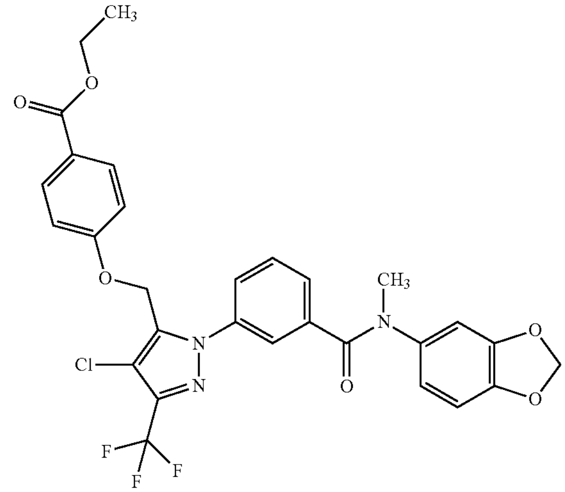 [SMILES: CCOC(=O)c1ccc(OCc2c(Cl)c(C(F)(F)F)nn2-c2cccc(C(=O)N(C)c3ccc4c(c3)OCO4)c2)cc1] | ethyl 4-[[2-[3-[1,3-benzodioxol-5-yl(methyl)carbamoyl]phenyl]-4-chloro-5-(trifluoromethyl)pyrazol-3-yl]methoxy]benzoate | C29H23ClF3N3O6 | +++ |
| 151 | 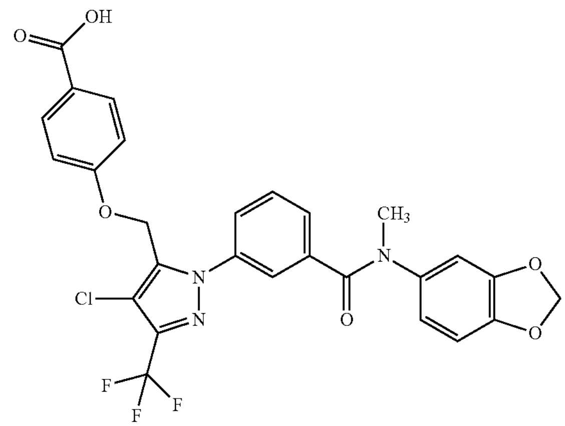 [SMILES: CN(C(=O)c1cccc(-n2nc(C(F)(F)F)c(Cl)c2COc2ccc(C(=O)O)cc2)c1)c1ccc2c(c1)OCO2] | 4-[[2-[3-[1,3-benzodioxol-5-yl(methyl)carbamoyl]phenyl]-4-chloro-5-(trifluoromethyl)pyrazol-3-yl]methoxy]benzoic acid | C27H19ClF3N3O6 | +++ |
| 152 | 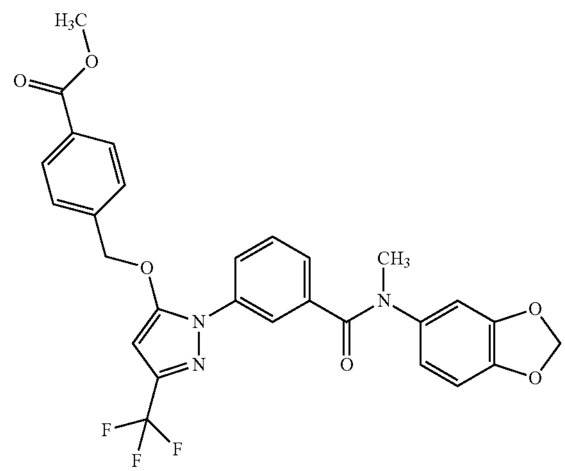 [SMILES: COC(=O)c1ccc(COc2cc(C(F)(F)F)nn2-c2cccc(C(=O)N(C)c3ccc4c(c3)OCO4)c2)cc1] | methyl 4-[[2-[3-[1,3-benzodioxol-5-yl(methyl)carbamoyl]phenyl]-5-(trifluoromethyl)pyrazol-3-yl]oxymethyl]benzoate | C28H22F3N3O6 | +++ |
| Int-153 | 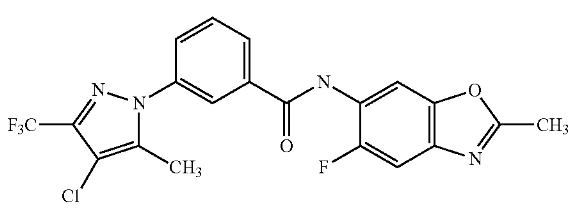 [SMILES: Cc1nc2cc(F)c(NC(=O)c3cccc(-n4nc(C(F)(F)F)c(Cl)c4C)c3)cc2o1] | 3-[4-chloro-5-methyl-3-(trifluoromethyl)pyrazol-1-yl]-N-(5-fluoro-2-methyl-1,3-benzoxazol-6-yl)benzamide | C20H13ClF4N4O2 | +++ |

TABLE 1-continued

| # | Substance Name | Substance Formula | EC50 |
|---|---|---|---|
| 154 | 3-[4-chloro-5-methyl-3-(trifluoromethyl)pyrazol-1-yl]-N-(5-fluoro-2-methyl-1,3-benzoxazol-6-yl)-N-methyl-benzamide | C21H15ClF4N4O2 | +++ |
| 155 | methyl 4-[[2-[3-[1,3-benzodioxol-5-yl(methyl)carbamoyl]phenyl]-4-chloro-5-(trifluoromethyl)pyrazol-3-yl]oxymethyl]benzoate | C28H21ClF3N3O6 | +++ |
| 156 | methyl 4-[[4-chloro-2-[3-[(6-chloro-1,3-benzodioxol-5-yl)-methyl-carbamoyl]phenyl]-5-(trifluoromethyl)pyrazol-3-yl]oxymethyl]benzoate | C28H20Cl2F3N3O6 | +++ |
| 157 | tert-butyl 4-[2-[3-[1,3-benzodioxol-5-yl(methyl)carbamoyl]phenyl]-4-chloro-5-(trifluoromethyl)pyrazol-3-yl]oxypiperidine-1-carboxylate | C29H30ClF3N4O6 | +++ |

TABLE 1-continued

| # | Compound structure | Substance Name | Substance Formula | EC$_{50}$ |
|---|---|---|---|---|
| 158 | 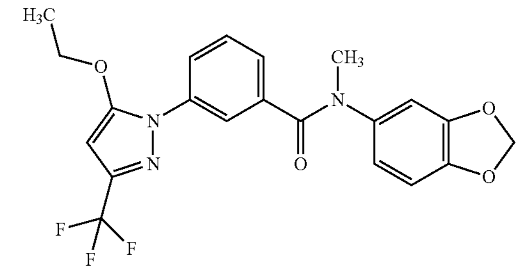 [SMILES: CCOc1cc(C(F)(F)F)nn1-c1cccc(C(=O)N(C)c2ccc3c(c2)OCO3)c1] | N-(1,3-benzodioxol-5-yl)-3-[5-ethoxy-3-(trifluoromethyl)pyrazol-1-yl]-N-methyl-benzamide | C21H18F3N3O4 | +++ |
| 159 | 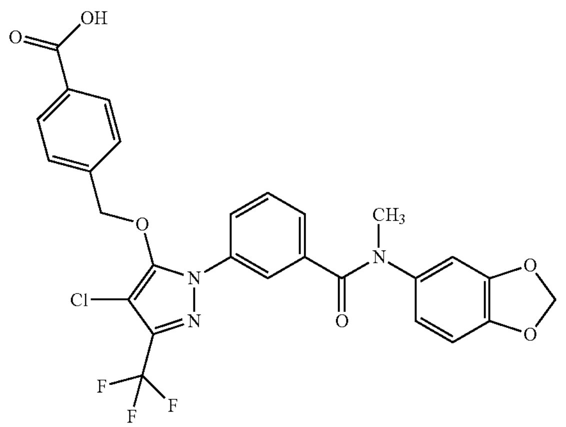 | 4-[[2-[3-[1,3-benzodioxol-5-yl(methyl)carbamoyl]phenyl]-4-chloro-5-(trifluoromethyl)pyrazol-3-yl]oxymethyl]benzoic acid | C27H19ClF3N3O6 | +++ |
| Int-160 | 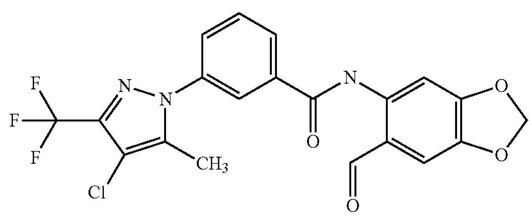 [SMILES: Cc1c(Cl)c(C(F)(F)F)nn1-c1cccc(C(=O)Nc2cc3c(cc2C=O)OCO3)c1] | 3-[4-chloro-5-methyl-3-(trifluoromethyl)pyrazol-1-yl]-N-(6-formyl-1,3-benzodioxol-5-yl)benzamide | C20H13ClF3N3O4 | + |
| 161 | 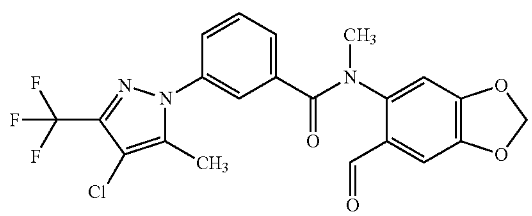 [SMILES: Cc1c(Cl)c(C(F)(F)F)nn1-c1cccc(C(=O)N(C)c2cc3c(cc2C=O)OCO3)c1] | 3-[4-chloro-5-methyl-3-(trifluoromethyl)pyrazol-1-yl]-N-(6-formyl-1,3-benzodioxol-5-yl)-N-methyl-benzamide | C21H15ClF3N3O4 | ++ |
| 162 | 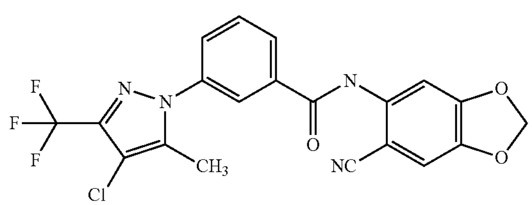 [SMILES: Cc1c(Cl)c(C(F)(F)F)nn1-c1cccc(C(=O)Nc2cc3c(cc2C#N)OCO3)c1] | 3-[4-chloro-5-methyl-3-(trifluoromethyl)pyrazol-1-yl]-N-(6-cyano-1,3-benzodioxol-5-yl)benzamide | C20H12ClF3N4O3 | + |
| 163 | 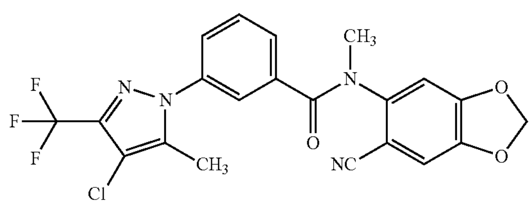 [SMILES: Cc1c(Cl)c(C(F)(F)F)nn1-c1cccc(C(=O)N(C)c2cc3c(cc2C#N)OCO3)c1] | 3-[4-chloro-5-methyl-3-(trifluoromethyl)pyrazol-1-yl]-N-(6-cyano-1,3-benzodioxol-5-yl)-N-methyl-benzamide | C21H14ClF3N4O3 | +++ |

TABLE 1-continued

| # | Compound structure | Substance Name | Substance Formula | $EC_{50}$ |
|---|---|---|---|---|
| 164 | 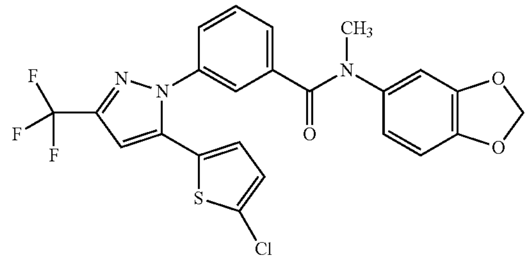 [SMILES: CN(C(=O)c1cccc(-n2nc(C(F)(F)F)cc2-c2ccc(Cl)s2)c1)c1ccc2c(c1)OCO2] | N-(1,3-benzodioxol-5-yl)-3-[5-(5-chloro-2-thienyl)-3-(trifluoromethyl)pyrazol-1-yl]-N-methyl-benzamide | C23H15ClF3N3O3S | +++ |
| 165 | 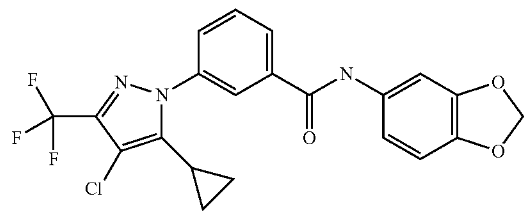 [SMILES: O=C(Nc1ccc2c(c1)OCO2)c1cccc(-n2nc(C(F)(F)F)c(Cl)c2C2CC2)c1] | N-(1,3-benzodioxol-5-yl)-3-[4-chloro-5-cyclopropyl-3-(trifluoromethyl)pyrazol-1-yl]benzamide | C21H15ClF3N3O3 | + |
| 166 | 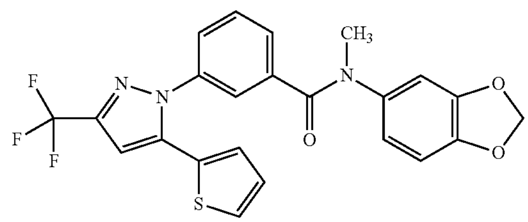 [SMILES: CN(C(=O)c1cccc(-n2nc(C(F)(F)F)cc2-c2cccs2)c1)c1ccc2c(c1)OCO2] | N-(1,3-benzodioxol-5-yl)-N-methyl-3-[5-(2-thienyl)-3-(trifluoromethyl)pyrazol-1-yl]benzamide | C23H16F3N3O3S | +++ |
| Int-167 | 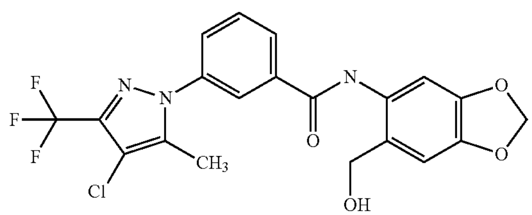 [SMILES: Cc1c(Cl)c(C(F)(F)F)nn1-c1cccc(C(=O)Nc2cc3c(cc2CO)OCO3)c1] | 3-[4-chloro-5-methyl-3-(trifluoromethyl)pyrazol-1-yl]-N-[6-(hydroxymethyl)-1,3-benzodioxol-5-yl]benzamide | C20H15ClF3N3O4 | +++ |
| 168 | 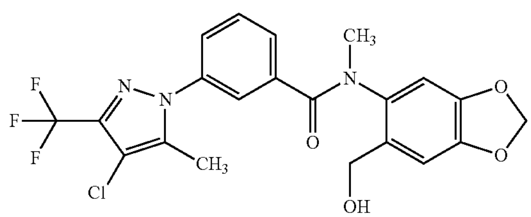 [SMILES: Cc1c(Cl)c(C(F)(F)F)nn1-c1cccc(C(=O)N(C)c2cc3c(cc2CO)OCO3)c1] | 3-[4-chloro-5-methyl-3-(trifluoromethyl)pyrazol-1-yl]-N-[6-(hydroxymethyl)-1,3-benzodioxol-5-yl]-N-methyl-benzamide | C21H17ClF3N3O4 | ++ |
| 169 | 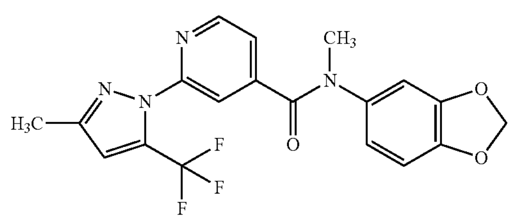 [SMILES: Cc1cc(C(F)(F)F)n(-c2cc(C(=O)N(C)c3ccc4c(c3)OCO4)ccn2)n1] | N-(1,3-benzodioxol-5-yl)-N-methyl-2-[3-methyl-5-(trifluoromethyl)pyrazol-1-yl]pyridine-4-carboxamide | C19H15F3N4O3 | + |
| 170 | 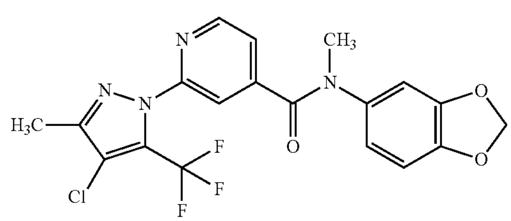 [SMILES: Cc1nn(-c2cc(C(=O)N(C)c3ccc4c(c3)OCO4)ccn2)c(C(F)(F)F)c1Cl] | N-(1,3-benzodioxol-5-yl)-2-[4-chloro-3-methyl-5-(trifluoromethyl)pyrazol-1-yl]-N-methyl-pyridine-4-carboxamide | C19H14ClF3N4O3 | + |

TABLE 1-continued

| # | Compound structure | Substance Name | Substance Formula | EC$_{50}$ |
|---|---|---|---|---|
| 171 | 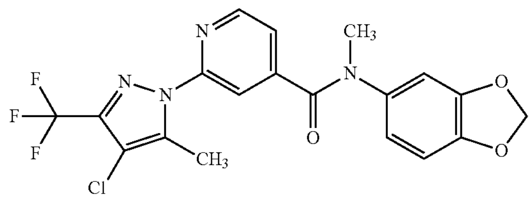 [SMILES: Cc1c(Cl)c(C(F)(F)F)nn1-c1cc(C(=O)N(C)c2ccc3c(c2)OCO3)ccn1] | N-(1,3-benzodioxol-5-yl)-2-[4-chloro-5-methyl-3-(trifluoromethyl)pyrazol-1-yl]-N-methyl-pyridine-4-carboxamide | C19H14ClF3N4O3 | +++ |
| Int-172 | 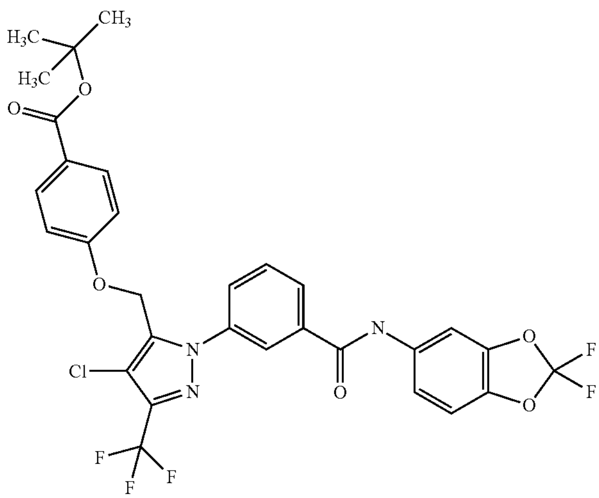 [SMILES: CC(C)(C)OC(=O)c1ccc(OCc2c(Cl)c(C(F)(F)F)nn2-c2cccc(C(=O)Nc3ccc4c(c3)OC(F)(F)O4)c2)cc1] | tert-butyl 4-[[4-chloro-2-[3-[(2,2-difluoro-1,3-benzodioxol-5-yl)carbamoyl]phenyl]-5-(trifluoromethyl)pyrazol-3-yl]methoxy]benzoate | C30H23ClF5N3O6 | + |
| 173 | 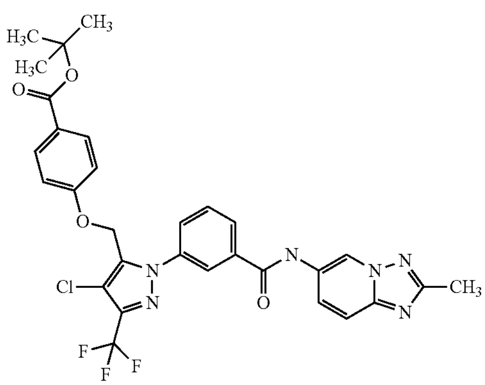 [SMILES: Cc1nc2ccc(NC(=O)c3cccc(-n4nc(C(F)(F)F)c(Cl)c4COc4ccc(C(=O)OC(C)(C)C)cc4)c3)cn2n1] | tert-butyl 4-[[4-chloro-2-[3-[(2-methyl-[1,2,4]triazolo[1,5-a]pyridin-6-yl)carbamoyl]phenyl]-5-(trifluoromethyl)pyrazol-3-yl]methoxy]benzoate | C30H26ClF3N6O4 | + |
| 174 | 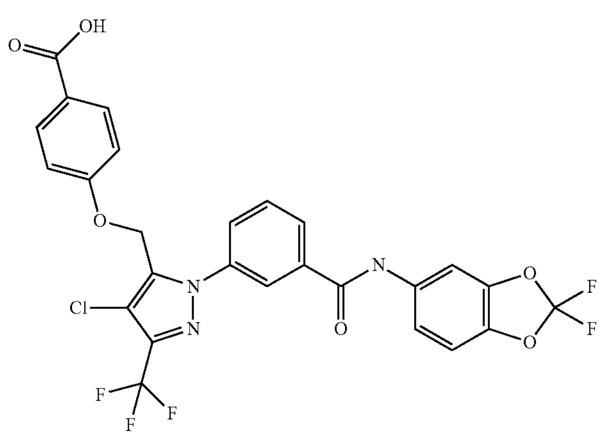 [SMILES: O=C(O)c1ccc(OCc2c(Cl)c(C(F)(F)F)nn2-c2cccc(C(=O)Nc3ccc4c(c3)OC(F)(F)O4)c2)cc1] | 4-[[4-chloro-2-[3-[(2,2-difluoro-1,3-benzodioxol-5-yl)carbamoyl]phenyl]-5-(trifluoromethyl)pyrazol-3-yl]methoxy]benzoic acid | C26H15ClF5N3O6 | + |

TABLE 1-continued

| # | Compound structure | Substance Name | Substance Formula | EC$_{50}$ |
|---|---|---|---|---|
| 175 | 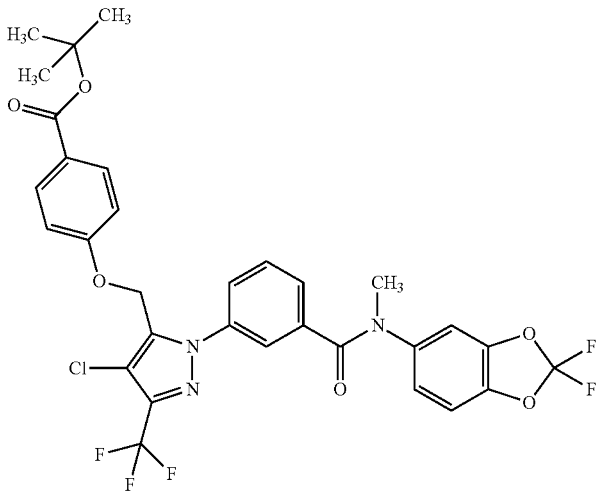 [SMILES: CN(C(=O)c1cccc(-n2nc(C(F)(F)F)c(Cl)c2COc2ccc(C(=O)OC(C)(C)C)cc2)c1)c1ccc2c(c1)OC(F)(F)O2] | tert-butyl 4-[[4-chloro-2-[3-[(2,2-difluoro-1,3-benzodioxol-5-yl)-methyl-carbamoyl]phenyl]-5-(trifluoromethyl)pyrazol-3-yl]methoxy]benzoate | C31H25ClF5N3O6 | +++ |
| 176 | 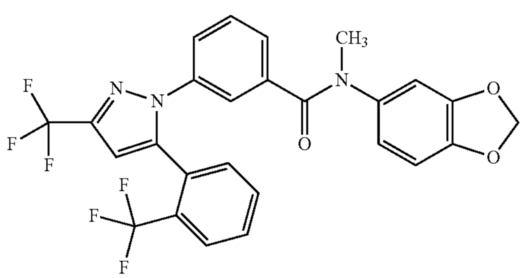 [SMILES: CN(C(=O)c1cccc(-n2nc(C(F)(F)F)cc2-c2ccccc2C(F)(F)F)c1)c1ccc2c(c1)OCO2] | N-(1,3-benzodioxol-5-yl)-N-methyl-3-[3-(trifluoromethyl)-5-[2-(trifluoromethyl)phenyl]pyrazol-1-yl]benzamide | C26H17F6N3O3 | +++ |
| 177 | 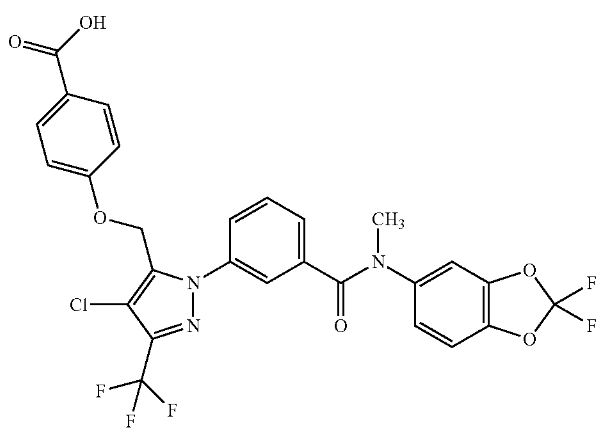 [SMILES: CN(C(=O)c1cccc(-n2nc(C(F)(F)F)c(Cl)c2COc2ccc(C(=O)O)cc2)c1)c1ccc2c(c1)OC(F)(F)O2] | 4-[[4-chloro-2-[3-[(2,2-difluoro-1,3-benzodioxol-5-yl)-methyl-carbamoyl]phenyl]-5-(trifluoromethyl)pyrazol-3-yl]methoxy]benzoic acid | C27H17ClF5N3O6 | +++ |
| Int-178 | 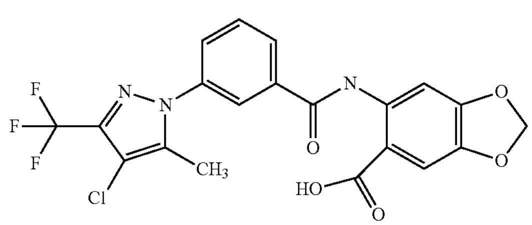 [SMILES: Cc1c(Cl)c(C(F)(F)F)nn1-c1cccc(C(=O)Nc2cc3c(cc2C(=O)O)OCO3)c1] | 6-[[3-[4-chloro-5-methyl-3-(trifluoromethyl)pyrazol-1-yl]benzoyl]amino]-1,3-benzodioxole-5-carboxylic acid | C20H13ClF3N3O5 | + |

TABLE 1-continued

| # | Compound structure | Substance Name | Substance Formula | EC$_{50}$ |
|---|---|---|---|---|
| 179 | 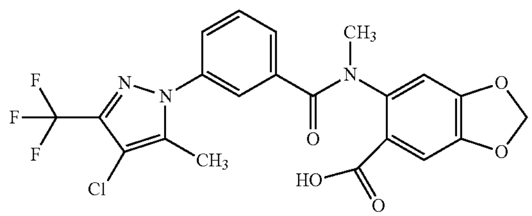 [SMILES: Cc1c(Cl)c(C(F)(F)F)nn1-c1cccc(C(=O)N(C)c2cc3c(cc2C(=O)O)OCO3)c1] | 6-[[3-[4-chloro-5-methyl-3-(trifluoromethyl)pyrazol-1-yl]benzoyl]-methyl-amino]-1,3-benzodioxole-5-carboxylic acid | C21H15ClF3N3O5 | + |
| 180 | 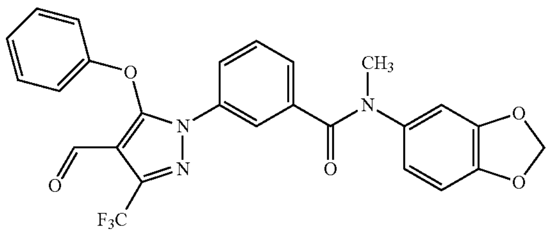 [SMILES: CN(C(=O)c1cccc(-n2nc(C(F)(F)F)c(C=O)c2Oc2ccccc2)c1)c1ccc2c(c1)OCO2] | N-(1,3-benzodioxol-5-yl)-3-[4-formyl-5-phenoxy-3-(trifluoromethyl)pyrazol-1-yl]-N-methyl-benzamide | C26H18F3N3O5 | +++ |
| 181 | 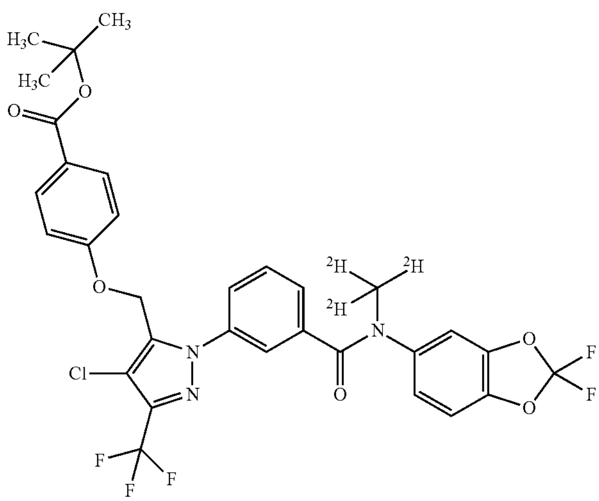 [SMILES: [2H]C([2H])([2H])N(C(=O)c1cccc(-n2nc(C(F)(F)F)c(Cl)c2COc2ccc(C(=O)OC(C)(C)C)cc2)c1)c1ccc2c(c1)OC(F)(F)O2] | tert-butyl 4-[[4-chloro-2-[3-[(2,2-difluoro-1,3-benzodioxol-5-yl)-(trideuteriomethyl)carbamoyl]phenyl]-5-(trifluoromethyl)pyrazol-3-yl]methoxy]benzoate | C31H22ClD3F5N3O6 | +++ |
| 182 | 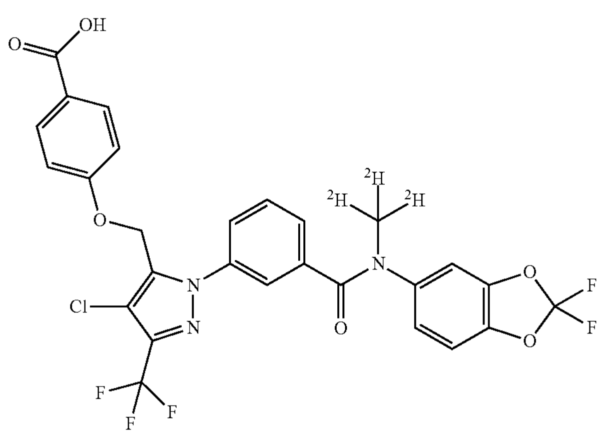 [SMILES: [2H]C([2H])([2H])N(C(=O)c1cccc(-n2nc(C(F)(F)F)c(Cl)c2COc2ccc(C(=O)O)cc2)c1)c1ccc2c(c1)OC(F)(F)O2] | 4-[[4-chloro-2-[3-[(2,2-difluoro-1,3-benzodioxol-5-yl)-(trideuteriomethyl)carbamoyl]phenyl]-5-(trifluoromethyl)pyrazol-3-yl]methoxy]benzoic acid | C27H14ClD3F5N3O6 | +++ |

TABLE 1-continued

| # | Compound structure | Substance Name | Substance Formula | EC₅₀ |
|---|---|---|---|---|
| 183 | 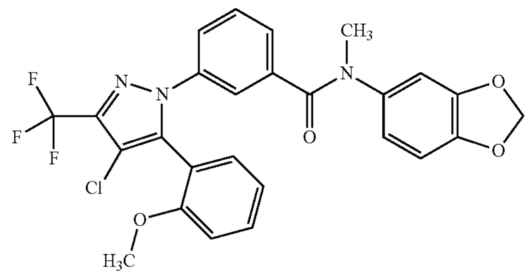 [SMILES: COc1ccccc1-c1c(Cl)c(C(F)(F)F)nn1-c1cccc(C(=O)N(C)c2ccc3c(c2)OCO3)c1] | N-(1,3-benzodioxol-5-yl)-3-[4-chloro-5-(2-methoxyphenyl)-3-(trifluoromethyl)pyrazol-1-yl]-N-methyl-benzamide | C26H19ClF3N3O4 | +++ |
| 184 | 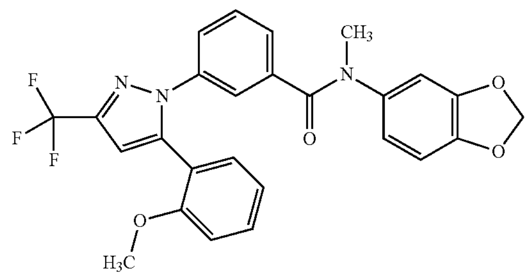 [SMILES: COc1ccccc1-c1cc(C(F)(F)F)nn1-c1cccc(C(=O)N(C)c2ccc3c(c2)OCO3)c1] | N-(1,3-benzodioxol-5-yl)-3-[5-(2-methoxyphenyl)-3-(trifluoromethyl)pyrazol-1-yl]-N-methyl-benzamide | C26H20F3N3O4 | +++ |
| 185 | 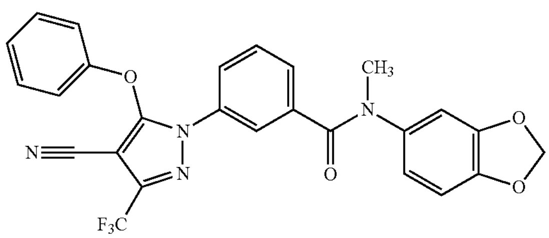 [SMILES: CN(C(=O)c1cccc(-n2nc(C(F)(F)F)c(C#N)c2Oc2ccccc2)c1)c1ccc2c(c1)OCO2] | N-(1,3-benzodioxol-5-yl)-3-[4-cyano-5-phenoxy-3-(trifluoromethyl)pyrazol-1-yl]-N-methyl-benzamide | C26H17F3N4O4 | +++ |
| 186 | 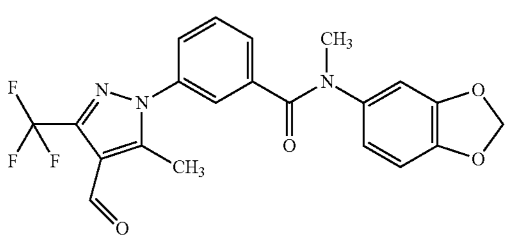 [SMILES: Cc1c(C=O)c(C(F)(F)F)nn1-c1cccc(C(=O)N(C)c2ccc3c(c2)OCO3)c1] | N-(1,3-benzodioxol-5-yl)-3-[4-formyl-5-methyl-3-(trifluoromethyl)pyrazol-1-yl]-N-methyl-benzamide | C21H16F3N3O4 | +++ |
| 187 | 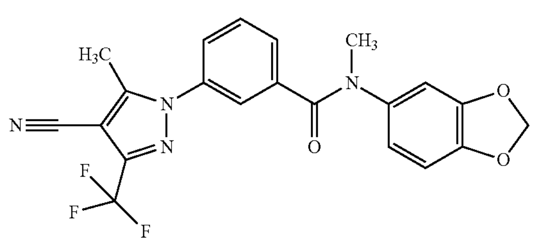 [SMILES: Cc1c(C#N)c(C(F)(F)F)nn1-c1cccc(C(=O)N(C)c2ccc3c(c2)OCO3)c1] | N-(1,3-benzodioxol-5-yl)-3-[4-cyano-5-methyl-3-(trifluoromethyl)pyrazol-1-yl]-N-methyl-benzamide | C21H15F3N4O3 | +++ |

TABLE 1-continued

| # | Compound structure | Substance Name | Substance Formula | EC$_{50}$ |
|---|---|---|---|---|
| 188 | 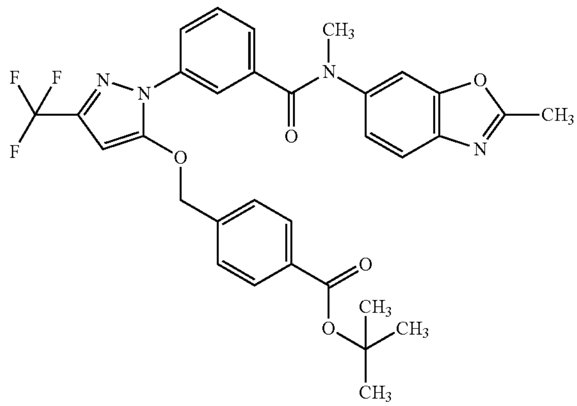 [SMILES: Cc1nc2ccc(N(C)C(=O)c3cccc(-n4nc(C(F)(F)F)cc4OCc4ccc(C(=O)OC(C)(C)C)cc4)c3)cc2o1] | tert-butyl 4-[[2-[3-[methyl-(2-methyl-1,3-benzoxazol-6-yl)carbamoyl]phenyl]-5-(trifluoromethyl)pyrazol-3-yl]oxymethyl]benzoate | C32H29F3N4O5 | +++ |
| 189 | 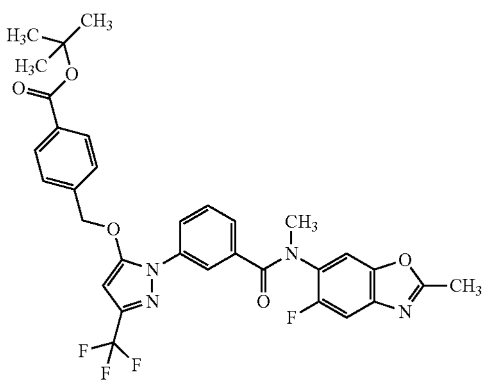 [SMILES: Cc1nc2cc(F)c(N(C)C(=O)c3cccc(-n4nc(C(F)(F)F)cc4OCc4ccc(C(=O)OC(C)(C)C)cc4)c3)cc2o1] | tert-butyl 4-[[2-[3-[(5-fluoro-2-methyl-1,3-benzoxazol-6-yl)-methyl-carbamoyl]phenyl]-5-(trifluoromethyl)pyrazol-3-yl]oxymethyl]benzoate | C32H28F4N4O5 | +++ |
| 190 | 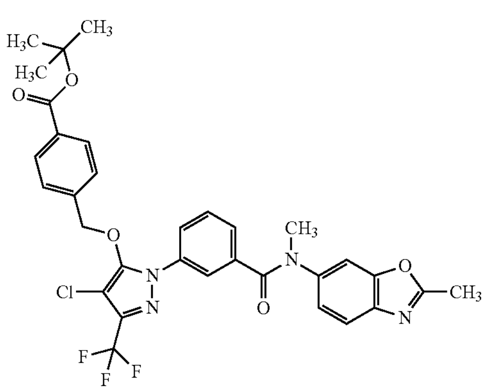 [SMILES: Cc1nc2ccc(N(C)C(=O)c3cccc(-n4nc(C(F)(F)F)c(Cl)c4OCc4ccc(C(=O)OC(C)(C)C)cc4)c3)cc2o1] | tert-butyl 4-[[4-chloro-2-[3-[methyl-(2-methyl-1,3-benzoxazol-6-yl)carbamoyl]phenyl]-5-(trifluoromethyl)pyrazol-3-yl]oxymethyl]benzoate | C32H28ClF3N4O5 | +++ |

| # | Substance Name | Substance Formula | EC$_{50}$ |
|---|---|---|---|
| 191 | tert-butyl 4-[[2-[3-[(2,2-difluoro-1,3-benzodioxol-5-yl)-methyl-carbamoyl]phenyl]-5-(trifluoromethyl)pyrazol-3-yl]oxymethyl]benzoate | C31H26F5N3O6 | +++ |
| 192 | N-(1,3-benzodioxol-5-yl)-N-methyl-3-[3-(2-pyridyl)-5-(trifluoromethyl)pyrazol-1-yl]benzamide | C24H17F3N4O3 | ++ |
| 193 | N-(1,3-benzodioxol-5-yl)-N-methyl-3-[5-(3-pyridyl)-3-(trifluoromethyl)pyrazol-1-yl]benzamide | C24H17F3N4O3 | +++ |
| 194 | N-(1,3-benzodioxol-5-yl)-N-methyl-3-[3-(3-pyridyl)-5-(trifluoromethyl)pyrazol-1-yl]benzamide | C24H17F3N4O3 | ++ |
| 195 | 4-[[2-[3-[methyl-(2-methyl-1,3-benzoxazol-6-yl)carbamoyl]phenyl]-5-(trifluoromethyl)pyrazol-3-yl]oxymethyl]benzoic acid | C28H21F3N4O5 | +++ |

TABLE 1-continued

| # | Compound structure | Substance Name | Substance Formula | EC$_{50}$ |
|---|---|---|---|---|
| 196 | 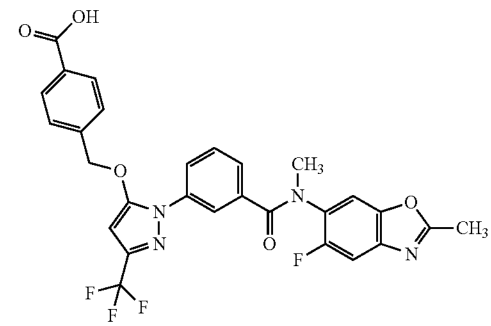 [SMILES: Cc1nc2cc(F)c(N(C)C(=O)c3cccc(-n4nc(C(F)(F)F)cc4OCc4ccc(C(=O)O)cc4)c3)cc2o1] | 4-[[2-[3-[(5-fluoro-2-methyl-1,3-benzoxazol-6-yl)-methyl-carbamoyl]phenyl]-5-(trifluoromethyl)pyrazol-3-yl]oxymethyl]benzoic acid | C28H20F4N4O5 | +++ |
| 197 | 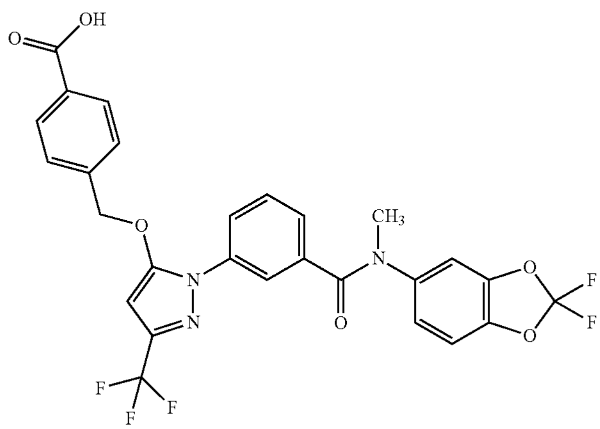 [SMILES: CN(C(=O)c1cccc(-n2nc(C(F)(F)F)cc2OCc2ccc(C(=O)O)cc2)c1)c1ccc2c(c1)OC(F)(F)O2] | 4-[[2-[3-[(2,2-difluoro-1,3-benzodioxol-5-yl)-methyl-carbamoyl]phenyl]-5-(trifluoromethyl)pyrazol-3-yl]oxymethyl]benzoic acid | C27H18F5N3O6 | +++ |
| 198 | 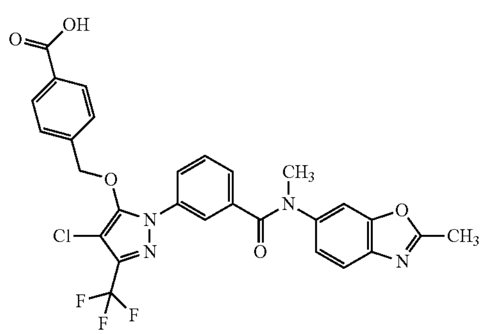 [SMILES: Cc1nc2ccc(N(C)C(=O)c3cccc(-n4nc(C(F)(F)F)c(Cl)c4OCc4ccc(C(=O)O)cc4)c3)cc2o1] | 4-[[4-chloro-2-[3-[methyl-(2-methyl-1,3-benzoxazol-6-yl)carbamoyl]phenyl]-5-(trifluoromethyl)pyrazol-3-yl]oxymethyl]benzoic acid | C28H20ClF3N4O5 | +++ |
| 200 | 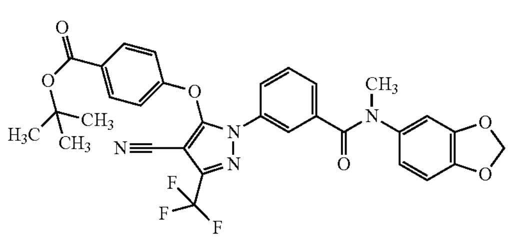 [SMILES: CN(C(=O)c1cccc(-n2nc(C(F)(F)F)c(C#N)c2Oc2ccc(C(=O)OC(C)(C)C)cc2)c1)c1ccc2c(c1)OCO2] | tert-butyl 4-[2-[3-[1,3-benzodioxol-5-yl(methyl)carbamoyl]phenyl]-4-cyano-5-(trifluoromethyl)pyrazol-3-yl]oxybenzoate | C31H25F3N4O6 | +++ |

TABLE 1-continued

| # | Compound structure | Substance Name | Substance Formula | EC$_{50}$ |
|---|---|---|---|---|
| 201 | 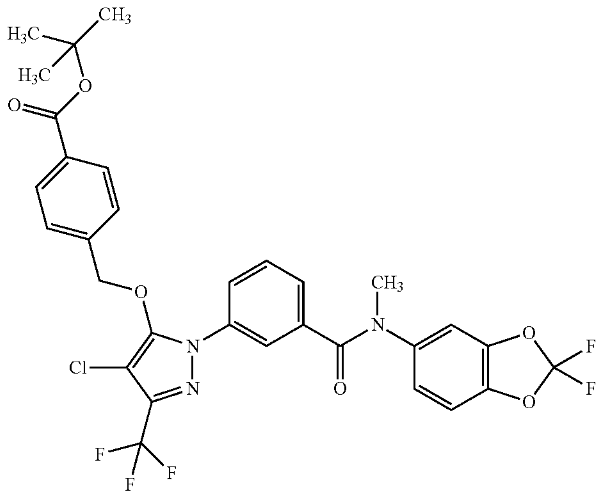 [SMILES: CN(C(=O)c1cccc(-n2nc(C(F)(F)F)c(Cl)c2OCc2ccc(C(=O)OC(C)(C)C)cc2)c1)c1ccc2c(c1)OC(F)(F)O2] | tert-butyl 4-[[4-chloro-2-[3-[(2,2-difluoro-1,3-benzodioxol-5-yl)-methyl-carbamoyl]phenyl]-5-(trifluoromethyl)pyrazol-3-yl]oxymethyl]benzoate | C31H25ClF5N3O6 | +++ |
| 202 | 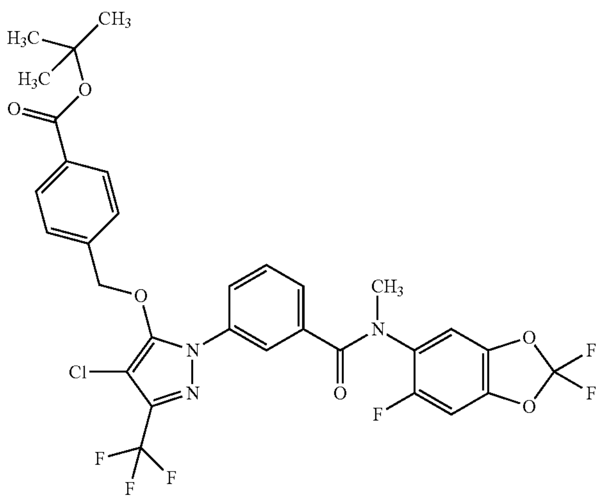 [SMILES: CN(C(=O)c1cccc(-n2nc(C(F)(F)F)c(Cl)c2OCc2ccc(C(=O)OC(C)(C)C)cc2)c1)c1cc2c(cc1F)OC(F)(F)O2] | tert-butyl 4-[[4-chloro-2-[3-[(5-fluoro-2-methyl-1,3-benzoxazol-6-yl)-methyl-carbamoyl]phenyl]-5-(trifluoromethyl)pyrazol-3-yl]oxymethyl]benzoate | C32H27ClF4N4O5 | +++ |
| Int-203 | 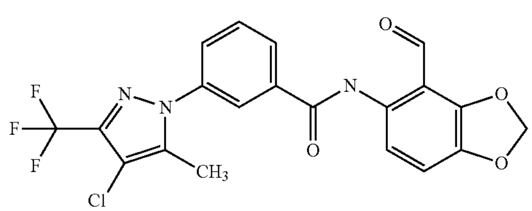 [SMILES: Cc1c(Cl)c(C(F)(F)F)nn1-c1cccc(C(=O)Nc2ccc3c(c2C=O)OCO3)c1] | 3-[4-chloro-5-methyl-3-(trifluoromethyl)pyrazol-1-yl]-N-(4-formyl-1,3-benzodioxol-5-yl)benzamide | C20H13ClF3N3O4 | + |
| 204 | 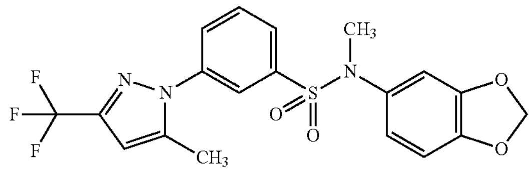 [SMILES: Cc1cc(C(F)(F)F)nn1-c1cccc(S(=O)(=O)N(C)c2ccc3c(c2)OCO3)c1] | N-(1,3-benzodioxol-5-yl)-N-methyl-3-[5-methyl-3-(trifluoromethyl)pyrazol-1-yl]benzenesulfonamide | C19H16F3N3O4S | ++ |
| 205 | 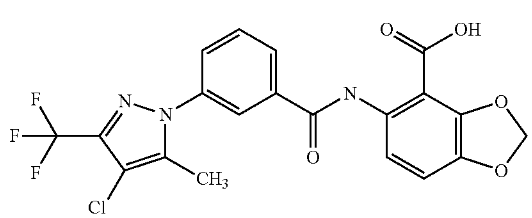 [SMILES: Cc1c(Cl)c(C(F)(F)F)nn1-c1cccc(C(=O)Nc2ccc3c(c2C(=O)O)OCO3)c1] | 5-[[3-[4-chloro-5-methyl-3-(trifluoromethyl)pyrazol-1-yl]benzoyl]amino]-1,3-benzodioxole-4-carboxylic acid | C20H13ClF3N3O5 | + |

TABLE 1-continued

| # | Compound structure | Substance Name | Substance Formula | EC$_{50}$ |
|---|---|---|---|---|
| 206 | 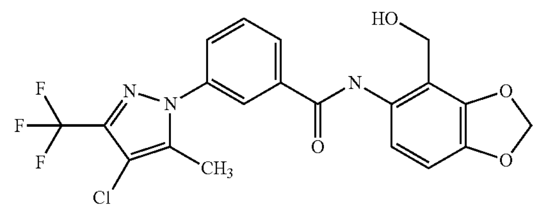 [SMILES: Cc1c(Cl)c(C(F)(F)F)nn1-c1cccc(C(=O)Nc2ccc3c(c2CO)OCO3)c1] | 3-[4-chloro-5-methyl-3-(trifluoromethyl)pyrazol-1-yl]-N-[4-(hydroxymethyl)-1,3-benzodioxol-5-yl]benzamide | C20H15ClF3N3O4 | + |
| 207 | 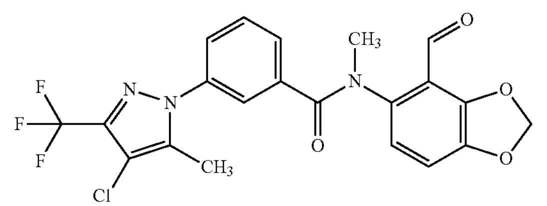 [SMILES: Cc1c(Cl)c(C(F)(F)F)nn1-c1cccc(C(=O)N(C)c2ccc3c(c2C=O)OCO3)c1] | 3-[4-chloro-5-methyl-3-(trifluoromethyl)pyrazol-1-yl]-N-(4-formyl-1,3-benzodioxol-5-yl)-N-methyl-benzamide | C21H15ClF3N3O4 | + |
| 208 | 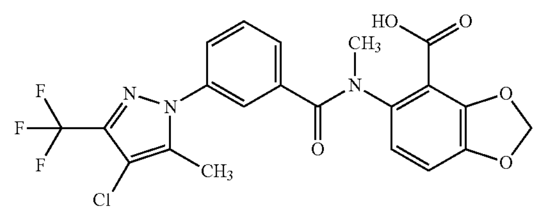 [SMILES: Cc1c(Cl)c(C(F)(F)F)nn1-c1cccc(C(=O)N(C)c2ccc3c(c2C(=O)O)OCO3)c1] | 5-[[3-[4-chloro-5-methyl-3-(trifluoromethyl)pyrazol-1-yl]benzoyl]-methyl-amino]-1,3-benzodioxole-4-carboxylic acid | C21H15ClF3N3O5 | + |
| 209 | 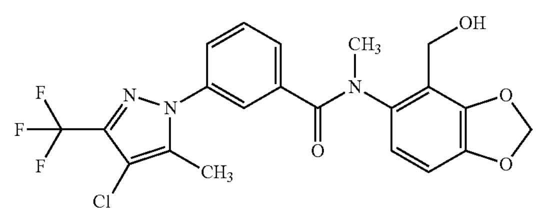 [SMILES: Cc1c(Cl)c(C(F)(F)F)nn1-c1cccc(C(=O)N(C)c2ccc3c(c2CO)OCO3)c1] | 3-[4-chloro-5-methyl-3-(trifluoromethyl)pyrazol-1-yl]-N-[4-(hydroxymethyl)-1,3-benzodioxol-5-yl]-N-methyl-benzamide | C21H17ClF3N3O4 | + |
| 210 | 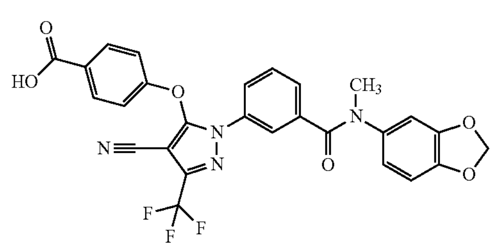 [SMILES: CN(C(=O)c1cccc(-n2nc(C(F)(F)F)c(C#N)c2Oc2ccc(C(=O)O)cc2)c1)c1ccc2c(c1)OCO2] | 4-[2-[3-[1,3-benzodioxol-5-yl(methyl)carbamoyl]phenyl]-4-cyano-5-(trifluoromethyl)pyrazol-3-yl]oxybenzoic acid | C27H17F3N4O6 | + |
| 211 | 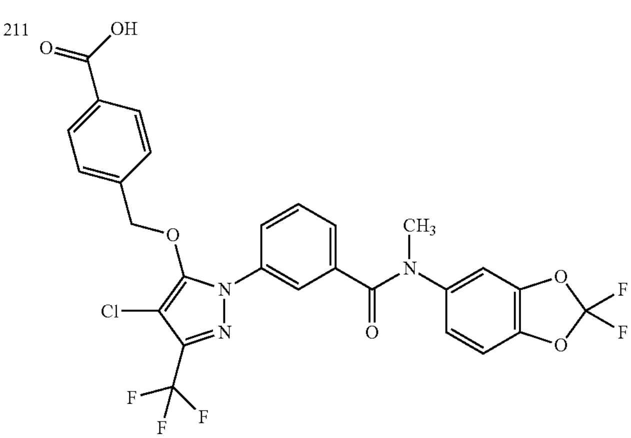 | 4-[[4-chloro-2-[3-[(2,2-difluoro-1,3-benzodioxol-5-yl)-methyl-carbamoyl]phenyl]-5-(trifluoromethyl)pyrazol-3-yl]oxymethyl]benzoic acid | C27H17ClF5N3O6 | +++ |

TABLE 1-continued

| # | Compound structure | Substance Name | Substance Formula | EC$_{50}$ |
|---|---|---|---|---|
| 212 | 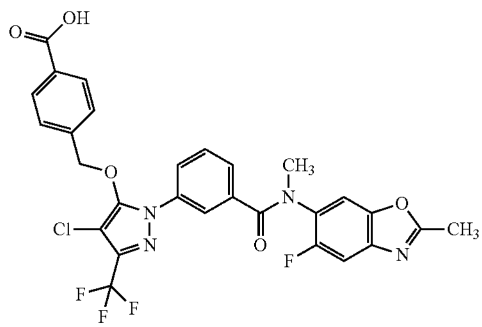 [SMILES: Cc1nc2cc(F)c(N(C)C(=O)c3cccc(-n4nc(C(F)(F)F)c(Cl)c4OCc4ccc(C(=O)O)cc4)c3)cc2o1] | 4-[[4-chloro-2-[3-[(5-fluoro-2-methyl-1,3-benzoxazol-6-yl)-methyl-carbamoyl]phenyl]-5-(trifluoromethyl)pyrazol-3-yl]oxymethyl]benzoic acid | C28H19ClF4N4O5 | +++ |
| 213 | 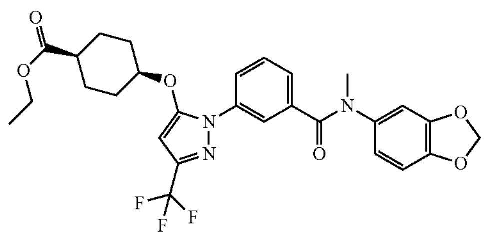 [SMILES: CCOC(=O)[C@H]1CC[C@@H](Oc2cc(C(F)(F)F)nn2-c2cccc(C(=O)N(C)c3ccc4c(c3)OCO4)c2)CC1] | ethyl-cis-4-[2-[3-[1,3-benzodioxol-5-yl(methyl)carbamoyl]phenyl]-5-(trifluoromethyl)pyrazol-3-yl]oxycyclohexanecarboxylate | C28H28F3N3O6 | |
| 214 | 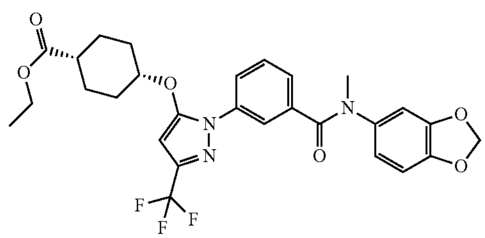 [SMILES: CCOC(=O)[C@H]1CC[C@@H](Oc2cc(C(F)(F)F)nn2-c2cccc(C(=O)N(C)c3ccc4c(c3)OCO4)c2)CC1] | ethyl 4-[2-[3-[1,3-benzodioxol-5-yl(methyl)carbamoyl]phenyl]-5-(trifluoromethyl)pyrazol-3-yl]oxycyclo-hexanecarboxylate | C28H28F3N3O6 | |
| 215 | 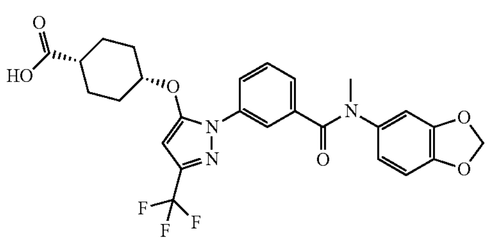 [SMILES: CN(C(=O)c1cccc(-n2nc(C(F)(F)F)cc2O[C@H]2CC[C@@H](C(=O)O)CC2)c1)c1ccc2c(c1)OCO2] | 4-[2-[3-[1,3-benzodioxol-5-yl(methyl)carbamoyl]phenyl]-5-(trifluoromethyl)pyrazol-3-yl]oxycyclohexanecarboxylic acid | C26H24F3N3O6 | +++ |
| 216 | 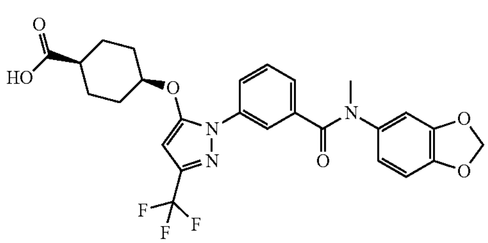 [SMILES: CN(C(=O)c1cccc(-n2nc(C(F)(F)F)cc2O[C@H]2CC[C@@H](C(=O)O)CC2)c1)c1ccc2c(c1)OCO2] | cis-4-[2-[3-[1,3-benzodioxol-5-yl(methyl)carbamoyl]phenyl]-5-(trifluoromethyl)pyrazol-3-yl]oxycyclo hexanecarboxylic acid | C26H24F3N3O6 | +++ |
| 217 | 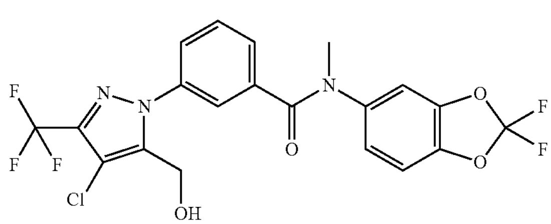 [SMILES: CN(C(=O)c1cccc(-n2nc(C(F)(F)F)c(Cl)c2CO)c1)c1ccc2c(c1)OC(F)(F)O2] | 3-[4-chloro-5-(hydroxymethyl)-3-(trifluoromethyl) pyrazol-1-yl]-N-(2,2-difluoro-1,3-benzodioxol-5-yl)-N-methyl-benzamide | C20H13ClF5N3O4 | +++ |

TABLE 1-continued

| # | Compound structure | Substance Name | Substance Formula | EC$_{50}$ |
|---|---|---|---|---|
| 218 | 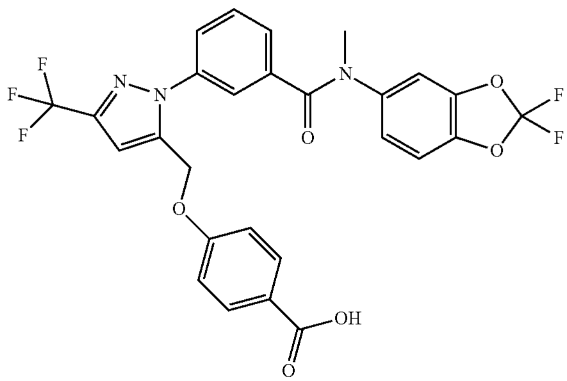 [SMILES: CN(C(=O)c1cccc(-n2nc(C(F)(F)F)cc2COc2ccc(C(=O)O)cc2)c1)c1ccc2c(c1)OC(F)(F)O2] | 4-[[2-[3-[(2,2-difluoro-1,3-benzodioxol-5-yl)-methyl-carbamoyl]phenyl]-5-(trifluoromethyl)pyrazol-3-yl]methoxy]benzoic acid | C27H18F5N3O6 | +++ |
| 223 | 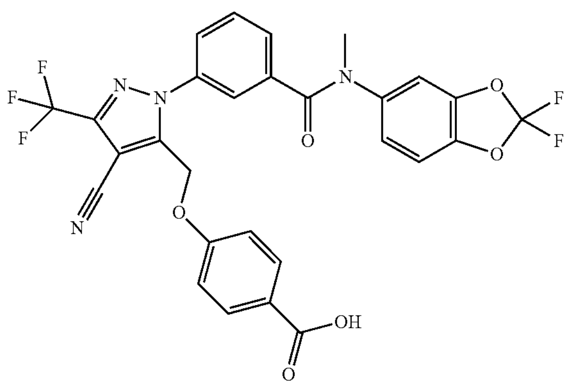 [SMILES: CN(C(=O)c1cccc(-n2nc(C(F)(F)F)c(C#N)c2COc2ccc(C(=O)O)cc2)c1)c1ccc2c(c1)OC(F)(F)O2] | 4-[[4-cyano-2-[3-[(2,2-difluoro-1,3-benzodioxol-5-yl)-methyl-carbamoyl]phenyl]-5-(trifluoromethyl)pyrazol-3-yl]oxymethyl]benzoic acid | C28H17F5N4O6 | +++ |
| 224 | 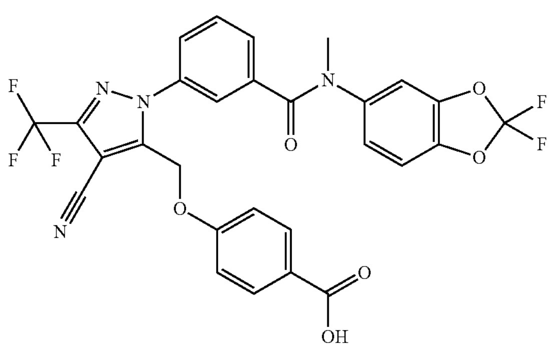 [SMILES: CN(C(=O)c1cccc(-n2nc(C(F)(F)F)c(C#N)c2COc2ccc(C(=O)O)cc2)c1)c1ccc2c(c1)OC(F)(F)O2] | 4-[[4-cyano-2-[3-[(2,2-difluoro-1,3-benzodioxol-5-yl)-methyl-carbamoyl]phenyl]-5-(trifluoromethyl)pyrazol-3-yl]methoxy]benzoic acid | C28H17F5N4O6 | +++ |
| 226 | 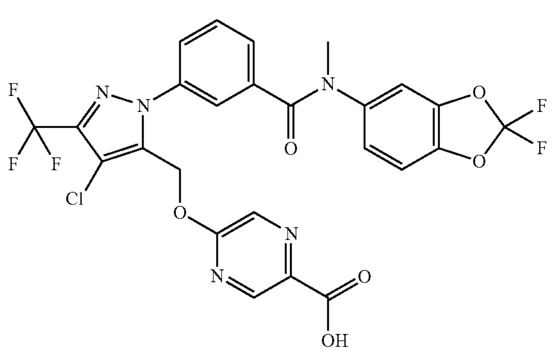 [SMILES: CN(C(=O)c1cccc(-n2nc(C(F)(F)F)c(Cl)c2COc2cnc(C(=O)O)cn2)c1)c1ccc2c(c1)OC(F)(F)O2] | 5-[[4-chloro-2-[3-[(2,2-difluoro-1,3-benzodioxol-5-yl)-methyl-carbamoyl]phenyl]-5-(trifluoromethyl)pyrazol-3-yl]methoxypyrazine-2-carboxylic acid | C25H15ClF5N5O6 | +++ |

TABLE 1-continued

| # | Compound structure | Substance Name | Substance Formula | EC$_{50}$ |
|---|---|---|---|---|
| 228 | 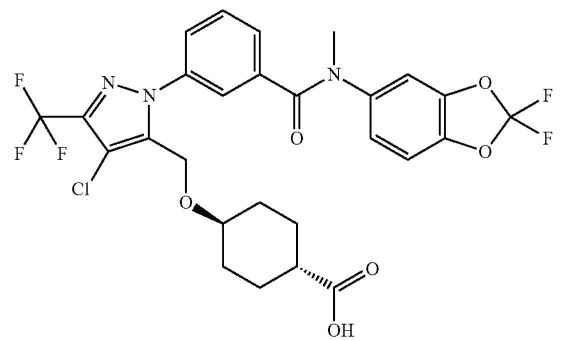 [SMILES: CN(C(=O)c1cccc(-n2nc(C(F)(F)F)c(Cl)c2CO[C@H]2CC[C@H](C(=O)O)CC2)c1)c1ccc2c(c1)OC(F)(F)O2] | Trans-4-[[4-chloro-2-[3-[(2,2-difluoro-1,3-benzodioxol-5-yl)-methyl-carbamoyl]phenyl]-5-(trifluoromethyl)pyrazol-3-yl]methoxy]cyclohexane-carboxylic acid | C27H23ClF5N3O6 | +++ |
| 233 | 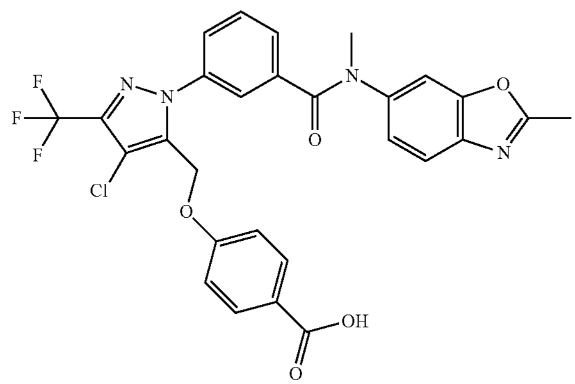 [SMILES: Cc1nc2ccc(N(C)C(=O)c3cccc(-n4nc(C(F)(F)F)c(Cl)c4COc4ccc(C(=O)O)cc4)c3)cc2o1] | 4-[[4-chloro-2-[3-[methyl-(2-methyl-1,3-benzoxazol-6-yl)carbamoyl]phenyl]-5-(trifluoromethyl)pyrazol-3-yl]methoxy]benzoic acid | C28H20ClF3N4O5 | +++ |
| 234 | 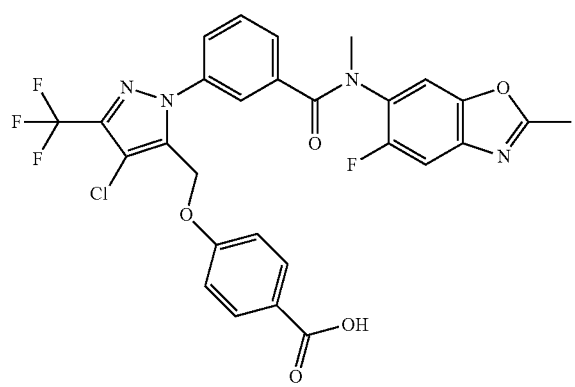 [SMILES: Cc1nc2cc(F)c(N(C)C(=O)c3cccc(-n4nc(C(F)(F)F)c(Cl)c4COc4ccc(C(=O)O)cc4)c3)cc2o1] | 4-[[4-chloro-2-[3-[(5-fluoro-2-methyl-1,3-benzoxazol-6-yl)-methyl-carbamoyl]phenyl]-5-(trifluoromethyl)pyrazol-3-yl]methoxy]benzoic acid | C28H19ClF4N4O5 | +++ |
| 236 | 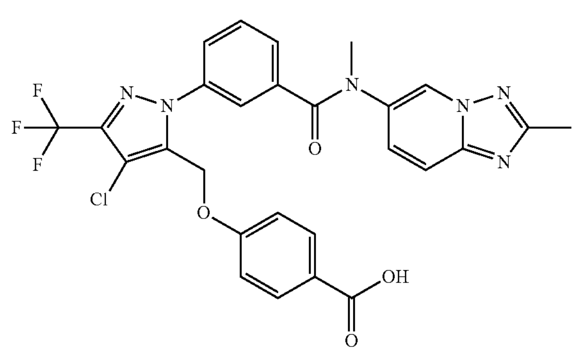 [SMILES: Cc1nc2ccc(N(C)C(=O)c3cccc(-n4nc(C(F)(F)F)c(Cl)c4COc4ccc(C(=O)O)cc4)c3)cn2n1] | 4-[[4-chloro-2-[3-[methyl-(2-methyl-[1,2,4]triazolo[1,5-a]pyridin-6-yl)carbamoyl]phenyl]-5-(trifluoromethyl)pyrazol-3-yl]methoxy]benzoic acid | C27H20ClF3N6O4 | +++ |

TABLE 1-continued

| # | Compound structure | Substance Name | Substance Formula | EC$_{50}$ |
|---|---|---|---|---|
| 238 | 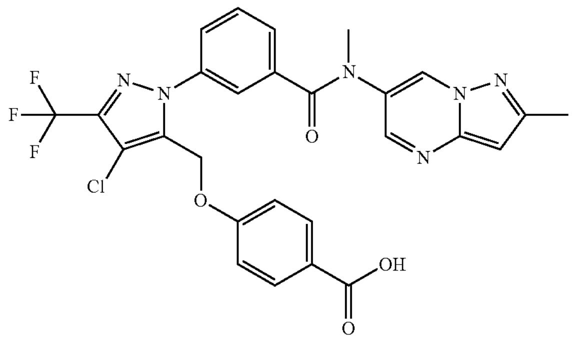 [SMILES: Cc1cc2ncc(N(C)C(=O)c3cccc(-n4nc(C(F)(F)F)c(Cl)c4COc4ccc(C(=O)O)cc4)c3)cn2n1] | 4-[[4-chloro-2-[3-[methyl-(2-methylpyrazolo[1,5-a]pyrimidin-6-yl)carbamoyl]phenyl]-5-(trifluoromethyl)pyrazol-3-yl]methoxy]benzoic acid | C27H20ClF3N6O4 | ++ |
| 239 | 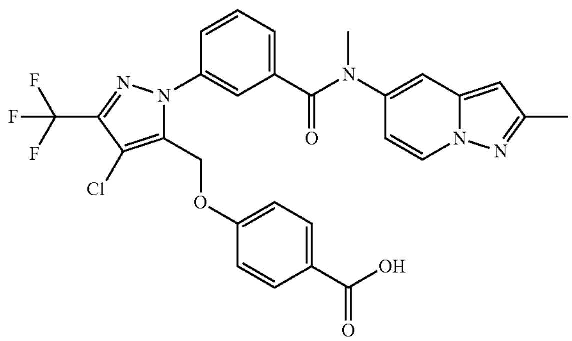 [SMILES: Cc1cc2cc(N(C)C(=O)c3cccc(-n4nc(C(F)(F)F)c(Cl)c4COc4ccc(C(=O)O)cc4)c3)ccn2n1] | 4-[[4-chloro-2-[3-[methyl-(2-methylpyrazolo[1,5-a]pyridin-5-yl)carbamoyl]phenyl]-5-(trifluoromethyl)pyrazol-3-yl]methoxy]benzoic acid | C28H21ClF3N5O4 | +++ |
| 245 | 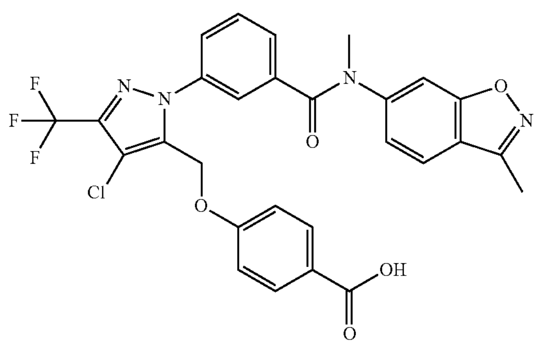 [SMILES: Cc1noc2cc(N(C)C(=O)c3cccc(-n4nc(C(F)(F)F)c(Cl)c4COc4ccc(C(=O)O)cc4)c3)ccc12] | 4-[[4-chloro-2-[3-[methyl-(3-methyl-1,2-benzoxazol-6-yl)carbamoyl]phenyl]-5-(trifluoromethyl)pyrazol-3-yl]methoxy]benzoic acid | C28H20ClF3N4O5 | +++ |
| 254 | 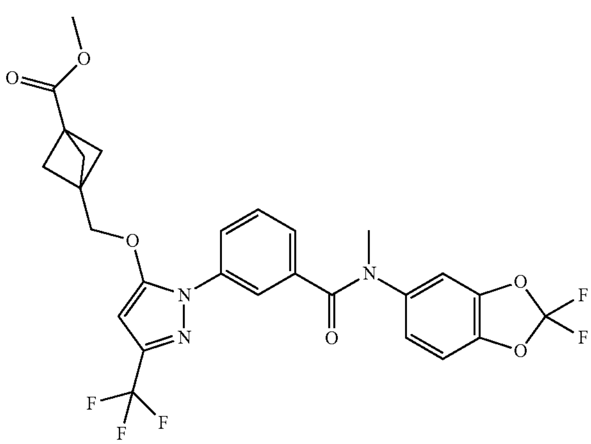 [SMILES: COC(=O)C12CC(COc3cc(C(F)(F)F)nn3-c3cccc(C(=O)N(C)c4ccc5c(c4)OC(F)(F)O5)c3)(C1)C2] | methyl 3-[[2-[3-[(2,2-difluoro-1,3-benzodioxol-5-yl)-methyl-carbamoyl]phenyl]-5-(trifluoromethyl)pyrazol-3-yl]oxymethyl]bicyclo[1.1.1]pentane-1-carboxylate | C27H22F5N3O6 | +++ |

| # | Compound structure | Substance Name | Substance Formula | $EC_{50}$ |
|---|---|---|---|---|
| 255 | 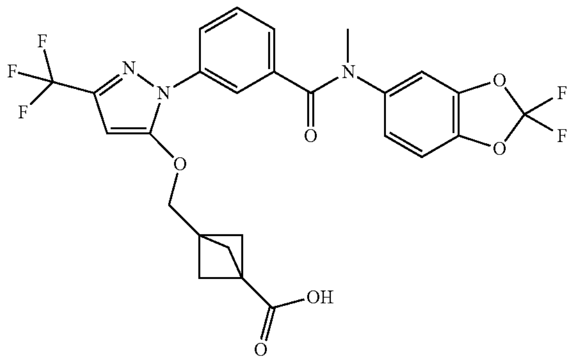 [SMILES: CN(C(=O)c1cccc(-n2nc(C(F)(F)F)cc2OCC23CC(C(=O)O)(C2)C3)c1)c1ccc2c(c1)OC(F)(F)O2] | 3-[[2-[3-[(2,2-difluoro-1,3-benzodioxol-5-yl)-methyl-carbamoyl]phenyl]-5-(trifluoromethyl)pyrazol-3-yl]oxymethyl]bicyclo[1.1.1]pentane-1-carboxylic acid | C26H20F5N3O6 | +++ |
| 256 | 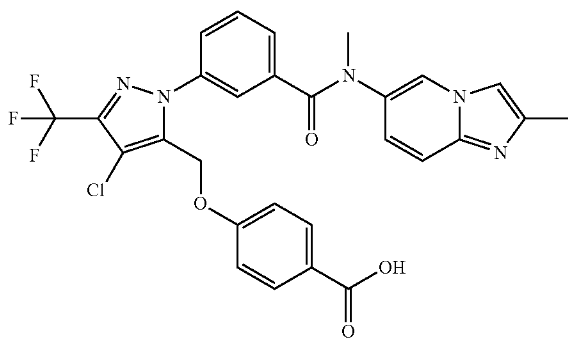 [SMILES: Cc1cn2cc(N(C)C(=O)c3cccc(-n4nc(C(F)(F)F)c(Cl)c4COc4ccc(C(=O)O)cc4)c3)ccc2n1] | 4-[[4-chloro-2-[3-[methyl-(2-methylimidazo[1,2-a]pyridin-6-yl)carbamoyl]phenyl]-5-(trifluoromethyl)pyrazol-3-yl]methoxy]benzoic acid | C28H21ClF3N5O4 | +++ |
| 257 | 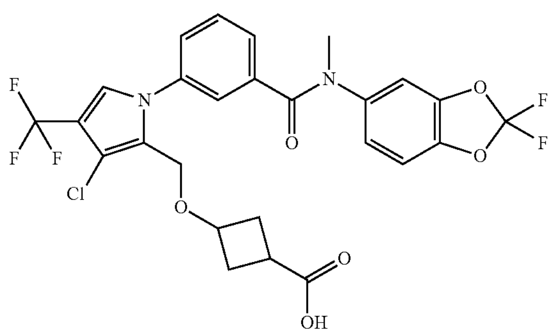 [SMILES: CN(C(=O)c1cccc(-n2cc(C(F)(F)F)c(Cl)c2COC2CC(C(=O)O)C2)c1)c1ccc2c(c1)OC(F)(F)O2] | 3-[[4-chloro-2-[3-[(2,2-difluoro-1,3-benzodioxol-5-yl)-methyl-carbamoyl]phenyl]-5-(trifluoromethyl)pyrazol-3-yl]methoxy]cyclobutane-carboxylic acid | C25H19ClF5N3O6 | +++ |
| 258 | 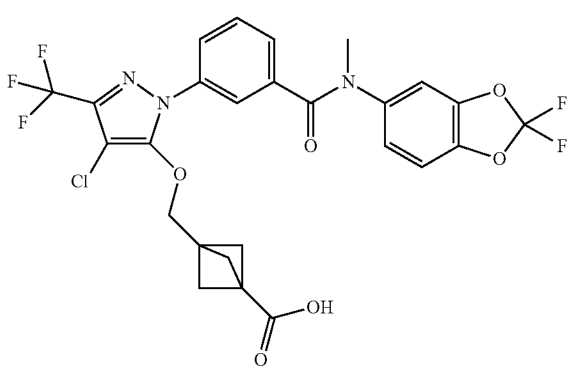 [SMILES: CN(C(=O)c1cccc(-n2nc(C(F)(F)F)c(Cl)c2OCC23CC(C(=O)O)(C2)C3)c1)c1ccc2c(c1)OC(F)(F)O2] | 3-[[4-chloro-2-[3-[(2,2-difluoro-1,3-benzodioxol-5-yl)-methyl-carbamoyl]phenyl]-5-(trifluoromethyl)pyrazol-3-yl]oxymethyl]bicyclo[1.1.1]pentane-1-carboxylic acid | C26H19ClF5N3O6 | +++ |

TABLE 1-continued

| # | Compound structure | Substance Name | Substance Formula | EC$_{50}$ |
|---|---|---|---|---|
| 259 | 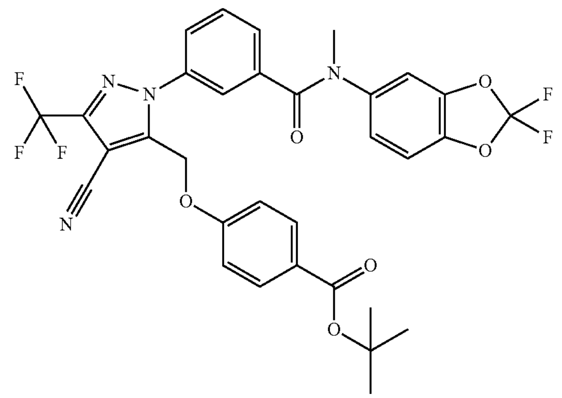 [SMILES: CN(C(=O)c1cccc(-n2nc(C(F)(F)F)c(C#N)c2COc2ccc(C(=O)OC(C)(C)C)cc2)c1)c1ccc2c(c1)OC(F)(F)O2] | tert-butyl 4-[[4-cyano-2-[3-[(2,2-difluoro-1,3-benzodioxol-5-yl)-methyl-carbamoyl]phenyl]-5-(trifluoromethyl)pyrazol-3-yl]methoxy]benzoate | C32H25F5N4O6 | +++ |
| 260 | 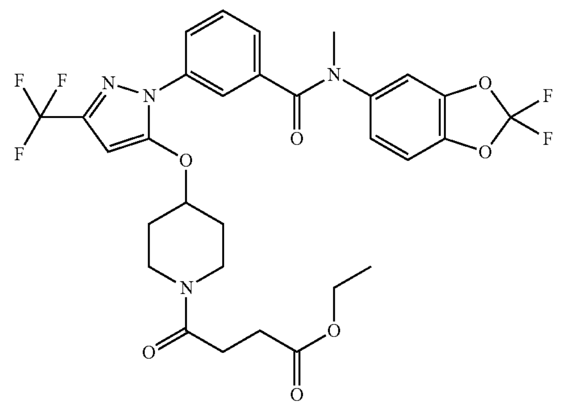 [SMILES: CCOC(=O)CCC(=O)N1CCC(Oc2cc(C(F)(F)F)nn2-c2cccc(C(=O)N(C)c3ccc4c(c3)OC(F)(F)O4)c2)CC1] | ethyl 4-[4-[2-[3-[(2,2-difluoro-1,3-benzodioxol-5-yl)-methyl-carbamoyl]phenyl]-5-(trifluoromethyl)pyrazol-3-yl]oxy-1-piperidyl]-4-oxo-butanoate | C30H29F5N4O7 | +++ |
| 261 | 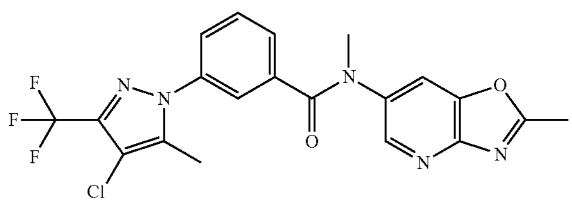 [SMILES: Cc1nc2ncc(N(C)C(=O)c3cccc(-n4nc(C(F)(F)F)c(Cl)c4C)c3)cc2o1] | 3-[4-chloro-5-methyl-3-(trifluoromethyl)pyrazol-1-yl]-N-methyl-N-(2-methyloxazolo[4,5-b]pyridin-6-yl)benzamide | C20H15ClF3N5O2 | ++ |
| 262 | 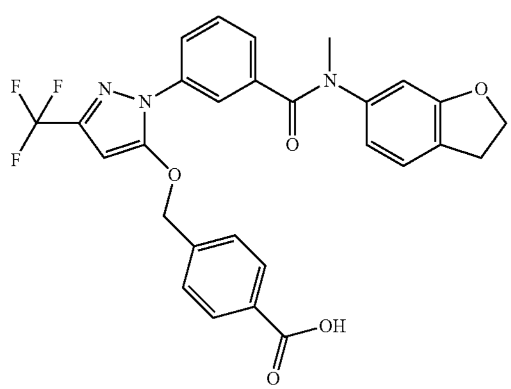 [SMILES: CN(C(=O)c1cccc(-n2nc(C(F)(F)F)cc2OCc2ccc(C(=O)O)cc2)c1)c1ccc2c(c1)OCC2] | 4-[[2-[3-[2,3-dihydrobenzofuran-6-yl(methyl)carbamoyl]phenyl]-5-(trifluoromethyl)pyrazol-3-yl]oxymethyl]benzoic acid | C28H22F3N3O5 | +++ |

TABLE 1-continued

| # | Compound structure | Substance Name | Substance Formula | EC$_{50}$ |
|---|---|---|---|---|
| 263 | 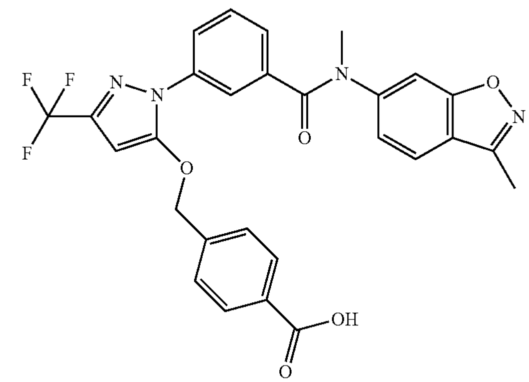 [SMILES: Cc1noc2cc(N(C)C(=O)c3cccc(-n4nc(C(F)(F)F)cc4OCc4ccc(C(=O)O)cc4)c3)ccc12] | 4-[[2-[3-[methyl-(3-methyl-1,2-benzoxazol-6-yl)carbamoyl]phenyl]-5-(trifluoromethyl)pyrazol-3-yl]oxymethyl]benzoic acid | C28H21F3N4O5 | + |
| 264 | 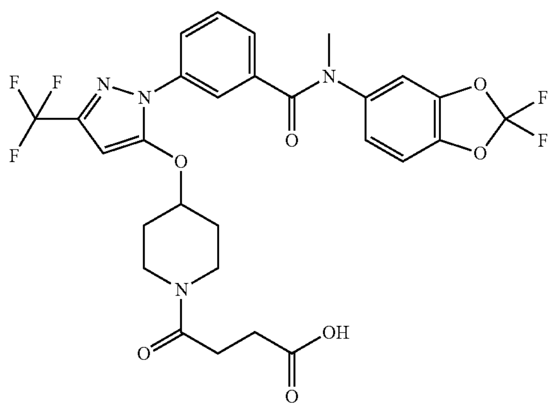 [SMILES: CN(C(=O)c1cccc(-n2nc(C(F)(F)F)cc2OC2CCN(C(=O)CCC(=O)O)CC2)c1)c1ccc2c(c1)OC(F)(F)O2] | 4-[4-[2-[3-[(2,2-difluoro-1,3-benzodioxol-5-yl)-methyl-carbamoyl]phenyl]-5-(trifluoromethyl)pyrazol-3-yl]oxy-1-piperidyl]-4-oxo-butanoic acid | C28H25F5N4O7 | ++ |
| 265 | 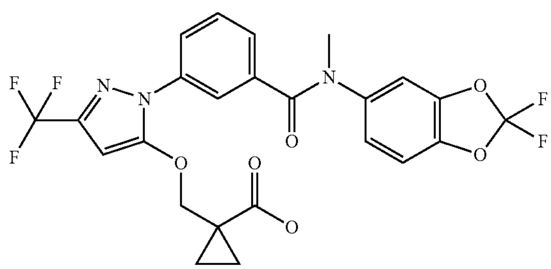 [SMILES: CN(C(=O)c1cccc(-n2nc(C(F)(F)F)cc2OCC2(C(=O)O)CC2)c1)c1ccc2c(c1)OC(F)(F)O2] | 1-[[2-[3-[(2,2-difluoro-1,3-benzodioxol-5-yl)-methyl-carbamoyl]phenyl]-5-(trifluoromethyl)pyrazol-3-yl]oxymethyl]cyclopropane-carboxylic acid | C24H18F5N3O6 | + |
| 266 | 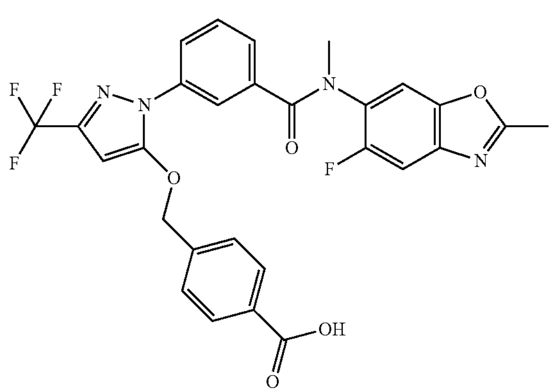 [SMILES: Cc1nc2cc(F)c(N(C)C(=O)c3cccc(-n4nc(C(F)(F)F)cc4OCc4ccc(C(=O)O)cc4)c3)cc2o1] | 4-[[2-[3-[(5-fluoro-2-methyl-1,3-benzoxazol-6-yl)-methyl-carbamoyl]phenyl]-5-(trifluoromethyl)pyrazol-3-yl]methoxy]benzoic acid | C28H20F4N4O5 | +++ |

TABLE 1-continued

| # | Compound structure | Substance Name | Substance Formula | EC$_{50}$ |
|---|---|---|---|---|
| 267 | 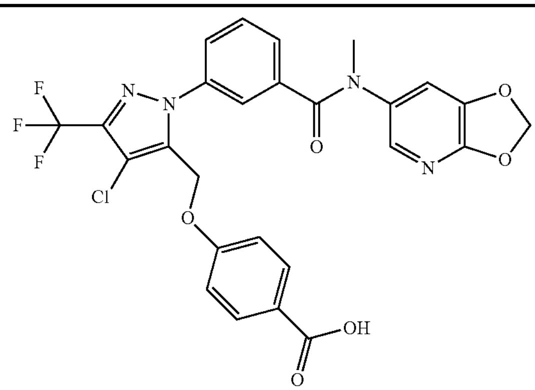 | 4-[[4-chloro-2-[3-[[1,3]dioxolo[4,5-b]pyridin-6-yl(methyl)carbamoyl]phenyl]-5-(trifluoromethyl)pyrazol-3-yl]methoxy]benzoic acid | C26H18ClF3N4O6 | +++ |
| 268 | 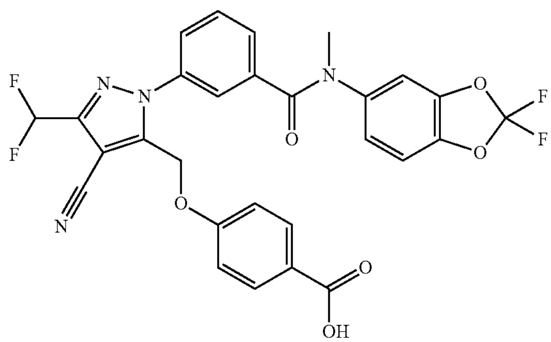 [SMILES: CN(C(=O)c1cccc(-n2nc(C(F)F)c(C#N)c2COc2ccc(C(=O)O)cc2)c1)c1ccc2c(c1)OC(F)(F)O2] | 4-[[4-cyano-2-[3-[(2,2-difluoro-1,3-benzodioxol-5-yl)-methyl-carbamoyl]phenyl]-5-(difluoromethyl)pyrazol-3-yl]methoxy]benzoic acid | C28H18F4N4O6 | +++ |
| 269 | 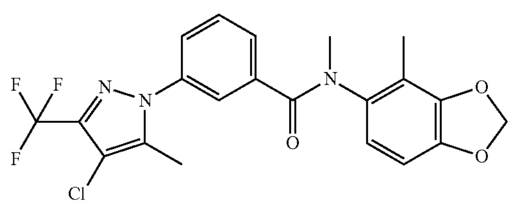 [SMILES: Cc1c(N(C)C(=O)c2cccc(-n3nc(C(F)(F)F)c(Cl)c3C)c2)ccc2c1OCO2] | 3-[4-chloro-5-methyl-3-(trifluoromethyl)pyrazol-1-yl]-N-methyl-N-(4-methyl-1,3-benzodioxol-5-yl)benzamide | C21H17ClF3N3O3 | + |

Transepithelial Electrical Conductance (TEEC)

FRT cells expressing F508del-CFTR were plated on HTS Transwell-24 well permeable supports (Code 3379, Corning Life Sciences) at a density of 200,000 cells/well. After six days, cells were incubated for 24 hrs with test correctors, vehicle, or VX-809. Compounds were dissolved in both basolateral (800 µL) and apical (300 µL) culture medium. After treatment, the culture medium was removed and replaced on both sides with a saline solution containing (in mM): 130 NaCl, 2.7 KCl, 1.5 KH$_2$PO$_4$, 1 CaCl$_2$), 0.5 MgCl$_2$, 10 glucose, 10 Na-Hepes (pH 7.4). The basolateral and apical side received 800 µL and 100 µL, respectively. The 24-well tray with cells was placed on a block heater (SBH 130D, Stuart) to keep the temperature at 37° C. during the entire experiment. After 10 min, the basal transepithelial electrical resistance (TEER) across each layer of FRT cells was measured with a STX100C electrode pair connected to an EVOM2 voltohmeter (World Precision Instruments). To stimulate F508del-CFTR, each well received (apical side) 50 µL of saline solution containing 60 µM forskolin and 150 µM genistein (final concentrations: 20 µM forskolin, 50 µM genistein). Forskolin was also pipetted in the basolateral medium to obtain the 20 µM concentration. After 10 min TEER was measured again in each well. To block F508del-CFTR function, the inhibitor PPQ-102 was used at the final concentration of 30 µM. To achieve the desired concentration, 75 µL of the apical solution in each well was replaced with an equal volume of saline solution containing 20 µM forskolin, 50 µM genistein, and 60 µM PPQ-102. After further 10 min, the transepithelial electrical resistance was measured. All values of TEER were converted to transepithelial electrical conductance (TEEC) using the formula TEEC=1/TEER. The parameter to indicate activity of F508del-CFTR in each well (ΔTEEC) was calculated from the difference in TEEC measured after maximal stimulation of F508del-CFTR with forskolin and genistein and after block with PPQ-102.

Corrector activities obtained on selected compounds tested at 5.0 µM (expressed as ΔTEEC values) are illustrated in table 2, wherein +: ΔTEEC<2000 µS; ++: 2000 µS<ΔTEEC<3000 µS; +++: ΔTEEC>3000 µS.

| # | Substance Name | activity |
|---|---|---|
| 009 | 3-(4-chloro-3,5-dimethyl-pyrazol-1-yl)-N-(2,2-difluoro-1,3-benzodioxol-5-yl)-N-methyl-benzamide | + |
| 075 | ethyl 2-[3-[1,3-benzodioxol-5-yl(methyl)carbamoyl]phenyl]-4-chloro-5-methyl-pyrazole-3-carboxylate | + |

-continued

| # | Substance Name | activity |
|---|---|---|
| 080 | 3-(4-chloro-3,5-dimethyl-pyrazol-1-yl)-N-(5-chloro-2-methyl-1,3-benzoxazol-6-yl)-N-methyl-benzamide | ++ |
| 089 | tert-butyl 2-[3-[1,3-benzodioxol-5-yl(methyl)carbamoyl]phenyl]-4-chloro-5-methyl-pyrazole-3-carboxylate | + |
| 090 | N-(1,3-benzodioxol-5-yl)-3-[4-chloro-5-methyl-3-(trifluoromethyl)pyrazol-1-yl]-N-methyl-benzamide | ++ |
| 098 | N-(1,3-benzodioxol-5-yl)-3-[4-bromo-5-methyl-3-(trifluoromethyl)pyrazol-1-yl]-N-methyl-benzamide | ++ |
| 099 | N-(1,3-benzodioxol-5-yl)-3-[3,5-dimethyl-4-(trifluoromethyl)pyrazol-1-yl]-N-methyl-benzamide | ++ |
| 100 | N-(1,3-benzodioxol-5-yl)-3-[5-isobutyl-3-(trifluoromethyl)pyrazol-1-yl]-N-methyl-benzamide | + |
| 108 | 3-[4-chloro-5-methyl-3-(trifluoromethyl)pyrazol-1-yl]-N-methyl-N-(2-methyl-1,3-benzoxazol-6-yl)benzamide | ++ |
| 113 | N-(1,3-benzodioxol-5-yl)-3-[4-chloro-5-ethoxy-3-(trifluoromethyl)pyrazol-1-yl]-N-methyl-benzamide | + |
| 125 | N-(1,3-benzodioxol-5-yl)-N-methyl-3-[5-phenyl-3-(trifluoromethyl)pyrazol-1-yl]benzamide | + |
| 141 | ethyl 4-[[2-[3-[1,3-benzodioxol-5-yl(methyl)carbamoyl]phenyl]-4-chloro-5-methyl-pyrazol-3-yl]methoxy]benzoate | ++ |
| 144 | 4-[[2-[3-[1,3-benzodioxol-5-yl(methyl)carbamoyl]phenyl]-4-chloro-5-methyl-pyrazol-3-yl]methoxy]benzoic acid | +++ |

Western Blot Analysis of F508del-CFTR Protein Maturation

Biochemical analysis of corrector effect was evaluated by determining the electrophoretic mobility of F508del-CFTR protein (Tomati et al., Sci Rep 5:12138, 2015). Under normal conditions, F508del-CFTR mostly migrates as a 150 kDa band that corresponds to the immature form of the protein (Band B). Active correctors cause appearance of the mature form of F508del-CFTR that migrates as a 180 kDa band (Band C). Cells expressing F508del-CFTR were grown to confluence on 60 mm diameter dishes and lysed in RIPA buffer containing a complete protease inhibitor (Roche). Lysate protein concentration was calculated using the BCA assay (Euroclone) following the manufacturer's instructions. Equal amounts of protein (30 µg total per lysate) were separated on 4-12% gradient NuPAGE Bis-Tris gels (Life Technologies) and analyzed by Western blotting. CFTR protein was detected with the mouse monoclonal anti-CFTR antibody (596, Cystic Fibrosis Foundation Therapeutics, University of North Carolina, Chapel Hill) diluted 1:5,000. GAPDH protein was detected with the mouse monoclonal anti-GAPDH antibody clone $6C_5$ (Santa Cruz Biotech Inc.) diluted 1:5,000. The secondary antibody was IgG goat anti-mouse (Ab 97023, Abcam) conjugated with horseradish peroxidase (HRP) and diluted 1:10,000. Proteins were visualized by chemiluminescence using the SuperSignal West Femto Substrate (Thermo Scientific). Chemiluminescence was monitored using the Molecular Imager ChemiDoc XRS System. Images were analyzed with ImageJ software (National Institutes of Health). Under control conditions, F508del-CFTR protein migrates as a 150 kDa.

FIG. 1 illustrates the analysis of electrophoretic mobility of mutant and wild type CFTR. The image shows a representative western blot experiment with lysates from parental FRT cells (no CFTR expressed), FRT cells expressing F508del-CFTR treated with correctors or vehicle, and FRT cells expressing wild type CFTR. In the immunoblot for CFTR, black and white arrowheads indicate the positions of band C and band B, respectively.

Short-Circuit Current Recordings on Human Bronchial Epithelial Cells

Human bronchial epithelial (HBE) cells obtained from CF patients (F508del/F508del genotype) were plated on Snapwell inserts (Code 3801, Corning Life Sciences) at a density of 500,000 cells per insert. Cells were cultured for two weeks in a differentiating medium whose compositions has been previously described (Scudieri et al., J Physiol 590: 6141-6155, 2012). For the first week, the medium was kept on both apical and basolateral sides of inserts (submerged condition). For the second week, the apical medium was removed (air-liquid condition, ALC). To test the activity of correctors, cells were treated for 24 hrs with compounds dissolved in the basolateral medium. After treatment, Snapwell inserts carrying differentiated bronchial epithelia were mounted in a vertical chamber resembling an Ussing system with internal fluid circulation. Both apical and basolateral hemichambers were filled with 5 mL of a Krebs bicarbonate solution containing (in mM): 126 NaCl, 0.38 $KH_2PO_4$, 2.13 $K_2HPO_4$, 1 $MgSO_4$, 1 $CaCl_2$, 24 $NaHCO_3$, and 10 glucose. Both sides were continuously bubbled with a gas mixture containing 5% $CO_2$-95% air and the temperature of the solution was kept at 37° C. The transepithelial voltage was short-circuited with a voltage-clamp (DVC-1000, World Precision Instruments) connected to the apical and basolateral chambers via Ag/AgCl electrodes and agar bridges (1 M KCl in 1% agar). The offset between voltage electrodes and the fluid resistance were canceled before experiments. The short-circuit current was recorded with a PowerLab 4/25 (ADInstruments) analogical to digital converter connected to a Macintosh computer. During recordings, cells were sequentially treated with: amiloride (10 µM, apical side) to block $Na^+$ absorption through ENaC channel; CPT-cAMP (100 µM, apical and basolateral side) plus VX-770 (1 µM, apical side) to stimulate F508del-CFTR activity; $CFTR_{inh}$-172 (10 µM, apical side) to fully inhibit F508del-CFTR. The difference between the current measured with CPT-cAMP plus potentiator and the current remaining after $CFTR_{inh}$-172 treatment ($\Delta I_{CFTR}$) was taken as the parameter reflecting F508del-CFTR expression in the apical membrane.

Activities of selected compounds on HBE cells (expressed as $\Delta I_{CFTR}$) are illustrated in table 3 wherein +: $\Delta I_{CFTR}<2.0$ µA; ++: 2.0 µA$<\Delta I_{CFTR}<3.0$ µA; +++: $\Delta I_{CFTR}>3.0$ µA.

TABLE 3

| # | Substance Name | activity |
|---|---|---|
| 009 | 3-(4-chloro-3,5-dimethyl-pyrazol-1-yl)-N-(2,2-difluoro-1,3-benzodioxol-5-yl)-N-methyl-benzamide | ++ |
| 075 | ethyl 2-[3-[1,3-benzodioxol-5-yl(methyl)carbamoyl]phenyl]-4-chloro-5-methyl-pyrazole-3-carboxylate | + |
| 080 | 3-(4-chloro-3,5-dimethyl-pyrazol-1-yl)-N-(5-chloro-2-methyl-1,3-benzoxazol-6-yl)-N-methyl-benzamide | ++ |
| 089 | tert-butyl 2-[3-[1,3-benzodioxol-5-yl(methyl)carbamoyl]phenyl]-4-chloro-5-methyl-pyrazole-3-carboxylate | +++ |
| 090 | N-(1,3-benzodioxol-5-yl)-3-[4-chloro-5-methyl-3-(trifluoromethyl)pyrazol-1-yl]-N-methyl-benzamide | +++ |

TABLE 3-continued

| # | Substance Name | activity |
|---|---|---|
| 098 | N-(1,3-benzodioxol-5-yl)-3-[4-bromo-5-methyl-3-(trifluoromethyl)pyrazol-1-yl]-N-methyl-benzamide | +++ |
| 099 | N-(1,3-benzodioxol-5-yl)-3-[3,5-dimethyl-4-(trifluoromethyl)pyrazol-1-yl]-N-methyl-benzamide | ++ |
| 100 | N-(1,3-benzodioxol-5-yl)-3-[5-isobutyl-3-(trifluoromethyl)pyrazol-1-yl]-N-methyl-benzamide | + |
| 108 | 3-[4-chloro-5-methyl-3-(trifluoromethyl)pyrazol-1-yl]-N-methyl-N-(2-methyl-1,3-benzoxazol-6-yl)benzamide | + |
| 113 | N-(1,3-benzodioxol-5-yl)-3-[4-chloro-5-ethoxy-3-(trifluoromethyl)pyrazol-1-yl]-N-methyl-benzamide | + |
| 125 | N-(1,3-benzodioxol-5-yl)-N-methyl-3-[5-phenyl-3-(trifluoromethyl)pyrazol-1-yl]benzamide | + |
| 141 | ethyl 4-[[2-[3-[1,3-benzodioxol-5-yl(methyl)carbamoyl]phenyl]-4-chloro-5-methyl-pyrazol-3-yl]methoxy]benzoate | +++ |
| 144 | 4-[[2-[3-[1,3-benzodioxol-5-yl(methyl)carbamoyl]phenyl]-4-chloro-5-methyl-pyrazol-3-yl]methoxy]benzoic acid | ++ |

The invention claimed is:

1. A compound, a pharmaceutically acceptable salt of said compound, or a solvate of said compound, wherein the compound is selected from the group consisting of:

| # | Substance Name |
|---|---|
| 4 | 3-(4-chloro-3,5-dimethyl-pyrazol-1-yl)-N-(2,3-dihydro-1,4-benzodioxin-6-yl)-N-ethyl-benzamide, |
| 7 | 3-(4-chloro-3,5-dimethyl-pyrazol-1-yl)-N-methyl-N-phenyl-benzamide, |
| 8 | 3-(4-chloro-3,5-dimethyl-pyrazol-1-yl)-N-methyl-N-(2,2,3,3-tetrafluoro-1,4-benzodioxin-6-yl)benzamide, |
| 9 | 3-(4-chloro-3,5-dimethyl-pyrazol-1-yl)-N-(2,2-difluoro-1,3-benzodioxol-5-yl)-N-methyl-benzamide |
| 10 | N-(2,3-dihydro-1,4-benzodioxin-6-yl)-N-methyl-3-pyrazol-1-yl-benzamide, |
| 11 | N-(2,3-dihydro-1,4-benzodioxin-6-yl)-3-(3,5-dimethylpyrazol-1-yl)-N-methyl-benzamide, |
| 14 | 3-(4-chloro-3,5-dimethyl-pyrazol-1-yl)-N-(3,4-dimethoxyphenyl)-N-methyl-benzamide, |
| 15 | N-(1,3-benzodioxol-5-yl)-3-(4-chloro-3,5-dimethyl-pyrazol-1-yl)-N-methyl-benzamide, |
| 17 | N-(2,3-dihydro-1,4-benzodioxin-6-yl)-3-(3,5-dimethylpyrazol-1-yl)-N-methyl-benzenesulfonamide, |
| 19 | 3-(4-chloro-3,5-dimethyl-pyrazol-1-yl)-N-(2,2-difluoro-1,3-benzodioxol-5-yl)-N-ethyl-benzamide, |
| 20 | 3-(4-chloro-3,5-dimethyl-pyrazol-1-yl)-N-(2,3-dihydro-1,4-benzodioxin-6-yl)-N-methyl-benzenesulfonamide, |
| 23 | 3-(4-chloro-3,5-dimethyl-pyrazol-1-yl)-N-indan-5-yl-N-methyl-benzamide, |
| 24 | 3-(4-chloro-3,5-dimethyl-pyrazol-1-yl)-N-methyl-N-(1-methylbenzimidazol-5-yl)benzamide, |
| 25 | 3-(4-chloro-3,5-dimethyl-pyrazol-1-yl)-N-methyl-N-(2-methyl-1,3-benzoxazol-5-yl)benzamide, |
| 29 | N-(1,3-benzoxazol-5-yl)-3-(4-chloro-3,5-dimethyl-pyrazol-1-yl)-N-methyl-benzamide, |
| 31 | 5-(4-chloro-3,5-dimethyl-pyrazol-1-yl)-N-(2,3-dihydro-1,4-benzodioxin-6-yl)-N,2-dimethyl-benzamide, |
| 32 | N-(6-chloro-2,3-dihydro-1,4-benzodioxin-7-yl)-3-(4-chloro-3,5-dimethyl-pyrazol-1-yl)-N-methyl-benzamide, |
| 33 | 3-(4-chloropyrazol-1-yl)-N-(2,3-dihydro-1,4-benzodioxin-6-yl)-N-methyl-benzamide, |
| 34 | 3-(4-chloro-3,5-dimethyl-pyrazol-1-yl)-N-(2,2-dimethyl-1,3-benzodioxol-5-yl)-N-methyl-benzamide, |
| 35 | 3-(4-chloro-3,5-dimethyl-pyrazol-1-yl)-N-(2,2-difluoro-1,3-benzodioxol-5-yl)-N-methyl-benzenesulfonamide, |
| 36 | 3-(4-chloro-3,5-dimethyl-pyrazol-1-yl)-N-(3,4-dihydro-2H-1,4-benzoxazin-7-yl)-N-methyl-benzamide; 2,2,2-trifluoroacetic acid, |
| 37 | 3-(4-tert-butyl-3,5-dimethyl-pyrazol-1-yl)-N-(2,3-dihydro-1,4-benzodioxin-6-yl)-N-methyl-benzamide, |
| 38 | 3-(4-chloro-3,5-dimethyl-pyrazol-1-yl)-N-(3,4-dihydro-2H-1,4-benzoxazin-6-yl)-N-methyl-benzamide; 2,2,2-trifluoroacetic acid, |
| 42 | 3-(4-chloro-3,5-dimethyl-pyrazol-1-yl)-N-methyl-N-(6-methyl-1,3-benzodioxol-5-yl)benzamide, |
| 43 | ethyl 1-[3-[1,3-benzodioxol-5-yl(methyl)carbamoyl] phenyl]-3,5-dimethyl-pyrazole-4-carboxylate, |
| 44 | 3-(4-chloro-3,5-dimethyl-pyrazol-1-yl)-N-methyl-N-tetralin-6-yl-benzamide, |
| 47 | 3-(4-chloro-3,5-dimethyl-pyrazol-1-yl)-N-methyl-N-(2-methyl-1,3-benzoxazol-6-yl)benzamide, |
| 48 | 1-[3-[1,3-benzodioxol-5-yl(methyl)carbamoyl]phenyl]-3,5-dimethyl-pyrazole-4-carboxylic acid, |
| 49 | N-(6-chloro-2,2-difluoro-1,3-benzodioxol-5-yl)-3-(4-chloro-3,5-dimethyl-pyrazol-1-yl)-N-methyl-benzamide, |
| 55 | 3-(4-chloro-3,5-dimethyl-pyrazol-1-yl)-N-(2-cyclopropyl-1,3-benzoxazol-5-yl)-N-methyl-benzamide, |
| 56 | 1-[3-[1,3-benzodioxol-5-yl(methyl)carbamoyl]phenyl]-3,5-dimethyl-pyrazole-4-carboxamide, |

-continued

| # | Substance Name |
|---|---|
| 57 | 3-(4-chloro-3,5-dimethyl-pyrazol-1-yl)-N-(1,3-dihydroisobenzofuran-5-yl)-N-methyl-benzamide, |
| 58 | 3-(4-chloro-3,5-dimethyl-pyrazol-1-yl)-N-(2,3-dihydrobenzofuran-5-yl)-N-methyl-benzamide, |
| 59 | 1-[3-[1,3-benzodioxol-5-yl(methyl)carbamoyl]phenyl]-N-(2-hydroxyethyl)-3,5-dimethyl-pyrazole-4-carboxamide, |
| 62 | 3-(4-chloro-3,5-dimethyl-pyrazol-1-yl)-N-(2-isopropyl-1,3-benzoxazol-5-yl)-N-methyl-benzamide, |
| 64 | 3-(4-chloro-3,5-dimethyl-pyrazol-1-yl)-N-(2-methoxy-1,3-benzoxazol-5-yl)-N-methyl-benzamide, |
| 65 | 2-[3-[1,3-benzodioxol-5-yl(methyl)carbamoyl]phenyl]-5-methyl-pyrazole-3-carboxylic acid, |
| 66 | 1-[3-[1,3-benzodioxol-5-yl(methyl)carbamoyl]phenyl]-5-methyl-pyrazole-3-carboxylic acid, |
| 67 | ethyl 1-[3-[1,3-benzodioxol-5-yl(methyl) carbamoyl]phenyl]-4-chloro-5-methyl-pyrazole-3-carboxylate, |
| 68 | 3-(4-chloro-3,5-dimethyl-pyrazol-1-yl)-N-(3-methoxyphenyl)-N-methyl-benzamide, |
| 69 | 1-[3-[1,3-benzodioxol-5-yl(methyl)carbamoyl]phenyl]-4-chloro-5-methyl-pyrazole-3-carboxylic acid, |
| 70 | N-(1,3-benzodioxol-5-yl)-3-[5-(hydroxymethyl)-3-methyl-pyrazol-1-yl]-N-methyl-benzamide, |
| 71 | N-(1,3-benzodioxol-5-yl)-3-(4-chloro-3,5-dimethyl-pyrazol-1-yl)-N-methyl-4-(trifluoromethyl)benzamide, |
| 72 | N-(1,3-benzodioxol-5-yl)-2-(4-chloro-3,5-dimethyl-pyrazol-1-yl)-N-methyl-pyrimidine-4-carboxamide, |
| 73 | N-(1,3-benzodioxol-5-yl)-3-[4-chloro-3-(hydroxymethyl)-5-methyl-pyrazol-1-yl]-N-methyl-benzamide, |
| 74 | 1-[3-[1,3-benzodioxol-5-yl(methyl)carbamoyl]phenyl]-4-chloro-5-methyl-pyrazole-3-carboxamide, |
| 75 | ethyl 2-[3-[1,3-benzodioxol-5-yl(methyl)carbamoyl]phenyl]-4-chloro-5-methyl-pyrazole-3-carboxylate, |
| 76 | 3-(4-chloro-3,5-dimethyl-pyrazol-1-yl)-N-(2-ethyl-1,3-benzoxazol-6-yl)-N-methyl-benzamide, |
| 77 | 3-(4-chloro-3,5-dimethyl-pyrazol-1-yl)-N-methyl-N-(2-methylimidazo[1,2-a]pyridin-6-yl)benzamide, |
| 78 | 3-(4-chloro-3,5-dimethyl-pyrazol-1-yl)-N-methyl-N-[2-(trifluoromethyl)-1,3-benzoxazol-5-yl]benzamide, |
| 79 | 3-(4-chloro-3,5-dimethyl-pyrazol-1-yl)-N-methyl-N-(2-methyl-[1,2,4]triazolo[1,5-a]pyridin-6-yl)benzamide, |
| 80 | 3-(4-chloro-3,5-dimethyl-pyrazol-1-yl)-N-(5-chloro-2-methyl-1,3-benzoxazol-6-yl)-N-methyl-benzamide, |
| 81 | N-(1,3-benzodioxol-5-yl)-3-(4-cyano-3,5-dimethyl-pyrazol-1-yl)-N-methyl-benzamide, |
| 82 | N-(1,3-benzodioxol-5-yl)-3-(4-chloro-3,5-dimethyl-pyrazol-1-yl)-N,4-dimethyl-benzamide, |
| 83 | 2-[3-[1,3-benzodioxol-5-yl(methyl)carbamoyl]phenyl]-4-chloro-5-methyl-pyrazole-3-carboxylic acid, |
| 84 | 2-[3-[1,3-benzodioxol-5-yl(methyl)carbamoyl]phenyl]-4-chloro-5-methyl-pyrazole-3-carboxamide, |
| 85 | 2-[3-[1,3-benzodioxol-5-yl(methyl)carbamoyl]phenyl]-4-chloro-N,5-dimethyl-pyrazole-3-carboxamide, |
| 86 | ethyl 1-[3-[1,3-benzodioxol-5-yl(methyl) carbamoyl]phenyl]-4-chloro-5-isopropyl-pyrazole-3-carboxylate, |
| 87 | ethyl 2-[3-[1,3-benzodioxol-5-yl(methyl)carbamoyl] phenyl]-4-chloro-5-isopropyl-pyrazole-3-carboxylate, |
| 88 | 2-[3-[1,3-benzodioxol-5-yl(methyl)carbamoyl]phenyl]-4-chloro-N,N,5-trimethyl-pyrazole-3-carboxamide, |
| 89 | tert-butyl 2-[3-[1,3-benzodioxol-5-yl(methyl) carbamoyl]phenyl]-4-chloro-5-methyl-pyrazole-3-carboxylate, |
| 90 | N-(1,3-benzodioxol-5-yl)-3-[4-chloro-5-methyl-3-(trifluoromethyl)pyrazol-1-yl]-N-methyl-benzamide, |
| 91 | N-(1,3-benzodioxol-5-yl)-N-methyl-3-[5-methyl-3-(trifluoromethyl)pyrazol-1-yl]benzamide, |
| 92 | N-(1,3-benzodioxol-5-yl)-3-(4-chloro-3,5-diethyl-pyrazol-1-yl)-N-methyl-benzamide, |
| 93 | N-(1,3-benzodioxol-5-yl)-3-(3,5-diethylpyrazol-1-yl)-N-methyl-benzamide, |
| 94 | N-(1,3-benzodioxol-5-yl)-3-(4-chloro-5-cyclopropyl-3-methyl-pyrazol-1-yl)-N-methyl-benzamide, |
| 95 | 3-[4-chloro-5-methyl-3-(trifluoromethyl)pyrazol-1-yl]-N-(2,2-difluoro-1,3-benzodioxol-5-yl)-N-methyl-benzamide, |
| 96 | 3-[4-chloro-5-methyl-3-(trifluoromethyl)pyrazol-1-yl]-N-(2,3-dihydro-1,4-benzodioxin-6-yl)-N-methyl-benzamide, |
| 97 | N-(1,3-benzodioxol-5-yl)-3-(5-cyclopropyl-3-methyl-pyrazol-1-yl)-N-methyl-benzamide, |
| 98 | N-(1,3-benzodioxol-5-yl)-3-[4-bromo-5-methyl-3-(trifluoromethyl)pyrazol-1-yl]-N-methyl-benzamide, |
| 99 | N-(1,3-benzodioxol-5-yl)-3-[3,5-dimethyl-4-(trifluoromethyl)pyrazol-1-yl]-N-methyl-benzamide, |

-continued

| # | Substance Name |
|---|---|
| 100 | N-(1,3-benzodioxol-5-yl)-3-[5-isobutyl-3-(trifluoromethyl)pyrazol-1-yl]-N-methyl-benzamide, |
| 101 | N-(1,3-benzodioxol-5-yl)-3-[4-chloro-5-isobutyl-3-(trifluoromethyl)pyrazol-1-yl]-N-methyl-benzamide, |
| 102 | N-(1,3-benzodioxol-5-yl)-3-[4-chloro-3-methyl-5-(trifluoromethyl)pyrazol-1-yl]-N-methyl-benzamide, |
| 103 | ethyl 4-chloro-2-[3-[2,3-dihydro-1,4-benzodioxin-6-yl(methyl)carbamoyl]phenyl]-5-methyl-pyrazole-3-carboxylate, |
| 104 | N-(1,3-benzodioxol-5-yl)-3-[4-cyclopropyl-5-methyl-3-(trifluoromethyl)pyrazol-1-yl]-N-methyl-benzamide, |
| 105 | N-(1,3-benzodioxol-5-yl)-3-[4-chloro-5-(hydroxymethyl)-3-methyl-pyrazol-1-yl]-N-methyl-benzamide, |
| 106 | N-(6-chloro-1,3-benzodioxol-5-yl)-3-[4-chloro-5-methyl-3-(trifluoromethyl)pyrazol-1-yl]-N-methyl-benzamide, |
| 107 | N-(1,3-benzodioxol-5-yl)-3-[4-chloro-5-(methoxymethyl)-3-methyl-pyrazol-1-yl]-N-methyl-benzamide, |
| 108 | 3-[4-chloro-5-methyl-3-(trifluoromethyl)pyrazol-1-yl]-N-methyl-N-(2-methyl-1,3-benzoxazol-6-yl)benzamide, |
| 109 | N-(1,3-benzodioxol-5-yl)-3-[4-chloro-5-[(R)-hydroxy (phenyl)methyl]-3-methyl-pyrazol-1-yl]-N-methyl-benzamide, |
| 110 | N-(6-chloro-1,3-benzodioxol-5-yl)-3-[4-chloro-5-isobutyl-3-(trifluoromethyl)pyrazol-1-yl]-N-methyl-benzamide, |
| 111 | N-(1,3-benzodioxol-5-yl)-3-[4-chloro-5-cyclopropyl-3-(trifluoromethyl)pyrazol-1-yl]-N-methyl-benzamide, |
| 112 | N-(1,3-benzodioxol-5-yl)-3-(4-chloro-5-formyl-3-methyl-pyrazol-1-yl)-N-methyl-benzamide, |
| 113 | N-(1,3-benzodioxol-5-yl)-3-[4-chloro-5-ethoxy-3-(trifluoromethyl)pyrazol-1-yl]-N-methyl-benzamide, |
| 114 | N-(1,3-benzodioxol-5-yl)-3-[4-chloro-5-[(1R)-1-hydroxyethyl]-3-methyl-pyrazol-1-yl]-N-methyl-benzamide, |
| 115 | N-(1,3-benzodioxol-5-yl)-3-[4-chloro-5-(1-hydroxy-1-methyl-ethyl)-3-methyl-pyrazol-1-yl]-N-methyl-benzamide, |
| 116 | 3-(5-acetyl-4-chloro-3-methyl-pyrazol-1-yl)-N-(1,3-benzodioxol-5-yl)-N-methyl-benzamide, |
| 117 | N-(1,3-benzodioxol-5-yl)-3-[4-chloro-5-[(R)-methoxy (phenyl)methyl]-3-methyl-pyrazol-1-yl]-N-methyl-benzamide, |
| 118 | N-(1,3-benzodioxol-5-yl)-3-[4-chloro-3-methyl-5-(phenoxymethyl)pyrazol-1-yl]-N-methyl-benzamide, |
| 119 | N-(1,3-benzodioxol-5-yl)-3-(5-benzoyl-4-chloro-3-methyl-pyrazol-1-yl)-N-methyl-benzamide, |
| 122 | 3-[4-chloro-5-methyl-3-(trifluoromethyl)pyrazol-1-yl]-N-methyl-N-(2-methylindazol-6-yl)benzamide, |
| 123 | N-(5-chloro-2-methyl-1,3-benzoxazol-6-yl)-3-[4-chloro-5-methyl-3-(trifluoromethyl)pyrazol-1-yl]-N-methyl-benzamide, |
| 124 | N-(1,3-benzodioxol-5-yl)-3-[4-chloro-5-phenyl-3-(trifluoromethyl)pyrazol-1-yl]-N-methyl-benzamide, |
| 125 | N-(1,3-benzodioxol-5-yl)-N-methyl-3-[5-phenyl-3-(trifluoromethyl)pyrazol-1-yl]benzamide, |
| 126 | N-(1,3-benzodioxol-5-yl)-3-[4-fluoro-5-methyl-3-(trifluoromethyl)pyrazol-1-yl]-N-methyl-benzamide, |
| 129 | N-(1,3-benzodioxol-5-yl)-3-[4-chloro-3-methyl-5-(5-methyl-1,3,4-oxadiazol-2-yl)pyrazol-1-yl]-N-methyl-benzamide, |
| 130 | ethyl 2-3-[1,3-benzodioxol-5-yl(methyl)carbamoyl]phenyl]-5-(trifluoromethyl)pyrazole-3-carboxylate, |
| 131 | N-(1,3-benzodioxol-5-yl)-3-[5-isopropoxy-3-(trifluoromethyl)pyrazol-1-yl]-N-methyl-benzamide, |
| 132 | N-(1,3-benzodioxol-5-yl)-3-[5-benzyloxy-3-(trifluoromethyl)pyrazol-1-yl]-N-methyl-benzamide, |
| 133 | N-(1,3-benzodioxol-5-yl)-N-methyl-3-[5-phenethyloxy-3-(trifluoromethyl)pyrazol-1-yl]benzamide, |
| 134 | N-(1,3-benzodioxol-5-yl)-3-[5-benzyloxy-4-chloro-3-(trifluoromethyl)pyrazol-1-yl]-N-methyl-benzamide, |
| 135 | 3-[4-chloro-5-cyclopropyl-3-(trifluoromethyl)pyrazol-1-yl]-N-ethyl-N-(2-methyl-1,3-benzoxazol-6-yl)benzamide, |
| 137 | 3-[4-chloro-5-cyclopropyl-3-(trifluoromethyl)pyrazol-1-yl]-N-methyl-N-(2-methyl-1,3-benzoxazol-6-yl)benzamide, |
| 139 | 3-[4-chloro-5-cyclopropyl-3-(trifluoromethyl)pyrazol-1-yl]-N-(5-chloro-2-methyl-1,3-benzoxazol-6-yl)-N-methyl-benzamide, |
| 140 | ethyl 3-[[2-[3-[1,3-benzodioxol-5-yl(methyl)carbamoyl] phenyl]-4-chloro-5-methyl-pyrazol-3-yl]methoxy]benzoate, |
| 141 | ethyl 4-[[2-[3-[1,3-benzodioxol-5-yl(methyl)carbamoyl] phenyl]-4-chloro-5-methyl-pyrazol-3-yl]methoxy]benzoate, |
| 142 | N-(1,3-benzodioxol-5-yl)-3-[4-chloro-5-isopropoxy-3-(trifluoromethyl)pyrazol-1-yl]-N-methyl-benzamide, |
| 143 | 3-[[2-[3-[1,3-benzodioxol-5-yl(methyl)carbamoyl]phenyl]-4-chloro-5-methyl-pyrazol-3-yl]methoxy]benzoic acid, |

-continued

| # | Substance Name |
|---|---|
| 144 | 4-[[2-[3-[1,3-benzodioxol-5-yl(methyl)carbamoyl]phenyl]-4-chloro-5-methyl-pyrazol-3-yl]methoxy]benzoic acid, |
| 145 | tert-butyl 2-[[3-[4-chloro-5-cyclopropyl-3-(trifluoromethyl)pyrazol-1-yl]benzoyl]-(2-methyl-1,3-benzoxazol-6-yl)amino]acetate, |
| 146 | 2-[[3-[4-chloro-5-cyclopropyl-3-(trifluoromethyl)pyrazol-1-yl]benzoyl]-(2-methyl-1,3-benzoxazol-6-yl)amino]acetic acid, |
| 147 | N-(1,3-benzodioxol-5-yl)-3-[5-(2-furyl)-3-(trifluoromethyl)pyrazol-1-yl]-N-methyl-benzamide, |
| 149 | 3-[4-chloro-5-methyl-3-(trifluoromethyl)pyrazol-1-yl]-N-methyl-N-(2-methyl-1,3-benzothiazol-6-yl)benzamide, |
| 150 | ethyl 4-[[2-[3-[1,3-benzodioxol-5-yl(methyl)carbamoyl] phenyl]-4-chloro-5-(trifluoromethyl)pyrazol-3-yl]methoxy]benzoate, |
| 151 | 4-[[2-[3-[1,3-benzodioxol-5-yl(methyl)carbamoyl]phenyl]-4-chloro-5-(trifluoromethyl)pyrazol-3-yl]methoxy]benzoic acid, |
| 152 | methyl 4-[[2-[3-[1,3-benzodioxol-5-yl(methyl)carbamoyl]phenyl]-5-(trifluoromethyl)pyrazol-3-yl]oxymethyl]benzoate, |
| 154 | 3-[4-chloro-5-methyl-3-(trifluoromethyl)pyrazol-1-yl]-N-(5-fluoro-2-methyl-1,3-benzoxazol-6-yl)-N-methyl-benzamide, |
| 155 | methyl 4-[[2-[3-[1,3-benzodioxol-5-yl(methyl)carbamoyl] phenyl]-4-chloro-5-(trifluoromethyl)pyrazol-3-yl]oxymethyl]benzoate, |
| 156 | methyl 4-[[4-chloro-2-[3-[(6-chloro-1,3-benzodioxol-5-yl)-methyl-carbamoyl]phenyl]-5-(trifluoromethyl)pyrazol-3-yl]oxymethyl]benzoate, |
| 157 | tert-butyl 4-[2-[3-[1,3-benzodioxol-5-yl(methyl) carbamoyl]phenyl]-4-chloro-5-(trifluoromethyl)pyrazol-3-yl]oxypiperidine-1-carboxylate, |
| 158 | N-(1,3-benzodioxol-5-yl)-3-[5-ethoxy-3-(trifluoromethyl) pyrazol-1-yl]-N-methyl-benzamide, |
| 159 | 4-[[2-[3-[1,3-benzodioxol-5-yl(methyl)carbamoyl]phenyl]-4-chloro-5-(trifluoromethyl)pyrazol-3-yl]oxymethyl] benzoic acid, |
| 161 | 3-[4-chloro-5-methyl-3-(trifluoromethyl)pyrazol-1-yl]-N-(6-formyl-1,3-benzodioxol-5-yl)-N-methyl-benzamide, |
| 163 | 3-[4-chloro-5-methyl-3-(trifluoromethyl)pyrazol-1-yl]-N-(6-cyano-1,3-benzodioxol-5-yl)-N-methyl-benzamide, |
| 164 | N-(1,3-benzodioxol-5-yl)-3-[5-(5-chloro-2-thienyl)-3-(trifluoromethyl)pyrazol-1-yl]-N-methyl-benzamide, |
| 166 | N-(1,3-benzodioxol-5-yl)-N-methyl-3-[5-(2-thienyl)-3-(trifluoromethyl)pyrazol-1-yl]benzamide, |
| 168 | 3-[4-chloro-5-methyl-3-(trifluoromethyl)pyrazol-1-yl]-N-[6-(hydroxymethyl)-1,3-benzodioxol-5-yl]-N-methyl-benzamide, |
| 169 | N-(1,3-benzodioxol-5-yl)-N-methyl-2-[3-methyl-5-(trifluoromethyl)pyrazol-1-yl]pyridine-4-carboxamide, |
| 170 | N-(1,3-benzodioxol-5-yl)-2-[4-chloro-3-methyl-5-(trifluoromethyl)pyrazol-1-yl]-N-methyl-pyridine-4-carboxamide, |
| 171 | N-(1,3-benzodioxol-5-yl)-2-[4-chloro-5-methyl-3-(trifluoromethyl)pyrazol-1-yl]-N-methyl-pyridine-4-carboxamide, |
| 175 | tert-butyl 4-[[4-chloro-2-[3-[(2,2-difluoro-1,3-benzodioxol-5-yl)-methyl-carbamoyl]phenyl]-5-(trifluoromethyl)pyrazol-3-yl]methoxy]benzoate, |
| 176 | N-(1,3-benzodioxol-5-yl)-N-methyl-3-[3-(trifluoromethyl)-5-[2-(trifluoromethyl)phenyl]pyrazol-1-yl]benzamide, |
| 177 | 4-[[4-chloro-2-[3-[(2,2-difluoro-1,3-benzodioxol-5-yl)-methyl-carbamoyl]phenyl]-5-(trifluoromethyl)pyrazol-3-yl]methoxy]benzoic acid, |
| 179 | 6-[[3-[4-chloro-5-methyl-3-(trifluoromethyl)pyrazol-1-yl]benzoyl]-methyl-amino]-1,3-benzodioxole-5-carboxylic acid, |
| 180 | N-(1,3-benzodioxol-5-yl)-3-[4-formyl-5-phenoxy-3-(trifluoromethyl)pyrazol-1-yl]-N-methyl-benzamide, |
| 183 | N-(1,3-benzodioxol-5-yl)-3-[4-chloro-5-(2-methoxyphenyl)-3-(trifluoromethyl)pyrazol-1-yl]-N-methyl-benzamide, |
| 184 | N-(1,3-benzodioxol-5-yl)-3-[5-(2-methoxyphenyl)-3-(trifluoromethyl)pyrazol-1-yl]-N-methyl-benzamide, |
| 185 | N-(1,3-benzodioxol-5-yl)-3-[4-cyano-5-phenoxy-3-(trifluoromethyl)pyrazol-1-yl]-N-methyl-benzamide, |
| 186 | N-(1,3-benzodioxol-5-yl)-3-[4-formyl-5-methyl-3-(trifluoromethyl)pyrazol-1-yl]-N-methyl-benzamide, |
| 187 | N-(1,3-benzodioxol-5-yl)-3-[4-cyano-5-methyl-3-(trifluoromethyl)pyrazol-1-yl]-N-methyl-benzamide, |
| 188 | tert-butyl 4-[[2-[3-[methyl-(2-methyl-1,3-benzoxazol-6-yl)carbamoyl]phenyl]-5-(trifluoromethyl)pyrazol-3-yl]oxymethyl]benzoate, |
| 189 | tert-butyl 4-[[2-[3-[(5-fluoro-2-methyl-1,3-benzoxazol-6-yl)-methyl-carbamoyl]phenyl]-5-(trifluoromethyl)pyrazol-3-yl]oxymethyl]benzoate, |
| 190 | tert-butyl 4-[[4-chloro-2-[3-[methyl-(2-methyl-1,3-benzoxazol-6-yl)carbamoyl]phenyl]-5-(trifluoromethyl)pyrazol-3-yl]oxymethyl]benzoate, |
| 191 | tert-butyl 4-[[2-[3-[(2,2-difluoro-1,3-benzodioxol-5-yl)-methyl-carbamoyl]phenyl]-5-(trifluoromethyl)pyrazol-3-yl]oxymethyl]benzoate, |
| 192 | N-(1,3-benzodioxol-5-yl)-N-methyl-3-[3-(2-pyridyl)-5-(trifluoromethyl)pyrazol-1-yl]benzamide, |
| 193 | N-(1,3-benzodioxol-5-yl)-N-methyl-3-[5-(3-pyridyl)-3-(trifluoromethyl)pyrazol-1-yl]benzamide, |

-continued

| # | Substance Name |
|---|---|
| 194 | N-(1,3-benzodioxol-5-yl)-N-methyl-3-[3-(3-pyridyl)-5-(trifluoromethyl)pyrazol-1-yl]benzamide, |
| 195 | 4-[[2-[3-[methyl-(2-methyl-1,3-benzoxazol-6-yl)carbamoyl]phenyl]-5-(trifluoromethyl)pyrazol-3-yl]oxymethyl]benzoic acid, |
| 196 | 4-[[2-[3-[(5-fluoro-2-methyl-1,3-benzoxazol-6-yl)-methyl-carbamoyl]phenyl]-5-(trifluoromethyl)pyrazol-3-yl]oxymethyl]benzoic acid, |
| 197 | 4-[[2-[3-[(2,2-difluoro-1,3-benzodioxol-5-yl)-methyl-carbamoyl]phenyl]-5-(trifluoromethyl)pyrazol-3-yl]oxymethyl]benzoic acid, |
| 198 | 4-[[4-chloro-2-[3-[methyl-(2-methyl-1,3-benzoxazol-6-yl)carbamoyl]phenyl]-5-(trifluoromethyl)pyrazol-3-yl]oxymethyl]benzoic acid, |
| 200 | tert-butyl 4-[2-[3-[1,3-benzodioxol-5-yl(methyl) carbamoyl]phenyl]-4-cyano-5-(trifluoromethyl)pyrazol-3-yl]oxybenzoate, |
| 201 | tert-butyl 4-[[4-chloro-2-[3-[(2,2-difluoro-1,3-benzodioxol-5-yl)-methyl-carbamoyl]phenyl]-5-(trifluoromethyl)pyrazol-3-yl]oxymethyl]benzoate, |
| 202 | tert-butyl 4-[[4-chloro-2-[3-[(5-fluoro-2-methyl-1,3-benzoxazol-6-yl)-methyl-carbamoyl]phenyl]-5-(trifluoromethyl)pyrazol-3-yl]oxymethyl]benzoate, |
| 204 | N-(1,3-benzodioxol-5-yl)-N-methyl-3-[5-methyl-3-(trifluoromethyl)pyrazol-1-yl]benzenesulfonamide, |
| 207 | 3-[4-chloro-5-methyl-3-(trifluoromethyl)pyrazol-1-yl]-N-(4-formyl-1,3-benzodioxol-5-yl)-N-methyl-benzamide, |
| 208 | 5-[[3-[4-chloro-5-methyl-3-(trifluoromethyl)pyrazol-1-yl]benzoyl]-methyl-amino]-1,3-benzodioxole-4-carboxylic acid, |
| 209 | 3-[4-chloro-5-methyl-3-(trifluoromethyl)pyrazol-1-yl]-N-[4-(hydroxymethyl)-1,3-benzodioxol-5-yl]-N-methyl-benzamide, |
| 210 | 4-[2-[3-[1,3-benzodioxol-5-yl(methyl)carbamoyl]phenyl]-4-cyano-5-(trifluoromethyl)pyrazol-3-yl]oxybenzoic acid, |
| 211 | 4-[[4-chloro-2-[3-[(2,2-difluoro-1,3-benzodioxol-5-yl)-methyl-carbamoyl]phenyl]-5-(trifluoromethyl)pyrazol-3-yl]oxymethyl]benzoic acid, |
| 212 | 4-[[4-chloro-2-[3-[(5-fluoro-2-methyl-1,3-benzoxazol-6-yl)-methyl-carbamoyl]phenyl]-5-(trifluoromethyl)pyrazol-3-yl]oxymethyl]benzoic acid, |
| 213 | ethyl-cis-4-[2-[3-[1,3-benzodioxol-5-yl(methyl)carbamoyl]phenyl]-5-(trifluoromethyl)pyrazol-3-yl]oxycyclohexanecarboxylate, |
| 214 | ethyl 4-[2-[3-[1,3-benzodioxol-5-yl(methyl)carbamoyl] phenyl]-5-(trifluoromethyl)pyrazol-3-yl]oxycyclo hexanecarboxylate, |
| 215 | 4-[2-[3-[1,3-benzodioxol-5-yl(methyl)carbamoyl]phenyl]-5-(trifluoromethyl)pyrazol-3-yl]oxycyclohexanecarboxylic acid, |
| 216 | cis-4-[2-[3-[1,3-benzodioxol-5-yl(methyl)carbamoyl] phenyl]-5-(trifluoromethyl)pyrazol-3-yl]oxycyclo hexanecarboxylic acid, |
| 217 | 3-[4-chloro-5-(hydroxymethyl)-3-(trifluoromethyl) pyrazol-1-yl]-N-(2,2-difluoro-1,3-benzodioxol-5-yl)-N-methyl-benzamide, |
| 218 | 4-[[2-[3-[(2,2-difluoro-1,3-benzodioxol-5-yl)-methyl-carbamoyl]phenyl]-5-(trifluoromethyl)pyrazol-3-yl]methoxy]benzoic acid, |
| 219 | 3-[4-chloro-5-isobutyl-3-(trifluoromethyl)pyrazol-1-yl]-N-(2,2-difluoro-1,3-benzodioxol-5-yl)-N-methyl-benzamide, |
| 220 | N-(2,2-difluoro-1,3-benzodioxol-5-yl)-3-[4-fluoro-5-methyl-3-(trifluoromethyl)pyrazol-1-yl]-N-methyl-benzamide, |
| 221 | 3-[4-chloro-5-cyclopropyl-3-(trifluoromethyl)pyrazol-1-yl]-N-(2,2-difluoro-1,3-benzodioxol-5-yl)-N-methyl-benzamide, |
| 222 | 4-[4-chloro-2-[3-[(2,2-difluoro-1,3-benzodioxol-5-yl)-methyl-carbamoyl]phenyl]-5-(trifluoromethyl)pyrazol-3-yl]oxycyclohexanecarboxylic acid, |
| 223 | 4-[[4-cyano-2-[3-[(2,2-difluoro-1,3-benzodioxol-5-yl)-methyl-carbamoyl]phenyl]-5-(trifluoromethyl)pyrazol-3-yl]oxymethyl]benzoic acid, |
| 224 | 4-[[4-cyano-2-[3-[(2,2-difluoro-1,3-benzodioxol-5-yl)-methyl-carbamoyl]phenyl]-5-(trifluoromethyl)pyrazol-3-yl]methoxy]benzoic acid, |
| 225 | 2-[[4-chloro-2-[3-[(2,2-difluoro-1,3-benzodioxol-5-yl)-methyl-carbamoyl]phenyl]-5-(trifluoromethyl)pyrazol-3-yl]methoxy]thiazole-5-carboxylic acid, |
| 226 | 5-[[4-chloro-2-[3-[(2,2-difluoro-1,3-benzodioxol-5-yl)-methyl-carbamoyl]phenyl]-5-(trifluoromethyl)pyrazol-3-yl]methoxy]pyrazine-2-carboxylic acid, |
| 227 | 3-[[4-chloro-2-[3-[(2,2-difluoro-1,3-benzodioxol-5-yl)-methyl-carbamoyl]phenyl]-5-(trifluoromethyl)pyrazol-3-yl]methoxy]bicyclo[1.1.1]pentane-1-carboxylic acid, |
| 228 | Trans-4-[[4-chloro-2-[3-[(2,2-difluoro-1,3-benzodioxol-5-yl)-methyl-carbamoyl]phenyl]-5-(trifluoromethyl)pyrazol-3-yl]methoxy]cyclohexanecarboxylic acid, |
| 229 | 3-[2-[3-[methyl-(2-methyl-1,3-benzoxazol-6-yl)carbamoyl]phenyl]-5-(trifluoromethyl)pyrazol-3-yl]oxycyclobutanecarboxylic acid, |
| 230 | N-(1,3-benzodioxol-5-yl)-4-[4-chloro-5-methyl-3-(trifluoromethyl)pyrazol-1-yl]-N-methyl-pyridine-2-carboxamide, |
| 231 | 4-[[4-chloro-2-[3-[(2,2-difluoro-1,3-benzodioxol-5-yl)-methyl-carbamoyl]phenyl]-5-(trifluoromethyl)pyrazol-3-yl]methoxy]-2-fluoro-benzoic acid, |
| 232 | 1-[2-[3-[1,3-benzodioxol-5-yl(methyl)carbamoyl]phenyl]-4-chloro-5-(trifluoromethyl)pyrazol-3-yl]piperidine-4-carboxylic acid, |
| 233 | 4-[[4-chloro-2-[3-[methyl-(2-methyl-1,3-benzoxazol-6-yl)carbamoyl]phenyl]-5-(trifluoromethyl)pyrazol-3-yl]methoxy]benzoic acid, |
| 234 | 4-[[4-chloro-2-[3-[(5-fluoro-2-methyl-1,3-benzoxazol-6-yl)-methyl-carbamoyl]phenyl]-5-(trifluoromethyl)pyrazol-3-yl]methoxy]benzoic acid, |
| 235 | 4-[1-[2-[3-[1,3-benzodioxol-5-yl(methyl)carbamoyl]phenyl]-4-chloro-5-(trifluoromethyl)pyrazol-3-yl]-1-methyl-ethoxy]benzoic acid, |

-continued

| # | Substance Name |
|---|---|
| 236 | 4-[[4-chloro-2-[3-[methyl-(2-methyl-[1,2,4]triazolo[1,5-a]pyridin-6-yl)carbamoyl]phenyl]-5-(trifluoromethyl)pyrazol-3-yl]methoxy]benzoic acid, |
| 237 | 4-[[4-chloro-2-[3-[methyl-(3-methyl-1H-pyrazolo[3,4-b]pyridin-5-yl)carbamoyl]phenyl]-5-(trifluoromethyl)pyrazol-3-yl]methoxy]benzoic acid, |
| 238 | 4-[[4-chloro-2-[3-[methyl-(2-methylpyrazolo[1,5-a]pyrimidin-6-yl)carbamoyl]phenyl]-5-(trifluoromethyl)pyrazol-3-yl]methoxy]benzoic acid, |
| 239 | 4-[[4-chloro-2-[3-[methyl-(2-methylpyrazolo[1,5-a]pyridin-5-yl)carbamoyl]phenyl]-5-(trifluoromethyl)pyrazol-3-yl]methoxy]benzoic acid, |
| 240 | 4-[[4-chloro-2-[3-[methyl(6-quinolyl)carbamoyl]phenyl]-5-(trifluoromethyl)pyrazol-3-yl]methoxy]benzoic acid, |
| 241 | 4-[[4-chloro-2-[3-[methyl-(2-methyloxazolo[4,5-b]pyridin-6-yl)carbamoyl]phenyl]-5-(trifluoromethyl)pyrazol-3-yl]methoxy]benzoic acid, |
| 242 | 1-[2-[3-[1,3-benzodioxol-5-yl(methyl)carbamoyl]phenyl]-4-chloro-5-(trifluoromethyl)pyrazol-3-yl]azetidine-3-carboxylic acid, |
| 243 | 4-[[4-chloro-2-[5-[(2,2-difluoro-1,3-benzodioxol-5-yl)-methyl-carbamoyl]-3-pyridyl]-5-(trifluoromethyl)pyrazol-3-yl]methoxy]benzoic acid, |
| 244 | 4-[[4-chloro-2-[3-[(1,1-dioxo-2,3-dihydrobenzothiophen-6-yl)-methyl-carbamoyl]phenyl]-5-(trifluoromethyl)pyrazol-3-yl]methoxy]benzoic acid, |
| 245 | 4-[[4-chloro-2-[3-[methyl-(3-methyl-1,2-benzoxazol-6-yl)carbamoyl]phenyl]-5-(trifluoromethyl)pyrazol-3-yl]methoxy]benzoic acid, |
| 246 | 3-[[4-chloro-2-[3-[(2,2-difluoro-1,3-benzodioxol-5-yl)-methyl-carbamoyl]phenyl]-5-(trifluoromethyl)pyrazol-3-yl]methoxy]isoxazole-5-carboxylic acid, |
| 247 | 4-[[4-chloro-2-[3-[(2,2-difluoro-1,3-benzodioxol-5-yl)-methyl-carbamoyl]phenyl]-5-(trifluoromethyl)pyrazol-3-yl]methoxy]pyrrolidine-2-carboxylic acid, |
| 248 | 6-[[4-chloro-2-[3-[(2,2-difluoro-1,3-benzodioxol-5-yl)-methyl-carbamoyl]phenyl]-5-(trifluoromethyl)pyrazol-3-yl]methoxy]pyridine-3-carboxylic acid, |
| 249 | 4-[[4-chloro-2-[3-[(3-hydroxyindan-5-yl)-methyl-carbamoyl]phenyl]-5-(trifluoromethyl)pyrazol-3-yl]methoxy]benzoic acid, |
| 250 | 4-[[4-chloro-2-[3-[(2,2-difluoro-[1,3]dioxolo[4,5-b]pyrazin-5-yl)-methyl-carbamoyl]phenyl]-5-(trifluoromethyl)pyrazol-3-yl]methoxy]benzoic acid, |
| 251 | 4-[[4-chloro-2-[3-[methyl-(2-methyloxazolo[4,5-b]pyridin-6-yl)carbamoyl]phenyl]-5-(trifluoromethyl)pyrazol-3-yl]methoxy]benzoic acid, |
| 252 | N-(2,2-difluoro-1,3-benzodioxol-5-yl)-N-methyl-3-[5-methyl-3-(p-tolylmethoxy)-6,7-dihydro-4H-pyrazolo[4,3-c]pyridin-2-yl]benzamide, |
| 253 | N-(2,2-difluoro-1,3-benzodioxol-5-yl)-N-methyl-3-[3-(p-tolylmethoxy)-4,5,6,7-tetrahydroindazol-2-yl]benzamide, |
| 254 | methyl 3-[[2-[3-[(2,2-difluoro-1,3-benzodioxol-5-yl)-methyl-carbamoyl]phenyl]-5-(trifluoromethyl)pyrazol-3-yl]oxymethyl]bicyclo[1.1.1]pentane-1-carboxylate, |
| 255 | 3-[[2-[3-[(2,2-difluoro-1,3-benzodioxol-5-yl)-methyl-carbamoyl]phenyl]-5-(trifluoromethyl)pyrazol-3-yl]oxymethyl]bicyclo[1.1.1]pentane-1-carboxylic acid, |
| 256 | 4-[[4-chloro-2-[3-[methyl-(2-methylimidazo[1,2-a]pyridin-6-yl)carbamoyl]phenyl]-5-(trifluoromethyl)pyrazol-3-yl]methoxy]benzoic acid, |
| 257 | 3-[[4-chloro-2-[3-[(2,2-difluoro-1,3-benzodioxol-5-yl)-methyl-carbamoyl]phenyl]-5-(trifluoromethyl)pyrazol-3-yl]methoxy]cyclobutanecarboxylic acid, |
| 258 | 3-[[4-chloro-2-[3-[(2,2-difluoro-1,3-benzodioxol-5-yl)-methyl-carbamoyl]phenyl]-5-(trifluoromethyl)pyrazol-3-yl]oxymethyl]bicyclo[1.1.1]pentane-1-carboxylic acid, |
| 259 | tert-butyl 4-[[4-cyano-2-[3-[(2,2-difluoro-1,3-benzodioxol-5-yl)-methyl-carbamoyl]phenyl]-5-(trifluoromethyl)pyrazol-3-yl]methoxy]benzoate, |
| 260 | ethyl 4-[2-[3-[(2,2-difluoro-1,3-benzodioxol-5-yl)-methyl-carbamoyl]phenyl]-5-(trifluoromethyl)pyrazol-3-yl]oxy-1-piperidyl]-4-oxo-butanoate, |
| 261 | 3-[4-chloro-5-methyl-3-(trifluoromethyl)pyrazol-1-yl]-N-methyl-N-(2-methyloxazolo[4,5-b]pyridin-6-yl)benzamide, |
| 262 | 4-[[2-[3-[2,3-dihydrobenzofuran-6-yl(methyl)carbamoyl]phenyl]-5-(trifluoromethyl)pyrazol-3-yl]oxymethyl]benzoic acid, |
| 263 | 4-[[2-[3-[methyl-(3-methyl-1,2-benzoxazol-6-yl)carbamoyl]phenyl]-5-(trifluoromethyl)pyrazol-3-yl]oxymethyl]benzoic acid, |
| 264 | 4-[4-[2-[3-[(2,2-difluoro-1,3-benzodioxol-5-yl)-methyl-carbamoyl]phenyl]-5-(trifluoromethyl)pyrazol-3-yl]oxy-1-piperidyl]-4-oxo-butanoic acid, |
| 265 | 1-[[2-[3-[(2,2-difluoro-1,3-benzodioxol-5-yl)-methyl-carbamoyl]phenyl]-5-(trifluoromethyl)pyrazol-3-yl]oxymethyl]cyclopropanecarboxylic acid, |
| 266 | 4-[[2-[3-[(5-fluoro-2-methyl-1,3-benzoxazol-6-yl)-methyl-carbamoyl]phenyl]-5-(trifluoromethyl)pyrazol-3-yl]methoxy]benzoic acid, |
| 267 | 4-[[4-chloro-2-[3-[[1,3]dioxolo[4,5-b]pyridin-6-yl(methyl)carbamoyl]phenyl]-5-(trifluoromethyl)pyrazol-3-yl]methoxy]benzoic acid, |
| 268 | 4-[[4-cyano-2-[3-[(2,2-difluoro-1,3-benzodioxol-5-yl)-methyl-carbamoyl]phenyl]-5-(difluoromethyl)pyrazol-3-yl]methoxy]benzoic acid, |
| 269 | 3-[4-chloro-5-methyl-3-(trifluoromethyl)pyrazol-1-yl]-N-methyl-N-(4-methyl-1,3-benzodioxol-5-yl)benzamide, |
| 270 | 4-[[4-chloro-2-[3-[(2,2-difluoro-1,3-benzodioxol-5-yl)-methyl-carbamoyl]phenyl]-5-(difluoromethyl)pyrazol-3-yl]methoxy]benzoic acid, |
| 271 | 4-[[4-chloro-5-(difluoromethyl)-2-[3-[methyl-(2-methyl-1,3-benzoxazol-6-yl)carbamoyl]phenyl]pyrazol-3-yl]methoxy]benzoic acid, |
| 272 | 4-[[4-chloro-2-[3-[[2-(difluoromethoxy)pyrimidin-5-yl]-methyl-carbamoyl]phenyl]-5-(trifluoromethyl)pyrazol-3-yl]methoxy]benzoic acid, |
| 273 | 4-[[4-chloro-5-(difluoromethyl)-2-[3-[methyl-(2-methyl-1,3-benzoxazol-6-yl)carbamoyl]phenyl]pyrazol-3-yl]oxymethyl]benzoic acid, |

| # | Substance Name |
|---|---|
| 274 | 4-[[2-[3-[(2,2-difluoro-1,3-benzodioxol-5-yl)-methyl-carbamoyl]phenyl]-5-(difluoromethyl)pyrazol-3-yl]methoxy]benzoic acid, |
| 275 | 4-[[4-chloro-2-[3-[(2,2-difluoro-3H-furo[3,2-b]pyridin-6-yl)-methyl-carbamoyl]phenyl]-5-(trifluoromethyl)pyrazol-3-yl]methoxy]benzoic acid, |
| 276 | 4-[[4-cyano-5-(difluoromethyl)-2-[3-[methyl-(2-methyloxazolo[4,5-b]pyridin-6-yl)carbamoyl]phenyl]pyrazol-3-yl]methoxy]benzoic acid, |
| 277 | 6-[[4-chloro-2-[3-[(2,2-difluoro-1,3-benzodioxol-5-yl)-methyl-carbamoyl]phenyl]-5-(trifluoromethyl)pyrazol-3-yl]methoxy]pyridazine-3-carboxylic acid, |
| 278 | 4-[[4-chloro-2-[3-[methyl-(2-methylpyrazolo[1,5-a]pyrimidin-6-yl)carbamoyl]phenyl]-5-(trifluoromethyl)pyrazol-3-yl]oxymethyl]benzoic acid, |
| 279 | 5-[[4-chloro-2-[3-[(2,2-difluoro-1,3-benzodioxol-5-yl)-methyl-carbamoyl]phenyl]-5-(trifluoromethyl)pyrazol-3-yl]methoxy]pyridine-2-carboxylic acid, |
| 280 | 6-[[4-chloro-2-[3-[[2-(difluoromethoxy)pyrimidin-5-yl]-methyl-carbamoyl]phenyl]-5-(trifluoromethyl)pyrazol-3-yl]methoxy]pyridine-3-carboxylic acid, |
| 281 | 5-[[2-[3-[(2,2-difluoro-1,3-benzodioxol-5-yl)-methyl-carbamoyl]phenyl]-5-(trifluoromethyl)pyrazol-3-yl]methoxy]pyridine-2-carboxylic acid, |
| 282 | 2-[[4-chloro-2-[3-[(2,2-difluoro-1,3-benzodioxol-5-yl)-methyl-carbamoyl]phenyl]-5-(trifluoromethyl)pyrazol-3-yl]methoxy]pyridine-4-carboxylic acid, |
| 283 | 4-[[4-cyano-2-[3-[[2-(difluoromethoxy)pyrimidin-5-yl]-methyl-carbamoyl]phenyl]-5-methyl-pyrazol-3-yl]methoxy]benzoic acid, |
| 284 | 4-[[4-cyano-5-methyl-2-[3-[methyl-(2-methyloxazolo[4,5-b]pyridin-6-yl)carbamoyl]phenyl]pyrazol-3-yl]methoxy]benzoic acid, |
| 285 | 4-[[5-methyl-2-[3-[methyl-(2-methylpyrazolo[1,5-a]pyrimidin-6-yl)carbamoyl]phenyl]pyrazol-3-yl]oxymethyl]benzoic acid, |
| 286 | 4-[[2-[3-[(2,2-difluoro-1,3-benzodioxol-5-yl)-methyl-carbamoyl]phenyl]-4,5,6,7-tetrahydroindazol-3-yl]oxymethyl]benzoic acid, and, |
| 287 | 4-[[2-[3-[(2,2-difluoro-1,3-benzodioxol-5-yl)-methyl-carbamoyl]phenyl]-5-methyl-6,7-dihydro-4H-pyrazolo[4,3-c]pyridin-3-yl]oxymethyl]benzoic acid. |

2. A pharmaceutical composition comprising a compound of claim 1 or a pharmaceutically acceptable salt of the compound or solvate of the compound.

\* \* \* \* \*

UNITED STATES PATENT AND TRADEMARK OFFICE
CERTIFICATE OF CORRECTION

PATENT NO. : 11,597,723 B2
APPLICATION NO. : 16/493457
DATED : March 7, 2023
INVENTOR(S) : Tiziano Bandiera et al.

It is certified that error appears in the above-identified patent and that said Letters Patent is hereby corrected as shown below:

On the Title Page

At Assignees (73), please delete "Gasiini" in the second applicant and replace it with "Gaslini."

At Assignees (73), please delete "FondaZione" in the third applicant and replace it with "Fondazione."

Signed and Sealed this
Seventeenth Day of December, 2024

Derrick Brent
*Acting Director of the United States Patent and Trademark Office*